United States Patent
Manoharan et al.

(10) Patent No.: US 8,796,436 B2
(45) Date of Patent: Aug. 5, 2014

(54) MODIFIED IRNA AGENTS

(71) Applicant: Alnylam Pharmaceuticals, Inc., Cambridge, MA (US)

(72) Inventors: Muthiah Manoharan, Cambridge, MA (US); Venkitasamy Kesavan, Cambridge, MA (US); Kallanthottathil Rajeev, Cambrige, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/849,003

(22) Filed: Mar. 22, 2013

(65) Prior Publication Data

US 2013/0211063 A1 Aug. 15, 2013

Related U.S. Application Data

(63) Continuation of application No. 12/714,298, filed on Feb. 26, 2010, now Pat. No. 8,507,661, and a continuation of application No. 10/916,185, filed on Aug. 10, 2004, now Pat. No. 7,745,608, and a continuation-in-part of application No. PCT/US2004/011829, filed on Apr. 16, 2004.

(60) Provisional application No. 60/493,986, filed on Aug. 8, 2003, provisional application No. 60/494,597, filed on Aug. 11, 2003, provisional application No. 60/506,341, filed on Sep. 26, 2003, provisional application No. 60/518,453, filed on Nov. 7, 2003, provisional application No. 60/463,772, filed on Apr. 17, 2003, provisional application No. 60/465,802, filed on Apr. 25, 2003, provisional application No. 60/469,612, filed on May 9, 2003, provisional application No. 60/510,246, filed on Oct. 9, 2003, provisional application No. 60/510,318, filed on Oct. 10, 2003, provisional application No. 60/503,414, filed on Sep. 15, 2003, provisional application No. 60/465,665, filed on Apr. 25, 2003.

(51) Int. Cl.
C07H 21/02 (2006.01)
C07H 21/04 (2006.01)

(52) U.S. Cl.
USPC .......................... 536/23.1; 536/22.1

(58) Field of Classification Search
None
See application file for complete search history.

(56) References Cited

U.S. PATENT DOCUMENTS

| | | |
|---|---|---|
| 4,572,912 A | 2/1986 | Yoshioka et al. |
| 5,328,470 A | 7/1994 | Nabel et al. |
| 5,519,134 A | 5/1996 | Acevedo et al. |
| 5,646,126 A | 7/1997 | Cheng et al. |
| 5,714,606 A | 2/1998 | Acevedo et al. |
| 6,147,204 A | 11/2000 | Gold et al. |
| 6,239,107 B1 | 5/2001 | Gozes et al. |
| 6,509,323 B1 | 1/2003 | Davis et al. |
| 2002/0016285 A1 | 2/2002 | Bhatt et al. |
| 2002/0086356 A1 | 7/2002 | Tuschl et al. |
| 2003/0008818 A1 | 1/2003 | Pun et al. |
| 2003/0170891 A1 | 9/2003 | McSwiggen |
| 2005/0107325 A1 | 5/2005 | Manoharan et al. |
| 2005/0119214 A1 | 6/2005 | Manoharan et al. |
| 2005/0164235 A1 | 7/2005 | Manoharan et al. |
| 2006/0058266 A1 | 3/2006 | Manoharan et al. |
| 2007/0179100 A1 | 8/2007 | Manoharan et al. |
| 2007/0275914 A1 | 11/2007 | Manoharan et al. |
| 2010/0240881 A1 | 9/2010 | Manoharan et al. |

FOREIGN PATENT DOCUMENTS

| | | |
|---|---|---|
| EP | 0023725 A1 | 2/1981 |
| WO | 9203464 A1 | 3/1992 |
| WO | 9518792 A1 | 7/1995 |
| WO | 0044895 A1 | 8/2000 |
| WO | 0044914 A1 | 8/2000 |
| WO | 0136646 A1 | 5/2001 |
| WO | 0175164 A2 | 10/2001 |
| WO | 0198273 A1 | 12/2001 |
| WO | 0244321 A2 | 6/2002 |
| WO | 02094185 A2 | 11/2002 |
| WO | 03012052 A2 | 2/2003 |
| WO | 03051839 A1 | 6/2003 |
| WO | 2004065601 A2 | 8/2004 |
| WO | 2004080406 A2 | 9/2004 |
| WO | 2004090108 A2 | 10/2004 |
| WO | 2004091515 A2 | 10/2004 |
| WO | 2004094345 A2 | 11/2004 |
| WO | 2005061499 A1 | 7/2005 |

OTHER PUBLICATIONS

Amarzguioui et al., "Tolerance for Mutations and Chemical Modifications in a siRNA," Nucleic Acids Research 31 (2):589-595 (2003).
Schwarz et al., "Asymmetry in the Assembly of the RNAi Enzyme Complex," Cell 115:199-208 (2003).
Sproat et al., "Synthesis of Modified Building Blocks Containing Amino or Thiol Moieties: Application of Modified oligodeoxyribonucleotides," Nucleosides Nucleotides 7:651-653 (1988).
Stetler-Stevenson et al., "Tumor Cell Interactions with the Extracellular Matrix During Invasion and Metastasis," Annu. Rev. Cell Biol. 9:541-573 (1993).
Stirchak, "Uncharged stereoregular nucleic acid analogs: 2. Morpholino nucleoside oligomers with carbamate internucleoside linkages," Nucleic Acids Res. 17:6129-6141 (1989).

(Continued)

*Primary Examiner* — Patrick Lewis
(74) *Attorney, Agent, or Firm* — Jeffrey N. Townes; LeClairRyan

(57) ABSTRACT

The invention relates to iRNA agents, which preferably include a monomer in which the ribose moiety has been replaced by a moiety other than ribose. The inclusion of such a monomer can allow for modulation of a property of the iRNA agent into which it is incorporated, e.g., by using the non-ribose moiety as a point to which a ligand or other entity, e.g., a lipophilic moiety. e.g., cholesterol, is directly, or indirectly, tethered. The invention also relates to methods of making and using such modified iRNA agents.

23 Claims, 28 Drawing Sheets

(56) References Cited

OTHER PUBLICATIONS

Strasser et al., "Apoptosis Signaling," Annu. Rev. Blochem. 69:217-245 (2000).
Tae et al., "Efforts toward expansion of the genetic alphabet: replication of DNA with three base pairs," J. Am. Chem. Soc. 123:7439-7440 (2001).
Takeda et al., "Convenient Methods for Syntheses of Active Carbamates, Ureas and Nitrosoureas Using N,N'-disuccinimido Carbonate (DSC)," Tetrahedron Lett. 24(42):4569-4572 (1983).
Tittensor, "The Preparation of Nucleoside Carbonates," J. Chem. Soc. (C), 2656-2662 (1971).
Truffert et al., "Synthesis, Purification and Characterization of Two Peptide-Oligonucleotide Conjugates as Potential Artificial Nucleases," Tetrahedron 52(8):3005-3016 (1996).
Valentijn et al., "Solid-phase Synthesis of Lysine-based Cluster Galactosides with High Affinity for the Asialoglycoprotein Receptor," Tetrahedron 3:759-770 (1997).
Verma et al., "Modified Oligonucleotides: Synthesis and Strategy for Users," Annu. Rev. Biochem. 67:99-134 (1998).
Vives et al., "A Truncated HIV-1 Tat Protein Basic Domain Rapidly Translocates through the Plasma Membrane and Accumulates in the Cell Nucleus," J. Biol. Chem. 272(25):16010-16017 (1997).
Weizman et al., "2,2'-Bipyridine ligandoside: a novel building block for modifying DNA with intra-duplex metal complexes," J. Am. Chem. Soc. 123:3375-3376 (2001).
Wender et al., "Oligocarbamate Molecular Transporters: Design, Synthesis, and Biological Evaluation of a New Class of Transporters for Drug Delivery," J. Am. Chem. Soc. 124:13382-13383 (2002).
Wengel, "Synthesis of 3'-C- and 4' C-Branched Oligodeoxynucicotides and the Development of Locked Nucleic Acid (LNA)," Acc. Chem. Res. 32:301-310 (1999).
Wijsman et al., "Solid-support synthesis of di- and tetramannosylated tetrathymidylic acid," Recl. Tray. Chim. Pays-Bas. 115:397-401 (1996).
Wilds et al., "Structural basis for recognition of guanosine by a synthetic tricyclic cytosine analogue: Guanidinium G-clamp," Helvetica Chimica Acta 86:966-978 (2003).
Wincott et al., "Synthesis, deprotection, analysis and purification of RNA and ribozymes," Nucleic Acids Res. 23 (14):2677-2684 (1995).
Wirz et al., "Facile chemoenzymic preparation of enantiomerically pure 2-methylglycerol derivatives as versatile tnfunctional C4-synthons," J. Org. Chem. 58:3980-3984 (1993).
Witzeman et al., "Transacetoacetylation with ten-Butyl Acetoacetate: Synthetic Applications," J. Org. Chem. 56:1713-1718 (1991).
Wu et al., "Efforts toward Expansion of the Genetic Alphabet: Optimization of Interbase Hydrophobic Interactions," J Am. Chem. Soc. 122:7621-7632 (2000).
Yokota, "Tumor progression and metastasis," Carcinogenesis 21:497-503 (2000).
Zhou et al., "Lipophilic polylysines mediate efficient DNA transfection in mammalian cells," J. of Controlled Release 19:269-274 (1992).
Zimmerman et al., "Model Studies Directed toward a General Triplex DNA Recognition Scheme: A Novel DNA Base That Binds a CG Base-Pair in an Organic Solvent," J. Am. Chem. Soc. 117:10769-10770 (1995).
Zitzmann et al., "Arginine-Glycine-Aspartic Acid (RGD)-Peptide Binds to Both Tumor and Tumor-Endothelial Cells in Vivo," Cancer Res. 62:5139-5143 (2002).
Amosova et al., "Effect of the 1-(2'-deoxy-beta-D-ribofuranosyl) 3-nitropyrrole residue on the stability of DNA duplexes and triplexes," Nucleic Acids Res. 25:1930-1934 (1997).
An et al., "Synthesis of Novel 3 '-C-MethyleneThymidine and 5-Methyluridine/Cytidine H-Phosphonates and Phosphonamidites for New Backbone Modification of Oligonucleotides," J. Org. Chem. 66:2789-2801 (2001).
Ausin et al., "Synthesis of Amino-and Guanidino-G-Clamp PNA Monomers," Organic Letters 4:4073-4075 (2002).

Aoki et al., "Potential tumor-targeting peptide vector of histidylated oligolysine conjugated to a tumor-homing RGD MOTIF," Cancer Gene Therapy 8:783-787 (2001).
Basbaum et al., "Focalized proteolysis: spatial and temporal regulation of extra cellular matrix degradation at the cell surface," Curr. Opin. Cell Biol. 8:731-738 (1996).
Benezra et al., "The Id proteins and angiogenesis," Oncogene 20(58):8334-8341 (2001).
Berger el al., "Universal bases for hybridization, replication and chain termination," Nucleic Acids Res. 28:2911-2914 (2000).
Bergstrom et al., "Synthesis, Structure, and Deoxyribonucleic Acid Sequencing with a Universal Nucleoside: 1-(2'-Deoxy-(B-D-ribofuranosyl)-3-nitropyrrole," Ant. Chem. Soc. 117:1201-1209 (1995).
Bernstein et al., "Role for a bidentate ribonucicase in the initiation step of RNA interference," Nature 409:363-366 (2001).
Birkedal-Hansen et al., "Matrix Metalloproteinases: A Review," Crit. Rev. Oral Biol. Med. 4:197-250(1993).
Boyd, "Invasion and metastasis," Cancer Metastasis Rev. 15(I):77-89 (1996).
Brinckerhoff et al., "Matrix metalloproteinases: a tail of a frog that became a prince," Nature Reviews 3:207-214 (2002).
Brotsehi et al., "A Stable DNA Duplex Containing a Non-Hydrogen-Bonding and Non-Shape-Complementary Base Couple: Interstrand Stacking as the Stability Determining Factor," Agnew Chem. Int. Ed. 40:3012-3014 (2001).
Chaloin et al., "Design of Carrier Peptide-Oligonucleotide Conjugates with Rapid Membrane Translocation and Nuclear Localization Properties," Biochem. Biophys. Res. Commun. 243:601-608 (1998).
Chao et al., "BCL-2 Family: Regulators of Cell Death," Annu. Rev. Immunol. 16:395-419 (1998).
Chen et al., "Gene therapy for brain tumors: regression of experimental gliomas by adenovirus-mediated gene transfer in vivo," Proc. Natl. Acad. Sci. USA 91:3054-3057 (1994).
Childs et al., "The MDR Superfamily of Genes and Its Biological Implications," Imp. Adv. Oncol. 21-36 (1994).
Chothia et al., "The Molecular Structure of Cell Adhesion Molecules," Anna. Rev. Binchem. 66:823-862 (1997).
Colledge et al., "Disruption of c-mos causes parthenogenetic development of unfertilized mouse eggs," Nature 370: 65-68 (1994).
Corey et al., "Protection of Hydroxyl Groups as tert-Butyldimcthylsilyl Derivatives," J. Am. Chem. Soc. 94:6190-6191 (1972).
Cormier et al., "Synthesis of hexanucleotide analogues containing diisopropylsilyl internucleotide linkages," Nucleic Acids Res. 16:4583-4594 (1988).
Cosstick et al, "Solid Phase Synthesis of Oligonucleotides Containing 3'-Thiothymidine," Tetrahedron Lett. 30 (35):4693-4696 (1989).
D'Ari, "Cycle-regulated genes and cell cycle regulation," Bioassays 23(7):563-565 (2001).
De et al., "Structure-Activity Relationships for Antiplasmodial Activity among 7-Substituted 4- Aminoquinolines," J. Med. Chem. 41:4918-4926 (1998).
Deller et al., "Cell surface receptors," Curr. Opin. Struct. Biol. 10(2):213-219 (2000).
Derossi et aL, "The Third Helix of the Antennapedia Homeodomain Translocates through Biological Membranes," J. Biol. Chem. 269(14):10444-10450 (1994).
Eckstein, "Oligonucleotides and Analogues, A practical approach," Table of Contents IRL Press (1991).
Edge et al., "Synthetic Analogues of Polynucleotides. Part VIII. Analogues of Oligonucleotides containing Carboxymethylthymidine," J. Chem. Soc. Perkin Trans. 1:1991-1996 (1972).
Elbashir el al., "RNA interference is mediated by 21-and 22-nucleotide RNAs," Genes and Dev. 15:188-200 (2001).
Elmquist et al., "VE-Cadherin-Derived Cell-Penetrating Peptide, pVEC, with Carrier Functions," Exp. Cell Res. 269:237-244 (2001).
Fang et al., "Fluoride-cleavable biotinylation phosphoramidite for 5'-end-labeling and affinity purification of synthetic oligonucleotides," Nucleic Acids Res. 31(2):708-715 (2003).
Fire et al., "Potent specific genetic interference by double-stranded RNA in Caenorhabditis elegans," Nature 391:806-811 (1998).

(56) References Cited

OTHER PUBLICATIONS

Fischer et al., "Cellular delivery of impermeable effector molecules in the form of conjugates with peptides capable of mediating membrane translocation" Bioconjugate Chem. 12:825-841 (2001).
Flanagan et al., "A cytosine analog that confers enhanced potency to antisense oligonucleotides," Proc. Natl. Acad. Sci. USA 96:3513-3518 (1999).
Fotedar et al., "Apoptosis and the cell cycle," Prog. Cell Cycle Res. 2:147-163 (1996).
Gante, "Azapeptides," Synthesis 405-413 (1989).
Gould et al., "Angiogenesis: An Expanding Universe," Hum. Pathol. 33(11):1061-1063 (2002).
Guckian et al., "Structure and Base Pairing Properties of a Replicable Nonpolar Isostere for Deoxyadenosine," J. Org. Chem. 63:9652-9656 (1998).
Hammond, "Argonaute2, a link between genetic and biochemical analyses of RNAi," Science 293:1146-1150 (2001).
Hashimoto et al., "Parthenogenetic activation of oocytes in c-mos-deficient mice," Nature 370:68-71 (1994).
Hanahan et al., "The Hallmarks of Cancer," Cell 100:57-70 (2000).
Haubner et al., "Glycosylated RGD-Containing Peptides: Tracer for Tumor Targeting and Angiogenesis Imaging with Improved Biokinetics," J. Nucl. Med. 42(2):326-336 (2001).
Holmes et al., "Steric inhibition of human immunodeficiency virus type-1 Tat-dependent trans-activation in vitro and in cells by oligonucleotides containing 2'-0-methyl G-clamp ribonucleoside analogues," Nucleic Acids Res. 31:2759-2768 (2003).
Holmes et al., "The Synthesis of 2'-O-Methyl G-Clamp Containing Oligonucleotides and Their Inhibition of the HIV-1 Tat-TAR Interaction," Nucleosides, Nucleotides & Nucleic Acids 22:1259-1262 (2003).
Hyrup et al., "Peptide Nucleic Acids (PNA): Synthesis, Properties and Potential Applications," Bioorganic & Medicinal Chemistry 4:5-23 (1996).
Iyer et al, "3H-1,2-Benzodithiole-3-one 1,1-Dioxide as an Improved Sulfurizing Reagent in the Solid-Phase Synthesis of Oligodeoxyribonucleoside Phosphorothioates," J. Am. Chem. Soc., 112:1253-1254 (1990).
Katajisto et al., "Solid-Phase Synthesis of Multiantennary Oligonucleotide Glycoconjugates Utilizing On-Support Oximation," Bioconjugate Chem. 15:890-896 (2004).
Kawasaki et al., "Uniformly Modified 2'-Deoxy-2'-fluoro Phosphorothioate Oligonucleotides as Nuclease-Resistant Antisense Compounds with High Affinity and Specificity for RNA Targets," J. Med. Chem. 36:831-841 (1993).
Ketting et al., "Dicer functions ill RNA interference and in synthesis of small RNA involved in developmental timing in *C. elegans*," Genes Dev. 15(20):2654-2659 (2001).
Krepela, "Cysteine proteinases in tumor cell growth and apoptosis," Neoplasma 48(5):332-349 (2001).
Kumar et al., "Express Protocol for Functionalization of Polymer Supports for Oligonucleotide Synthesis," Nucleosides & Nucleotides 15(4):879-888 (1996).
Lam et al., "A new type of synthetic peptide library for identifying ligand-binding activity," Nature 354:82-84 (1991).
Lan et al., "Minor Groove Hydration is Critical to the Stability of DNA Duplexes," J. Am. Chem. Soc. 122:6512-6513 (2000).
Larock, "Table of Contents from Comprehensive Organic Transformation," VCH Publishers, Inc. (1989).
Levin et al., "Rapid, One-Pot Conversion of Aryl Fluorides into Phenols with 2-Butyn-1-OL and Potassium t-Butoxide in Dmso," Synthetic Communications 32(9):1401-1406 (2002).
Limbach et al. "Summary: the modified nucleosides of RNA," Nucleic Acids Res. 22:2183-2196 (1994).
Lindgren et al., "Cell-penetrating peptides," Tips 21:99-103 (2000).
Liu et al., "Bi-stranded, multisite replication of a base pair between difluorotoluene and adenine: confirmation by 'inverse' sequencing," Chem. Biol. 4:919-926 (1997).
Loakes, "The applications of universal DNA base analogues," NAR 29:2437-2447 (2001).

Loakes, "Survey and Summary: The Applications of Universal DNA base analogues" Nucleic Acid Res. 29:2437-2117 (2001).
Maier et al., "Nuclease resistance of oligonucleotides containing the tricyclic cytosine analogues phenoxazine and 9-(2-aminoethoxy)-phenoxazine ("G-clamp") and origins of their nuclease resistance properties" Biochem. 41:1323-1327 (2002).
Manoharan, "Oligonucleotide Conjugates as Potential Antisense Drugs with Improved Uptake, Biodistribution, Targeted Delivery, and Mechanism of Action," Antisense Nucleic Acid Drug Devel. 12:103-128 (2002).
Martin, "Stereoselektive Synthese von 2'-0-(2-Methoxyethyl)ribonucleosiden: Nachbargruppenbeteiligung der methyoxyethosy-Gruppe bei der Ribosylierung von Heterocyclen," Helv. Chim. Acta 79:1930-1938 (1996) (English abstract only).
Matray et al., "Selective and Stable DNA Base Pairing without Hydrogen Bonds," J. Am. Chem. Soc. 120:6191-6192 (1998).
Matrisian, "Cancer biology: Extracellular proteinases in malignancy," Curr. Biol. 9(20):R776-778 (1999).
McMinn et al., "Efforts toward Expansion of the Genetic Alphabet; DNA Polymerase Recognition of a Highly Stable, Self-Pairing Hydrophobic Base," J. Am. Chem. Soc. 121:11585-11586 (1999).
Mendelsohn et al., "The EGF receptor family as target for cancer therapy," Oncogene, 19(56):6550-6565 (2000).
Mi et al., "Characterization of a Class of Cationic Peptides Able to Facilitate Efficient Protein Transduction in Vitro and in Vivo," Mol. Ther. 2(4):339-347 (2000).
Mignatti et al., "Biology and Biochemistry of proteinases in Tumor Invasion," Physiol. Rev. 73:161-195 (1993).
Mitchell et al., "Polyarginine enters cells more efficiently than other polycationic homopolymers," J. Pept. Res. 56:318-325 (2000).
Morales et al., "Importance of Terminal Base Pair Hydrogen-Bonding in 3'-End Proofreading by the Klenow Fragment of DNA Polymerase I," Biochem. 39:2626-2632 (2000).
Moran et al., "Difluorotoluene, a Nonpolar Isostere for Thymine, Codes Specifically and Efficiently for Adenine in DNA Replication," J. Am. Chem. Soc. 119:2056-2057 (1997).
Mullauer et al., "Mutations in apoptosis genes; a pathogenetic factor for human disease," Mutat. Res. 488(3):211-231 (2001).
Nakata et al., "A Formal Total Synthesis of Erythromycin A. 2. A Convergent Synthesis of Woodward's Caramate Intermediate," Tetrahedron Lett. 29(18):2223-2226 (1988).
Noguchi et al., "Total Synthesis of Analogs of Topostin B, A DNA Topoisomerase I Inhibitor. Part 1. Synthesis of Fragments of Topostin B-1 Analogs," Tetrahedron 51:10531-10544 (1995).
Nakatani et al., "Recognition of a Single Guanine Bulge by 2-Acylamino-1, 8-naphthyridine," J. Am. Chem. Soc. 122:2172-2177 (2000).
Nakatani et al., "Specific binding of 2-amino-1,8-naphthyridine into a single guanine bulge as evidenced by photooxidation of GG doublet," Bioorg. Med. Chem. Lett. 11:335-337 (2001).
Normanno et al., "The role of EGF-Related Peptides in Tumor Growth," Front. Biosci. 6:D685-707 (2001).
Nykanen et al., "ATP requirements and small interfering RNA structure in the RNA interference pathway," Cell 107:309-321 (2001).
Norton, "ID helix-loop-helix proteins in cell growth, differentiation and tumorigenesis," J. Cell Sci. 113(22):3897-3905 (2000).
Ogawa et al., "Efforts toward the Expansion of the Genetic Alphabet Information Storage and Replication with Unnatural Hydrophobic Base Pairs," J. Am. Chem. Soc. 122:3274-3287 (2000).
Ogawa et al., "Rational Design of an Unnatural Base Pair with Increased Kinetic Selectivity," J. Am. Chem. Soc. 122:8803-8804 (2000).
Oliver et al., "Effect of the universal base 3-nitropyrrole on the selectivity of neighboring natural bases" Organic Lett. 3:1977-1980 (2001).
Opalinska et al., "Nucleic-Acid Therapeutic: Basic Principles and Recent Applications," Nature Reviews Drug Discovery, 1:503-514 (2002).
Parise et al., New aspects of integrin signaling in cancer, Semin. Cancer Biol. 10(6):407-414 (2000).
Patri et al., "Dendritic polymer macromolecular carriers for drug delivery," Curr. Opin. Chem. Biol. 6:466-471 (2002).

(56) References Cited

OTHER PUBLICATIONS

Pooga et al., "Cell penetration by transportation," FASEB J. 12:67-77 (2000).

Pirrung et al., "A universal, photocleavable DNA base: nitropiperonyl 2'-deoxyriboside," J. Org. Chem. 66:2067-2071 (2001).

Prakash et al., "Synthesis of 2'-O'[2-[(N,N-Dimethylamino)oxy]ethyl]Modified Nucleosides and Oligonucleotides," J. Org. Chem. 67:357-369 (2002).

Prusiner et al., "Prion Protein Biology," Cell 93(3):337-348 (1998).

Quintana et al., "Design and Function of a Dendrimer-Based Therapeutic Nanodevice Targeted to Tumor Cells Through the Folate Receptor," Pharma Res. 19(9):1310-1316 (2002).

Rajeev el al., "High-Affinity Peptide Nucleic Acid Oligomers Containing Tricyclic Cytosine Analogues," Organic Letters 4:4395-4398 (2002).

Rajeev et al., "2'-Modified-2-thiothymidine Oligonucleotides," Org. Lett. 5(17):3005-3008 (2003).

Reed, "Mechanisms of Apoptosis" Am. J. Pathol. 157(5):1415-1430 (2000).

Rogers et al. "Mild conversion of electron deficient aryl fluorides to phenols using 2-(methylsulfonyl)ethanol," Tetrahedron Lett. 43:3585-3587 (2002).

Rubinstein et al., "Recent Advances in Cytokines, Cytokine Receptors and Signal Transduction," Cytokine Growth Factor Rev. 9(2):175-181 (1998).

Rump et al., "Preparation of Conugates of Oligodeoxynucleotides and Lipid Structures and their Interaction with Low-Density Lipoprotein," Bioconjugate Chem. 9(3):341-349 (1998).

Safar et al., "Molecular studies of prion diseases," Prog. Brain Res. 117:421-434 (1998).

Sajiki et al, "Highly chemoselective Hydrogenation with retention of the epoxide function using a heterogeneous Pd/C—Ethylenediamine catalyst and THF," Chem. Eur. J. 6(12):2200-2204 (2000).

Simeoni et al., "Insight into the mechanism of the peptide-based gene delivery system MPG: implications for delivery of siRNA into mammalian cells," Nucl. Acids Res. 31(11):2717-2724 (2003).

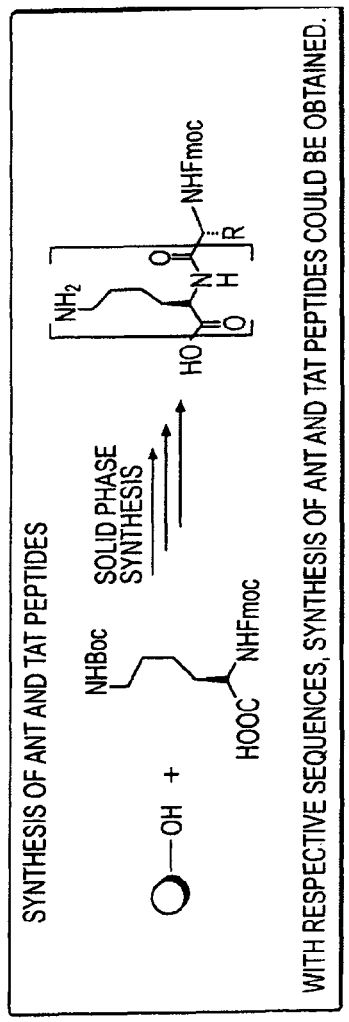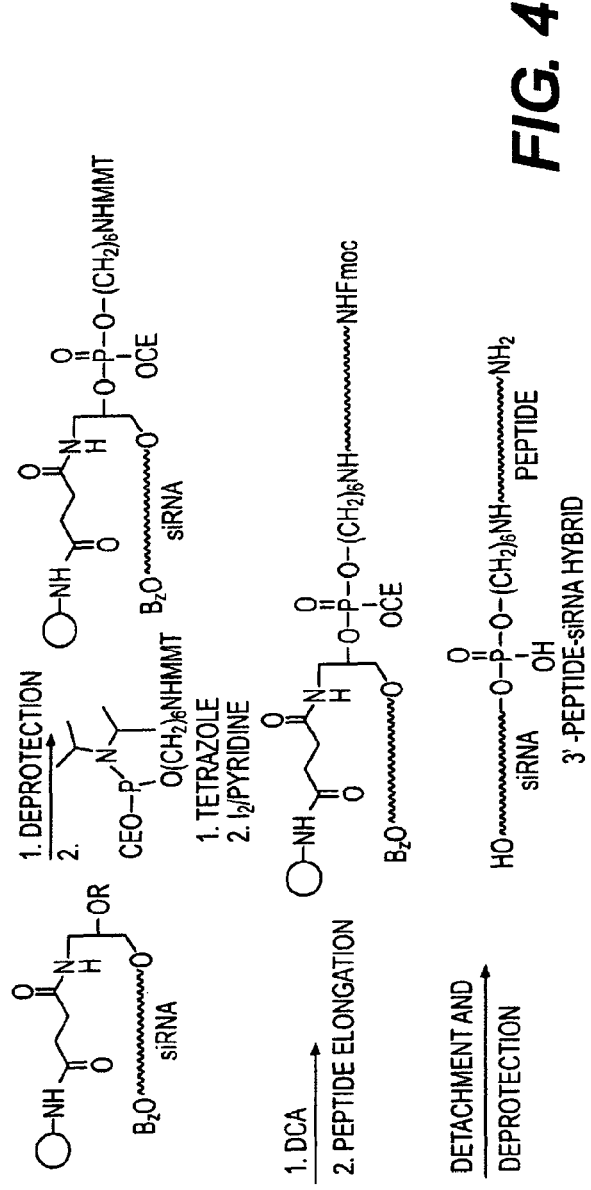
FIG. 4

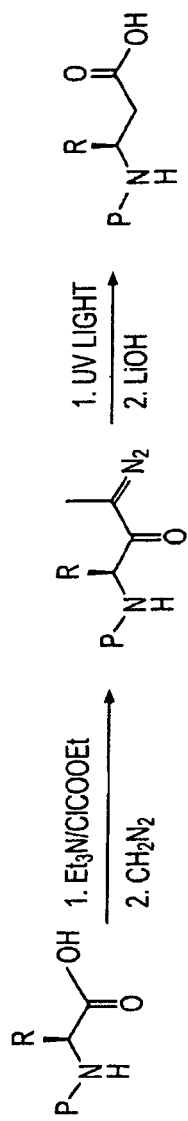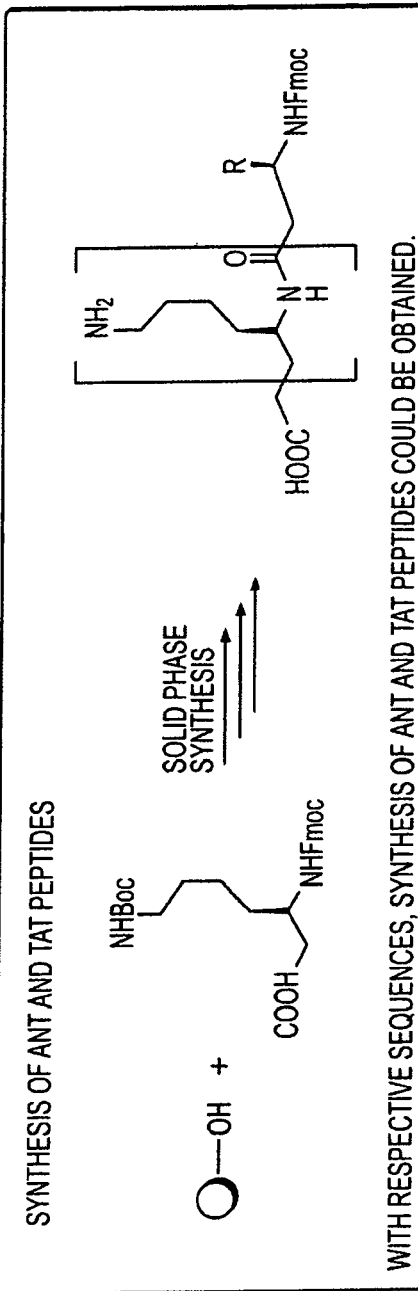
FIG. 8

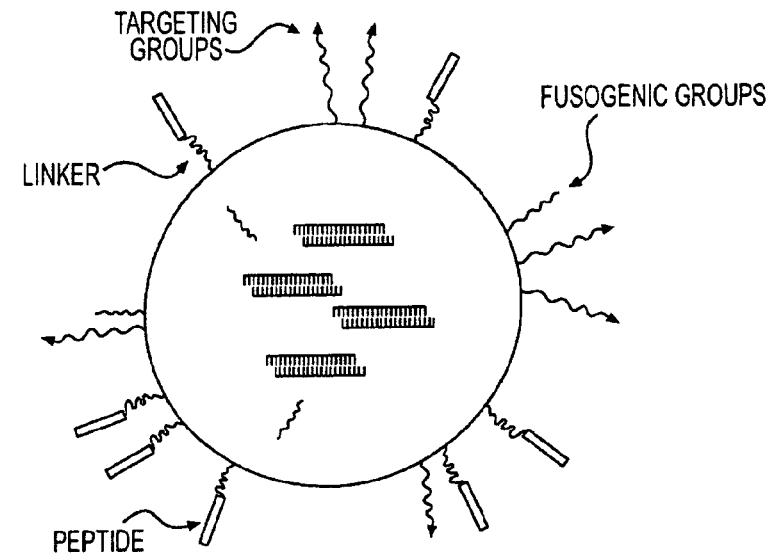
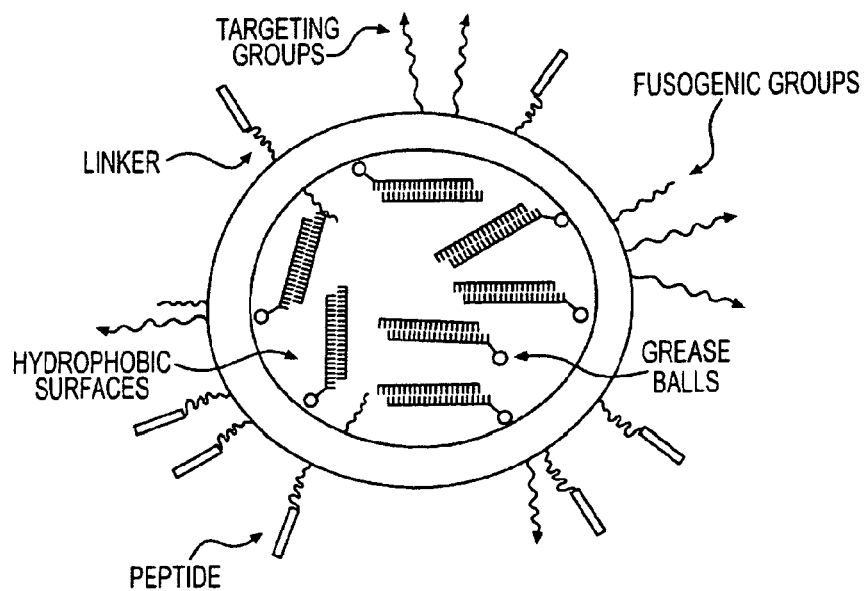
FIG. 11

FIG. 21

MODIFIED IRNA AGENTS

CROSS-REFERENCE TO RELATED APPLICATIONS

This application is a continuation of U.S. application Ser. No. 12/714,298, filed Feb. 26, 2010, which is a continuation of U.S. application Ser. No. 10/916,185, filed Aug. 10, 2004, now U.S. Pat. No. 7,745,608, which is a continuation-in-part of International Application No. PCT/US2004/011829, filed on Apr. 16, 2004, which claims the benefit of U.S. Provisional Application No. 60/493,986, filed on Aug. 8, 2003; U.S. Provisional Application No. 60/494,597, filed on Aug. 11, 2003; U.S. Provisional Application No. 60/506,341, filed on Sep. 26, 2003; U.S. Provisional Application No. 60/518,453, filed on Nov. 7, 2003; U.S. Provisional Application No. 60/463,772, filed on Apr. 17, 2003; U.S. Provisional Application No. 60/465,802, filed on Apr. 25, 2003; U.S. Provisional Application No. 60/469,612, filed on May 9, 2003; U.S. Provisional Application No. 60/510,246, filed on Oct. 9, 2003; U.S. Provisional Application No. 60/510,318, filed on Oct. 10, 2003; U.S. Provisional Application No. 60/503,414, filed on Sep. 15, 2003; U.S. Provisional Application No. 60/465,665, filed on Apr. 25, 2003; International Application No.: PCT/US04/07070, filed on Mar. 8, 2004; International Application No.: PCT/US2004/10586, filed on Apr. 5, 2004; International Application No.: PCT/US2004/11255, filed on Apr. 9, 2004; and International Application No.: PCT/US2004/011822, filed on Apr. 16, 2004. The contents of all of these prior applications are hereby incorporated by reference in their entireties.

TECHNICAL FIELD

The invention relates to iRNA agents, which preferably include a monomer in which the ribose moiety has been replaced by a moiety other than ribose. The inclusion of such a monomer can allow for modulation of a property of the iRNA agent into which it is incorporated, e.g., by using the non-ribose moiety as a point to which a ligand or other entity, e.g., a lipophilic moiety. e.g., cholesterol, is directly, or indirectly, tethered. The invention also relates to methods of making and using such modified iRNA agents.

BACKGROUND

RNA interference or "RNAi" is a term initially coined by Fire and co-workers to describe the observation that double-stranded RNA (dsRNA) can block gene expression when it is introduced into worms (Fire et al. (1998) *Nature* 391, 806-811). Short dsRNA directs gene-specific, post-transcriptional silencing in many organisms, including vertebrates, and has provided a new tool for studying gene function. RNAi may involve mRNA degradation.

SUMMARY

The inventor has discovered, inter alia, that the ribose sugar of one or more ribonucleotide subunits of an iRNA agent can be replaced with another moiety, e.g., a non-carbohydrate (preferably cyclic) carrier. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The carriers further include (i) at least two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" in some embodiments refers to a constituent ring atom of the cyclic carrier, e.g., a carbon atom or a heteroatom (distinct from an atom which provides a backbone attachment point), that connects a selected moiety. The moiety can be, e.g., a ligand, e.g., a targeting or delivery moiety, or a moiety which alters a physical property. One of the most preferred moieties is a moiety which promotes entry into a cell, e.g., a lipophilic moiety, e.g., cholesterol. While not wishing to be bound by theory it is believed the attachment of a lipohilic agent increases the lipophilicity of an iRNA agent. Optionally, the selected moiety is connected by an intervening tether to the cyclic carrier. Thus, it will often include a functional group, e.g., an amino group, or generally, provide a bond, that is suitable for incorporation or tethering of another chemical entity, e.g., a ligand to the constituent ring.

Incorporation of one or more RRMSs described herein into an RNA agent, e.g., an iRNA agent, particularly when tethered to an appropriate entity, can confer one or more new properties to the RNA agent and/or alter, enhance or modulate one or more existing properties in the RNA molecule. E.g., it can alter one or more of lipophilicity or nuclease resistance. Incorporation of one or more RRMSs described herein into an iRNA agent can, particularly when the RRMS is tethered to an appropriate entity, modulate, e.g., increase, binding affinity of an iRNA agent to a target mRNA, change the geometry of the duplex form of the iRNA agent, alter distribution or target the iRNA agent to a particular part of the body, or modify the interaction with nucleic acid binding proteins (e.g., during RISC formation and strand separation).

Accordingly, in one aspect, the invention features, an iRNA agent preferably comprising a first strand and a second strand, wherein at least one subunit having a formula (I) is incorporated into at least one of said strands:

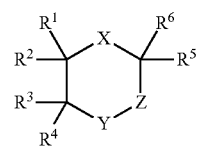

(I)

wherein:
X is N(CO)R$^7$, NR$^7$ or CH$_2$;
Y is NR$^8$, O, S, CR$^9$R$^{10}$, or absent;
Z is CR$^{11}$R$^{12}$ or absent;
Each of R$^1$, R$^2$, R$^3$, R$^4$, R$^9$, and R$^{10}$ is, independently, H, OR$^a$, OR$^b$, (CH$_2$)$_n$OR$^a$, or (CH$_2$)$_n$OR$^b$, provided that at least one of R$^1$, R$^2$, R$^3$, R$^4$, R$^9$, and R$^{10}$ is OR$^a$ or OR$^b$ and that at least one of R$^1$, R$^2$, R$^3$, R$^4$, R$^9$, and R$^{10}$ is (CH$_2$)$_n$OR$^a$, or (CH$_2$)$_n$OR$^b$ (when the RRMS is terminal, one of R$^1$, R$^2$, R$^3$, R$^4$, R$^9$, and R$^{10}$ will include R$^a$ and one will include R$^b$; when the RRMSS is internal, two of R$^1$, R$^2$, R$^3$, R$^4$, R$^9$, and R$^{10}$ will each include an $R^b$); further provided that preferably $OR^a$ may only be present with $(CH_2)_nOR^b$ and $(CH_2)_nOR^a$ may only be present with $OR^b$;

Each of $R^5$, $R^6$, $R^{11}$, and $R^{12}$ is, independently, H, $C_1$-$C_6$ alkyl optionally substituted with 1-3 $R^{13}$, or $C(O)NHR^7$; or $R^5$ and $R^{11}$ together are $C_3$-$C_8$ cycloalkyl optionally substituted with $R^{14}$;

$R^7$ can be a ligand, e.g., $R^7$ can be $R^d$, or $R^7$ can be a ligand tethered indirectly to the carrier, e.g., through a tethering moiety, e.g., $C_1$-$C_{20}$ alkyl substituted with $NR^cR^d$; or $C_1$-$C_{20}$ alkyl substituted with $NHC(O)R^d$;

$R^8$ is $C_1$-$C_6$ alkyl;
$R^{13}$ is hydroxy, $C_1$-$C_4$ alkoxy, or halo;
$R^{14}$ is $NR^cR^7$;
$R^a$ is H or:

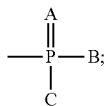

$R^b$ is H or:

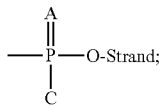

Each of A and C is, independently, O or S;
B is OH, O⁻, or

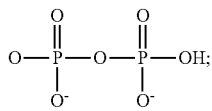

$R^c$ is H or $C_1$-$C_6$ alkyl;
$R^d$ is H or a ligand, e.g., a lipophilic ligand, e.g., cholesterol; and
n is 1-4.

Embodiments can include one or more of the following features.

The iRNA agent can be 21 nucleotides in length and there can be a duplex region of about 19 pairs.

The iRNA agent can include a duplex region between 17 and 23 pairs in length.

$R^1$ can be $CH_2OR^a$ and $R^3$ can be $OR^b$; or $R^1$ can be $CH_2OR^a$ and $R^9$ can be $OR^b$; or $R^1$ can be $CH_2OR^a$ and $R^2$ can be $OR^b$.

$R^1$ can be $CH_2OR^b$ and $R^3$ can be $OR^b$; or $R^1$ can be $CH_2OR^b$ and $R^9$ can be $OR^b$; or $R^1$ can be $CH_2OR^b$ and $R^2$ can be $OR^b$; or $R^1$ can be $CH_2OR^b$ and $R^3$ can be $OR^a$; or $R^1$ can be $CH_2OR^b$ and $R^9$ can be $OR^a$; or $R^1$ can be $CH_2OR^b$ and $R^2$ can be $OR^a$. $R^1$ can be $OR^a$ and $R^3$ can be $CH_2OR^b$; or $R^1$ can be $OR^a$ and $R^9$ can be $CH_2OR^b$; or $R^1$ can be $OR^a$ and $R^2$ can be $CH_2OR^b$.

$R^1$ can be $OR^b$ and $R^3$ can be $CH_2OR^b$; or $R^1$ can be $OR^b$ and $R^9$ can be $CH_2OR^b$; or $R^1$ can be $OR^b$ and $R^2$ can be $CH_2OR^b$; or $R^1$ can be $OR^b$ and $R^3$ can be $CH_2OR^a$; or $R^1$ can be $OR^b$ and $R^9$ can be $CH_2OR^a$; or $R^1$ can be $OR^b$ and $R^2$ can be $CH_2OR^a$.

$R^3$ can be $CH_2OR^a$ and $R^9$ can be $OR^b$; or $R^3$ can be $CH_2OR^a$ and $R^4$ can be $OR^b$.

$R^3$ can be $CH_2OR^b$ and $R^9$ can be $OR^b$; or $R^3$ can be $CH_2OR^b$ and $R^4$ can be $OR^b$; or $R^3$ can be $CH_2OR^b$ and $R^9$ can be $OR^a$; or $R^3$ can be $CH_2OR^b$ and $R^4$ can be $OR^a$.

$R^3$ can be $OR^b$ and $R^9$ can be $CH_2OR^a$; or $R^3$ can be $OR^b$ and $R^4$ can be $CH_2OR^a$; or $R^3$ can be $OR^b$ and $R^9$ can be $CH_2OR^b$; or $R^3$ can be $OR^b$ and $R^4$ can be $CH_2OR^b$.

$R^3$ can be $OR^a$ and $R^9$ can be $CH_2OR^b$; or $R^3$ can be $OR^a$ and $R^4$ can be $CH_2OR^b$.

$R^9$ can be $CH_2OR^a$ and $R^{10}$ can be $OR^b$.

$R^9$ can be $CH_2OR^b$ and $R^{10}$ can be $OR^b$; or $R^9$ can be $CH_2OR^b$ and $R^{10}$ can be $OR^a$.

In a preferred embodiment the ribose is replaced with a pyrroline scaffold or with a 4-hydroxyproline-derived scaffold, and X is $N(CO)R^7$ or $NR^7$, Y is $CR^9R^{10}$, and Z is absent.

$R^1$ and $R^3$ can be cis or $R^1$ and $R^3$ can be trans.

n can be 1.

A can be O or S.

$R^1$ can be $(CH_2)_nOR^b$ and $R^3$ can be $OR^b$; or $R^1$ can be $(CH_2)_nOR^a$ and $R^3$ can be $OR^b$.

$R^7$ can be $(CH_2)_5NHR^d$ or $(CH_2)_5NHR^d$. $R^d$ can be chosen from a folic acid radical; a cholesterol radical; a carbohydrate radical; a vitamin A radical; a vitamin E radical; a vitamin K radical. Preferably, $R^d$ is a cholesterol radical.

$R^1$ can be $OR^b$ and $R^3$ can be $(CH_2)_nOR^b$; or $R^1$ can be $OR^b$ and $R^3$ can be $(CH_2)_nOR^a$; or $R^1$ can be $OR^a$ and $R^3$ can be $(CH_2)_nOR^b$; or $R^1$ can be $(CH_2)_nOR^b$ and $R^9$ can be $OR^a$.

$R^1$ and $R^9$ can be cis or $R^1$ and $R^9$ can be trans.

$R^1$ can be $OR^a$ and $R^9$ can be $(CH_2)_nOR^b$; or $R^1$ can be $(CH_2)_nOR^b$ and $R^9$ can be $OR^b$; or $R^1$ can be $(CH_2)_nOR^a$ and $R^9$ can be $OR^b$; or $R^1$ can be $OR^b$ and $R^9$ can be $(CH_2)_nOR^b$; or $R^1$ can be $OR^b$ and $R^9$ can be $(CH_2)_nOR^a$.

$R^3$ can be $(CH_2)_nOR^b$ and $R^9$ can be $OR^a$; or $R^3$ can be $(CH_2)_nOR^b$ and $R^9$ can be $OR^b$; or $R^3$ can be $(CH_2)_nOR^a$ and $R^9$ can be $OR^b$; or $R^3$ can be $OR^a$ and $R^9$ can be $(CH_2)_nOR^b$; $R^3$ can be $OR^b$ and $R^9$ can be $(CH_2)_nOR^b$; or $R^3$ can be $OR^b$ and $R^9$ can be $(CH_2)_nOR^a$.

$R^3$ and $R^9$ can be cis or $R^3$ and $R^9$ can be trans.

In other preferred embodiments the ribose is replaced with a piperidine scaffold, and X is $N(CO)R^7$ or $NR^7$, Y is $CR^9R^{10}$, and Z is $CR^{11}R^{12}$.

$R^9$ can be $(CH_2)_nOR^b$ and $R^{10}$ can be $OR^a$.

n can be 1 or 2.

$R^9$ can be $(CH_2)_nOR^b$ and $R^{10}$ can be $OR^b$; or $R^9$ can be $(CH_2)_nOR^a$ and $R^{10}$ can be $OR^b$.

A can be O or S.

$R^7$ can be $(CH_2)_5NHR^d$ or $(CH_2)_5NHR^d$. $R^d$ can be selected from a folic acid radical; a cholesterol radical; a carbohydrate radical; a vitamin A radical; a vitamin E radical; a vitamin K radical. Preferably, $R^d$ is a cholesterol radical.

$R^3$ can be $(CH_2)_nOR^b$ and $R^4$ can be $OR^a$; or $R^3$ can be $(CH_2)_nOR^b$ and $R^4$ can be $OR^b$; or $R^3$ can be $(CH_2)_nOR^a$ and $R^4$ can be $OR^b$.

$R^1$ can be $(CH_2)_nOR^b$ and $R^2$ can be $OR^a$; or $R^1$ can be $(CH_2)_nOR^b$ and $R^2$ can be $OR^b$; or $R^1$ can be $(CH_2)_nOR^a$ and $R^2$ can be $OR^b$.

$R^3$ can be $(CH_2)_nOR^b$ and $R^9$ can be $OR^a$.

$R^3$ and $R^9$ can be cis, or $R^3$ and $R^9$ can be trans.

$R^3$ can be $(CH_2)_nOR^b$ and $R^9$ can be $OR^b$; or $R^3$ can be $(CH_2)_nOR^b$ and $R^9$ can be $OR^a$; or $R^3$ can be $(CH_2)_nOR^a$ and $R^9$ can be $OR^b$.

$R^1$ can be $(CH_2)_nOR^b$ and $R^3$ can be $OR^a$.

$R^1$ and $R^3$ can be cis, or $R^1$ and $R^3$ can be trans.

$R^3$ can be $OR^a$ and $R^9$ can be $(CH_2)_nOR^b$.

$R^1$ can be $OR^a$ and $R^3$ can be $(CH_2)_nOR^b$.

In other preferred embodiments the ribose is replaced with a piperazine scaffold, and X is $N(CO)R^7$ or $NR^7$, Y is $NR^8$, and Z is $CR^{11}R^{12}$.

$R^1$ can be $(CH_2)_nOR^b$ and $R^3$ can be $OR^a$.

$R^1$ and $R^3$ can be cis or $R^1$ and $R^3$ can be trans.

n can be 1.

$R^1$ can be $(CH_2)_nOR^b$ and $R^3$ can be $OR^b$; or $R^1$ can be $(CH_2)_nOR^a$ and $R^3$ can be $OR^b$.

A can be O or S, preferably S.

$R^7$ can be $(CH_2)_5NHR^d$ or $(CH_2)_5NHR^d$. $R^d$ can be chosen from the group of a folic acid radical; a cholesterol radical; a carbohydrate radical; a vitamin A radical; a vitamin E radical; a vitamin K radical. Preferably, $R^d$ is a cholesterol radical.

$R^8$ can be $CH_3$.

$R^1$ can be $OR^a$ and $R^3$ can be $(CH_2)_nOR^b$.

In other preferred embodiments the ribose is replaced with a morpholino scaffold, and X is $N(CO)R^7$ or $NR^7$, Y is O, and Z is $CR^{11}R^{12}$.

$R^1$ can be $(CH_2)_nOR^b$ and $R^3$ can be $OR^a$.

$R^1$ and $R^3$ can be cis, or $R^1$ and $R^3$ can be trans.

n can be 1.

$R^1$ can be $(CH_2)_nOR^b$ and $R^3$ can be $OR^b$; of $R^1$ can be $(CH_2)_nOR^a$ and $R^3$ can be $OR^b$.

A can be O or S.

$R^7$ can be $(CH_2)_5NHR^d$ or $(CH_2)_5NHR^d$. $R^d$ can be chosen from the group of a folic acid radical; a cholesterol radical; a carbohydrate radical; a vitamin A radical; a vitamin E radical; a vitamin K radical. Preferably, $R^d$ is a cholesterol radical.

$R^8$ can be $CH_3$.

$R^1$ can be $OR^a$ and $R^3$ can be $(CH_2)_nOR^b$.

In other preferred embodiments the ribose is replaced with a decalin scaffold, and X is $CH_2$; Y is $CR^9R^{10}$; and Z is $CR^{11}R^{12}$; and $R^5$ and $R^{11}$ together are $C^6$ cycloalkyl.

$R^6$ can be $C(O)NHR^7$.

$R^{12}$ can be hydrogen.

$R^6$ and $R^{12}$ can be trans.

$R^3$ can be $OR^a$ and $R^9$ can be $(CH_2)_nOR^b$.

$R^3$ and $R^9$ can be cis, or $R^3$ and $R^9$ can be trans.

n can be 1 or 2.

$R^3$ can be $OR^b$ and $R^9$ can be $(CH_2)_nOR^b$; or $R^3$ can be $OR^b$ and $R^9$ can be $(CH_2)_nOR^a$.

A can be O or S.

$R^7$ can be $(CH_2)_5NHR^d$ or $(CH_2)_5NHR^d$. $R^d$ can be chosen from the group of a folic acid radical; a cholesterol radical; a carbohydrate radical; a vitamin A radical; a vitamin E radical; a vitamin K radical. Preferably, $R^d$ is a cholesterol radical.

In other preferred embodiments the ribose is replaced with a decalin/indane scaffold, e.g., X is $CH_2$; Y is $CR^9R^{10}$; and Z is $CR^{11}R^{12}$; and $R^5$ and $R^{11}$ together are $C^5$ cycloalkyl.

$R^6$ can be $CH_3$.

$R^{12}$ can be hydrogen.

$R^6$ and $R^{12}$ can be trans.

$R^3$ can be $OR^a$ and $R^9$ can be $(CH_2)_nOR^b$.

$R^3$ and $R^9$ can be cis, or $R^3$ and $R^9$ can be trans.

n can be 1 or 2.

$R^3$ can be $OR^b$ and $R^9$ can be $(CH_2)_nOR^a$; or $R^3$ can be $OR^b$ and $R^9$ can be $(CH_2)_nOR^a$.

A can be O or S.

$R^{14}$ can be $N(CH3)R^7$. $R^7$ can be $(CH_2)_5NHR^d$ or $(CH_2)_5NHR^d$. $R^d$ can be chosen from the group of a folic acid radical; a cholesterol radical; a carbohydrate radical; a vitamin A radical; a vitamin E radical; a vitamin K radical. Preferably, $R^d$ is a cholesterol radical.

In another aspect, this invention features an iRNA agent comprising a first strand and a second strand, wherein at least one subunit having a formula (II) is incorporated into at least one of said strands:

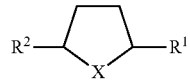

(II)

X is $N(CO)R^7$ or $NR^7$;

Each of $R^1$ and $R^2$ is, independently, $OR^a$, $OR^b$, $(CH_2)_nOR^a$, or $(CH_2)_nOR^b$, provided that one of $R^1$ and $R^2$ is $OR^a$ or $OR^b$ and the other is $(CH_2)_nOR^a$ or $(CH_2)_nOR^b$ (when the RRMS is terminal, one of $R^1$ or $R^2$ will include $R^a$ and one will include $R^b$; when the RRMSS is internal, both $R^1$ and $R^2$ will each include an $R^b$); further provided that preferably $OR^a$ may only be present with $(CH_2)_nOR^b$ and $(CH_2)_nOR^a$ may only be present with $OR^b$;

$R^7$ is $C_1$-$C_{20}$ alkyl substituted with $NR^cR^d$;

$R^8$ is $C_1$-$C_6$ alkyl;

$R^{13}$ is hydroxy, $C_1$-$C_4$ alkoxy, or halo;

$R^{14}$ is $NR^cR^7$;

$R^a$ is:

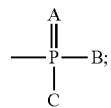

$R^b$ is

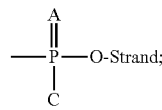

Each of A and C is, independently, O or S;

B is OH, O⁻, or

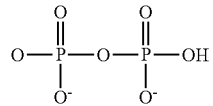

$R^c$ is H or $C_1$-$C_6$ alkyl;

$R^d$ is H or a ligand; and n is 1-4.

Embodiments can include one or more of the features described above.

In a further aspect, this invention features an iRNA agent having a first strand and a second strand, wherein at least one subunit having a formula (I) or formula (II) is incorporated into at least one of said strands.

In one aspect, this invention features an iRNA agent having a first strand and a second strand, wherein at least two subunits having a formula (I) and/or formula (II) are incorporated into at least one of said strands.

In another aspect, this invention provides a method of making an iRNA agent described herein having a first strand and a second strand in which at least one subunit of formula (I) and/or (II) is incorporated in the strands. The method includes contacting the first strand with the second strand.

In a further aspect, this invention provides a method of modulating expression of a target gene, the method includes administering an iRNA agent described herein having a first strand and a second strand in which at least one subunit of formula (I) and/or (II) is incorporated in the strands. to a subject.

In one aspect, this invention features a pharmaceutical composition having an iRNA agent described herein having a first strand and a second strand in which at least one subunit of formula (I) and/or (II) is incorporated in the strands and a pharmaceutically acceptable carrier.

RRMSs described herein may be incorporated into any double-stranded RNA-like molecule described herein, e.g., an iRNA agent. An iRNA agent may include a duplex comprising a hybridized sense and antisense strand, in which the antisense strand and/or the sense strand may include one or more of the RRMSs described herein. An RRMS can be introduced at one or more points in one or both strands of a double-stranded iRNA agent. An RRMS can be placed at or near (within 1, 2, or 3 positions) of the 3' or 5' end of the sense strand or at near (within 2 or 3 positions of) the 3' end of the antisense strand. In some embodiments it is preferred to not have an RRMS at or near (within 1, 2, or 3 positions of) the 5' end of the antisense strand. An RRMS can be internal, and will preferably be positioned in regions not critical for antisense binding to the target.

In an embodiment, an iRNA agent may have an RRMS at (or within 1, 2, or 3 positions of) the 3' end of the antisense strand. In an embodiment, an iRNA agent may have an RRMS at (or within 1, 2, or 3 positions of) the 3' end of the antisense strand and at (or within 1, 2, or 3 positions of) the 3' end of the sense strand. In an embodiment, an iRNA agent may have an RRMS at (or within 1, 2, or 3 positions of) the 3' end of the antisense strand and an RRMS at the 5' end of the sense strand, in which both ligands are located at the same end of the iRNA agent.

In certain embodiments, two ligands are tethered, preferably, one on each strand and are hydrophobic moieties. While not wishing to be bound by theory, it is believed that pairing of the hydrophobic ligands can stabilize the iRNA agent via intermolecular van der Waals interactions.

In an embodiment, an iRNA agent may have an RRMS at (or within 1, 2, or 3 positions of) the 3' end of the antisense strand and an RRMS at the 5' end of the sense strand, in which both RRMSs may share the same ligand (e.g., cholic acid) via connection of their individual tethers to separate positions on the ligand. A ligand shared between two proximal RRMSs is referred to herein as a "hairpin ligand."

In other embodiments, an iRNA agent may have an RRMS at the 3' end of the sense strand and an RRMS at an internal position of the sense strand. An iRNA agent may have an RRMS at an internal position of the sense strand; or may have an RRMS at an internal position of the antisense strand; or may have an RRMS at an internal position of the sense strand and an RRMS at an internal position of the antisense strand.

In preferred embodiments the iRNA agent includes a first and second sequences, which are preferably two separate molecules as opposed to two sequences located on the same strand, have sufficient complementarity to each other to hybridize (and thereby form a duplex region), e.g., under physiological conditions, e.g., under physiological conditions but not in contact with a helicase or other unwinding enzyme.

It is preferred that the first and second sequences be chosen such that the ds iRNA agent includes a single strand or unpaired region at one or both ends of the molecule. Thus, a ds iRNA agent contains first and second sequences, preferable paired to contain an overhang, e.g., one or two 5' or 3' overhangs but preferably a 3' overhang of 2-3 nucleotides. Most embodiments will have a 3' overhang. Preferred sRNA agents will have single-stranded overhangs, preferably 3' overhangs, of 1 or preferably 2 or 3 nucleotides in length at each end. The overhangs can be the result of one strand being longer than the other, or the result of two strands of the same length being staggered. 5' ends are preferably phosphorylated.

Other modifications to sugars, bases, or backbones described herein can be incorporated into the iRNA agents.

The iRNA agents can take an architecture or structure described herein. The iRNA agents can be palindromic, or double targeting, as described herein.

The iRNA agents can have a sequence such that a non-canonical or other than canonical Watson-Crick structure is formed between two monomers of the iRNA agent or between a strand of the iRNA agent and another sequence, e.g., a target or off-target sequence, as is described herein.

The iRNA agent can be selected to target any of a broad spectrum of genes, including any of the genes described herein.

In a preferred embodiment the iRNA agent has an architecture (architecture refers to one or more of overall length, length of a duplex region, the presence, number, location, or length of overhangs, single strand versus double strand form) described herein. E.g., the iRNA agent can be less than 30 nucleotides in length, e.g., 21-23 nucleotides. Preferably, the iRNA is 21 nucleotides in length and there is a duplex region of about 19 pairs. In one embodiment, the iRNA is 21 nucleotides in length, and the duplex region of the iRNA is 19 nucleotides. In another embodiment, the iRNA is greater than 30 nucleotides in length.

In some embodiment the duplex region of the iRNA agent will have, mismatches. Preferably it will have no more than 1, 2, 3, 4, or 5 bases, which do not form canonical Watson-Crick pairs or which do not hybridize. Overhangs are discussed in detail elsewhere herein but are preferably about 2 nucleotides in length. The overhangs can be complementary to the gene sequences being targeted or can be other sequence. TT is a preferred overhang sequence. The first and second iRNA agent sequences can also be joined, e.g., by additional bases to form a hairpin, or by other non-base linkers.

In addition of the RRMS-containing bases the iRNA agents described herein can include nuclease resistant monomers (NRMs).

In another aspect, the invention features an iRNA agent to which is conjugated a lipophilic moiety, e.g., cholesterol, e.g., by conjugation to an RRMS of an iRNA agent. In a preferred embodiment, the lipophilic moiety enhances entry of the iRNA agent into a cell. In a preferred embodiment, the cell is part of an organism, tissue, or cell line, e.g., a primary cell line, immortalized cell line, or any type of cell line disclosed herein. Thus, the conjugated iRNA agent an be used to silence a target gene in an organism, e.g., a mammal, e.g., a human, or to silence a target gene in a cell line or in cells which are outside an organism.

The lipophilic moiety can be chosen, for example, from the group consisting of a lipid, cholesterol, oleyl, retinyl, cholesteryl residues, cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine. A preferred lipophilic moiety is cholesterol.

The iRNA agent can have a first strand and a second strand, wherein at least one subunit having formula (I) or formula (II) is incorporated into at least one of the strands. The iRNA agent can have one or more of any of the features described herein. For example, when the subunit is of formula (I), $R^d$ can be cholesterol; X can be $N(CO)R^7$ or $NR^7$, Y can be $CR^9R^{10}$, and Z can be absent, and $R^1$ can be $(CH_2)_nOR^b$ and $R^3$ can be $OR^a$; X can be $N(CO)R^7$ or $NR^7$, Y can be $CR^9R^{10}$, and Z can be $CR^{11}R^{12}$, and $R^9$ can be $(CH_2)_nOR^b$ and $R^{10}$ can be $OR^a$; X can be $N(CO)R^7$ or $NR^7$, Y can be $NR^8$, and Z can be $CR^{11}R^{12}$, and $R^1$ can be $(CH_2)_nOR^b$ and $R^3$ can be $OR^a$; X can be $CH_2$; Y can be $CR^9R^{10}$; and Z can be $CR^{11}R^{12}$, in which $R^6$ can be $C(O)NHR^7$; or X can be $CH_2$; Y can be $CR^9R^{10}$; and Z can be $CR^{11}R^{12}$, in which $R^{11}$ or $R^{12}$ can be $C(O)NHR^7$ or $R^5$ and $R^{11}$ together can be $C_5$ or $C_6$ cycloalkyl substituted with $N(CH3)R^7$.

In a preferred embodiment, the lipophilic moiety, e.g., a cholesterol, enhances entry of the iRNA agent into a synoviocyte, myocyte, keratinocyte, hepatocyte, leukocyte, endothelial cell (e.g., a kidney cell), B-cell, T-cell, epithelial cell, mesodermal cell, myeloid cell, neural cell, neoplastic cell, mast cell, or fibroblast cell. In certain aspects, a myocyte can be a smooth muscle cell or a cardiac myocyte, a fibroblast cell can be a dermal fibroblast, and a leukocyte can be a monocyte. In another preferred embodiment, the cell can be from an adherent tumor cell line derived from a tissue, such as bladder, lung, breast, cervix, colon, pancreas, prostate, kidney, liver, skin, or nervous system (e.g., central nervous system).

In a preferred embodiment, the iRNA agent targets a protein tyrosine phosphatase (PTP-1B) gene or a MAP kinase gene, such as ERK1, ERK2, JNK1, JNK2, or p38. In a preferred embodiment, these iRNA agents are used to silence genes in a fibroblast cell.

In a preferred embodiment, the iRNA agent targets an MDR, Myc, Myb, c-Myc, N-Myc, L-Myc, c-Myb, a-Myb, b-Myb, v-Myb, cyclin D1, Cyclin D2, cyclin E, CDK4, cdc25A, CDK2, or CDK4 gene. In a preferred embodiment, these iRNA agents are used to silence genes in an epithelial cell or mesodermal cell.

In a preferred embodiment, the iRNA agent targets a G72 or DAAO gene. In a preferred embodiment, these iRNA agents are used to silence genes in a neural cell.

In a preferred embodiment, the iRNA agent targets a gene of the telomerase pathway, such as a TERT or TR/TERC. In a preferred embodiment, these iRNA agents are used to silence genes in a keratinocyte.

In a preferred embodiment, the iRNA agent targets an interleukin gene, such as IL-1, IL-2, IL-5, IL-8, IL-10, IL-15, IL-16, IL-17, or IL-18. In another preferred embodiment, the iRNA agent targets an interleukin receptor gene, or a chromosomal translocation, such as BCR-ABL, TEL-AML-1, EWS-FLI1, EWS-ERG, TLS-FUS, PAX3-FKHR, or AML-ETO. In a preferred embodiment, these iRNA agents are used to silence genes in a lymphoma or a leukemia cell.

In a preferred embodiment, the iRNA agent targets a GRB2 associated binding protein. In a preferred embodiment, these iRNA agents are used to silence genes in a mast cell.

In a preferred embodiment, the iRNA agent targets a growth factor or growth factor receptor, such as a TGFbeta or TGFbeta Receptor; PDGF or PDGFR; VEGF or VEGFr1, VEGFr2, or VEGFr3; or IGF-1R, DAF-2, or InR. In another preferred embodiment, the iRNA agent targets PRL1, PRL2, PRL3, protein kinase C (PKC), PKC receptor, MDR1, TERT, TR/TERC, cyclin D1, NF-KappaB, REL-A, REL-B, PCNA, CHK-1, c-fos, jun, or BCL-2. In a preferred embodiment, these iRNA agents are used to silence genes in an adherent tumor cell line.

In a preferred embodiment, the iRNA agent targets an exogenous gene of a genetically modified cell. An exogenous gene can be, for example, a viral or bacterial gene that derives from an organism that has invaded or infected the cell, or the exogenous gene can be any gene introduced into the cell by natural or artificial means, such as by a genetic recombination event. An iRNA agent can target a viral gene, for example, such as a hepatitis viral gene (e.g., a gene of an HAV, HBV, or HCV). Alternatively, or in addition, the iRNA agent can silence a reporter gene, such as GFP or beta galatosidase and the like. These iRNA agents can be used to silence exogenous genes in an adherent tumor cell line.

In a preferred embodiment, the iRNA agent to which the lipophilic moiety is conjugated silences at least one gene, e.g., any gene described herein, in any one of a number of cell lines including, but not limited to, a 3T3, DLD2, THP1, Raw264.7, IC21, P388D1, U937, HL60, SEM-K2, WEHI-231, HB56, TIB55, Jurkat, J45.01, K562, EL4, LRMB, Bcl-1, BC-3, TF1, CTLL-2, C1R, Rat6, VERO, MRC5, CV1, Cos7, RPTE, A10, T24, J82, A549, A375, ARH-77, Calu1, SW480, SW620, SKOV3, SK-UT, CaCo2, A375, C8161, CCRF-CEM, MCF-7, MDA-MB-231, MOLT, mIMCD-3, NHDF, HeLa, HeLa-S3, Huh1, Huh4, Huh7, HUVEC, HASMC, HEKn, HEKa, MiaPaCell, Panc1, PC-3, LNCaP, HepG2, or U87 cell line. Cell lines are available from a variety of sources known to those with skill in the art (see, e.g., the American Type Culture Collection (ATCC) (Manassus, Va.)).

In another aspect, the invention provides, methods of silencing a target gene by providing an iRNA agent to which a lipophilic moiety is conjugated, e.g., a lipophilic conjugated iRNA agent described herein, to a cell. In a preferred embodiment the conjugated iRNA agent an be used to silence a target gene in an organism, e.g., a mammal, e.g., a human, or to silence a target gene in a cell line or in cells which are outside an organism. In the case of a whole organism, the method can be used to silence a gene, e.g., a gene described herein, and treat a condition mediated by the gene. In the case of use on a cell which is not part of an organism, e.g., a primary cell line, secondary cell line, tumor cell line, or transformed or immortalized cell line, the iRNA agent to which a lipophilic moiety is conjugated can be used to silence a gene, e.g., one described herein. Cells which are not part of a whole organism can be used in an initial screen to determine if an iRNA agent is effective in silencing a gene. A test in cells which are not part of a whole organism can be followed by testing the iRNA agent in a whole animal. In preferred embodiments, the iRNA agent which is conjugated to a lipophilic moiety is administered to an organism, or contacted with a cell which is not part of an organism, in the absence of (or in a reduced amount of) other reagents that facilitate or enhance delivery, e.g., a compound which enhances transit through the cell membrane. (A reduced amount can be an amount of such reagent which is reduced in comparison to what would be needed to get an equal amount of nonconjugated iRNA agent into the target cell). E.g., the iRNA agent which is conjugated to a lipophilic moiety is administered to an organism, or contacted with a cell which is not part of an organism, in the absence (or reduced amount) of: an additional lipophilic moiety; a transfection agent, e.g., concentrations of an ion or other substance which substantially alters cell permeability to an iRNA agent; a transfecting agent such as Lipofectamine™ (Invitrogen, Carlsbad, Calif.), Lipofectamine 2000™, TransIT-TKO™ (Minis, Madison, Wis.), FuGENE 6 (Roche, Indianapolis, Ind.), polyethylenimine, X-tremeGENE Q2 (Roche, Indianapolis, Ind.), DOTAP, DOSPER, Metafectene™ (Biontex, Munich, Germany), and the like.

In a preferred embodiment the iRNA agent is suitable for delivery to a cell in vivo, e.g., to a cell in an organism. In another aspect, the iRNA agent is suitable for delivery to a cell in vitro, e.g., to a cell in a cell line.

An iRNA agent to which a lipophilic moiety is attached can target any gene described herein and can be delivered to any cell type described herein, e.g., a cell type in an organism, tissue, or cell line. Delivery of the iRNA agent can be in vivo, e.g., to a cell in an organism, or in vitro, e.g., to a cell in a cell line.

In another aspect, the invention provides compositions of iRNA agents described herein, and in particular compositions of an iRNA agent to which a lipophilic moiety is conjugated, e.g., a lipophilic conjugated iRNA agent described herein. In a preferred embodiment the composition is a pharmaceutically acceptable composition.

In preferred embodiments, the composition, e.g., pharmaceutically acceptable composition, is free of, has a reduced amount of, or is essentially free of other reagents that facilitate or enhance delivery, e.g., compounds which enhance transit through the cell membrane. (A reduced amount can be an amount of such reagent which is reduced in comparison to what would be needed to get an equal amount of nonconjugated iRNA agent into the target cell). E.g., the composition is free of, has a reduced amount of, or is essentially free of: an additional lipophilic moiety; a transfection agent, e.g., concentrations of an ion or other substance which substantially alters cell permeability to an iRNA agent; a transfecting agent such as Lipofectamine™ (Invitrogen, Carlsbad, Calif.), Lipofectamine 2000™, TransIT-TKO™ (Minis, Madison, Wis.), FuGENE 6 (Roche, Indianapolis, Ind.), polyethylenimine, X-tremeGENE Q2 (Roche, Indianapolis, Ind.), DOTAP, DOSPER, Metafectene™ (Biontex, Munich, Germany), and the like.

In a preferred embodiment the composition is suitable for delivery to a cell in vivo, e.g., to a cell in an organism. In another aspect, the iRNA agent is suitable for delivery to a cell in vitro, e.g., to a cell in a cell line.

The RRMS-containing iRNA agents can be used in any of the methods described herein, e.g., to target any of the genes described herein or to treat any of the disorders described herein. They can be incorporated into any of the formulations, modes of delivery, delivery modalities, kits or preparations, e.g., pharmaceutical preparations, described herein. E.g, a kit which includes one or more of the iRNA agents described herein, a sterile container in which the iRNA agent is disclosed, and instructions for use.

The methods and compositions of the invention, e.g., the RRSM-containing iRNA agents described herein, can be used with any of the iRNA agents described herein. In addition, the methods and compositions of the invention can be used for the treatment of any disease or disorder described herein, and for the treatment of any subject, e.g., any animal, any mammal, such as any human.

The methods and compositions of the invention, e.g., the RRMS-containing iRNA agents described herein, can be used with any dosage and/or formulation described herein, as well as with any route of administration described herein.

The non-ribose scaffolds, as well as monomers and dimers of the RRMSs described herein are within the invention An "RNA agent" as used herein, is an unmodified RNA, modified RNA, or nucleoside surrogate, all of which are defined herein, see the section herein entitled RNA Agents. While numerous modified RNAs and nucleoside surrogates are described herein, preferred examples include those which include one or more RRMS. Preferred examples are those which also a 2' sugar modification, a modification in a single strand overhang, preferably a 3' single strand overhang, or, particularly if single stranded, a 5' modification which includes one or more phosphate groups or one or more analogs of a phosphate group.

An "iRNA agent" as used herein, is an RNA agent which can, or which can be cleaved into an RNA agent which can, down regulate the expression of a target gene, preferably an endogenous or pathogen target RNA. While not wishing to be bound by theory, an iRNA agent may act by one or more of a number of mechanisms, including post-transcriptional cleavage of a target mRNA sometimes referred to in the art as RNAi, or pre-transcriptional or pre-translational mechanisms. An iRNA agent can include a single strand or can include more than one strands, e.g., it can be a double stranded iRNA agent. If the iRNA agent is a single strand it is particularly preferred that it include a 5' modification which includes one or more phosphate groups or one or more analogs of a phosphate group.

The details of one or more embodiments of the invention are set forth in the accompanying drawings and the description below. Other features and advantages of the invention will be apparent from the description and drawings, and from the claims. This application incorporates all cited references, patents, and patent applications by references in their entirety for all purposes.

DESCRIPTION OF DRAWINGS

FIG. 4 is a general reaction scheme for 3' conjugation of peptide into iRNA.

FIG. 8 is a general reaction scheme for the synthesis of β-methyl amino acids and Ant and Tat peptides.

FIG. 11 is a schematic representation of peptide carriers.

58), Duplex #8 (SEQ ID NO. 59/SEQ ID NO. 60), Duplex #9 (SEQ ID NO. 45/SEQ ID NO. 46), Duplex #10 (SEQ ID NO. 47/SEQ ID NO. 48), Duplex #11 (SEQ ID NO. 49/SEQ ID NO. 50), and Duplex #12 (SEQ ID NO. 51/SEQ ID NO. 52).

Figure 16:
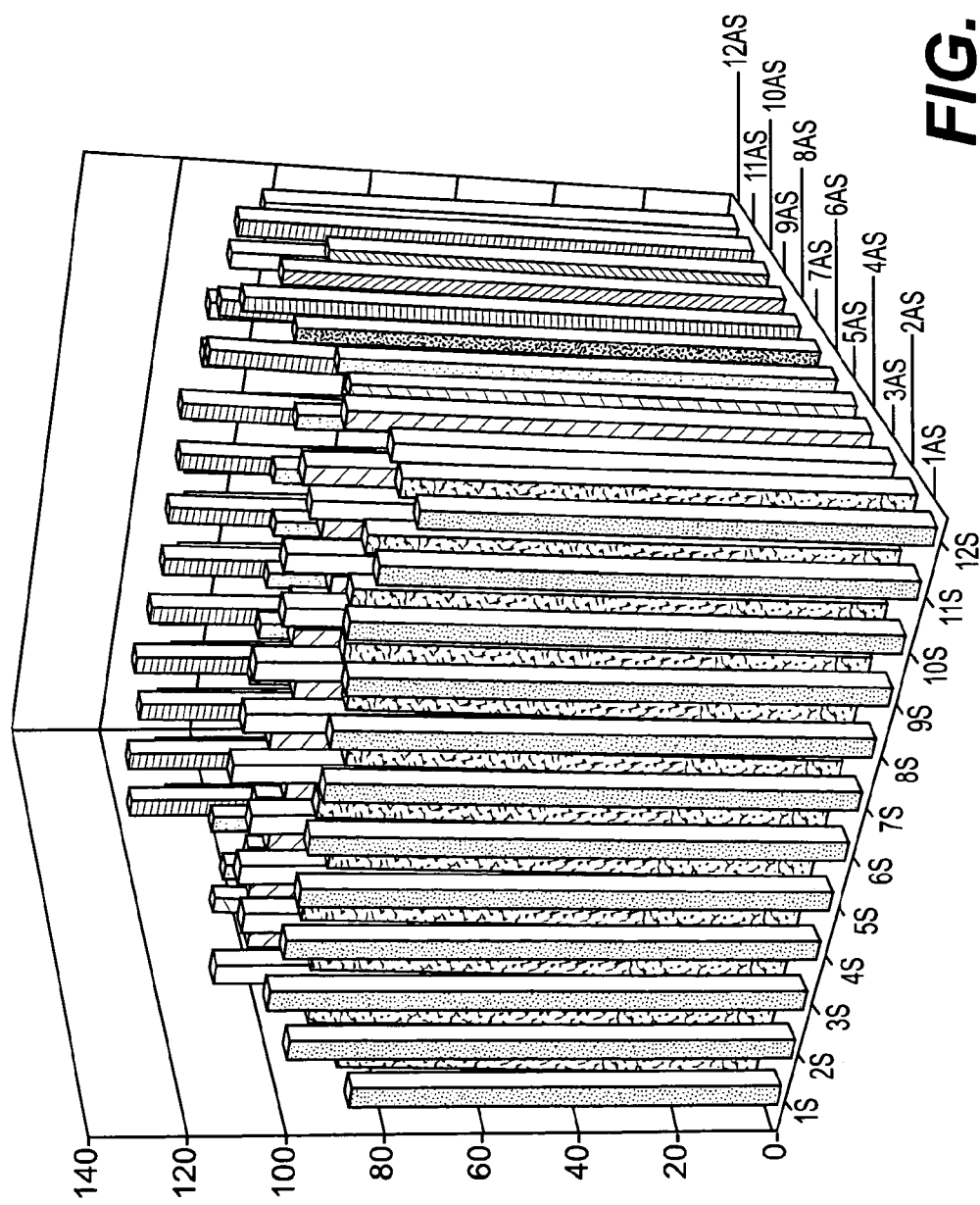

FIG. 16 is a graphical representation of relative cell viability results.

Figure 17:
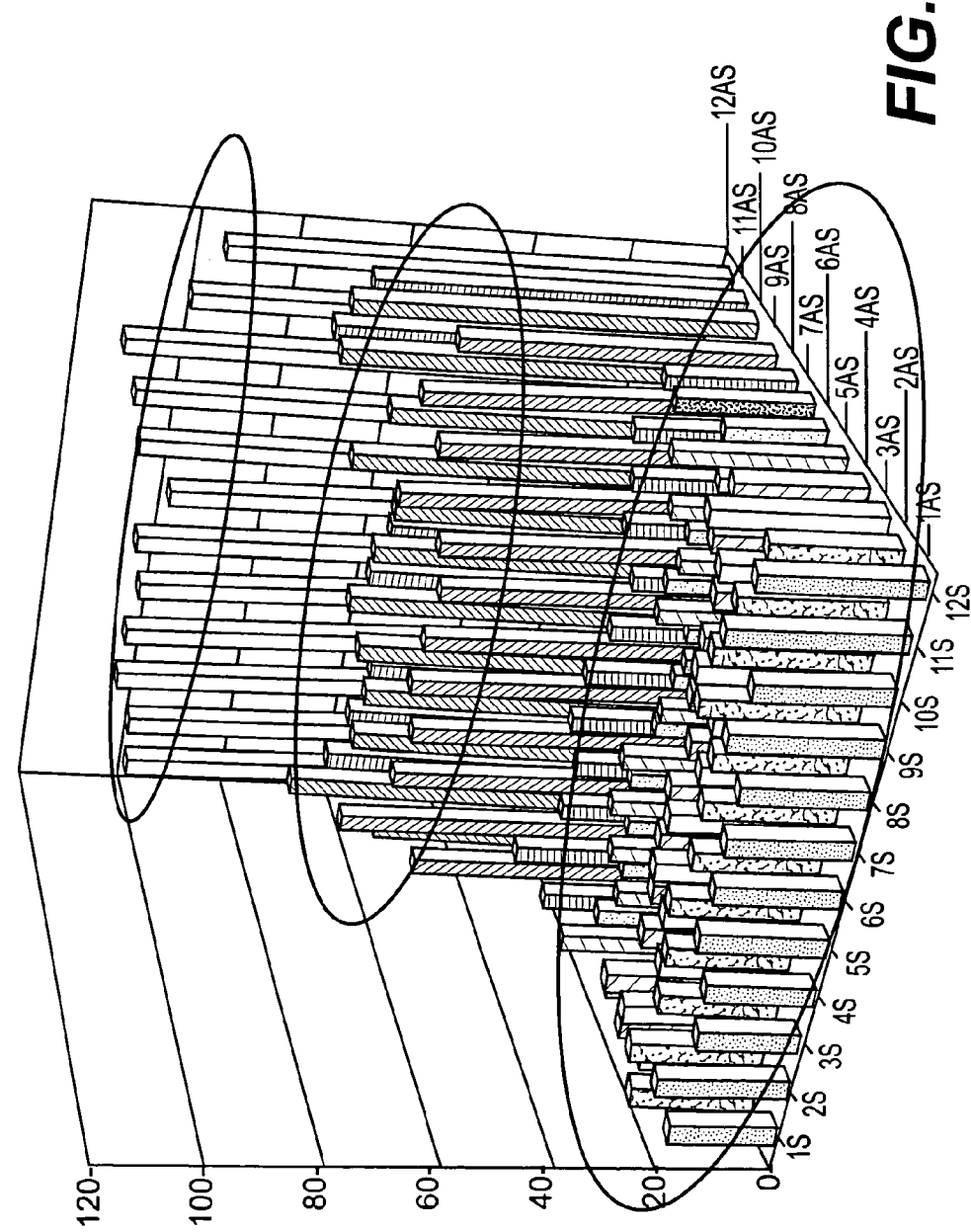

FIG. 17 is a graphical representation of gene silencing activity results.

Figure 18:
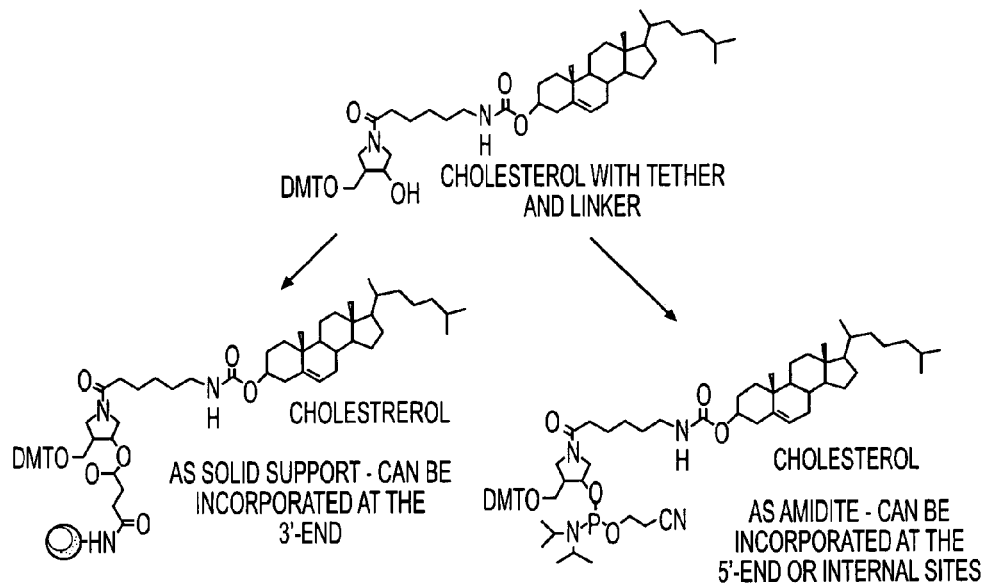

FIG. 18. is a list of representative cholesterol-tethered RRMS monomers.

Figure 19:
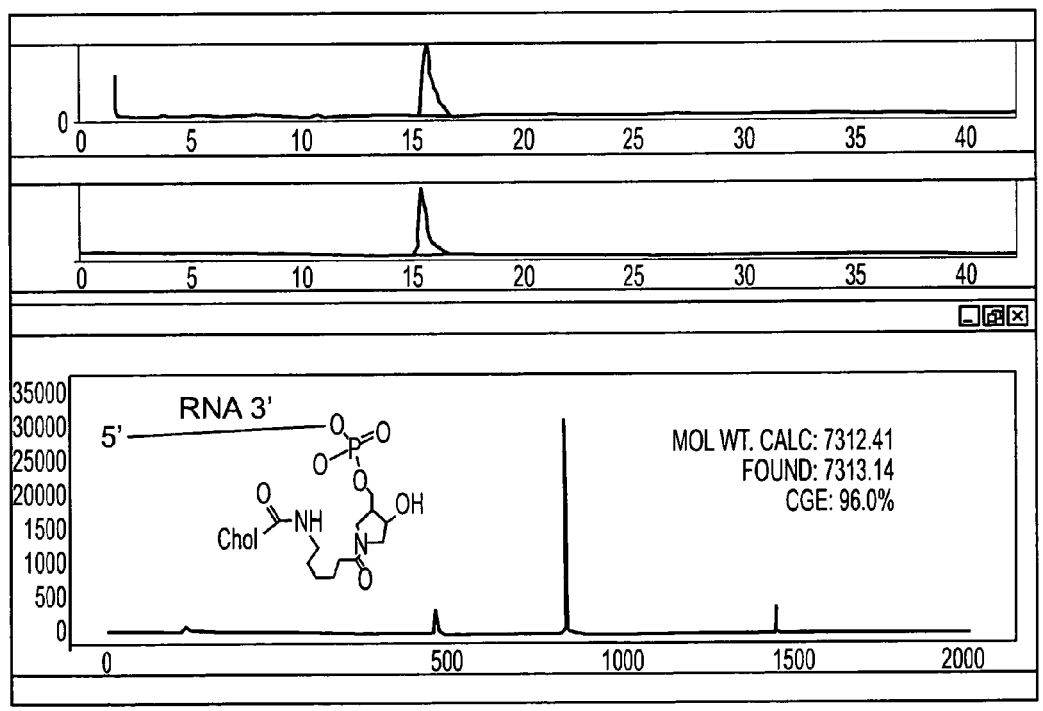

FIG. 19 shows LCMS data for a 3' cholesterol conjugate after PAGE purification.

Figure 20:
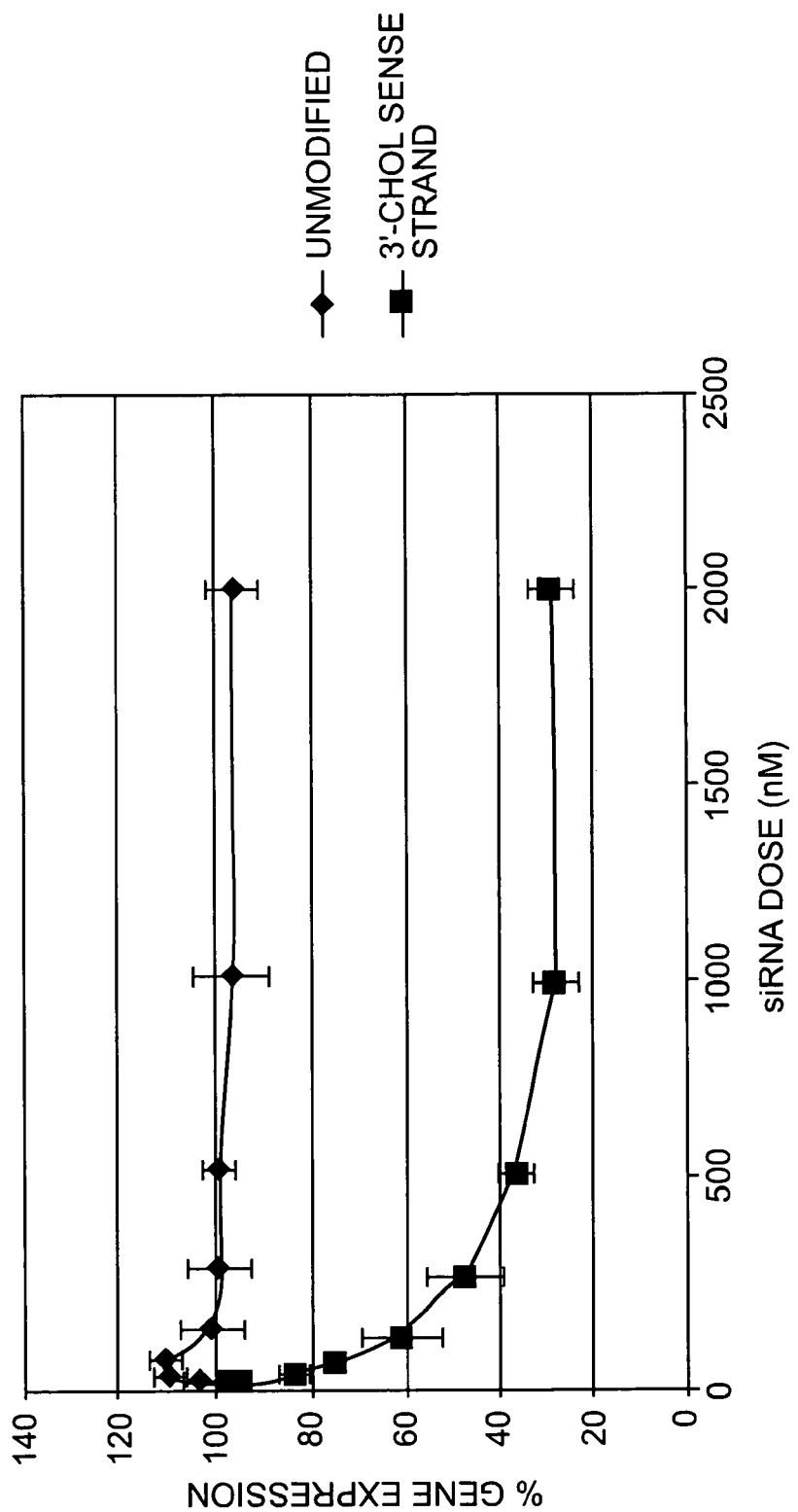

FIG. 20 is a graphical representation of Luc silencing with no transfection reagent.

Figure 21:
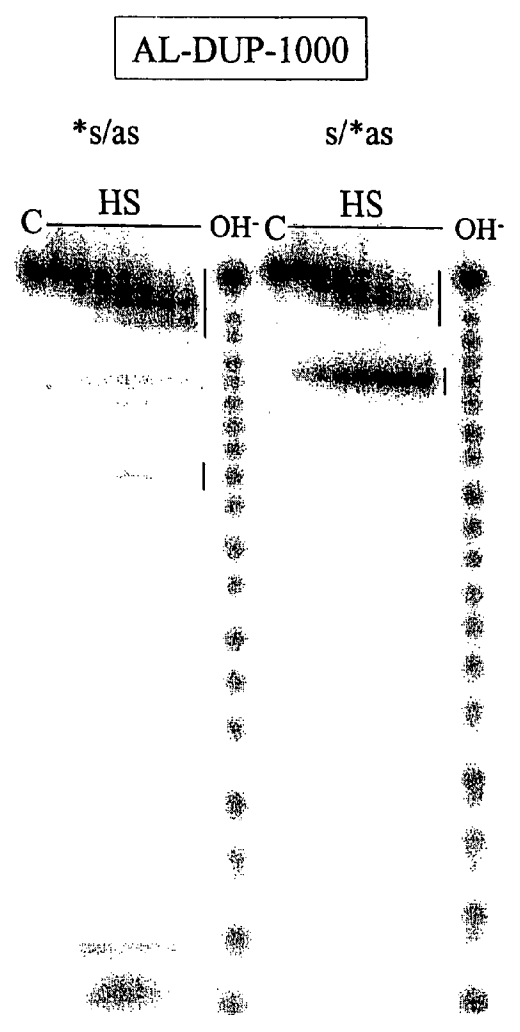

FIG. 21 is a denaturing gel analysis of the human serum stability assay for AL-DUP-1000. C is the 4 hour time point for siRNA duplex incubated in PBS buffer alone, OH— is the partial alkaline hydrolysis marker, *s/as represents siRNA duplex containing 5' end-labeled sense RNA and s/*as represents duplex containing 5' end-labeled antisense RNA. Samples were incubated in 90% human serum and time points were assayed at 10 seconds, 5 min, 15 min, 30 min, 1 hour, 2 hours and 4 hours. Black lines to the right of bands indicate exonucleolytic degradation fragments and the red lines highlight a few of the endonucleolytic degradation fragment.

Figure 22:
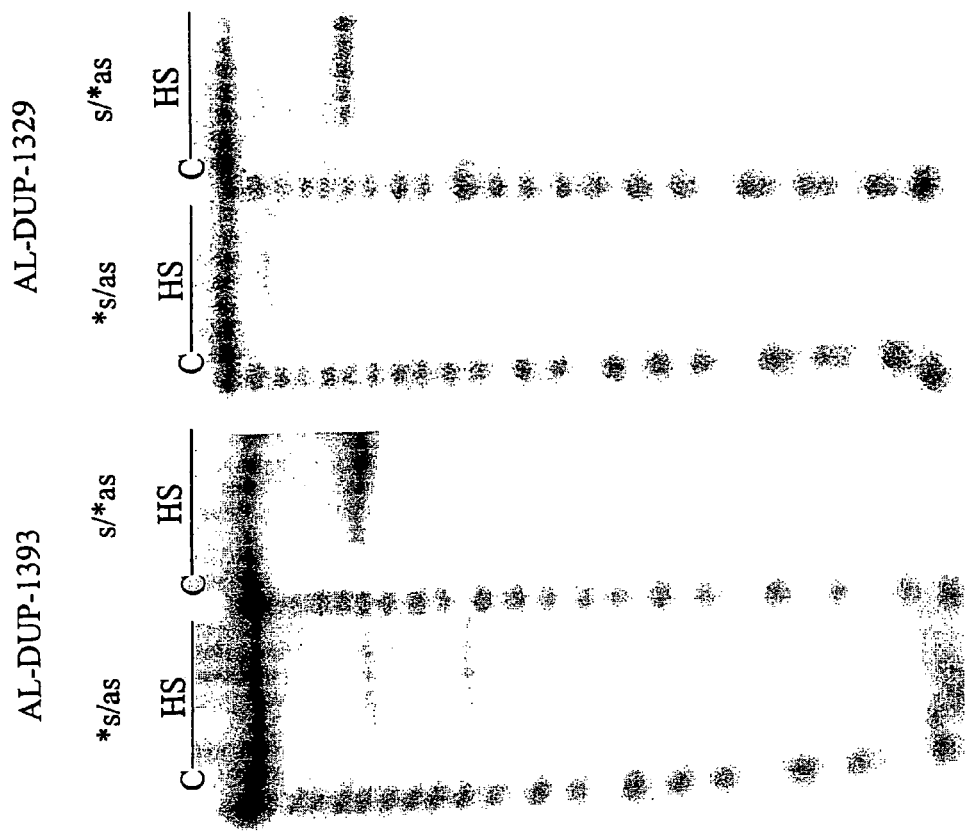

FIG. 22A is a denaturing gel analysis of the human serum stability assay for AL-DUP-1393. C is the 4 hour time point for each siRNA duplex incubated in PBS buffer alone, *s/as represents siRNA duplex containing 5' end-labeled sense RNA and s/*as represents duplex containing 5' end-labeled antisense RNA. Samples were assayed at 10 seconds, 15 min, 30 min, 1 hour, 2 hours and 4 hours.

FIG. 22B is a denaturing gel analysis of the human serum stability assay for AL-DUP-1329. The lanes are labeled and the experiment was performed as described for FIG. 22A.

Figure 23:
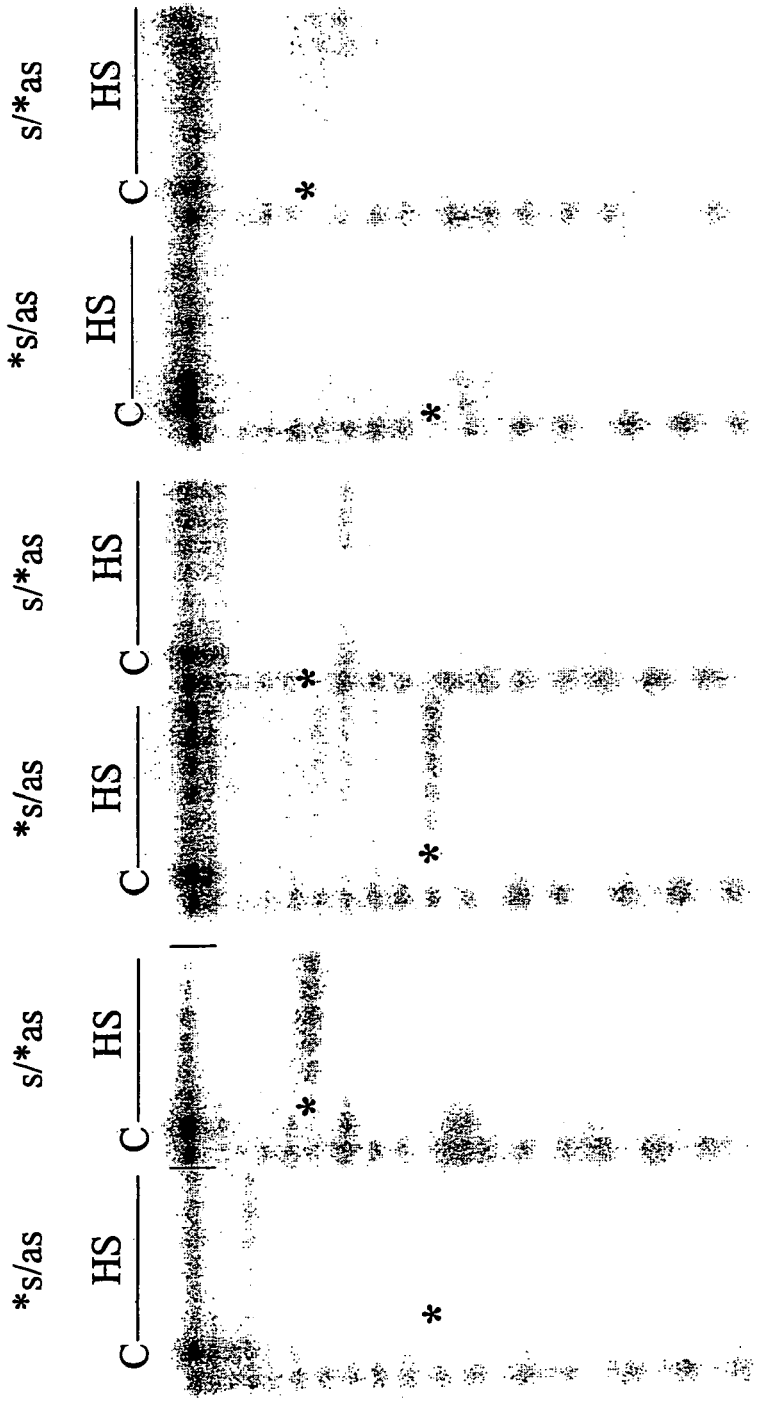

FIG. 23 is a denaturing gel analysis of AL-DUP-1036, AL-DUP-13ff, and AL-DUP-1363 (see Table 8 for sequences). Black vertical lines highlight regions where exonuclease cleavage is suppressed, stars indicate sites of strong endonucleolytic cleavage in the antisense strand and weaker endonucleolytic cleavage in the sense strand. C is the 4 hour time point for each siRNA duplex incubated in PBS buffer alone, *s/as represents siRNA duplex containing 5' end-labeled sense RNA and s/*as represents duplex containing 5' end-labeled antisense RNA. Samples were assayed at 10 seconds, 15 min, 30 min, 1 hour, 2 hours and 4 hours.

Figure 24:
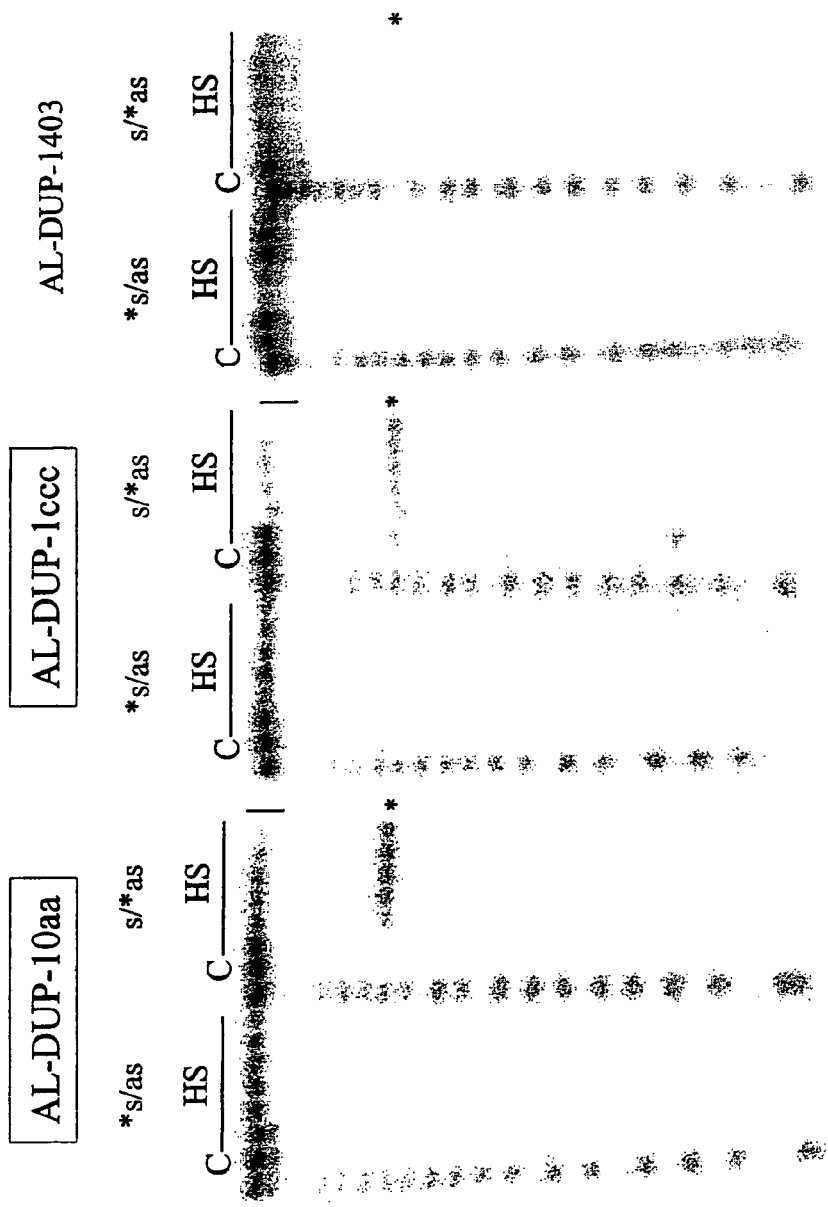

FIG. 24. Human serum stability profile of siRNA duplexes containing cationic modifications. Denaturing gel analysis of AL-DUP-10aa (alkylamino-dT), AL-DUP-1ccc (abasic pyrrolidine cationic), and AL-DUP-1403 (see Table 9 for sequences). Black line highlights region where exonuclease cleavage is suppressed and red star indicates site of strong endonucleolytic cleavage in the antisense strand. C is the 4 hour time point for each siRNA duplex incubated in PBS buffer alone, *s/as represents siRNA duplex containing 5' end-labeled sense RNA and s/*as represents duplex containing 5' end-labeled antisense RNA. Samples were assayed at 10 seconds, 15 min, 30 min, 1 hour, 2 hours and 4 hours.

Figure 25:
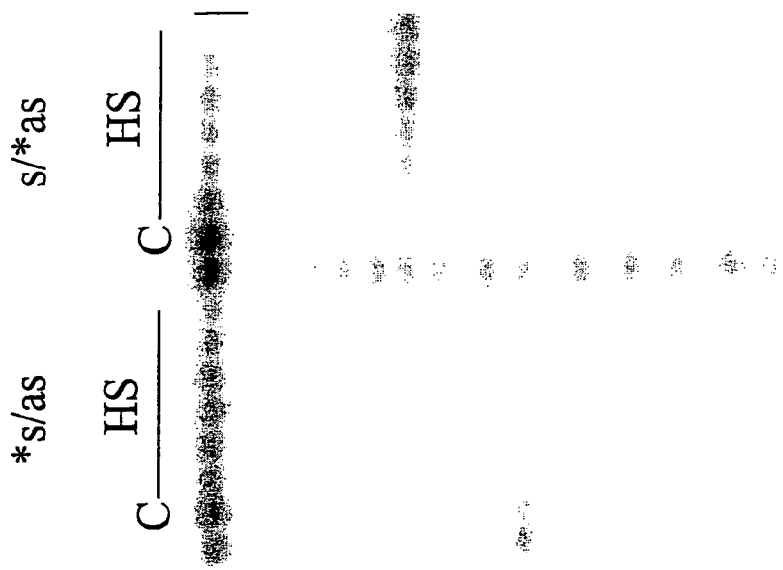

FIG. 25 is a denaturing gel analysis of the human serum stability assay for AL-DUP-1069. The black vertical line highlights the region where exonuclease cleavage is suppressed. C is the 4 hour time point for each siRNA duplex incubated in PBS buffer alone, *s/as represents siRNA duplex containing 5' end-labeled sense RNA and s/*as represents duplex containing 5' end-labeled antisense RNA. Samples were assayed at 10 seconds, 15 min, 30 min, 1 hour, 2 hours and 4 hours.

DETAILED DESCRIPTION

Double-stranded (dsRNA) directs the sequence-specific silencing of mRNA through a process known as RNA interference (RNAi). The process occurs in a wide variety of organisms, including mammals and other vertebrates.

It has been demonstrated that 21-23 nt fragments of dsRNA are sequence-specific mediators of RNA silencing, e.g., by causing RNA degradation. While not wishing to be bound by theory, it may be that a molecular signal, which may be merely the specific length of the fragments, present in these 21-23 nt fragments recruits cellular factors that mediate RNAi. Described herein are methods for preparing and administering these 21-23 nt fragments, and other iRNAs agents, and their use for specifically inactivating gene function. The use of iRNAs agents (or recombinantly produced or chemically synthesized oligonucleotides of the same or similar nature) enables the targeting of specific mRNAs for silencing in mammalian cells. In addition, longer dsRNA agent fragments can also be used, e.g., as described below.

Although, in mammalian cells, long dsRNAs can induce the interferon response which is frequently deleterious, sRNAs do not trigger the interferon response, at least not to an extent that is deleterious to the cell and host. In particular, the length of the iRNA agent strands in an sRNA agent can be less than 31, 30, 28, 25, or 23 nt, e.g., sufficiently short to avoid inducing a deleterious interferon response. Thus, the administration of a composition of sRNA agent (e.g., formulated as described herein) to a mammalian cell can be used to silence expression of a target gene while circumventing the interferon response. Further, use of a discrete species of iRNA agent can be used to selectively target one allele of a target gene, e.g., in a subject heterozygous for the allele.

Moreover, in one embodiment, a mammalian cell is treated with an iRNA agent that disrupts a component of the interferon response, e.g., double stranded RNA (dsRNA)-activated protein kinase PKR. Such a cell can be treated with a second iRNA agent that includes a sequence complementary to a target RNA and that has a length that might otherwise trigger the interferon response.

In a typical embodiment, the subject is a mammal such as a cow, horse, mouse, rat, dog, pig, goat, or a primate. The subject can be a dairy mammal (e.g., a cow, or goat) or other farmed animal (e.g., a chicken, turkey, sheep, pig, fish, shrimp). In a much preferred embodiment, the subject is a human, e.g., a normal individual or an individual that has, is diagnosed with, or is predicted to have a disease or disorder.

Further, because iRNA agent mediated silencing persists for several days after administering the iRNA agent composition, in many instances, it is possible to administer the composition with a frequency of less than once per day, or, for some instances, only once for the entire therapeutic regimen. For example, treatment of some cancer cells may be mediated by a single bolus administration, whereas a chronic viral infection may require regular administration, e.g., once per week or once per month.

A number of exemplary routes of delivery are described that can be used to administer an iRNA agent to a subject. In addition, the iRNA agent can be formulated according to an exemplary method described herein.

Ligand-Conjugated Monomer Subunits and Monomers for Oligonucleotide Synthesis

DEFINITIONS

The term "halo" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). Alkyl and haloalkyl groups may be optionally inserted with O, N, or S. The terms "aralkyl" refers to an alkyl moiety in which an alkyl hydrogen atom is replaced by an aryl group. Aralkyl includes groups in which more than one hydrogen atom has been replaced by an aryl group. Examples of "aralkyl" include benzyl, 9-fluorenyl, benzhydryl, and trityl groups.

The term "alkenyl" refers to a straight or branched hydrocarbon chain containing 2-8 carbon atoms and characterized in having one or more double bonds. Examples of a typical alkenyl include, but not limited to, allyl, propenyl, 2-butenyl, 3-hexenyl and 3-octenyl groups. The term "alkynyl" refers to a straight or branched hydrocarbon chain containing 2-8 carbon atoms and characterized in having one or more triple bonds. Some examples of a typical alkynyl are ethynyl, 2-propynyl, and 3-methylbutynyl, and propargyl. The $sp^2$ and $sp^3$ carbons may optionally serve as the point of attachment of the alkenyl and alkynyl groups, respectively.

The terms "alkylamino" and "dialkylamino" refer to —NH (alkyl) and —N(alkyl)$_2$ radicals respectively. The term "aralkylamino" refers to a —NH(aralkyl) radical. The term "alkoxy" refers to an —O-alkyl radical, and the terms "cycloalkoxy" and "aralkoxy" refer to an —O— cycloalkyl and O-aralkyl radicals respectively. The term "siloxy" refers to a $R_3SiO$— radical. The term "mercapto" refers to an SH radical. The term "thioalkoxy" refers to an —S-alkyl radical.

The term "alkylene" refers to a divalent alkyl (i.e., —R—), e.g., —CH$_2$—, —CH$_2$CH$_2$—, and —CH$_2$CH$_2$CH$_2$—. The term "alkylenedioxo" refers to a divalent species of the structure —O—R—O—, in which R represents an alkylene.

The term "aryl" refers to an aromatic monocyclic, bicyclic, or tricyclic hydrocarbon ring system, wherein any ring atom can be substituted. Examples of aryl moieties include, but are not limited to, phenyl, naphthyl, anthracenyl, and pyrenyl.

The term "cycloalkyl" as employed herein includes saturated cyclic, bicyclic, tricyclic, or polycyclic hydrocarbon groups having 3 to 12 carbons, wherein any ring atom can be substituted. The cycloalkyl groups herein described may also contain fused rings. Fused rings are rings that share a common carbon-carbon bond or a common carbon atom (e.g., spiro-fused rings). Examples of cycloalkyl moieties include, but are not limited to, cyclohexyl, adamantyl, and norbornyl.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heterocyclyl groups herein described may also contain fused rings. Fused rings are rings that share a common carbon-carbon bond or a common carbon atom (e.g., spiro-fused rings). Examples of heterocyclyl include, but are not limited to tetrahydrofuranyl, tetrahydropyranyl, piperidinyl, morpholino, pyrrolinyl and pyrrolidinyl.

The term "cycloalkenyl" as employed herein includes partially unsaturated, nonaromatic, cyclic, bicyclic, tricyclic, or polycyclic hydrocarbon groups having 5 to 12 carbons, preferably 5 to 8 carbons, wherein any ring atom can be substituted. The cycloalkenyl groups herein described may also contain fused rings. Fused rings are rings that share a common carbon-carbon bond or a common carbon atom (e.g., spiro-fused rings). Examples of cycloalkenyl moieties include, but are not limited to cyclohexenyl, cyclohexadienyl, or norbornenyl.

The term "heterocycloalkenyl" refers to a partially saturated, nonaromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heterocycloalkenyl groups herein described may also contain fused rings. Fused rings are rings that share a common carbon-carbon bond or a common carbon atom (e.g., spiro-fused rings). Examples of heterocycloalkenyl include but are not limited to tetrahydropyridyl and dihydropyran.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heteroaryl groups herein described may also contain fused rings that share a common carbon-carbon bond.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Suitable substituents include, without limitation, alkyl, alkenyl, alkynyl, alkoxy, halo, hydroxy, cyano, nitro, amino, $SO_3H$, sulfate, phosphate, perfluoroalkyl, perfluoroalkoxy, methylenedioxy, ethylenedioxy, carboxyl, oxo, thioxo, imino (alkyl, aryl, aralkyl), $S(O)_n$alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl. In one aspect, the substituents on a group are independently any one single, or any subset of the aforementioned substituents.

The terms "adeninyl, cytosinyl, guaninyl, thyminyl, and uracilyl" and the like refer to radicals of adenine, cytosine, guanine, thymine, and uracil.

A "protected" moiety refers to a reactive functional group, e.g., a hydroxyl group or an amino group, or a class of molecules, e.g., sugars, having one or more functional groups, in which the reactivity of the functional group is temporarily blocked by the presence of an attached protecting group. Protecting groups useful for the monomers and methods described herein can be found, e.g., in Greene, T. W., *Protective Groups in Organic Synthesis* (John Wiley and Sons: New York), 1981, which is hereby incorporated by reference.

General

Figure 1:
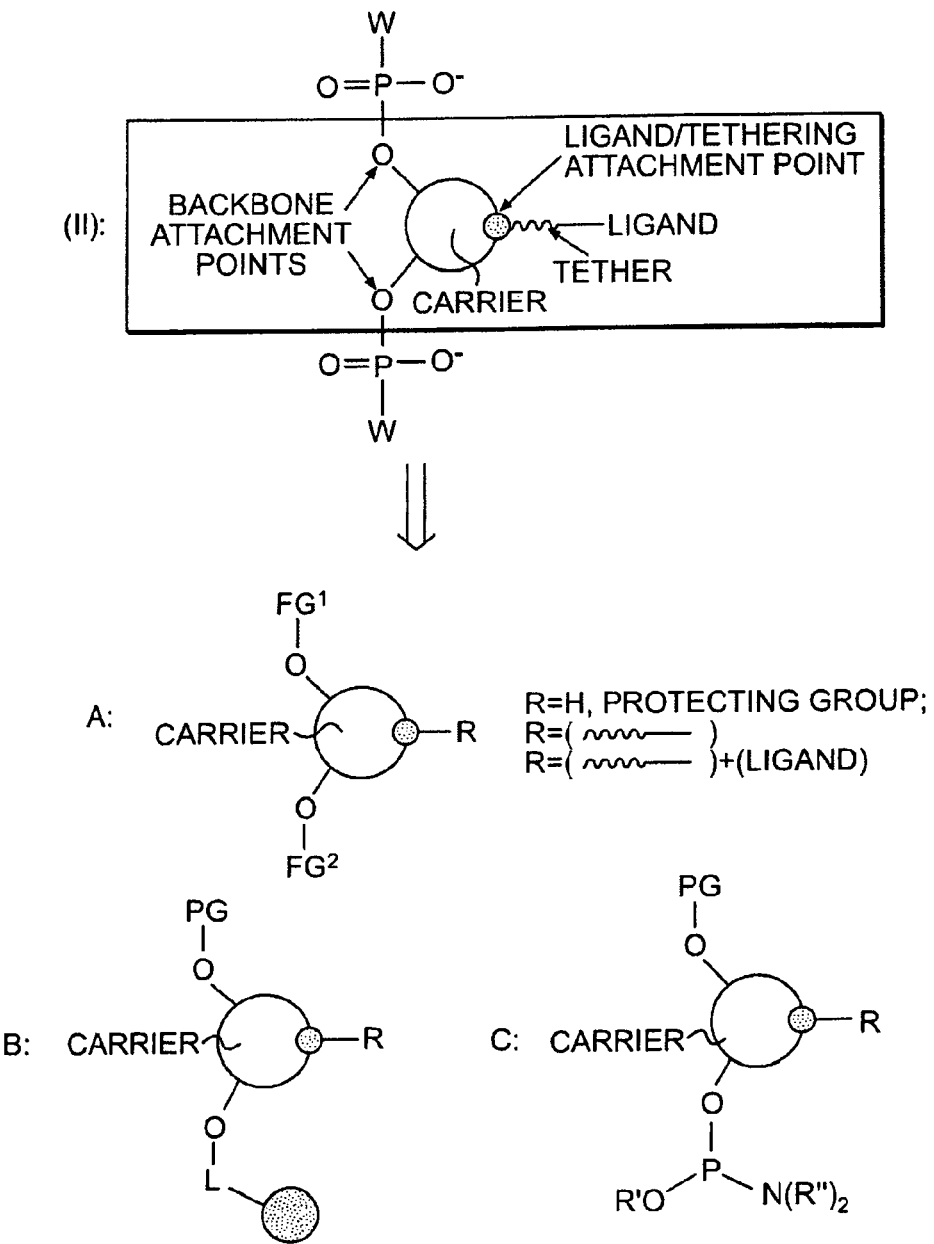
FIG. 1 a general synthetic scheme for incorporation of RRMS monomers into an oligonucleotide.

An RNA agent, e.g., an iRNA agent, containing a preferred, but nonlimiting ligand-conjugated monomer subunit is presented as formula (II) below and in the scheme in FIG. 1. The carrier (also referred to in some embodiments as a "linker") can be a cyclic or acyclic moiety and includes two "backbone attachment points" (e.g., hydroxyl groups) and a ligand. The ligand can be directly attached (e.g., conjugated) to the carrier or indirectly attached (e.g., conjugated) to the carrier by an intervening tether (e.g., an acyclic chain of one or more atoms; or a nucleobase, e.g., a naturally occurring nucleobase optionally having one or more chemical modifications, e.g., an unusual base; or a universal base). The carrier therefore also includes a "ligand or tethering attachment point" for the ligand and tether/tethered ligand, respectively.

The ligand-conjugated monomer subunit may be the 5' or 3' terminal subunit of the RNA molecule, i.e., one of the two "W" groups may be a hydroxyl group, and the other "W" group may be a chain of two or more unmodified or modified ribonucleotides. Alternatively, the ligand-conjugated monomer subunit may occupy an internal position, and both "W" groups may be one or more unmodified or modified ribonucleotides. More than one ligand-conjugated monomer subunit may be present in a RNA molecule, e.g., an iRNA agent. Preferred positions for inclusion of a tethered ligand-conjugated monomer subunits, e.g., one in which a lipophilic moiety, e.g., cholesterol, is tethered to the carrier are at the 3' terminus, the 5' terminus, or an internal position of the sense strand.

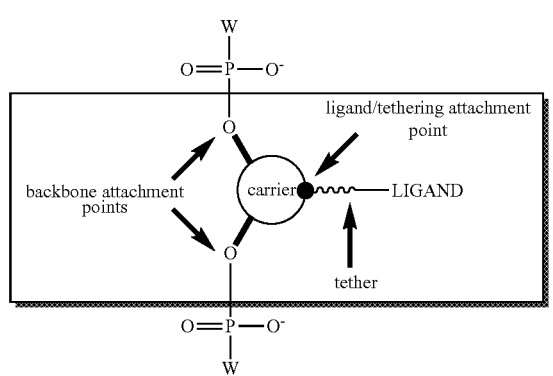

The modified RNA molecule of formula (II) can be obtained using oligonucleotide synthetic methods known in the art. In a preferred embodiment, the modified RNA molecule of formula (II) can be prepared by incorporating one or more of the corresponding monomer compounds (see, e.g., A, B, and C below and in the scheme in FIG. 1) into a growing sense or antisense strand, utilizing, e.g., phosphoramidite or H-phosphonate coupling strategies.

The monomers, e.g., a ligand-conjugated monomer, generally include two differently functionalized hydroxyl groups ($OFG^1$ and $OFG^2$), which are linked to the carrier molecule (see A below and in FIG. 1), and a ligand/tethering attachment point. As used herein, the term "functionalized hydroxyl group" means that the hydroxyl proton has been replaced by another substituent. As shown in representative structures B and C below and in FIG. 1, one hydroxyl group ($OFG^1$) on the carrier is functionalized with a protecting group (PG). The other hydroxyl group ($OFG^2$) can be functionalized with either (1) a liquid or solid phase synthesis support reagent (solid circle) directly or indirectly through a linker, L, as in B, or (2) a phosphorus-containing moiety, e.g., a phosphoramidite as in C. The tethering attachment point may be connected to a hydrogen atom, a suitable protecting group, a tether, or a tethered ligand at the time that the monomer is incorporated into the growing sense or antisense strand (see variable "R" in A below). Thus, the tethered ligand can be, but need not be attached to the monomer at the time that the monomer is incorporated into the growing strand. In certain embodiments, the tether, the ligand or the tethered ligand may be linked to a "precursor" ligand-conjugated monomer subunit after a "precursor" ligand-conjugated monomer subunit has been incorporated into the strand. The wavy line used below (and elsewhere herein) refers to a connection, and can represent a direct bond between the moiety and the attachment point or a tethering molecule which is interposed between the moiety and the attachment point. Directly tethered means the moiety is bound directly to the attachment point. Indirectly tethered means that there is a tether molecule interposed between the attachment point and the moiety.

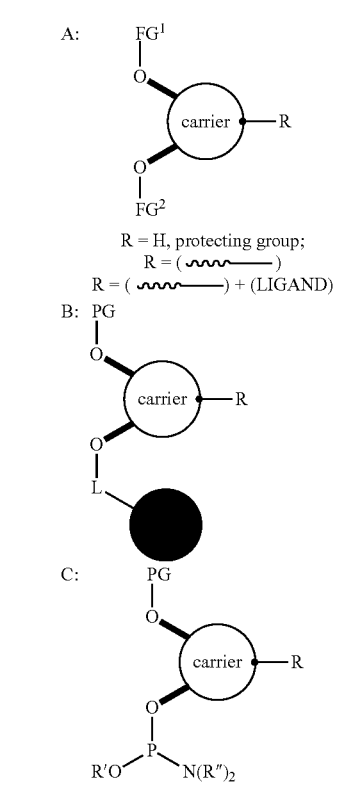

The ($OFG^1$) protecting group may be selected as desired, e.g., from T. W. Greene and P. G. M. Wuts, *Protective Groups in Organic Synthesis,* 2d. Ed., John Wiley and Sons (1991). The protecting group is preferably stable under amidite synthesis conditions, storage conditions, and oligonucleotide synthesis conditions. Hydroxyl groups, —OH, are nucleophilic groups (i.e., Lewis bases), which react through the oxygen with electrophiles (i.e., Lewis acids). Hydroxyl groups in which the hydrogen has been replaced with a protecting group, e.g., a triarylmethyl group or a trialkylsilyl group, are essentially unreactive as nucleophiles in displacement reactions. Thus, the protected hydroxyl group is useful in preventing e.g., homocoupling of compounds exemplified by structure C during oligonucleotide synthesis. In some embodiments, a preferred protecting group is the dimethoxytrityl group. In other embodiments, a preferred protecting group is a silicon-based protecting group having the formula below:

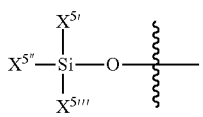

Figure 2A:
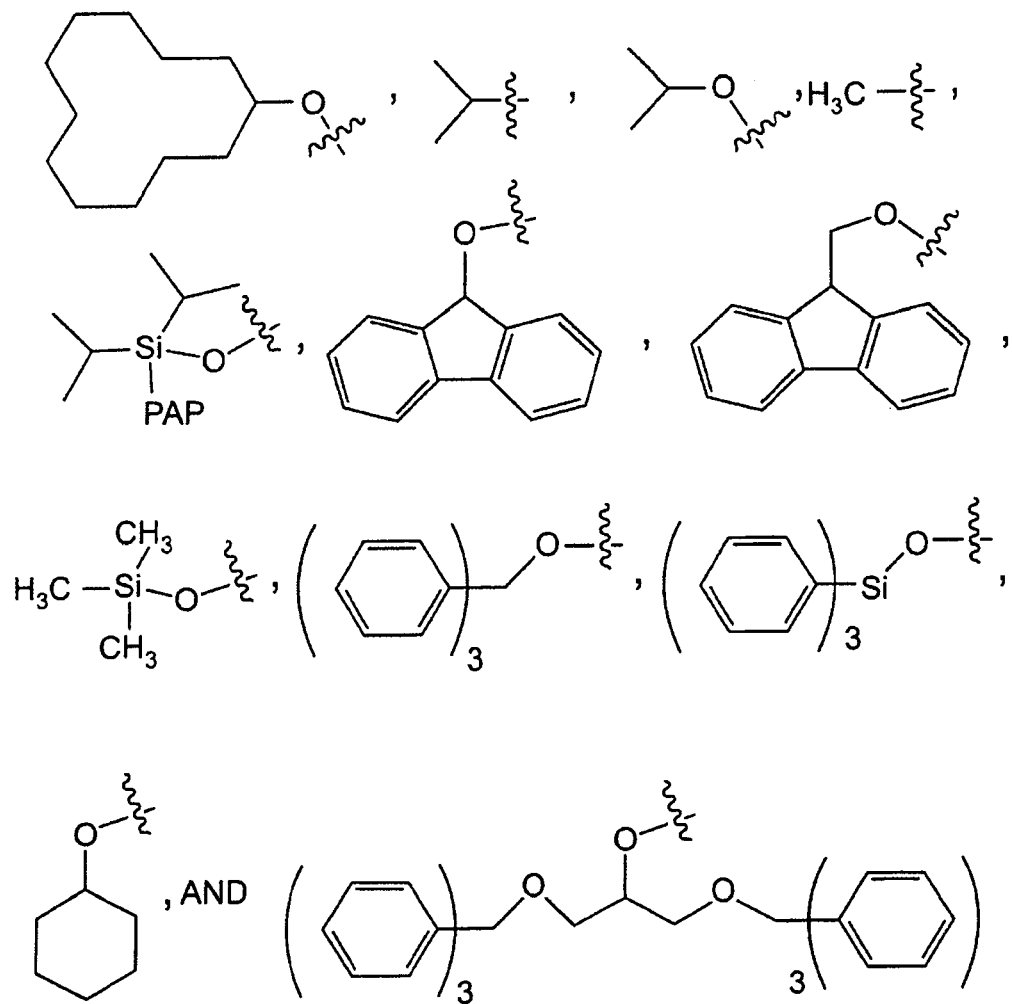
FIG. 2A is a list of substituents that may be present on silicon in OFG[1].

$X^{5'}$, $X^{5''}$, and $X^{5'''}$ can be selected from substituted or unsubstituted alkyl, cycloalkyl, aryl, araklyl, heteroaryl, alkoxy, cycloalkoxy, aralkoxy, aryloxy, heteroaryloxy, or siloxy (i.e., $R_3SiO-$, the three "R" groups can be any combination of the above listed groups). $X^{5'}$, $X^{5''}$, and $X^{5'''}$ may all be the same or different; also contemplated is a combination in which two of $X^{5'}$, $X^{5''}$, and $X^{5'''}$ are identical and the third is different. In certain embodiments $X^{5'}$, $X^{5''}$, and $X^{5'''}$ include at least one alkoxy or siloxy groups and may be any one of the groups listed in FIG. 2A, a preferred combination includes $X^{5'}$, $X^{5''}$=trimethylsiloxy and $X^{5'''}$=1, 3-(triphenylmethoxy)-2-propoxy or cyclododecyloxy.

Other preferred combinations of $X^{5'}$, $X^{5''}$, and $X^{5'''}$ include those that result in $OFG^1$ groups that meet the deprotection and stability criteria delineated below. The group is preferably stable under amidite synthesis conditions, storage conditions, and oligonucleotide synthesis conditions. Rapid removal, i.e., less than one minute, of the silyl group from e.g., a support-bound oligonucleotide is desirable because it can reduce synthesis times and thereby reduce exposure time of the growing oligonucleotide chain to the reagents. Oligonucleotide synthesis can be improved if the silyl protecting group is visible during deprotection, e.g., from the addition of a chromophore silyl substituent.

Selection of silyl protecting groups can be complicated by the competing demands of the essential characteristics of stability and facile removal, and the need to balance these competitive goals. Most substituents that increase stability can also increase the reaction time required for removal of the silyl group, potentially increasing the level of difficulty in removal of the group.

The addition of alkoxy and siloxy substituents to $OFG^1$ silicon-containing protecting groups increases the susceptibility of the protecting groups to fluoride cleavage of the silylether bonds. Increasing the steric bulk of the substituents preserves stability while not decreasing fluoride lability to an equal extent. An appropriate balance of substituents on the silyl group makes a silyl ether a viable nucleoside protecting group.

Candidate $OFG^1$ silicon-containing protecting groups may be tested by exposing a tetrahydrofuran solution of a preferred carrier bearing the candidate $OFG^1$ group to five molar equivalents of tetrahydrofuran at room temperature. The reaction time may be determined by monitoring the disappearance of the starting material by thin layer chromatography.

When the $OFG^2$ in B includes a linker, e.g., a relatively long organic linker, connected to a soluble or insoluble support reagent, solution or solid phase synthesis techniques can be employed to build up a chain of natural and/or modified ribonucleotides once $OFG^1$ is deprotected and free to react as a nucleophile with another nucleoside or monomer containing an electrophilic group (e.g., an amidite group). Alternatively, a natural or modified ribonucleotide or oligoribonucleotide chain can be coupled to monomer C via an amidite group or H-phosphonate group at $OFG^2$. Subsequent to this operation, $OFG^1$ can be deblocked, and the restored nucleophilic hydroxyl group can react with another nucleoside or monomer containing an electrophilic group. R' can be substituted or unsubstituted alkyl or alkenyl. In preferred embodiments, R' is methyl, allyl or 2-cyanoethyl. R" may a $C_1$-$C_{10}$ alkyl group, preferably it is a branched group containing three or more carbons, e.g., isopropyl.

$OFG^2$ in B can be hydroxyl functionalized with a linker, which in turn contains a liquid or solid phase synthesis support reagent at the other linker terminus. The support reagent can be any support medium that can support the monomers described herein. The monomer can be attached to an insoluble support via a linker, L, which allows the monomer (and the growing chain) to be solubilized in the solvent in which the support is placed. The solubilized, yet immobilized, monomer can react with reagents in the surrounding solvent; unreacted reagents and soluble by-products can be readily washed away from the solid support to which the monomer or monomer-derived products is attached. Alternatively, the monomer can be attached to a soluble support moiety, e.g., polyethylene glycol (PEG) and liquid phase synthesis techniques can be used to build up the chain. Linker and support medium selection is within skill of the art. Generally the linker may be $-C(O)(CH_2)_qC(O)-$, or $-C(O)(CH_2)_qS-$, in which q can be 0, 1, 2, 3, or 4; preferably, it is oxalyl, succinyl or thioglycolyl. Standard control pore glass solid phase synthesis supports can not be used in conjunction with fluoride labile 5' silyl protecting groups because the glass is degraded by fluoride with a significant reduction in the amount of full-length product. Fluoride-stable polystyrene based supports or PEG are preferred.

The ligand/tethering attachment point can be any divalent, trivalent, tetravalent, pentavalent or hexavalent atom. In some embodiments, ligand/tethering attachment point can be a carbon, oxygen, nitrogen or sulfur atom. For example, a ligand/tethering attachment point precursor functional group can have a nucleophilic heteroatom, e.g., $-SH$, $-NH_2$, secondary amino, $ONH_2$, or $NH_2NH_2$. As another example, the ligand/tethering attachment point precursor functional group can be an olefin, e.g., $-CH=CH_2$, and the precursor functional group can be attached to a ligand, a tether, or tethered ligand using, e.g., transition metal catalyzed carbon-carbon (for example olefin metathesis) processes or cycloadditions (e.g., Diels-Alder). As a further example, the ligand/tethering attachment point precursor functional group can be an electrophilic moiety, e.g., an aldehyde. When the carrier is a cyclic carrier, the ligand/tethering attachment point can be an endocyclic atom (i.e., a constituent atom in the cyclic moiety, e.g., a nitrogen atom) or an exocyclic atom (i.e., an atom or group of atoms attached to a constituent atom in the cyclic moiety).

The carrier can be any organic molecule containing attachment points for $OFG^1$, $OFG^2$, and the ligand. In certain embodiments, carrier is a cyclic molecule and may contain heteroatoms (e.g., O, N or S). E.g., carrier molecules may include aryl (e.g., benzene, biphenyl, etc.), cycloalkyl (e.g., cyclohexane, cis or trans decalin, etc.), or heterocyclyl (piperazine, pyrrolidine, etc.). In other embodiments, the carrier can be an acyclic moiety, e.g., based on serinol. Any of the above cyclic systems may include substituents in addition to $OFG^1$, $OFG^2$, and the ligand.

Sugar-Based Monomers

In some embodiments, the carrier molecule is an oxygen containing heterocycle. Preferably the carrier is a ribose sugar as shown in structure LCM-I. In this embodiment, the monomer, e.g., a ligand-conjugated monomer is a nucleoside.

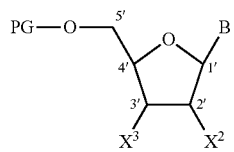

LCM-I

"B" represents a nucleobase, e.g., a naturally occurring nucleobase optionally having one or more chemical modifications, e.g., and unusual base; or a universal base.

As used herein, an "unusual" nucleobase can include any one of the following:
2-methyladeninyl,
N6-methyladeninyl,
2-methylthio-N6-methyladeninyl,
N6-isopentenyladeninyl,
2-methylthio-N6-isopentenyladeninyl,
N6-(cis-hydroxyisopentenyl)adeninyl,
2-methylthio-N6-(cis-hydroxyisopentenyl)adeninyl,
N6-glycinylcarbamoyladeninyl,
N6-threonylcarbamoyladeninyl,
2-methylthio-N6-threonyl carbamoyladeninyl,
N6-methyl-N6-threonylcarbamoyladeninyl,
N6-hydroxynorvalylcarbamoyladeninyl,
2-methylthio-N6-hydroxynorvalyl carbamoyladeninyl,
N6,N6-dimethyladeninyl,
3-methylcytosinyl,
5-methylcytosinyl,
2-thiocytosinyl,
5-formylcytosinyl,

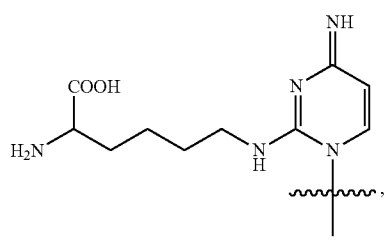 [SMILES: *n1ccc(=N)nc1NCCCCC(N)C(=O)O]

N4-methylcytosinyl,
5-hydroxymethylcytosinyl,
1-methylguaninyl,
N2-methylguaninyl,
7-methylguaninyl,
N2,N2-dimethylguaninyl,

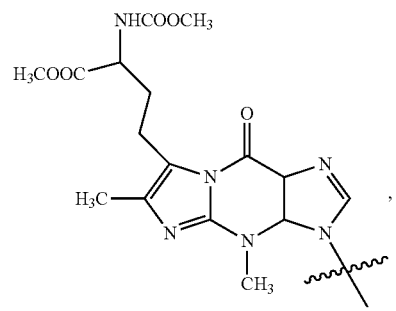

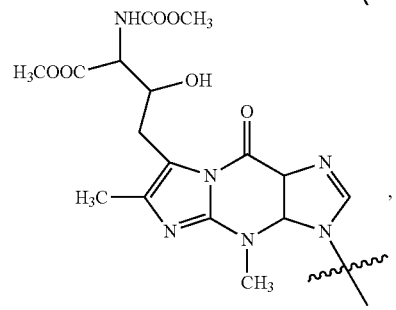

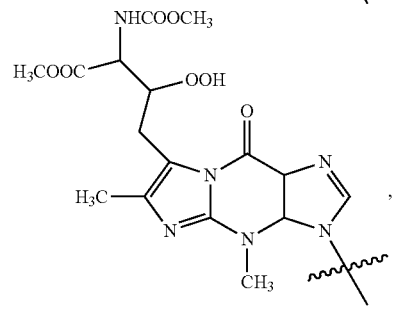

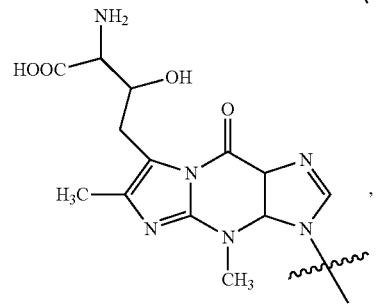

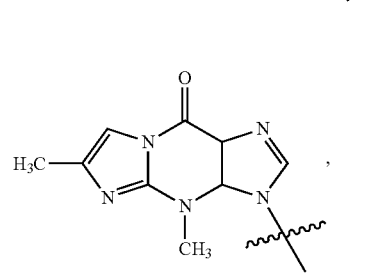

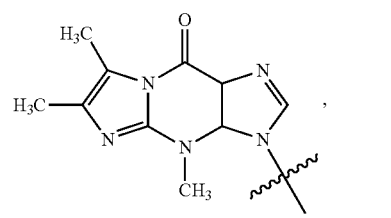

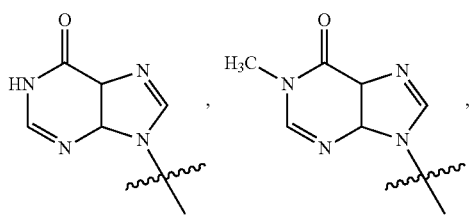

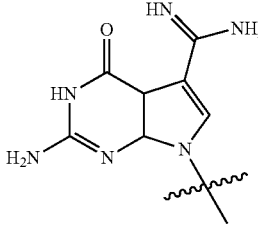

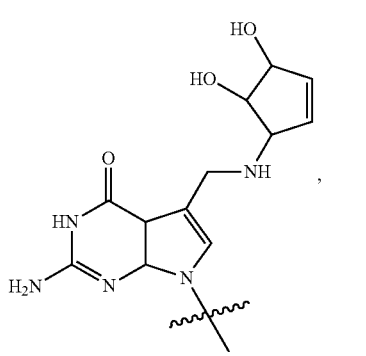

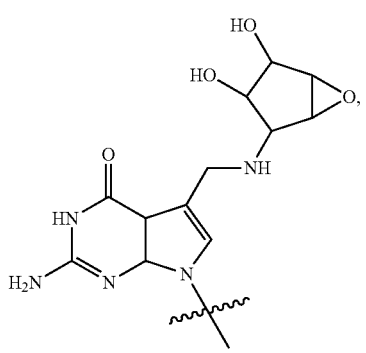

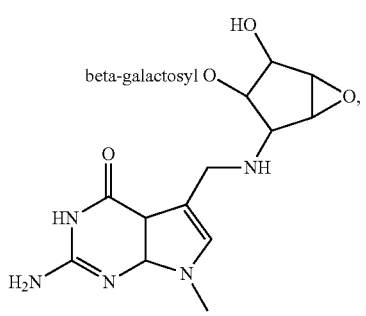

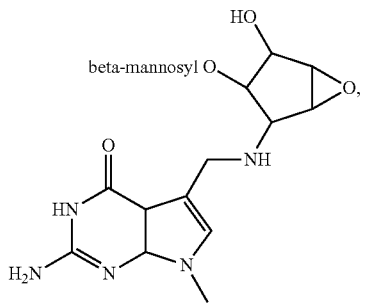

N2,7-dimethylguaninyl,
N2,N2,7-trimethylguaninyl,
1-methylguaninyl,
7-cyano-7-deazaguaninyl,
7-aminomethyl-7-deazaguaninyl,
pseudouracilyl,
dihydrouracilyl,
5-methyluracilyl,
1-methylpseudouracilyl,
2-thiouracilyl,
4-thiouracilyl,
2-thiothyminyl,
5-methyl-2-thiouracilyl,
3-(3-amino-3-carboxypropyl)uracilyl,
5-hydroxyuracilyl,
5-methoxyuracilyl,
uracilyl 5-oxyacetic acid,
uracilyl 5-oxyacetic acid methyl ester,
5-(carboxyhydroxymethyl)uracilyl,
5-(carboxyhydroxymethyl)uracilyl methyl ester,
5-methoxycarbonylmethyluracilyl,
5-methoxycarbonylmethyl-2-thiouracilyl,
5-aminomethyl-2-thiouracilyl,
5-methylaminomethyluracilyl,
5-methylaminomethyl-2-thiouracilyl,
5-methylaminomethyl-2-selenouracilyl,
5-carbamoylmethyluracilyl,
5-carboxymethylaminomethyluracilyl,
5-carboxymethylaminomethyl-2-thiouracilyl,
3-methyluracilyl,
1-methyl-3-(3-amino-3-carboxypropyl)pseudouracilyl,
5-carboxymethyluracilyl,
5-methyldihydrouracilyl, or
3-methylpseudouracilyl.

A universal base can form base pairs with each of the natural DNA/RNA bases, exhibiting relatively little discrimination between them. In general, the universal bases are non-hydrogen bonding, hydrophobic, aromatic moieties which can stabilize e.g., duplex RNA or RNA-like molecules, via stacking interactions. A universal base can also include hydrogen bonding substituents. As used herein, a "universal base" can include anthracenes, pyrenes or any one of the following:

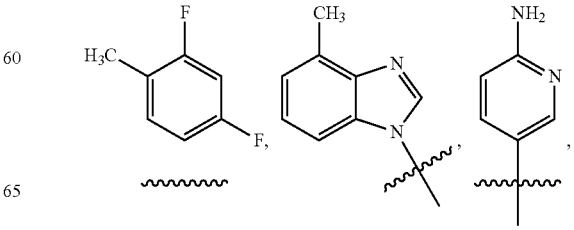

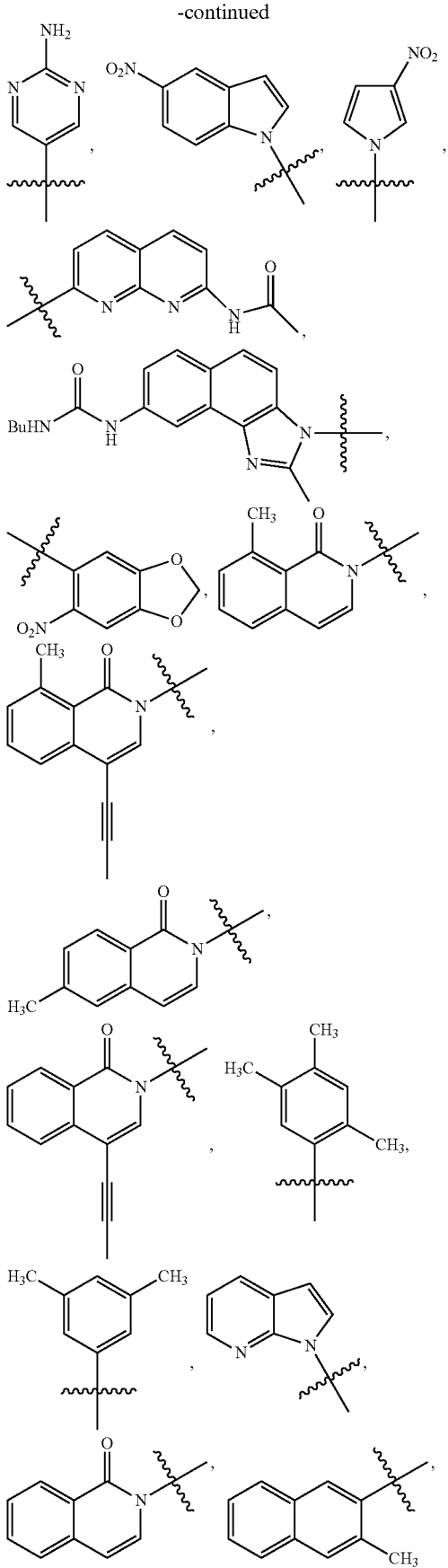

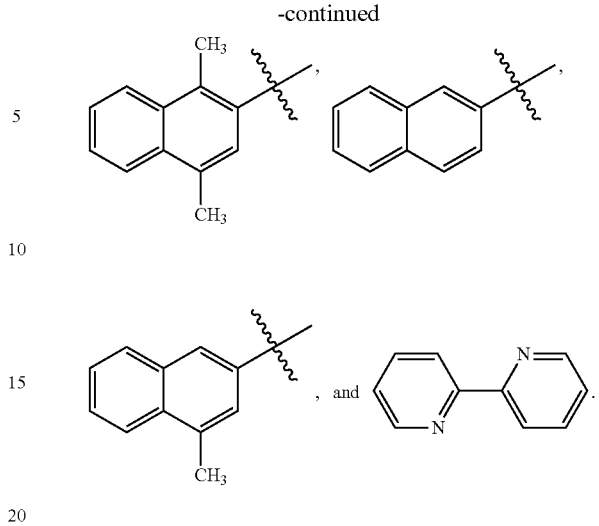

In some embodiments, B can form part of a tether that connects a ligand to the carrier. For example, the tether can be B—CH=CH—C(O)NH—(CH$_2$)$_5$—NHC(O)-LIGAND. In a preferred embodiment, the double bond is trans, and the ligand is a substituted or unsubstituted cholesterolyl radical (e.g., attached through the D-ring side chain or the C-3 hydroxyl); an aralkyl moiety having at least one sterogenic center and at least one substituent on the aryl portion of the aralkyl group; or a nucleobase. In certain embodiments, B, in the tether described above, is uracilyl or a universal base, e.g., an aryl moiety, e.g., phenyl, optionally having additional substituents, e.g., one or more fluoro groups. B can be substituted at any atom with the remainder of the tether.

$X^2$ can include "oxy" or "deoxy" substituents in place of the 2'-OH; or be a ligand or a tethered ligand.

Examples of "oxy"-substituents include alkoxy or aryloxy (OR, e.g., R=H, alkyl, cycloalkyl, aryl, aralkyl, heteroaryl, sugar, or protecting group); polyethyleneglycols (PEG), O(CH$_2$CH$_2$O)$_n$CH$_2$CH$_2$OR; "locked" nucleic acids (LNA) in which the 2' hydroxyl is connected, e.g., by a methylene bridge, to the 4' carbon of the same ribose sugar; O-PROTECTED AMINE (AMINE=NH$_2$; alkylamino, dialkylamino, heterocyclyl, arylamino, diaryl amino, heteroaryl amino, or diheteroaryl amino, ethylene diamine, polyamino) and aminoalkoxy, O(CH$_2$)$_n$PROTECTED AMINE, (e.g., AMINE=NH$_2$; alkylamino, dialkylamino, heterocyclyl, arylamino, diaryl amino, heteroaryl amino, or diheteroaryl amino, ethylene diamine, polyamino), and orthoester. Amine protecting groups can include formyl, amido, benzyl, allyl, etc.

Figure 2B:
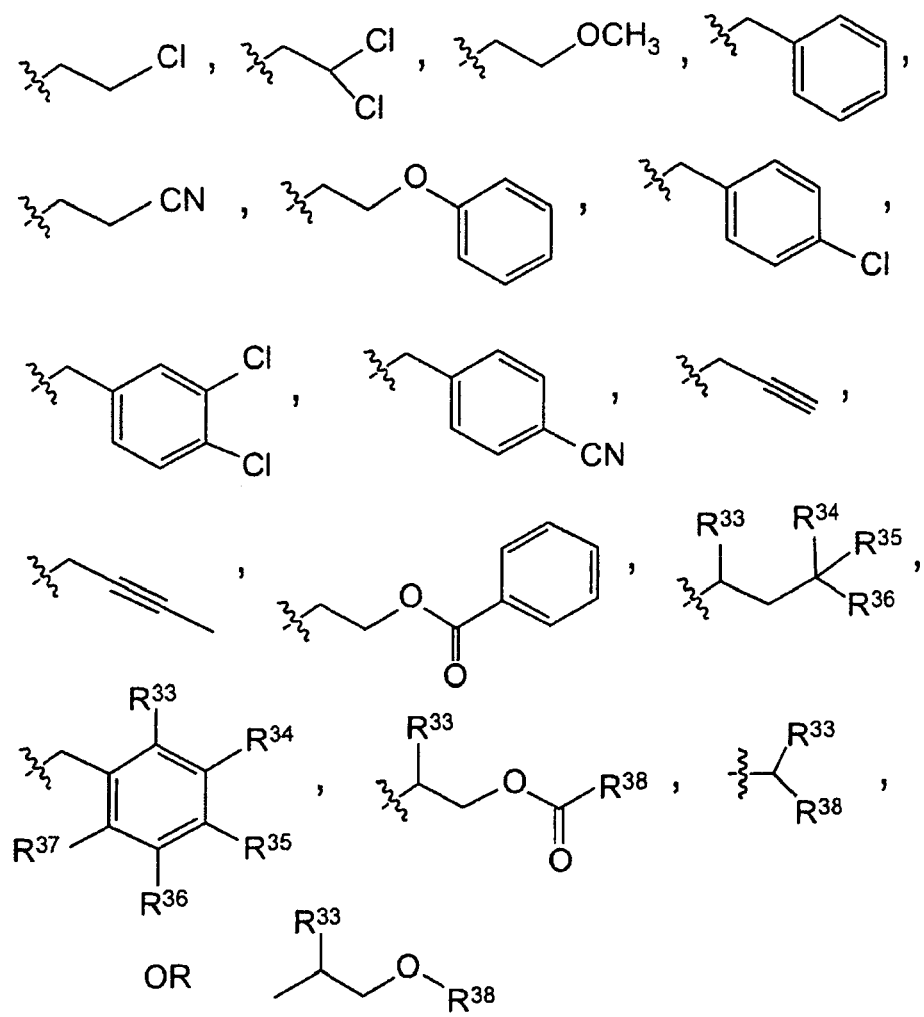
FIG. 2B is a list of substituents that may be present on the C2'-orthoester group.

Preferred orthoesters have the general formula J. The groups $R^{31}$ and $R^{32}$ may be the same or different and can be any combination of the groups listed in FIG. 2B. A preferred orthoester is the "ACE" group, shown below as structure K.

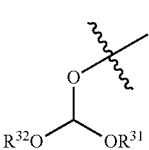

J

K

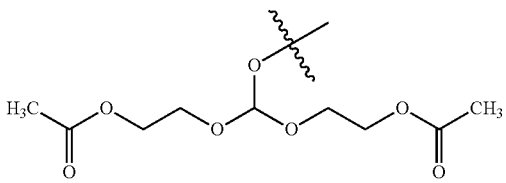

"Deoxy" substituents include hydrogen (i.e. deoxyribose sugars); halo (e.g., fluoro); protected amino (e.g. $NH_2$; alkylamino, dialkylamino, heterocyclyl, arylamino, diaryl amino, heteroaryl amino, diheteroaryl amino, or amino acid in which all amino are protected); fully protected polyamino (e.g., $NH(CH_2CH_2NH)_nCH_2CH_2$-AMINE, wherein AMINE=$NH_2$; alkylamino, dialkylamino, heterocyclyl, arylamino, diaryl amino, heteroaryl amino, or diheteroaryl amino and all amino groups are protected), —NHC(O)R (R=alkyl, cycloalkyl, aryl, aralkyl, heteroaryl or sugar), cyano; alkyl-thio-alkyl; thioalkoxy; and alkyl, cycloalkyl, aryl, alkenyl and alkynyl, which may be optionally substituted with e.g., a protected amino functionality. Preferred substitutents are 2'-methoxyethyl, 2'-OCH3, 2'-O-allyl, 2'-C-allyl, and 2'-fluoro.

$X^3$ is as described for $OFG^2$ above.

PG can be a triarylmethyl group (e.g., a dimethoxytrityl group) or $Si(X^{5'})(X^{5''})(X^{5'''})$ in which $(X^{5'})$, $(X^{5''})$, and $(X^{5'''})$ are as described elsewhere.

Sugar Replacement-Based Monomers, e.g., Ligand-Conjugated Monomers (Cyclic)

Cyclic sugar replacement-based monomers, e.g., sugar replacement-based ligand-conjugated monomers, are also referred to herein as ribose replacement monomer subunit (RRMS) monomer compounds. Preferred carriers have the general formula (LCM-2) provided below (In that structure preferred backbone attachment points can be chosen from $R^1$ or $R^2$; $R^3$ or $R^4$; or $R^9$ and $R^{10}$ if Y is $CR^9R^{10}$ (two positions are chosen to give two backbone attachment points, e.g., $R^1$ and $R^4$, or $R^4$ and $R^9$)). Preferred tethering attachment points include $R^7$; $R^5$ or $R^6$ when X is $CH_2$. The carriers are described below as an entity, which can be incorporated into a strand. Thus, it is understood that the structures also encompass the situations wherein one (in the case of a terminal position) or two (in the case of an internal position) of the attachment points, e.g., $R^1$ or $R^2$; $R^3$ or $R^4$; or $R^9$ or $R^{10}$ (when Y is $CR^9R^{10}$), is connected to the phosphate, or modified phosphate, e.g., sulfur containing, backbone. E.g., one of the above-named R groups can be —$CH_2$—, wherein one bond is connected to the carrier and one to a backbone atom, e.g., a linking oxygen or a central phosphorus atom.)

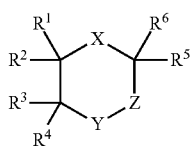

(LCM-2)

in which,
X is $N(CO)R^7$, $NR^7$ or $CH_2$;
Y is $NR^8$, O, S, $CR^9R^{10}$;
Z is $CR^{11}R^{12}$ or absent;

Each of $R^1$, $R^2$, $R^3$, $R^4$, $R^9$, and $R^{10}$ is, independently, H, $OR^a$, or $(CH_2)_nOR^b$, provided that at least two of $R^1$, $R^2$, $R^3$, $R^4$, $R^9$, and $R^{10}$ are $OR^a$ and/or $(CH_2)_nOR^b$;

Each of $R^5$, $R^6$, $R^{11}$, and $R^{12}$ is, independently, a ligand, H, $C_1$-$C_6$ alkyl optionally substituted with 1-3 $R^{13}$, or C(O)$NHR^7$; or $R^5$ and $R^{11}$ together are $C_3$-$C_8$ cycloalkyl optionally substituted with $R^{14}$;

$R^7$ can be a ligand, e.g., $R^7$ can be $R^d$, or $R^7$ can be a ligand tethered indirectly to the carrier, e.g., through a tethering moiety, e.g., $C_1$-$C_{20}$ alkyl substituted with $NR^cR^d$; or $C_1$-$C_{20}$ alkyl substituted with $NHC(O)R^d$;

$R^8$ is H or $C_1$-$C_6$ alkyl;
$R^{13}$ is hydroxy, $C_1$-$C_4$ alkoxy, or halo;
$R^{14}$ is $NR^cR^7$;
$R^{15}$ is $C_1$-$C_6$ alkyl optionally substituted with cyano, or $C_2$-$C_6$ alkenyl;
$R^{16}$ is $C_1$-$C_{10}$ alkyl;
$R^{17}$ is a liquid or solid phase support reagent;
L is —$C(O)(CH_2)_qC(O)$—, or —$C(O)(CH_2)_qS$—;
$R^a$ is a protecting group, e.g., $CAr_3$; (e.g., a dimethoxytrityl group) or $Si(X^{5'})(X^{5''})(X^{5'''})$ in which $(X^{5'})$, $(X^{5''})$, and $(X^{5'''})$ are as described elsewhere.
$R^b$ is $P(O)(O^-)H$, $P(OR^{15})N(R^{16})_2$ or $L$-$R^{17}$;
$R^c$ is H or $C_1$-$C_6$ alkyl;
$R^d$ is H or a ligand;
Each Ar is, independently, $C_6$-$C_{10}$ aryl optionally substituted with $C_1$-$C_4$ alkoxy;
n is 1-4; and q is 0-4.

Exemplary carriers include those in which, e.g., X is $N(CO)R^7$ or $NR^7$, Y is $CR^9R^{10}$, and Z is absent; or X is $N(CO)R^7$ or $NR^7$, Y is $CR^9R^{10}$, and Z is $CR^{11}R^{12}$; or X is $N(CO)R^7$ or $NR^7$, Y is $NR^8$, and Z is $CR^{11}R^{12}$; or X is $N(CO)R^7$ or $NR^7$, Y is O, and Z is $CR^{11}R^{12}$; or X is $CH_2$; Y is $CR^9R^{10}$; Z is $CR^{11}R^{12}$, and $R^5$ and $R^{11}$ together form $C_6$ cycloalkyl (H, z=2), or the indane ring system, e.g., X is $CH_2$; Y is $CR^9R^{10}$; Z is $CR^{11}R^{12}$, and $R^5$ and $R^{11}$ together form $C_5$ cycloalkyl (H, z=1).

In certain embodiments, the carrier may be based on the pyrroline ring system or the 4-hydroxyproline ring system, e.g., X is $N(CO)R^7$ or $NR^7$, Y is $CR^9R^{10}$, and Z is absent (D). $OFG^1$ is preferably attached to a primary carbon, e.g., an exocyclic alkylene

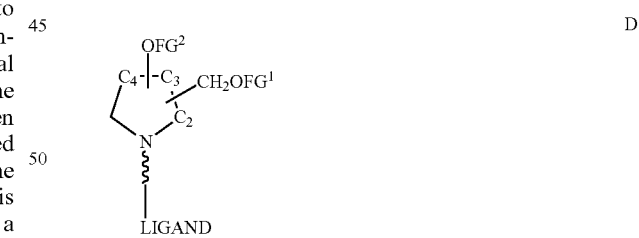

D group, e.g., a methylene group, connected to one of the carbons in the five-membered ring (—$CH_2OFG^1$ in D). $OFG^2$ is preferably attached directly to one of the carbons in the five-membered ring (—$OFG^2$ in D). For the pyrroline-based carriers, —$CH_2OFG^1$ may be attached to C-2 and $OFG^2$ may be attached to C-3; or —$CH_2OFG^1$ may be attached to C-3 and $OFG^2$ may be attached to C-4. In certain embodiments, $CH_2OFG^1$ and $OFG^2$ may be geminally substituted to one of the above-referenced carbons. For the 3-hydroxyproline-based carriers, —$CH_2OFG^1$ may be attached to C-2 and $OFG^2$ may be attached to C-4. The pyrroline- and 4-hydroxyproline-based monomers may therefore contain linkages (e.g., carbon-carbon bonds) wherein bond rotation is restricted about that particular linkage, e.g. restriction resulting from the presence of a ring. Thus, $CH_2OFG^1$ and $OFG^2$ may be cis or trans with respect to one another in any of the pairings delineated above Accordingly, all cis/trans isomers are expressly included. The monomers may also contain one or more asymmetric centers and thus occur as racemates and racemic mixtures, single enantiomers, individual diastereomers and diastereomeric mixtures. All such isomeric forms of the monomers are expressly included (e.g., the centers bearing $CH_2OFG^1$ and $OFG^2$ can both have the R configuration; or both have the S configuration; or one center can have the R configuration and the other center can have the S configuration and vice versa). The tethering attachment point is preferably nitrogen. Preferred examples of carrier D include the following:

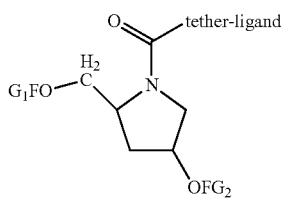

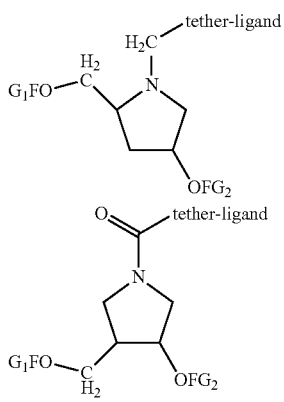

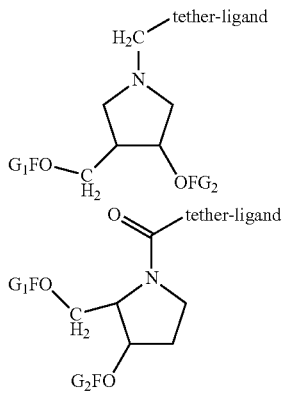

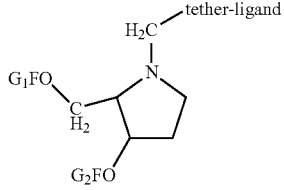

In certain embodiments, the carrier may be based on the piperidine ring system (E), e.g., X is $N(CO)R^7$ or $NR^7$, Y is $CR^9R^{10}$, and Z is $CR^{11}R^{12}$. $OFG^1$ is preferably

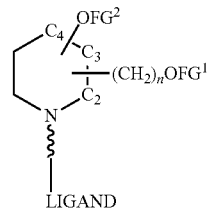

attached to a primary carbon, e.g., an exocyclic alkylene group, e.g., a methylene group (n=1) or ethylene group (n=2), connected to one of the carbons in the six-membered ring [—$(CH_2)_nOFG^1$ in E]. $OFG^2$ is preferably attached directly to one of the carbons in the six-membered ring (—$OFG^2$ in E). —$(CH_2)_nOFG^1$ and $OFG^2$ may be disposed in a geminal manner on the ring, i.e., both groups may be attached to the same carbon, e.g., at C-2, C-3, or C-4. Alternatively, —$(CH_2)_n$ $OFG^1$ and $OFG^2$ may be disposed in a vicinal manner on the ring, i.e., both groups may be attached to adjacent ring carbon atoms, e.g., —$(CH_2)_nOFG^1$ may be attached to C-2 and $OFG^2$ may be attached to C-3; —$(CH_2)_nOFG^1$ may be attached to C-3 and $OFG^2$ may be attached to C-2; —$(CH_2)_nOFG^1$ may be attached to C-3 and $OFG^2$ may be attached to C-4; or —$(CH_2)_n$ $OFG^1$ may be attached to C-4 and $OFG^2$ may be attached to C-3. The piperidine-based monomers may therefore contain linkages (e.g., carbon-carbon bonds) wherein bond rotation is restricted about that particular linkage, e.g. restriction resulting from the presence of a ring. Thus, —$(CH_2)_nOFG^1$ and $OFG^2$ may be cis or trans with respect to one another in any of the pairings delineated above. Accordingly, all cis/trans isomers are expressly included. The monomers may also contain one or more asymmetric centers and thus occur as racemates and racemic mixtures, single enantiomers, individual diastereomers and diastereomeric mixtures. All such isomeric forms of the monomers are expressly included (e.g., the centers bearing $CH_2OFG^1$ and $OFG^2$ can both have the R configuration; or both have the S configuration; or one center can have the R configuration and the other center can have the S configuration and vice versa). The tethering attachment point is preferably nitrogen.

In certain embodiments, the carrier may be based on the piperazine ring system (F), e.g., X is $N(CO)R^7$ or $NR^7$, Y is $NR^8$, and Z is $CR^{11}R^{12}$, or the morpholine ring system (G), e.g., X is $N(CO)R^7$ or $NR^7$, Y is O, and Z is $CR^{11}R^{12}$. $OFG^1$ is preferably

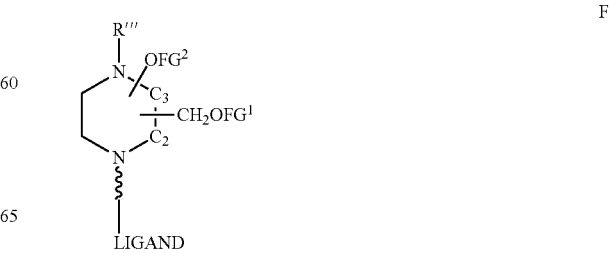

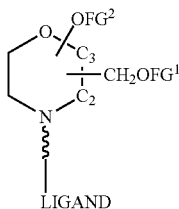

G attached to a primary carbon, e.g., an exocyclic alkylene group, e.g., a methylene group, connected to one of the carbons in the six-membered ring (—CH$_2$OFG$^1$ in F or G). OFG$^2$ is preferably attached directly to one of the carbons in the six-membered rings (—OFG$^2$ in F or G). For both F and G, —CH$_2$OFG$^1$ may be attached to C-2 and OFG$^2$ may be attached to C-3; or vice versa. In certain embodiments, CH$_2$OFG$^1$ and OFG$^2$ may be geminally substituted to one of the above-referenced carbons. The piperazine- and morpholine-based monomers may therefore contain linkages (e.g., carbon-carbon bonds) wherein bond rotation is restricted about that particular linkage, e.g. restriction resulting from the presence of a ring. Thus, CH$_2$OFG$^1$ and OFG$^2$ may be cis or trans with respect to one another in any of the pairings delineated above. Accordingly, all cis/trans isomers are expressly included. The monomers may also contain one or more asymmetric centers and thus occur as racemates and racemic mixtures, single enantiomers, individual diastereomers and diastereomeric mixtures. All such isomeric forms of the monomers are expressly included (e.g., the centers bearing CH$_2$OFG$^1$ and OFG$^2$ can both have the R configuration; or both have the S configuration; or one center can have the R configuration and the other center can have the S configuration and vice versa). R'" can be, e.g., C$_1$-C$_6$ alkyl, preferably CH$_3$. The tethering attachment point is preferably nitrogen in both F and G.

In certain embodiments, the carrier may be based on the decalin ring system, e.g., X is CH$_2$; Y is CR$^9$R$^{10}$; Z is CR$^{11}$R$^{12}$, and R$^5$ and R$^{11}$ together form C$_6$ cycloalkyl (H, z=2), or the indane ring system, e.g., X is CH$_2$; Y is CR$^9$R$^{10}$; Z is CR$^{11}$R$^{12}$, and R$^5$ and R$^{11}$ together form C$_5$ cycloalkyl (H, z=1). OFG$^1$ is preferably attached to a primary carbon,

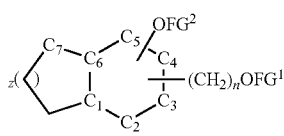

H e.g., an exocyclic methylene group (n=1) or ethylene group (n=2) connected to one of C-2, C-3, C-4, or C-5 [—(CH$_2$)$_n$ OFG$^1$ in H]. OFG$^2$ is preferably attached directly to one of C-2, C-3, C-4, or C-5 (—OFG$^2$ in H). —(CH$_2$)$_n$OFG$^1$ and OFG$^2$ may be disposed in a geminal manner on the ring, i.e., both groups may be attached to the same carbon, e.g., at C-2, C-3, C-4, or C-5.

Alternatively, —(CH$_2$)$_n$OFG$^1$ and OFG$^2$ may be disposed in a vicinal manner on the ring, i.e., both groups may be attached to adjacent ring carbon atoms, e.g., —(CH$_2$)$_n$OFG$^1$ may be attached to C-2 and OFG$^2$ may be attached to C-3; —(CH$_2$)$_n$OFG$^1$ may be attached to C-3 and OFG$^2$ may be attached to C-2; —(CH$_2$)$_n$OFG$^1$ may be attached to C-3 and OFG$^2$ may be attached to C-4; or —(CH$_2$)$_n$OFG$^1$ may be attached to C-4 and OFG$^2$ may be attached to C-3; —(CH$_2$)$_n$ OFG$^1$ may be attached to C-4 and OFG$^2$ may be attached to C-5; or —(CH$_2$)$_n$OFG$^1$ may be attached to C-5 and OFG$^2$ may be attached to C-4. The decalin or indane-based monomers may therefore contain linkages (e.g., carbon-carbon bonds) wherein bond rotation is restricted about that particular linkage, e.g. restriction resulting from the presence of a ring. Thus, —(CH$_2$)$_n$OFG$^1$ and OFG$^2$ may be cis or trans with respect to one another in any of the pairings delineated above. Accordingly, all cis/trans isomers are expressly included. The monomers may also contain one or more asymmetric centers and thus occur as racemates and racemic mixtures, single enantiomers, individual diastereomers and diastereomeric mixtures. All such isomeric forms of the monomers are expressly included (e.g., the centers bearing CH$_2$OFG$^1$ and OFG$^2$ can both have the R configuration; or both have the S configuration; or one center can have the R configuration and the other center can have the S configuration and vice versa). In a preferred embodiment, the substituents at C-1 and C-6 are trans with respect to one another. The tethering attachment point is preferably C-6 or C-7.

Other carriers may include those based on 3-hydroxyproline (J). Thus, —(CH$_2$)$_n$OFG$^1$ and OFG$^2$ may be cis or trans with respect to one another. Accordingly, all cis/trans isomers are expressly included. The monomers may also contain one or more asymmetric centers

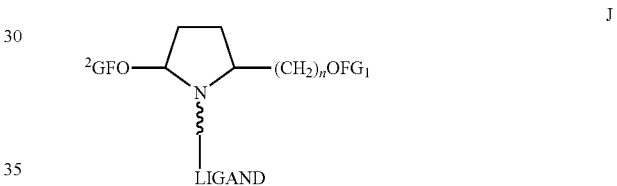

J and thus occur as racemates and racemic mixtures, single enantiomers, individual diastereomers and diastereomeric mixtures. All such isomeric forms of the monomers are expressly included (e.g., the centers bearing CH$_2$OFG$^1$ and OFG$^2$ can both have the R configuration; or both have the S configuration; or one center can have the R configuration and the other center can have the S configuration and vice versa). The tethering attachment point is preferably nitrogen.

Figure 3:
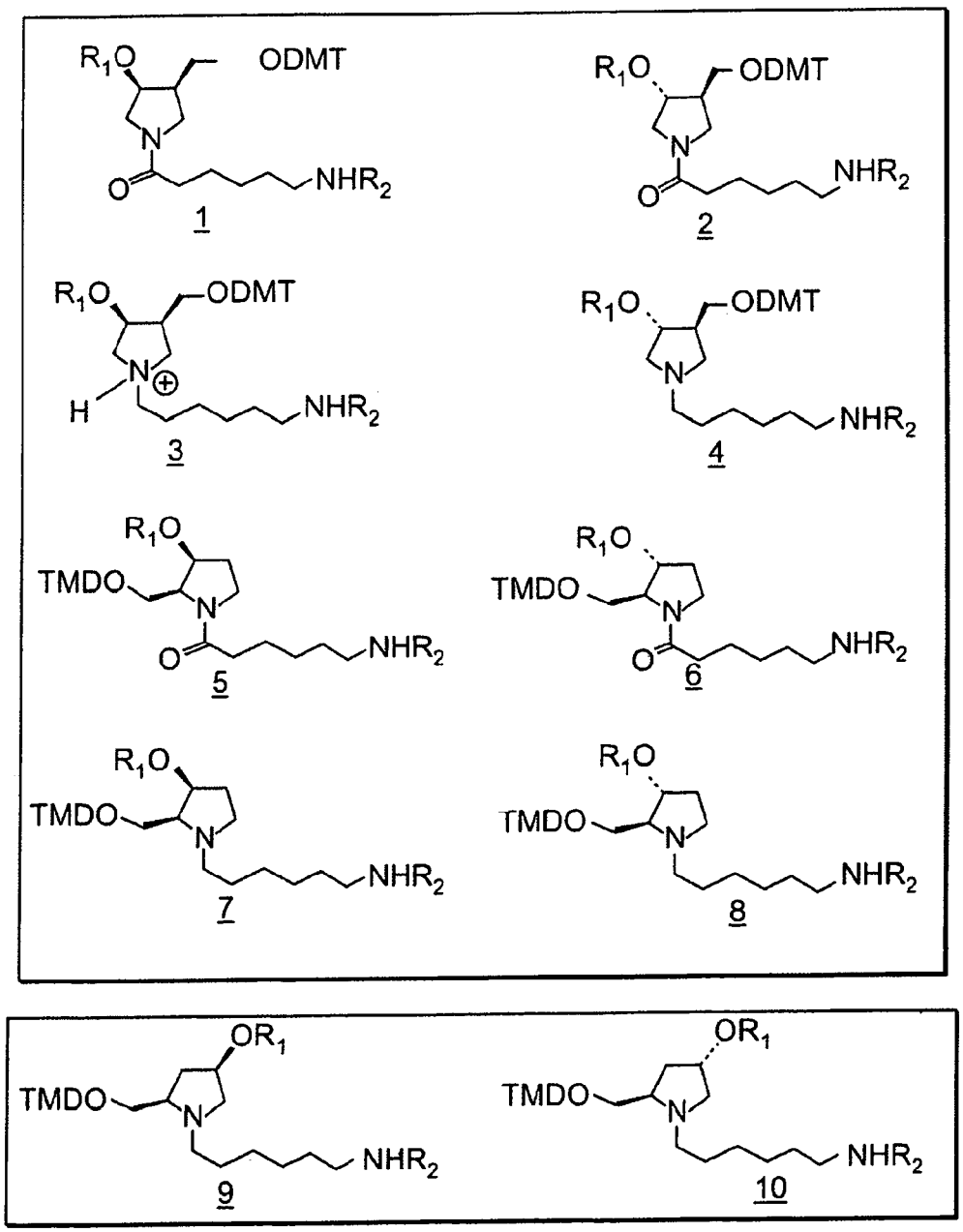
FIG. 3 is list of representative RRMS cyclic carriers. Panel 1 shows pyrroline-based RRMSs; panel 2 shows 3-hydroxyproline-based RRMSs; panel 3 shows piperidine-based RRMSs; panel 4 shows morpholine and piperazine-based RRMSs; and panel 5 shows decalin-based RRMSs. R1 is succinate or phosphoramidate and R2 is H or a conjugate ligand.
Figure 3:
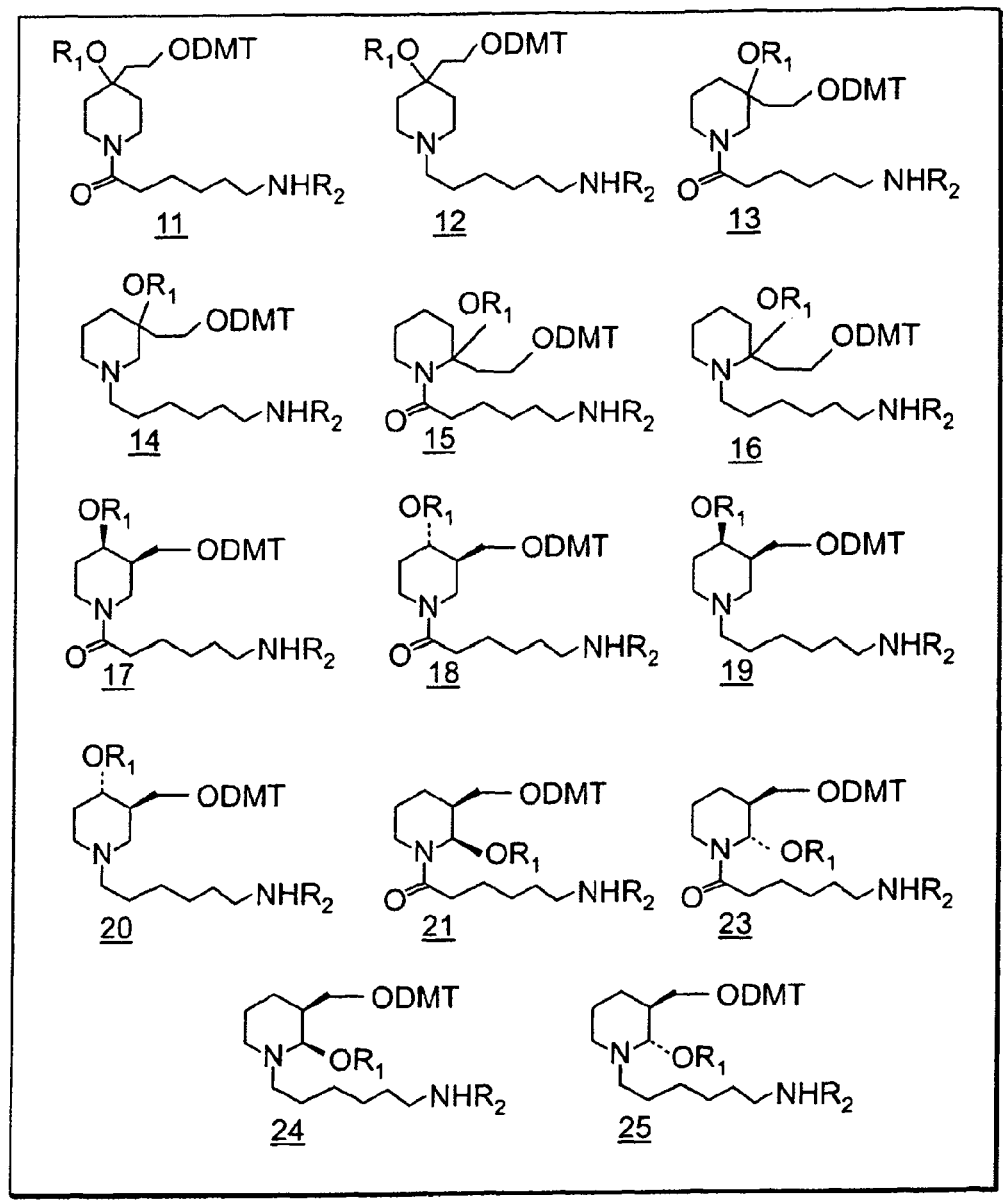
Figure 3:
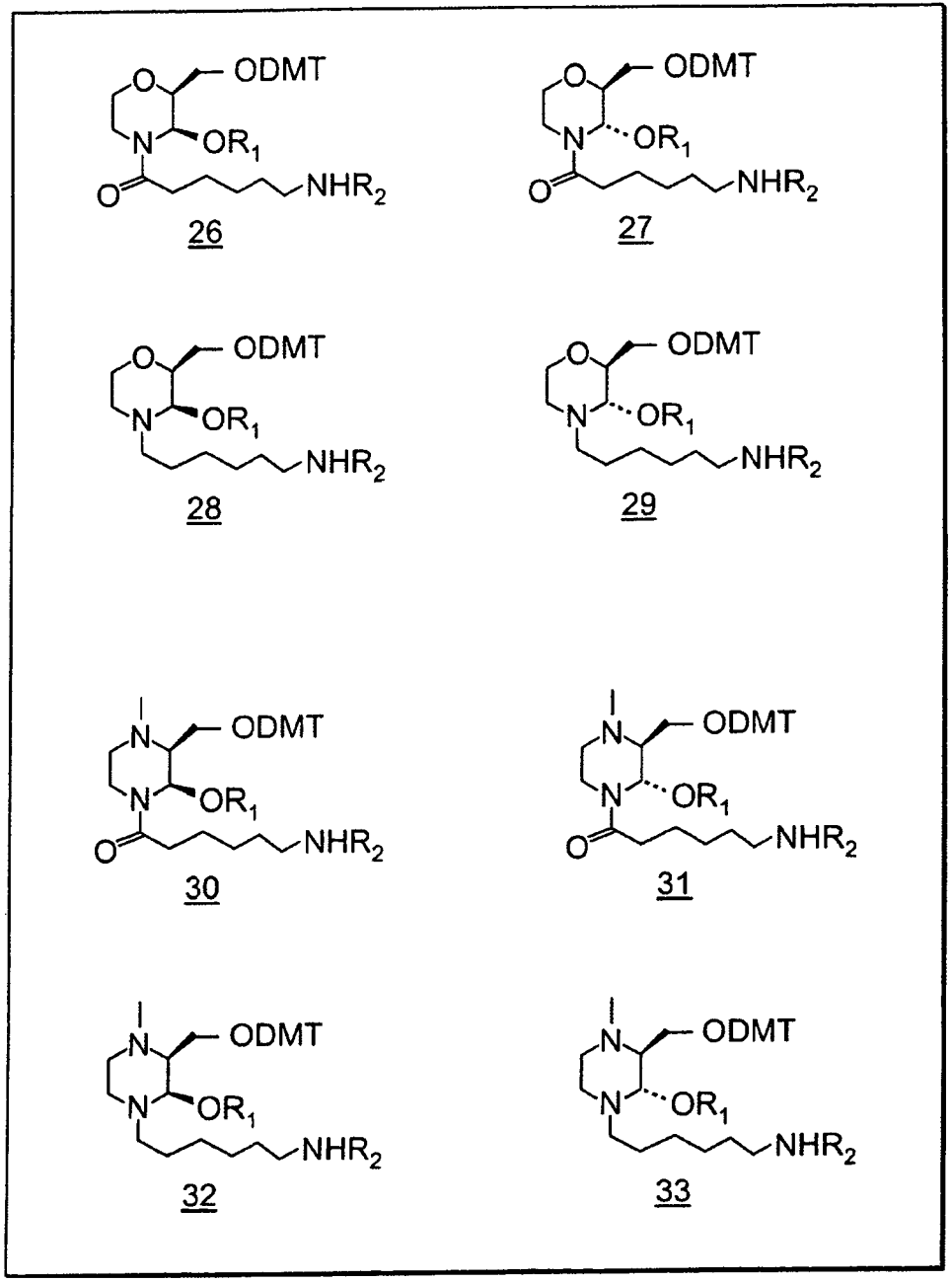
Figure 3:
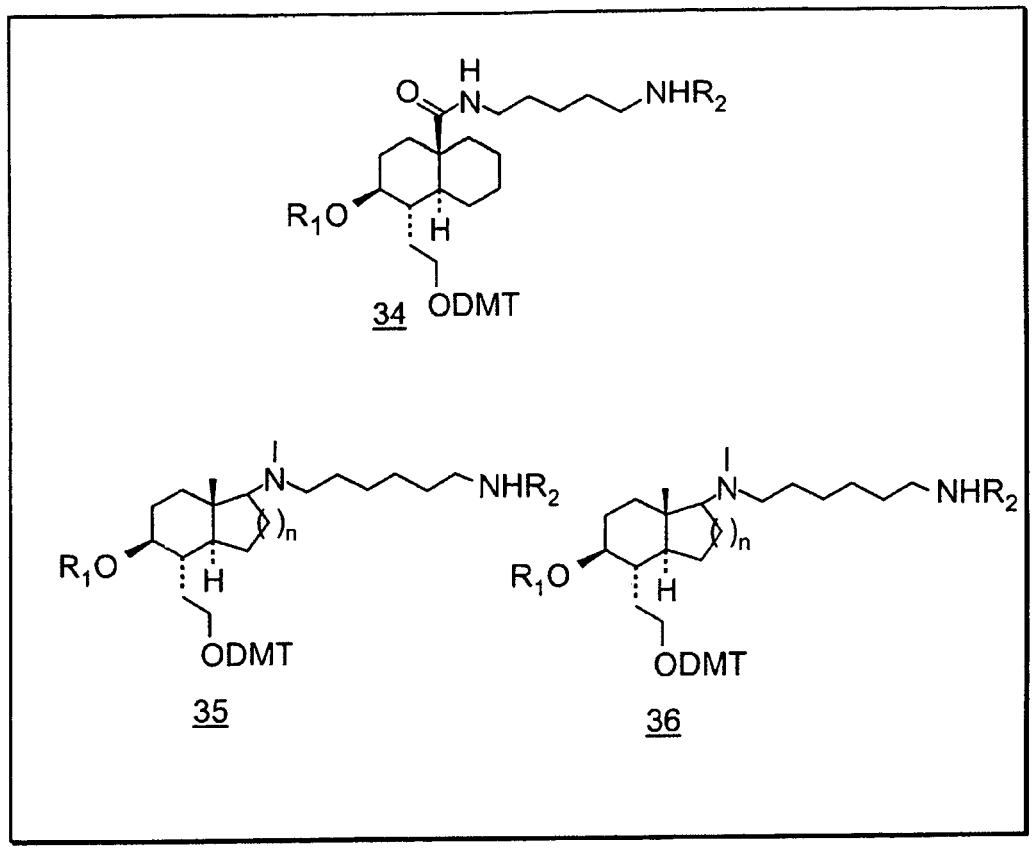

Representative cyclic, sugar replacement-based carriers are shown in FIG. 3.

Sugar Replacement-Based Monomers (Acyclic)

Acyclic sugar replacement-based monomers, e.g., sugar replacement-based ligand-conjugated monomers, are also referred to herein as ribose replacement monomer subunit (RRMS) monomer compounds. Preferred acyclic carriers can have formula LCM-3 or LCM-4 below.

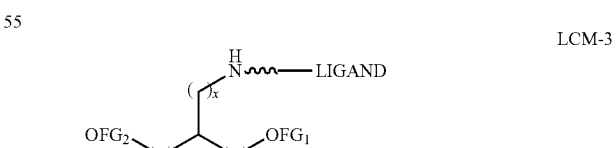

LCM-3

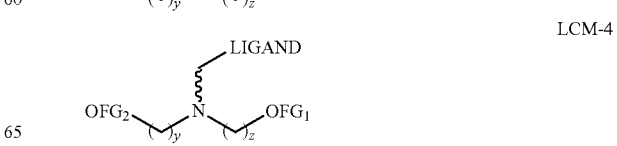

LCM-4

In some embodiments, each of x, y, and z can be, independently of one another, 0, 1, 2, or 3. In formula LCM-3, when y and z are different, then the tertiary carbon can have either the R or S configuration. In preferred embodiments, x is zero and y and z are each 1 in formula LCM-3 (e.g., based on serinol), and y and z are each 1 in formula LCM-3. Each of formula LCM-3 or LCM-4 below can optionally be substituted, e.g., with hydroxy, alkoxy, perhaloalkyl.

Tethers

In certain embodiments, a moiety, e.g., a ligand may be connected indirectly to the carrier via the intermediacy of an intervening tether. Tethers are connected to the carrier at a tethering attachment point (TAP) and may include any $C_1$-$C_{100}$ carbon-containing moiety, (e.g. $C_1$-$C_{75}$, $C_1$-$C_{50}$, $C_1$-$C_{20}$, $C_1$-$C_{10}$; $C_1$, $C_2$, $C_3$, $C_4$, $C_5$, $C_6$, $C_7$, $C_8$, $C_9$, or $C_{10}$), preferably having at least one nitrogen atom. In preferred embodiments, the nitrogen atom forms part of a terminal amino or amido (NHC(O)—) group on the tether, which may serve as a connection point for the ligand. Preferred tethers (underlined) include TAP-(CH$_2$)$_n$NH—; TAP-C(O)(CH$_2$)$_n$NH—; TAP-NR""(CH$_2$)$_n$NH—, TAP-C(O)—(CH$_2$)$_n$—C(O)—; TAP-C(O)—(CH$_2$)$_n$—C(O)O—; TAP-C(O)—O—; TAP-C(O)—(CH$_2$)$_n$—NH—C(O)—; TAP-C(O)—(CH$_2$)$_n$; TAP-C(O)—NH—; TAP-C(O)—; TAP-(CH$_2$)$_n$C(O)—; TAP-(CH$_2$)$_n$—C(O)O—; TAP-(CH$_2$)$_n$—; or TAP-(CH$_2$)$_n$—NH—C(O)—; in which n is 1-20 (e.g., 1, 2, 3, 4, 5, 6, 7, 8, 9, 10, 11, 12, 13, 14, 15, 16, 17, 18, 19, or 20) and R"" is $C_1$-$C_6$ alkyl. Preferably, n is 5, 6, or 11. In other embodiments, the nitrogen may form part of a terminal oxyamino group, e.g., —ONH$_2$, or hydrazino group, —NHNH$_2$. The tether may optionally be substituted, e.g., with hydroxy, alkoxy, perhaloalkyl, and/or optionally inserted with one or more additional heteroatoms, e.g., N, O, or S. Preferred tethered ligands may include, e.g., TAP -(CH$_2$)$_n$NH(LIGAND); TAP-C(O)(CH$_2$)$_n$NH(LIGAND); TAP-NR""(CH$_2$)$_n$NH(LIGAND); TAP -(CH$_2$)$_n$ONH(LIGAND); TAP-C(O)(CH$_2$)$_n$ONH(LIGAND); TAP-NR""(CH$_2$)$_n$ONH(LIGAND); TAP-(CH$_2$)$_n$NHNH$_2$(LIGAND), TAP-C(O)(CH$_2$)$_n$NHNH$_2$(LIGAND); TAP-NR""(CH$_2$)$_n$NHNH$_2$(LIGAND); TAP-C(O)—(CH$_2$)$_n$—C(O)(LIGAND); TAP-C(O)—(CH$_2$)$_n$—C(O)O(LIGAND); TAP-C(O)—O(LIGAND); TAP-C(O)—(CH$_2$)$_n$—NH—C(O)(LIGAND); TAP-C(O)—(CH$_2$)$_n$(LIGAND); TAP-C(O)—NH(LIGAND); TAP-C(O)(LIGAND); TAP-(CH$_2$)$_n$—C(O)(LIGAND); TAP-(CH$_2$)$_n$—C(O)O(LIGAND); TAP-(CH$_2$)$_n$(LIGAND); or TAP-(CH$_2$)$_n$—NH—C(O)(LIGAND). In some embodiments, amino terminated tethers (e.g., NH$_2$, ONH$_2$, NH$_2$NH$_2$) can form an imino bond (i.e., C=N) with the ligand. In some embodiments, amino terminated tethers (e.g., NH$_2$, ONH$_2$, NH$_2$NH$_2$) can acylated, e.g., with C(O)CF$_3$.

In some embodiments, the tether can terminate with a mercapto group (i.e., SH) or an olefin (e.g., CH=CH$_2$). For example, the tether can be TAP-(CH$_2$)$_n$—SH, TAP-C(O)(CH$_2$)$_n$SH, TAP-(CH$_2$)$_n$—(CH=CH$_2$), or TAP-C(O)(CH$_2$)$_n$(CH=CH$_2$), in which n can be as described elsewhere. The tether may optionally be substituted, e.g., with hydroxy, alkoxy, perhaloalkyl, and/or optionally inserted with one or more additional heteroatoms, e.g., N, O, or S. The double bond can be cis or trans or E or Z.

In other embodiments the tether may include an electrophilic moiety, preferably at the terminal position of the tether. Preferred electrophilic moieties include, e.g., an aldehyde, alkyl halide, mesylate, tosylate, nosylate, or brosylate, or an activated carboxylic acid ester, e.g. an NHS ester, or a pentafluorophenyl ester. Preferred tethers (underlined) include TAP-(CH$_2$)$_n$CHO; TAP-C(O)(CH$_2$)$_n$CHO; or TAP-NR""(CH$_2$)$_n$CHO, in which n is 1-6 and R"" is $C_1$-$C_6$ alkyl; or TAP-(CH$_2$)$_n$C(O)ONHS; TAP-C(O)(CH$_2$)$_n$ONHS; or TAP-NR""(CH$_2$)$_n$C(O)ONHS, in which n is 1-6 and R"" is $C_1$-$C_6$ alkyl; TAP-(CH$_2$)$_n$C(O)OC$_6$F$_5$; TAP-C(O)(CH$_2$)$_n$C(O)OC$_6$F$_5$; or TAP-NR""(CH$_2$)$_n$C(O)OC$_6$F$_5$, in which n is 1-11 and R"" is $C_1$-$C_6$ alkyl; or —(CH$_2$)$_n$CH$_2$LG; TAP-C(O)(CH$_2$)$_n$CH$_2$LG; or TAP-NR""(CH$_2$)$_n$CH$_2$LG, in which n can be as described elsewhere and R"" is $C_1$-$C_6$ alkyl (LG can be a leaving group, e.g., halide, mesylate, tosylate, nosylate, brosylate). Tethering can be carried out by coupling a nucleophilic group of a ligand, e.g., a thiol or amino group with an electrophilic group on the tether.

In other embodiments, it can be desirable for the monomer to include a phthalimido group (K) at the terminal position of the tether.

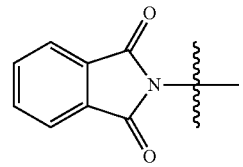

K

In other embodiments, other protected amino groups can be at the terminal position of the tether, e.g., alloc, monomethoxy trityl (MMT), trifluoroacetyl, Fmoc, or aryl sulfonyl (e.g., the aryl portion can be ortho-nitrophenyl or ortho, para-dinitrophenyl).

Any of the tethers described herein may further include one or more additional linking groups, e.g., —O—(CH$_2$)$_n$—, —(CH$_2$)$_n$—SS—, —(CH$_2$)$_n$—, or —(CH=CH)—.

Tethered Ligands

A wide variety of entities, e.g., ligands, can be tethered to an iRNA agent, e.g., to the carrier of a ligand-conjugated monomer subunit. Examples are described below in the context of a ligand-conjugated monomer subunit but that is only preferred, entities can be coupled at other points to an iRNA agent.

Preferred moieties are ligands, which are coupled, preferably covalently, either directly or indirectly via an intervening tether, to the carrier. In preferred embodiments, the ligand is attached to the carrier via an intervening tether. As discussed above, the ligand or tethered ligand may be present on the ligand-conjugated monomer \ when the ligand-conjugated monomer is incorporated into the growing strand. In some embodiments, the ligand may be incorporated into a "precursor" ligand-conjugated monomer subunit after a "precursor" ligand-conjugated monomer subunit has been incorporated into the growing strand. For example, a monomer having, e.g., an amino-terminated tether, e.g., TAP-(CH$_2$)$_n$NH$_2$ may be incorporated into a growing sense or antisense strand. In a subsequent operation, i.e., after incorporation of the precursor monomer subunit into the strand, a ligand having an electrophilic group, e.g., a pentafluorophenyl ester or aldehyde group, can subsequently be attached to the precursor ligand-conjugated monomer by coupling the electrophilic group of the ligand with the terminal nucleophilic group of the precursor ligand-conjugated monomer subunit tether.

In preferred embodiments, a ligand alters the distribution, targeting or lifetime of an iRNA agent into which it is incorporated. In preferred embodiments a ligand provides an enhanced affinity for a selected target, e.g, molecule, cell or cell type, compartment, e.g., a cellular or organ compartment, tissue, organ or region of the body, as, e.g., compared to a species absent such a ligand.

Preferred ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics.

Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl) methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic moieties, e.g., cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g, cholesterol, cholic acid, adamantane acetic acid, 1-pyrene butyric acid, dihydrotestosterone, glycerol (e.g., esters and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl)glycerol, 1,3-bis-O(octaadecyl)glycerol), geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, $[MPEG]_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose. The ligand can be, for example, a lipopolysaccharide, an activator of p38 MAP kinase, or an activator of NF-κB.

The ligand can be a substance, e.g, a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the iRNA agent into the cell by activating an inflammatory response, for example. Exemplary ligands that would have such an effect include tumor necrosis factor alpha (TNFalpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

Peptides that target markers enriched in proliferating cells can be used. E.g., RGD containing peptides and petomimetics can target cancer cells, in particular cells that exhibit an $I_v\theta_3$ integrin. Thus, one could use RGD peptides, cyclic peptides containing RGD, RGD peptides that include D-amino acids, as well as synthetic RGD mimics. In addition to RGD, one can use other moieties that target the $I_v$-$\theta_3$ integrin ligand. Generally, such ligands can be used to control proliferating cells and angiogeneis. Preferred conjugates of this type include an iRNA agent that targets PECAM-1, VEGF, or other cancer gene, e.g., a cancer gene described herein.

The iRNA agents of the invention are particularly useful when targeted to the liver. An iRNA agent can be targeted to the liver by incorporation of a monomer derivatized with a ligand which targets to the liver. For example, a liver-targeting agent can be a lipophilic moiety. Preferred lipophilic moieties include lipid, cholesterols, oleyl, retinyl, or cholesteryl residues. Other lipophilic moieties that can function as liver-targeting agents include cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine.

An iRNA agent can also be targeted to the liver by association with a low-density lipoprotein (LDL), such as lactosylated LDL. Polymeric carriers complexed with sugar residues can also function to target iRNA agents to the liver.

A targeting agent that incorporates a sugar, e.g., galactose and/or analogues thereof, is particularly useful. These agents target, in particular, the parenchymal cells of the liver. For example, a targeting moiety can include more than one or preferably two or three galactose moieties, spaced about 15 angstroms from each other. The targeting moiety can alternatively be lactose (e.g., three lactose moieties), which is glucose coupled to a galactose. The targeting moiety can also be N-Acetyl-Galactosamine, N-Ac-Glucosamine. A mannose or mannose-6-phosphate targeting moiety can be used for macrophage targeting.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long (see Table 1, for example).

TABLE 1

Exemplary Cell Permeation Peptides

| Cell Permeation Peptide | Amino acid Sequence | Reference |
|---|---|---|
| Penetratin | RQIKIWFQNRRMKWKK (SEQ ID NO: 1) | Derossi et al., J. Biol. Chem. 269:10444, 1994 |
| Tat fragment (48-60) | GRKKRRQRRRPPQC (SEQ ID NO: 2) | Vives et al., J. Biol. Chem., 272:16010, 1997 |
| Signal Sequence-based peptide | GALFLGWLGAAGSTMGAWSQPKKKRKV (SEQ ID NO: 3) | Chaloin et al., Biochem. Biophys. Res. Commun., 243:601, 1998 |
| PVEC | LLIILRRRIRKQAHAHSK (SEQ ID NO: 4) | Elmquist et al., Exp. Cell Res., 269:237, 2001 |
| Transportan | GWTLNSAGYLLKINLKALAALAKKIL (SEQ ID NO: 5) | Pooga et al., FASEB J., 12:67, 1998 |
| Amphiphilic model peptide | KLALKLALKALKAALKLA (SEQ ID NO: 6) | Oehlke et al., Mol. Ther., 2:339, 2000 |
| Arg$_9$ | RRRRRRRRR (SEQ ID NO: 7) | Mitchel et al., J. Pept. Res., 56:318, 2000 |
| Bacterial cell wall permeating | KFFKFFKFFK (SEQ ID NO: 8) | |
| LL-37 | LLGDFFRKSKEKIGKEFKRIVQRIKDFLRN LVPRTES (SEQ ID NO: 9) | |
| Cecropin P1 | SWLSKTAKKLENSAKKRISEGIAIAIQGGPR (SEQ ID NO: 10) | |

TABLE 1-continued

Exemplary Cell Permeation Peptides

| Cell Permeation Peptide | Amino acid Sequence | Reference |
|---|---|---|
| α-defensin | ACYCRIPACIAGERRYGTCIYQGRLWAFCC (SEQ ID NO: 11) | |
| b-defensin | DHYNCVSSGGQCLYSACPIFTKIQGTCYR GKAKCCK (SEQ ID NO: 12) | |
| Bactenecin | RKCRIVVIRVCR (SEQ ID NO: 13) | |
| PR-39 | RRRPRPPYLPRPRPPPFFPPRLPPRIPPGFPP RFPPRFPGKR-NH2 (SEQ ID NO: 14) | |
| Indolicidin | ILPWKWPWWPWRR-NH2 (SEQ ID NO: 15) | |

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO:16). An RFGF analogue (e.g., amino acid sequence AALLPVLLAAP (SEQ ID NO:17)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO:18)) and the Drosophila Antennapedia protein (RQIKIWFQNRRMKWKK (SEQ ID NO:19)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Preferably the peptide or peptidomimetic tethered to an iRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide moiety can be used to target a tumor cell, such as an endothelial tumor cell or a breast cancer tumor cell (Zitzmann et al., Cancer Res., 62:5139-43, 2002). An RGD peptide can facilitate targeting of an iRNA agent to tumors of a variety of other tissues, including the lung, kidney, spleen, or liver (Aoki et al., Cancer Gene Therapy 8:783-787, 2001). Preferably, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing $\alpha_\nu\beta_3$ (Haubner et al., Jour. Nucl. Med., 42:326-336, 2001).

Peptides that target markers enriched in proliferating cells can be used. E.g., RGD containing peptides and peptidomimetics can target cancer cells, in particular cells that exhibit an $I_\nu\theta_3$ integrin. Thus, one could use RGD peptides, cyclic peptides containing RGD, RGD peptides that include D-amino acids, as well as synthetic RGD mimics. In addition to RGD, one can use other moieties that target the $I_\nu$-$\theta_3$ integrin ligand. Generally, such ligands can be used to control proliferating cells and angiogeneis. Preferred conjugates of this type include an iRNA agent that targets PECAM-1, VEGF, or other cancer gene, e.g., a cancer gene described herein.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

In one embodiment, a targeting peptide tethered to an ligand-conjugated monomer can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, $H_2A$ peptides, Xenopus peptides, esculentinis-1, and caerins. A number of factors will preferably be considered to maintain the integrity of helix stability. For example, a maximum number of helix stabilization residues will be utilized (e.g., leu, ala, or lys), and a minimum number helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix. Formation of salt bridges between residues with opposite charges, separated by i±3, or i±4 positions can provide stability. For example, cationic residues such as lysine, arginine, homo-arginine, ornithine or histidine can form salt bridges with the anionic residues glutamate or aspartate.

Peptide and petidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides.

In some embodiments, the ligand can be any of the nucleobases described herein.

In some embodiments, the ligand can be a substituted amine, e.g. dimethylamino. In certain embodiments the substituted amine can be rendered cationic, e.g., by quaternization, e.g., protonation or alkylation. In certain embodiments, the substituted amine can be at the terminal position of a relatively hydrophobic chain, e.g., an alkylene chain.

In some embodiments, the ligand can be one of the following triterpenes:

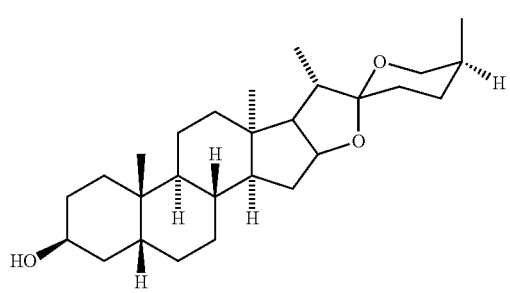
Sarsasapogenin

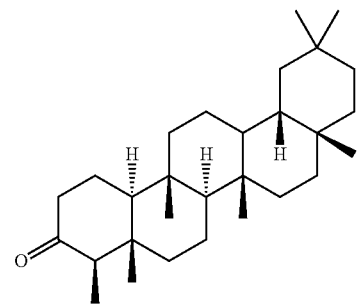
Friedelin

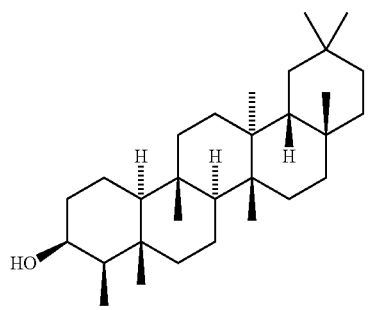
Epifriedelanol

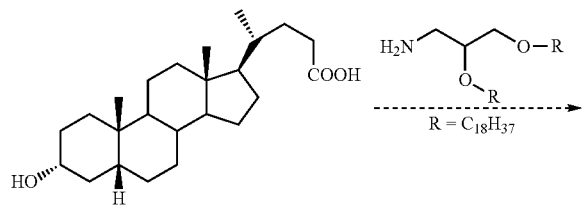
Lithocholic acid $R = C_{18}H_{37}$

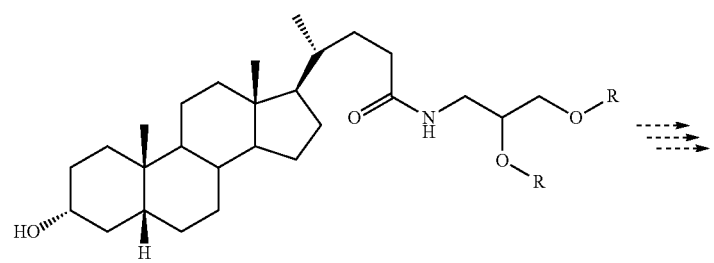

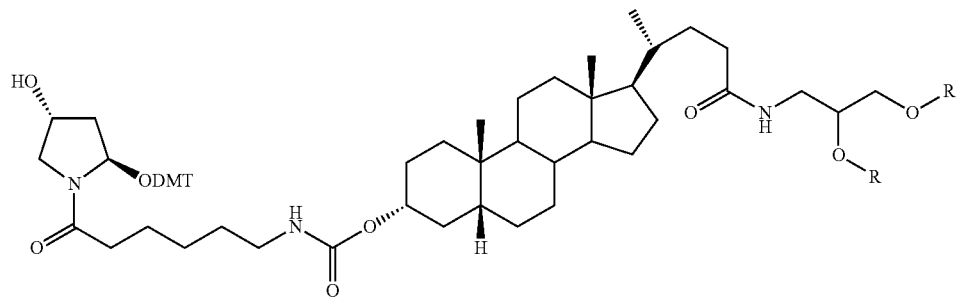

In some embodiments, the ligand can be substituted or unsubstituted cholesterol, or a stereoisomer thereof or one of the following steroids:

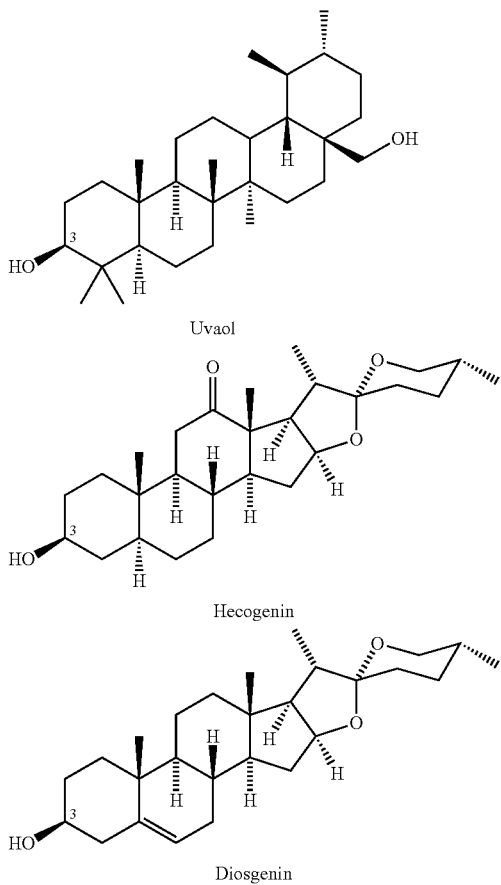

Uvaol

Hecogenin

Diosgenin

Methods for Making iRNA Agents

A listing of ribonucleosides containing the unusual bases described herein are described in "The RNA Modification Database" maintained by Pamela F. Crain, Jef Rozenski and James A. McCloskey; Departments of Medicinal Chemistry and Biochemistry, University of Utah, Salt Lake City, Utah 84112, USA (RNAmods@lib.med.utah.edu)

The 5' silyl protecting group can be used in conjunction with acid labile orthoesters at the 2' position of ribonucleosides to synthesize oligonucleotides via phosphoramidite chemistry. Final deprotection conditions are known not to significantly degrade RNA products. Functional groups on the unusual and universal bases are blocked during oligonucleotide synthesis with protecting groups that are compatible with the operations being performed that are described herein. All syntheses can be can be conducted in any automated or manual synthesizer on large, medium, or small scale. The syntheses may also be carried out in multiple well plates or glass slides.

The 5'-O-silyl group can be removed via exposure to fluoride ions, which can include any source of fluoride ion, e.g., those salts containing fluoride ion paired with inorganic counterions e.g., cesium fluoride and potassium fluoride or those salts containing fluoride ion paired with an organic counterion, e.g., a tetraalkylammonium fluoride. A crown ether catalyst can be utilized in combination with the inorganic fluoride in the deprotection reaction. Preferred fluoride ion source are tetrabutylammonium fluoride or aminehydrofluorides (e.g., combining aqueous HF with triethylamine in a dipolar aprotic solvent, e.g., dimethylformamide).

The choice of protecting groups for use on the phosphite triesters and phosphotriesters can alter the stability of the triesters towards fluoride. Methyl protection of the phosphotriester or phosphitetriester can stabilize the linkage against fluoride ions and improve process yields.

Since ribonucleosides have a reactive 2' hydroxyl substituent, it can be desirable to protect the reactive 2' position in RNA with a protecting group that is compatible with a 5'-β-silyl protecting group, e.g. one stable to fluoride. Orthoesters meet this criterion and can be readily removed in a final acid deprotection step that can result in minimal RNA degradation.

Tetrazole catalysts can be used in the standard phosphoramidite coupling reaction. Preferred catalysts include e.g. tetrazole, S-ethyl-tetrazole, p-nitrophenyltetrazole.

The general process is as follows. Nucleosides are suitably protected and functionalized for use in solid-phase or solution-phase synthesis of RNA oligonucleotides. The 2'-hydroxyl group in a ribonucleotide can be modified using a tris orthoester reagent. The 2'-hydroxyl can be modified to yield a 2'-O-orthoester nucleoside by reacting the ribonucleoside with the tris orthoester reagent in the presence of an acidic catalyst, e.g., pyridinium p-toluene sulfonate. This reaction is known to those skilled in the art. The product can then be subjected to further protecting group reactions (e.g., 5'-O-silylation) and functionalizations (e.g., 3'-O-phosphitylation) to produce a desired reagent (e.g., nucleoside phosphoramidite) for incorporation within an oligonucleotide or polymer by reactions known to those skilled in the art.

Preferred orthoesters include those comprising ethylene glycol ligands which are protected with acyl or ester protecting groups. Specifically, the preferred acyl group is acetyl. The nucleoside reagents may then be used by those skilled in the art to synthesize RNA oligonucleotides on commercially available synthesizer instruments, e.g. Gene Assembler Plus (Pharmacia), 380B (Applied Biosystems). Following synthesis (either solution-phase or solid-phase) of an oligonucleotide or polymer, the product can be subjected to one or more reactions using non-acidic reagents. One of these reactions may be strong basic conditions, for example, 40% methylamine in water for 10 minutes at 55.degree. C., which will remove the acyl protecting groups from the ethylene glycol ligands but leave the orthoester moiety attached. The resultant orthoester may be left attached when the polymer or oligonucleotide is used in subsequent applications, or it may be removed in a final mildly-acidic reaction, for example, 10 minutes at 55.degree. C. in 50 mM acetic acid, pH 3.0, followed by addition of equal volume of 150 mM TRIS buffer for 10 minutes at 55.degree. C.

Universal bases are described in "Survey and Summary: The Applications of Universal DNA base analogues" Loakes, D., *Nucleic Acid Research* 2001, 29, 2437, which is incorporated by reference in its entirety. Specific examples are described in the following: Liu, D.; Moran, S.; Kool, E. T. *Chem. Biol.*, 1997, 4, 919-926; Morales, J. C.; Kool, E. T. *Biochemistry*, 2000, 39, 2626-2632; Matray, T, J.; Kool, E. T. *J. Am. Chem. Soc.*, 1998, 120, 6191-6192; Moran, S. Ren, R. X.-F.; Rumney IV, S.; Kool, E. T. *J. Am. Chem. Soc.*, 1997, 119, 2056-2057; Guckian, K. M.; Morales, J. C.; Kool, E. T. *J. Org. Chem.*, 1998, 63, 9652-9656; Berger, M.; Wu. Y.; Ogawa, A. K.; McMinn, D. L.; Schultz, P. G.; Romesberg, F. E. *Nucleic Acids Res.*, 2000, 28, 2911-2914; Ogawa, A. K.; Wu, Y.; McMinn, D. L.; Liu, J.; Schultz, P. G.; Romesberg, F. E. *J. Am. Chem. Soc.*, 2000, 122, 3274-3287; Ogawa, A. K.;

Wu. Y.; Berger, M.; Schultz, P. G.; Romesberg, F. E. *J. Am. Chem. Soc.*, 2000, 122, 8803-8804; Tae, E. L.; Wu, Y.; Xia, G.; Schultz, P. G.; Romesberg, F. E. *J. Am. Chem. Soc.*, 2001, 123, 7439-7440; Wu, Y.; Ogawa, A. K.; Berger, M.; McMinn, D. L.; Schultz, P. G.; Romesberg, F. E. *J. Am. Chem. Soc.*, 2000, 122, 7621-7632.; McMinn, D. L.; Ogawa. A. K.; Wu, Y.; Liu, J.; Schultz, P. G.; Romesberg, F. E. *J. Am. Chem. Soc.*, 1999, 121, 11585-11586; Brotschi, C.; Haberli, A.; Leumann, C, J. *Angew. Chem. Int. Ed.*, 2001, 40, 3012-3014; Weizman, H.; Tor, Y. *J. Am. Chem. Soc.*, 2001, 123, 3375-3376; Lan, T.; McLaughlin, L. W. *J. Am. Chem. Soc.*, 2000, 122, 6512-13.

As discussed above, the monomers and methods described herein can be used in the preparation of modified RNA molecules, or polymeric molecules comprising any combination of monomer compounds described herein and/or natural or modified ribonucleotides in which one or more subunits contain an unusual or universal base. Modified RNA molecules include e.g. those molecules containing a chemically or stereochemically modified nucleoside (e.g., having one or more backbone modifications, e.g., phosphorothioate or P-alkyl; having one or more sugar modifications, e.g., 2'-OCH$_3$ or 2'-F; and/or having one or more base modifications, e.g., 5-alkylamino or 5-allylamino) or a nucleoside surrogate.

Coupling of 5'-hydroxyl groups with phosphoramidites forms phosphite ester intermediates, which in turn are oxidized e.g., with iodine, to the phosphate diester. Alternatively, the phosphites may be treated with e.g., sulfur, selenium, amino, and boron reagents to form modified phosphate backbones. Linkages between the monomers described herein and a nucleoside or oligonucleotide chain can also be treated with iodine, sulfur, selenium, amino, and boron reagents to form unmodified and modified phosphate backbones respectively. Similarly, the monomers described herein may be coupled with nucleosides or oligonucleotides containing any of the modifications or nucleoside surrogates described herein.

Figure 5:
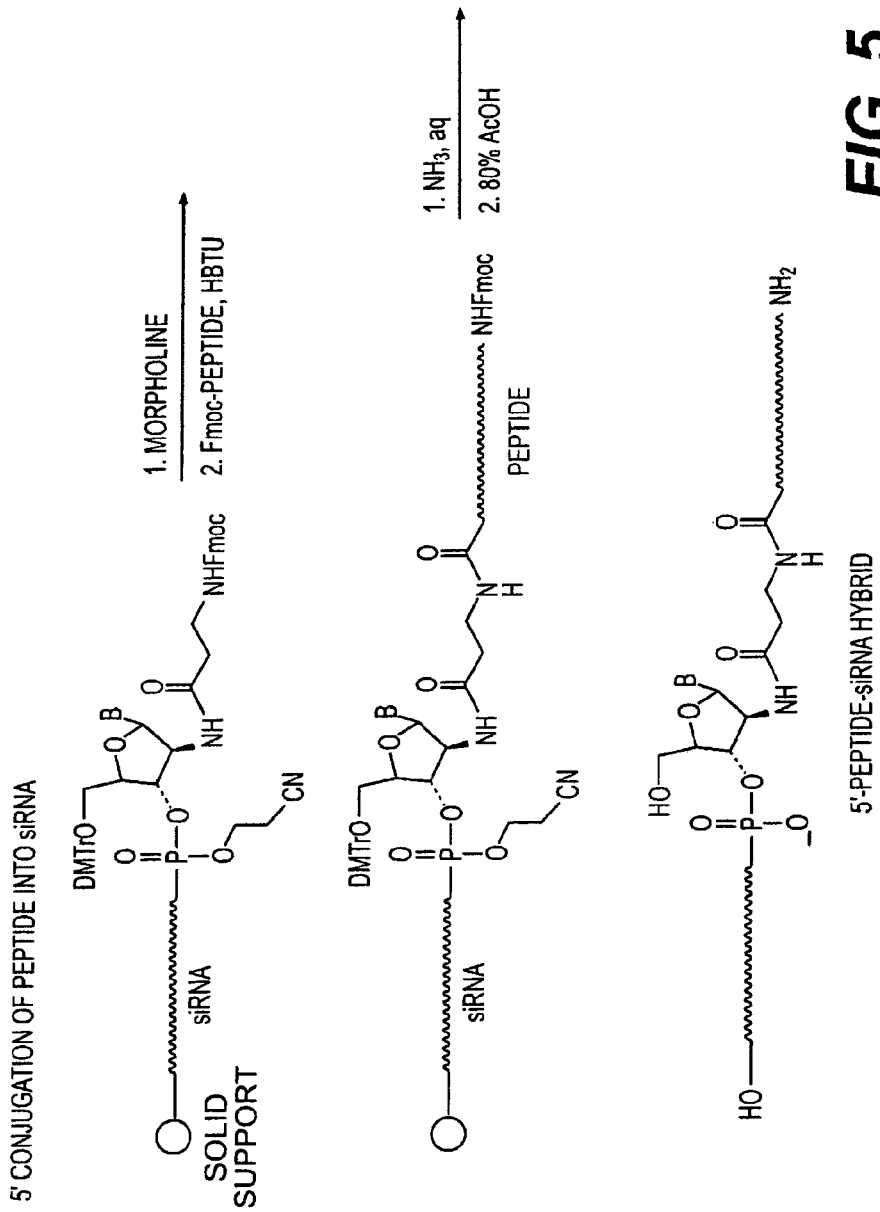
FIG. 5 is a general reaction scheme for 5' conjugation of peptide into iRNA.

The synthesis and purification of oligonucleotide peptide conjugates can be performed by established methods. See, for example, Trufert et al., Tetrahedron, 52:3005, 1996; and Manoharan, "Oligonucleotide Conjugates in Antisense Technology," in *Antisense Drug Technology*, ed. S. T. Crooke, Marcel Dekker, Inc., 2001. Exemplary methods are shown in FIGS. 4 and 5.

Figure 6:
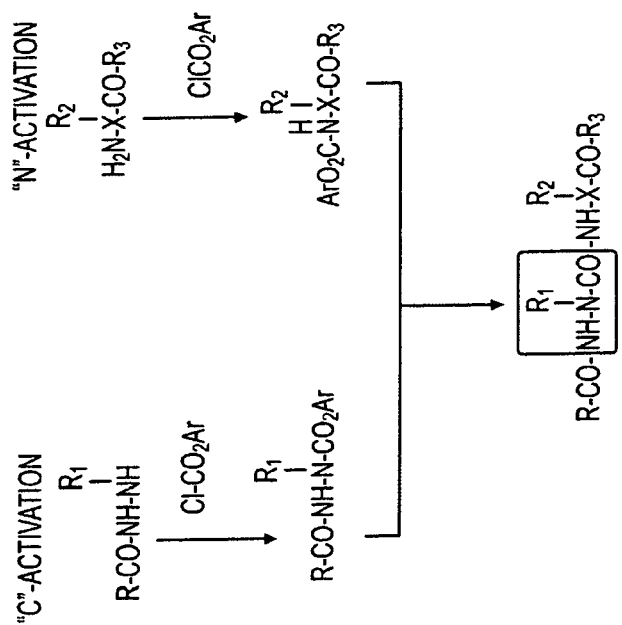
FIG. 6 is a general reaction scheme for the synthesis of aza-peptides.

In one embodiment of the invention, a peptidomimetic can be modified to create a constrained peptide that adopts a distinct and specific preferred conformation, which can increase the potency and selectivity of the peptide. For example, the constrained peptide can be an azapeptide (Gante, Synthesis, 405-413, 1989). An azapeptide is synthesized by replacing the α-carbon of an amino acid with a nitrogen atom without changing the structure of the amino acid side chain. For example, the azapeptide can be synthesized by using hydrazine in traditional peptide synthesis coupling methods, such as by reacting hydrazine with a "carbonyl donor," e.g., phenylchloroformate. A general azapeptide synthesis is shown in FIG. 6.

Figure 7:
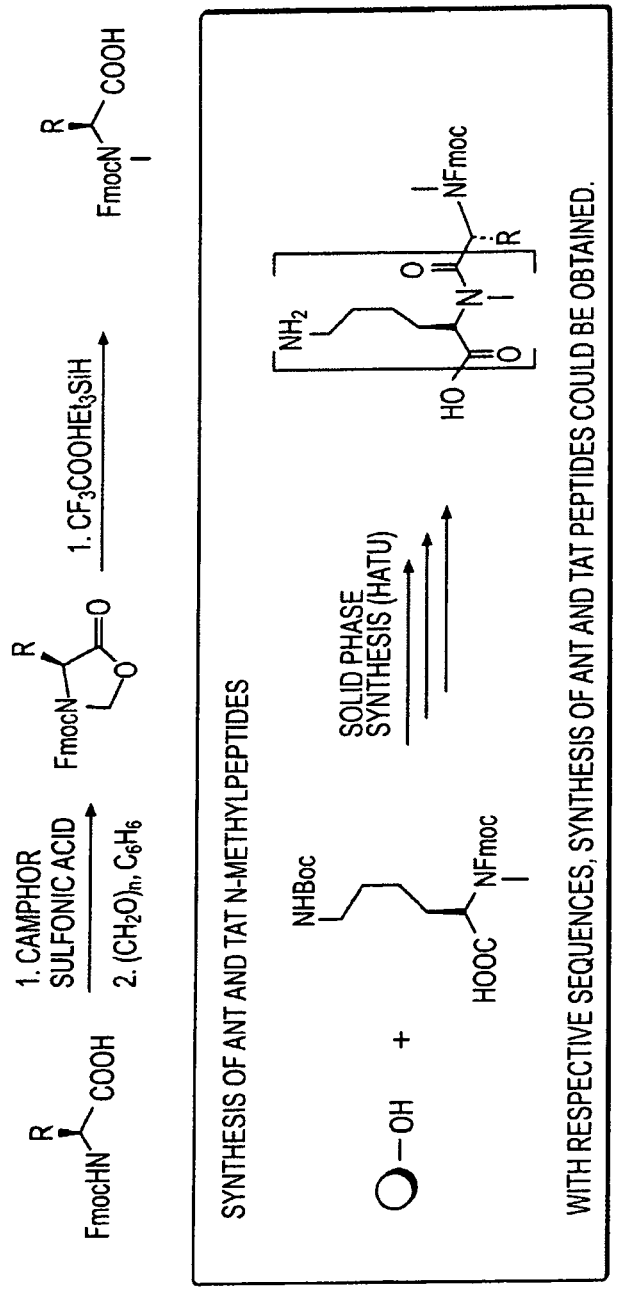
FIG. 7 is a general reaction scheme for the synthesis of N-methyl amino acids and peptides.

In one embodiment of the invention, a peptide or peptidomimetic (e.g., a peptide or peptidomimetic tethered to an ligand-conjugated monomer) can be an N-methyl peptide. N-methyl peptides are composed of N-methyl amino acids, which provide an additional methyl group in the peptide backbone, thereby potentially providing additional means of resistance to proteolytic cleavage. N-methyl peptides can by synthesized by methods known in the art (see, for example, Lindgren et al., Trends Pharmacol. Sci. 21:99, 2000; *Cell Penetrating Peptides: Processes and Applications*, Langel, ed., CRC Press, Boca Raton, Fla., 2002; Fische et al., Bioconjugate. Chem. 12: 825, 2001; Wander et al., J. Am. Chem. Soc., 124:13382, 2002). For example, an Ant or Tat peptide can be an N-methyl peptide. An exemplary synthesis is shown in FIG. 7.

In one embodiment of the invention, a peptide or peptidomimetic (e.g., a peptide or peptidomimetic tethered to a ligand-conjugated monomer) can be a β-peptide. β-peptides form stable secondary structures such as helices, pleated sheets, turns and hairpins in solutions. Their cyclic derivatives can fold into nanotubes in the solid state. β-peptides are resistant to degradation by proteolytic enzymes. β-peptides can be synthesized by methods known in the art. For example, an Ant or Tat peptide can be a β-peptide. An exemplary synthesis is shown in FIG. 8.

Figure 9:
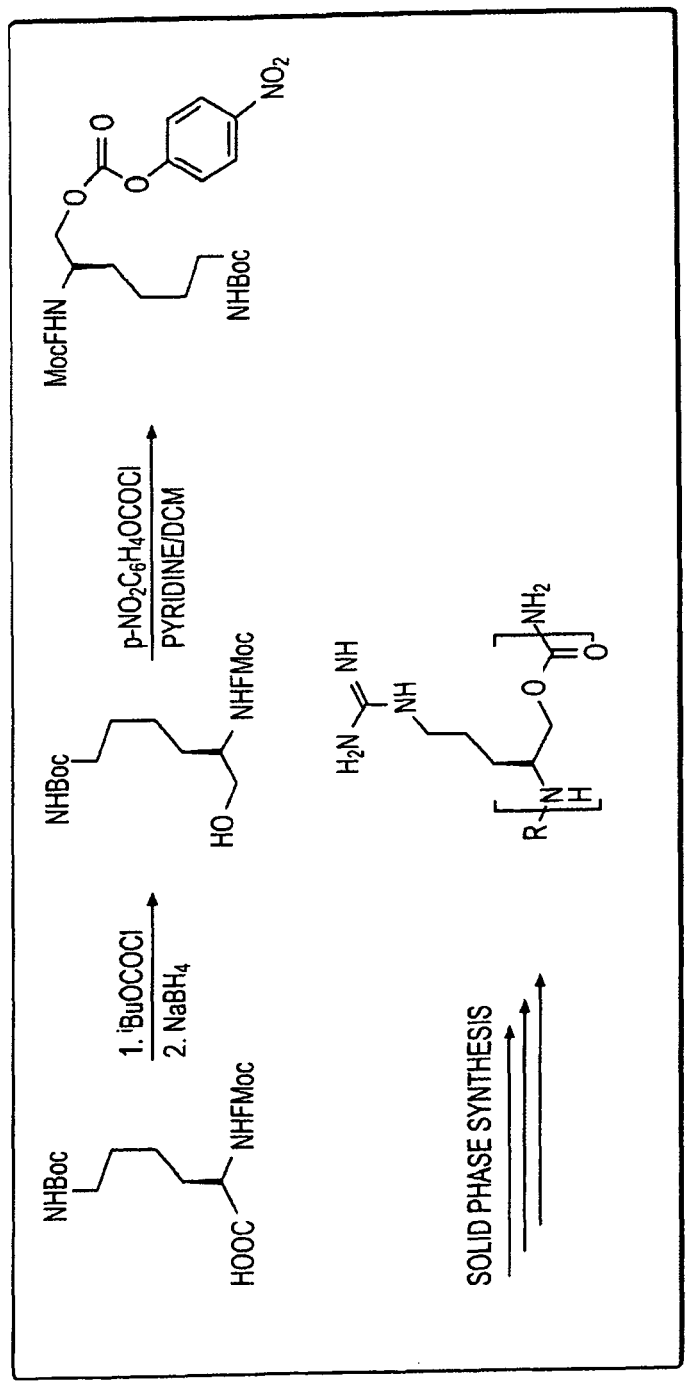
FIG. 9 is a general reaction scheme for the synthesis of Ant and Tat oligocarbamates.

In one embodiment of the invention, a peptide or peptidomimetic (e.g., a peptide or peptidomimetic tethered to a ligand-conjugated monomer) can be a oligocarbamate. Oligocarbamate peptides are internalized into a cell by a transport pathway facilitated by carbamate transporters. For example, an Ant or Tat peptide can be an oligocarbamate. An exemplary synthesis is shown in FIG. 9.

Figure 10:
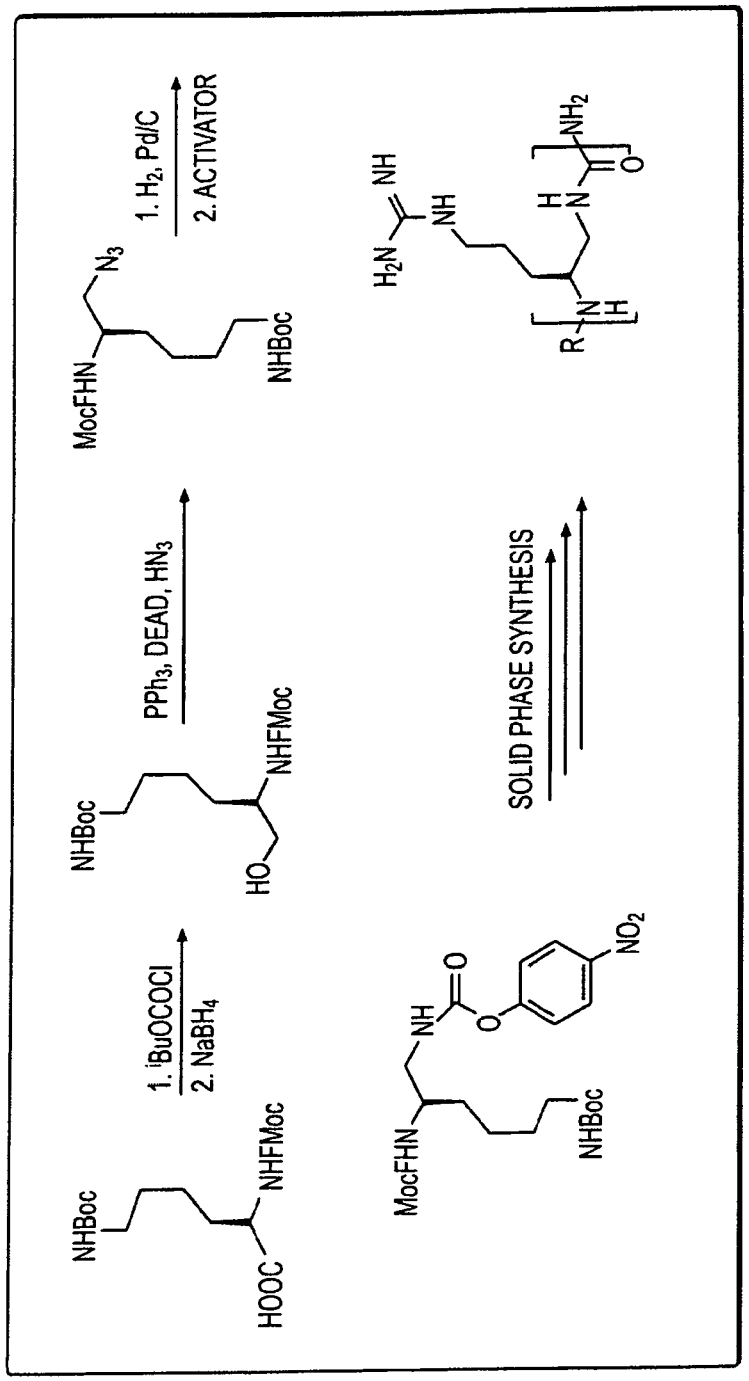
FIG. 10 is a general reaction scheme for the synthesis of Ant and Tat oligoureas.

In one embodiment of the invention, a peptide or peptidomimetic (e.g., a peptide or peptidomimetic tethered to a ligand-conjugated monomer) can be an oligourea conjugate (or an oligothiourea conjugate), in which the amide bond of a peptidomimetic is replaced with a urea moiety. Replacement of the amide bond provides increased resistance to degradation by proteolytic enzymes, e.g., proteolytic enzymes in the gastrointestinal tract. In one embodiment, an oligourea conjugate is tethered to an iRNA agent for use in oral delivery. The backbone in each repeating unit of an oligourea peptidomimetic can be extended by one carbon atom in comparison with the natural amino acid. The single carbon atom extension can increase peptide stability and lipophilicity, for example. An oligourea peptide can therefore be advantageous when an iRNA agent is directed for passage through a bacterial cell wall, or when an iRNA agent must traverse the blood-brain barrier, such as for the treatment of a neurological disorder. In one embodiment, a hydrogen bonding unit is conjugated to the oligourea peptide, such as to create an increased affinity with a receptor. For example, an Ant or Tat peptide can be an oligourea conjugate (or an oligothiourea conjugate). An exemplary synthesis is shown in FIG. 10.

The siRNA peptide conjugates of the invention can be affiliated with, e.g., tethered to, ligand-conjugated monomers occurring at various positions on an iRNA agent. For example, a peptide can be terminally conjugated, on either the sense or the antisense strand, or a peptide can be bisconjugated (one peptide tethered to each end, one conjugated to the sense strand, and one conjugated to the antisense strand). In another option, the peptide can be internally conjugated, such as in the loop of a short hairpin iRNA agent. In yet another option, the peptide can be affiliated with a complex, such as a peptide-carrier complex.

A peptide-carrier complex consists of at least a carrier molecule, which can encapsulate one or more iRNA agents (such as for delivery to a biological system and/or a cell), and a peptide moiety tethered to the outside of the carrier molecule, such as for targeting the carrier complex to a particular tissue or cell type. A carrier complex can carry additional targeting molecules on the exterior of the complex, or fusogenic agents to aid in cell delivery. The one or more iRNA agents encapsulated within the carrier can be conjugated to lipophilic molecules, which can aid in the delivery of the agents to the interior of the carrier.

A carrier molecule or structure can be, for example, a micelle, a liposome (e.g., a cationic liposome), a nanoparticle, a microsphere, or a biodegradable polymer. A peptide moiety can be tethered to the carrier molecule by a variety of linkages, such as a disulfide linkage, an acid labile linkage, a peptide-based linkage, an oxyamino linkage or a hydrazine linkage. For example, a peptide-based linkage can be a GFLG peptide. Certain linkages will have particular advantages, and the advantages (or disadvantages) can be considered depending on the tissue target or intended use. For example, peptide based linkages are stable in the blood stream but are susceptible to enzymatic cleavage in the lysosomes. A schematic of preferred carriers is shown in FIG. 11.

The protected monomer compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Other synthetic chemistry transformations, protecting groups (e.g., for hydroxyl, amino, etc. present on the bases) and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The protected monomer compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds described herein can also contain linkages (e.g., carbon-carbon bonds, carbon-nitrogen bonds, e.g., amides) or substituents that can restrict bond rotation, e.g. restriction resulting from the presence of a ring or double bond. Accordingly, all cis/trans, E/Z isomers, and rotational isomers (rotamers) are expressly included herein. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

Representative ligand-conjugated monomers and typical syntheses for preparing ligand-conjugated monomers and related compounds described herein are provided below. As discussed elsewhere, protecting groups for ligand-conjugated monomer hydroxyl groups, e.g., OFG$^1$, include but are not limited to the dimethoxytrityl group (DMT). For example, it can be desirable in some embodiments to use silicon-based protecting groups as a protecting group for OFG$^1$. Silicon-based protecting groups can therefore be used in conjunction with or in place of the DMT group as necessary or desired. Thus, the ligand-conjugated monomers and syntheses delineated below, which feature the DMT protecting group as a protecting group for OFG$^1$, is not to be construed as limiting in any way to the invention.

Synthesis of Pyrroline Carrier

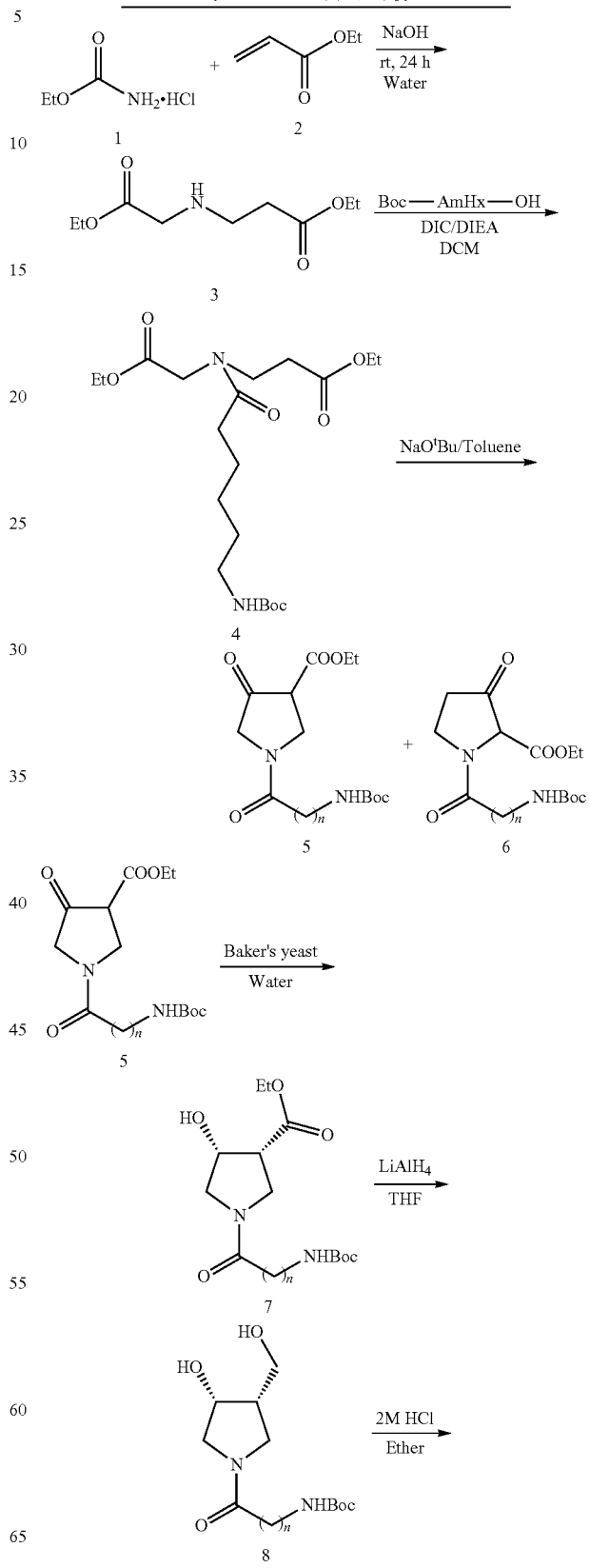

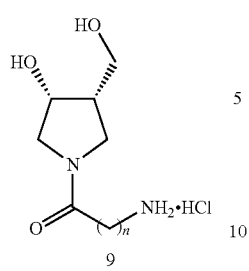
9
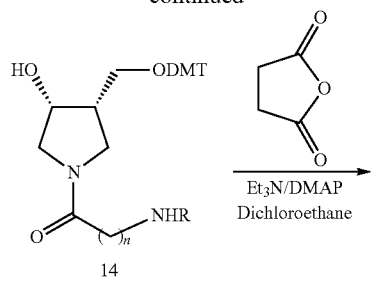
14
Scheme 2. Synthesis of cis-(-(2R, 3S)-pyrrolidine diol
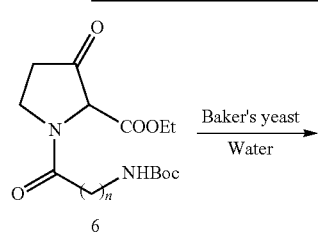
6
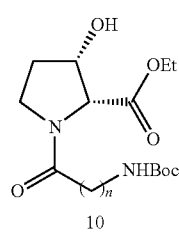
10
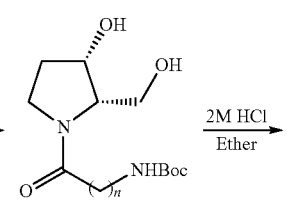
11
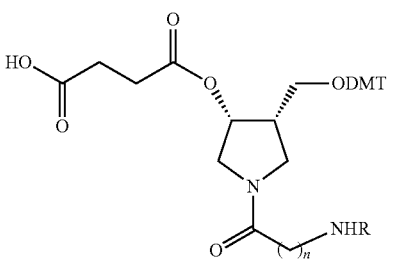
15
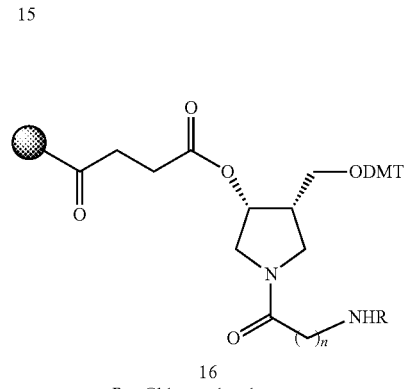
16
R = Chlosterol carbamate
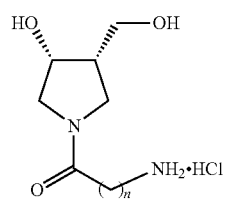
12
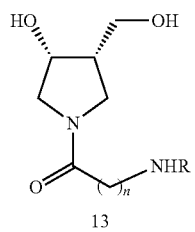
9
13
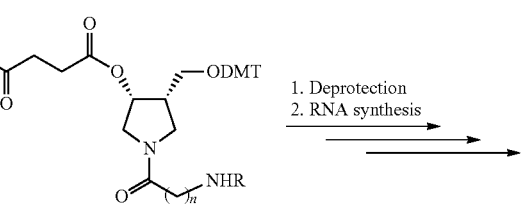
R = Chlosterol carbamate
or any lipophilic molecule
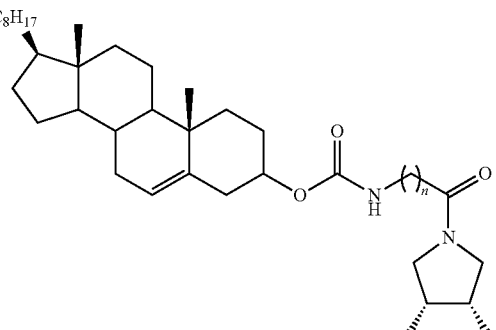
siRNA 51
-continued
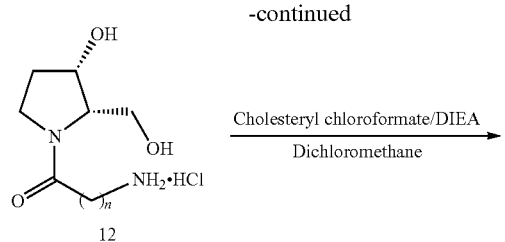
12
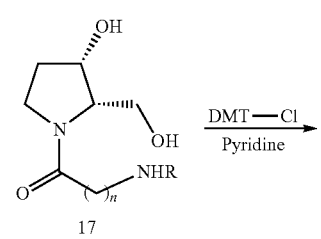
17
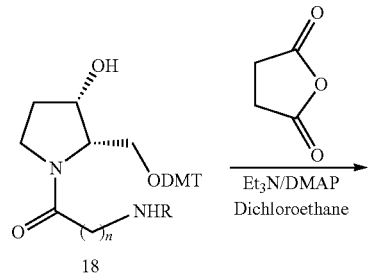
18
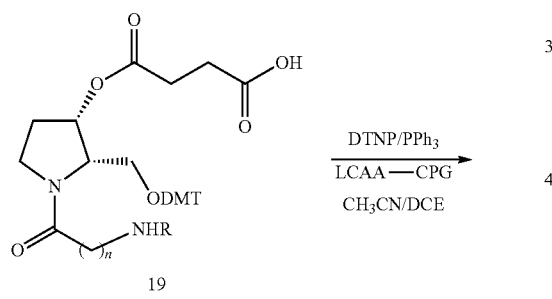
19
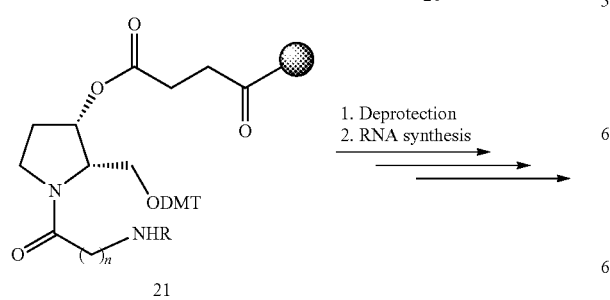
20
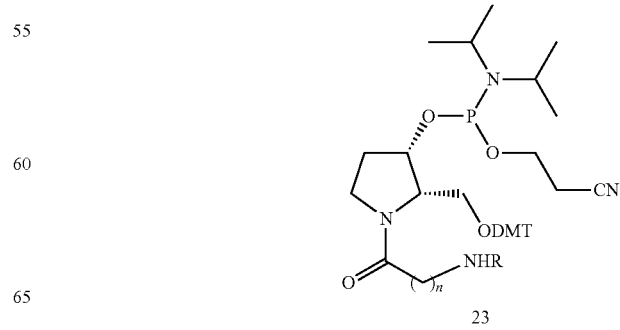
21
52
-continued
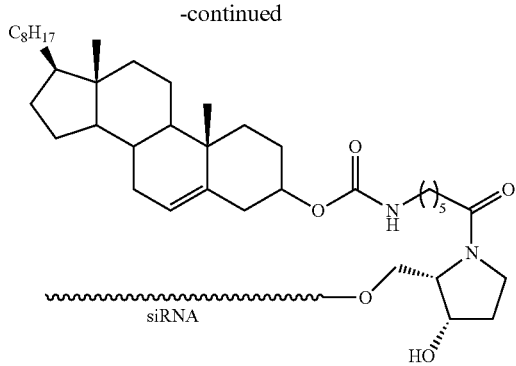
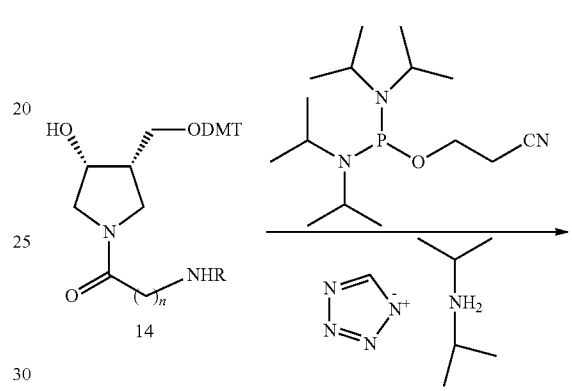
14
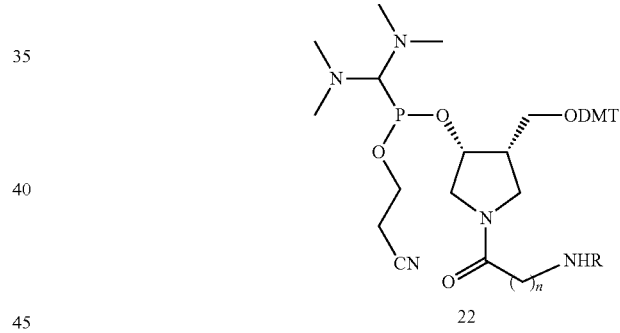
22
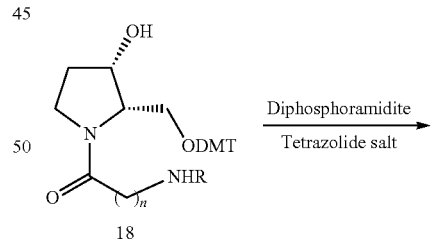
18
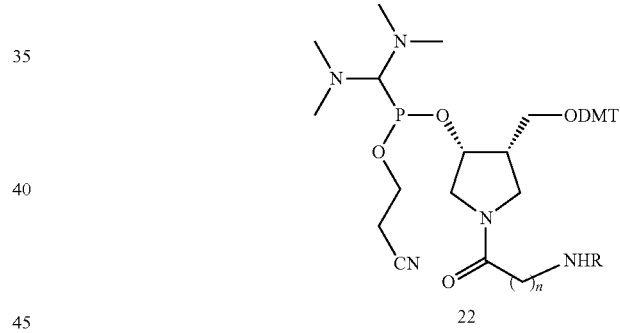
23

Synthesis of 5'-Labelled siRNA
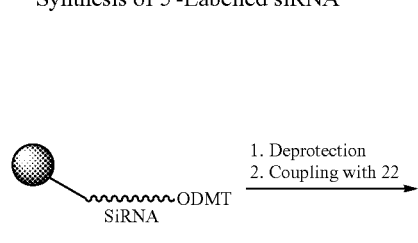
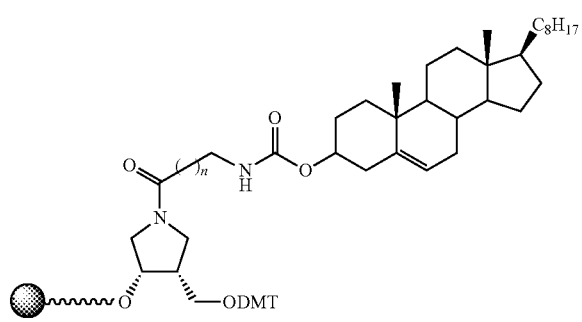
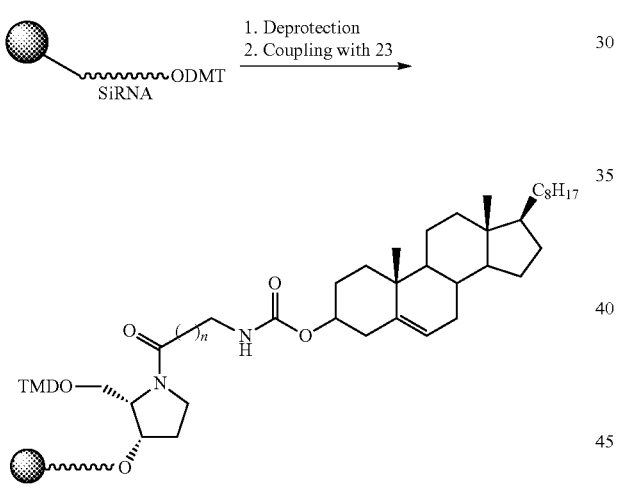
-continued
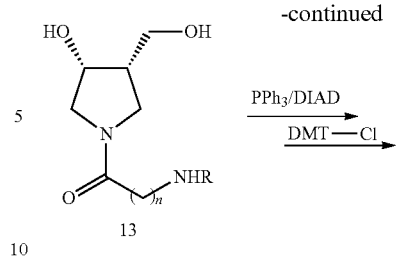
13
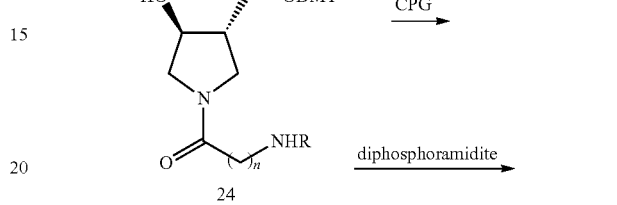
24
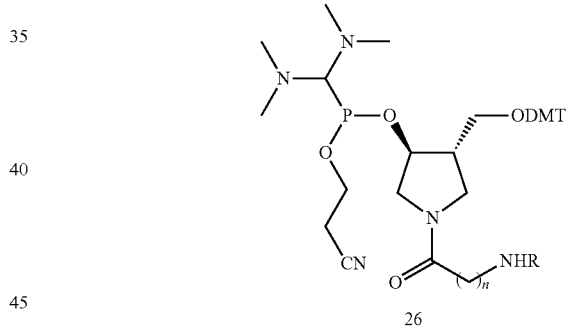
25 & 26 can be used for 3',5'-conjugation respectively.
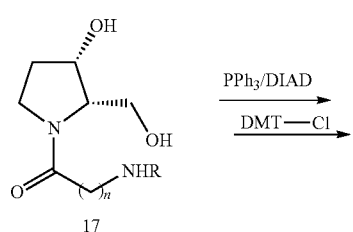
17

-continued
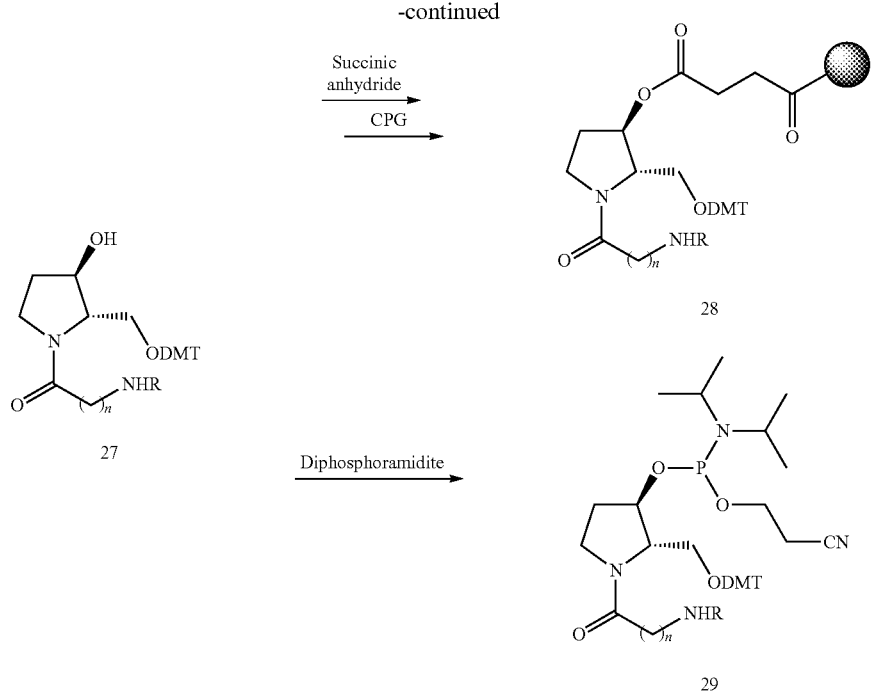
Synthesis of Pthalimido Derivative
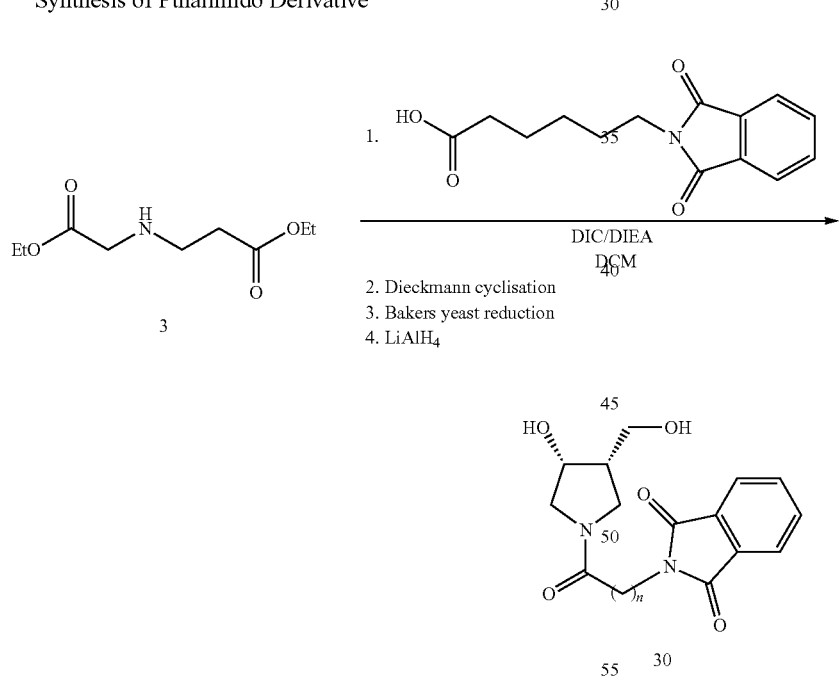
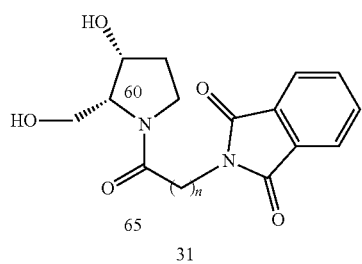

30 and 31 can be converted to similar derivatives as shown in schemes 2-4 for 3' and 5' conjugation of siRNA
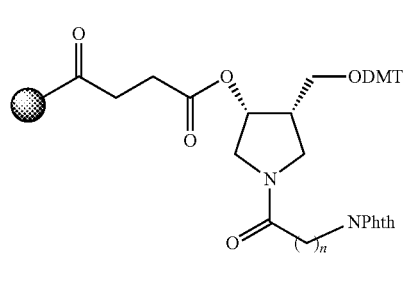
32
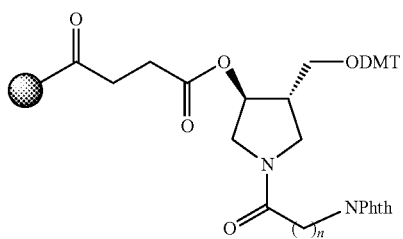
36
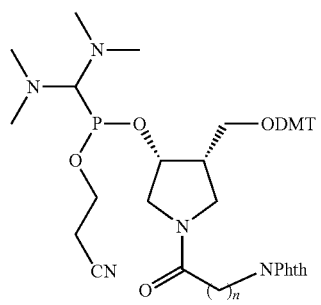
33
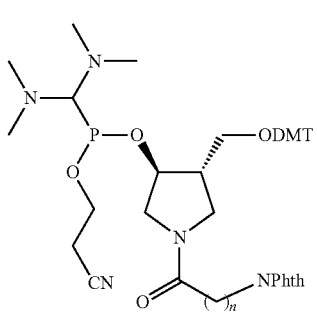
37
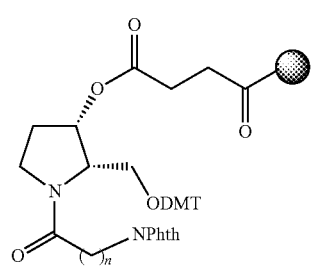
34
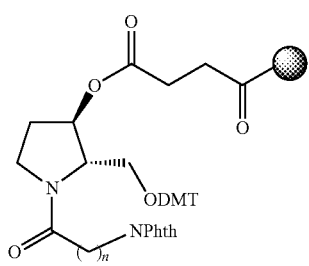
38
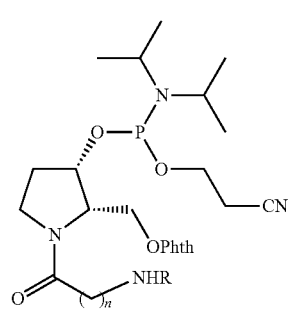
35

Synthesis of Thalimido Derivative
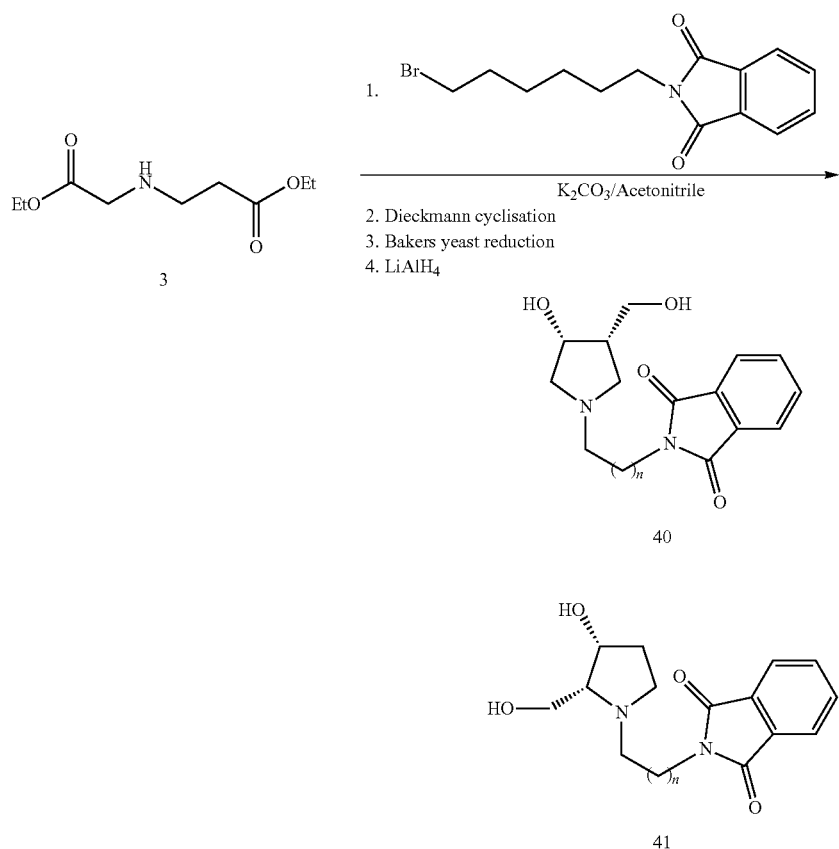
40 and 41 can be converted to similar derivatives as shown in schemes 2-4 for 3' and 5' conjugation of siRNA
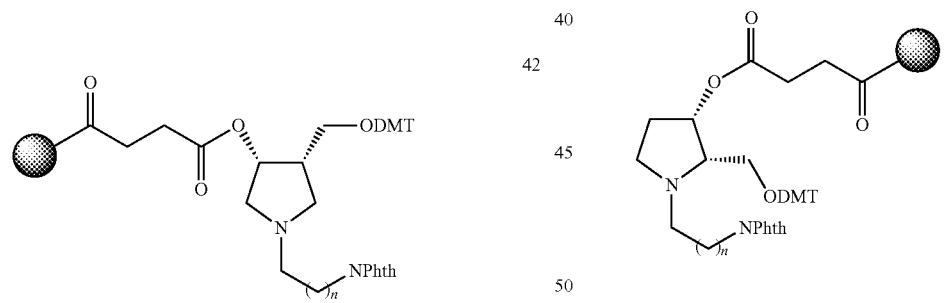
-continued
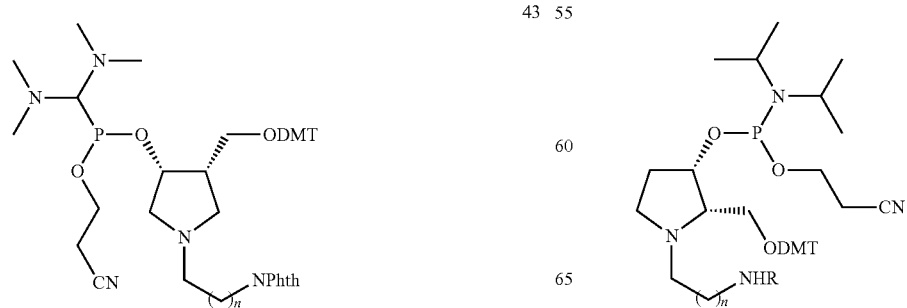

46
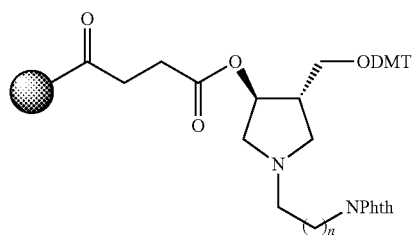
47
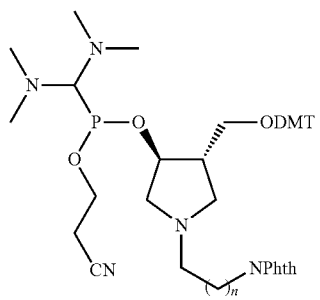
48
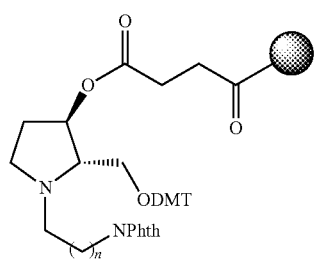
49
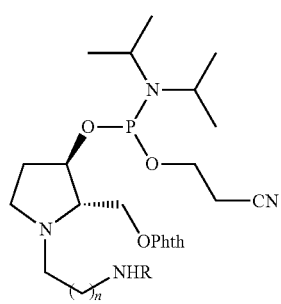
Synthesis of N-Alkyl Pyrroline Derivatives
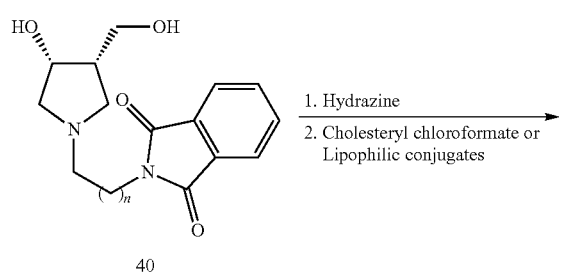
40
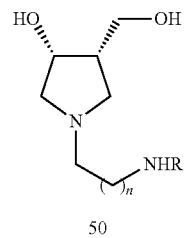
50
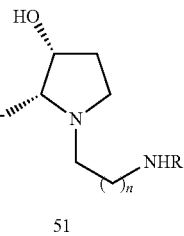
41
51
Intermediates 50 and 51 can be converted to analogs which could be conjugated with siRNA using similar reactions
52
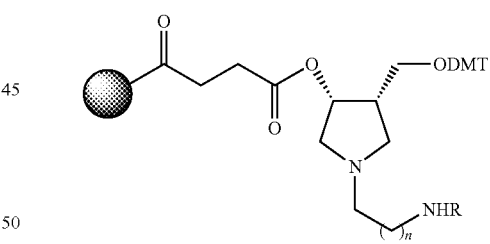
53
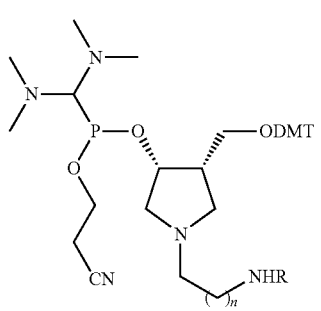

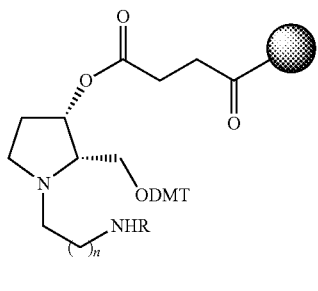
54
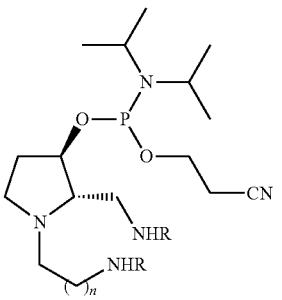
59
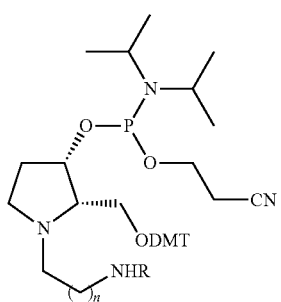
55
Piperidine Series Ligands:
Similar to pyrroline series piperidine series can be synthesised
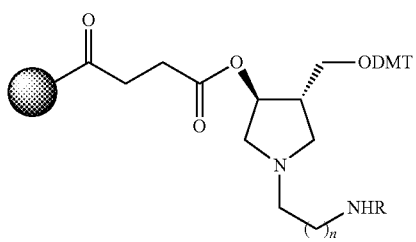
56
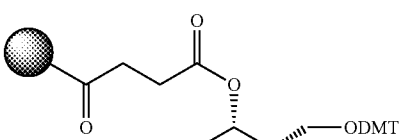
60
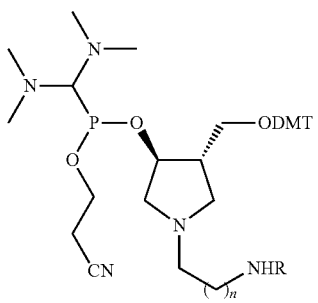
57
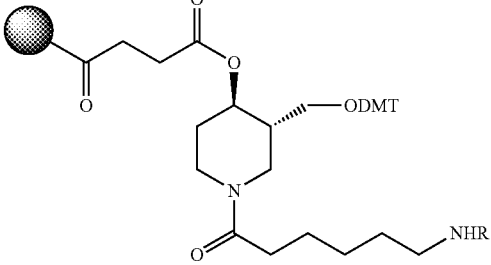
61
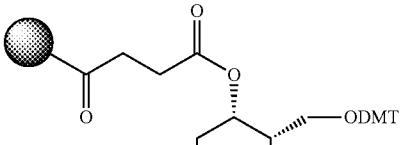
62
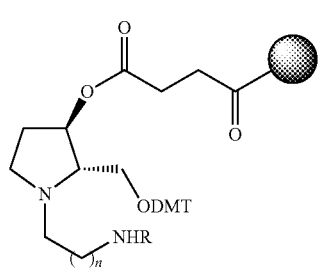
58
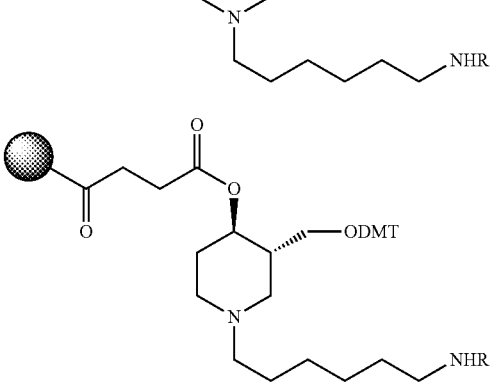
63

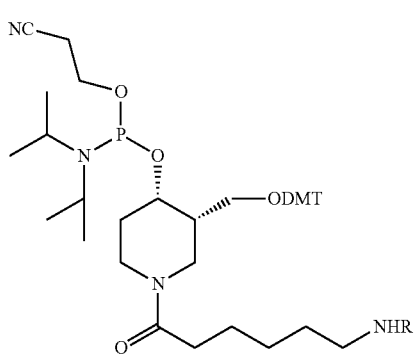
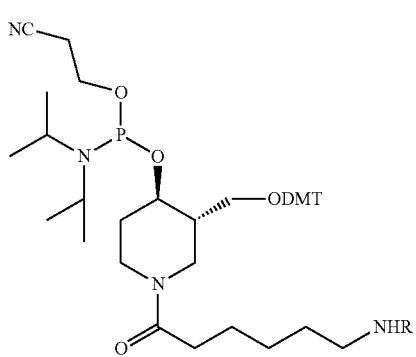
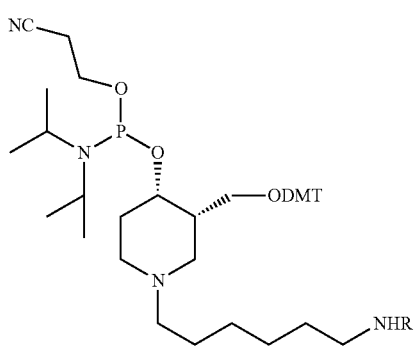
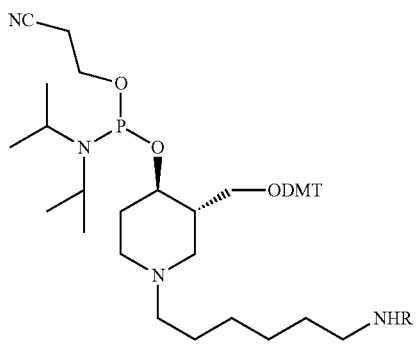
Piperidine Series Ligands:
Similar to pyrroline series piperidine series can be synthesised
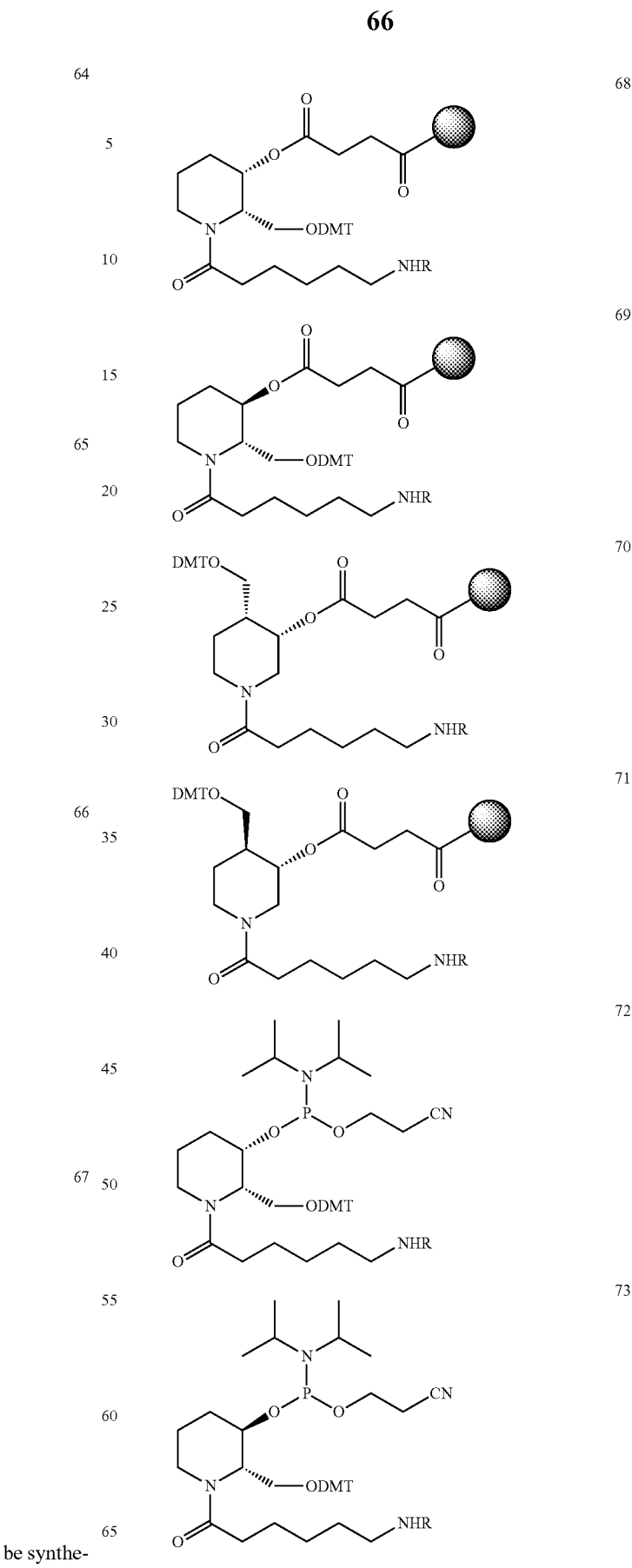

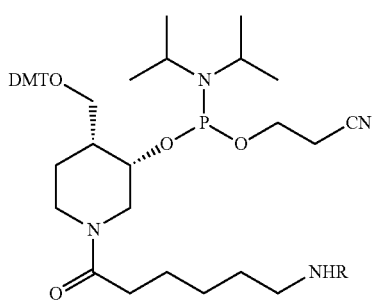
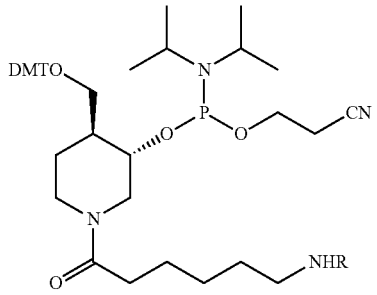
Hydroxy Proline Series Linkers:
From commercially available cis-3-hydroxy proline and (s)-pyrrolidone carboxylate
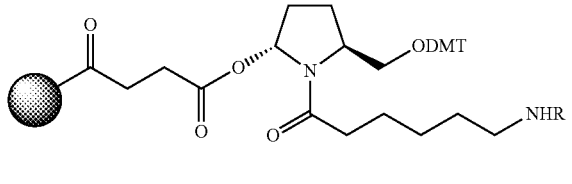
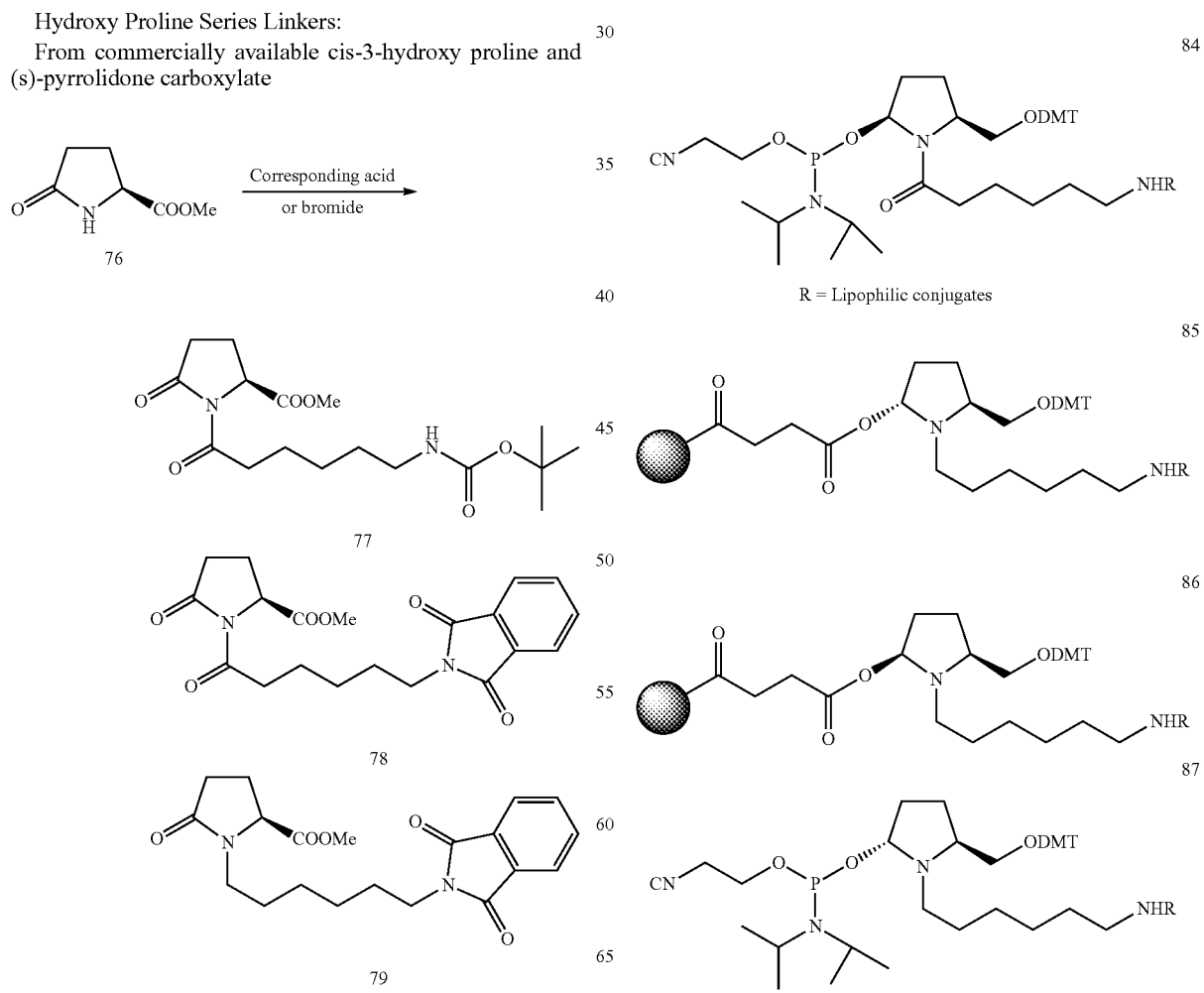
R = Lipophilic conjugates

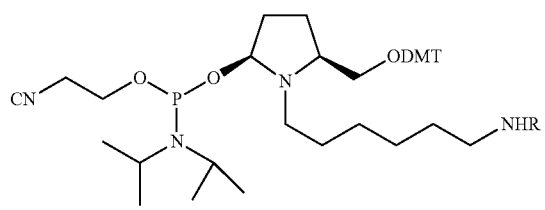
R = Lipophilic conjugates
Phthalimide Derivative to Stabilise siRNA
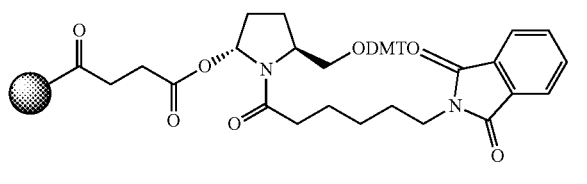
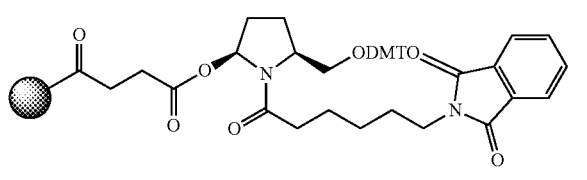
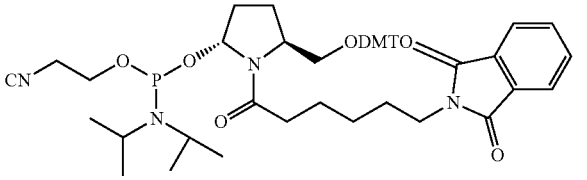
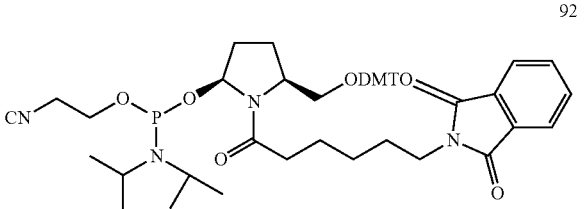
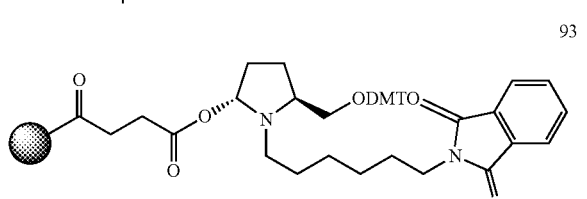
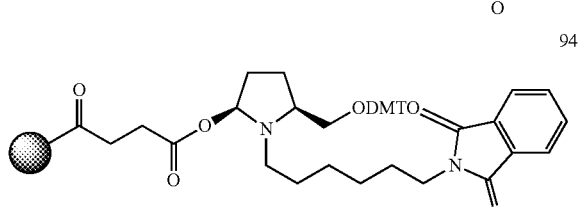
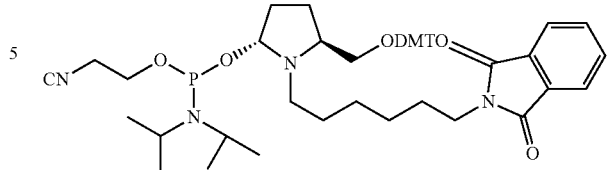
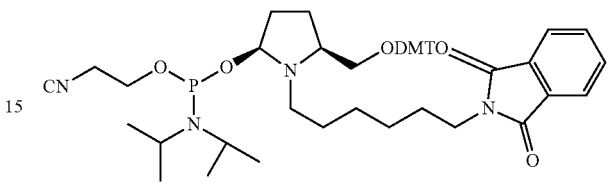
4-Hydroxy Proline Derivatives
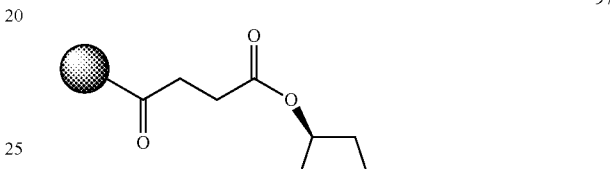
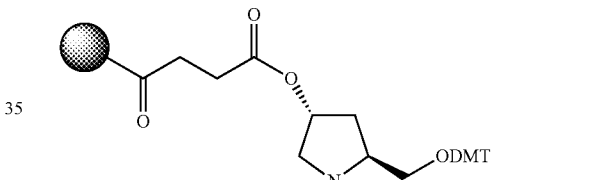
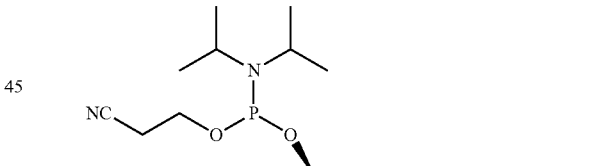
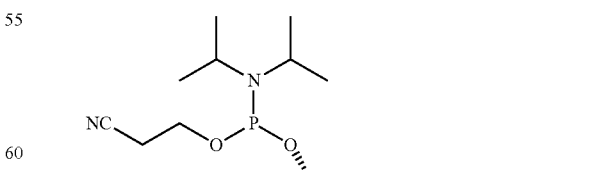
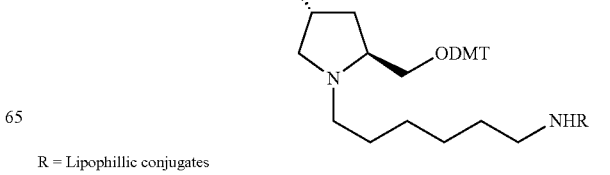
R = Lipophillic conjugates

Phthalimido Derivatives
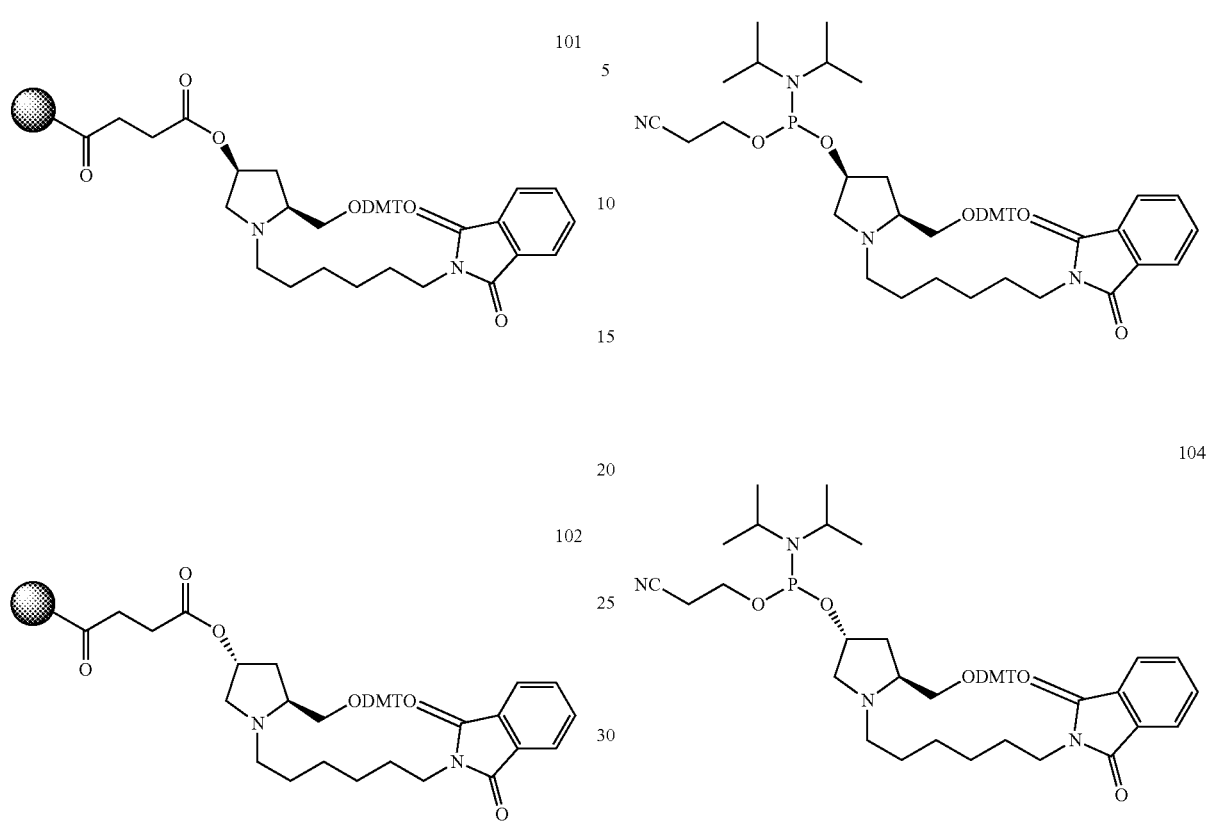
Synthesis of 6-Membered Linker
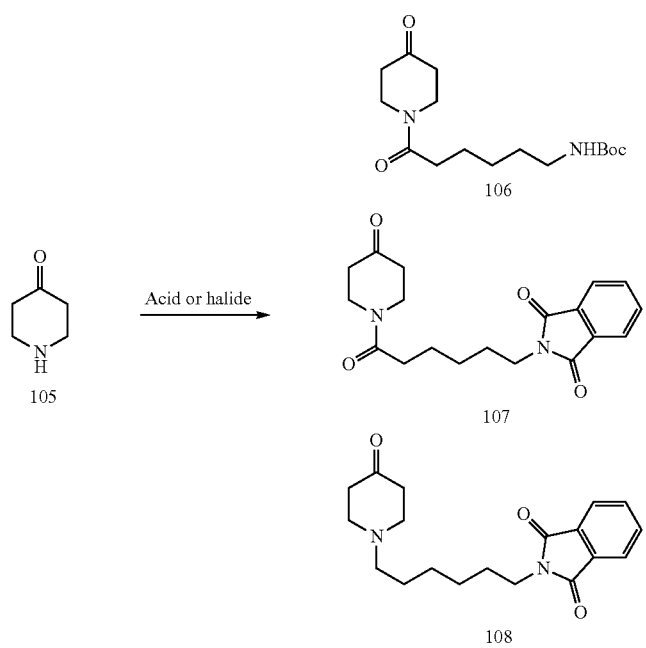

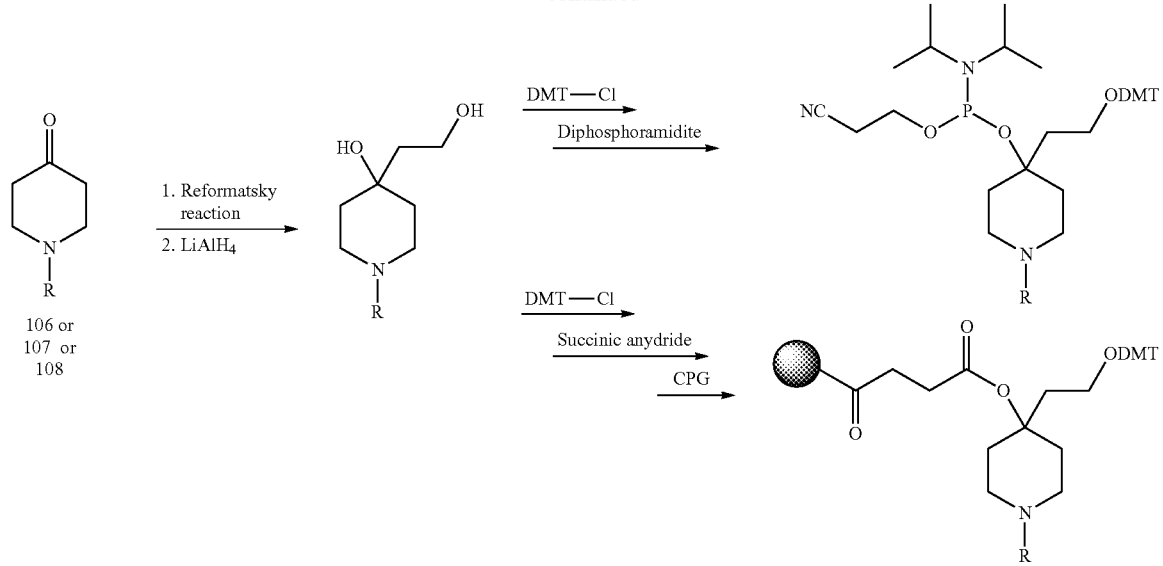
Simliar reaction can be carried out with 2-piperidone and 3-piperidone
Linkers from 4-Piperidone
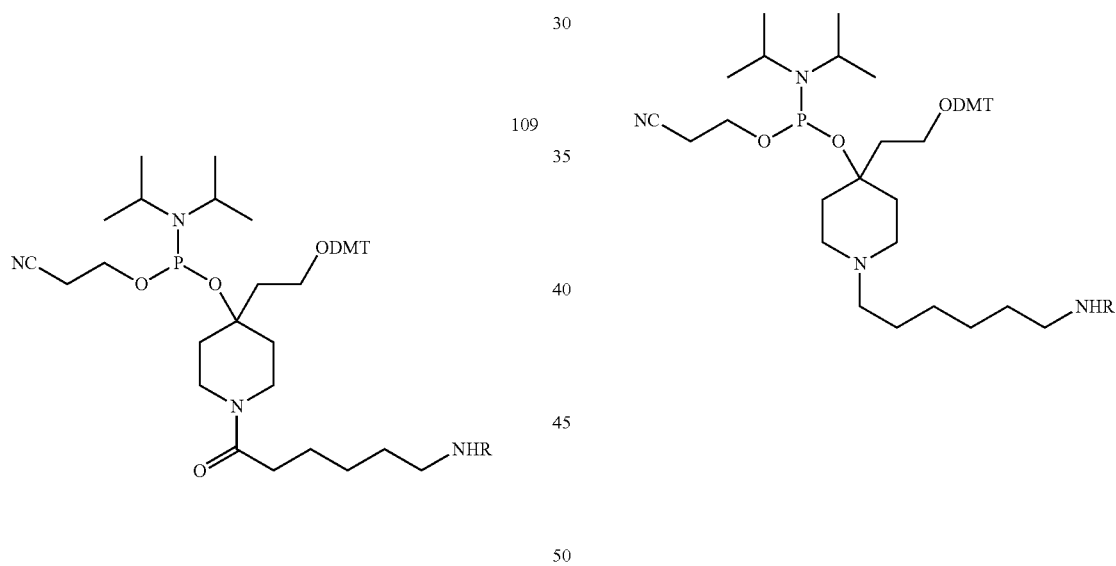
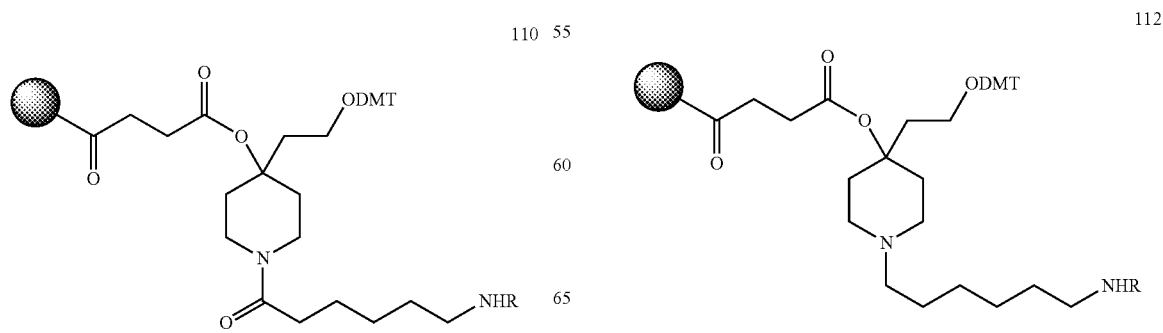

76
Linkers from 3-Piperidone
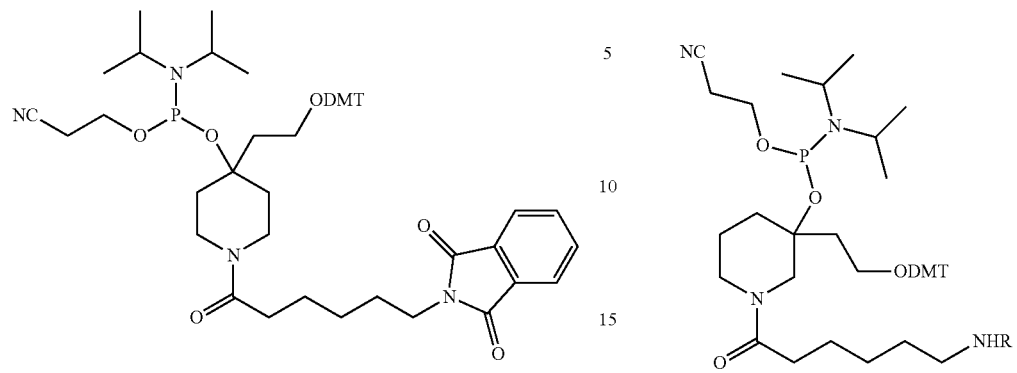
113
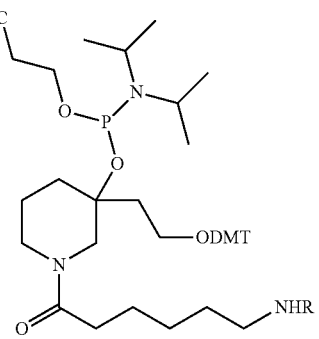
117
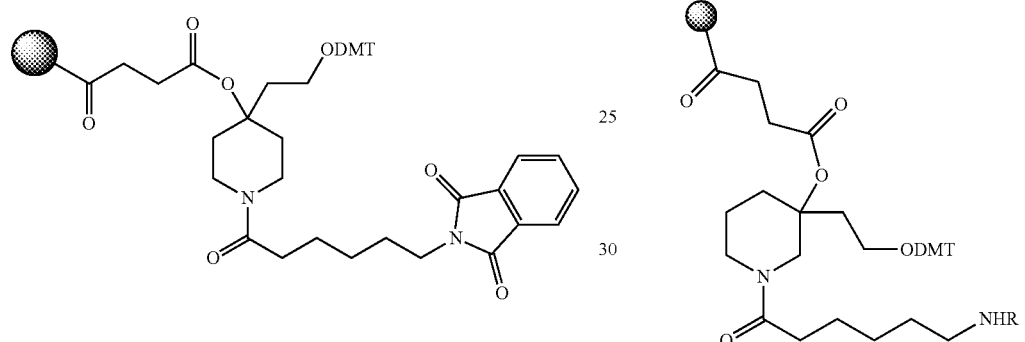
114
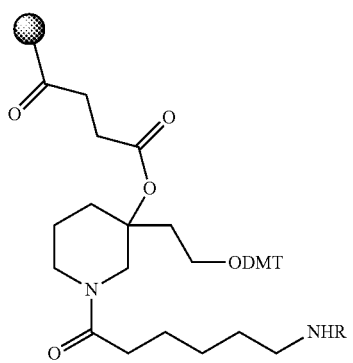
118
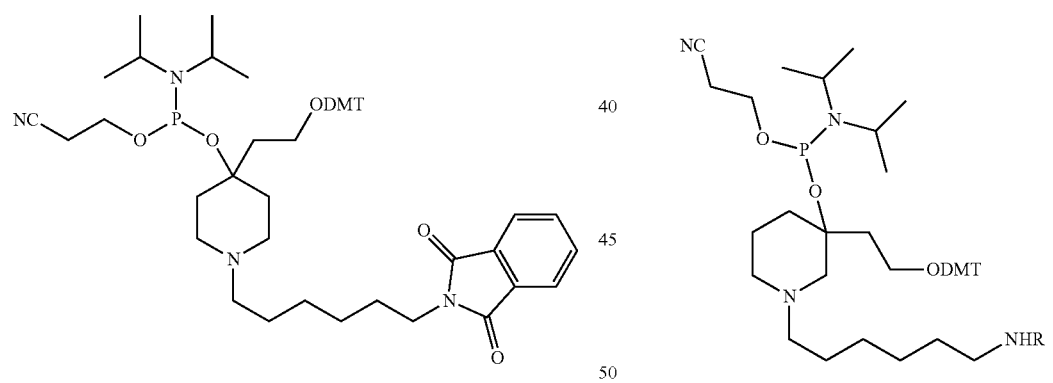
115
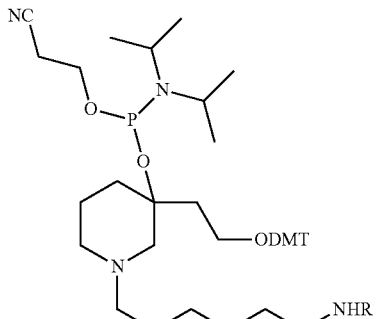
119
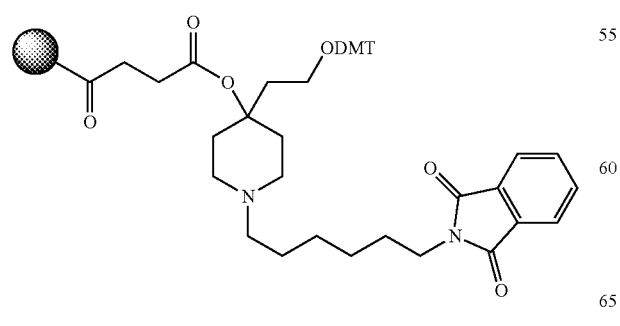
116
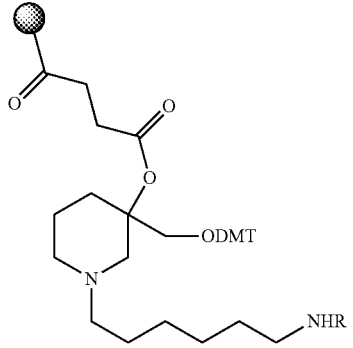
120

77
-continued
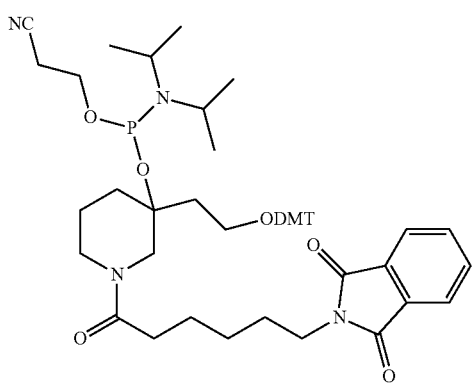
121
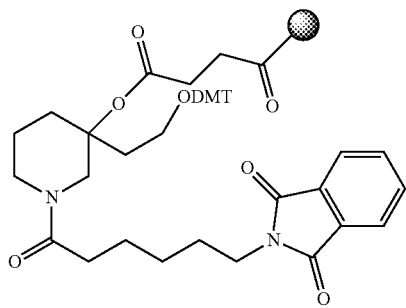
122
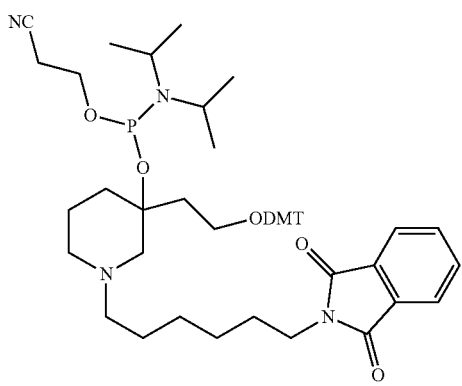
123
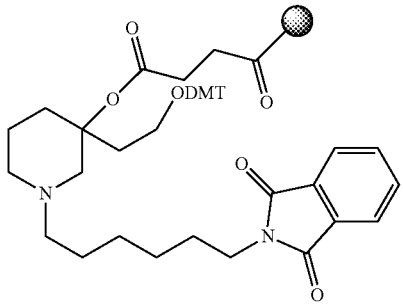
124
78
Linkers from 2-Piperidone
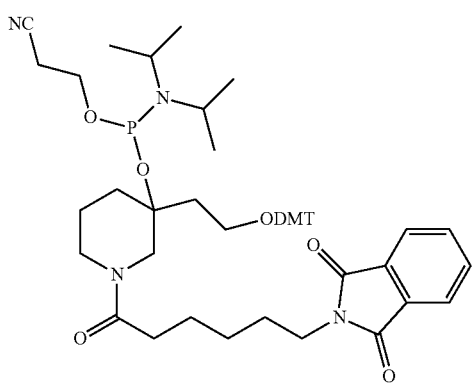
125
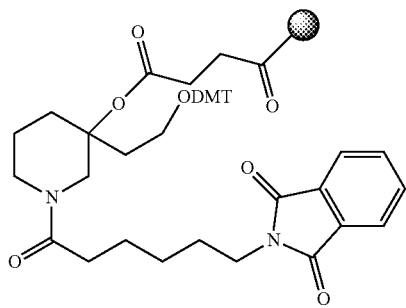
126
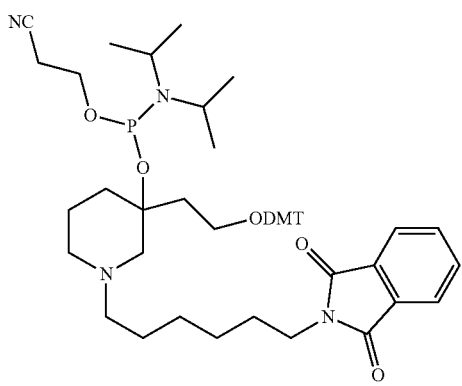
127
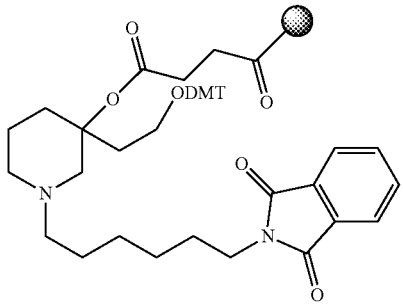
128
129
130

79
-continued
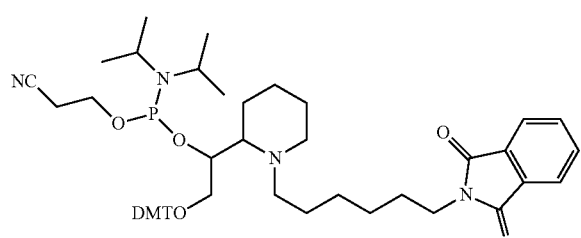
131
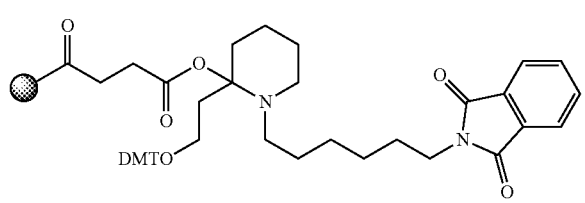
132
Conjugation Through Decalin System
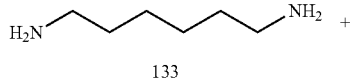
133
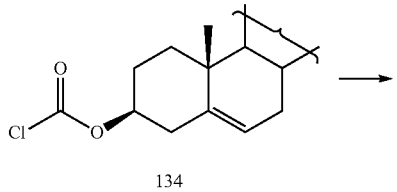
134
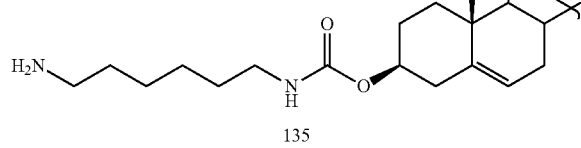
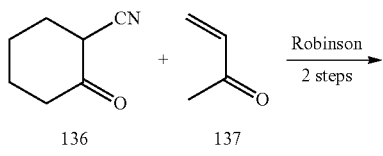
136  137
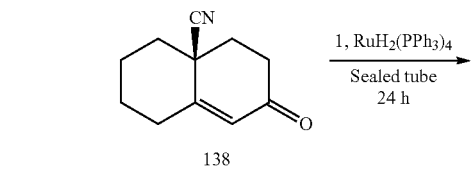
138
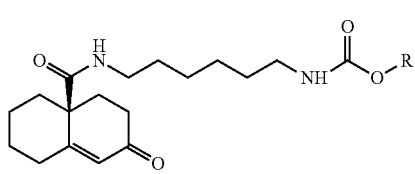
R = Cholesterol
139
80
-continued
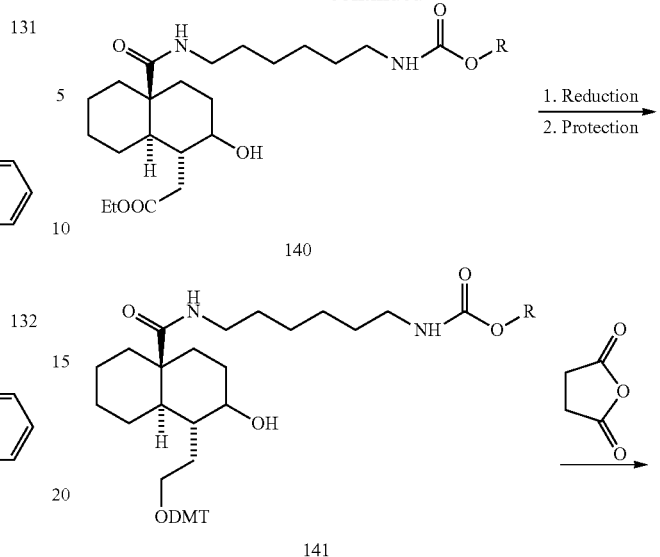
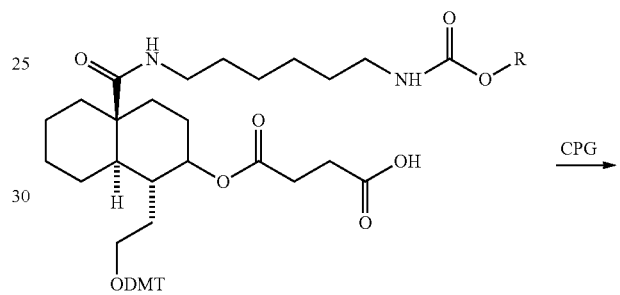
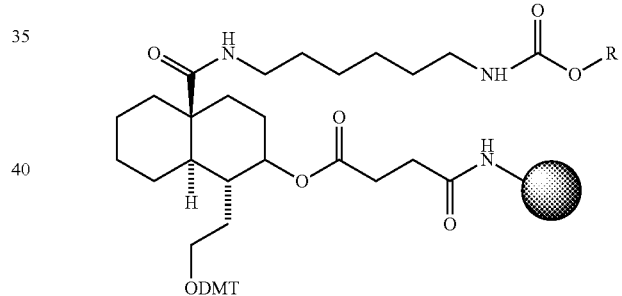
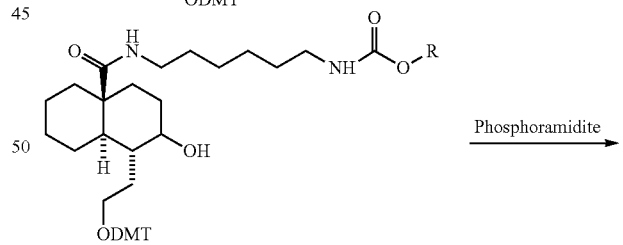
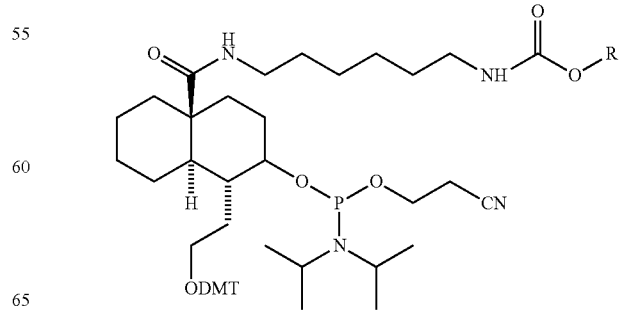

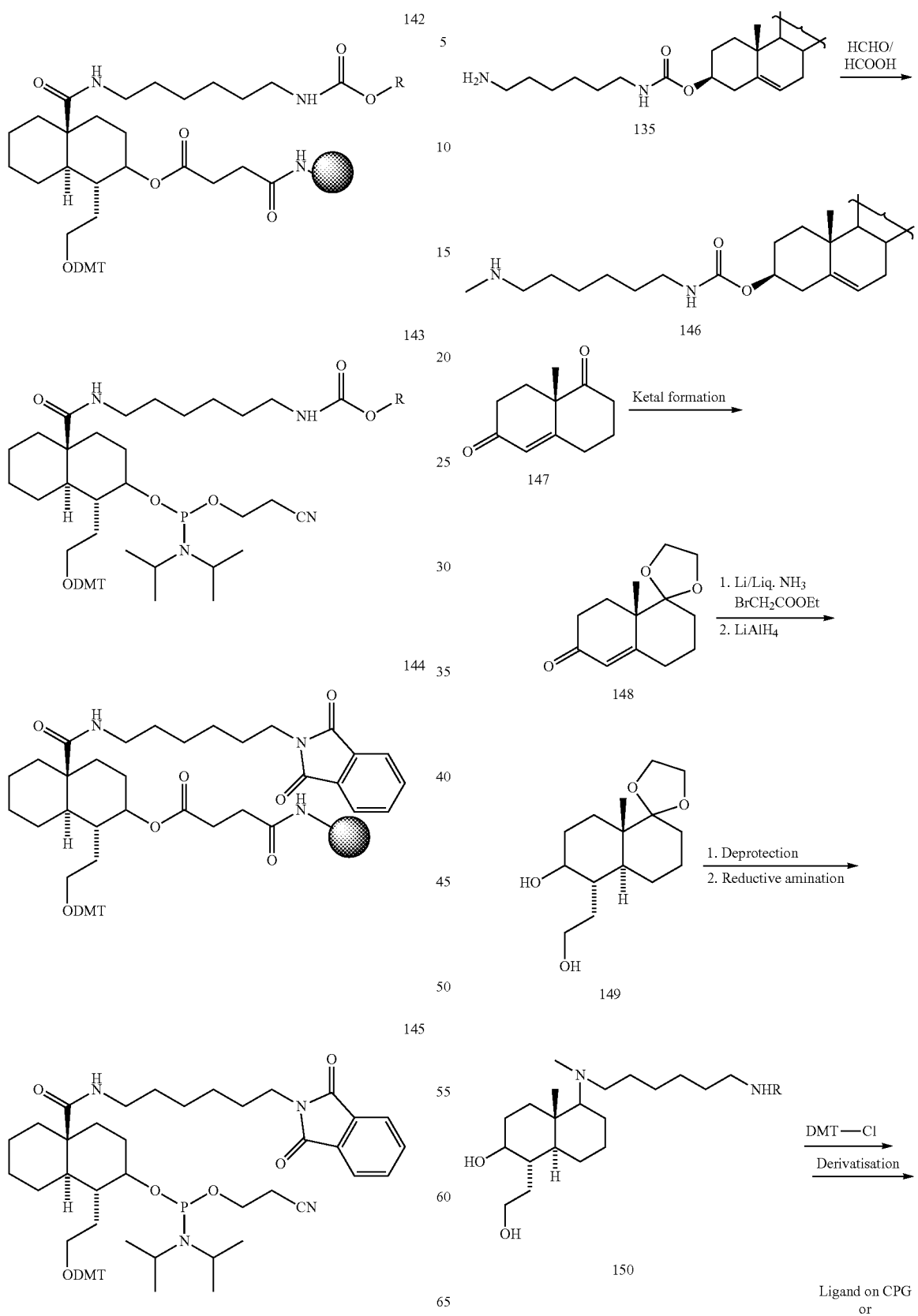

Conjugates from Wieland-Miescher Ketone
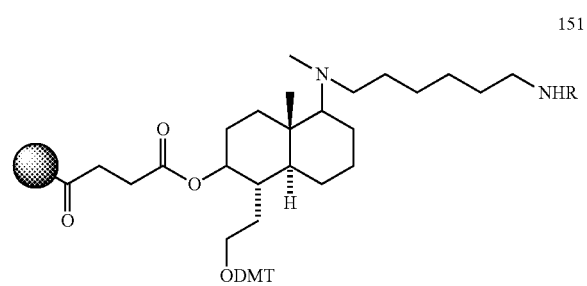
151
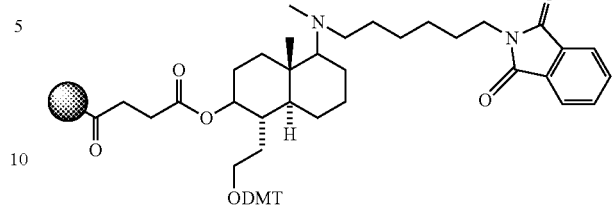
153
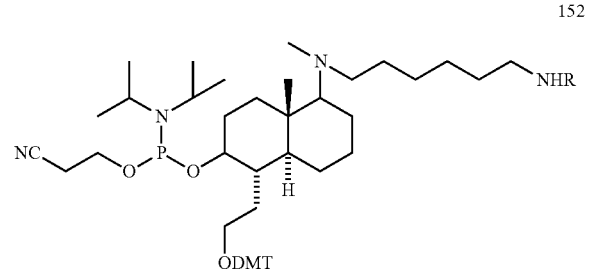
152
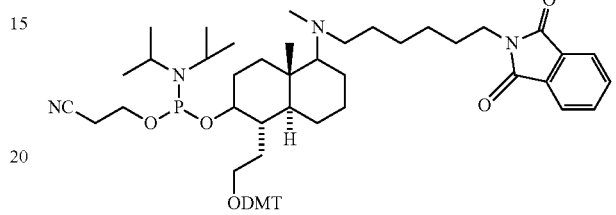
154
Synthesis of Pyrroline Linker:
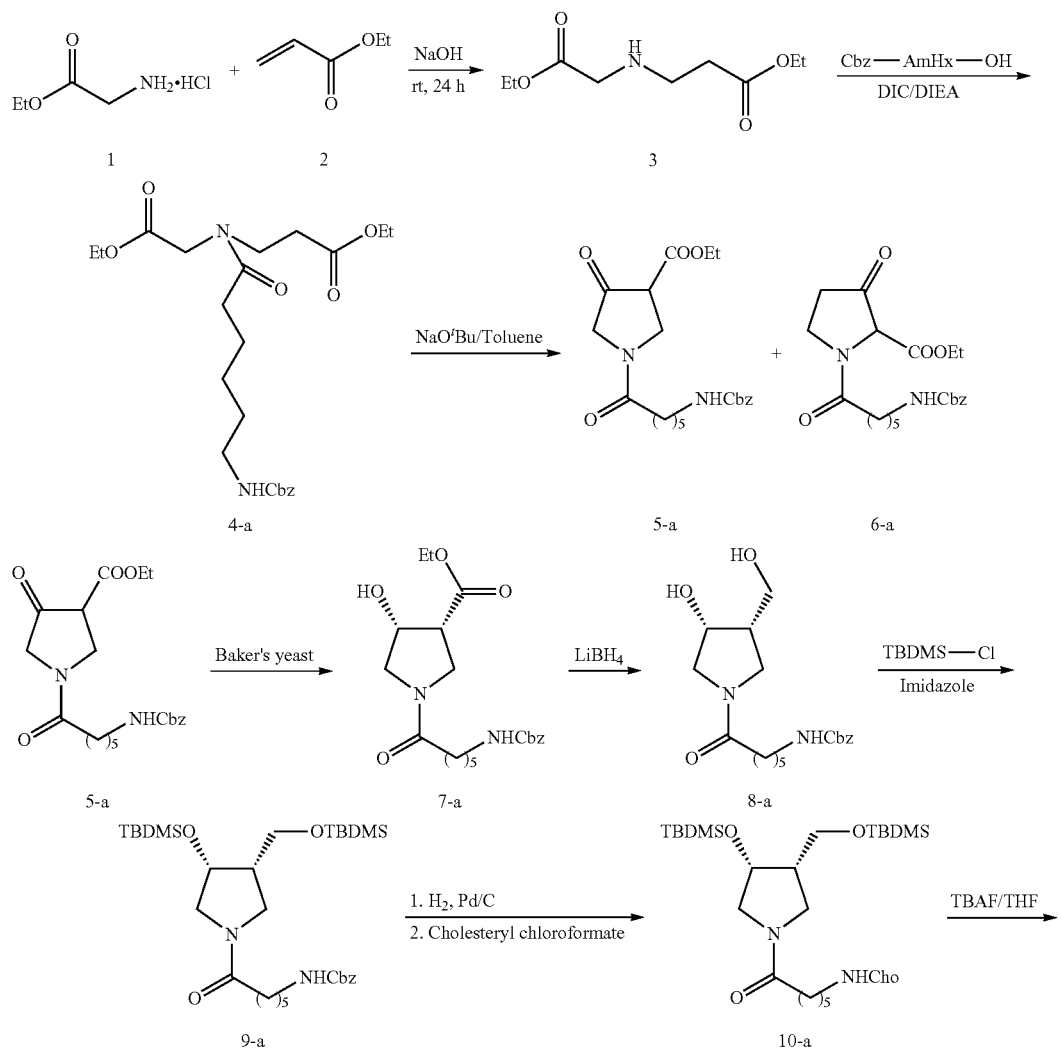

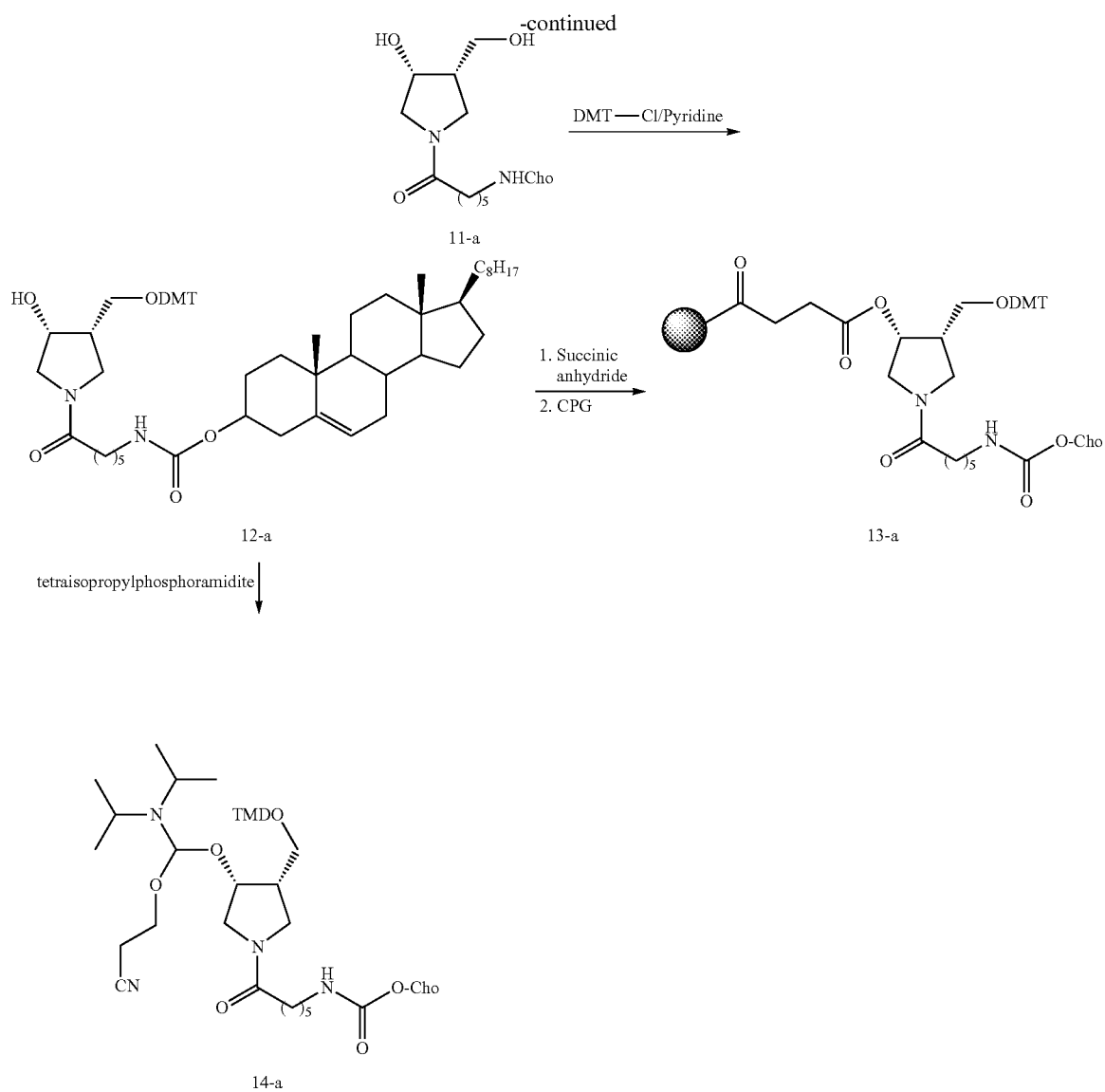
Solid Phase Synthesis and Post-Synthesis Conjugation:
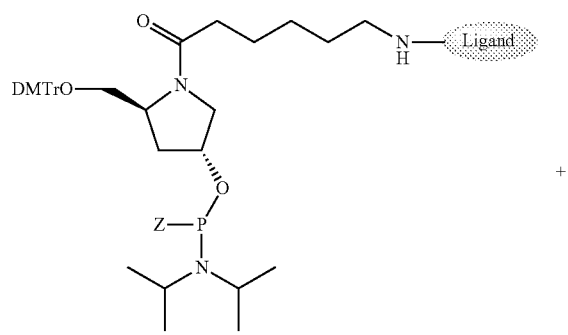

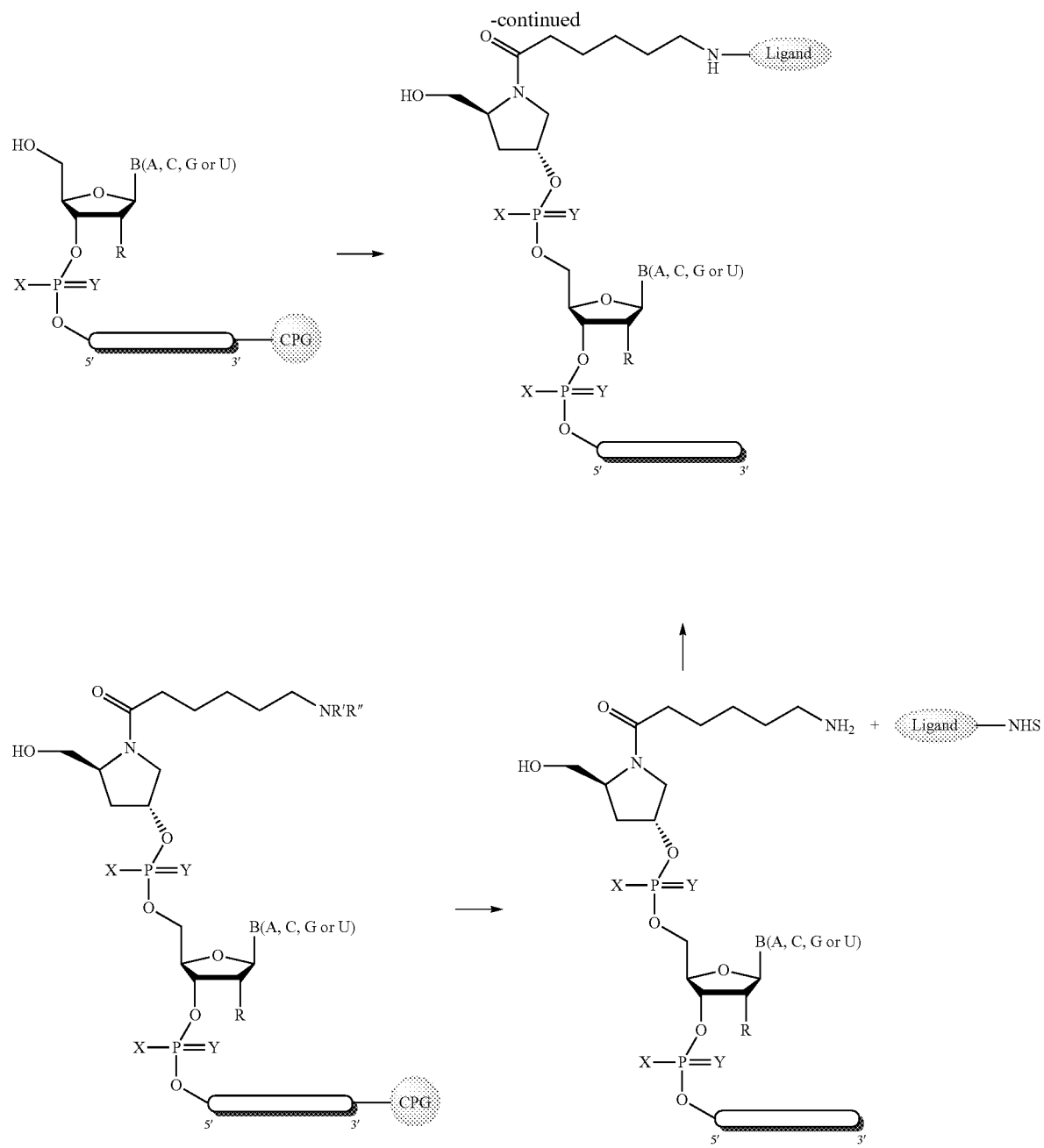
Exemplary Ligand Conjugated Monomers
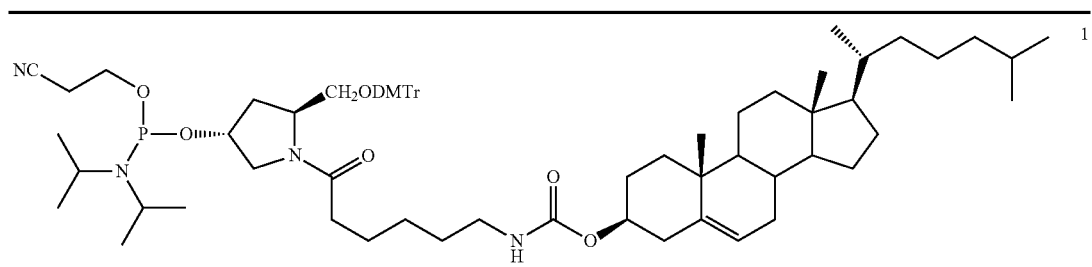

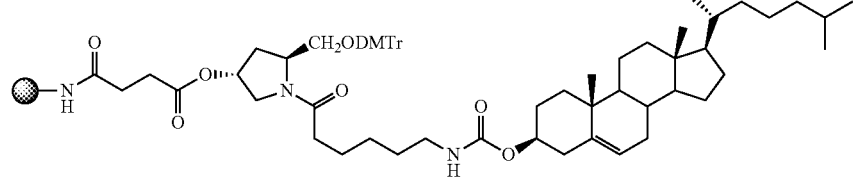
9
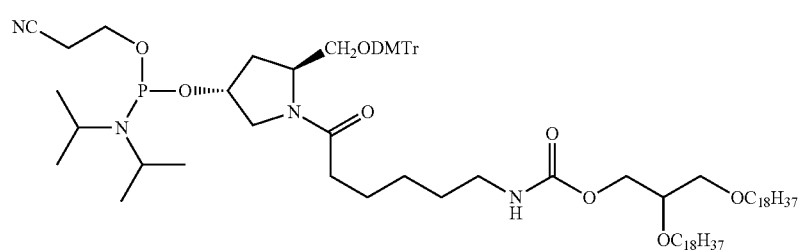
13
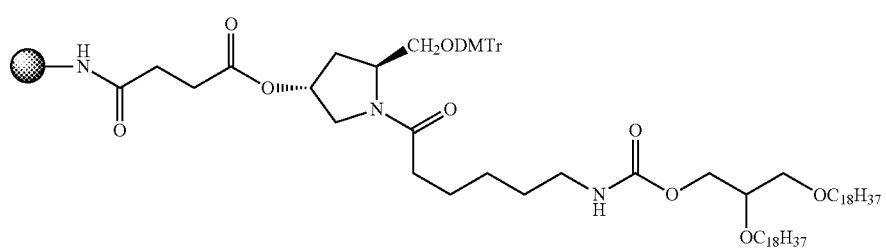
15
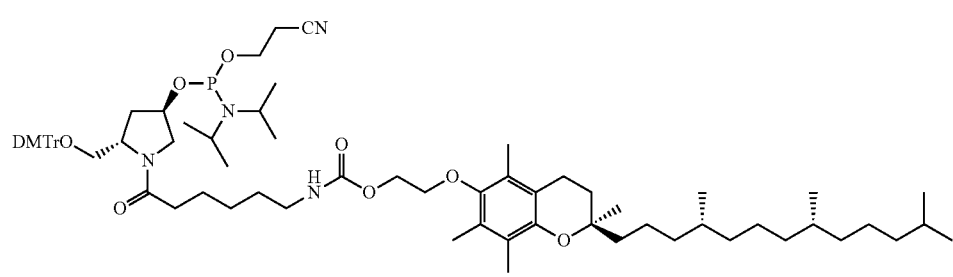
20
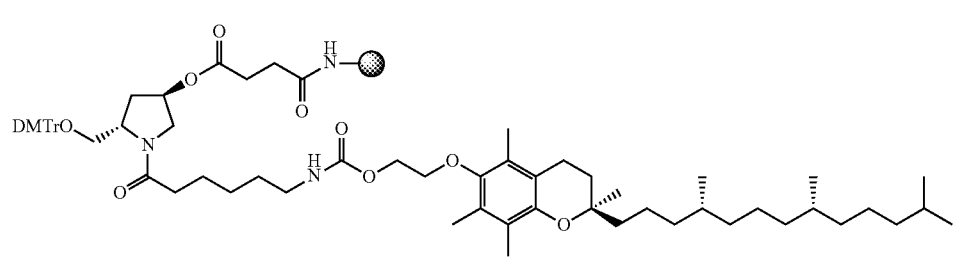
22

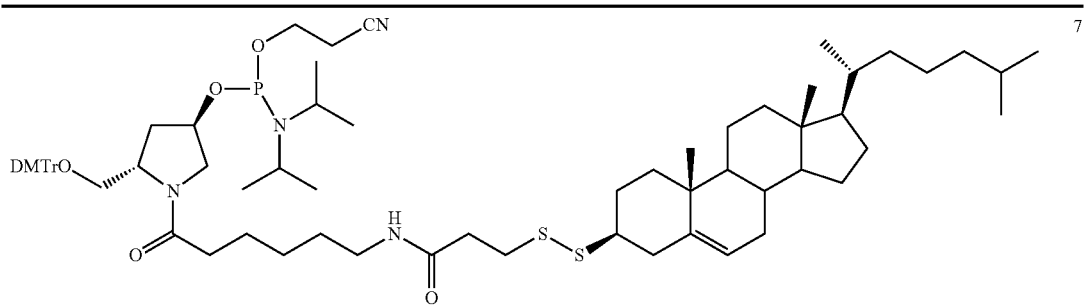
26
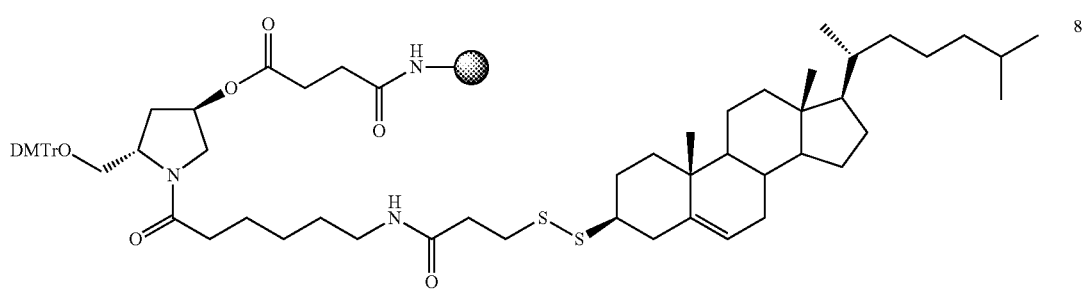
28
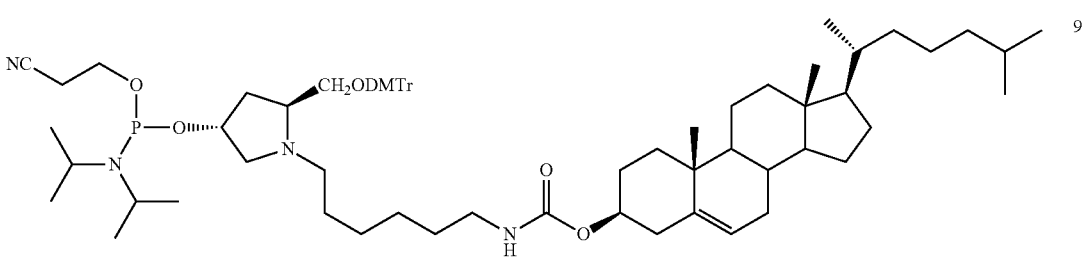
33
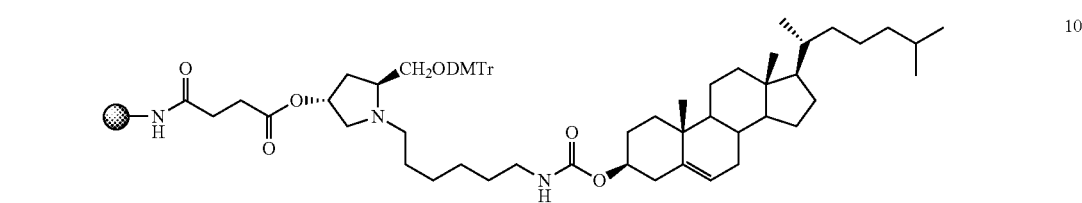
35
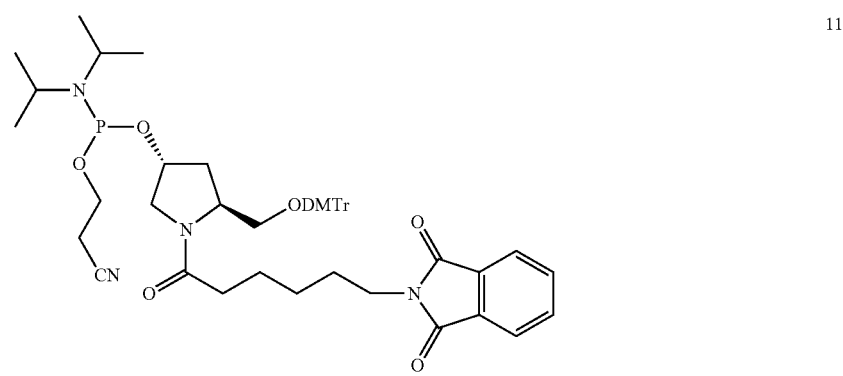
45a

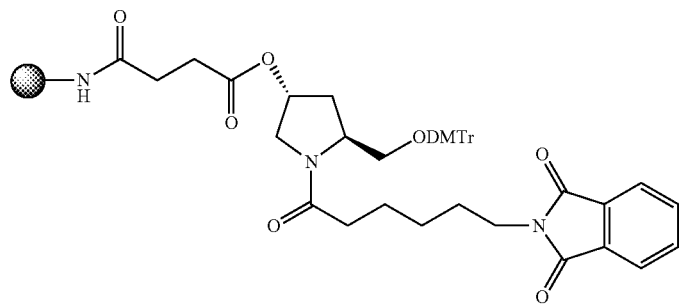
46a
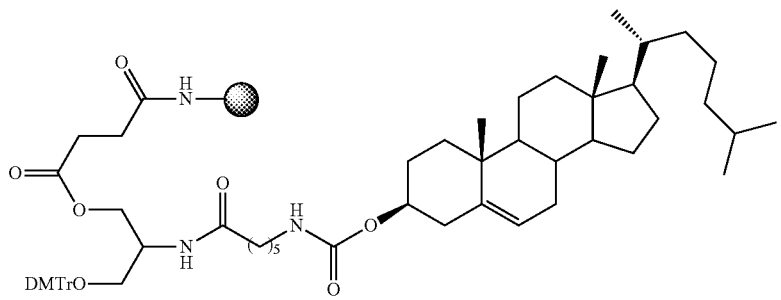
55
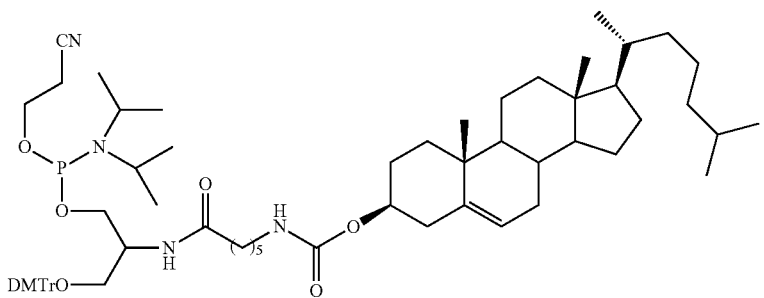
56
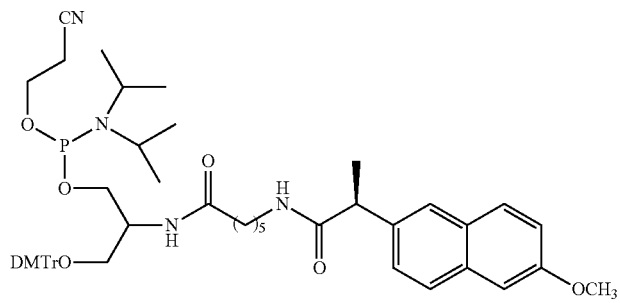
209a

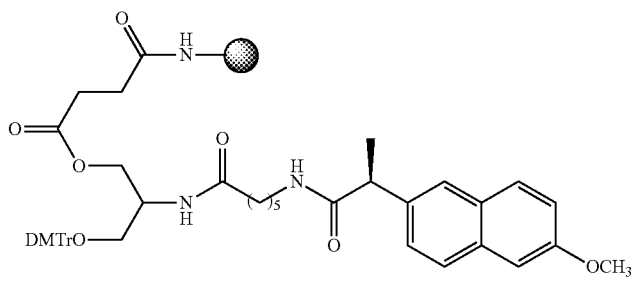
16
208a
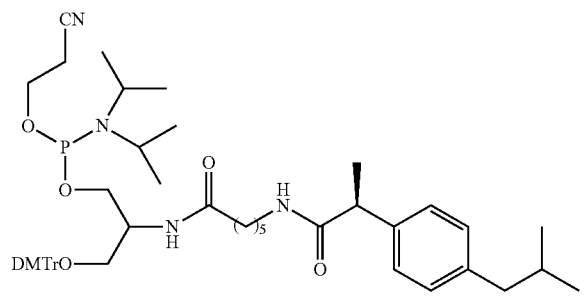
17
209b
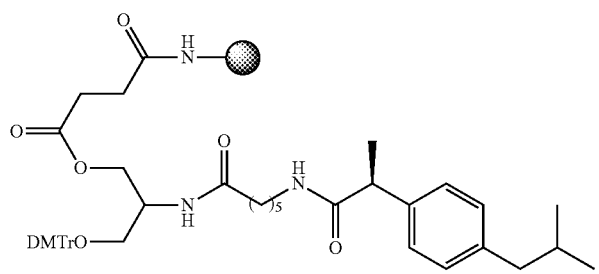
18
208b
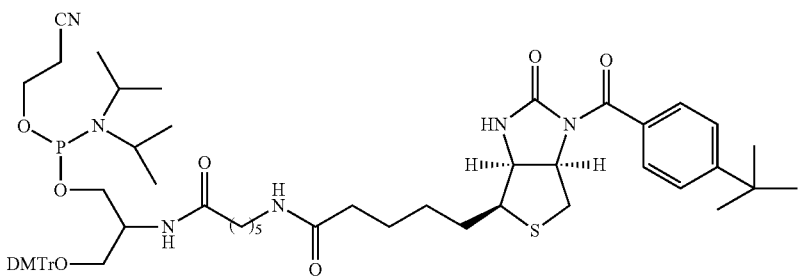
19
223
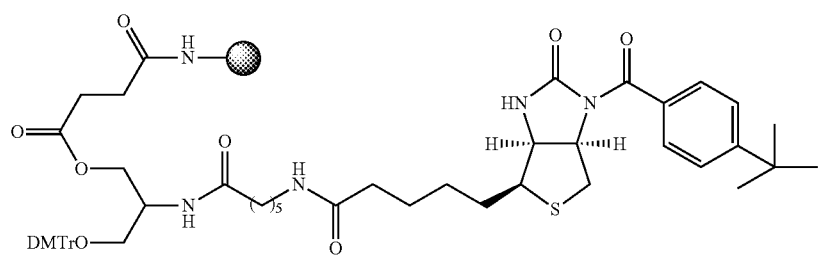
20
224

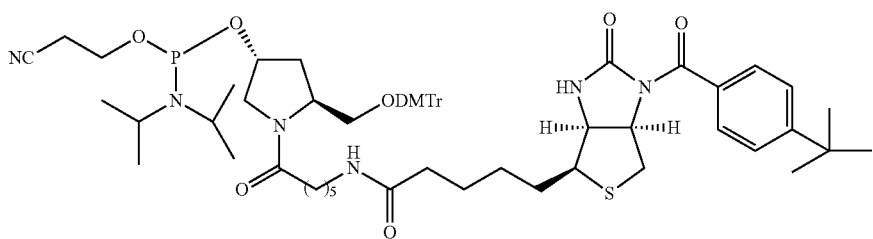
229a
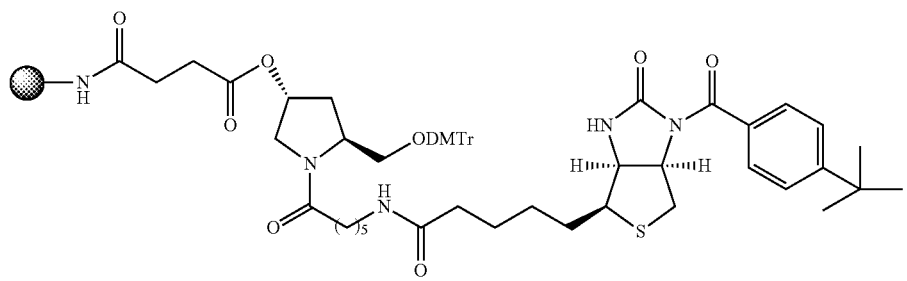
230a
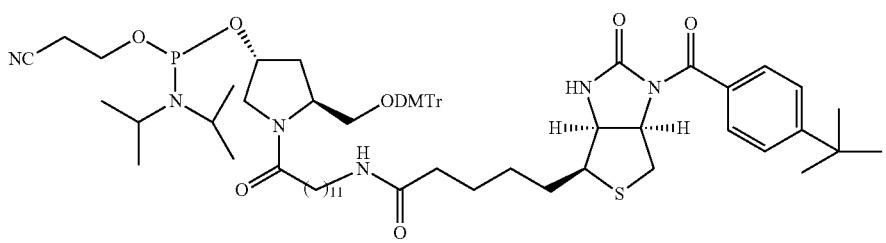
229b
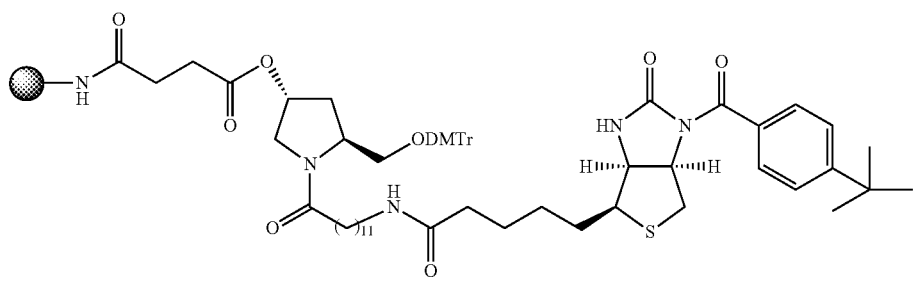
230b
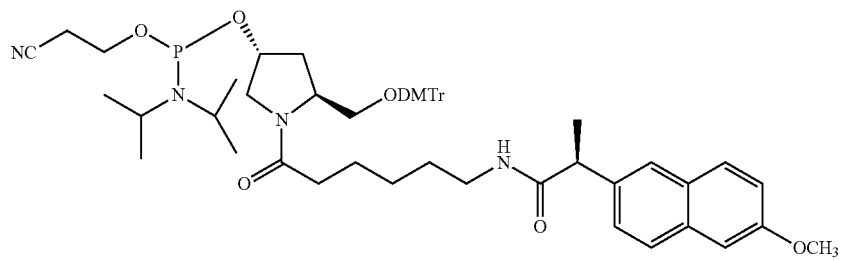
212a

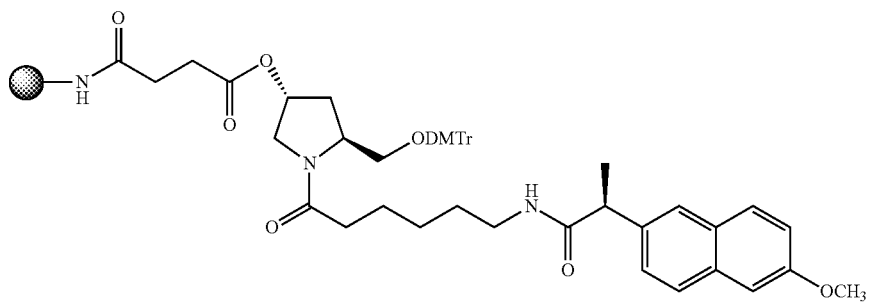
211a
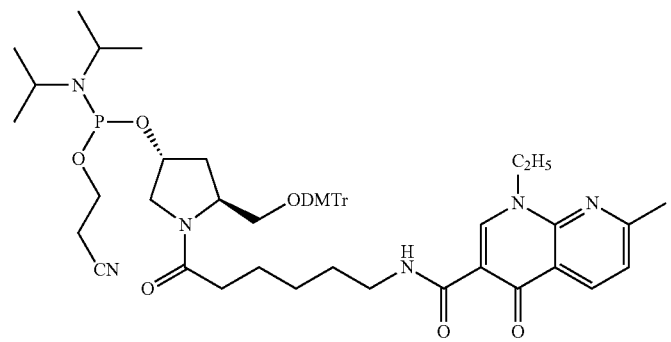
100
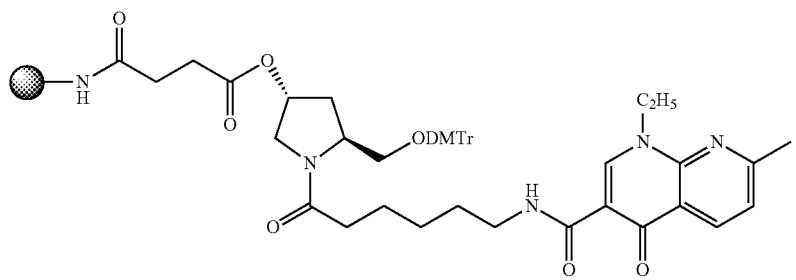
102
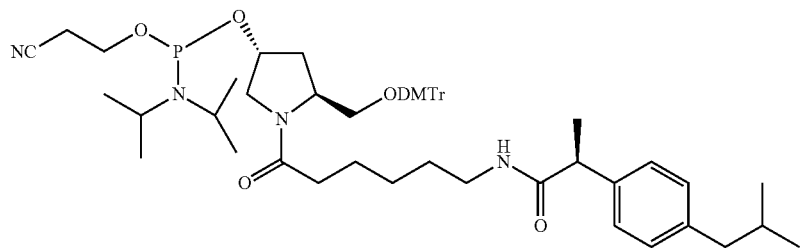
212b

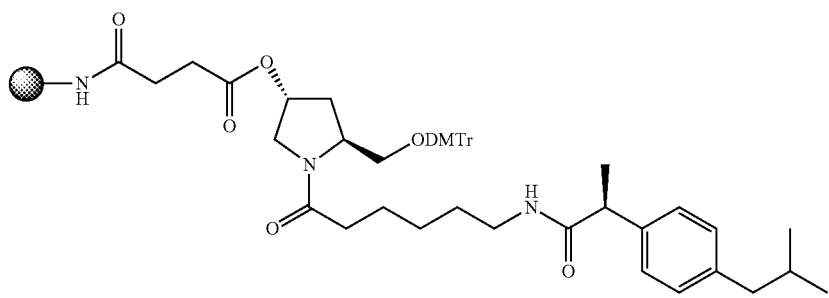
211b
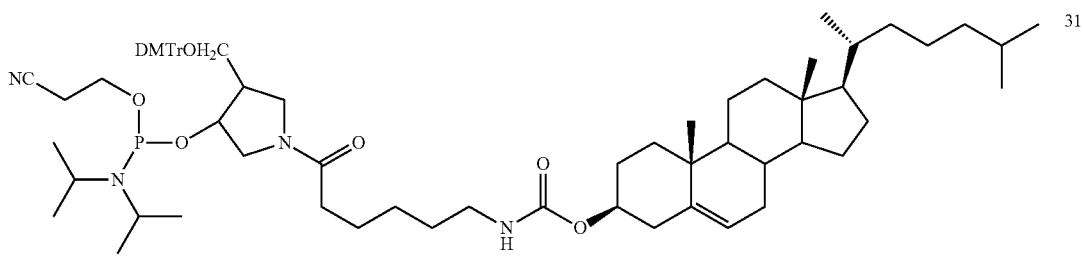
67
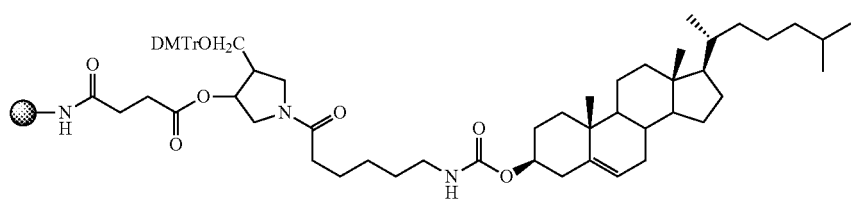
69
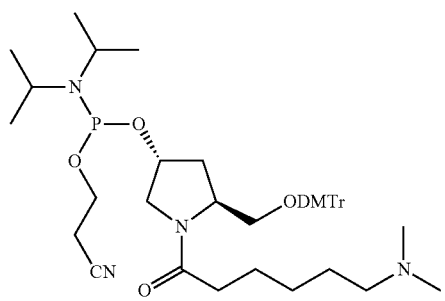
95
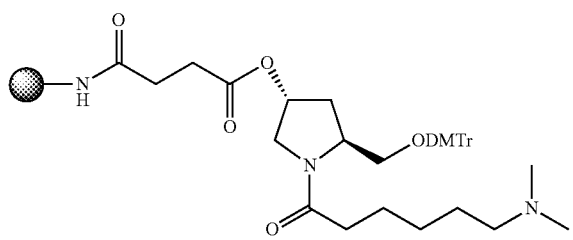
97

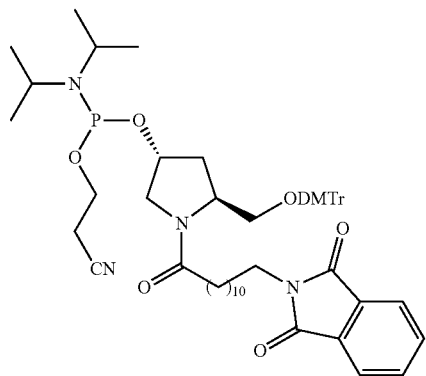
45b
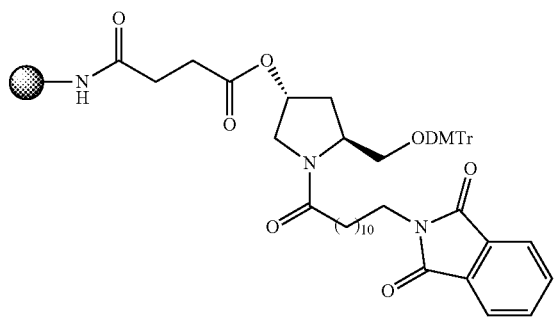
46b
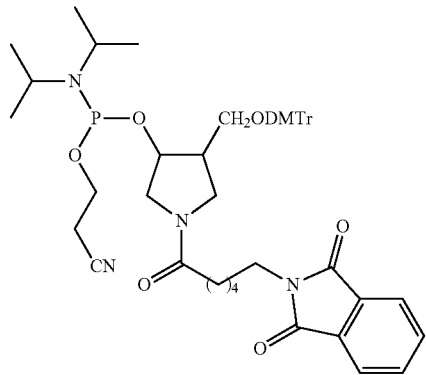
78
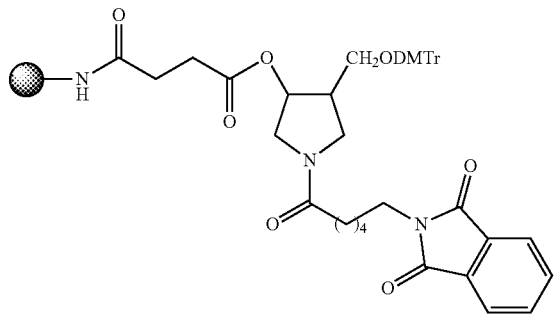
80

-continued
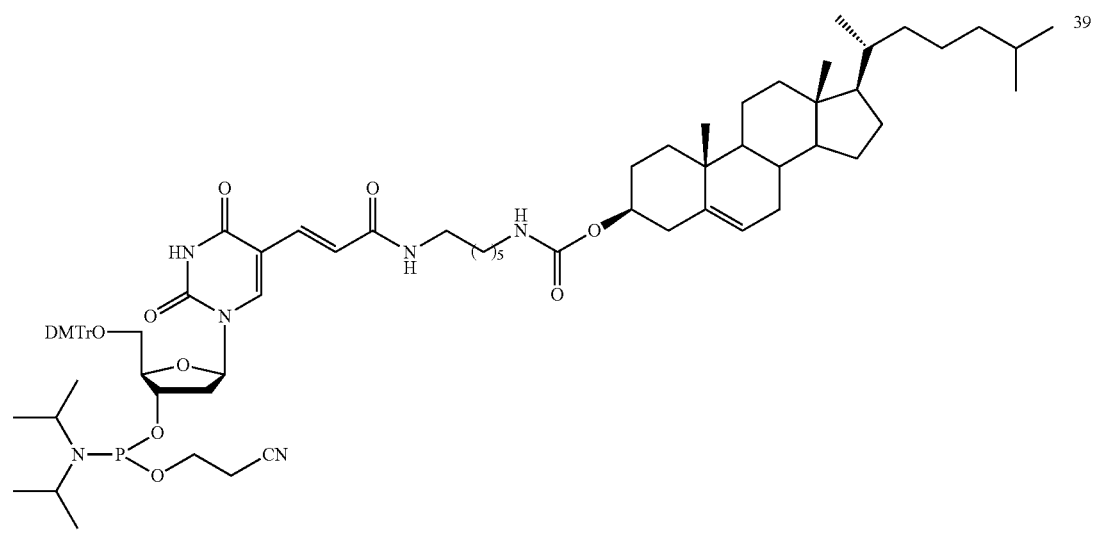
216a
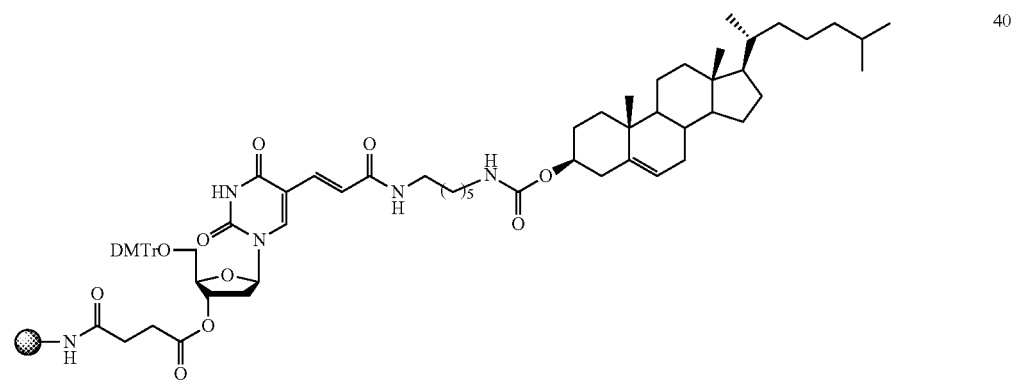
215a
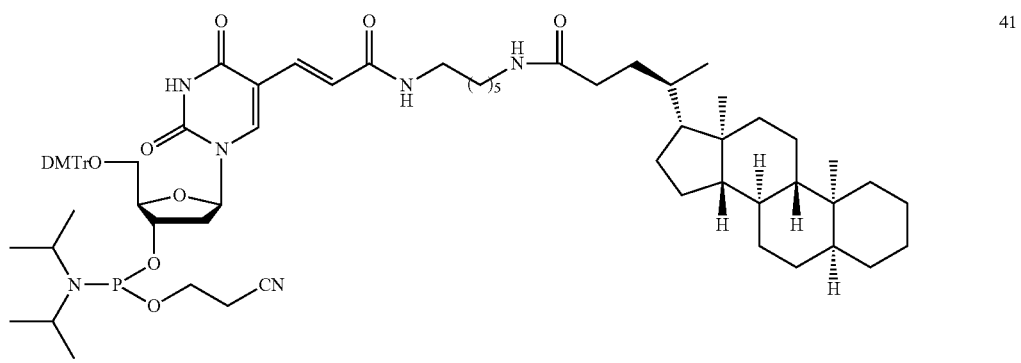
216b

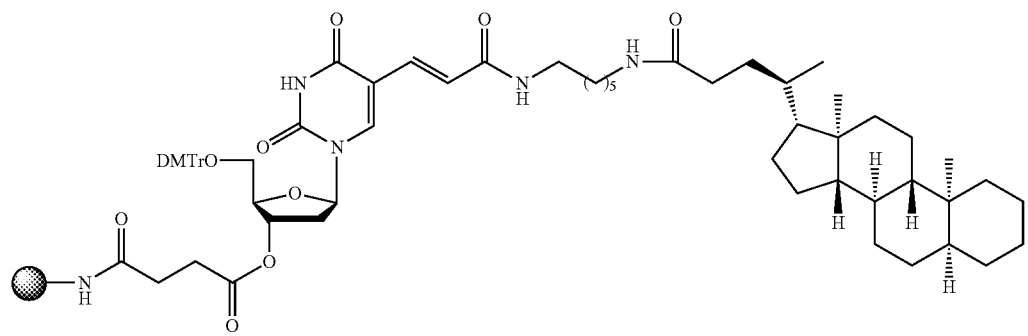
215b
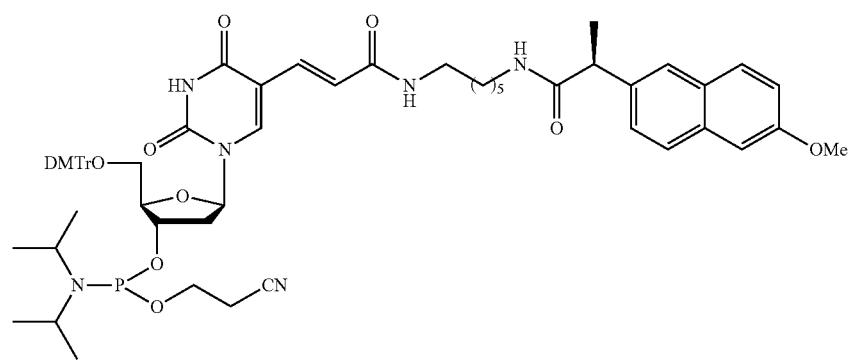
243a
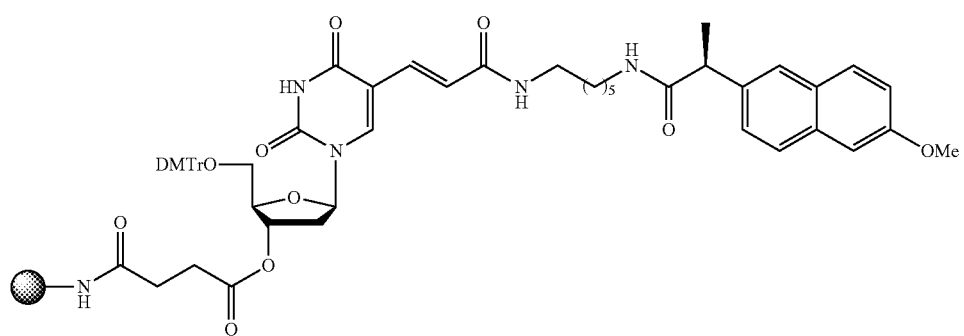
242a
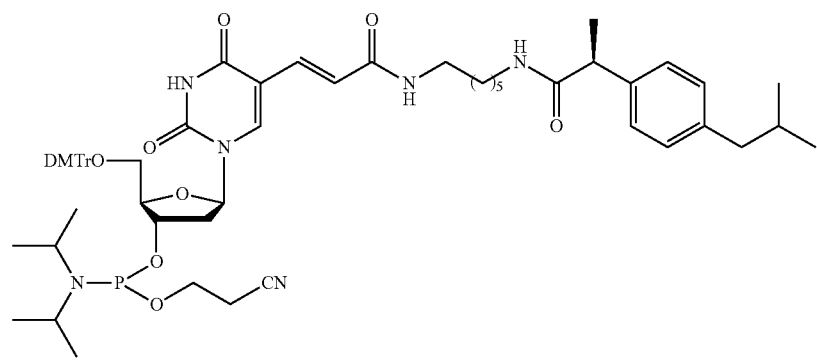
243b

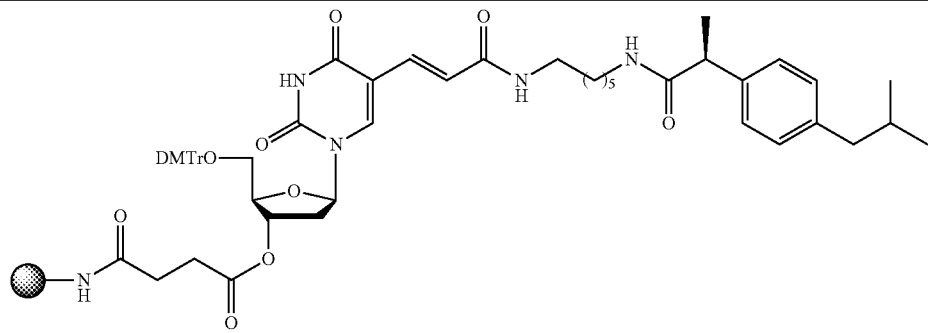
242b
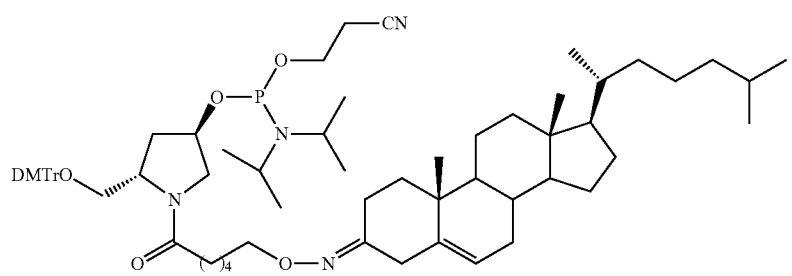
236a
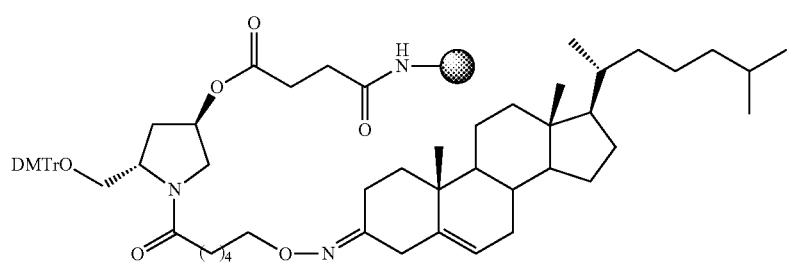
237a
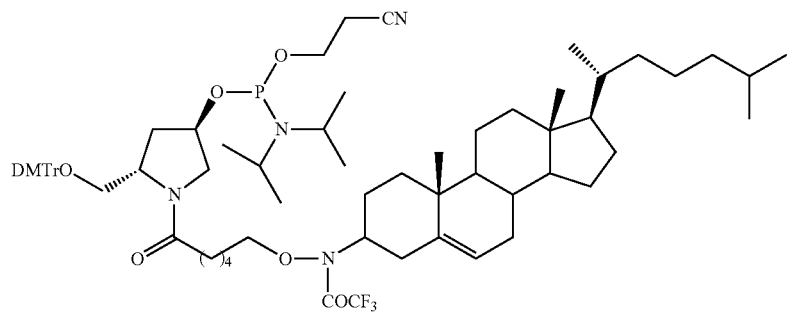
239a

-continued
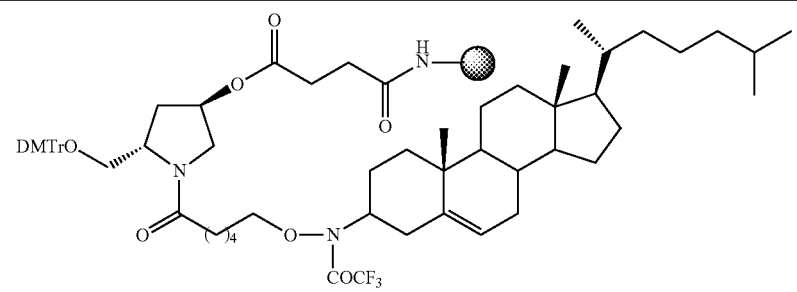
240a
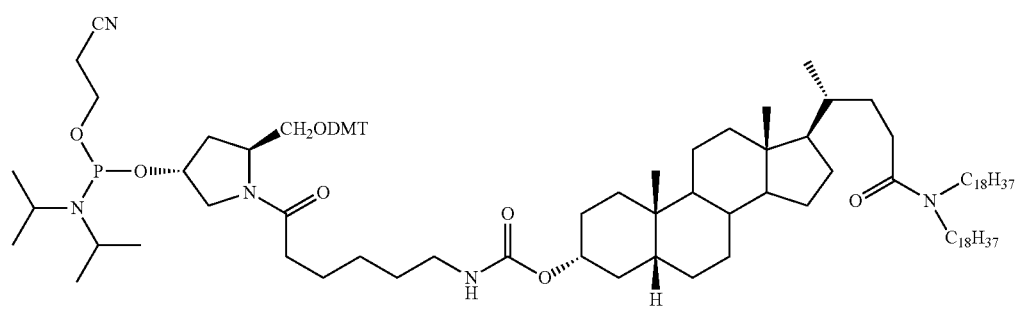
85
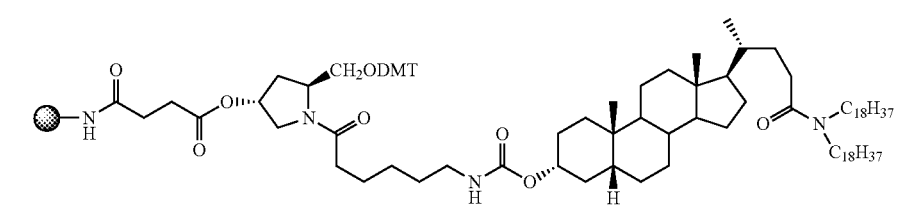
87
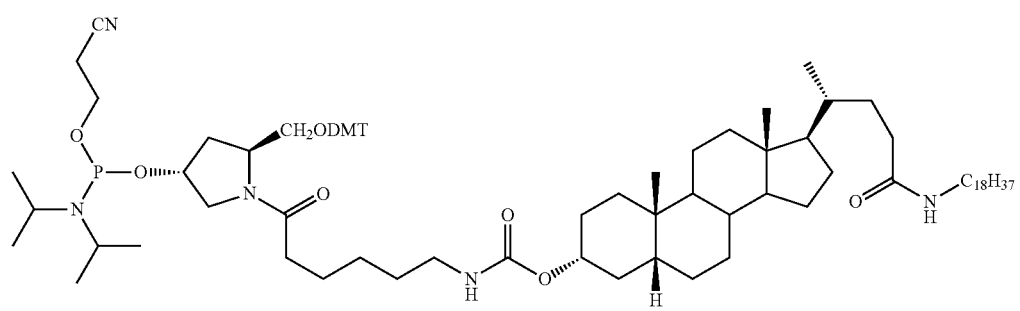
91
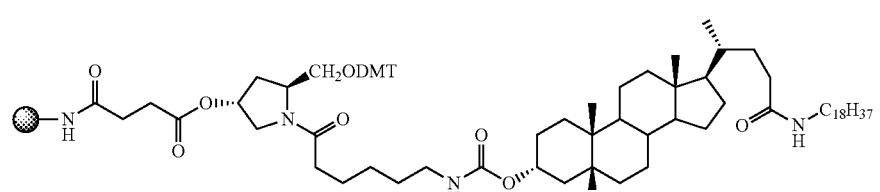
93

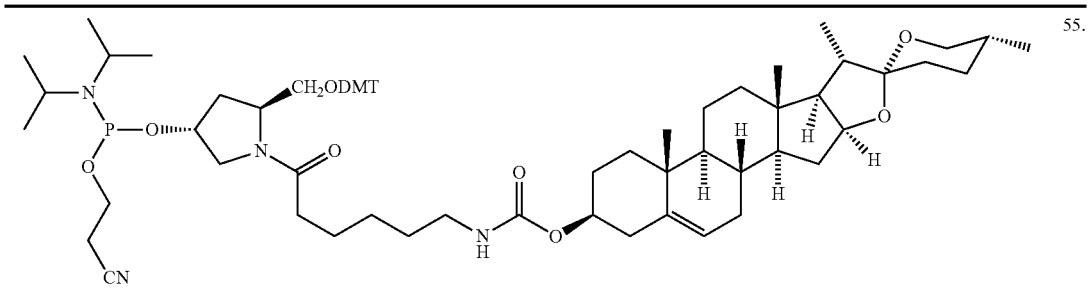

106
Diosgenin

55.

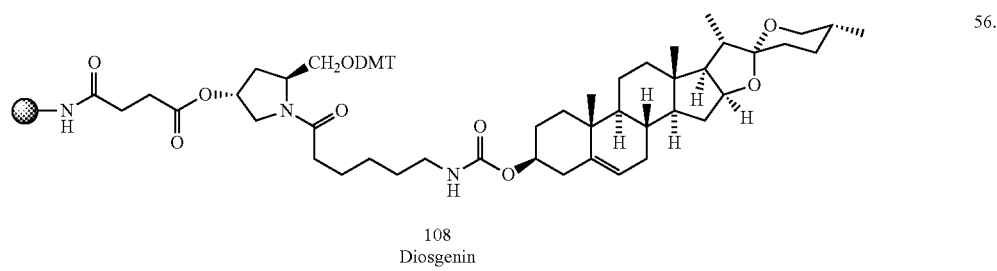

108
Diosgenin

56.

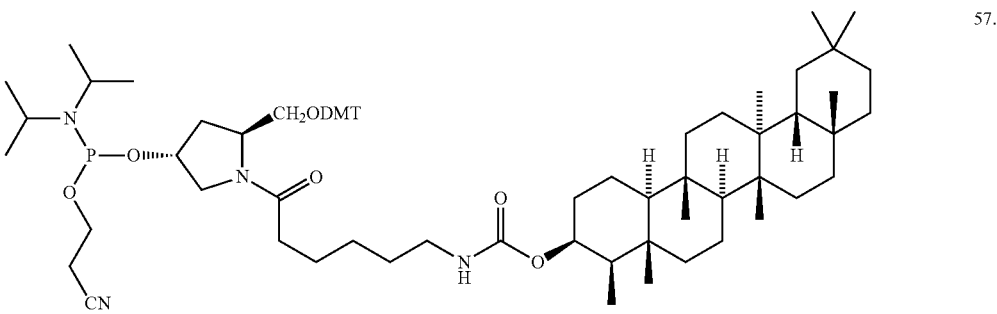

112
Epifriedelanol

57.

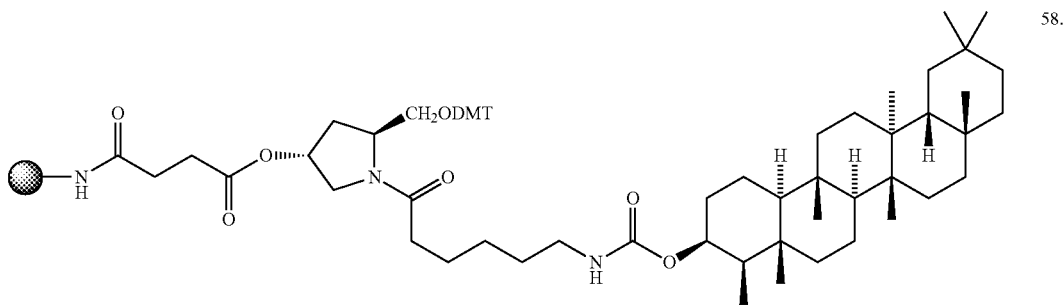

114
Epifriedelanol

58.

Targeting

The iRNA agents of the invention are particularly useful when targeted to the liver. The chemical modifications described herein can be combined with the compounds and methods described in U.S. Provisional Application 60/462,097, filed on Apr. 9, 2003, which is hereby incorporated by reference; and U.S. Provisional Application 60/461,915, filed on Apr. 10, 2003, which is hereby incorporated by reference. For example, an iRNA agent can be targeted to the liver by incorporation of an RRMS containing a ligand that targets the liver, e.g., a lipophilic moiety. Preferred lipophilic moieties include lipid, cholesterols, oleyl, retinyl, or cholesteryl residues. Other lipophilic moieties that can function as liver-targeting agents include cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine.

An iRNA agent can also be targeted to the liver by association with a low-density lipoprotein (LDL), such as lactosylated LDL. Polymeric carriers complexed with sugar residues can also function to target iRNA agents to the liver.

Conjugation of an iRNA agent with a serum albumin (SA), such as human serum albumin, can also be used to target the iRNA agent to a non-kidney tissue, such as the liver.

An iRNA agent targeted to the liver by an RRMS targeting moiety described herein can target a gene expressed in the liver. For example, the iRNA agent can target p21(WAF1/DIP1), P27(KIP1), the α-fetoprotein gene, beta-catenin, or c-MET, such as for treating a cancer of the liver. In another embodiment, the iRNA agent can target apoB-100, such as for the treatment of an HDL/LDL cholesterol imbalance; dyslipidemias, e.g., familial combined hyperlipidemia (FCHL), or acquired hyperlipidemia; hypercholesterolemia; statin-resistant hypercholesterolemia; coronary artery disease (CAD); coronary heart disease (CHD); or atherosclerosis. In another embodiment, the iRNA agent can target forkhead homologue in rhabdomyosarcoma (FKHR); glucagon; glucagon receptor; glycogen phosphorylase; PPAR-Gamma Coactivator (PGC-1); Fructose-1,6-bisphosphatase; glucose-6-phosphatase; glucose-6-phosphate translocator; glucokinase inhibitory regulatory protein; or phosphoenolpyruvate carboxykinase (PEPCK), such as to inhibit hepatic glucose production in a mammal, such as a human, such as for the treatment of diabetes. In another embodiment, an iRNA agent targeted to the liver can target Factor V, e.g., the Leiden Factor V allele, such as to reduce the tendency to form a blood clot. An iRNA agent targeted to the liver can include a sequence which targets hepatitis virus (e.g., Hepatitis A, B, C, D, E, F, G, or H). For example, an iRNA agent of the invention can target any one of the nonstructural proteins of HCV: NS3, 4A, 4B, 5A, or 5B. For the treatment of hepatitis B, an iRNA agent can target the protein X (HBx) gene, for example.

A targeting agent that incorporates a sugar, e.g., galactose and/or analogues thereof, can be useful. These agents target, for example, the parenchymal cells of the liver. For example, a targeting moiety can include more than one or preferably two or three galactose moieties, spaced about 15 angstroms from each other. The targeting moiety can alternatively be lactose (e.g., three lactose moieties), which is glucose coupled to a galactose. The targeting moiety can also be N-Acetyl-Galactosamine, N-Ac-Glucosamine. A mannose or mannose-6-phosphate targeting moiety can be used for macrophage targeting.

The iRNA agents of the invention are particularly useful when targeted to the kidney. The chemical modifications described herein can be combined with the compounds and methods described in U.S. Provisional Application 60/460,783, filed on Apr. 3, 2003, which is hereby incorporated by reference; and 60/503,414, filed on Sep. 15, 2003, which is hereby incorporated by reference. An iRNA agent can be targeted to the kidney by incorporation of an RRMS containing a ligand that targets the kidney.

An iRNA agent targeted to the kidney by an RRMS targeting moiety described herein can target a gene expressed in the kidney.

Ligands on RRMSs can include folic acid, glucose, cholesterol, cholic acid, Vitamin E, Vitamin K, or Vitamin A.

Conjugation with a Lipophilic Moiety which Promotes Entry into Cells

RNAi agents can be modified so as to enhance entry into cells, e.g., by conjugation with a lipophilic moiety. A lipophilic moiety can be attached to an RNAi agent in a number of ways but a preferred mode of attachment is by attachment to an RRMS, e.g., pyrroline-based RRMS. The lipohilic moiety can be attached at the N atom of a pyrroline-based RRMS. Examples of lipophilic moieties include cholesterols, lipid, oleyl, retinyl, or cholesteryl residues. Other lipophilic moieties include cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine. Cholesterol is a particularly preferred example.

The lipohilic moiety can be attached at the 3' terminus, the 5' terminus, or internally, preferably on the sense strand. The lipohilic moiety can be attached to an RRMS, e.g., a pyrroline-based RRMS which is at the 3' terminus, the 5' terminus, or internal, in the sense strand. The attachment can be direct or through a tethering molecule. Tethers, spacers or linkers discussed herein can be used to attach the moiety to the RRMS.

An iRNA agent to which one or more lipophilic (e.g., cholesterol) molecules is conjugated (referred to herein as an "iRNA-lipophilic conjugate") can be delivered in vivo, e.g., to a cell, such as a cell of a tissue in a subject, such as a mammalian subject (e.g., a human or mouse). Alternatively, or in addition, the iRNA agent can be delivered in vitro, e.g., to a cell in a cell line. Cell lines can be, for example, from a vertebrate organism, such as a mammal (e.g., a human or a mouse). Delivery of an iRNA-cholesterol conjugate to a cell line can be in the absence of other transfection reagents. For example, delivery of an iRNA-lipophilic conjugate to a cell can be in the absence of, or optionally, in the presence of, Lipofectamine™ (Invitrogen, Carlsbad, Calif.), Lipofectamine 2000™, TransIT-TKO™ (Mirus, Madison, Wis.), FuGENE 6 (Roche, Indianapolis, Ind.), polyethylenimine, X-tremeGENE Q2 (Roche, Indianapolis, Ind.), DOTAP, DOSPER, or Metafectene™ (Biontex, Munich, Germany), or another transfection reagent. Exemplary cell lines can be provided by the American Type Culture Collection (ATCC) (Manassus, Va.). An iRNA-lipophilic conjugate can be delivered to a cell line, such as any cell line described herein, to target a specific gene for downregulation.

In one example, an iRNA-lipophilic conjugate can be delivered to a primary cell line, e.g., a synoviocyte (such as type B), cardiac myocyte, keratinocyte, hepatocyte, smooth muscle cell, endothelial cell, or dermal fibroblast cell line.

In another example, an iRNA-lipophilic conjugate can be delivered to monocyte, or myeloid cell line, e.g., a THP1, Raw264.7, IC21, P388D1, U937, or HL60 cell line.

In another example, an iRNA-lipophilic conjugate can be delivered to lymphoma, or leukemia cell line, e.g., an SEM-K2, WEHI-231, HB56, TIB55, Jurkat, K562, EL4, LRMB, Bcl-1, or TF1 cell line. For example, an iRNA-lipophilic conjugate can be delivered to a lymphoma cell line to target a specific gene for down regulation. An iRNA-lipophilic agent can target (down-regulate) a gene in a Jurkat cell line, for example, that encodes an immune factor, such as an interleukin gene, e.g., IL-1, IL-2, IL-5, IL-6, IL-8, IL-10, IL-15, IL-16, IL-17, or IL-18. In another aspect, an iRNA-lipophilic conjugate can target a gene that encodes a receptor of an interleukin.

An iRNA-lipophilic conjugate can target a gene resulting from a chromosomal translocation, such as BCR-ABL, TEL-AML-1, EWS-FLI1, EWS-ERG, TLS-FUS, PAX3-FKHR, or AML1-ETO. For example, an iRNA-lipophilic conjugate that targets a gene resulting from a chromosomal translocation can be delivered to a leukemia cell line, e.g., any of the leukemia cell lines discussed above.

An iRNA-lipophilic conjugate can be delivered to an immortalized cell line, including immortalized cell lines from a variety of different tissue types, including but not limited to T-cells, fibroblast cells, epithelial cells (e.g., kidney epithelial cells) and muscle cells (e.g., smooth muscle cells). Exemplary immortalized cell lines are CTLL-2 (T-cell), Rat 6 (fibroblast), VERO (fibroblast), MRC5 (fibroblast), CV1 (fibroblast), Cos7 (fibroblast), RPTE (kidney epithelial), and A10 (smooth muscle) cell lines.

An iRNA-lipophilic conjugate can be delivered to a mast cell line, for example. An iRNA-lipophilic conjugate delivered to a mast cell line can target, for example, a gene encoding a GRB2 associated binding protein (e.g., GAB2).

An iRNA-lipophilic conjugate can be delivered to an adherent tumor cell line, including tumor cell lines from a variety of different tissue types including but not limited to cancers of the bladder, lung, breast, cervix, colon, pancreas, prostate, and liver, melanomas, and glioblastomas. Exemplary tumor cell lines include the T24 (bladder), J82 (bladder), A549 (lung), Calu1 (lung), SW480 (colon), SW620 (colon), CaCo2 (colon), A375 (melanoma), C8161 (melanoma), MCF-7 (breast), MDA-MB-231 (breast), HeLa (cervical), HeLa S3 (cervical), MiaPaCall (pancreas), Panc1 (pancreas), PC-3 (prostate), LNCaP (prostate), HepG2 (hepatocellular), and U87 (glioblastoma) cell lines. An iRNA-lipophilic conjugate that targets a specific gene can be delivered to an adherent tumor cell line. For example, an iRNA-lipophilic conjugate that targets a growth factor or growth factor receptor, such as a TGF-beta (e.g., TGF-beta 1) or TGF-beta receptor gene, can be delivered to an A549 or HepG2 cell line, a DLD2 colon carcinoma line, or a SKOV3 adenocarcinoma cell line. Other exemplary target growth factor genes include platelet derived growth factor (PDGF) and PDGF-Receptor (PDGFR), vascular endothelial growth factor (VEGF) and VEGF receptor genes (e.g., VEGFr1, VEGFr2, or VEGFr3), and insulin-growth factor receptors, such as type I insulin-growth factor (IGF) receptors, including IGF-1R, DAF-2 and InR.

In another example, an iRNA-lipophilic conjugate that targets one or more genes in a protein tyrosine phosphatase type IVA (PRL3, also called PTP4A3) gene family (e.g., PRL1, PRL2, or PRL3), or a gene in a PRL3 pathway, can be delivered to an A549 cell line, or to a cultured colorectal epithelial cell line.

In another example, an iRNA-lipophilic conjugate can target one or more protein kinase C genes in an adherent tumor cell line, such as in a mouse Lewis lung carcinoma, B16 melanoma, mouse mammary adenocarcinoma or fibrosarcoma; or a human lung carcinoma, bladder carcinoma, pancreatic cancer, gastric cancer, breast cancer, thyroid carcinoma, or melanoma. An iRNA-lipophilic conjugate can target a gene encoding a PKC isoforms, such as PKC-alpha, PKC beta I, PKC beta II, PKC gamma, PKC delta, PKC epsilon, and/or PKC zeta, or a gene encoding one or more receptors of a protein kinase C polypeptide.

In another example, an iRNA-lipophilic conjugate can target a gene encoding a P-glycoprotein, such as a gene in the multidrug resistance (MDR) gene family, e.g., MDR1. An iRNA-lipophilic conjugate that targets an MDR gene can be delivered, for example, to a human KB carcinoma cell line, a human leukemia or ovarian carcinoma cell line, or a lung carcinoma cell line such as A549.

In another example, an iRNA-lipophilic conjugate can target a gene encoding a gene in the telomerase pathway, such as TERT or the telomerase template RNA (TR/TERC). An iRNA-lipophilic conjugate that targets a gene in the telomerase pathway can be delivered, for example, to a human cancer cell line, e.g., a breast, cervical, endometrial, meningeal, lung, testicular, or ovarian cancer cell line.

In another example, an iRNA-lipophilic conjugate delivered to an adherent cell line (e.g., a HeLa, parathyroid adenoma, or A549 cell line) can target a cyclin gene, such as cyclin D1.

In another example, an iRNA-lipophilic conjugate delivered to an adherent cell line (e.g., a HeLa cell line) can target an NF-kappaB or REL-A gene, or a gene encoding a ligand or receptor of an NF-kappaB or REL-A polypeptide, or a gene encoding a subunit of NF-kappaB, such as REL-B, REL, NF-kappaB1 or NF-kappaB2.

In another example, an iRNA-lipophilic conjugate delivered to an adherent cell line (e.g., a HeLa or A549 cell line) can target a gene encoding proliferating cell nuclear antigen (PCNA), a checkpoint kinase gene (CHK-1), or a c-fos gene. Further, an iRNA-lipophilic conjugate can target any gene in a PCNA, CHK-1, or c-fos pathway. For example an iRNA-lipophilic conjugate can down-regulate a gene encoding jun, which is in the c-fos pathway.

In another example, an iRNA-lipophilic conjugate delivered to an adherent cell line (e.g., an A549, T24, or A375 cell line) can target a gene encoding BCL2.

The cell lines described herein can be used to test iRNA-lipophilic conjugates that target exogenous, such as pathogenic or viral, nucleic acids. For example, an iRNA-lipophilic conjugate that targets a hepatitis viral gene can be delivered to a human hepatoma cell line, such as a HepG2 or Huh cell line, e.g., Huh1, Huh4, Huh7, and the like, that has been infected with the virus (e.g., an HAV, HBV, or HCV). For example, an iRNA-lipophilic conjugate that targets an HCV gene, such as in an infected Huh cell line, can target a conserved region of the HCV genome, such as the 5'-non-coding region (NCR), the 5' end of the core protein coding region, or the 3'-NCR.

The cell lines described herein can be also be used to test iRNA-lipophilic conjugates that target exogenous recombinant nucleic acids, such as reporter genes (e.g., GFP, lacZ, beta-galactosidase, and the like), that are transfected (transiently or stably) into the cell lines.

In one aspect, an iRNA-lipophilic conjugate can be delivered to a B-cell line, e.g., BC-3, C1R, or ARH-77 cells. In another aspect, an iRNA-lipophilic conjugate can be delivered to T-cells, e.g., J45.01, MOLT, and CCRF-CEM cells. An iRNA-lipophilic conjugate can target an endogenous or exogenous nucleic acid. For example, development of an iRNA-lipophilic conjugate that targets an HIV gene can be tested against an exogenous HIV nucleic acid in a B cell or T cell line, or in a macrophage or endothelial cell culture system.

An iRNA-lipophilic conjugate can be delivered to cells derived from endoderm, epithelium, or mesoderm. For example, an iRNA-lipophilic conjugate can be delivered to cells of the HeLa or MCF7 epithelial cell lines, to cells of the HUVEC endothelial cell line, or to cells of an SK-UT or HASMC mesodermal cell line. In one example, an iRNA-lipophilic agent that targets a TGF-beta nucleic acid or TGF-beta receptor nucleic acid can be delivered to a vascular smooth muscle cell line, e.g., the kidney fibroblast 293 cell line. Other exemplary targets of iRNA-lipophilic conjugates delivered to fibroblast cells, such as 293 cells, included a protein tyrosine phosphatase-1B (PTP-1B) gene or MAP kinase gene (e.g., ERK1, ERK2, JNK1, JNK2, and p38). In another example, an iRNA-lipophilic conjugate that targets an MDR gene for down-regulation can be delivered to the human intestinal epithelial cell line, Caco-2.

In one example, an iRNA-lipophilic conjugate delivered to a cell line, such as an epithelial or mesodermal cell line (e.g., a HeLa or HASMC cell line, respectively), can target a gene encoding a Myc or Myb polypeptide, e.g., c-Myc, N-Myc, L-Myc, c-Myb, a-Myb, b-Myb, and v-Myb, or a gene in the Myc or Myb gene pathway, such as cyclin D1, cyclin D2, cyclin E, CDK4, cdc25A, CDK2, or CDK4.

In one example, an iRNA-lipophilic conjugate that targets a gene expressed in the nervous system, such as in the brain, e.g, a G72 or D-amino acid oxidase (DAAO) gene, can be delivered to a cultured neuronal cell line, such as an hNT cell line.

In another example, an iRNA-lipophilic conjugate can target a gene encoding a gene in the telomerase pathway, such as TERT or TR/TERC. An iRNA-lipophilic conjugate that targets a gene in the telomerase pathway can be delivered, for example, to a human keratinocyte cell line, such as a HEK cell line, e.g., HEKn or HEKa.

In another example, an iRNA-lipophilic conjugate delivered to a tissue-specific cell-line, such as a HEK (keratinocyte), HuVEC (endothelial), 3T3 (fibroblast), or NHDF (fibroblast) cell line, can target a gene encoding BCL-2, or VEGF or a VEGF receptor (e.g., VEGFr1, VEGFr2, or VEGFr3).

An iRNA-lipophilic conjugate can be delivered to a subgroup of cells derived from a particular tissue. For example, an iRNA-lipophilic conjugate can be delivered to a proximal tubular kidney cell line, such as the mouse cell line mIMCD-3. An iRNA-lipophilic conjugate that targets a TGF-beta nucleic acid or TGF-beta receptor nucleic acid, for example, can be delivered to a cell line derived from prostate tissue, e.g., a PC3 or RWPE prostate cell line. An iRNA-lipophilic conjugate delivered to a prostate tissue cell line can alternatively target a polycomb group gene, such as EZH2.

In another example, an iRNA-lipophilic conjugate can be delivered to pancreatic islet b-cells, where for example, it targets a gastric inhibitory polypeptide (GIP) gene, or a GIP-receptor gene.

The iRNA-lipophilic conjugates described herein are not limited in the cell lines to which they can be applied or to the nucleic acids to which they can target.

iRNA Agent Structure

The monomers described herein can be used to make oligonucleotides which are useful as iRNA agents, e.g., RNA molecules, (double-stranded; single-stranded) that mediate RNAi, e.g., with respect to an endogenous gene of a subject or to a gene of a pathogen. In most cases the iRNA agent will incorporate monomers described herein together with naturally occurring nucleosides or nucleotides or with other modified nucleosides or nucleotides. The modified monomers can be present at any position in the iRNA agent, e.g., at the terminii or in the middle region of an iRNA agent or in a duplex region or in an unpaired region. In a preferred embodiment iRNA agent can have any architecture, e.g., architecture described herein. E.g., it can be incorporated into an iRNA agent having an overhang structure, a hairpin or other single strand structure or a two-strand structure, as described herein.

An "RNA agent" as used herein, is an unmodified RNA, modified RNA, or nucleoside surrogate, all of which are defined herein (see, e.g., the section below entitled RNA Agents). While numerous modified RNAs and nucleoside surrogates are described, preferred examples include those which have greater resistance to nuclease degradation than do unmodified RNAs. Preferred examples include those which have a 2' sugar modification, a modification in a single strand overhang, preferably a 3' single strand overhang, or, particularly if single stranded, a 5' modification which includes one or more phosphate groups or one or more analogs of a phosphate group.

An "iRNA agent" as used herein, is an RNA agent which can, or which can be cleaved into an RNA agent which can, down regulate the expression of a target gene, preferably an endogenous or pathogen target RNA. While not wishing to be bound by theory, an iRNA agent may act by one or more of a number of mechanisms, including post-transcriptional cleavage of a target mRNA sometimes referred to in the art as RNAi, or pre-transcriptional or pre-translational mechanisms. An iRNA agent can include a single strand or can include more than one strands, e.g., it can be a double stranded iRNA agent. If the iRNA agent is a single strand it is particularly preferred that it include a 5' modification which includes one or more phosphate groups or one or more analogs of a phosphate group.

The RRMS-containing iRNA agent should include a region of sufficient homology to the target gene, and be of sufficient length in terms of nucleotides, such that the iRNA agent, or a fragment thereof, can mediate down regulation of the target gene. (For ease of exposition the term nucleotide or ribonucleotide is sometimes used herein in reference to one or more monomeric subunits of an RNA agent. It will be understood herein that the usage of the term "ribonucleotide" or "nucleotide", herein can, in the case of a modified RNA or nucleotide surrogate, also refer to a modified nucleotide, or surrogate replacement moiety at one or more positions.) Thus, the iRNA agent is or includes a region which is at least partially, and in some embodiments fully, complementary to the target RNA. It is not necessary that there be perfect complementarity between the iRNA agent and the target, but the correspondence must be sufficient to enable the iRNA agent, or a cleavage product thereof, to direct sequence specific silencing, e.g., by RNAi cleavage of the target RNA, e.g., mRNA.

Complementarity, or degree of homology with the target strand, is most critical in the antisense strand. While perfect complementarity, particularly in the antisense strand, is often desired some embodiments can include, particularly in the antisense strand, one or more but preferably 6, 5, 4, 3, 2, or fewer mismatches (with respect to the target RNA). The mismatches, particularly in the antisense strand, are most tolerated in the terminal regions and if present are preferably in a terminal region or regions, e.g., within 6, 5, 4, or 3 nucleotides of the 5' and/or 3' terminus. The sense strand need only be sufficiently complementary with the antisense strand to maintain the over all double strand character of the molecule.

As discussed elsewhere herein, an iRNA agent will often be modified or include nucleoside surrogates in addition to the ribose replacement modification subunit (RRMS). Single stranded regions of an iRNA agent will often be modified or include nucleoside surrogates, e.g., the unpaired region or regions of a hairpin structure, e.g., a region which links two complementary regions, can have modifications or nucleoside surrogates. Modification to stabilize one or more 3'- or 5'-terminus of an iRNA agent, e.g., against exonucleases, or to favor the antisense sRNA agent to enter into RISC are also favored. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis.

iRNA agents include: molecules that are long enough to trigger the interferon response (which can be cleaved by Dicer (Bernstein et al. 2001. Nature, 409:363-366) and enter a RISC (RNAi-induced silencing complex)); and, molecules which are sufficiently short that they do not trigger the interferon response (which molecules can also be cleaved by Dicer and/or enter a RISC), e.g., molecules which are of a size which allows entry into a RISC, e.g., molecules which resemble Dicer-cleavage products. Molecules that are short enough that they do not trigger an interferon response are termed sRNA agents or shorter iRNA agents herein. "sRNA agent or shorter iRNA agent" as used herein, refers to an iRNA agent, e.g., a double stranded RNA agent or single strand agent, that is sufficiently short that it does not induce a deleterious interferon response in a human cell, e.g., it has a duplexed region of less than 60 but preferably less than 50, 40, or 30 nucleotide pairs. The sRNA agent, or a cleavage product thereof, can down regulate a target gene, e.g., by inducing RNAi with respect to a target RNA, preferably an endogenous or pathogen target RNA.

Each strand of an sRNA agent can be equal to or less than 30, 25, 24, 23, 22, 21, or 20 nucleotides in length. The strand is preferably at least 19 nucleotides in length. For example, each strand can be between 21 and 25 nucleotides in length. Preferred sRNA agents have a duplex region of 17, 18, 19, 29, 21, 22, 23, 24, or 25 nucleotide pairs, and one or more overhangs, preferably one or two 3' overhangs, of 2-3 nucleotides.

In addition to homology to target RNA and the ability to down regulate a target gene, an iRNA agent will preferably have one or more of the following properties:

(1) it will be of the Formula 1, 2, 3, or 4 set out in the RNA Agent section below;
(2) if single stranded it will have a 5' modification which includes one or more phosphate groups or one or more analogs of a phosphate group;
(3) it will, despite modifications, even to a very large number, or all of the nucleosides, have an antisense strand that can present bases (or modified bases) in the proper three dimensional framework so as to be able to form correct base pairing and form a duplex structure with a homologous target RNA which is sufficient to allow down regulation of the target, e.g., by cleavage of the target RNA;
(4) it will, despite modifications, even to a very large number, or all of the nucleosides, still have "RNA-like" properties, i.e., it will possess the overall structural, chemical and physical properties of an RNA molecule, even though not exclusively, or even partly, of ribonucleotide-based content. For example, an iRNA agent can contain, e.g., a sense and/or an antisense strand in which all of the nucleotide sugars contain e.g., 2' fluoro in place of 2' hydroxyl. This deoxyribonucleotide-containing agent can still be expected to exhibit RNA-like properties. While not wishing to be bound by theory, the electronegative fluorine prefers an axial orientation when attached to the C2' position of ribose. This spatial preference of fluorine can, in turn, force the sugars to adopt a $C_{3'}$-endo pucker. This is the same puckering mode as observed in RNA molecules and gives rise to the RNA-characteristic A-family-type helix. Further, since fluorine is a good hydrogen bond acceptor, it can participate in the same hydrogen bonding interactions with water molecules that are known to stabilize RNA structures. (Generally, it is preferred that a modified moiety at the 2' sugar position will be able to enter into H-bonding which is more characteristic of the OH moiety of a ribonucleotide than the H moiety of a deoxyribonucleotide. A preferred iRNA agent will: exhibit a $C_{3'}$-endo pucker in all, or at least 50, 75, 80, 85, 90, or 95% of its sugars; exhibit a $C_{3'}$-endo pucker in a sufficient amount of its sugars that it can give rise to a the RNA-characteristic A-family-type helix; will have no more than 20, 10, 5, 4, 3, 2, or 1 sugar which is not a $C_{3'}$-endo pucker structure. These limitations are particularly preferably in the antisense strand;
(5) regardless of the nature of the modification, and even though the RNA agent can contain deoxynucleotides or modified deoxynucleotides, particularly in overhang or other single strand regions, it is preferred that DNA molecules, or any molecule in which more than 50, 60, or 70% of the nucleotides in the molecule, or more than 50, 60, or 70% of the nucleotides in a duplexed region are deoxyribonucleotides, or modified deoxyribonucleotides which are deoxy at the 2' position, are excluded from the definition of RNA agent.

A "single strand iRNA agent" as used herein, is an iRNA agent which is made up of a single molecule. It may include a duplexed region, formed by intra-strand pairing, e.g., it may be, or include, a hairpin or pan-handle structure. Single strand iRNA agents are preferably antisense with regard to the target molecule. In preferred embodiments single strand iRNA agents are 5' phosphorylated or include a phosphoryl analog at the 5' prime terminus. 5'-phosphate modifications include those which are compatible with RISC mediated gene silencing. Suitable modifications include: 5'-monophosphate ((HO)2(O)P—O-5'); 5'-diphosphate ((HO)2(O)P—O—P (HO)(O)—O-5'); 5'-triphosphate ((HO)2(O)P—O—(HO) (O)P—O—P(HO)(O)—O-5'); 5'-guanosine cap (7-methylated or non-methylated) (7m-G-O-5'-(HO)(O)P—O—(HO) (O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS) (S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, (OH)2(O)P-5'-CH2—), 5'-alkyletherphosphonates (R=alkylether=methoxymethyl (MeOCH2-), ethoxymethyl, etc., e.g. RP(OH)(O)—O-5'-). (These modifications can also be used with the antisense strand of a double stranded iRNA.)

A single strand iRNA agent should be sufficiently long that it can enter the RISC and participate in RISC mediated cleavage of a target mRNA. A single strand iRNA agent is at least 14, and more preferably at least 15, 20, 25, 29, 35, 40, or 50 nucleotides in length. It is preferably less than 200, 100, or 60 nucleotides in length.

Hairpin iRNA agents will have a duplex region equal to or at least 17, 18, 19, 29, 21, 22, 23, 24, or 25 nucleotide pairs. The duplex region will preferably be equal to or less than 200, 100, or 50, in length. Preferred ranges for the duplex region are 15-30, 17 to 23, 19 to 23, and 19 to 21 nucleotides pairs in length. The hairpin will preferably have a single strand overhang or terminal unpaired region, preferably the 3', and preferably of the antisense side of the hairpin. Preferred overhangs are 2-3 nucleotides in length.

A "double stranded (ds) iRNA agent" as used herein, is an iRNA agent which includes more than one, and preferably two, strands in which interchain hybridization can form a region of duplex structure.

The antisense strand of a double stranded iRNA agent should be equal to or at least, 14, 15, 16 17, 18, 19, 25, 29, 40, or 60 nucleotides in length. It should be equal to or less than 200, 100, or 50, nucleotides in length. Preferred ranges are 17 to 25, 19 to 23, and 19 to 21 nucleotides in length.

The sense strand of a double stranded iRNA agent should be equal to or at least 14, 15, 16 17, 18, 19, 25, 29, 40, or 60 nucleotides in length. It should be equal to or less than 200, 100, or 50, nucleotides in length. Preferred ranges are 17 to 25, 19 to 23, and 19 to 21 nucleotides in length.

The double strand portion of a double stranded iRNA agent should be equal to or at least, 14, 15, 16 17, 18, 19, 20, 21, 22, 23, 24, 25, 29, 40, or 60 nucleotide pairs in length. It should be equal to or less than 200, 100, or 50, nucleotides pairs in length. Preferred ranges are 15-30, 17 to 23, 19 to 23, and 19 to 21 nucleotides pairs in length.

In many embodiments, the ds iRNA agent is sufficiently large that it can be cleaved by an endogenous molecule, e.g., by Dicer, to produce smaller ds iRNA agents, e.g., sRNAs agents It may be desirable to modify one or both of the antisense and sense strands of a double strand iRNA agent. In some cases they will have the same modification or the same class of modification but in other cases the sense and antisense strand will have different modifications, e.g., in some cases it is desirable to modify only the sense strand. It may be desirable to modify only the sense strand, e.g., to inactivate it, e.g., the sense strand can be modified in order to inactivate the sense strand and prevent formation of an active sRNA/protein or RISC. This can be accomplished by a modification which prevents 5'-phosphorylation of the sense strand, e.g., by modification with a 5'-O-methyl ribonucleotide (see Nykänen et al., (2001) ATP requirements and small interfering RNA structure in the RNA interference pathway. Cell 107, 309-321.) Other modifications which prevent phosphorylation can also be used, e.g., simply substituting the 5'-OH by H rather than O-Me. Alternatively, a large bulky group may be added to the 5'-phosphate turning it into a phosphodiester linkage, though this may be less desirable as phosphodiesterases can cleave such a linkage and release a functional sRNA 5'-end. Antisense strand modifications include 5' phosphorylation as well as any of the other 5' modifications discussed herein, particularly the 5' modifications discussed above in the section on single stranded iRNA molecules.

It is preferred that the sense and antisense strands be chosen such that the ds iRNA agent includes a single strand or unpaired region at one or both ends of the molecule. Thus, a ds iRNA agent contains sense and antisense strands, preferable paired to contain an overhang, e.g., one or two 5' or 3' overhangs but preferably a 3' overhang of 2-3 nucleotides. Most embodiments will have a 3' overhang. Preferred sRNA agents will have single-stranded overhangs, preferably 3' overhangs, of 1 or preferably 2 or 3 nucleotides in length at each end. The overhangs can be the result of one strand being longer than the other, or the result of two strands of the same length being staggered. 5' ends are preferably phosphorylated.

Preferred lengths for the duplexed region is between 15 and 30, most preferably 18, 19, 20, 21, 22, and 23 nucleotides in length, e.g., in the sRNA agent range discussed above. sRNA agents can resemble in length and structure the natural Dicer processed products from long dsRNAs. Embodiments in which the two strands of the sRNA agent are linked, e.g., covalently linked are also included. Hairpin, or other single strand structures which provide the required double stranded region, and preferably a 3' overhang are also within the invention.

The isolated iRNA agents described herein, including ds iRNA agents and sRNA agents can mediate silencing of a target RNA, e.g., mRNA, e.g., a transcript of a gene that encodes a protein. For convenience, such mRNA is also referred to herein as mRNA to be silenced. Such a gene is also referred to as a target gene. In general, the RNA to be silenced is an endogenous gene or a pathogen gene. In addition, RNAs other than mRNA, e.g., tRNAs, and viral RNAs, can also be targeted.

As used herein, the phrase "mediates RNAi" refers to the ability to silence, in a sequence specific manner, a target RNA. While not wishing to be bound by theory, it is believed that silencing uses the RNAi machinery or process and a guide RNA, e.g., an sRNA agent of 21 to 23 nucleotides.

As used herein, "specifically hybridizable" and "complementary" are terms which are used to indicate a sufficient degree of complementarity such that stable and specific binding occurs between a compound of the invention and a target RNA molecule. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 5 nucleotides.

In one embodiment, an iRNA agent is "sufficiently complementary" to a target RNA, e.g., a target mRNA, such that the iRNA agent silences production of protein encoded by the target mRNA. In another embodiment, the iRNA agent is "exactly complementary" (excluding the RRMS containing subunit(s)) to a target RNA, e.g., the target RNA and the iRNA agent anneal, preferably to form a hybrid made exclusively of Watson-Crick basepairs in the region of exact complementarity. A "sufficiently complementary" target RNA can include an internal region (e.g., of at least 10 nucleotides) that is exactly complementary to a target RNA. Moreover, in some embodiments, the iRNA agent specifically discriminates a single-nucleotide difference. In this case, the iRNA agent only mediates RNAi if exact complementary is found in the region (e.g., within 7 nucleotides of) the single-nucleotide difference.

As used herein, the term "oligonucleotide" refers to a nucleic acid molecule (RNA or DNA) preferably of length less than 100, 200, 300, or 400 nucleotides.

RNA agents discussed herein include otherwise unmodified RNA as well as RNA which have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al., (1994) Summary: the modified nucleosides of RNA, Nucleic Acids Res. 22: 2183-2196. Such rare or unusual RNAs, often termed modified RNAs (apparently because the are typically the result of a post transcriptionally modification) are within the term unmodified RNA, as used herein. Modified RNA as used herein refers to a molecule in which one or more of the components of the nucleic acid, namely sugars, bases, and phosphate moieties, are different from that which occur in nature, preferably different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone. Examples of all of the above are discussed herein.

Much of the discussion below refers to single strand molecules. In many embodiments of the invention a double stranded iRNA agent, e.g., a partially double stranded iRNA agent, is required or preferred. Thus, it is understood that that double stranded structures (e.g. where two separate molecules are contacted to form the double stranded region or where the double stranded region is formed by intramolecular pairing (e.g., a hairpin structure)) made of the single stranded structures described below are within the invention. Preferred lengths are described elsewhere herein.

As nucleic acids are polymers of subunits or monomers, many of the modifications described below occur at a position which is repeated within a nucleic acid, e.g., a modification of a base, or a phosphate moiety, or the a non-linking O of a phosphate moiety. In some cases the modification will occur at all of the subject positions in the nucleic acid but in many, and in fact in most cases it will not. By way of example, a modification may only occur at a 3' or 5' terminal position, may only occur in a terminal regions, e.g. at a position on a terminal nucleotide or in the last 2, 3, 4, 5, or 10 nucleotides of a strand. A modification may occur in a double strand region, a single strand region, or in both. A modification may occur only in the double strand region of an RNA or may only occur in a single strand region of an RNA. E.g., a phosphorothioate modification at a non-linking O position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. The 5' end or ends can be phosphorylated.

In some embodiments it is particularly preferred, e.g., to enhance stability, to include particular bases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang will be modified, e.g., with a modification described herein. Modifications can include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. Overhangs need not be homologous with the target sequence.

Modifications and nucleotide surrogates are discussed below.

FORMULA 1

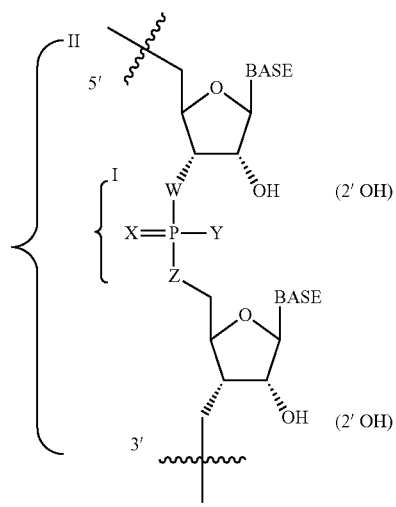

The scaffold presented above in Formula 1 represents a portion of a ribonucleic acid. The basic components are the ribose sugar, the base, the terminal phosphates, and phosphate internucleotide linkers. Where the bases are naturally occurring bases, e.g., adenine, uracil, guanine or cytosine, the sugars are the unmodified 2' hydroxyl ribose sugar (as depicted) and W, X, Y, and Z are all O, Formula 1 represents a naturally occurring unmodified oligoribonucleotide.

Unmodified oligoribonucleotides may be less than optimal in some applications, e.g., unmodified oligoribonucleotides can be prone to degradation by e.g., cellular nucleases. Nucleases can hydrolyze nucleic acid phosphodiester bonds. However, chemical modifications to one or more of the above RNA components can confer improved properties, and, e.g., can render oligoribonucleotides more stable to nucleases. Unmodified oligoribonucleotides may also be less than optimal in terms of offering tethering points for attaching ligands or other moieties to an iRNA agent.

Modified nucleic acids and nucleotide surrogates can include one or more of:

(i) alteration, e.g., replacement, of one or both of the non-linking (X and Y) phosphate oxygens and/or of one or more of the linking (W and Z) phosphate oxygens (When the phosphate is in the terminal position, one of the positions W or Z will not link the phosphate to an additional element in a naturally occurring ribonucleic acid. However, for simplicity of terminology, except where otherwise noted, the W position at the 5' end of a nucleic acid and the terminal Z position at the 3' end of a nucleic acid, are within the term "linking phosphate oxygens" as used herein.);

(ii) alteration, e.g., replacement, of a constituent of the ribose sugar, e.g., of the 2' hydroxyl on the ribose sugar, or wholesale replacement of the ribose sugar with a structure other than ribose, e.g., as described herein;

(iii) wholesale replacement of the phosphate moiety (bracket I) with "dephospho" linkers;

(iv) modification or replacement of a naturally occurring base;

(v) replacement or modification of the ribose-phosphate backbone (bracket II);

(vi) modification of the 3' end or 5' end of the RNA, e.g., removal, modification or replacement of a terminal phosphate group or conjugation of a moiety, e.g. a fluorescently labeled moiety, to either the 3' or 5' end of RNA.

The terms replacement, modification, alteration, and the like, as used in this context, do not imply any process limitation, e.g., modification does not mean that one must start with a reference or naturally occurring ribonucleic acid and modify it to produce a modified ribonucleic acid bur rather modified simply indicates a difference from a naturally occurring molecule.

It is understood that the actual electronic structure of some chemical entities cannot be adequately represented by only one canonical form (i.e. Lewis structure). While not wishing to be bound by theory, the actual structure can instead be some hybrid or weighted average of two or more canonical forms, known collectively as resonance forms or structures. Resonance structures are not discrete chemical entities and exist only on paper. They differ from one another only in the placement or "localization" of the bonding and nonbonding electrons for a particular chemical entity. It can be possible for one resonance structure to contribute to a greater extent to the hybrid than the others. Thus, the written and graphical descriptions of the embodiments of the present invention are made in terms of what the art recognizes as the predominant resonance form for a particular species. For example, any phosphoroamidate (replacement of a nonlinking oxygen with nitrogen) would be represented by X=O and Y=N in the above figure.

Specific modifications are discussed in more detail below.

The Phosphate Group

The phosphate group is a negatively charged species. The charge is distributed equally over the two non-linking oxygen atoms (i.e., X and Y in Formula 1 above). However, the phosphate group can be modified by replacing one of the oxygens with a different substituent. One result of this modification to RNA phosphate backbones can be increased resistance of the oligoribonucleotide to nucleolytic breakdown. Thus while not wishing to be bound by theory, it can be desirable in some embodiments to introduce alterations which result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. Unlike the situation where only one of X or Y is altered, the phosphorus center in the phosphorodithioates is achiral which precludes the formation of oligoribonucleotides diastereomers. Diastereomer formation can result in a preparation in which the individual diastereomers exhibit varying resistance to nucleases. Further, the hybridization affinity of RNA containing chiral phosphate groups can be lower relative to the corresponding unmodified RNA species. Thus, while not wishing to be bound by theory, modifications to both X and Y which eliminate the chiral center, e.g. phosphorodithioate formation, may be desirable in that they cannot produce diastereomer mixtures. Thus, X can be any one of S, Se, B, C, H, N, or OR (R is alkyl or aryl). Thus Y can be any one of S, Se, B, C, H, N, or OR (R is alkyl or aryl). Replacement of X and/or Y with sulfur is preferred.

The phosphate linker can also be modified by replacement of a linking oxygen (i.e., W or Z in Formula 1) with nitrogen (bridged phosphoroamidates), sulfur (bridged phosphorothioates) and carbon (bridged methylenephosphonates). The replacement can occur at a terminal oxygen (position W (3') or position Z (5'). Replacement of W with carbon or Z with nitrogen is preferred.

Candidate agents can be evaluated for suitability as described below.

The Sugar Group

A modified RNA can include modification of all or some of the sugar groups of the ribonucleic acid. E.g., the 2' hydroxyl group (OH) can be modified or replaced with a number of different "oxy" or "deoxy" substituents. While not being bound by theory, enhanced stability is expected since the hydroxyl can no longer be deprotonated to form a 2' alkoxide ion. The 2' alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE (AMINE=$NH_2$; alkylamino, dialkylamino, heterocyclyl, arylamino, diaryl amino, heteroaryl amino, or diheteroaryl amino, ethylene diamine, polyamino) and aminoalkoxy, $O(CH_2)_nAMINE$, (e.g., AMINE=$NH_2$; alkylamino, dialkylamino, heterocyclyl, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Preferred substitutents are 2'-methoxyethyl, 2'-OCH3, 2'-O-allyl, 2'-C— allyl, and 2'-fluoro.

The sugar group can also contain one or more carbons that possess the opposite stereochemical configuration than that of the corresponding carbon in ribose. Thus, a modified RNA can include nucleotides containing e.g., arabinose, as the sugar.

Modified RNAs can also include "abasic" sugars, which lack a nucleobase at C-1'. These abasic sugars can also be further contain modifications at one or more of the constituent sugar atoms.

To maximize nuclease resistance, the 2' modifications can be used in combination with one or more phosphate linker modifications (e.g., phosphorothioate). The so-called "chimeric" oligonucleotides are those that contain two or more different modifications.

The modification can also entail the wholesale replacement of a ribose structure with another entity at one or more sites in the iRNA agent. These modifications are described in section entitled Ribose Replacements for RRMSs.

Candidate modifications can be evaluated as described below.

Replacement of the Phosphate Group

The phosphate group can be replaced by non-phosphorus containing connectors (cf. Bracket I in Formula 1 above). While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methylenecarbonylamino and methylenemethylimino groups.

Candidate modifications can be evaluated as described below.

Replacement of Ribophosphate Backbone

Oligonucleotide-mimicking scaffolds can also be constructed wherein the phosphate linker and ribose sugar are replaced by nuclease resistant nucleoside or nucleotide surrogates (see Bracket II of Formula 1 above). While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone.

Examples include the mophilino, cyclobutyl, pyrrolidine and peptide nucleic acid (PNA) nucleoside surrogates. A preferred surrogate is a PNA surrogate.

Candidate modifications can be evaluated as described below.

Terminal Modifications

The 3' and 5' ends of an oligonucleotide can be modified. Such modifications can be at the 3' end, 5' end or both ends of the molecule. They can include modification or replacement of an entire terminal phosphate or of one or more of the atoms of the phosphate group. E.g., the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a spacer. The terminal atom of the spacer can connect to or replace the linking atom of the phosphate group or the C-3' or C-5' O, N, S or C group of the sugar. Alternatively, the spacer can connect to or replace the terminal atom of a nucleotide surrogate (e.g., PNAs). These spacers or linkers can include e.g., —(CH$_2$)$_n$—, —(CH$_2$)$_n$N—, —(CH$_2$)$_n$O—, —(CH$_2$)$_n$S—, O(CH$_2$CH$_2$O)$_n$CH$_2$CH$_2$OH (e.g., n=3 or 6), abasic sugars, amide, carboxy, amine, oxyamine, oxyimine, thioether, disulfide, thiourea, sulfonamide, or morpholino, or biotin and fluorescein reagents. When a spacer/phosphate-functional molecular entity-spacer/phosphate array is interposed between two strands of iRNA agents, this array can substitute for a hairpin RNA loop in a hairpin-type RNA agent. The 3' end can be an —OH group. While not wishing to be bound by theory, it is believed that conjugation of certain moieties can improve transport, hybridization, and specificity properties. Again, while not wishing to be bound by theory, it may be desirable to introduce terminal alterations that improve nuclease resistance. Other examples of terminal modifications include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)litho-cholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles).

Terminal modifications can be added for a number of reasons, including as discussed elsewhere herein to modulate activity or to modulate resistance to degradation. Terminal modifications useful for modulating activity include modification of the 5' end with phosphate or phosphate analogs. E.g., in preferred embodiments iRNA agents, especially antisense strands, are 5' phosphorylated or include a phosphoryl analog at the 5' prime terminus. 5'-phosphate modifications include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, (OH)2(O)P-5'-CH2—), 5'-alkyletherphosphonates (R=alkylether=methoxymethyl (MeOCH2—), ethoxymethyl, etc., e.g. RP(OH)(O)—O-5'-).

Terminal modifications can also be useful for monitoring distribution, and in such cases the preferred groups to be added include fluorophores, e.g., fluorscein or an Alexa dye, e.g., Alexa 488. Terminal modifications can also be useful for enhancing uptake, useful modifications for this include cholesterol. Terminal modifications can also be useful for cross-linking an RNA agent to another moiety; modifications useful for this include mitomycin C.

Candidate modifications can be evaluated as described below.

The Bases

Adenine, guanine, cytosine and uracil are the most common bases found in RNA. These bases can be modified or replaced to provide RNA's having improved properties. E.g., nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases, e.g., "unusual bases" and "universal bases" described herein, can be employed. Examples include without limitation 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6, N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, N$^4$-acetyl cytosine, 2-thiocytosine, N6-methyladenine, N6-isopentyladenine, 2-methylthio-N6-isopentenyladenine, N-methylguanines, or O-alkylated bases. Further purines and pyrimidines include those disclosed in U.S. Pat. No. 3,687,808, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

Generally, base changes are less preferred for promoting stability, but they can be useful for other reasons, e.g., some, e.g., 2,6-diaminopurine and 2 amino purine, are fluorescent. Modified bases can reduce target specificity. This should be taken into consideration in the design of iRNA agents.

Candidate modifications can be evaluated as described below.

Evaluation of Candidate RNA's

One can evaluate a candidate RNA agent, e.g., a modified RNA, for a selected property by exposing the agent or modified molecule and a control molecule to the appropriate conditions and evaluating for the presence of the selected property. For example, resistance to a degradent can be evaluated as follows. A candidate modified RNA (and preferably a control molecule, usually the unmodified form) can be exposed to degradative conditions, e.g., exposed to a milieu, which includes a degradative agent, e.g., a nuclease. E.g., one can use a biological sample, e.g., one that is similar to a milieu, which might be encountered, in therapeutic use, e.g., blood or a cellular fraction, e.g., a cell-free homogenate or disrupted cells. The candidate and control could then be evaluated for resistance to degradation by any of a number of approaches. For example, the candidate and control could be labeled, preferably prior to exposure, with, e.g., a radioactive or enzymatic label, or a fluorescent label, such as Cy3 or Cy5. Control and modified RNA's can be incubated with the degradative agent, and optionally a control, e.g., an inactivated, e.g., heat inactivated, degradative agent. A physical parameter, e.g., size, of the modified and control molecules are then determined. They can be determined by a physical method, e.g., by polyacrylamide gel electrophoresis or a sizing column, to assess whether the molecule has maintained its original length, or assessed functionally. Alternatively, Northern blot analysis can be used to assay the length of an unlabeled modified molecule.

A functional assay can also be used to evaluate the candidate agent. A functional assay can be applied initially or after an earlier non-functional assay, (e.g., assay for resistance to degradation) to determine if the modification alters the ability of the molecule to silence gene expression. For example, a cell, e.g., a mammalian cell, such as a mouse or human cell, can be co-transfected with a plasmid expressing a fluorescent protein, e.g., GFP, and a candidate RNA agent homologous to the transcript encoding the fluorescent protein (see, e.g., WO 00/44914). For example, a modified dsRNA homologous to the GFP mRNA can be assayed for the ability to inhibit GFP expression by monitoring for a decrease in cell fluorescence, as compared to a control cell, in which the transfection did not include the candidate dsRNA, e.g., controls with no agent added and/or controls with a non-modified RNA added. Efficacy of the candidate agent on gene expression can be assessed by comparing cell fluorescence in the presence of the modified and unmodified dsRNA agents.

In an alternative functional assay, a candidate dsRNA agent homologous to an endogenous mouse gene, preferably a maternally expressed gene, such as c-mos, can be injected into an immature mouse oocyte to assess the ability of the agent to inhibit gene expression in vivo (see, e.g., WO 01/36646). A phenotype of the oocyte, e.g., the ability to maintain arrest in metaphase II, can be monitored as an indicator that the agent is inhibiting expression. For example, cleavage of c-mos mRNA by a dsRNA agent would cause the oocyte to exit metaphase arrest and initiate parthenogenetic development (Colledge et al. Nature 370: 65-68, 1994; Hashimoto et al. Nature, 370:68-71, 1994). The effect of the modified agent on target RNA levels can be verified by Northern blot to assay for a decrease in the level of target mRNA, or by Western blot to assay for a decrease in the level of target protein, as compared to a negative control. Controls can include cells in which with no agent is added and/or cells in which a non-modified RNA is added.

REFERENCES

General References

The oligoribonucleotides and oligoribonucleosides used in accordance with this invention may be with solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL Press, 1991 (especially Chapter 1, Modern machine-aided methods of oligodeoxyribonucleotide synthesis, Chapter 2, Oligoribonucleotide synthesis, Chapter 3,2'-O-Methyloligoribonucleotide-s: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and. Chapter 7, Oligodeoxynucleotides containing modified bases. Other particularly useful synthetic procedures, reagents, blocking groups and reaction conditions are described in Martin, P., *Helv. Chim. Acta,* 1995, 78, 486-504; Beaucage, S. L. and Iyer, R. P., *Tetrahedron,* 1992, 48, 2223-2311 and Beaucage, S. L. and Iyer, R. P., *Tetrahedron,* 1993, 49, 6123-6194, or references referred to therein.

Modification described in WO 00/44895, WO01/75164, or WO02/44321 can be used herein.

The disclosure of all publications, patents, and published patent applications listed herein are hereby incorporated by reference.

Phosphate Group References

The preparation of phosphinate oligoribonucleotides is described in U.S. Pat. No. 5,508,270. The preparation of alkyl phosphonate oligoribonucleotides is described in U.S. Pat. No. 4,469,863. The preparation of phosphoramidite oligoribonucleotides is described in U.S. Pat. No. 5,256,775 or U.S. Pat. No. 5,366,878. The preparation of phosphotriester oligoribonucleotides is described in U.S. Pat. No. 5,023,243. The preparation of borano phosphate oligoribonucleotide is described in U.S. Pat. Nos. 5,130,302 and 5,177,198. The preparation of 3'-Deoxy-3'-amino phosphoramidate oligoribonucleotides is described in U.S. Pat. No. 5,476,925. 3'-Deoxy-3'-methylenephosphonate oligoribonucleotides is described in An, H, et al. *J. Org. Chem.* 2001, 66, 2789-2801. Preparation of sulfur bridged nucleotides is described in Sproat et al. *Nucleosides Nucleotides* 1988, 7,651 and Crosstick et al. *Tetrahedron Lett.* 1989, 30, 4693.

Sugar Group References

Modifications to the 2' modifications can be found in Verma, S. et al. *Annu. Rev. Biochem.* 1998, 67, 99-134 and all references therein. Specific modifications to the ribose can be found in the following references: 2'-fluoro (Kawasaki et. al., *J. Med. Chem.,* 1993, 36, 831-841), 2'-MOE (Martin, P. *Helv. Chim. Acta* 1996, 79, 1930-1938), "LNA" (Wengel, J. *Acc. Chem. Res.* 1999, 32, 301-310).

Replacement of the Phosphate Group References

Methylenemethylimino linked oligoribonucleosides, also identified herein as MMI linked oligoribonucleosides, methylenedimethylhydrazo linked oligoribonucleosides, also identified herein as MDH linked oligoribonucleosides, and methylenecarbonylamino linked oligonucleosides, also identified herein as amide-3 linked oligoribonucleosides, and methyleneaminocarbonyl linked oligonucleosides, also identified herein as amide-4 linked oligoribonucleosides as well as mixed backbone compounds having, as for instance, alternating MMI and PO or PS linkages can be prepared as is described in U.S. Pat. Nos. 5,378,825, 5,386,023, 5,489,677 and in published PCT applications PCT/US92/04294 and PCT/US92/04305 (published as WO 92/20822 WO and 92/20823, respectively). Formacetal and thioformacetal linked oligoribonucleosides can be prepared as is described in U.S. Pat. Nos. 5,264,562 and 5,264,564. Ethylene oxide linked oligoribonucleosides can be prepared as is described in U.S. Pat. No. 5,223,618. Siloxane replacements are described in Cormier, J. F. et al. *Nucleic Acids Res.* 1988, 16, 4583. Carbonate replacements are described in Tittensor, J. R. *J. Chem. Soc. C* 1971, 1933. Carboxymethyl replacements are described in Edge, M. D. et al. *J. Chem. Soc. Perkin Trans.* 11972, 1991. Carbamate replacements are described in Stirchak, E. P. *Nucleic Acids Res.* 1989, 17, 6129.

Replacement of the Phosphate-Ribose Backbone References

Cyclobutyl sugar surrogate compounds can be prepared as is described in U.S. Pat. No. 5,359,044. Pyrrolidine sugar surrogate can be prepared as is described in U.S. Pat. No. 5,519,134. Morpholino sugar surrogates can be prepared as is described in U.S. Pat. Nos. 5,142,047 and 5,235,033, and other related patent disclosures. Peptide Nucleic Acids (PNAs) are known per se and can be prepared in accordance with any of the various procedures referred to in Peptide Nucleic Acids (PNA): Synthesis, Properties and Potential Applications, Bioorganic & Medicinal Chemistry, 1996, 4, 5-23. They may also be prepared in accordance with U.S. Pat. No. 5,539,083.

Terminal Modification References

Terminal modifications are described in Manoharan, M. et al. *Antisense and Nucleic Acid Drug Development* 12, 103-128 (2002) and references therein.

Bases References

N-2 substituted purine nucleoside amidites can be prepared as is described in U.S. Pat. No. 5,459,255. 3-Deaza purine nucleoside amidites can be prepared as is described in U.S. Pat. No. 5,457,191. 5,6-Substituted pyrimidine nucleoside amidites can be prepared as is described in U.S. Pat. No. 5,614,617. 5-Propynyl pyrimidine nucleoside amidites can be prepared as is described in U.S. Pat. No. 5,484,908. Additional references can be disclosed in the above section on base modifications.

Preferred iRNA Agents

Preferred RNA agents have the following structure (see Formula 2 below):

Referring to Formula 2 above, $R^1$, $R^2$, and $R^3$ are each, independently, H, (i.e. abasic nucleotides), adenine, guanine, cytosine and uracil, inosine, thymine, xanthine, hypoxanthine, nubularine, tubercidine, isoguanisine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl) uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, 7-deazaguanine, N6, N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, $N^4$-acetyl cytosine, 2-thiocytosine, N6-methyladenine, N6-isopentyladenine, 2-methylthio-N6-isopentenyladenine, N-methylguanines, or O-alkylated bases.

$R^4$, $R^5$, and $R^6$ are each, independently, $OR^8$, $O(CH_2CH_2O)_mCH_2CH_2OR^8$; $O(CH_2)_nR^9$; $O(CH_2)_nOR^9$, H; halo; $NH_2$; $NHR^8$; $N(R^8)_2$; $NH(CH_2CH_2NH)_m$ $CH_2CH_2NHR^9$; $NHC(O)R^8$; cyano; mercapto, $SR^8$; alkylthio-alkyl; alkyl, aralkyl, cycloalkyl, aryl, heteroaryl, alkenyl, alkynyl, each of which may be optionally substituted with halo, hydroxy, oxo, nitro, haloalkyl, alkyl, alkaryl, aryl, aralkyl, alkoxy, aryloxy, amino, alkylamino, dialkylamino, heterocyclyl, arylamino, diaryl amino, heteroaryl amino, diheteroaryl amino, acylamino, alkylcarbamoyl, arylcarbamoyl, aminoalkyl, alkoxycarbonyl, carboxy, hydroxyalkyl, alkanesulfonyl, alkanesulfonamido, arenesulfonamido, aralkylsulfonamido, alkylcarbonyl, acyloxy, cyano, or ureido; or $R^4$, $R^5$, or $R^6$ together combine with $R^7$ to form an [—O—$CH_2$—] covalently bound bridge between the sugar 2' and 4' carbons.

$A^1$ is:

FORMULA 2

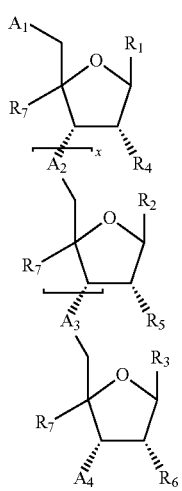

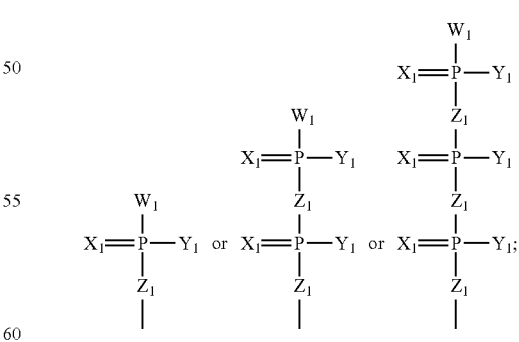

H; OH; $OCH_3$; $W^1$; an abasic nucleotide; or absent;

(a preferred A1, especially with regard to anti-sense strands, is chosen from 5'-monophosphate ((HO)2(O)P—O-5'), 5'-diphosphate ((HO)2(O)P—O—P(HO)(O)—O-5'), 5'-triphosphate ((HO)2(O)P—O—(HO)(O)P—O—P(HO) (O)—O-5'), 5'-guanosine cap (7-methylated or non-methylated) (7m-G-O-5'-(HO)(O)P—O—(HO)(O)P—O—P(HO)(O)—O-5'), 5'-adenosine cap (Appp), and any modified or unmodified nucleotide cap structure (N—O-5'-(HO)(O)P-β-(HO)(O)P—O—P(HO)(O)—O-5'), 5'-monothiophosphate (phosphorothioate; (HO)2(S)P—O-5'), 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)2(O)P—NH-5', (HO)(NH$_2$)(O)P—O-5'), 5'-alkylphosphonates (R=alkyl=methyl, ethyl, isopropyl, propyl, etc., e.g. RP(OH)(O)—O-5'-, (OH)$_2$(O)P-5'-CH$_2$—), 5'-alkyletherphosphonates (R=alkylether=methoxymethyl (MeOCH$_2$—), ethoxymethyl, etc., e.g. RP(OH)(O)—O-5'-)).

$A^2$ is:

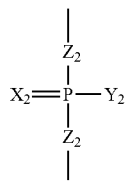

$A^3$ is:

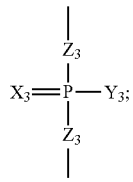

and
$A^4$ is:

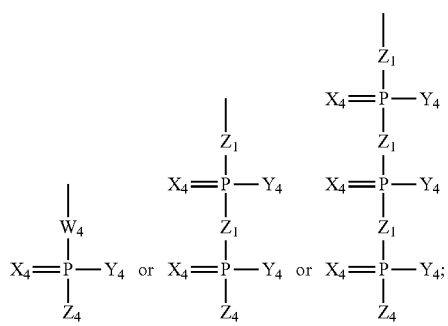

H; $Z^4$; an inverted nucleotide; an abasic nucleotide; or absent.

$W^1$ is OH, $(CH_2)_n R^{10}$, $(CH_2)_n NHR^{10}$, $(CH_2)_n OR^{10}$, $(CH_2)_n SR^{10}$; $O(CH_2)_n R^{10}$; $O(CH_2)_n OR^{10}$, $O(CH_2)_n NR^{10}$, $O(CH_2)_n SR^{10}$; $O(CH_2)_n SS(CH_2)_n OR^{10}$, $O(CH_2)_n C(O)OR^{10}$, $NH(CH_2)_n R^{10}$; $NH(CH_2)_n NR^{10}$; $NH(CH_2)_n OR^{10}$, $NH(CH_2)_n SR^{10}$; $S(CH_2)_n R^{10}$, $S(CH_2)_n NR^{10}$, $S(CH_2)_n OR^{10}$, $S(CH_2)_n SR^{10} O(CH_2CH_2O)_m CH_2CH_2OR^{10}$; $O(CH_2CH_2O)_m CH_2CH_2NHR^{10}$, $NH(CH_2CH_2NH)_m CH_2CH_2NHR^{10}$; $Q-R^{10}$, $O-Q-R^{10} N-Q-R^{10}$, $S-Q-R^{10}$ or —O—. $W^4$ is O, CH$_2$, NH, or S.

$X^1$, $X^2$, $X^3$, and $X^4$ are each, independently, O or S.

$Y^1$, $Y^2$, $Y^3$, and $Y^4$ are each, independently, OH, O⁻, OR$^8$, S, Se, BH$_3^-$, H, NHR$^9$, N(R$^9$)$_2$ alkyl, cycloalkyl, aralkyl, aryl, or heteroaryl, each of which may be optionally substituted.

$Z^1$, $Z^2$, and $Z^3$ are each independently O, CH$_2$, NH, or S. $Z^4$ is OH, $(CH_2)_n R^{10}$, $(CH_2)_n NHR^{10}$, $(CH_2)_n OR^{10}$, $(CH_2)_n SR^{10}$; $O(CH_2)_n R^{10}$; $O(CH_2)_n OR^{10}$, $O(CH_2)_n NR^{10}$, $O(CH_2)_n SR^{10}$, $O(CH_2)_n SS(CH_2)_n OR^{10}$, $O(CH_2)_n C(O)OR^{10}$; $NH(CH_2)_n R^{10}$; $NH(CH_2)_n NR^{10}$; $NH(CH_2)_n OR^{10}$, $NH(CH_2)_n SR^{10}$; $S(CH_2)_n R^{10}$, $S(CH_2)_n NR^{10}$, $S(CH_2)_n OR^{10}$, $S(CH_2)_n SR^{10} O(CH_2CH_2O)_m CH_2CH_2OR^{10}$, $O(CH_2CH_2O)_m CH_2CH_2NHR^{10}$, $NH(CH_2CH_2NH)_m CH_2CH_2NHR^{10}$; $Q-R^{10}$, $O-Q-R^{10} N-Q-R^{10}$, $S-Q-R^{10}$.

x is 5-100, chosen to comply with a length for an RNA agent described herein.

$R^7$ is H; or is together combined with $R^4$, $R^5$, or $R^6$ to form an [—O—CH$_2$—] covalently bound bridge between the sugar 2' and 4' carbons.

$R^8$ is alkyl, cycloalkyl, aryl, aralkyl, heterocyclyl, heteroaryl, amino acid, or sugar; $R^9$ is NH$_2$, alkylamino, dialkylamino, heterocyclyl, arylamino, diaryl amino, heteroaryl amino, diheteroaryl amino, or amino acid; and $R^{10}$ is H; fluorophore (pyrene, TAMRA, fluorescein, Cy3 or Cy5 dyes); sulfur, silicon, boron or ester protecting group; intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipohilic carriers (cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino; alkyl, cycloalkyl, aryl, aralkyl, heteroaryl; radiolabelled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles); or an RNA agent. m is 0-1,000,000, and n is 0-20. Q is a spacer selected from the group consisting of abasic sugar, amide, carboxy, oxyamine, oxyimine, thioether, disulfide, thiourea, sulfonamide, or morpholino, biotin or fluorescein reagents.

Preferred RNA agents in which the entire phosphate group has been replaced have the following structure (see Formula 3 below):

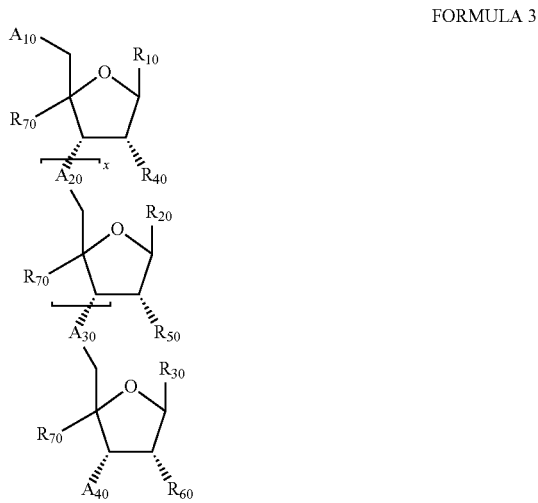

FORMULA 3

Referring to Formula 3, $A^{10}$-$A^{40}$ is L-G-L; $A^{10}$ and/or $A^{40}$ may be absent, in which L is a linker, wherein one or both L may be present or absent and is selected from the group consisting of $CH_2(CH_2)_g$; $N(CH_2)_g$; $O(CH_2)_g$; $S(CH_2)_g$. G is a functional group selected from the group consisting of siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino.

$R^{10}$, $R^{20}$, and $R^{30}$ are each, independently, H, (i.e. abasic nucleotides), adenine, guanine, cytosine and uracil, inosine, thymine, xanthine, hypoxanthine, nubularine, tubercidine, isoguanisine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, 7-deazaguanine, N6, N6-dimethyladenine, 2,6-diaminopurine, 5-amino-allyl-uracil, N3-methyluracil substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, N4-acetyl cytosine, 2-thiocytosine, N6-methyladenine, N6-isopentyladenine, 2-methylthio-N6-isopentenyladenine, N-methylguanines, or O-alkylated bases.

$R^{40}$, $R^{50}$, and $R^{60}$ are each, independently, $OR^8$, $O(CH_2CH_2O)_mCH_2CH_2OR^8$; $O(CH_2)_nR^9$; $O(CH_2)_nOR^9$, H; halo; $NH_2$; $NHR^8$; $N(R^8)_2$; $NH(CH_2CH_2NH)_mCH_2CH_2R^9$; $NHC(O)R^8$; cyano; mercapto, $SR^7$; alkyl-thio-alkyl; alkyl, aralkyl, cycloalkyl, aryl, heteroaryl, alkenyl, alkynyl, each of which may be optionally substituted with halo, hydroxy, oxo, nitro, haloalkyl, alkyl, alkaryl, aryl, aralkyl, alkoxy, aryloxy, amino, alkylamino, dialkylamino, heterocyclyl, arylamino, diaryl amino, heteroaryl amino, diheteroaryl amino, acylamino, alkylcarbamoyl, arylcarbamoyl, aminoalkyl, alkoxycarbonyl, carboxy, hydroxyalkyl, alkanesulfonyl, alkanesulfonamido, arenesulfonamido, aralkylsulfonamido, alkylcarbonyl, acyloxy, cyano, and ureido groups; or $R^{40}$, $R^{50}$, or $R^{60}$ together combine with $R^{70}$ to form an [—O—$CH_2$—] covalently bound bridge between the sugar 2' and 4' carbons.

x is 5-100 or chosen to comply with a length for an RNA agent described herein.

$R^{70}$ is H; or is together combined with $R^{40}$, $R^{50}$, or $R^{60}$ to form an [—O—$CH_2$—] covalently bound bridge between the sugar 2' and 4' carbons.

$R^8$ is alkyl, cycloalkyl, aryl, aralkyl, heterocyclyl, heteroaryl, amino acid, or sugar; and $R^9$ is $NH_2$, alkylamino, dialkylamino, heterocyclyl, arylamino, diaryl amino, heteroaryl amino, diheteroaryl amino, or amino acid. m is 0-1,000,000, n is 0-20, and g is 0-2.

Preferred nucleoside surrogates have the following structure (see Formula 4 below):

$$SLR^{100}\text{-}(M\text{-}SLR^{200})_x\text{-}M\text{-}SLR^{300} \quad \text{FORMULA 4}$$

S is a nucleoside surrogate selected from the group consisting of mophilino, cyclobutyl, pyrrolidine and peptide nucleic acid. L is a linker and is selected from the group consisting of $CH_2(CH_2)_g$; $N(CH_2)_g$; $O(CH_2)_g$; $S(CH_2)_g$; —C(O)(CH_2)_n— or may be absent. M is an amide bond; sulfonamide; sulfinate; phosphate group; modified phosphate group as described herein; or may be absent.

$R^{100}$, $R^{200}$, and $R^{300}$ are each, independently, H (i.e., abasic nucleotides), adenine, guanine, cytosine and uracil, inosine, thymine, xanthine, hypoxanthine, nubularine, tubercidine, isoguanisine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, 7-deazaguanine, N6, N6-dimethyladenine, 2,6-diaminopurine, 5-amino-allyl-uracil, N3-methyluracil substituted 1, 2, 4,-triazoles, 2-pyridinones, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, N4-acetyl cytosine, 2-thiocytosine, N6-methyladenine, N6-isopentyladenine, 2-methylthio-N6-isopentenyladenine, N-methylguanines, or O-alkylated bases.

x is 5-100, or chosen to comply with a length for an RNA agent described herein; and g is 0-2.

Nuclease Resistant Monomers

The monomers and methods described herein can be used to prepare an RNA, e.g., an iRNA agent, that incorporates a nuclease resistant monomer (NRM), such as those described herein and those described in copending, co-owned U.S. Provisional Application Ser. No. 60/469,612, filed on May 9, 2003, and International Application No. PCT/US04/07070, both of which are hereby incorporated by reference.

An iRNA agent can include monomers which have been modified so as to inhibit degradation, e.g., by nucleases, e.g., endonucleases or exonucleases, found in the body of a subject. These monomers are referred to herein as NRMs, or nuclease resistance promoting monomers or modifications. In many cases these modifications will modulate other properties of the iRNA agent as well, e.g., the ability to interact with a protein, e.g., a transport protein, e.g., serum albumin, or a member of the RISC(RNA-induced Silencing Complex), or the ability of the first and second sequences to form a duplex with one another or to form a duplex with another sequence, e.g., a target molecule.

While not wishing to be bound by theory, it is believed that modifications of the sugar, base, and/or phosphate backbone in an iRNA agent can enhance endonuclease and exonuclease resistance, and can enhance interactions with transporter proteins and one or more of the functional components of the RISC complex. Preferred modifications are those that increase exonuclease and endonuclease resistance and thus prolong the half-life of the iRNA agent prior to interaction with the RISC complex, but at the same time do not render the iRNA agent resistant to endonuclease activity in the RISC complex. Again, while not wishing to be bound by any theory, it is believed that placement of the modifications at or near the 3' and/or 5' end of antisense strands can result in iRNA agents that meet the preferred nuclease resistance criteria delineated above. Again, still while not wishing to be bound by any theory, it is believed that placement of the modifications at e.g., the middle of a sense strand can result in iRNA agents that are relatively less likely to undergo off-targeting.

Modifications described herein can be incorporated into any double-stranded RNA and RNA-like molecule described herein, e.g., an iRNA agent. An iRNA agent may include a duplex comprising a hybridized sense and antisense strand, in which the antisense strand and/or the sense strand may include one or more of the modifications described herein. The anti sense strand may include modifications at the 3' end and/or the 5' end and/or at one or more positions that occur 1-6 (e.g., 1-5, 1-4, 1-3, 1-2) nucleotides from either end of the strand. The sense strand may include modifications at the 3' end and/or the 5' end and/or at any one of the intervening positions between the two ends of the strand. The iRNA agent may also include a duplex comprising two hybridized antisense strands. The first and/or the second antisense strand may include one or more of the modifications described herein. Thus, one and/or both antisense strands may include modifications at the 3' end and/or the 5' end and/or at one or more positions that occur 1-6 (e.g., 1-5, 1-4, 1-3, 1-2) nucleotides from either end of the strand. Particular configurations are discussed below.

Modifications that can be useful for producing iRNA agents that meet the preferred nuclease resistance criteria delineated above can include one or more of the following chemical and/or stereochemical modifications of the sugar, base, and/or phosphate backbone:

(i) chiral ($S_P$) thioates. Thus, preferred NRMs include nucleotide dimers with an enriched or pure for a particular chiral form of a modified phosphate group containing a heteroatom at the nonbridging position, e.g., Sp or Rp, at the position X, where this is the position normally occupied by the oxygen. The atom at X can also be S, Se, $Nr_2$, or $Br_3$. When X is S, enriched or chirally pure Sp linkage is preferred. Enriched means at least 70, 80, 90, 95, or 99% of the preferred form. Such NRMs are discussed in more detail below;

(ii) attachment of one or more cationic groups to the sugar, base, and/or the phosphorus atom of a phosphate or modified phosphate backbone moiety. Thus, preferred NRMs include monomers at the terminal position derivatized at a cationic group. As the 5' end of an antisense sequence should have a terminal —OH or phosphate group this NRM is preferably not used at the 5' end of an anti-sense sequence. The group should be attached at a position on the base which minimizes interference with H bond formation and hybridization, e.g., away form the face which interacts with the complementary base on the other strand, e.g, at the 5' position of a pyrimidine or a 7-position of a purine. These are discussed in more detail below;

(iii) nonphosphate linkages at the termini. Thus, preferred NRMs include Non-phosphate linkages, e.g., a linkage of 4 atoms which confers greater resistance to cleavage than does a phosphate bond. Examples include 3' $CH2-NCH_3$—O—$CH2-5'$ and 3' CH2-NH—(O=)—CH2-5';

(iv) 3'-bridging thiophosphates and 5'-bridging thiophosphates. Thus, preferred NRM's can included these structures;

(v) L-RNA, 2'-5' linkages, inverted linkages, a-nucleosides. Thus, other preferred NRM's include: L nucleosides and dimeric nucleotides derived from L-nucleosides; 2'-5' phosphate, non-phosphate and modified phosphate linkages (e.g., thiophosphates, phosphoramidates and boronophosphates); dimers having inverted linkages, e.g., 3'-3' or 5'-5' linkages; monomers having an alpha linkage at the 1' site on the sugar, e.g., the structures described herein having an alpha linkage;

(vi) conjugate groups. Thus, preferred NRM's can include e.g., a targeting moiety or a conjugated ligand described herein conjugated with the monomer, e.g., through the sugar, base, or backbone;

(vi) abasic linkages. Thus, preferred NRM's can include an abasic monomer, e.g., an abasic monomer as described herein (e.g., a nucleobaseless monomer); an aromatic or heterocyclic or polyheterocyclic aromatic monomer as described herein.; and (vii) 5'-phosphonates and 5'-phosphate prodrugs. Thus, preferred NRM's include monomers, preferably at the terminal position, e.g., the 5' position, in which one or more atoms of the phosphate group is derivatized with a protecting group, which protecting group or groups, are removed as a result of the action of a component in the subject's body, e.g, a carboxyesterase or an enzyme present in the subject's body. E.g., a phosphate prodrug in which a carboxy esterase cleaves the protected molecule resulting in the production of a thioate anion which attacks a carbon adjacent to the O of a phosphate and resulting in the production of an unprotected phosphate.

One or more different NRM modifications can be introduced into an iRNA agent or into a sequence of an iRNA agent. An NRM modification can be used more than once in a sequence or in an iRNA agent. As some NRM's interfere with hybridization the total number incorporated, should be such that acceptable levels of iRNA agent duplex formation are maintained.

In some embodiments NRM modifications are introduced into the terminal the cleavage site or in the cleavage region of a sequence (a sense strand or sequence) which does not target a desired sequence or gene in the subject. This can reduce off-target silencing.

Chiral $S_P$ Thioates

A modification can include the alteration, e.g., replacement, of one or both of the non-linking (X and Y) phosphate oxygens and/or of one or more of the linking (W and Z) phosphate oxygens. Formula X below depicts a phosphate moiety linking two sugar/sugar surrogate-base moieties, $SB_1$ and $SB_2$.

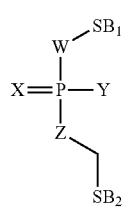

FORMULA X

In certain embodiments, one of the non-linking phosphate oxygens in the phosphate backbone moiety (X and Y) can be replaced by any one of the following: S, Se, $BR_3$ (R is hydrogen, alkyl, aryl, etc.), C (i.e., an alkyl group, an aryl group, etc.), H, $NR_2$ (R is hydrogen, alkyl, aryl, etc.), or OR (R is alkyl or aryl). The phosphorus atom in an unmodified phosphate group is achiral. However, replacement of one of the non-linking oxygens with one of the above atoms or groups of atoms renders the phosphorus atom chiral; in other words a phosphorus atom in a phosphate group modified in this way is a stereogenic center. The stereogenic phosphorus atom can possess either the "R" configuration (herein $R_P$) or the "S" configuration (herein $S_P$). Thus if 60% of a population of stereogenic phosphorus atoms have the $R_P$ configuration, then the remaining 40% of the population of stereogenic phosphorus atoms have the $S_P$ configuration.

In some embodiments, iRNA agents, having phosphate groups in which a phosphate non-linking oxygen has been replaced by another atom or group of atoms, may contain a population of stereogenic phosphorus atoms in which at least about 50% of these atoms (e.g., at least about 60% of these atoms, at least about 70% of these atoms, at least about 80% of these atoms, at least about 90% of these atoms, at least about 95% of these atoms, at least about 98% of these atoms, at least about 99% of these atoms) have the $S_P$ configuration. Alternatively, iRNA agents having phosphate groups in which a phosphate non-linking oxygen has been replaced by another atom or group of atoms may contain a population of stereogenic phosphorus atoms in which at least about 50% of these atoms (e.g., at least about 60% of these atoms, at least about 70% of these atoms, at least about 80% of these atoms, at least about 90% of these atoms, at least about 95% of these atoms, at least about 98% of these atoms, at least about 99% of these atoms) have the $R_P$ configuration. In other embodiments, the population of stereogenic phosphorus atoms may have the $S_P$ configuration and may be substantially free of stereogenic phosphorus atoms having the $R_P$ configuration. In still other embodiments, the population of stereogenic phosphorus atoms may have the $R_P$ configuration and may be substantially free of stereogenic phosphorus atoms having the $S_P$ configuration. As used herein, the phrase "substantially free of stereogenic phosphorus atoms having the $R_P$ configuration" means that moieties containing stereogenic phosphorus atoms having the $R_P$ configuration cannot be detected by conventional methods known in the art (chiral HPLC, $^1$H NMR analysis using chiral shift reagents, etc.). As used herein, the phrase "substantially free of stereogenic phosphorus atoms having the $S_P$ configuration" means that moieties containing stereogenic phosphorus atoms having the $S_P$ configuration cannot be detected by conventional methods known in the art (chiral HPLC, $^1$H NMR analysis using chiral shift reagents, etc.).

In a preferred embodiment, modified iRNA agents contain a phosphorothioate group, i.e., a phosphate groups in which a phosphate non-linking oxygen has been replaced by a sulfur atom. In an especially preferred embodiment, the population of phosphorothioate stereogenic phosphorus atoms may have the $S_P$ configuration and be substantially free of stereogenic phosphorus atoms having the $R_P$ configuration.

Phosphorothioates may be incorporated into iRNA agents using dimers e.g., formulas X-1 and X-2. The former can be used to introduce phosphorothioate

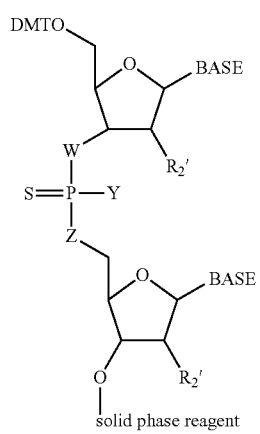

at the 3' end of a strand, while the latter can be used to introduce this modification at the 5' end or at a position that occurs e.g., 1, 2, 3, 4, 5, or 6 nucleotides from either end of the strand. In the above formulas, Y can be 2-cyanoethoxy, W and Z can be O, $R_{2'}$ can be, e.g., a substituent that can impart the C-3 endo configuration to the sugar (e.g., OH, F, OCH$_3$), DMT is dimethoxytrityl, and "BASE" can be a natural, unusual, or a universal base.

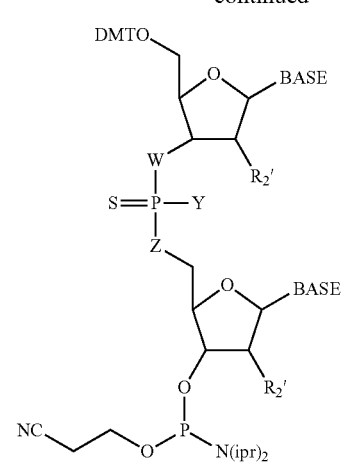

X-1 and X-2 can be prepared using chiral reagents or directing groups that can result in phosphorothioate-containing dimers having a population of stereogenic phosphorus atoms having essentially only the $R_P$ configuration (i.e., being substantially free of the $S_P$ configuration) or only the $S_P$ configuration (i.e., being substantially free of the $R_P$ configuration). Alternatively, dimers can be prepared having a population of stereogenic phosphorus atoms in which about 50% of the atoms have the $R_P$ configuration and about 50% of the atoms have the $S_P$ configuration. Dimers having stereogenic phosphorus atoms with the $R_P$ configuration can be identified and separated from dimers having stereogenic phosphorus atoms with the $S_P$ configuration using e.g., enzymatic degradation and/or conventional chromatography techniques.

Cationic Groups

Modifications can also include attachment of one or more cationic groups to the sugar, base, and/or the phosphorus atom of a phosphate or modified phosphate backbone moiety. A cationic group can be attached to any atom capable of substitution on a natural, unusual or universal base. A preferred position is one that does not interfere with hybridization, i.e., does not interfere with the hydrogen bonding interactions needed for base pairing. A cationic group can be attached e.g., through the C2' position of a sugar or analogous position in a cyclic or acyclic sugar surrogate. Cationic groups can include e.g., protonated amino groups, derived from e.g., O-AMINE (AMINE=NH$_2$; alkylamino, dialkylamino, heterocyclyl, arylamino, diaryl amino, heteroaryl amino, or diheteroaryl amino, ethylene diamine, polyamino); aminoalkoxy, e.g., O(CH$_2$)$_n$AMINE, (e.g., AMINE=NH$_2$; alkylamino, dialkylamino, heterocyclyl, arylamino, diaryl amino, heteroaryl amino, or diheteroaryl amino, ethylene diamine, polyamino); amino (e.g. NH$_2$; alkylamino, dialkylamino, heterocyclyl, arylamino, diaryl amino, heteroaryl amino, diheteroaryl amino, or amino acid); or NH(CH$_2$CH$_2$NH)$_n$CH$_2$CH$_2$-AMINE (AMINE=NH$_2$; alkylamino, dialkylamino, heterocyclyl, arylamino, diaryl amino, heteroaryl amino, or diheteroaryl amino).

Nonphosphate Linkages

Modifications can also include the incorporation of nonphosphate linkages at the 5' and/or 3' end of a strand. Examples of nonphosphate linkages which can replace the phosphate group include methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methyl phosphonate and hydroxylamino groups.

3'-bridging thiophosphates and 5'-bridging thiophosphates; locked-RNA, 2'-5' linkages, inverted linkages, α-nucleosides; conjugate groups; abasic linkages; and 5'-phosphonates and 5'-phosphate prodrugs Referring to formula X above, modifications can include replacement of one of the bridging or linking phosphate oxygens in the phosphate backbone moiety (W and Z). Unlike the situation where only one of X or Y is altered, the phosphorus center in the phosphorodithioates is achiral which precludes the formation of iRNA agents containing a stereogenic phosphorus atom.

Modifications can also include linking two sugars via a phosphate or modified phosphate group through the 2' position of a first sugar and the 5' position of a second sugar. Also contemplated are inverted linkages in which both a first and second sugar are eached linked through the respective 3' positions. Modified RNA's can also include "abasic" sugars, which lack a nucleobase at C-1'. The sugar group can also contain one or more carbons that possess the opposite stereochemical configuration than that of the corresponding carbon in ribose. Thus, a modified iRNA agent can include nucleotides containing e.g., arabinose, as the sugar. In another subset of this modification, the natural, unusual, or universal base may have the α-configuration. Modifications can also include L-RNA.

Modifications can also include 5'-phosphonates, e.g., P(O)(O$^-$)$_2$—X—C$^{5'}$-sugar (X=CH2, CF2, CHF and 5'-phosphate prodrugs, e.g., P(O)[OCH2CH2SC(O)R]$_2$CH$_2$C$^{5'}$-sugar. In the latter case, the prodrug groups may be decomposed via reaction first with carboxy esterases. The remaining ethyl thiolate group via intramolecular S$_N$2 displacement can depart as episulfide to afford the underivatized phosphate group.

Modification can also include the addition of conjugating groups described elsewhere herein, which are preferably attached to an iRNA agent through any amino group available for conjugation.

Nuclease resistant modifications include some which can be placed only at the terminus and others which can go at any position. Generally the modifications that can inhibit hybridization so it is preferably to use them only in terminal regions, and preferable to not use them at the cleavage site or in the cleavage region of an sequence which targets a subject sequence or gene. The can be used anywhere in a sense sequence, provided that sufficient hybridization between the two sequences of the iRNA agent is maintained. In some embodiments it is desirable to put the NRM at the cleavage site or in the cleavage region of a sequence which does not target a subject sequence or gene, as it can minimize off-target silencing.

In addition, an iRNA agent described herein can have an overhang which does not form a duplex structure with the other sequence of the iRNA agent—it is an overhang, but it does hybridize, either with itself, or with another nucleic acid, other than the other sequence of the iRNA agent.

In most cases, the nuclease-resistance promoting modifications will be distributed differently depending on whether the sequence will target a sequence in the subject (often referred to as an anti-sense sequence) or will not target a sequence in the subject (often referred to as a sense sequence). If a sequence is to target a sequence in the subject, modifications which interfere with or inhibit endonuclease cleavage should not be inserted in the region which is subject to RISC mediated cleavage, e.g., the cleavage site or the cleavage region (As described in Elbashir et al., 2001, Genes and Dev. 15: 188, hereby incorporated by reference, cleavage of the target occurs about in the middle of a 20 or 21 nt guide RNA, or about 10 or 11 nucleotides upstream of the first nucleotide which is complementary to the guide sequence. As used herein cleavage site refers to the nucleotide on either side of the cleavage site, on the target or on the iRNA agent strand which hybridizes to it. Cleavage region means an nucleotide with 1, 2, or 3 nucleotides of the cleave site, in either direction.)

Such modifications can be introduced into the terminal regions, e.g., at the terminal position or with 2, 3, 4, or 5 positions of the terminus, of a sequence which targets or a sequence which does not target a sequence in the subject.

An iRNA agent can have a first and a second strand chosen from the following:

a first strand which does not target a sequence and which has an NRM modification at or within 1, 2, 3, 4, 5, or 6 positions from the 3' end;

a first strand which does not target a sequence and which has an NRM modification at or within 1, 2, 3, 4, 5, or 6 positions from the 5' end;

a first strand which does not target a sequence and which has an NRM modification at or within 1, 2, 3, 4, 5, or 6 positions from the 3' end and which has a NRM modification at or within 1, 2, 3, 4, 5, or 6 positions from the 5' end;

a first strand which does not target a sequence and which has an NRM modification at the cleavage site or in the cleavage region;

a first strand which does not target a sequence and which has an NRM modification at the cleavage site or in the cleavage region and one or more of an NRM modification at or within 1, 2, 3, 4, 5, or 6 positions from the 3' end, a NRM modification at or within 1, 2, 3, 4, 5, or 6 positions from the 5' end, or NRM modifications at or within 1, 2, 3, 4, 5, or 6 positions from both the 3' and the 5' end; and a second strand which targets a sequence and which has an NRM modification at or within 1, 2, 3, 4, 5, or 6 positions from the 3' end;

a second strand which targets a sequence and which has an NRM modification at or within 1, 2, 3, 4, 5, or 6 positions from the 5' end (5' end NRM modifications are preferentially not at the terminus but rather at a position 1, 2, 3, 4, 5, or 6 away from the 5' terminus of an antisense strand);

a second strand which targets a sequence and which has an NRM modification at or within 1, 2, 3, 4, 5, or 6 positions from the 3' end and which has a NRM modification at or within 1, 2, 3, 4, 5, or 6 positions from the 5' end;

a second strand which targets a sequence and which preferably does not have an NRM modification at the cleavage site or in the cleavage region;

a second strand which targets a sequence and which does not have an NRM modification at the cleavage site or in the cleavage region and one or more of an NRM modification at or within 1, 2, 3, 4, 5, or 6 positions from the 3' end, a NRM modification at or within 1, 2, 3, 4, 5, or 6 positions from the 5' end, or NRM modifications at or within 1, 2, 3, 4, 5, or 6 positions from both the 3' and the 5' end (5' end NRM modifications are preferentially not at the terminus but rather at a position 1, 2, 3, 4, 5, or 6 away from the 5' terminus of an antisense strand).

An iRNA agent can also target two sequences and can have a first and second strand chosen from:

a first strand which targets a sequence and which has an NRM modification at or within 1, 2, 3, 4, 5, or 6 positions from the 3' end;

a first strand which targets a sequence and which has an NRM modification at or within 1, 2, 3, 4, 5, or 6 positions from the 5' end (5' end NRM modifications are preferentially not at the terminus but rather at a position 1, 2, 3, 4, 5, or 6 away from the 5' terminus of an antisense strand);

a first strand which targets a sequence and which has an NRM modification at or within 1, 2, 3, 4, 5, or 6 positions from the 3' end and which has a NRM modification at or within 1, 2, 3, 4, 5, or 6 positions from the 5' end;

a first strand which targets a sequence and which preferably does not have an NRM modification at the cleavage site or in the cleavage region;

a first strand which targets a sequence and which dose not have an NRM modification at the cleavage site or in the cleavage region and one or more of an NRM modification at or within 1, 2, 3, 4, 5, or 6 positions from the 3' end, a NRM modification at or within 1, 2, 3, 4, 5, or 6 positions from the 5' end, or NRM modifications at or within 1, 2, 3, 4, 5, or 6 positions from both the 3' and the 5' end (5' end NRM modifications are preferentially not at the terminus but rather at a position 1, 2, 3, 4, 5, or 6 away from the 5' terminus of an antisense strand) and a second strand which targets a sequence and which has an NRM modification at or within 1, 2, 3, 4, 5, or 6 positions from the 3' end;

a second strand which targets a sequence and which has an NRM modification at or within 1, 2, 3, 4, 5, or 6 positions from the 5' end (5' end NRM modifications are preferentially not at the terminus but rather at a position 1, 2, 3, 4, 5, or 6 away from the 5' terminus of an antisense strand);

a second strand which targets a sequence and which has an NRM modification at or within 1, 2, 3, 4, 5, or 6 positions from the 3' end and which has a NRM modification at or within 1, 2, 3, 4, 5, or 6 positions from the 5' end;

a second strand which targets a sequence and which preferably does not have an NRM modification at the cleavage site or in the cleavage region;

a second strand which targets a sequence and which dose not have an NRM modification at the cleavage site or in the cleavage region and one or more of an NRM modification at or within 1, 2, 3, 4, 5, or 6 positions from the 3' end, a NRM modification at or within 1, 2, 3, 4, 5, or 6 positions from the 5' end, or NRM modifications at or within 1, 2, 3, 4, 5, or 6 positions from both the 3' and the 5' end (5' end NRM modifications are preferentially not at the terminus but rather at a position 1, 2, 3, 4, 5, or 6 away from the 5' terminus of an antisense strand).

Ribose Mimics

The monomers and methods described herein can be used to prepare an RNA, e.g., an iRNA agent, that incorporates a ribose mimic, such as those described herein and those described in copending co-owned U.S. Provisional Application Ser. No. 60/454,962, filed on Mar. 13, 2003, and International Application No. PCT/US04/07070, both of which are hereby incorporated by reference.

Thus, an aspect of the invention features an iRNA agent that includes a secondary hydroxyl group, which can increase efficacy and/or confer nuclease resistance to the agent. Nucleases, e.g., cellular nucleases, can hydrolyze nucleic acid phosphodiester bonds, resulting in partial or complete degradation of the nucleic acid. The secondary hydroxy group confers nuclease resistance to an iRNA agent by rendering the iRNA agent less prone to nuclease degradation relative to an iRNA which lacks the modification. While not wishing to be bound by theory, it is believed that the presence of a secondary hydroxyl group on the iRNA agent can act as a structural mimic of a 3' ribose hydroxyl group, thereby causing it to be less susceptible to degradation.

The secondary hydroxyl group refers to an "OH" radical that is attached to a carbon atom substituted by two other carbons and a hydrogen. The secondary hydroxyl group that confers nuclease resistance as described above can be part of any acyclic carbon-containing group. The hydroxyl may also be part of any cyclic carbon-containing group, and preferably one or more of the following conditions is met (1) there is no ribose moiety between the hydroxyl group and the terminal phosphate group or (2) the hydroxyl group is not on a sugar moiety which is coupled to a base. The hydroxyl group is located at least two bonds (e.g., at least three bonds away, at least four bonds away, at least five bonds away, at least six bonds away, at least seven bonds away, at least eight bonds away, at least nine bonds away, at least ten bonds away, etc.) from the terminal phosphate group phosphorus of the iRNA agent. In preferred embodiments, there are five intervening bonds between the terminal phosphate group phosphorus and the secondary hydroxyl group.

Preferred iRNA agent delivery modules with five intervening bonds between the terminal phosphate group phosphorus and the secondary hydroxyl group have the following structure (see formula Y below):

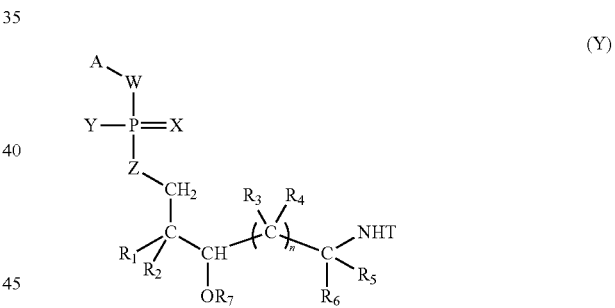

(Y)

Referring to formula Y, A is an iRNA agent, including any iRNA agent described herein. The iRNA agent may be connected directly or indirectly (e.g., through a spacer or linker) to "W" of the phosphate group. These spacers or linkers can include e.g., —$(CH_2)_n$—, —$(CH_2)_nN$—, —$(CH_2)_nO$—, —$(CH_2)_nS$—, $O(CH_2CH_2O)_nCH_2CH_2OH$ (e.g., n=3 or 6), abasic sugars, amide, carboxy, amine, oxyamine, oxyimine, thioether, disulfide, thiourea, sulfonamide, or morpholino, or biotin and fluorescein reagents.

The iRNA agents can have a terminal phosphate group that is unmodified (e.g., W, X, Y, and Z are O) or modified. In a modified phosphate group, W and Z can be independently NH, O, or S; and X and Y can be independently S, Se, $BH_3^-$, $C_1$-$C_6$ alkyl, $C_6$-$C_{10}$ aryl, H, O, $O^-$, alkoxy or amino (including alkylamino, arylamino, etc.). Preferably, W, X and Z are O and Y is S.

$R_1$ and $R_3$ are each, independently, hydrogen; or $C_1$-$C_{100}$ alkyl, optionally substituted with hydroxyl, amino, halo, phosphate or sulfate and/or may be optionally inserted with N, O, S, alkenyl or alkynyl.

$R_2$ is hydrogen; $C_1$-$C_{100}$ alkyl, optionally substituted with hydroxyl, amino, halo, phosphate or sulfate and/or may be optionally inserted with N, O, S, alkenyl or alkynyl; or, when n is 1, $R_2$ may be taken together with $R_4$ or $R_6$ to form a ring of 5-12 atoms.

$R_4$ is hydrogen; $C_1$-$C_{100}$ alkyl, optionally substituted with hydroxyl, amino, halo, phosphate or sulfate and/or may be optionally inserted with N, O, S, alkenyl or alkynyl; or, when n is 1, $R_4$ may be taken together with $R_2$ or $R_5$ to form a ring of 5-12 atoms.

$R_5$ is hydrogen, $C_1$-$C_{100}$ alkyl optionally substituted with hydroxyl, amino, halo, phosphate or sulfate and/or may be optionally inserted with N, O, S, alkenyl or alkynyl; or, when n is 1, $R_5$ may be taken together with $R_4$ to form a ring of 5-12 atoms.

$R_6$ is hydrogen, $C_1$-$C_{100}$ alkyl, optionally substituted with hydroxyl, amino, halo, phosphate or sulfate and/or may be optionally inserted with N, O, S, alkenyl or alkynyl, or, when n is 1, $R_6$ may be taken together with $R_2$ to form a ring of 6-10 atoms;

$R_7$ is hydrogen, $C_1$-$C_{100}$ alkyl, or $C(O)(CH_2)_q C(O)NHR_9$; T is hydrogen or a functional group; n and q are each independently 1-100; $R_8$ is $C_1$-$C_{10}$ alkyl or $C_6$-$C_{10}$ aryl; and $R_9$ is hydrogen, C1-C10 alkyl, C6-C10 aryl or a solid support agent.

Preferred embodiments may include one of more of the following subsets of iRNA agent delivery modules.

In one subset of RNAi agent delivery modules, A can be connected directly or indirectly through a terminal 3' or 5' ribose sugar carbon of the RNA agent.

In another subset of RNAi agent delivery modules, X, W, and Z are O and Y is S.

In still yet another subset of RNAi agent delivery modules, n is 1, and $R_2$ and $R_6$ are taken together to form a ring containing six atoms and $R_4$ and $R_5$ are taken together to form a ring containing six atoms. Preferably, the ring system is a trans-decalin. For example, the RNAi agent delivery module of this subset can include a compound of Formula (Y-1):

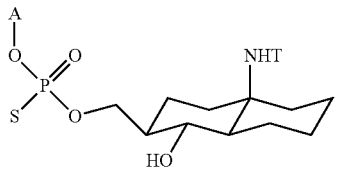

The functional group can be, for example, a targeting group (e.g., a steroid or a carbohydrate), a reporter group (e.g., a fluorophore), or a label (an isotopically labelled moiety). The targeting group can further include protein binding agents, endothelial cell targeting groups (e.g., RGD peptides and mimetics), cancer cell targeting groups (e.g., folate Vitamin B12, Biotin), bone cell targeting groups (e.g., bisphosphonates, polyglutamates, polyaspartates), multivalent mannose (for e.g., macrophage testing), lactose, galactose, N-acetyl-galactosamine, monoclonal antibodies, glycoproteins, lectins, melanotropin, or thyrotropin.

As can be appreciated by the skilled artisan, methods of synthesizing the compounds of the formulae herein will be evident to those of ordinary skill in the art. The synthesized compounds can be separated from a reaction mixture and further purified by a method such as column chromatography, high pressure liquid chromatography, or recrystallization. Additionally, the various synthetic steps may be performed in an alternate sequence or order to give the desired compounds.

Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Palindromes

The monomers and methods described herein can be used to prepare an RNA, e.g., an iRNA agent, having a palindrome structure as described herein and those described in one or more of U.S. Provisional Application Ser. No. 60/452,682, filed Mar. 7, 2003; U.S. Provisional Application Ser. No. 60/462,894, filed Apr. 14, 2003; and International Application No. PCT/US04/07070, filed Mar. 8, 2004, all of which are hereby incorporated by reference. The iRNA agents of the invention can target more than one RNA region. For example, an iRNA agent can include a first and second sequence that are sufficiently complementary to each other to hybridize. The first sequence can be complementary to a first target RNA region and the second sequence can be complementary to a second target RNA region. The first and second sequences of the iRNA agent can be on different RNA strands, and the mismatch between the first and second sequences can be less than 50%, 40%, 30%, 20%, 10%, 5%, or 1%. The first and second sequences of the iRNA agent are on the same RNA strand, and in a related embodiment more than 50%, 60%, 70%, 80%, 90%, 95%, or 1% of the iRNA agent can be in bimolecular form. The first and second sequences of the iRNA agent can be fully complementary to each other.

The first target RNA region can be encoded by a first gene and the second target RNA region can encoded by a second gene, or the first and second target RNA regions can be different regions of an RNA from a single gene. The first and second sequences can differ by at least 1 nucleotide.

The first and second target RNA regions can be on transcripts encoded by first and second sequence variants, e.g., first and second alleles, of a gene. The sequence variants can be mutations, or polymorphisms, for example. The first target RNA region can include a nucleotide substitution, insertion, or deletion relative to the second target RNA region, or the second target RNA region can a mutant or variant of the first target region.

The first and second target RNA regions can comprise viral or human RNA regions. The first and second target RNA regions can also be on variant transcripts of an oncogene or include different mutations of a tumor suppressor gene transcript. In addition, the first and second target RNA regions can correspond to hot-spots for genetic variation.

The compositions of the invention can include mixtures of iRNA agent molecules. For example, one iRNA agent can contain a first sequence and a second sequence sufficiently complementary to each other to hybridize, and in addition the first sequence is complementary to a first target RNA region and the second sequence is complementary to a second target RNA region. The mixture can also include at least one additional iRNA agent variety that includes a third sequence and a fourth sequence sufficiently complementary to each other to hybridize, and where the third sequence is complementary to a third target RNA region and the fourth sequence is complementary to a fourth target RNA region. In addition, the first or second sequence can be sufficiently complementary to the third or fourth sequence to be capable of hybridizing to each other. The first and second sequences can be on the same or different RNA strands, and the third and fourth sequences can be on the same or different RNA strands.

The target RNA regions can be variant sequences of a viral or human RNA, and in certain embodiments, at least two of the target RNA regions can be on variant transcripts of an oncogene or tumor suppressor gene. The target RNA regions can correspond to genetic hot-spots.

Methods of making an iRNA agent composition can include obtaining or providing information about a region of an RNA of a target gene (e.g., a viral or human gene, or an oncogene or tumor suppressor, e.g., p53), where the region has high variability or mutational frequency (e.g., in humans). In addition, information about a plurality of RNA targets within the region can be obtained or provided, where each RNA target corresponds to a different variant or mutant of the gene (e.g., a region including the codon encoding p53 248Q and/or p53 249S). The iRNA agent can be constructed such that a first sequence is complementary to a first of the plurality of variant RNA targets (e.g., encoding 249Q) and a second sequence is complementary to a second of the plurality of variant RNA targets (e.g., encoding 249S), and the first and second sequences can be sufficiently complementary to hybridize.

Sequence analysis, e.g., to identify common mutants in the target gene, can be used to identify a region of the target gene that has high variability or mutational frequency. A region of the target gene having high variability or mutational frequency can be identified by obtaining or providing genotype information about the target gene from a population.

Expression of a target gene can be modulated, e.g., down-regulated or silenced, by providing an iRNA agent that has a first sequence and a second sequence sufficiently complementary to each other to hybridize. In addition, the first sequence can be complementary to a first target RNA region and the second sequence can be complementary to a second target RNA region.

An iRNA agent can include a first sequence complementary to a first variant RNA target region and a second sequence complementary to a second variant RNA target region. The first and second variant RNA target regions can correspond to first and second variants or mutants of a target gene, e.g., viral gene, tumor suppressor or oncogene. The first and second variant target RNA regions can include allelic variants, mutations (e.g., point mutations), or polymorphisms of the target gene. The first and second variant RNA target regions can correspond to genetic hot-spots.

A plurality of iRNA agents (e.g., a panel or bank) can be provided.

Other than Canonical Watson-Crick Duplex Structures

The monomers and methods described herein can be used to prepare an RNA, e.g., an iRNA agent, having monomers which can form other than a canonical Watson-Crick pairing with another monomer, e.g., a monomer on another strand, such as those described herein and those described in U.S. Provisional Application Ser. No. 60/465,665, filed Apr. 25, 2003, and International Application No. PCT/US04/07070, filed Mar. 8, 2004, both of which are hereby incorporated by reference.

The use of "other than canonical Watson-Crick pairing" between monomers of a duplex can be used to control, often to promote, melting of all or part of a duplex. The iRNA agent can include a monomer at a selected or constrained position that results in a first level of stability in the iRNA agent duplex (e.g., between the two separate molecules of a double stranded iRNA agent) and a second level of stability in a duplex between a sequence of an iRNA agent and another sequence molecule, e.g., a target or off-target sequence in a subject. In some cases the second duplex has a relatively greater level of stability, e.g., in a duplex between an anti-sense sequence of an iRNA agent and a target mRNA. In this case one or more of the monomers, the position of the monomers in the iRNA agent, and the target sequence (sometimes referred to herein as the selection or constraint parameters), are selected such that the iRNA agent duplex is has a comparatively lower free energy of association (which while not wishing to be bound by mechanism or theory, is believed to contribute to efficacy by promoting disassociation of the duplex iRNA agent in the context of the RISC) while the duplex formed between an anti-sense targeting sequence and its target sequence, has a relatively higher free energy of association (which while not wishing to be bound by mechanism or theory, is believed to contribute to efficacy by promoting association of the anti-sense sequence and the target RNA).

In other cases the second duplex has a relatively lower level of stability, e.g., in a duplex between a sense sequence of an iRNA agent and an off-target mRNA. In this case one or more of the monomers, the position of the monomers in the iRNA agent, and an off-target sequence, are selected such that the iRNA agent duplex is has a comparatively higher free energy of association while the duplex formed between a sense targeting sequence and its off-target sequence, has a relatively lower free energy of association (which while not wishing to be bound by mechanism or theory, is believed to reduce the level of off-target silencing by contribute to efficacy by promoting disassociation of the duplex formed by the sense strand and the off-target sequence).

Thus, inherent in the structure of the iRNA agent is the property of having a first stability for the intra-iRNA agent duplex and a second stability for a duplex formed between a sequence from the iRNA agent and another RNA, e.g., a target mRNA. As discussed above, this can be accomplished by judicious selection of one or more of the monomers at a selected or constrained position, the selection of the position in the duplex to place the selected or constrained position, and selection of the sequence of a target sequence (e.g., the particular region of a target gene which is to be targeted). The iRNA agent sequences which satisfy these requirements are sometimes referred herein as constrained sequences. Exercise of the constraint or selection parameters can e, e.g., by inspection, or by computer assisted methods. Exercise of the parameters can result in selection of a target sequence and of particular monomers to give a desired result in terms of the stability, or relative stability, of a duplex.

Thus, in another aspect, the invention features, an iRNA agent which includes: a first sequence which targets a first target region and a second sequence which targets a second target region. The first and second sequences have sufficient complementarity to each other to hybridize, e.g., under physiological conditions, e.g., under physiological conditions but not in contact with a helicase or other unwinding enzyme. In a duplex region of the iRNA agent, at a selected or constrained position, the first target region has a first monomer, and the second target region has a second monomer. The first and second monomers occupy complementary or corresponding positions. One, and preferably both monomers are selected such that the stability of the pairing of the monomers contribute to a duplex between the first and second sequence will differ form the stability of the pairing between the first or second sequence with a target sequence.

Usually, the monomers will be selected (selection of the target sequence may be required as well) such that they form a pairing in the iRNA agent duplex which has a lower free energy of dissociation, and a lower Tm, than will be possessed by the paring of the monomer with its complementary monomer in a duplex between the iRNA agent sequence and a target RNA duplex.

The constraint placed upon the monomers can be applied at a selected site or at more than one selected site. By way of example, the constraint can be applied at more than 1, but less than 3, 4, 5, 6, or 7 sites in an iRNA agent duplex.

A constrained or selected site can be present at a number of positions in the iRNA agent duplex. E.g., a constrained or selected site can be present within 3, 4, 5, or 6 positions from either end, 3' or 5' of a duplexed sequence. A constrained or selected site can be present in the middle of the duplex region, e.g., it can be more than 3, 4, 5, or 6, positions from the end of a duplexed region.

In some embodiment the duplex region of the iRNA agent will have, mismatches, in addition to the selected or constrained site or sites. Preferably it will have no more than 1, 2, 3, 4, or 5 bases, which do not form canonical Watson-Crick pairs or which do not hybridize. Overhangs are discussed in detail elsewhere herein but are preferably about 2 nucleotides in length. The overhangs can be complementary to the gene sequences being targeted or can be other sequence. TT is a preferred overhang sequence. The first and second iRNA agent sequences can also be joined, e.g., by additional bases to form a hairpin, or by other non-base linkers.

The monomers can be selected such that: first and second monomers are naturally occurring ribonuceotides, or modified ribonucleotides having naturally occurring bases, and when occupying complementary sites either do not pair and have no substantial level of H-bonding, or form a non canonical Watson-Crick pairing and form a non-canonical pattern of H bonding, which usually have a lower free energy of dissociation than seen in a canonical Watson-Crick pairing, or otherwise pair to give a free energy of association which is less than that of a preselected value or is less, e.g., than that of a canonical pairing. When one (or both) of the iRNA agent sequences duplexes with a target, the first (or second) monomer forms a canonical Watson-Crick pairing with the base in the complementary position on the target, or forms a non canonical Watson-Crick pairing having a higher free energy of dissociation and a higher Tm than seen in the paring in the iRNA agent. The classical Watson-Crick parings are as follows: A-T, G-C, and A-U. Non-canonical Watson-Crick pairings are known in the art and can include, U-U, G-G, G-$A_{trans}$, G-$A_{cis}$, and GU.

The monomer in one or both of the sequences is selected such that, it does not pair, or forms a pair with its corresponding monomer in the other sequence which minimizes stability (e.g., the H bonding formed between the monomer at the selected site in the one sequence and its monomer at the corresponding site in the other sequence are less stable than the H bonds formed by the monomer one (or both) of the sequences with the respective target sequence. The monomer is one or both strands is also chosen to promote stability in one or both of the duplexes made by a strand and its target sequence. E.g., one or more of the monomers and the target sequences are selected such that at the selected or constrained position, there is are no H bonds formed, or a non canonical pairing is formed in the iRNA agent duplex, or otherwise they otherwise pair to give a free energy of association which is less than that of a preselected value or is less, e.g., than that of a canonical pairing, but when one (or both) sequences form a duplex with the respective target, the pairing at the selected or constrained site is a canonical Watson-Crick paring.

The inclusion of such a monomers will have one or more of the following effects: it will destabilize the iRNA agent duplex, it will destabilize interactions between the sense sequence and unintended target sequences, sometimes referred to as off-target sequences, and duplex interactions between the a sequence and the intended target will not be destabilized.

By way of example:

The monomer at the selected site in the first sequence includes an A (or a modified base which pairs with T), and the monomer in at the selected position in the second sequence is chosen from a monomer which will not pair or which will form a non-canonical pairing, e.g., G. These will be useful in applications wherein the target sequence for the first sequence has a T at the selected position. In embodiments where both target duplexes are stabilized it is useful wherein the target sequence for the second strand has a monomer which will form a canonical Watson-Crick pairing with the monomer selected for the selected position in the second strand.

The monomer at the selected site in the first sequence includes U (or a modified base which pairs with A), and the monomer in at the selected position in the second sequence is chosen from a monomer which will not pair or which will form a non-canonical pairing, e.g., U or G. These will be useful in applications wherein the target sequence for the first sequence has a T at the selected position. In embodiments where both target duplexes are stabilized it is useful wherein the target sequence for the second strand has a monomer which will form a canonical Watson-Crick pairing with the monomer selected for the selected position in the second strand.

The monomer at the selected site in the first sequence includes a G (or a modified base which pairs with C), and the monomer in at the selected position in the second sequence is chosen from a monomer which will not pair or which will form a non-canonical pairing, e.g., G, $A_{cis}$, $A_{trans}$, or U. These will be useful in applications wherein the target sequence for the first sequence has a T at the selected position. In embodiments where both target duplexes are stabilized it is useful wherein the target sequence for the second strand has a monomer which will form a canonical Watson-Crick pairing with the monomer selected for the selected position in the second strand.

The monomer at the selected site in the first sequence includes a C (or a modified base which pairs with G), and the monomer in at the selected position in the second sequence is chosen a monomer which will not pair or which will form a non-canonical pairing. These will be useful in applications wherein the target sequence for the first sequence has a T at the selected position. In embodiments where both target duplexes are stabilized it is useful wherein the target sequence for the second strand has a monomer which will form a canonical Watson-Crick pairing with the monomer selected for the selected position in the second strand.

A non-naturally occurring or modified monomer or monomers can be chosen such that when a non-naturally occurring or modified monomer occupies a positions at the selected or constrained position in an iRNA agent they exhibit a first free energy of dissociation and when one (or both) of them pairs with a naturally occurring monomer, the pair exhibits a second free energy of dissociation, which is usually higher than that of the pairing of the first and second monomers. E.g., when the first and second monomers occupy complementary positions they either do not pair and have no substantial level of H-bonding, or form a weaker bond than one of them would form with a naturally occurring monomer, and reduce the stability of that duplex, but when the duplex dissociates at least one of the strands will form a duplex with a target in which the selected monomer will promote stability, e.g., the monomer will form a more stable pair with a naturally occurring monomer in the target sequence than the pairing it formed in the iRNA agent.

An example of such a pairing is 2-amino A and either of a 2-thio pyrimidine analog of U or T.

When placed in complementary positions of the iRNA agent these monomers will pair very poorly and will minimize stability. However, a duplex is formed between 2 amino A and the U of a naturally occurring target, or a duplex is between 2-thio U and the A of a naturally occurring target or 2-thio T and the A of a naturally occurring target will have a relatively higher free energy of dissociation and be more stable. This is shown in the FIG. 12.

Figure 12:
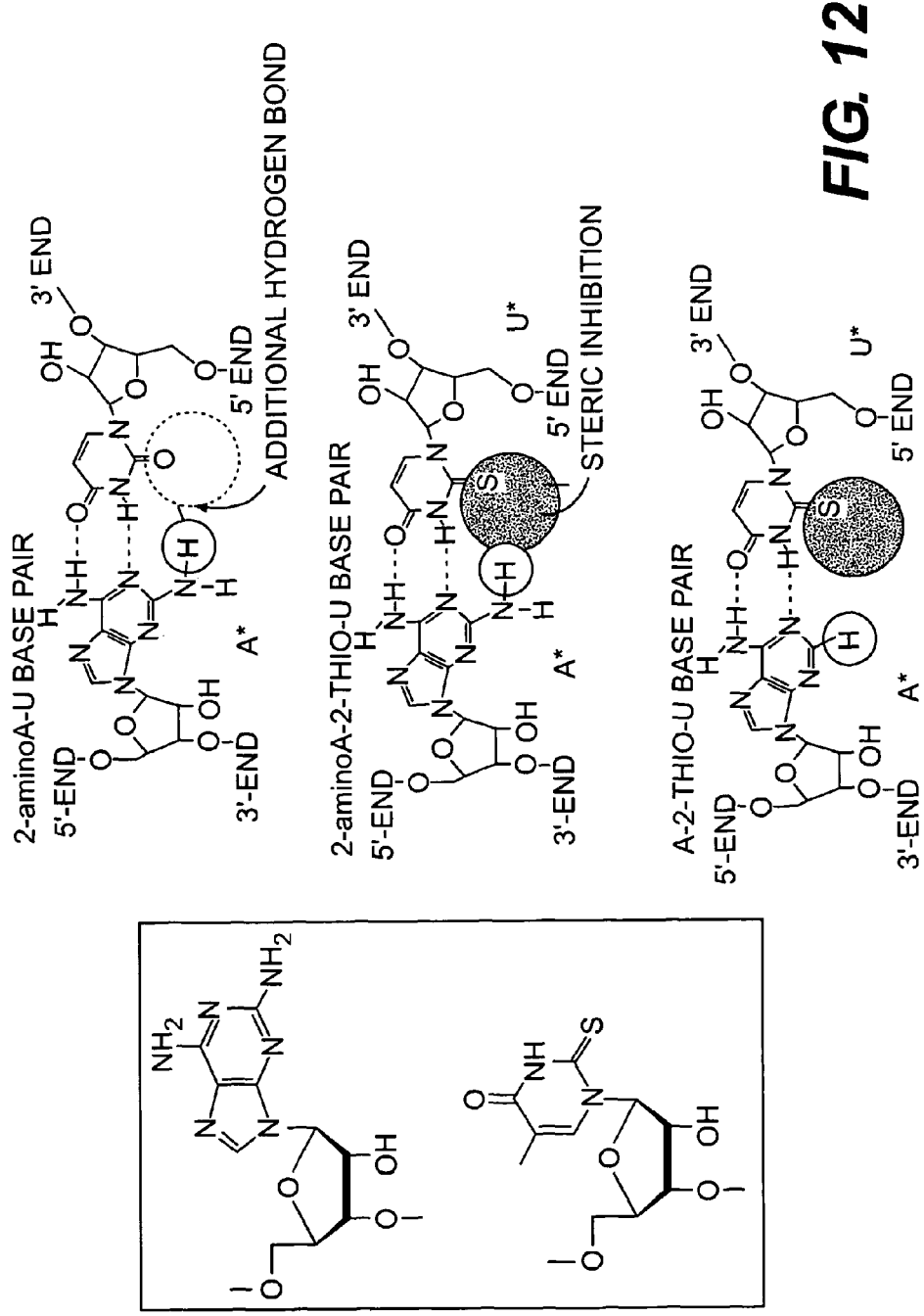
FIG. 12 is a structural representation of base pairing in psuedocomplementary siRNA[2].

The pair shown in FIG. 12 (the 2-amino A and the 2-s U and T) is exemplary. In another embodiment, the monomer at the selected position in the sense strand can be a universal pairing moiety. A universal pairing agent will form some level of H bonding with more than one and preferably all other naturally occurring monomers. An examples of a universal pairing moiety is a monomer which includes 3-nitro pyrrole. (Examples of other candidate universal base analogs can be found in the art, e.g., in Loakes, 2001, NAR 29: 2437-2447, hereby incorporated by reference. Examples can also be found in the section on Universal Bases below.) In these cases the monomer at the corresponding position of the anti-sense strand can be chosen for its ability to form a duplex with the target and can include, e.g., A, U, G, or C.

iRNA agents of the invention can include:

A sense sequence, which preferably does not target a sequence in a subject, and an anti-sense sequence, which targets a target gene in a subject. The sense and anti-sense sequences have sufficient complementarity to each other to hybridize, e.g., under physiological conditions, e.g., under physiological conditions but not in contact with a helicase or other unwinding enzyme. In a duplex region of the iRNA agent, at a selected or constrained position, the monomers are selected such that:

The monomer in the sense sequence is selected such that, it does not pair, or forms a pair with its corresponding monomer in the anti-sense strand which minimizes stability (e.g., the H bonding formed between the monomer at the selected site in the sense strand and its monomer at the corresponding site in the anti-sense strand are less stable than the H bonds formed by the monomer of the anti-sense sequence and its canonical Watson-Crick partner or, if the monomer in the anti-sense strand includes a modified base, the natural analog of the modified base and its canonical Watson-Crick partner).

The monomer is in the corresponding position in the anti-sense strand is selected such that it maximizes the stability of a duplex it forms with the target sequence, e.g., it forms a canonical Watson-Crick paring with the monomer in the corresponding position on the target stand;

Optionally, the monomer in the sense sequence is selected such that, it does not pair, or forms a pair with its corresponding monomer in the anti-sense strand which minimizes stability with an off-target sequence.

The inclusion of such a monomers will have one or more of the following effects: it will destabilize the iRNA agent duplex, it will destabilize interactions between the sense sequence and unintended target sequences, sometimes referred to as off-target sequences, and duplex interactions between the anti-sense strand and the intended target will not be destabilized.

The constraint placed upon the monomers can be applied at a selected site or at more than one selected site. By way of example, the constraint can be applied at more than 1, but less than 3, 4, 5, 6, or 7 sites in an iRNA agent duplex.

A constrained or selected site can be present at a number of positions in the iRNA agent duplex. E.g., a constrained or selected site can be present within 3, 4, 5, or 6 positions from either end, 3' or 5' of a duplexed sequence. A constrained or selected site can be present in the middle of the duplex region, e.g., it can be more than 3, 4, 5, or 6, positions from the end of a duplexed region.

In some embodiment the duplex region of the iRNA agent will have, mismatches, in addition to the selected or constrained site or sites. Preferably it will have no more than 1, 2, 3, 4, or 5 bases, which do not form canonical Watson-Crick pairs or which do not hybridize. Overhangs are discussed in detail elsewhere herein but are preferably about 2 nucleotides in length. The overhangs can be complementary to the gene sequences being targeted or can be other sequence. TT is a preferred overhang sequence. The first and second iRNA agent sequences can also be joined, e.g., by additional bases to form a hairpin, or by other non-base linkers.

The monomers can be selected such that: first and second monomers are naturally occurring ribonucleotides, or modified ribonucleotides having naturally occurring bases, and when occupying complementary sites either do not pair and have no substantial level of H-bonding, or form a non canonical Watson-Crick pairing and form a non-canonical pattern of H bonding, which usually have a lower free energy of dissociation than seen in a canonical Watson-Crick pairing, or otherwise pair to give a free energy of association which is less than that of a preselected value or is less, e.g., than that of a canonical pairing. When one (or both) of the iRNA agent sequences duplexes with a target, the first (or second) monomer forms a canonical Watson-Crick pairing with the base in the complementary position on the target, or forms a non canonical Watson-Crick pairing having a higher free energy of dissociation and a higher Tm than seen in the paring in the iRNA agent. The classical Watson-Crick parings are as follows: A-T, G-C, and A-U. Non-canonical Watson-Crick pairings are known in the art and can include, U-U, G-G, G-A$_{trans}$, G-A$_{cis}$, and GU.

The monomer in one or both of the sequences is selected such that, it does not pair, or forms a pair with its corresponding monomer in the other sequence which minimizes stability (e.g., the H bonding formed between the monomer at the selected site in the one sequence and its monomer at the corresponding site in the other sequence are less stable than the H bonds formed by the monomer one (or both) of the sequences with the respective target sequence. The monomer is one or both strands is also chosen to promote stability in one or both of the duplexes made by a strand and its target sequence. E.g., one or more of the monomers and the target sequences are selected such that at the selected or constrained position, there is are no H bonds formed, or a non canonical pairing is formed in the iRNA agent duplex, or otherwise they otherwise pair to give a free energy of association which is less than that of a preselected value or is less, e.g., than that of a canonical pairing, but when one (or both) sequences form a duplex with the respective target, the pairing at the selected or constrained site is a canonical Watson-Crick paring.

The inclusion of such a monomers will have one or more of the following effects: it will destabilize the iRNA agent duplex, it will destabilize interactions between the sense sequence and unintended target sequences, sometimes referred to as off-target sequences, and duplex interactions between the a sequence and the intended target will not be destabilized.

By way of example:

The monomer at the selected site in the first sequence includes an A (or a modified base which pairs with T), and the monomer in at the selected position in the second sequence is chosen from a monomer which will not pair or which will form a non-canonical pairing, e.g., G. These will be useful in applications wherein the target sequence for the first sequence has a T at the selected position. In embodiments where both target duplexes are stabilized it is useful wherein the target sequence for the second strand has a monomer which will form a canonical Watson-Crick pairing with the monomer selected for the selected position in the second strand.

The monomer at the selected site in the first sequence includes U (or a modified base which pairs with A), and the monomer in at the selected position in the second sequence is chosen from a monomer which will not pair or which will form a non-canonical pairing, e.g., U or G. These will be useful in applications wherein the target sequence for the first sequence has a T at the selected position. In embodiments where both target duplexes are stabilized it is useful wherein the target sequence for the second strand has a monomer which will form a canonical Watson-Crick pairing with the monomer selected for the selected position in the second strand.

The monomer at the selected site in the first sequence includes a G (or a modified base which pairs with C), and the monomer in at the selected position in the second sequence is chosen from a monomer which will not pair or which will form a non-canonical pairing, e.g., G, $A_{cis}$, $A_{trans}$, or U. These will be useful in applications wherein the target sequence for the first sequence has a T at the selected position. In embodiments where both target duplexes are stabilized it is useful wherein the target sequence for the second strand has a monomer which will form a canonical Watson-Crick pairing with the monomer selected for the selected position in the second strand.

The monomer at the selected site in the first sequence includes a C (or a modified base which pairs with G), and the monomer in at the selected position in the second sequence is chosen a monomer which will not pair or which will form a non-canonical pairing. These will be useful in applications wherein the target sequence for the first sequence has a T at the selected position. In embodiments where both target duplexes are stabilized it is useful wherein the target sequence for the second strand has a monomer which will form a canonical Watson-Crick pairing with the monomer selected for the selected position in the second strand.

A non-naturally occurring or modified monomer or monomers can be chosen such that when a non-naturally occurring or modified monomer occupies a positions at the selected or constrained position in an iRNA agent they exhibit a first free energy of dissociation and when one (or both) of them pairs with a naturally occurring monomer, the pair exhibits a second free energy of dissociation, which is usually higher than that of the pairing of the first and second monomers. E.g., when the first and second monomers occupy complementary positions they either do not pair and have no substantial level of H-bonding, or form a weaker bond than one of them would form with a naturally occurring monomer, and reduce the stability of that duplex, but when the duplex dissociates at least one of the strands will form a duplex with a target in which the selected monomer will promote stability, e.g., the monomer will form a more stable pair with a naturally occurring monomer in the target sequence than the pairing it formed in the iRNA agent.

An example of such a pairing is 2-amino A and either of a 2-thio pyrimidine analog of U or T.

When placed in complementary positions of the iRNA agent these monomers will pair very poorly and will minimize stability. However, a duplex is formed between 2 amino A and the U of a naturally occurring target, or a duplex is between 2-thio U and the A of a naturally occurring target or 2-thio T and the A of a naturally occurring target will have a relatively higher free energy of dissociation and be more stable.

The monomer at the selected position in the sense strand can be a universal pairing moiety. A universal pairing agent will form some level of H bonding with more than one and preferably all other naturally occurring monomers. An examples of a universal pairing moiety is a monomer which includes 3-nitro pyrrole. (Examples of other candidate universal base analogs can be found in the art, e.g., in Loakes, 2001, NAR 29: 2437-2447, hereby incorporated by reference. Examples can also be found in the section on Universal Bases below.) In these cases the monomer at the corresponding position of the anti-sense strand can be chosen for its ability to form a duplex with the target and can include, e.g., A, U, G, or C.

iRNA agents of the invention can include:

A sense sequence, which preferably does not target a sequence in a subject, and an anti-sense sequence, which targets a target gene in a subject. The sense and anti-sense sequences have sufficient complementarity to each other to hybridize, e.g., under physiological conditions, e.g., under physiological conditions but not in contact with a helicase or other unwinding enzyme. In a duplex region of the iRNA agent, at a selected or constrained position, the monomers are selected such that:

The monomer in the sense sequence is selected such that, it does not pair, or forms a pair with its corresponding monomer in the anti-sense strand which minimizes stability (e.g., the H bonding formed between the monomer at the selected site in the sense strand and its monomer at the corresponding site in the anti-sense strand are less stable than the H bonds formed by the monomer of the anti-sense sequence and its canonical Watson-Crick partner or, if the monomer in the anti-sense strand includes a modified base, the natural analog of the modified base and its canonical Watson-Crick partner);

The monomer is in the corresponding position in the anti-sense strand is selected such that it maximizes the stability of a duplex it forms with the target sequence, e.g., it forms a canonical Watson-Crick paring with the monomer in the corresponding position on the target stand;

Optionally, the monomer in the sense sequence is selected such that, it does not pair, or forms a pair with its corresponding monomer in the anti-sense strand which minimizes stability with an off-target sequence.

The inclusion of such a monomers will have one or more of the following effects: it will destabilize the iRNA agent duplex, it will destabilize interactions between the sense sequence and unintended target sequences, sometimes referred to as off-target sequences, and duplex interactions between the anti-sense strand and the intended target will not be destabilized.

The constraint placed upon the monomers can be applied at a selected site or at more than one selected site. By way of example, the constraint can be applied at more than 1, but less than 3, 4, 5, 6, or 7 sites in an iRNA agent duplex.

A constrained or selected site can be present at a number of positions in the iRNA agent duplex. E.g., a constrained or selected site can be present within 3, 4, 5, or 6 positions from either end, 3' or 5' of a duplexed sequence. A constrained or selected site can be present in the middle of the duplex region, e.g., it can be more than 3, 4, 5, or 6, positions from the end of a duplexed region.

The iRNA agent can be selected to target a broad spectrum of genes, including any of the genes described herein.

In a preferred embodiment the iRNA agent has an architecture (architecture refers to one or more of overall length, length of a duplex region, the presence, number, location, or length of overhangs, sing strand versus double strand form) described herein.

E.g., the iRNA agent can be less than 30 nucleotides in length, e.g., 21-23 nucleotides. Preferably, the iRNA is 21 nucleotides in length and there is a duplex region of about 19 pairs. In one embodiment, the iRNA is 21 nucleotides in length, and the duplex region of the iRNA is 19 nucleotides. In another embodiment, the iRNA is greater than 30 nucleotides in length.

In some embodiment the duplex region of the iRNA agent will have, mismatches, in addition to the selected or constrained site or sites. Preferably it will have no more than 1, 2, 3, 4, or 5 bases, which do not form canonical Watson-Crick pairs or which do not hybridize. Overhangs are discussed in detail elsewhere herein but are preferably about 2 nucleotides in length. The overhangs can be complementary to the gene sequences being targeted or can be other sequence. TT is a preferred overhang sequence. The first and second iRNA agent sequences can also be joined, e.g., by additional bases to form a hairpin, or by other non-base linkers.

One or more selection or constraint parameters can be exercised such that: monomers at the selected site in the sense and anti-sense sequences are both naturally occurring ribonucleotides, or modified ribonucleotides having naturally occurring bases, and when occupying complementary sites in the iRNA agent duplex either do not pair and have no substantial level of H-bonding, or form a non-canonical Watson-Crick pairing and thus form a non-canonical pattern of H bonding, which generally have a lower free energy of dissociation than seen in a Watson-Crick pairing, or otherwise pair to give a free energy of association which is less than that of a preselected value or is less, e.g., than that of a canonical pairing. When one, usually the anti-sense sequence of the iRNA agent sequences forms a duplex with another sequence, generally a sequence in the subject, and generally a target sequence, the monomer forms a classic Watson-Crick pairing with the base in the complementary position on the target, or forms a non-canonical Watson-Crick pairing having a higher free energy of dissociation and a higher Tm than seen in the paring in the iRNA agent. Optionally, when the other sequence of the iRNA agent, usually the sense sequences forms a duplex with another sequence, generally a sequence in the subject, and generally an off-target sequence, the monomer fails to forms a canonical Watson-Crick pairing with the base in the complementary position on the off target sequence, e.g., it forms or forms a non-canonical Watson-Crick pairing having a lower free energy of dissociation and a lower Tm.

By way of example:

the monomer at the selected site in the anti-sense stand includes an A (or a modified base which pairs with T), the corresponding monomer in the target is a T, and the sense strand is chosen from a base which will not pair or which will form a noncanonical pair, e.g., G;

the monomer at the selected site in the anti-sense stand includes a U (or a modified base which pairs with A), the corresponding monomer in the target is an A, and the sense strand is chosen from a monomer which will not pair or which will form a non-canonical pairing, e.g., U or G;

the monomer at the selected site in the anti-sense stand includes a C (or a modified base which pairs with G), the corresponding monomer in the target is a G, and the sense strand is chosen a monomer which will not pair or which will form a non-canonical pairing, e.g., G, $A_{cis}$, $A_{trans}$, or U; or the monomer at the selected site in the anti-sense stand includes a G (or a modified base which pairs with C), the corresponding monomer in the target is a C, and the sense strand is chosen from a monomer which will not pair or which will form a non-canonical pairing.

In another embodiment a non-naturally occurring or modified monomer or monomers is chosen such that when it occupies complementary a position in an iRNA agent they exhibit a first free energy of dissociation and when one (or both) of them pairs with a naturally occurring monomer, the pair exhibits a second free energy of dissociation, which is usually higher than that of the pairing of the first and second monomers. E.g., when the first and second monomers occupy complementary positions they either do not pair and have no substantial level of H-bonding, or form a weaker bond than one of them would form with a naturally occurring monomer, and reduce the stability of that duplex, but when the duplex dissociates at least one of the strands will form a duplex with a target in which the selected monomer will promote stability, e.g., the monomer will form a more stable pair with a naturally occurring monomer in the target sequence than the pairing it formed in the iRNA agent.

An example of such a pairing is 2-amino A and either of a 2-thio pyrimidine analog of U or T. As is discussed above, when placed in complementary positions of the iRNA agent these monomers will pair very poorly and will minimize stability. However, a duplex is formed between 2 amino A and the U of a naturally occurring target, or a duplex is formed between 2-thio U and the A of a naturally occurring target or 2-thio T and the A of a naturally occurring target will have a relatively higher free energy of dissociation and be more stable.

The monomer at the selected position in the sense strand can be a universal pairing moiety. A universal pairing agent will form some level of H bonding with more than one and preferably all other naturally occurring monomers. An examples of a universal pairing moiety is a monomer which includes 3-nitro pyrrole. Examples of other candidate universal base analogs can be found in the art, e.g., in Loakes, 2001, NAR 29: 2437-2447, hereby incorporated by reference. In these cases the monomer at the corresponding position of the anti-sense strand can be chosen for its ability to form a duplex with the target and can include, e.g., A, U, G, or C.

In another aspect, the invention features, an iRNA agent which includes:

a sense sequence, which preferably does not target a sequence in a subject, and an anti-sense sequence, which targets a plurality of target sequences in a subject, wherein the targets differ in sequence at only 1 or a small number, e.g., no more than 5, 4, 3 or 2 positions. The sense and anti-sense sequences have sufficient complementarity to each other to hybridize, e.g., under physiological conditions, e.g., under physiological conditions but not in contact with a helicase or other unwinding enzyme. In the sequence of the anti-sense strand of the iRNA agent is selected such that at one, some, or all of the positions which correspond to positions that differe in sequence between the target sequences, the anti-sense strand will include a monomer which will form H-bonds with at least two different target sequences. In a preferred example the anti-sense sequence will include a universal or promiscuous monomer, e.g., a monomer which includes 5-nitro pyrrole, 2-amino A, 2-thio U or 2-thio T, or other universal base referred to herein.

In a preferred embodiment the iRNA agent targets repeated sequences (which differ at only one or a small number of positions from each other) in a single gene, a plurality of genes, or a viral genome, e.g., the HCV genome.

Figure 13:
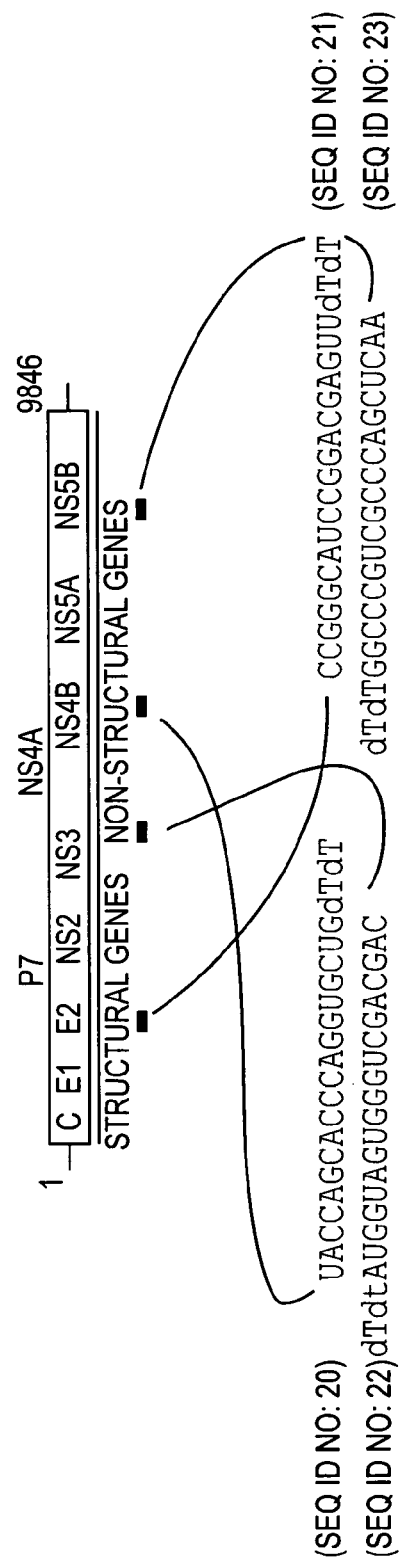
FIG. 13 is a schematic representation of dual targeting siRNAs designed to target the HCV genome.
Figure 14:
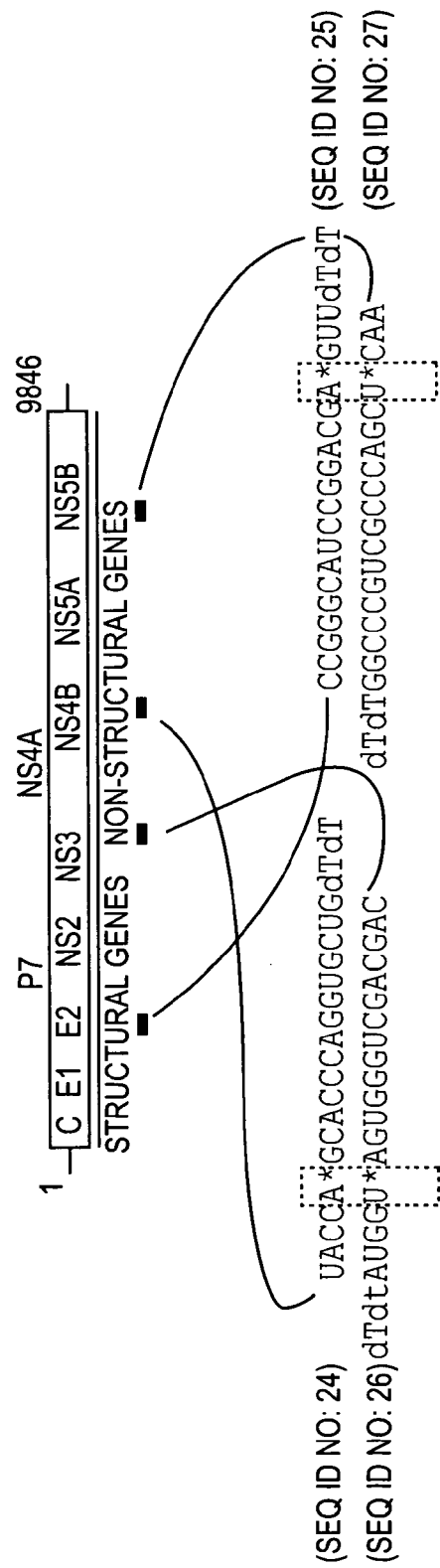
FIG. 14 is a schematic representation of psuedocomplementary, bifunctional siRNAs designed to target the HCV genome.

An embodiment is illustrated in the FIGS. 13 and 14.

In another aspect, the invention features, determining, e.g., by measurement or calculation, the stability of a pairing between monomers at a selected or constrained position in the iRNA agent duplex, and preferably determining the stability for the corresponding pairing in a duplex between a sequence form the iRNA agent and another RNA, e.g., a target sequence. The determinations can be compared. An iRNA agent thus analysed can be used in the development of a further modified iRNA agent or can be administered to a subject. This analysis can be performed successively to refine or desing optimized iRNA agents.

In another aspect, the invention features, a kit which includes one or more of the following an iRNA described herein, a sterile container in which the iRNA agent is disclosed, and instructions for use.

In another aspect, the invention features, an iRNA agent containing a constrained sequence made by a method described herein. The iRNA agent can target one or more of the genes referred to herein.

iRNA agents having constrained or selected sites, e.g., as described herein, can be used in any way described herein. Accordingly, they iRNA agents having constrained or selected sites, e.g., as described herein, can be used to silence a target, e.g., in any of the methods described herein and to target any of the genes described herein or to treat any of the disorders described herein. iRNA agents having constrained or selected sites, e.g., as described herein, can be incorporated into any of the formulations or preparations, e.g., pharmaceutical or sterile preparations described herein. iRNA agents having constrained or selected sites, e.g., as described herein, can be administered by any of the routes of administration described herein.

The term "other than canonical Watson-Crick pairing" as used herein, refers to a pairing between a first monomer in a first sequence and a second monomer at the corresponding position in a second sequence of a duplex in which one or more of the following is true: (1) there is essentially no pairing between the two, e.g., there is no significant level of H bonding between the monomers or binding between the monomers does not contribute in any significant way to the stability of the duplex; (2) the monomers are a non-canonical paring of monomers having a naturally occurring bases, i.e., they are other than A-T, A-U, or G-C, and they form monomer-monomer H bonds, although generally the H bonding pattern formed is less strong than the bonds formed by a canonical pairing; or (3) at least one of the monomers includes a non-naturally occurring bases and the H bonds formed between the monomers is, preferably formed is less strong than the bonds formed by a canonical pairing, namely one or more of A-T, A-U, G-C.

The term "off-target" as used herein, refers to as a sequence other than the sequence to be silenced.

Universal Bases: "wild-cards"; shape-based complementarity

Bi-stranded, multisite replication of a base pair between difluorotoluene and adenine: confirmation by 'inverse' sequencing. Liu, D.; Moran, S.; Kool, E. T. *Chem. Biol.,* 1997, 4, 919-926)

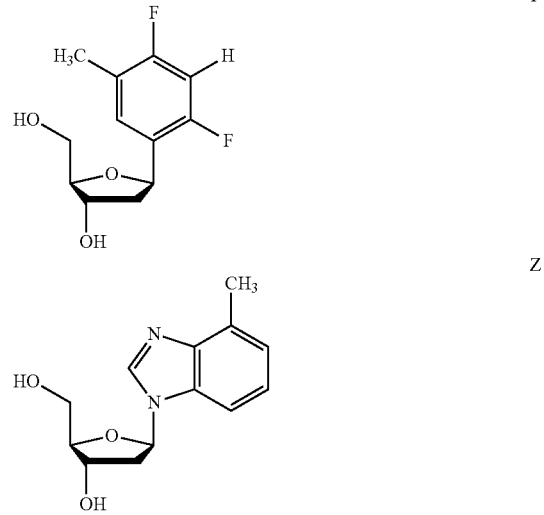

(Importance of terminal base pair hydrogen-bonding in 3'-end proofreading by the Klenow fragment of DNA polymerase I. Morales, J. C.; Kool, E. T. *Biochemistry,* 2000, 39, 2626-2632)

(Selective and stable DNA base pairing without hydrogen bonds. Matray, T, J.; Kool, E. T. *J. Am. Chem. Soc.,* 1998, 120, 6191-6192)

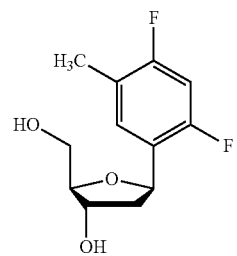

(Difluorotoluene, a nonpolar isostere for thymine, codes specifically and efficiently for adenine in DNA replication. Moran, S. Ren, R. X.-F.; Rumney IV, S.; Kool, E. T. *J. Am. Chem. Soc.,* 1997, 119, 2056-2057)

(Structure and base pairing properties of a replicable nonpolar isostere for deoxyadenosine. Guckian, K. M.; Morales, J. C.; Kool, E. T. *J. Org. Chem.,* 1998, 63, 9652-9656)

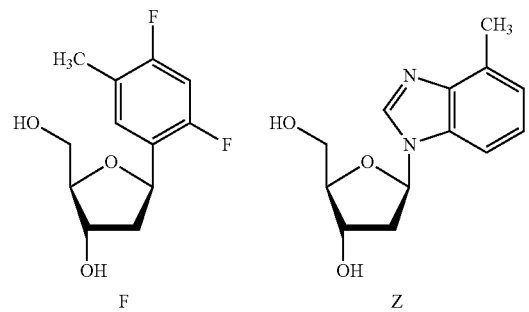

-continued
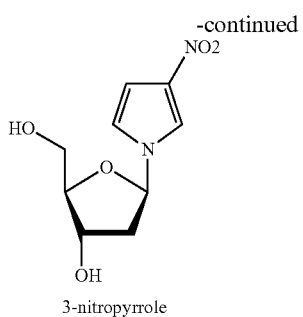
3-nitropyrrole
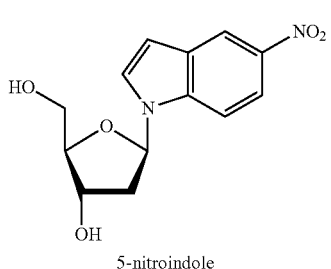
5-nitroindole
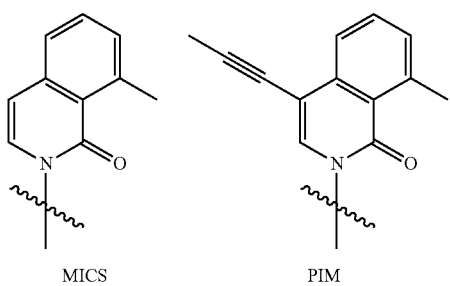
MICS    PIM
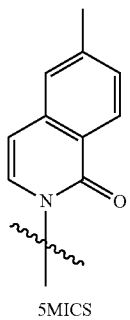
5MICS
(Universal bases for hybridization, replication and chain termination. Berger, M.; Wu. Y.; Ogawa, A. K.; McMinn, D. L.; Schultz, P. G.; Romesberg, F. E. *Nucleic Acids Res.*, 2000, 28, 2911-2914)
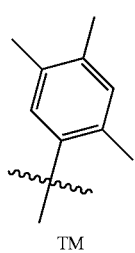
TM
-continued
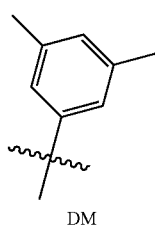
DM
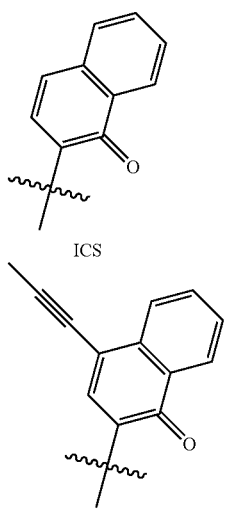
ICS
PICS
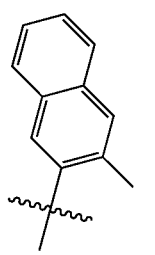
2MN
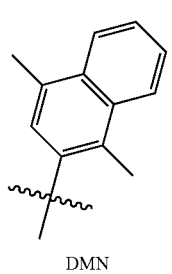
DMN
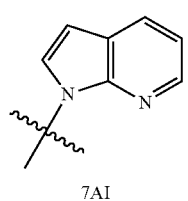
7AI

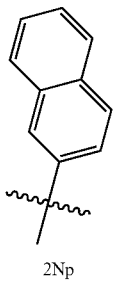

2Np

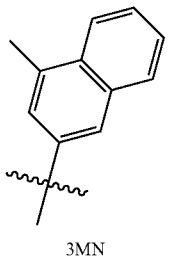

3MN (1. Efforts toward the expansion of the genetic alphabet: Information storage and replication with unnatural hydrophobic base pairs. Ogawa, A. K.; Wu, Y.; McMinn, D. L.; Liu, J.; Schultz, P. G.; Romesberg, F. E. *J. Am. Chem. Soc.,* 2000, 122, 3274-3287. 2. Rational design of an unnatural base pair with increased kinetic selectivity. Ogawa, A. K.; Wu. Y.; Berger, M.; Schultz, P. G.; Romesberg, F. E. *J. Am. Chem. Soc.,* 2000, 122, 8803-8804)

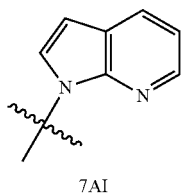 [SMILES: *n1ccc2cccnc21]

7AI (Efforts toward expansion of the genetic alphabet: replication of DNA with three base pairs. Tae, E. L.; Wu, Y.; Xia, G.; Schultz, P. G.; Romesberg, F. E. *J. Am. Chem. Soc.,* 2001, 123, 7439-7440)

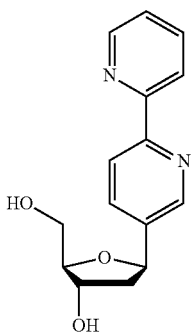

(1. Efforts toward expansion of the genetic alphabet: Optimization of interbase hydrophobic interactions. Wu, Y.; Ogawa, A. K.; Berger, M.; McMinn, D. L.; Schultz, P. G.; Romesberg, F. E. *J. Am. Chem. Soc.,* 2000, 122, 7621-7632. 2. Efforts toward expansion of genetic alphabet: DNA polymerase recognition of a highly stable, self-pairing hydrophobic base. McMinn, D. L.; Ogawa. A. K.; Wu, Y.; Liu, J.; Schultz, P. G.; Romesberg, F. E. *J. Am. Chem. Soc.,* 1999, 121, 11585-11586)

(A stable DNA duplex containing a non-hydrogen-bonding and non-shape complementary base couple: Interstrand stacking as the stability determining factor. Brotschi, C.; Haberli, A.; Leumann, C, *J. Angew. Chem. Int. Ed.,* 2001, 40, 3012-3014)

(2,2'-Bipyridine Ligandoside: A novel building block for modifying DNA with intra-duplex metal complexes. Weizman, H.; Tor, Y. *J. Am. Chem. Soc.,* 2001, 123, 3375-3376)

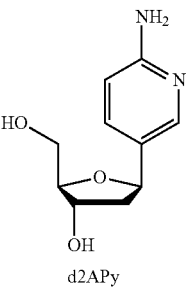

d2APy

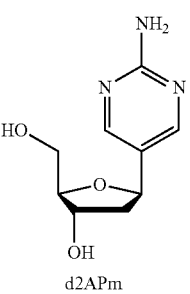

d2APm (Minor groove hydration is critical to the stability of DNA duplexes. Lan, T.; McLaughlin, L. W. *J. Am. Chem. Soc.,* 2000, 122, 6512-13)

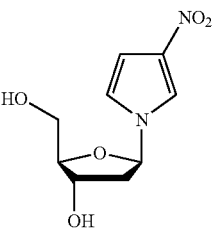

(Effect of the Universal base 3-nitropyrrole on the selectivity of neighboring natural bases. Oliver, J. S.; Parker, K. A.; Suggs, J. W. *Organic Lett.,* 2001, 3, 1977-1980. 2. Effect of the 1-(2'-deoxy-β-D-ribofuranosyl)-3-nitropyrrol residue on the stability of DNA duplexes and triplexes. Amosova, O.; George J.; Fresco, J. R. *Nucleic Acids Res.,* 1997, 25, 1930-1934. 3. Synthesis, structure and deoxyribonucleic acid sequencing with a universal nucleosides: 1-(2'-deoxy-β-D-ribofuranosyl)-3-nitropyrrole. Bergstrom, D. E.; Zhang, P.; Toma, P. H.; Andrews, P. C.; Nichols, R. *J. Am. Chem. Soc.,* 1995, 117, 1201-1209)

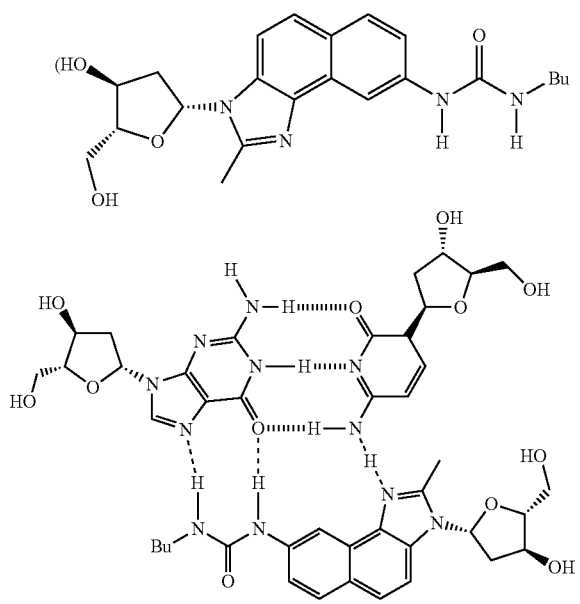

(Model studies directed toward a general triplex DNA recognition scheme: a novel DNA base that binds a CG base-pair in an organic solvent. Zimmerman, S. C.; Schmitt, P. *J. Am. Chem. Soc.*, 1995, 117, 10769-10770)

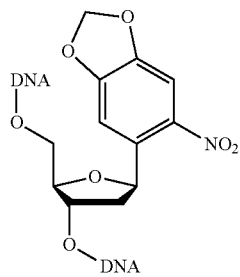

(A universal, photocleavable DNA base: nitropiperonyl 2'-deoxyriboside. *J. Org. Chem.*, 2001, 66, 2067-2071)

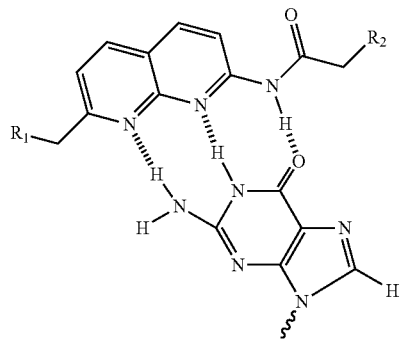

(Recognition of a single guanine bulge by 2-acylamino-1, 8-naphthyridine. Nakatani, K.; Sando, S.; Saito, I. *J. Am. Chem. Soc.*, 2000, 122, 2172-2177. b. Specific binding of 2-amino-1,8-naphthyridine into single guanine bulge as evidenced by photooxidation of GC doublet, Nakatani, K.; Sando, S.; Yoshida, K.; Saito, I. *Bioorg. Med. Chem. Lett.*, 2001, 11, 335-337)

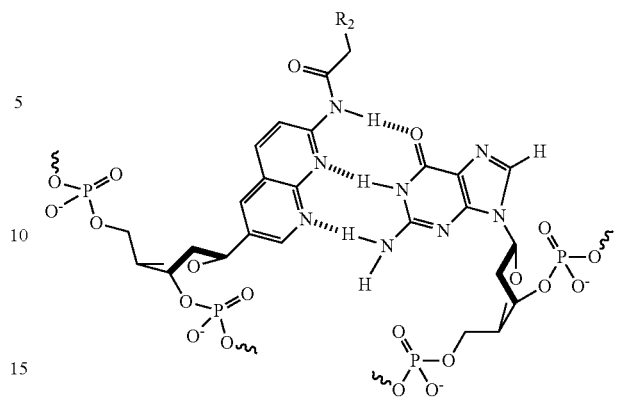

Asymmetrical Modifications

The monomers and methods described herein can be used to prepare an RNA, e.g., an iRNA agent, that can be asymmetrically modified as described herein, and as described in International Application Serial No. PCT/US04/07070, filed Mar. 8, 2004, which is hereby incorporated by reference.

An asymmetrically modified iRNA agent is one in which a strand has a modification which is not present on the other strand. An asymmetrical modification is a modification found on one strand but not on the other strand. Any modification, e.g., any modification described herein, can be present as an asymmetrical modification. An asymmetrical modification can confer any of the desired properties associated with a modification, e.g., those properties discussed herein. E.g., an asymmetrical modification can: confer resistance to degradation, an alteration in half life; target the iRNA agent to a particular target, e.g., to a particular tissue; modulate, e.g., increase or decrease, the affinity of a strand for its complement or target sequence; or hinder or promote modification of a terminal moiety, e.g., modification by a kinase or other enzymes involved in the RISC mechanism pathway. The designation of a modification as having one property does not mean that it has no other property, e.g., a modification referred to as one which promotes stabilization might also enhance targeting.

While not wishing to be bound by theory or any particular mechanistic model, it is believed that asymmetrical modification allows an iRNA agent to be optimized in view of the different or "asymmetrical" functions of the sense and antisense strands. For example, both strands can be modified to increase nuclease resistance, however, since some changes can inhibit RISC activity, these changes can be chosen for the sense stand. In addition, since some modifications, e.g., targeting moieties, can add large bulky groups that, e.g., can interfere with the cleavage activity of the RISC complex, such modifications are preferably placed on the sense strand. Thus, targeting moieties, especially bulky ones (e.g. cholesterol), are preferentially added to the sense strand. In one embodiment, an asymmetrical modification in which a phosphate of the backbone is substituted with S, e.g., a phosphorothioate modification, is present in the antisense strand, and a 2' modification, e.g., 2' OMe is present in the sense strand. A targeting moiety can be present at either (or both) the 5' or 3' end of the sense strand of the iRNA agent. In a preferred example, a P of the backbone is replaced with S in the antisense strand, 2'OMe is present in the sense strand, and a targeting moiety is added to either the 5' or 3' end of the sense strand of the iRNA agent.

In a preferred embodiment an asymmetrically modified iRNA agent has a modification on the sense strand which modification is not found on the antisense strand and the antisense strand has a modification which is not found on the sense strand.

Each strand can include one or more asymmetrical modifications. By way of example: one strand can include a first asymmetrical modification which confers a first property on the iRNA agent and the other strand can have a second asymmetrical modification which confers a second property on the iRNA. E.g., one strand, e.g., the sense strand can have a modification which targets the iRNA agent to a tissue, and the other strand, e.g., the antisense strand, has a modification which promotes hybridization with the target gene sequence.

In some embodiments both strands can be modified to optimize the same property, e.g., to increase resistance to nucleolytic degradation, but different modifications are chosen for the sense and the antisense strands, e.g., because the modifications affect other properties as well. E.g., since some changes can affect RISC activity these modifications are chosen for the sense strand.

In an embodiment one strand has an asymmetrical 2' modification, e.g., a 2' OMe modification, and the other strand has an asymmetrical modification of the phosphate backbone, e.g., a phosphorothioate modification. So, in one embodiment the antisense strand has an asymmetrical 2' OMe modification and the sense strand has an asymmetrical phosphorothioate modification (or vice versa). In a particularly preferred embodiment the RNAi agent will have asymmetrical 2'-O alkyl, preferably, 2'-OMe modifications on the sense strand and asymmetrical backbone P modification, preferably a phosphothioate modification in the antisense strand. There can be one or multiple 2'-OMe modifications, e.g., at least 2, 3, 4, 5, or 6, of the subunits of the sense strand can be so modified. There can be one or multiple phosphorothioate modifications, e.g., at least 2, 3, 4, 5, or 6, of the subunits of the antisense strand can be so modified. It is preferable to have an iRNA agent wherein there are multiple 2'-OMe modifications on the sense strand and multiple phosphorothioate modifications on the antisense strand. All of the subunits on one or both strands can be so modified. A particularly preferred embodiment of multiple asymmetric modification on both strands has a duplex region about 20-21, and preferably 19, subunits in length and one or two 3' overhangs of about 2 subunits in length.

Asymmetrical modifications are useful for promoting resistance to degradation by nucleases, e.g., endonucleases. iRNA agents can include one or more asymmetrical modifications which promote resistance to degradation. In preferred embodiments the modification on the antisense strand is one which will not interfere with silencing of the target, e.g., one which will not interfere with cleavage of the target. Most if not all sites on a strand are vulnerable, to some degree, to degradation by endonucleases. One can determine sites which are relatively vulnerable and insert asymmetrical modifications which inhibit degradation. It is often desirable to provide asymmetrical modification of a UA site in an iRNA agent, and in some cases it is desirable to provide the UA sequence on both strands with asymmetrical modification. Examples of modifications which inhibit endonucleolytic degradation can be found herein. Particularly favored modifications include: 2' modification, e.g., provision of a 2' OMe moiety on the U, especially on a sense strand; modification of the backbone, e.g., with the replacement of an O with an S, in the phosphate backbone, e.g., the provision of a phosphorothioate modification, on the U or the A or both, especially on an antisense strand; replacement of the U with a C5 amino linker; replacement of the A with a G (sequence changes are preferred to be located on the sense strand and not the antisense strand); and modification of the at the 2', 6', 7', or 8' position. Preferred embodiments are those in which one or more of these modifications are present on the sense but not the antisense strand, or embodiments where the antisense strand has fewer of such modifications.

Asymmetrical modification can be used to inhibit degradation by exonucleases. Asymmetrical modifications can include those in which only one strand is modified as well as those in which both are modified. In preferred embodiments the modification on the antisense strand is one which will not interfere with silencing of the target, e.g., one which will not interfere with cleavage of the target. Some embodiments will have an asymmetrical modification on the sense strand, e.g., in a 3' overhang, e.g., at the 3' terminus, and on the antisense strand, e.g., in a 3' overhang, e.g., at the 3' terminus. If the modifications introduce moieties of different size it is preferable that the larger be on the sense strand. If the modifications introduce moieties of different charge it is preferable that the one with greater charge be on the sense strand.

Examples of modifications which inhibit exonucleolytic degradation can be found herein. Particularly favored modifications include: 2' modification, e.g., provision of a 2' OMe moiety in a 3' overhang, e.g., at the 3' terminus (3' terminus means at the 3' atom of the molecule or at the most 3' moiety, e.g., the most 3' P or 2' position, as indicated by the context); modification of the backbone, e.g., with the replacement of a P with an S, e.g., the provision of a phosphorothioate modification, or the use of a methylated P in a 3' overhang, e.g., at the 3' terminus; combination of a 2' modification, e.g., provision of a 2' O Me moiety and modification of the backbone, e.g., with the replacement of a P with an S, e.g., the provision of a phosphorothioate modification, or the use of a methylated P, in a 3' overhang, e.g., at the 3' terminus; modification with a 3' alkyl; modification with an abasic pyrrolidine in a 3' overhang, e.g., at the 3' terminus; modification with naproxene, ibuprofen, or other moieties which inhibit degradation at the 3' terminus. Preferred embodiments are those in which one or more of these modifications are present on the sense but not the antisense strand, or embodiments where the antisense strand has fewer of such modifications.

Modifications, e.g., those described herein, which affect targeting can be provided as asymmetrical modifications. Targeting modifications which can inhibit silencing, e.g., by inhibiting cleavage of a target, can be provided as asymmetrical modifications of the sense strand. A biodistribution altering moiety, e.g., cholesterol, can be provided in one or more, e.g., two, asymmetrical modifications of the sense strand. Targeting modifications which introduce moieties having a relatively large molecular weight, e.g., a molecular weight of more than 400, 500, or 1000 daltons, or which introduce a charged moiety (e.g., having more than one positive charge or one negative charge) can be placed on the sense strand.

Modifications, e.g., those described herein, which modulate, e.g., increase or decrease, the affinity of a strand for its compliment or target, can be provided as asymmetrical modifications. These include: 5 methyl U; 5 methyl C; pseudouridine, Locked nucleic acids, 2 thio U and 2-amino-A. In some embodiments one or more of these is provided on the antisense strand.

iRNA agents have a defined structure, with a sense strand and an antisense strand, and in many cases short single strand overhangs, e.g., of 2 or 3 nucleotides are present at one or both 3' ends. Asymmetrical modification can be used to optimize the activity of such a structure, e.g., by being placed selectively within the iRNA. E.g., the end region of the iRNA agent defined by the 5' end of the sense strand and the 3' end of the antisense strand is important for function. This region can include the terminal 2, 3, or 4 paired nucleotides and any 3' overhang. In preferred embodiments asymmetrical modifications which result in one or more of the following are used: modifications of the 5' end of the sense strand which inhibit kinase activation of the sense strand, including, e.g., attachments of conjugates which target the molecule or the use modifications which protect against 5' exonucleolytic degradation; or modifications of either strand, but preferably the sense strand, which enhance binding between the sense and antisense strand and thereby promote a "tight" structure at this end of the molecule.

The end region of the iRNA agent defined by the 3' end of the sense strand and the 5' end of the antisense strand is also important for function. This region can include the terminal 2, 3, or 4 paired nucleotides and any 3' overhang. Preferred embodiments include asymmetrical modifications of either strand, but preferably the sense strand, which decrease binding between the sense and antisense strand and thereby promote an "open" structure at this end of the molecule. Such modifications include placing conjugates which target the molecule or modifications which promote nuclease resistance on the sense strand in this region. Modification of the antisense strand which inhibit kinase activation are avoided in preferred embodiments.

Exemplary modifications for asymmetrical placement in the sense strand include the following:

(a) backbone modifications, e.g., modification of a backbone P, including replacement of P with S, or P substituted with alkyl or allyl, e.g., Me, and dithioates (S—P=S); these modifications can be used to promote nuclease resistance;

(b) 2'-O alkyl, e.g., 2'-OMe, 3'-O alkyl, e.g., 3'-OMe (at terminal and/or internal positions); these modifications can be used to promote nuclease resistance or to enhance binding of the sense to the antisense strand, the 3' modifications can be used at the 5' end of the sense strand to avoid sense strand activation by RISC;

(c) 2'-5' linkages (with 2'-H, 2'-OH and 2'-OMe and with P=O or P=S) these modifications can be used to promote nuclease resistance or to inhibit binding of the sense to the antisense strand, or can be used at the 5' end of the sense strand to avoid sense strand activation by RISC;

(d) L sugars (e.g., L ribose, L-arabinose with 2'-H, 2'-OH and 2'-OMe); these modifications can be used to promote nuclease resistance or to inhibit binding of the sense to the antisense strand, or can be used at the 5' end of the sense strand to avoid sense strand activation by RISC;

(e) modified sugars (e.g., locked nucleic acids (LNA's), hexose nucleic acids (HNA's) and cyclohexene nucleic acids (CeNA's)); these modifications can be used to promote nuclease resistance or to inhibit binding of the sense to the antisense strand, or can be used at the 5' end of the sense strand to avoid sense strand activation by RISC;

(f) nucleobase modifications (e.g., C-5 modified pyrimidines, N-2 modified purines, N-7 modified purines, N-6 modified purines), these modifications can be used to promote nuclease resistance or to enhance binding of the sense to the antisense strand;

(g) cationic groups and Zwitterionic groups (preferably at a terminus), these modifications can be used to promote nuclease resistance;

(h) conjugate groups (preferably at terminal positions), e.g., naproxen, biotin, cholesterol, ibuprofen, folic acid, peptides, and carbohydrates; these modifications can be used to promote nuclease resistance or to target the molecule, or can be used at the 5' end of the sense strand to avoid sense strand activation by RISC.

Exemplary modifications for asymmetrical placement in the antisense strand include the following:

(a) backbone modifications, e.g., modification of a backbone P, including replacement of P with S, or P substituted with alkyl or allyl, e.g., Me, and dithioates (S—P=S);

(b) 2'-O alkyl, e.g., 2'-OMe, (at terminal positions);

(c) 2'-5' linkages (with 2'-H, 2'-OH and 2'-OMe) e.g., terminal at the 3' end); e.g., with P=O or P=S preferably at the 3'-end, these modifications are preferably excluded from the 5' end region as they may interfere with RISC enzyme activity such as kinase activity;

(d) L sugars (e.g., L ribose, L-arabinose with 2'-H, 2'-OH and 2'-OMe); e.g., terminal at the 3' end; e.g., with P=O or P=S preferably at the 3'-end, these modifications are preferably excluded from the 5' end region as they may interfere with kinase activity;

(e) modified sugars (e.g., LNA's, HNA's and CeNA's); these modifications are preferably excluded from the 5' end region as they may contribute to unwanted enhancements of paring between the sense and antisense strands, it is often preferred to have a "loose" structure in the 5' region, additionally, they may interfere with kinase activity;

(f) nucleobase modifications (e.g., C-5 modified pyrimidines, N-2 modified purines, N-7 modified purines, N-6 modified purines);

(g) cationic groups and Zwitterionic groups (preferably at a terminus);

conjugate groups (preferably at terminal positions), e.g., naproxen, biotin, cholesterol, ibuprofen, folic acid, peptides, and carbohydrates, but bulky groups or generally groups which inhibit RISC activity should are less preferred.

The 5'-OH of the antisense strand should be kept free to promote activity. In some preferred embodiments modifications that promote nuclease resistance should be included at the 3' end, particularly in the 3' overhang.

In another aspect, the invention features a method of optimizing, e.g., stabilizing, an iRNA agent. The method includes selecting a sequence having activity, introducing one or more asymmetric modifications into the sequence, wherein the introduction of the asymmetric modification optimizes a property of the iRNA agent but does not result in a decrease in activity.

The decrease in activity can be less than a preselected level of decrease. In preferred embodiments decrease in activity means a decrease of less than 5, 10, 20, 40, or 50% activity, as compared with an otherwise similar iRNA lacking the introduced modification. Activity can, e.g., be measured in vivo, or in vitro, with a result in either being sufficient to demonstrate the required maintenance of activity.

The optimized property can be any property described herein and in particular the properties discussed in the section on asymmetrical modifications provided herein. The modification can be any asymmetrical modification, e.g., an asymmetric modification described in the section on asymmetrical modifications described herein. Particularly preferred asymmetric modifications are 2'-O alkyl modifications, e.g., 2'-OMe modifications, particularly in the sense sequence, and modifications of a backbone O, particularly phosphorothioate modifications, in the antisense sequence.

In a preferred embodiment a sense sequence is selected and provided with an asymmetrical modification, while in other embodiments an antisense sequence is selected and provided with an asymmetrical modification. In some embodiments both sense and antisense sequences are selected and each provided with one or more asymmetrical modifications.

Multiple asymmetric modifications can be introduced into either or both of the sense and antisense sequence. A sequence can have at least 2, 4, 6, 8, or more modifications and all or substantially all of the monomers of a sequence can be modified.

Table 2 shows examples having strand I with a selected modification and strand II with a selected modification.

TABLE 2

Exemplary strand I- and strand II-modifications

| Strand I | Strand II |
| --- | --- |
| Nuclease Resistance (e.g., 2'-OMe) | Biodistribution (e.g., P=S) |
| Biodistribution conjugate (e.g., Lipophile) | Protein Binding Functionality (e.g., Naproxen) |
| Tissue Distribution Functionality (e.g., Carbohydrates) | Cell Targeting Functionality (e.g., Folate for cancer cells) |
| Tissue Distribution Functionality (e.g., Kidney Cell Targetingmoieties) | Fusogenic Functionality (e.g., Polyethylene imines) |
| Cancer Cell Targeting (e.g., RGD peptides and imines) | Fusogenic Functionality (e.g., peptides) |
| Nuclease Resistance (e.g. 2'-OMe), | Increase in binding Affinity (5-Me-C, 5-Me-U, 2-thio-U, 2-amino-A, G-clamp, LNA) |
| Tissue Distribution Functionality | RISC activity improving Functionality |
| Helical conformation changing Functionalities | Tissue Distribution Functionality (P=S; lipophile, carbohydrates) |

Z-X-Y Architecture

The monomers and methods described herein can be used to prepare an RNA, e.g., an iRNA agent, having a Z-X-Y architecture or structure such as those described herein and those described in copending, co-owned U.S. Provisional Application Ser. No. 60/510,246, filed on Oct. 9, 2003, which is hereby incorporated by reference, copending, co-owned U.S. Provisional Application Ser. No. 60/510,318, filed on Oct. 10, 2003, which is hereby incorporated by reference, and copending, co-owned International Application No. PCT/US04/07070, filed Mar. 8, 2004.

Thus, an iRNA agent can have a first segment, the Z region, a second segment, the X region, and optionally a third region, the Y region:

Z—X—Y.

It may be desirable to modify subunits in one or both of Z and/or Y on one hand and X on the other hand. In some cases they will have the same modification or the same class of modification but it will more often be the case that the modifications made in Z and/or Y will differ from those made in X.

The Z region typically includes a terminus of an iRNA agent. The length of the Z region can vary, but will typically be from 2-14, more preferably 2-10, subunits in length. It typically is single stranded, i.e., it will not base pair with bases of another strand, though it may in some embodiments self associate, e.g., to form a loop structure. Such structures can be formed by the end of a strand looping back and forming an intrastrand duplex. E.g., 2, 3, 4, 5 or more intra-strand bases pairs can form, having a looped out or connecting region, typically of 2 or more subunits which do not pair. This can occur at one or both ends of a strand. A typical embodiment of a Z region is a single strand overhang, e.g., an over hang of the length described elsewhere herein. The Z region can thus be or include a 3' or 5' terminal single strand. It can be sense or antisense strand but if it is antisense it is preferred that it is a 3-overhang. Typical inter-subunit bonds in the Z region include: P=O; P=S; S—P=S; P—NR$_2$; and P—BR$_2$.

Chiral P=X, where X is S, N, or B) inter-subunit bonds can also be present. (These inter-subunit bonds are discussed in more detail elsewhere herein.) Other preferred Z region subunit modifications (also discussed elsewhere herein) can include: 3'-OR, 3'SR, 2'-OMe, 3'-OMe, and 2'OH modifications and moieties; alpha configuration bases; and 2' arabino modifications.

The X region will in most cases be duplexed, in the case of a single strand iRNA agent, with a corresponding region of the single strand, or in the case of a double stranded iRNA agent, with the corresponding region of the other strand. The length of the X region can vary but will typically be between 10-45 and more preferably between 15 and 35 subunits. Particularly preferred region X's will include 17, 18, 19, 29, 21, 22, 23, 24, or 25 nucleotide pairs, though other suitable lengths are described elsewhere herein and can be used. Typical X region subunits include 2'-OH subunits. In typical embodiments phosphate inter-subunit bonds are preferred while phosphorothioate or non-phosphate bonds are absent. Other modifications preferred in the X region include: modifications to improve binding, e.g., nucleobase modifications; cationic nucleobase modifications; and C-5 modified pyrimidines, e.g., allylamines. Some embodiments have 4 or more consecutive 2'OH subunits. While the use of phosphorothioate is sometimes non preferred they can be used if they connect less than 4 consecutive 2'OH subunits.

The Y region will generally conform to the parameters set out for the Z regions. However, the X and Z regions need not be the same, different types and numbers of modifications can be present, and in fact, one will usually be a 3' overhang and one will usually be a 5' overhang.

In a preferred embodiment the iRNA agent will have a Y and/or Z region each having ribonucleosides in which the 2'-OH is substituted, e.g., with 2'-OMe or other alkyl; and an X region that includes at least four consecutive ribonucleoside subunits in which the 2'-OH remains unsubstituted.

The subunit linkages (the linkages between subunits) of an iRNA agent can be modified, e.g., to promote resistance to degradation. Numerous examples of such modifications are disclosed herein, one example of which is the phosphorothioate linkage. These modifications can be provided between the subunits of any of the regions, Y, X, and Z. However, it is preferred that their occurrences minimized and in particular it is preferred that consecutive modified linkages be avoided.

In a preferred embodiment the iRNA agent will have a Y and Z region each having ribonucleosides in which the 2'-OH is substituted, e.g., with 2'-OMe; and an X region that includes at least four consecutive subunits, e.g., ribonucleoside subunits in which the 2'-OH remains unsubstituted.

As mentioned above, the subunit linkages of an iRNA agent can be modified, e.g., to promote resistance to degradation. These modifications can be provided between the subunits of any of the regions, Y, X, and Z. However, it is preferred that they are minimized and in particular it is preferred that consecutive modified linkages be avoided.

Thus, in a preferred embodiment, not all of the subunit linkages of the iRNA agent are modified and more preferably the maximum number of consecutive subunits linked by other than a phosphodiester bond will be 2, 3, or 4. Particularly preferred iRNA agents will not have four or more consecutive subunits, e.g., 2'-hydroxyl ribonucleoside subunits, in which each subunits is joined by modified linkages—i.e. linkages that have been modified to stabilize them from degradation as compared to the phosphodiester linkages that naturally occur in RNA and DNA.

It is particularly preferred to minimize the occurrence in region X. Thus, in preferred embodiments each of the nucleoside subunit linkages in X will be phosphodiester linkages, or if subunit linkages in region X are modified, such modifications will be minimized. E.g., although the Y and/or Z regions can include inter subunit linkages which have been stabilized against degradation, such modifications will be minimized in the X region, and in particular consecutive modifications will be minimized. Thus, in preferred embodiments the maximum number of consecutive subunits linked by other than a phosphodiester bond will be 2, 3, or 4. Particularly preferred X regions will not have four or more consecutive subunits, e.g., 2'-hydroxyl ribonucleoside subunits, in which each subunits is joined by modified linkages—i.e. linkages that have been modified to stabilize them from degradation as compared to the phosphodiester linkages that naturally occur in RNA and DNA.

In a preferred embodiment Y and/or Z will be free of phosphorothioate linkages, though either or both may contain other modifications, e.g., other modifications of the subunit linkages.

In a preferred embodiment region X, or in some cases, the entire iRNA agent, has no more than 3 or no more than 4 subunits having identical 2' moieties.

In a preferred embodiment region X, or in some cases, the entire iRNA agent, has no more than 3 or no more than 4 subunits having identical subunit linkages.

In a preferred embodiment one or more phosphorothioate linkages (or other modifications of the subunit linkage) are present in Y and/or Z, but such modified linkages do not connect two adjacent subunits, e.g., nucleosides, having a 2' modification, e.g., a 2'-O-alkyl moiety. E.g., any adjacent 2'-O-alkyl moieties in the Y and/or Z, are connected by a linkage other than a phosphorothioate linkage.

In a preferred embodiment each of Y and/or Z independently has only one phosphorothioate linkage between adjacent subunits, e.g., nucleosides, having a 2' modification, e.g., 2'-O-alkyl nucleosides. If there is a second set of adjacent subunits, e.g., nucleosides, having a 2' modification, e.g., 2'-O-alkyl nucleosides, in Y and/or Z that second set is connected by a linkage other than a phosphorothioate linkage, e.g., a modified linkage other than a phosphorothioate linkage.

In a preferred embodiment each of Y and/or Z independently has more than one phosphorothioate linkage connecting adjacent pairs of subunits, e.g., nucleosides, having a 2' modification, e.g., 2'-O-alkyl nucleosides, but at least one pair of adjacent subunits, e.g., nucleosides, having a 2' modification, e.g., 2'-O-alkyl nucleosides, are be connected by a linkage other than a phosphorothioate linkage, e.g., a modified linkage other than a phosphorothioate linkage.

In a preferred embodiment one of the above recited limitation on adjacent subunits in Y and or Z is combined with a limitation on the subunits in X. E.g., one or more phosphorothioate linkages (or other modifications of the subunit linkage) are present in Y and/or Z, but such modified linkages do not connect two adjacent subunits, e.g., nucleosides, having a 2' modification, e.g., a 2'-O-alkyl moiety. E.g., any adjacent 2'-O-alkyl moieties in the Y and/or Z, are connected by a linkage other than a phosphorothioate linkage. In addition, the X region has no more than 3 or no more than 4 identical subunits, e.g., subunits having identical 2' moieties or the X region has no more than 3 or no more than 4 subunits having identical subunit linkages.

A Y and/or Z region can include at least one, and preferably 2, 3 or 4 of a modification disclosed herein. Such modifications can be chosen, independently, from any modification described herein, e.g., from nuclease resistant subunits, subunits with modified bases, subunits with modified intersubunit linkages, subunits with modified sugars, and subunits linked to another moiety, e.g., a targeting moiety. In a preferred embodiment more than 1 of such subunits can be present but in some embodiments it is preferred that no more than 1, 2, 3, or 4 of such modifications occur, or occur consecutively. In a preferred embodiment the frequency of the modification will differ between Y and/or Z and X, e.g., the modification will be present one of Y and/or Z or X and absent in the other.

An X region can include at least one, and preferably 2, 3 or 4 of a modification disclosed herein. Such modifications can be chosen, independently, from any modification described herein, e.g., from nuclease resistant subunits, subunits with modified bases, subunits with modified intersubunit linkages, subunits with modified sugars, and subunits linked to another moiety, e.g., a targeting moiety. In a preferred embodiment more than 1 of such subunits can b present but in some embodiments it is preferred that no more than 1, 2, 3, or 4 of such modifications occur, or occur consecutively.

An RRMS (described elsewhere herein) can be introduced at one or more points in one or both strands of a double-stranded iRNA agent. An RRMS can be placed in a Y and/or Z region, at or near (within 1, 2, or 3 positions) of the 3' or 5' end of the sense strand or at near (within 2 or 3 positions of) the 3' end of the antisense strand. In some embodiments it is preferred to not have an RRMS at or near (within 1, 2, or 3 positions of) the 5' end of the antisense strand. An RRMS can be positioned in the X region, and will preferably be positioned in the sense strand or in an area of the antisense strand not critical for antisense binding to the target.

Differential Modification of Terminal Duplex Stability

In one aspect, the monomers and methods described herein can be used to prepare an iRNA agent having differential modification of terminal duplex stability (DMTDS).

In addition, the monomers and methods described herein can be used to prepare iRNA agents having DMTDS and another element described herein. E.g., the monomers and methods described herein can be used to prepare an iRNA agent described herein, e.g., a palindromic iRNA agent, an iRNA agent having a non canonical pairing, an iRNA agent which targets a gene described herein, e.g., a gene active in the kidney, an iRNA agent having an architecture or structure described herein, an iRNA associated with an amphipathic delivery agent described herein, an iRNA associated with a drug delivery module described herein, an iRNA agent administered as described herein, or an iRNA agent formulated as described herein, which also incorporates DMTDS.

iRNA agents can be optimized by increasing the propensity of the duplex to disassociate or melt (decreasing the free energy of duplex association), in the region of the 5' end of the antisense strand duplex. This can be accomplished, e.g., by the inclusion of subunits which increase the propensity of the duplex to disassociate or melt in the region of the 5' end of the antisense strand. It can also be accomplished by the attachment of a ligand that increases the propensity of the duplex to disassociate of melt in the region of the 5' end. While not wishing to be bound by theory, the effect may be due to promoting the effect of an enzyme such as helicase, for example, promoting the effect of the enzyme in the proximity of the 5' end of the antisense strand.

The inventors have also discovered that iRNA agents can be optimized by decreasing the propensity of the duplex to disassociate or melt (increasing the free energy of duplex association), in the region of the 3' end of the antisense strand duplex. This can be accomplished, e.g., by the inclusion of subunits which decrease the propensity of the duplex to disassociate or melt in the region of the 3' end of the antisense strand. It can also be accomplished by the attachment of ligand that decreases the propensity of the duplex to dissociate of melt in the region of the 5' end.

Modifications which increase the tendency of the 5' end of the duplex to dissociate can be used alone or in combination with other modifications described herein, e.g., with modifications which decrease the tendency of the 3' end of the duplex to dissociate. Likewise, modifications which decrease the tendency of the 3' end of the duplex to dissociate can be used alone or in combination with other modifications described herein, e.g., with modifications which increase the tendency of the 5' end of the duplex to dissociate.

Decreasing the Stability of the AS 5' End of the Duplex

Subunit pairs can be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation:

A:U is preferred over G:C;
G:U is preferred over G:C;
I:C is preferred over G:C (I=inosine);
mismatches, e.g., non-canonical or other than canonical pairings (as described elsewhere herein) are preferred over canonical (A:T, A:U, G:C) pairings;
pairings which include a universal base are preferred over canonical pairings.

A typical ds iRNA agent can be diagrammed as follows:

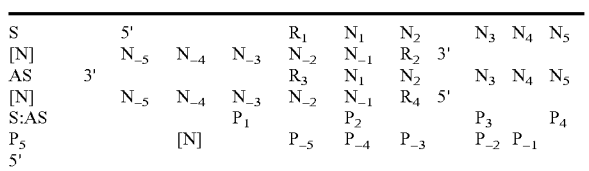

S indicates the sense strand; AS indicates antisense strand; $R_1$ indicates an optional (and nonpreferred) 5' sense strand overhang; $R_2$ indicates an optional (though preferred) 3' sense overhang; $R_3$ indicates an optional (though preferred) 3' antisense sense overhang; $R_4$ indicates an optional (and nonpreferred) 5' antisense overhang; N indicates subunits; [N] indicates that additional subunit pairs may be present; and $P_x$, indicates a paring of sense $N_x$ and antisense N. Overhangs are not shown in the P diagram. In some embodiments a 3' AS overhang corresponds to region Z, the duplex region corresponds to region X, and the 3' S strand overhang corresponds to region Y, as described elsewhere herein. (The diagram is not meant to imply maximum or minimum lengths, on which guidance is provided elsewhere herein.)

It is preferred that pairings which decrease the propensity to form a duplex are used at 1 or more of the positions in the duplex at the 5' end of the AS strand. The terminal pair (the most 5' pair in terms of the AS strand) is designated as $P_{-1}$, and the subsequent pairing positions (going in the 3' direction in terms of the AS strand) in the duplex are designated, $P_{-2}$, $P_{-3}$, $P_{-4}$, $P_{-5}$, and so on. The preferred region in which to modify to modulate duplex formation is at $P_{-5}$ through $P_{-1}$, more preferably $P_{-4}$ through $P_{-1}$, more preferably $P_{-3}$ through $P_{-1}$. Modification at $P_{-1}$, is particularly preferred, alone or with modification(s) other position(s), e.g., any of the positions just identified. It is preferred that at least 1, and more preferably 2, 3, 4, or 5 of the pairs of one of the recited regions be chosen independently from the group of:

A:U
G:U
I:C
mismatched pairs, e.g., non-canonical or other than canonical pairings or pairings which include a universal base.

In preferred embodiments the change in subunit needed to achieve a pairing which promotes dissociation will be made in the sense strand, though in some embodiments the change will be made in the antisense strand.

In a preferred embodiment the at least 2, or 3, of the pairs in $P_{-1}$, through $P_{-4}$, are pairs which promote dissociation.

In a preferred embodiment the at least 2, or 3, of the pairs in $P_{-1}$, through $P_{-4}$, are A:U.

In a preferred embodiment the at least 2, or 3, of the pairs in $P_{-1}$, through $P_{-4}$, are G:U.

In a preferred embodiment the at least 2, or 3, of the pairs in $P_{-1}$, through $P_{-4}$, are I:C.

In a preferred embodiment the at least 2, or 3, of the pairs in $P_{-1}$, through $P_{-4}$, are mismatched pairs, e.g., non-canonical or other than canonical pairings.

In a preferred embodiment the at least 2, or 3, of the pairs in $P_{-1}$, through $P_{-4}$, are pairings which include a universal base.

Increasing the Stability of the AS 3' End of the Duplex

Subunit pairs can be ranked on the basis of their propensity to promote stability and inhibit dissociation or melting (e.g., on the free energy of association or dissociation of a particular pairing, the simplest approach is to examine the pairs on an individual pair basis, though next neighbor or similar analysis can also be used). In terms of promoting duplex stability:

G:C is preferred over A:U
Watson-Crick matches (A:T, A:U, G:C) are preferred over non-canonical or other than canonical pairings
analogs that increase stability are preferred over Watson-Crick matches (A:T, A:U, G:C)
2-amino-A:U is preferred over A:U
2-thio U or 5 Me-thio-U:A are preferred over U:A
G-clamp (an analog of C having 4 hydrogen bonds):G is preferred over C:G
guanadinium-G-clamp:G is preferred over C:G
psuedo uridine:A is preferred over U:A
sugar modifications, e.g., 2' modifications, e.g., 2'F, ENA, or LNA, which enhance binding are preferred over non-modified moieties and can be present on one or both strands to enhance stability of the duplex. It is preferred that pairings which increase the propensity to form a duplex are used at 1 or more of the positions in the duplex at the 3' end of the AS strand. The terminal pair (the most 3' pair in terms of the AS strand) is designated as $P_1$, and the subsequent pairing positions (going in the 5' direction in terms of the AS strand) in the duplex are designated, $P_2$, $P_3$, $P_4$, $P_5$, and so on. The preferred region in which to modify to modulate duplex formation is at $P_5$ through $P_1$, more preferably $P_4$ through $P_1$, more preferably $P_3$ through $P_1$. Modification at $P_1$, is particularly preferred, alone or with modification(s) at other position(s), e.g., any of the positions just identified. It is preferred that at least 1, and more preferably 2, 3, 4, or 5 of the pairs of the recited regions be chosen independently from the group of:

G:C
a pair having an analog that increases stability over Watson-Crick matches (A:T, A:U, G:C)
2-amino-A:U
2-thio U or 5 Me-thio-U:A
G-clamp (an analog of C having 4 hydrogen bonds):G
guanadinium-G-clamp:G
psuedo uridine:A a pair in which one or both subunits has a sugar modification, e.g., a 2' modification, e.g., 2'F, ENA, or LNA, which enhance binding.

In a preferred embodiment the at least 2, or 3, of the pairs in $P_{-1}$, through $P_{-4}$, are pairs which promote duplex stability.

In a preferred embodiment the at least 2, or 3, of the pairs in $P_1$, through $P_4$, are G:C.

In a preferred embodiment the at least 2, or 3, of the pairs in $P_1$, through $P_4$, are a pair having an analog that increases stability over Watson-Crick matches.

In a preferred embodiment the at least 2, or 3, of the pairs in $P_1$, through $P_4$, are 2-amino-A:U.

In a preferred embodiment the at least 2, or 3, of the pairs in $P_1$, through $P_4$, are 2-thio U or 5 Me-thio-U:A.

In a preferred embodiment the at least 2, or 3, of the pairs in $P_1$, through $P_4$, are G-clamp:G.

In a preferred embodiment the at least 2, or 3, of the pairs in $P_1$, through $P_4$, are guanidinium-G-clamp:G.

In a preferred embodiment the at least 2, or 3, of the pairs in $P_1$, through $P_4$, are psuedo uridine:A.

In a preferred embodiment the at least 2, or 3, of the pairs in $P_1$, through $P_4$, are a pair in which one or both subunits has a sugar modification, e.g., a 2' modification, e.g., 2'F, ENA, or LNA, which enhances binding.

G-clamps and guanidinium G-clamps are discussed in the following references: Holmes and Gait, "The Synthesis of 2'-O-Methyl G-Clamp Containing Oligonucleotides and Their Inhibition of the HIV-1 Tat-TAR Interaction," Nucleosides, Nucleotides & Nucleic Acids, 22:1259-1262, 2003; Holmes et al., "Steric inhibition of human immunodeficiency virus type-1 Tat-dependent trans-activation in vitro and in cells by oligonucleotides containing 2'-O-methyl G-clamp ribonucleoside analogues," Nucleic Acids Research, 31:2759-2768, 2003; Wilds, et al., "Structural basis for recognition of guanosine by a synthetic tricyclic cytosine analogue: Guanidinium G-clamp," Helvetica Chimica Acta, 86:966-978, 2003; Rajeev, et al., "High-Affinity Peptide Nucleic Acid Oligomers Containing Tricyclic Cytosine Analogues," Organic Letters, 4:4395-4398, 2002; Ausin, et al., "Synthesis of Amino- and Guanidino-G-Clamp PNA Monomers," Organic Letters, 4:4073-4075, 2002; Maier et al., "Nuclease resistance of oligonucleotides containing the tricyclic cytosine analogues phenoxazine and 9-(2-aminoethoxy)-phenoxazine ("G-clamp") and origins of their nuclease resistance properties," Biochemistry, 41:1323-7, 2002; Flanagan, et al., "A cytosine analog that confers enhanced potency to antisense oligonucleotides," Proceedings Of The National Academy Of Sciences Of The United States Of America, 96:3513-8, 1999.

Simultaneously Decreasing the Stability of the AS 5' End of the Duplex and Increasing the Stability of the AS 3' End of the Duplex As is discussed above, an iRNA agent can be modified to both decrease the stability of the AS 5' end of the duplex and increase the stability of the AS 3' end of the duplex. This can be effected by combining one or more of the stability decreasing modifications in the AS 5' end of the duplex with one or more of the stability increasing modifications in the AS 3' end of the duplex. Accordingly a preferred embodiment includes modification in $P_{-5}$ through $P_{-i}$, more preferably $P_{-1}$ through $P_{-1}$ and more preferably $P_{-3}$ through $P_{-1}$. Modification at $P_{-1}$, is particularly preferred, alone or with other position, e.g., the positions just identified. It is preferred that at least 1, and more preferably 2, 3, 4, or 5 of the pairs of one of the recited regions of the AS 5' end of the duplex region be chosen independently from the group of:

A:U
G:U
I:C
mismatched pairs, e.g., non-canonical or other than canonical pairings which include a universal base; and
a modification in $P_5$ through $P_1$, more preferably $P_4$ through $P_1$ and more preferably $P_3$ through $P_1$. Modification at $P_1$, is particularly preferred, alone or with other position, e.g., the positions just identified. It is preferred that at least 1, and more preferably 2, 3, 4, or 5 of the pairs of one of the recited regions of the AS 3' end of the duplex region be chosen independently from the group of:
G:C
a pair having an analog that increases stability over Watson-Crick matches (A:T, A:U, G:C)
2-amino-A:U
2-thio U or 5 Me-thio-U:A
G-clamp (an analog of C having 4 hydrogen bonds):G
guanadinium-G-clamp:G
psuedo uridine:A
a pair in which one or both subunits has a sugar modification, e.g., a 2' modification, e.g., 2'F, ENA, or LNA, which enhance binding.

The invention also includes methods of selecting and making iRNA agents having DMTDS. E.g., when screening a target sequence for candidate sequences for use as iRNA agents one can select sequences having a DMTDS property described herein or one which can be modified, preferably with as few changes as possible, especially to the AS strand, to provide a desired level of DMTDS.

The invention also includes, providing a candidate iRNA agent sequence, and modifying at least one P in $P_{-5}$ through $P_{-1}$ and/or at least one P in $P_5$ through $P_1$ to provide a DMTDS iRNA agent.

DMTDS iRNA agents can be used in any method described herein, e.g., to silence any gene disclosed herein, to treat any disorder described herein, in any formulation described herein, and generally in and/or with the methods and compositions described elsewhere herein. DMTDS iRNA agents can incorporate other modifications described herein, e.g., the attachment of targeting agents or the inclusion of modifications which enhance stability, e.g., the inclusion of nuclease resistant monomers or the inclusion of single strand overhangs (e.g., 3' AS overhangs and/or 3' S strand overhangs) which self associate to form intrastrand duplex structure. Preferably these iRNA agents will have an architecture described herein.

Other Embodiments

An RNA, e.g., an iRNA agent, can be produced in a cell in vivo, e.g., from exogenous DNA templates that are delivered into the cell. For example, the DNA templates can be inserted into vectors and used as gene therapy vectors. Gene therapy vectors can be delivered to a subject by, for example, intravenous injection, local administration (U.S. Pat. No. 5,328, 470), or by stereotactic injection (see, e.g., Chen et al., Proc. Natl. Acad. Sci. USA 91:3054-3057, 1994). The pharmaceutical preparation of the gene therapy vector can include the gene therapy vector in an acceptable diluent, or can comprise a slow release matrix in which the gene delivery vehicle is imbedded. The DNA templates, for example, can include two transcription units, one that produces a transcript that includes the top strand of an iRNA agent and one that produces a transcript that includes the bottom strand of an iRNA agent. When the templates are transcribed, the iRNA agent is produced, and processed into sRNA agent fragments that mediate gene silencing.

In Vivo Delivery

An iRNA agent can be linked, e.g., noncovalently linked to a polymer for the efficient delivery of the iRNA agent to a subject, e.g., a mammal, such as a human. The iRNA agent can, for example, be complexed with cyclodextrin. Cyclodextrins have been used as delivery vehicles of therapeutic compounds. Cyclodextrins can form inclusion complexes with drugs that are able to fit into the hydrophobic cavity of the cyclodextrin. In other examples, cyclodextrins form non-covalent associations with other biologically active molecules such as oligonucleotides and derivatives thereof. The use of cyclodextrins creates a water-soluble drug delivery complex, that can be modified with targeting or other functional groups. Cyclodextrin cellular delivery system for oligonucleotides described in U.S. Pat. No. 5,691,316, which is hereby incorporated by reference, are suitable for use in methods of the invention. In this system, an oligonucleotide is noncovalently complexed with a cyclodextrin, or the oligonucleotide is covalently bound to adamantine which in turn is non-covalently associated with a cyclodextrin.

The delivery molecule can include a linear cyclodextrin copolymer or a linear oxidized cyclodextrin copolymer having at least one ligand bound to the cyclodextrin copolymer. Delivery systems, as described in U.S. Pat. No. 6,509,323, herein incorporated by reference, are suitable for use in methods of the invention. An iRNA agent can be bound to the linear cyclodextrin copolymer and/or a linear oxidized cyclodextrin copolymer. Either or both of the cyclodextrin or oxidized cyclodextrin copolymers can be crosslinked to another polymer and/or bound to a ligand.

A composition for iRNA delivery can employ an "inclusion complex," a molecular compound having the characteristic structure of an adduct. In this structure, the "host molecule" spatially encloses at least part of another compound in the delivery vehicle. The enclosed compound (the "guest molecule") is situated in the cavity of the host molecule without affecting the framework structure of the host. A "host" is preferably cyclodextrin, but can be any of the molecules suggested in U.S. Patent Publ. 2003/0008818, herein incorporated by reference.

Cyclodextrins can interact with a variety of ionic and molecular species, and the resulting inclusion compounds belong to the class of "host-guest" complexes. Within the host-guest relationship, the binding sites of the host and guest molecules should be complementary in the stereoelectronic sense. A composition of the invention can contain at least one polymer and at least one therapeutic agent, generally in the form of a particulate composite of the polymer and therapeutic agent, e.g., the iRNA agent. The iRNA agent can contain one or more complexing agents. At least one polymer of the particulate composite can interact with the complexing agent in a host-guest or a guest-host interaction to form an inclusion complex between the polymer and the complexing agent. The polymer and, more particularly, the complexing agent can be used to introduce functionality into the composition. For example, at least one polymer of the particulate composite has host functionality and forms an inclusion complex with a complexing agent having guest functionality. Alternatively, at least one polymer of the particulate composite has guest functionality and forms an inclusion complex with a complexing agent having host functionality. A polymer of the particulate composite can also contain both host and guest functionalities and form inclusion complexes with guest complexing agents and host complexing agents. A polymer with functionality can, for example, facilitate cell targeting and/or cell contact (e.g., targeting or contact to a kidney cell), intercellular trafficking, and/or cell entry and release.

Upon forming the particulate composite, the iRNA agent may or may not retain its biological or therapeutic activity. Upon release from the therapeutic composition, specifically, from the polymer of the particulate composite, the activity of the iRNA agent is restored. Accordingly, the particulate composite advantageously affords the iRNA agent protection against loss of activity due to, for example, degradation and offers enhanced bioavailability. Thus, a composition may be used to provide stability, particularly storage or solution stability, to an iRNA agent or any active chemical compound. The iRNA agent may be further modified with a ligand prior to or after particulate composite or therapeutic composition formation. The ligand can provide further functionality. For example, the ligand can be a targeting moiety.

Physiological Effects

The iRNA agents described herein can be designed such that determining therapeutic toxicity is made easier by the complementarity of the iRNA agent with both a human and a non-human animal sequence. By these methods, an iRNA agent can consist of a sequence that is fully complementary to a nucleic acid sequence from a human and a nucleic acid sequence from at least one non-human animal, e.g., a non-human mammal, such as a rodent, ruminant or primate. For example, the non-human mammal can be a mouse, rat, dog, pig, goat, sheep, cow, monkey, Pan paniscus, Pan troglodytes, Macaca mulatto, or Cynomolgus monkey. The sequence of the iRNA agent could be complementary to sequences within homologous genes, e.g., oncogenes or tumor suppressor genes, of the non-human mammal and the human. By determining the toxicity of the iRNA agent in the non-human mammal, one can extrapolate the toxicity of the iRNA agent in a human. For a more strenuous toxicity test, the iRNA agent can be complementary to a human and more than one, e.g., two or three or more, non-human animals.

The methods described herein can be used to correlate any physiological effect of an iRNA agent on a human, e.g., any unwanted effect, such as a toxic effect, or any positive, or desired effect.

Delivery Module

The monomers and methods described herein can be used to prepare an RNA, e.g., an iRNA agent described herein, that can be used with a drug delivery conjugate or module, such as those described herein and those described in copending, co-owned U.S. Provisional Application Ser. No. 60/454,265, filed on Mar. 12, 2003, and International Application Serial No. PCT/US04/07070, filed Mar. 8, 2004, both of which are hereby incorporated by reference.

The iRNA agents can be complexed to a delivery agent that features a modular complex. The complex can include a carrier agent linked to one or more of (preferably two or more, more preferably all three of): (a) a condensing agent (e.g., an agent capable of attracting, e.g., binding, a nucleic acid, e.g., through ionic or electrostatic interactions); (b) a fusogenic agent (e.g., an agent capable of fusing and/or being transported through a cell membrane, e.g., an endosome membrane); and (c) a targeting group, e.g., a cell or tissue targeting agent, e.g., a lectin, glycoprotein, lipid or protein, e.g., an antibody, that binds to a specified cell type such as a kidney cell.

An iRNA agent, e.g., iRNA agent or sRNA agent described herein, can be linked, e.g., coupled or bound, to the modular complex. The iRNA agent can interact with the condensing agent of the complex, and the complex can be used to deliver an iRNA agent to a cell, e.g., in vitro or in vivo. For example, the complex can be used to deliver an iRNA agent to a subject in need thereof, e.g., to deliver an iRNA agent to a subject having a disorder, e.g., a disorder described herein, such as a disease or disorder of the kidney.

The fusogenic agent and the condensing agent can be different agents or the one and the same agent. For example, a polyamino chain, e.g., polyethyleneimine (PEI), can be the fusogenic and/or the condensing agent.

The delivery agent can be a modular complex. For example, the complex can include a carrier agent linked to one or more of (preferably two or more, more preferably all three of):

(a) a condensing agent (e.g., an agent capable of attracting, e.g., binding, a nucleic acid, e.g., through ionic interaction), (b) a fusogenic agent (e.g., an agent capable of fusing and/or being transported through a cell membrane, e.g., an endosome membrane), and (c) a targeting group, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, Neproxin, or an RGD peptide or RGD peptide mimetic.

Carrier Agents

The carrier agent of a modular complex described herein can be a substrate for attachment of one or more of: a condensing agent, a fusogenic agent, and a targeting group. The carrier agent would preferably lack an endogenous enzymatic activity. The agent would preferably be a biological molecule, preferably a macromolecule. Polymeric biological carriers are preferred. It would also be preferred that the carrier molecule be biodegradable.

The carrier agent can be a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin or hyaluronic acid); or lipid. The carrier molecule can also be a recombinant or synthetic molecule, such as a synthetic polymer, e.g., a synthetic polyamino acid. Examples of polyamino acids include polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Other useful carrier molecules can be identified by routine methods.

A carrier agent can be characterized by one or more of: (a) is at least 1 Da in size; (b) has at least 5 charged groups, preferably between 5 and 5000 charged groups; (c) is present in the complex at a ratio of at least 1:1 carrier agent to fusogenic agent; (d) is present in the complex at a ratio of at least 1:1 carrier agent to condensing agent; (e) is present in the complex at a ratio of at least 1:1 carrier agent to targeting agent.

Fusogenic Agents

A fusogenic agent of a modular complex described herein can be an agent that is responsive to, e.g., changes charge depending on, the pH environment. Upon encountering the pH of an endosome, it can cause a physical change, e.g., a change in osmotic properties which disrupts or increases the permeability of the endosome membrane. Preferably, the fusogenic agent changes charge, e.g., becomes protonated, at pH lower than physiological range. For example, the fusogenic agent can become protonated at pH 4.5-6.5. The fusogenic agent can serve to release the iRNA agent into the cytoplasm of a cell after the complex is taken up, e.g., via endocytosis, by the cell, thereby increasing the cellular concentration of the iRNA agent in the cell.

In one embodiment, the fusogenic agent can have a moiety, e.g., an amino group, which, when exposed to a specified pH range, will undergo a change, e.g., in charge, e.g., protonation. The change in charge of the fusogenic agent can trigger a change, e.g., an osmotic change, in a vesicle, e.g., an endocytic vesicle, e.g., an endosome. For example, the fusogenic agent, upon being exposed to the pH environment of an endosome, will cause a solubility or osmotic change substantial enough to increase the porosity of (preferably, to rupture) the endosomal membrane.

The fusogenic agent can be a polymer, preferably a polyamino chain, e.g., polyethyleneimine (PEI). The PEI can be linear, branched, synthetic or natural. The PEI can be, e.g., alkyl substituted PEI, or lipid substituted PEI.

In other embodiments, the fusogenic agent can be polyhistidine, polyimidazole, polypyridine, polypropyleneimine, mellitin, or a polyacetal substance, e.g., a cationic polyacetal. In some embodiment, the fusogenic agent can have an alpha helical structure. The fusogenic agent can be a membrane disruptive agent, e.g., mellittin.

A fusogenic agent can have one or more of the following characteristics: (a) is at least 1Da in size; (b) has at least 10 charged groups, preferably between 10 and 5000 charged groups, more preferably between 50 and 1000 charged groups; (c) is present in the complex at a ratio of at least 1:1 fusogenic agent to carrier agent; (d) is present in the complex at a ratio of at least 1:1 fusogenic agent to condensing agent; (e) is present in the complex at a ratio of at least 1:1 fusogenic agent to targeting agent.

Other suitable fusogenic agents can be tested and identified by a skilled artisan. The ability of a compound to respond to, e.g., change charge depending on, the pH environment can be tested by routine methods, e.g., in a cellular assay. For example, a test compound is combined or contacted with a cell, and the cell is allowed to take up the test compound, e.g., by endocytosis. An endosome preparation can then be made from the contacted cells and the endosome preparation compared to an endosome preparation from control cells. A change, e.g., a decrease, in the endosome fraction from the contacted cell vs. the control cell indicates that the test compound can function as a fusogenic agent. Alternatively, the contacted cell and control cell can be evaluated, e.g., by microscopy, e.g., by light or electron microscopy, to determine a difference in endosome population in the cells. The test compound can be labeled. In another type of assay, a modular complex described herein is constructed using one or more test or putative fusogenic agents. The modular complex can be constructed using a labeled nucleic acid instead of the iRNA. The ability of the fusogenic agent to respond to, e.g., change charge depending on, the pH environment, once the modular complex is taken up by the cell, can be evaluated, e.g., by preparation of an endosome preparation, or by microscopy techniques, as described above. A two-step assay can also be performed, wherein a first assay evaluates the ability of a test compound alone to respond to, e.g., change charge depending on, the pH environment; and a second assay evaluates the ability of a modular complex that includes the test compound to respond to, e.g., change charge depending on, the pH environment.

Condensing Agent

The condensing agent of a modular complex described herein can interact with (e.g., attracts, holds, or binds to) an iRNA agent and act to (a) condense, e.g., reduce the size or charge of the iRNA agent and/or (b) protect the iRNA agent, e.g., protect the iRNA agent against degradation. The condensing agent can include a moiety, e.g., a charged moiety, that can interact with a nucleic acid, e.g., an iRNA agent, e.g., by ionic interactions. The condensing agent would preferably be a charged polymer, e.g., a polycationic chain. The condensing agent can be a polylysine (PLL), spermine, spermidine, polyamine, pseudopeptide-polyamine, peptidomimetic polyamine, dendrimer polyamine, arginine, amidine, protamine, cationic lipid, cationic porphyrin, quarternary salt of a polyamine, or an alpha helical peptide.

A condensing agent can have the following characteristics: (a) at least 1Da in size; (b) has at least 2 charged groups, preferably between 2 and 100 charged groups; (c) is present in the complex at a ratio of at least 1:1 condensing agent to carrier agent; (d) is present in the complex at a ratio of at least 1:1 condensing agent to fusogenic agent; (e) is present in the complex at a ratio of at least 1:1 condensing agent to targeting agent.

Other suitable condensing agents can be tested and identified by a skilled artisan, e.g., by evaluating the ability of a test agent to interact with a nucleic acid, e.g., an iRNA agent. The ability of a test agent to interact with a nucleic acid, e.g., an iRNA agent, e.g., to condense or protect the iRNA agent, can be evaluated by routine techniques. In one assay, a test agent is contacted with a nucleic acid, and the size and/or charge of the contacted nucleic acid is evaluated by a technique suitable to detect changes in molecular mass and/or charge. Such techniques include non-denaturing gel electrophoresis, immunological methods, e.g., immunoprecipitation, gel filtration, ionic interaction chromatography, and the like. A test agent is identified as a condensing agent if it changes the mass and/or charge (preferably both) of the contacted nucleic acid, compared to a control. A two-step assay can also be performed, wherein a first assay evaluates the ability of a test compound alone to interact with, e.g., bind to, e.g., condense the charge and/or mass of, a nucleic cid; and a second assay evaluates the ability of a modular complex that includes the test compound to interact with, e.g., bind to, e.g., condense the charge and/or mass of, a nucleic acid.

Amphipathic Delivery Agents

The monomers and methods described herein can be used to prepare an RNA, e.g., an iRNA agent described herein, that can be used with an amphipathic delivery conjugate or module, such as those described herein and those described in copending, co-owned U.S. Provisional Application Ser. No. 60/455,050, filed on Mar. 13, 2003, and International Application Serial No. PCT/US04/07070, filed Mar. 8, 2004, which is hereby incorporated by reference.

An amphipathic molecule is a molecule having a hydrophobic and a hydrophilic region. Such molecules can interact with (e.g., penetrate or disrupt) lipids, e.g., a lipid bylayer of a cell. As such, they can serve as delivery agent for an associated (e.g., bound) iRNA (e.g., an iRNA or sRNA described herein). A preferred amphipathic molecule to be used in the compositions described herein (e.g., the amphipathic iRNA constructs described herein) is a polymer. The polymer may have a secondary structure, e.g., a repeating secondary structure.

One example of an amphipathic polymer is an amphipathic polypeptide, e.g., a polypeptide having a secondary structure such that the polypeptide has a hydrophilic and a hybrophobic face. The design of amphipathic peptide structures (e.g., alpha-helical polypeptides) is routine to one of skill in the art. For example, the following references provide guidance: Grell et al. (2001) "Protein design and folding: template trapping of self-assembled helical bundles" J Pept Sci 7(3): 146-51; Chen et al. (2002) "Determination of stereochemistry stability coefficients of amino acid side-chains in an amphipathic alpha-helix" J Pept Res 59(1):18-33; Iwata et al. (1994) "Design and synthesis of amphipathic 3(10)-helical peptides and their interactions with phospholipid bilayers and ion channel formation" J Biol Chem 269(7):4928-33; Cornut et al. (1994) "The amphipathic alpha-helix concept. Application to the de novo design of ideally amphipathic Leu, Lys peptides with hemolytic activity higher than that of melittin" FEBS Lett 349(1):29-33; Negrete et al. (1998) "Deciphering the structural code for proteins: helical propensities in domain classes and statistical multiresidue information in alpha-helices," Protein Sci 7(6):1368-79.

Another example of an amphipathic polymer is a polymer made up of two or more amphipathic subunits, e.g., two or more subunits containing cyclic moieties (e.g., a cyclic moiety having one or more hydrophilic groups and one or more hydrophobic groups). For example, the subunit may contain a steroid, e.g., cholic acid; or a aromatic moiety. Such moieties preferably can exhibit atropisomerism, such that they can form opposing hydrophobic and hydrophilic faces when in a polymer structure.

The ability of a putative amphipathic molecule to interact with a lipid membrane, e.g., a cell membrane, can be tested by routine methods, e.g., in a cell free or cellular assay. For example, a test compound is combined or contacted with a synthetic lipid bilayer, a cellular membrane fraction, or a cell, and the test compound is evaluated for its ability to interact with, penetrate or disrupt the lipid bilayer, cell membrane or cell. The test compound can labeled in order to detect the interaction with the lipid bilayer, cell membrane or cell. In another type of assay, the test compound is linked to a reporter molecule or an iRNA agent (e.g., an iRNA or sRNA described herein) and the ability of the reporter molecule or iRNA agent to penetrate the lipid bilayer, cell membrane or cell is evaluated. A two-step assay can also be performed, wherein a first assay evaluates the ability of a test compound alone to interact with a lipid bilayer, cell membrane or cell; and a second assay evaluates the ability of a construct (e.g., a construct described herein) that includes the test compound and a reporter or iRNA agent to interact with a lipid bilayer, cell membrane or cell.

An amphipathic polymer useful in the compositions described herein has at least 2, preferably at least 5, more preferably at least 10, 25, 50, 100, 200, 500, 1000, 2000, 50000 or more subunits (e.g., amino acids or cyclic subunits). A single amphipathic polymer can be linked to one or more, e.g., 2, 3, 5, 10 or more iRNA agents (e.g., iRNA or sRNA agents described herein). In some embodiments, an amphipathic polymer can contain both amino acid and cyclic subunits, e.g., aromatic subunits.

The invention features a composition that includes an iRNA agent (e.g., an iRNA or sRNA described herein) in association with an amphipathic molecule. Such compositions may be referred to herein as "amphipathic iRNA constructs." Such compositions and constructs are useful in the delivery or targeting of iRNA agents, e.g., delivery or targeting of iRNA agents to a cell. While not wanting to be bound by theory, such compositions and constructs can increase the porosity of, e.g., can penetrate or disrupt, a lipid (e.g., a lipid bilayer of a cell), e.g., to allow entry of the iRNA agent into a cell.

In one aspect, the invention relates to a composition comprising an iRNA agent (e.g., an iRNA or sRNA agent described herein) linked to an amphipathic molecule. The iRNA agent and the amphipathic molecule may be held in continuous contact with one another by either covalent or noncovalent linkages.

The amphipathic molecule of the composition or construct is preferably other than a phospholipid, e.g., other than a micelle, membrane or membrane fragment.

The amphipathic molecule of the composition or construct is preferably a polymer. The polymer may include two or more amphipathic subunits. One or more hydrophilic groups and one or more hydrophobic groups may be present on the polymer. The polymer may have a repeating secondary structure as well as a first face and a second face. The distribution of the hydrophilic groups and the hydrophobic groups along the repeating secondary structure can be such that one face of the polymer is a hydrophilic face and the other face of the polymer is a hydrophobic face.

The amphipathic molecule can be a polypeptide, e.g., a polypeptide comprising an α-helical conformation as its secondary structure.

In one embodiment, the amphipathic polymer includes one or more subunits containing one or more cyclic moiety (e.g., a cyclic moiety having one or more hydrophilic groups and/or one or more hydrophobic groups). In one embodiment, the polymer is a polymer of cyclic moieties such that the moieties have alternating hydrophobic and hydrophilic groups. For example, the subunit may contain a steroid, e.g., cholic acid. In another example, the subunit may contain an aromatic moiety. The aromatic moiety may be one that can exhibit atropisomerism, e.g., a 2,2'-bis(substituted)-1-1'-binaphthyl or a 2,2'-bis(substituted) biphenyl. A subunit may include an aromatic moiety of Formula (M):

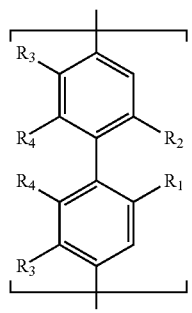

(M)

The invention features a composition that includes an iRNA agent (e.g., an iRNA or sRNA described herein) in association with an amphipathic molecule. Such compositions may be referred to herein as "amphipathic iRNA constructs." Such compositions and constructs are useful in the delivery or targeting of iRNA agents, e.g., delivery or targeting of iRNA agents to a cell. While not wanting to be bound by theory, such compositions and constructs can increase the porosity of, e.g., can penetrate or disrupt, a lipid (e.g., a lipid bilayer of a cell), e.g., to allow entry of the iRNA agent into a cell.

In one aspect, the invention relates to a composition comprising an iRNA agent (e.g., an iRNA or sRNA agent described herein) linked to an amphipathic molecule. The iRNA agent and the amphipathic molecule may be held in continuous contact with one another by either covalent or noncovalent linkages.

The amphipathic molecule of the composition or construct is preferably other than a phospholipid, e.g., other than a micelle, membrane or membrane fragment.

The amphipathic molecule of the composition or construct is preferably a polymer. The polymer may include two or more amphipathic subunits. One or more hydrophilic groups and one or more hydrophobic groups may be present on the polymer. The polymer may have a repeating secondary structure as well as a first face and a second face. The distribution of the hydrophilic groups and the hydrophobic groups along the repeating secondary structure can be such that one face of the polymer is a hydrophilic face and the other face of the polymer is a hydrophobic face.

The amphipathic molecule can be a polypeptide, e.g., a polypeptide comprising an α-helical conformation as its secondary structure.

In one embodiment, the amphipathic polymer includes one or more subunits containing one or more cyclic moiety (e.g., a cyclic moiety having one or more hydrophilic groups and/or one or more hydrophobic groups). In one embodiment, the polymer is a polymer of cyclic moieties such that the moieties have alternating hydrophobic and hydrophilic groups. For example, the subunit may contain a steroid, e.g., cholic acid. In another example, the subunit may contain an aromatic moiety. The aromatic moiety may be one that can exhibit atropisomerism, e.g., a 2,2'-bis(substituted)-1-1'-binaphthyl or a 2,2'-bis(substituted) biphenyl. A subunit may include an aromatic moiety of Formula (M):

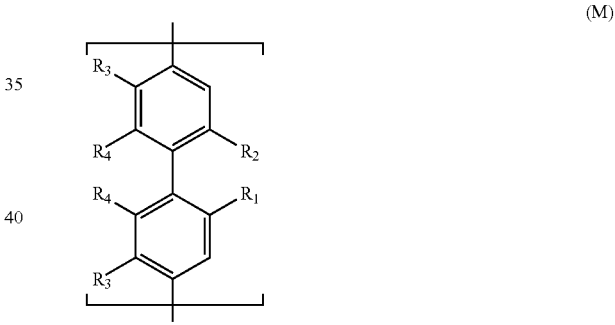

Referring to Formula M, $R_1$ is $C_1$-$C_{100}$ alkyl optionally substituted with aryl, alkenyl, alkynyl, alkoxy or halo and/or optionally inserted with O, S, alkenyl or alkynyl; $C_1$-$C_{100}$ perfluoroalkyl; or $OR_5$.

$R_2$ is hydroxy; nitro; sulfate; phosphate; phosphate ester; sulfonic acid; $OR_6$; or $C_1$-$C_{100}$ alkyl optionally substituted with hydroxy, halo, nitro, aryl or alkyl sulfinyl, aryl or alkyl sulfonyl, sulfate, sulfonic acid, phosphate, phosphate ester, substituted or unsubstituted aryl, carboxyl, carboxylate, amino carbonyl, or alkoxycarbonyl, and/or optionally inserted with O, NH, S, S(O), $SO_2$, alkenyl, or alkynyl.

$R_3$ is hydrogen, or when taken together with $R_4$ forms a fused phenyl ring.

$R_4$ is hydrogen, or when taken together with $R_3$ forms a fused phenyl ring.

$R_5$ is $C_1$-$C_{1-100}$ alkyl optionally substituted with aryl, alkenyl, alkynyl, alkoxy or halo and/or optionally inserted with O, S, alkenyl or alkynyl; or $C_1$-$C_{100}$ perfluoroalkyl; and $R_6$ is $C_1$-$C_{100}$ alkyl optionally substituted with hydroxy, halo, nitro, aryl or alkyl sulfinyl, aryl or alkyl sulfonyl, sulfate, sulfonic acid, phosphate, phosphate ester, substituted or unsubstituted aryl, carboxyl, carboxylate, amino carbonyl, or alkoxycarbonyl, and/or optionally inserted with O, NH, S, S(O), SO$_2$, alkenyl, or alkynyl.

Increasing Cellular Uptake of dsRNAs

A method of the invention that can include the administration of an iRNA agent and a drug that affects the uptake of the iRNA agent into the cell. The drug can be administered before, after, or at the same time that the iRNA agent is administered. The drug can be covalently linked to the iRNA agent. The drug can be, for example, a lipopolysaccharide, an activator of p38 MAP kinase, or an activator of NF-κB. The drug can have a transient effect on the cell.

The drug can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The drug can also increase the uptake of the iRNA agent into the cell by activating an inflammatory response, for example. Exemplary drug's that would have such an effect include tumor necrosis factor alpha (TNFalpha), interleukin-1 beta, or gamma interferon.

iRNA Conjugates

An iRNA agent can be coupled, e.g., covalently coupled, to a second agent. For example, an iRNA agent used to treat a particular disorder can be coupled to a second therapeutic agent, e.g., an agent other than the iRNA agent. The second therapeutic agent can be one which is directed to the treatment of the same disorder. For example, in the case of an iRNA used to treat a disorder characterized by unwanted cell proliferation, e.g., cancer, the iRNA agent can be coupled to a second agent which has an anti-cancer effect. For example, it can be coupled to an agent which stimulates the immune system, e.g., a CpG motif, or more generally an agent that activates a toll-like receptor and/or increases the production of gamma interferon.

iRNA Production

An iRNA can be produced, e.g., in bulk, by a variety of methods. Exemplary methods include: organic synthesis and RNA cleavage, e.g., in vitro cleavage.

Organic Synthesis

An iRNA can be made by separately synthesizing each respective strand of a double-stranded RNA molecule. The component strands can then be annealed.

A large bioreactor, e.g., the OligoPilot II from Pharmacia Biotec AB (Uppsala Sweden), can be used to produce a large amount of a particular RNA strand for a given iRNA. The OligoPilotII reactor can efficiently couple a nucleotide using only a 1.5 molar excess of a phosphoramidite nucleotide. To make an RNA strand, ribonucleotides amidites are used. Standard cycles of monomer addition can be used to synthesize the 21 to 23 nucleotide strand for the iRNA. Typically, the two complementary strands are produced separately and then annealed, e.g., after release from the solid support and deprotection.

Organic synthesis can be used to produce a discrete iRNA species. The complementary of the species to a particular target gene can be precisely specified. For example, the species may be complementary to a region that includes a polymorphism, e.g., a single nucleotide polymorphism. Further the location of the polymorphism can be precisely defined. In some embodiments, the polymorphism is located in an internal region, e.g., at least 4, 5, 7, or 9 nucleotides from one or both of the termini.

dsRNA Cleavage iRNAs can also be made by cleaving a larger ds iRNA. The cleavage can be mediated in vitro or in vivo. For example, to produce iRNAs by cleavage in vitro, the following method can be used:

In vitro transcription. dsRNA is produced by transcribing a nucleic acid (DNA) segment in both directions. For example, the HiScribe™ RNAi transcription kit (New England Biolabs) provides a vector and a method for producing a dsRNA for a nucleic acid segment that is cloned into the vector at a position flanked on either side by a T7 promoter. Separate templates are generated for T7 transcription of the two complementary strands for the dsRNA. The templates are transcribed in vitro by addition of T7 RNA polymerase and dsRNA is produced. Similar methods using PCR and/or other RNA polymerases (e.g., T3 or SP6 polymerase) can also be used. In one embodiment, RNA generated by this method is carefully purified to remove endotoxins that may contaminate preparations of the recombinant enzymes.

In vitro cleavage. dsRNA is cleaved in vitro into iRNAs, for example, using a Dicer or comparable RNAse III-based activity. For example, the dsRNA can be incubated in an in vitro extract from *Drosophila* or using purified components, e.g. a purified RNAse or RISC complex (RNA-induced silencing complex). See, e.g., Ketting et al. *Genes Dev* 2001 Oct. 15; 15(20):2654-9. and Hammond *Science* 2001 Aug. 10; 293 (5532):1146-50.

dsRNA cleavage generally produces a plurality of iRNA species, each being a particular 21 to 23 nt fragment of a source dsRNA molecule. For example, iRNAs that include sequences complementary to overlapping regions and adjacent regions of a source dsRNA molecule may be present.

Regardless of the method of synthesis, the iRNA preparation can be prepared in a solution (e.g., an aqueous and/or organic solution) that is appropriate for formulation. For example, the iRNA preparation can be precipitated and redissolved in pure double-distilled water, and lyophilized. The dried iRNA can then be resuspended in a solution appropriate for the intended formulation process.

Synthesis of modified and nucleotide surrogate iRNA agents is discussed below.

Formulation

The iRNA agents described herein can be formulated for administration to a subject For ease of exposition the formulations, compositions and methods in this section are discussed largely with regard to unmodified iRNA agents. It should be understood, however, that these formulations, compositions and methods can be practiced with other iRNA agents, e.g., modified iRNA agents, and such practice is within the invention.

A formulated iRNA composition can assume a variety of states. In some examples, the composition is at least partially crystalline, uniformly crystalline, and/or anhydrous (e.g., less than 80, 50, 30, 20, or 10% water). In another example, the iRNA is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the iRNA composition is formulated in a manner that is compatible with the intended method of administration (see, below).

In particular embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

A iRNA preparation can be formulated in combination with another agent, e.g., another therapeutic agent or an agent that stabilizes a iRNA, e.g., a protein that complexes with iRNA to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the iRNA preparation includes another iRNA agent, e.g., a second iRNA that can mediated RNAi with respect to a second gene, or with respect to the same gene. Still other preparation can include at least 3, 5, ten, twenty, fifty, or a hundred or more different iRNA species. Such iRNAs can mediated RNAi with respect to a similar number of different genes.

In one embodiment, the iRNA preparation includes at least a second therapeutic agent (e.g., an agent other than an RNA or a DNA). For example, a iRNA composition for the treatment of a viral disease, e.g. HIV, might include a known antiviral agent (e.g., a protease inhibitor or reverse transcriptase inhibitor). In another example, a iRNA composition for the treatment of a cancer might further comprise a chemotherapeutic agent.

Exemplary formulations are discussed below:

Liposomes

For ease of exposition the formulations, compositions and methods in this section are discussed largely with regard to unmodified iRNA agents. It should be understood, however, that these formulations, compositions and methods can be practiced with other iRNA agents, e.g., modified iRNA s agents, and such practice is within the invention. An iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof) preparation can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the iRNA composition. The lipophilic material isolates the aqueous interior from an aqueous exterior, which typically does not include the iRNA composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the iRNA are delivered into the cell where the iRNA can specifically bind to a target RNA and can mediate RNAi. In some cases the liposomes are also specifically targeted, e.g., to direct the iRNA to particular cell types, e.g., to cells of the kidney, such as those described herein.

A liposome containing a iRNA can be prepared by a variety of methods.

In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The iRNA preparation is then added to the micelles that include the lipid component. The cationic groups on the lipid interact with the iRNA and condense around the iRNA to form a liposome. After condensation, the detergent is removed, e.g., by dialysis, to yield a liposomal preparation of iRNA.

If necessary a carrier compound that assists in condensation can be added during the condensation reaction, e.g., by controlled addition. For example, the carrier compound can be a polymer other than a nucleic acid (e.g., spermine or spermidine). pH can also adjusted to favor condensation.

Further description of methods for producing stable polynucleotide delivery vehicles, which incorporate a polynucleotide/cationic lipid complex as structural components of the delivery vehicle, are described in, e.g., WO 96/37194. Liposome formation can also include one or more aspects of exemplary methods described in Felgner, P. L. et al., *Proc. Natl. Acad. Sci.*, USA 8:7413-7417, 1987; U.S. Pat. No. 4,897,355; U.S. Pat. No. 5,171,678; Bangham, et al. *M. Mol. Biol.* 23:238, 1965; Olson, et al. *Biochim. Biophys. Acta* 557:9, 1979; Szoka, et al. *Proc. Natl. Acad. Sci.* 75: 4194, 1978; Mayhew, et al. *Biochim. Biophys. Acta* 775:169, 1984; Kim, et al. *Biochim. Biophys. Acta* 728:339, 1983; and Fukunaga, et al. *Endocrinol.* 115:757, 1984. Commonly used techniques for preparing lipid aggregates of appropriate size for use as delivery vehicles include sonication and freeze-thaw plus extrusion (see, e.g., Mayer, et al. *Biochim. Biophys. Acta* 858:161, 1986). Microfluidization can be used when consistently small (50 to 200 nm) and relatively uniform aggregates are desired (Mayhew, et al. *Biochim. Biophys. Acta* 775:169, 1984). These methods are readily adapted to packaging iRNA preparations into liposomes.

Liposomes that are pH-sensitive or negatively-charged, entrap nucleic acid molecules rather than complex with them. Since both the nucleic acid molecules and the lipid are similarly charged, repulsion rather than complex formation occurs. Nevertheless, some nucleic acid molecules are entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 19, (1992) 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and in vivo include U.S. Pat. No. 5,283,185; U.S. Pat. No. 5,171,678; WO 94/00569; WO 93/24640; WO 91/16024; Felgner, *J. Biol. Chem.* 269:2550, 1994; Nabel, *Proc. Natl. Acad. Sci.* 90:11307, 1993; Nabel, *Human Gene Ther.* 3:649, 1992; Gershon, *Biochem.* 32:7143, 1993; and Strauss *EMBO J.* 11:417, 1992.

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver iRNAs to macrophages.

Further advantages of liposomes include: liposomes obtained from natural phospholipids are biocompatible and biodegradable; liposomes can incorporate a wide range of water and lipid soluble drugs; liposomes can protect encapsulated iRNAs in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of iRNA (see, e.g., Felgner, P. L. et al., Proc. Natl. Acad. Sci., USA 8:7413-7417, 1987 and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wis.) and dipalmitoylphosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., Biochim. Biophys. Res. Commun. 179:280, 1991). Lipopolylysine, made by conjugating polylysine to DOPE, has been reported to be effective for transfection in the presence of serum (Zhou, X. et al., Biochim. Biophys. Acta 1065:8, 1991). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer iRNA, into the skin. In some implementations, liposomes are used for delivering iRNA to epidermal cells and also to enhance the penetration of iRNA into dermal tissues, e.g., into skin. For example, the liposomes can be applied topically. Topical delivery of drugs formulated as liposomes to the skin has been documented (see, e.g., Weiner et al., Journal of Drug Targeting, 1992, vol. 2, 405-410 and du Plessis et al., Antiviral Research, 18, 1992, 259-265; Mannino, R. J. and Fould-Fogerite, S., Biotechniques 6:682-690, 1988; Itani, T. et al. Gene 56:267-276. 1987; Nicolau, C. et al. Meth. Enz. 149: 157-176, 1987; Straubinger, R. M. and Papahadjopoulos, D. Meth. Enz. 101:512-527, 1983; Wang, C. Y. and Huang, L., Proc. Natl. Acad. Sci. USA 84:7851-7855, 1987).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with iRNA are useful for treating a dermatological disorder.

Liposomes that include iRNA can be made highly deformable. Such deformability can enable the liposomes to penetrate through pore that are smaller than the average radius of the liposome. For example, transfersomes are a type of deformable liposomes. Transferosomes can be made by adding surface edge activators, usually surfactants, to a standard liposomal composition. Transfersomes that include iRNA can be delivered, for example, subcutaneously by infection in order to deliver iRNA to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transferosomes can be self-optimizing (adaptive to the shape of pores, e.g., in the skin), self-repairing, and can frequently reach their targets without fragmenting, and often self-loading. The iRNA agents can include an RRMS tethered to a moiety which improves association with a liposome.

Surfactants

For ease of exposition the formulations, compositions and methods in this section are discussed largely with regard to unmodified iRNA agents. It should be understood, however, that these formulations, compositions and methods can be practiced with other iRNA agents, e.g., modified iRNA agents, and such practice is within the invention. Surfactants find wide application in formulations such as emulsions (including microemulsions) and liposomes (see above). iRNA (or a precursor, e.g., a larger dsRNA which can be processed into a iRNA, or a DNA which encodes a iRNA or precursor) compositions can include a surfactant. In one embodiment, the iRNA is formulated as an emulsion that includes a surfactant. The most common way of classifying and ranking the properties of the many different types of surfactants, both natural and synthetic, is by the use of the hydrophile/lipophile balance (HLB). The nature of the hydrophilic group provides the most useful means for categorizing the different surfactants used in formulations (Rieger, in "Pharmaceutical Dosage Forms," Marcel Dekker, Inc., New York, N.Y., 1988, p. 285).

If the surfactant molecule is not ionized, it is classified as a nonionic surfactant. Nonionic surfactants find wide application in pharmaceutical products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in "Pharmaceutical Dosage Forms," Marcel Dekker, Inc., New York, N.Y., 1988, p. 285).

Micelles and Other Membranous Formulations

For ease of exposition the micelles and other formulations, compositions and methods in this section are discussed largely with regard to unmodified iRNA agents. It should be understood, however, that these micelles and other formulations, compositions and methods can be practiced with other iRNA agents, e.g., modified iRNA agents, and such practice is within the invention. The iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof)) composition can be provided as a micellar formulation. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the iRNA composition, an alkali metal $C_8$ to $C_{22}$ alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing is preferred in order to provide smaller size micelles.

In one method a first micellar composition is prepared which contains the iRNA composition and at least the alkali metal alkyl sulphate. The first micellar composition is then mixed with at least three micelle forming compounds to form a mixed micellar composition. In another method, the micellar composition is prepared by mixing the iRNA composition, the alkali metal alkyl sulphate and at least one of the micelle forming compounds, followed by addition of the remaining micelle forming compounds, with vigorous mixing.

Phenol and/or m-cresol may be added to the mixed micellar composition to stabilize the formulation and protect against bacterial growth. Alternatively, phenol and/or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e. there is one phase. If there are two phases, it is necessary to shake the dispenser prior to dispensing a portion of the contents, e.g. through a metered valve. The dispensed dose of pharmaceutical agent is propelled from the metered valve in a fine spray.

The preferred propellants are hydrogen-containing chlorofluorocarbons, hydrogen-containing fluorocarbons, dimethyl ether and diethyl ether. Even more preferred is HFA 134a (1,1,1,2 tetrafluoroethane).

The specific concentrations of the essential ingredients can be determined by relatively straightforward experimentation. For absorption through the oral cavities, it is often desirable to increase, e.g. at least double or triple, the dosage for through injection or administration through the gastrointestinal tract.

The iRNA agents can include an RRMS tethered to a moiety which improves association with a micelle or other membranous formulation.

Particles

For ease of exposition the particles, formulations, compositions and methods in this section are discussed largely with regard to unmodified iRNA agents. It should be understood, however, that these particles, formulations, compositions and methods can be practiced with other iRNA agents, e.g., modified iRNA agents, and such practice is within the invention. In another embodiment, an iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof) preparations may be incorporated into a particle, e.g., a microparticle. Microparticles can be produced by spray-drying, but may also be produced by other methods including lyophilization, evaporation, fluid bed drying, vacuum drying, or a combination of these techniques. See below for further description.

Sustained-Release Formulations.

An iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof) described herein can be formulated for controlled, e.g., slow release. Controlled release can be achieved by disposing the iRNA within a structure or substance which impedes its release. E.g., iRNA can be disposed within a porous matrix or in an erodable matrix, either of which allow release of the iRNA over a period of time.

Polymeric particles, e.g., polymeric in microparticles can be used as a sustained-release reservoir of iRNA that is taken up by cells only released from the microparticle through biodegradation. The polymeric particles in this embodiment should therefore be large enough to preclude phagocytosis (e.g., larger than 10 µm and preferably larger than 20 µm). Such particles can be produced by the same methods to make smaller particles, but with less vigorous mixing of the first and second emulsions. That is to say, a lower homogenization speed, vortex mixing speed, or sonication setting can be used to obtain particles having a diameter around 100 µm rather than 10 µm. The time of mixing also can be altered.

Larger microparticles can be formulated as a suspension, a powder, or an implantable solid, to be delivered by intramuscular, subcutaneous, intradermal, intravenous, or intraperitoneal injection; via inhalation (intranasal or intrapulmonary); orally; or by implantation. These particles are useful for delivery of any iRNA when slow release over a relatively long term is desired. The rate of degradation, and consequently of release, varies with the polymeric formulation.

Microparticles preferably include pores, voids, hollows, defects or other interstitial spaces that allow the fluid suspension medium to freely permeate or perfuse the particulate boundary. For example, the perforated microstructures can be used to form hollow, porous spray dried microspheres.

Polymeric particles containing iRNA (e.g., a sRNA) can be made using a double emulsion technique, for instance. First, the polymer is dissolved in an organic solvent. A preferred polymer is polylactic-co-glycolic acid (PLGA), with a lactic/glycolic acid weight ratio of 65:35, 50:50, or 75:25. Next, a sample of nucleic acid suspended in aqueous solution is added to the polymer solution and the two solutions are mixed to form a first emulsion. The solutions can be mixed by vortexing or shaking, and in a preferred method, the mixture can be sonicated. Most preferable is any method by which the nucleic acid receives the least amount of damage in the form of nicking, shearing, or degradation, while still allowing the formation of an appropriate emulsion. For example, acceptable results can be obtained with a Vibra-cell model VC-250 sonicator with a ⅛" microtip probe, at setting #3.

Spray-Drying.

An iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof)) can be prepared by spray drying. Spray dried iRNA can be administered to a subject or be subjected to further formulation. A pharmaceutical composition of iRNA can be prepared by spray drying a homogeneous aqueous mixture that includes a iRNA under conditions sufficient to provide a dispersible powdered composition, e.g., a pharmaceutical composition. The material for spray drying can also include one or more of: a pharmaceutically acceptable excipient, or a dispersibility-enhancing amount of a physiologically acceptable, water-soluble protein. The spray-dried product can be a dispersible powder that includes the iRNA.

Spray drying is a process that converts a liquid or slurry material to a dried particulate form. Spray drying can be used to provide powdered material for various administrative routes including inhalation. See, for example, M. Sacchetti and M. M. Van Oort in: Inhalation Aerosols: Physical and Biological Basis for Therapy, A. J. Hickey, ed. Marcel Dekkar, New York, 1996.

Spray drying can include atomizing a solution, emulsion, or suspension to form a fine mist of droplets and drying the droplets. The mist can be projected into a drying chamber (e.g., a vessel, tank, tubing, or coil) where it contacts a drying gas. The mist can include solid or liquid pore forming agents. The solvent and pore forming agents evaporate from the droplets into the drying gas to solidify the droplets, simultaneously forming pores throughout the solid. The solid (typically in a powder, particulate form) then is separated from the drying gas and collected.

Spray drying includes bringing together a highly dispersed liquid, and a sufficient volume of air (e.g., hot air) to produce evaporation and drying of the liquid droplets. The preparation to be spray dried can be any solution, course suspension, slurry, colloidal dispersion, or paste that may be atomized using the selected spray drying apparatus. Typically, the feed is sprayed into a current of warm filtered air that evaporates the solvent and conveys the dried product to a collector. The spent air is then exhausted with the solvent. Several different types of apparatus may be used to provide the desired product. For example, commercial spray dryers manufactured by Buchi Ltd. or Niro Corp. can effectively produce particles of desired size.

Spray-dried powdered particles can be approximately spherical in shape, nearly uniform in size and frequently hollow. There may be some degree of irregularity in shape depending upon the incorporated medicament and the spray drying conditions. In many instances the dispersion stability of spray-dried microspheres appears to be more effective if an inflating agent (or blowing agent) is used in their production. Particularly preferred embodiments may comprise an emulsion with an inflating agent as the disperse or continuous phase (the other phase being aqueous in nature). An inflating agent is preferably dispersed with a surfactant solution, using, for instance, a commercially available microfluidizer at a pressure of about 5000 to 15,000 psi. This process forms an emulsion, preferably stabilized by an incorporated surfactant, typically comprising submicron droplets of water immiscible blowing agent dispersed in an aqueous continuous phase. The formation of such dispersions using this and other techniques are common and well known to those in the art. The blowing agent is preferably a fluorinated compound (e.g. perfluorohexane, perfluorooctyl bromide, perfluorodecalin, perfluorobutyl ethane) which vaporizes during the spray-drying process, leaving behind generally hollow, porous aerodynamically light microspheres. As will be discussed in more detail below, other suitable blowing agents include chloroform, freons, and hydrocarbons. Nitrogen gas and carbon dioxide are also contemplated as a suitable blowing agent.

Although the perforated microstructures are preferably formed using a blowing agent as described above, it will be appreciated that, in some instances, no blowing agent is required and an aqueous dispersion of the medicament and surfactant(s) are spray dried directly. In such cases, the formulation may be amenable to process conditions (e.g., elevated temperatures) that generally lead to the formation of hollow, relatively porous microparticles. Moreover, the medicament may possess special physicochemical properties (e.g., high crystallinity, elevated melting temperature, surface activity, etc.) that make it particularly suitable for use in such techniques.

The perforated microstructures may optionally be associated with, or comprise, one or more surfactants. Moreover, miscible surfactants may optionally be combined with the suspension medium liquid phase. It will be appreciated by those skilled in the art that the use of surfactants may further increase dispersion stability, simplify formulation procedures or increase bioavailability upon administration. Of course combinations of surfactants, including the use of one or more in the liquid phase and one or more associated with the perforated microstructures are contemplated as being within the scope of the invention. By "associated with or comprise" it is meant that the structural matrix or perforated microstructure may incorporate, adsorb, absorb, be coated with or be formed by the surfactant.

Surfactants suitable for use include any compound or composition that aids in the formation and maintenance of the stabilized respiratory dispersions by forming a layer at the interface between the structural matrix and the suspension medium. The surfactant may comprise a single compound or any combination of compounds, such as in the case of co-surfactants. Particularly preferred surfactants are substantially insoluble in the propellant, nonfluorinated, and selected from the group consisting of saturated and unsaturated lipids, nonionic detergents, nonionic block copolymers, ionic surfactants, and combinations of such agents. It should be emphasized that, in addition to the aforementioned surfactants, suitable (i.e. biocompatible) fluorinated surfactants are compatible with the teachings herein and may be used to provide the desired stabilized preparations.

Lipids, including phospholipids, from both natural and synthetic sources may be used in varying concentrations to form a structural matrix. Generally, compatible lipids comprise those that have a gel to liquid crystal phase transition greater than about 40° C. Preferably, the incorporated lipids are relatively long chain (i.e. $C_6$-$C_{22}$) saturated lipids and more preferably comprise phospholipids. Exemplary phospholipids useful in the disclosed stabilized preparations comprise egg phosphatidylcholine, dilauroylphosphatidylcholine, dioleylphosphatidylcholine, dipalmitoylphosphatidylcholine, disteroylphosphatidylcholine, short-chain phosphatidylcholines, phosphatidylethanolamine, dioleylphosphatidylethanolamine, phosphatidylserine, phosphatidylglycerol, phosphatidylinositol, glycolipids, ganglioside GM1, sphingomyelin, phosphatidic acid, cardiolipin; lipids bearing polymer chains such as, polyethylene glycol, chitin, hyaluronic acid, or polyvinylpyrrolidone; lipids bearing sulfonated mono-, di-, and polysaccharides; fatty acids such as palmitic acid, stearic acid, and oleic acid; cholesterol, cholesterol esters, and cholesterol hemisuccinate. Due to their excellent biocompatibility characteristics, phospholipids and combinations of phospholipids and poloxamers are particularly suitable for use in the stabilized dispersions disclosed herein.

Compatible nonionic detergents comprise: sorbitan esters including sorbitan trioleate (Spans™ 85), sorbitan sesquioleate, sorbitan monooleate, sorbitan monolaurate, polyoxyethylene (20) sorbitan monolaurate, and polyoxyethylene (20) sorbitan monooleate, oleyl polyoxyethylene (2) ether, stearyl polyoxyethylene (2) ether, lauryl polyoxyethylene (4) ether, glycerol esters, and sucrose esters. Other suitable nonionic detergents can be easily identified using McCutcheon's Emulsifiers and Detergents (McPublishing Co., Glen Rock, N.J.). Preferred block copolymers include diblock and triblock copolymers of polyoxyethylene and polyoxypropylene, including poloxamer 188 (Pluronic™ F68), poloxamer 407 (Pluronic™ F-127), and poloxamer 338. Ionic surfactants such as sodium sulfosuccinate, and fatty acid soaps may also be utilized. In preferred embodiments, the microstructures may comprise oleic acid or its alkali salt.

In addition to the aforementioned surfactants, cationic surfactants or lipids are preferred especially in the case of delivery of an iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof). Examples of suitable cationic lipids include: DOTMA, N-[-(2,3-dioleyloxy)propyl]-N,N,N-trimethylammonium-chloride; DOTAP,1,2-dioleyloxy-3-(trimethylammonio)propane; and DOTB, 1,2-dioleyl-3-(4'-trimethylammonio)butanoyl-sn-glycerol.

Polycationic amino acids such as polylysine, and polyarginine are also contemplated.

For the spraying process, such spraying methods as rotary atomization, pressure atomization and two-fluid atomization can be used. Examples of the devices used in these processes include "Parubisu [phonetic rendering] Mini-Spray GA-32" and "Parubisu Spray Drier DL-41", manufactured by Yamato Chemical Co., or "Spray Drier CL-8,""Spray Drier L-8," "Spray Drier FL-12,""Spray Drier FL-16" or "Spray Drier FL-20," manufactured by Okawara Kakoki Co., can be used for the method of spraying using rotary-disk atomizer.

While no particular restrictions are placed on the gas used to dry the sprayed material, it is recommended to use air, nitrogen gas or an inert gas. The temperature of the inlet of the gas used to dry the sprayed materials such that it does not cause heat deactivation of the sprayed material. The range of temperatures may vary between about 50° C. to about 200° C., preferably between about 50° C. and 100° C. The temperature of the outlet gas used to dry the sprayed material, may vary between about 0° C. and about 150° C., preferably between 0° C. and 90° C., and even more preferably between 0° C. and 60° C.

The spray drying is done under conditions that result in substantially amorphous powder of homogeneous constitution having a particle size that is respirable, a low moisture content and flow characteristics that allow for ready aerosolization. Preferably the particle size of the resulting powder is such that more than about 98% of the mass is in particles having a diameter of about 10 µm or less with about 90% of the mass being in particles having a diameter less than 5 µm. Alternatively, about 95% of the mass will have particles with a diameter of less than 10 µm with about 80% of the mass of the particles having a diameter of less than 5 µm.

The dispersible pharmaceutical-based dry powders that include the iRNA preparation may optionally be combined with pharmaceutical carriers or excipients which are suitable for respiratory and pulmonary administration. Such carriers may serve simply as bulking agents when it is desired to reduce the iRNA concentration in the powder which is being delivered to a patient, but may also serve to enhance the stability of the iRNA compositions and to improve the dispersibility of the powder within a powder dispersion device in order to provide more efficient and reproducible delivery of the iRNA and to improve handling characteristics of the iRNA such as flowability and consistency to facilitate manufacturing and powder filling.

Such carrier materials may be combined with the drug prior to spray drying, i.e., by adding the carrier material to the purified bulk solution. In that way, the carrier particles will be formed simultaneously with the drug particles to produce a homogeneous powder. Alternatively, the carriers may be separately prepared in a dry powder form and combined with the dry powder drug by blending. The powder carriers will usually be crystalline (to avoid water absorption), but might in some cases be amorphous or mixtures of crystalline and amorphous. The size of the carrier particles may be selected to improve the flowability of the drug powder, typically being in the range from 25 µm to 100 µm. A preferred carrier material is crystalline lactose having a size in the above-stated range.

Powders prepared by any of the above methods will be collected from the spray dryer in a conventional manner for subsequent use. For use as pharmaceuticals and other purposes, it will frequently be desirable to disrupt any agglomerates which may have formed by screening or other conventional techniques. For pharmaceutical uses, the dry powder formulations will usually be measured into a single dose, and the single dose sealed into a package. Such packages are particularly useful for dispersion in dry powder inhalers, as described in detail below. Alternatively, the powders may be packaged in multiple-dose containers.

Methods for spray drying hydrophobic and other drugs and components are described in U.S. Pat. Nos. 5,000,888; 5,026,550; 4,670,419, 4,540,602; and 4,486,435. Bloch and Speison (1983) Pharm. Acta Helv 58:14-22 teaches spray drying of hydrochlorothiazide and chlorthalidone (lipophilic drugs) and a hydrophilic adjuvant (pentaerythritol) in azeotropic solvents of dioxane-water and 2-ethoxyethanol-water. A number of Japanese Patent application Abstracts relate to spray drying of hydrophilic-hydrophobic product combinations, including JP 806766; JP 7242568; JP 7101884; JP 7101883; JP 71018982; JP 7101881; and JP 4036233. Other foreign patent publications relevant to spray drying hydrophilic-hydrophobic product combinations include FR 2594693; DE 2209477; and WO 88/07870.

Lyophilization.

An iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof) preparation can be made by lyophilization. Lyophilization is a freeze-drying process in which water is sublimed from the composition after it is frozen. The particular advantage associated with the lyophilization process is that biologicals and pharmaceuticals that are relatively unstable in an aqueous solution can be dried without elevated temperatures (thereby eliminating the adverse thermal effects), and then stored in a dry state where there are few stability problems. With respect to the instant invention such techniques are particularly compatible with the incorporation of nucleic acids in perforated microstructures without compromising physiological activity. Methods for providing lyophilized particulates are known to those of skill in the art and it would clearly not require undue experimentation to provide dispersion compatible microstructures in accordance with the teachings herein. Accordingly, to the extent that lyophilization processes may be used to provide microstructures having the desired porosity and size, they are conformance with the teachings herein and are expressly contemplated as being within the scope of the instant invention.

Targeting

For ease of exposition the formulations, compositions and methods in this section are discussed largely with regard to unmodified iRNAs. It should be understood, however, that these formulations, compositions and methods can be practiced with other iRNA agents, e.g., modified iRNA agents, and such practice is within the invention.

In some embodiments, an iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof) is targeted to a particular cell. For example, a liposome or particle or other structure that includes a iRNA can also include a targeting moiety that recognizes a specific molecule on a target cell. The targeting moiety can be a molecule with a specific affinity for a target cell. Targeting moieties can include antibodies directed against a protein found on the surface of a target cell, or the ligand or a receptor-binding portion of a ligand for a molecule found on the surface of a target cell. For example, the targeting moiety can recognize a cancer-specific antigen of the kidney (e.g., G250, CA15-3, CA19-9, CEA, or HER2/neu) or a viral antigen, thus delivering the iRNA to a cancer cell or a virus-infected cell. Exemplary targeting moieties include antibodies (such as IgM, IgG, IgA, IgD, and the like, or a functional portions thereof), ligands for cell surface receptors (e.g., ectodomains thereof).

Table 3 provides a number of antigens which can be used to target an iRNA to a selected cell, such as when targeting of the iRNA agent to a tissue other than the kidney is desired.

TABLE 3

Targeting Antigens

| ANTIGEN | Exemplary tumor tissue |
|---|---|
| CEA (carcinoembryonic antigen) | colon, breast, lung |
| PSA (prostate specific antigen) | prostate cancer |
| CA-125 | ovarian cancer |
| CA 15-3 | breast cancer |
| CA 19-9 | breast cancer |
| HER2/neu | breast cancer |
| α-feto protein | testicular cancer, hepatic cancer |
| β-HCG (human chorionic gonadotropin) | testicular cancer, choriocarcinoma |
| MUC-1 | breast cancer |
| Estrogen receptor | breast cancer, uterine cancer |
| Progesterone receptor | breast cancer, uterine cancer |
| EGFr (epidermal growth factor receptor) | bladder cancer |

In one embodiment, the targeting moiety is attached to a liposome. For example, U.S. Pat. No. 6,245,427 describes a method for targeting a liposome using a protein or peptide. In another example, a cationic lipid component of the liposome is derivatized with a targeting moiety. For example, WO 96/37194 describes converting N-glutaryldioleoylphosphatidyl ethanolamine to a N-hydroxysuccinimide activated ester. The product was then coupled to an RGD peptide.

Genes and Diseases

In one aspect, the invention features, a method of treating a subject at risk for or afflicted with unwanted cell proliferation, e.g., malignant or nonmalignant cell proliferation. The method includes:

providing an iRNA agent, e.g., an sRNA or iRNA agent described herein, e.g., an iRNA having a structure described herein, where the iRNA is homologous to and can silence, e.g., by cleavage, a gene which promotes unwanted cell proliferation;

administering an iRNA agent, e.g., an sRNA or iRNA agent described herein to a subject, preferably a human subject, thereby treating the subject.

In a preferred embodiment the gene is a growth factor or growth factor receptor gene, a kinase, e.g., a protein tyrosine, serine or threonine kinase gene, an adaptor protein gene, a gene encoding a G protein superfamily molecule, or a gene encoding a transcription factor.

In a preferred embodiment the iRNA agent silences the PDGF beta gene, and thus can be used to treat a subject having or at risk for a disorder characterized by unwanted PDGF beta expression, e.g., testicular and lung cancers.

In another preferred embodiment the iRNA agent silences the Erb-B gene, and thus can be used to treat a subject having or at risk for a disorder characterized by unwanted Erb-B expression, e.g., breast cancer.

In a preferred embodiment the iRNA agent silences the Src gene, and thus can be used to treat a subject having or at risk for a disorder characterized by unwanted Src expression, e.g., colon cancers.

In a preferred embodiment the iRNA agent silences the CRK gene, and thus can be used to treat a subject having or at risk for a disorder characterized by unwanted CRK expression, e.g., colon and lung cancers.

In a preferred embodiment the iRNA agent silences the GRB2 gene, and thus can be used to treat a subject having or at risk for a disorder characterized by unwanted GRB2 expression, e.g., squamous cell carcinoma.

In another preferred embodiment the iRNA agent silences the RAS gene, and thus can be used to treat a subject having or at risk for a disorder characterized by unwanted RAS expression, e.g., pancreatic, colon and lung cancers, and chronic leukemia.

In another preferred embodiment the iRNA agent silences the MEKK gene, and thus can be used to treat a subject having or at risk for a disorder characterized by unwanted MEKK expression, e.g., squamous cell carcinoma, melanoma or leukemia.

In another preferred embodiment the iRNA agent silences the JNK gene, and thus can be used to treat a subject having or at risk for a disorder characterized by unwanted JNK expression, e.g., pancreatic or breast cancers.

In a preferred embodiment the iRNA agent silences the RAF gene, and thus can be used to treat a subject having or at risk for a disorder characterized by unwanted RAF expression, e.g., lung cancer or leukemia.

In a preferred embodiment the iRNA agent silences the Erk1/2 gene, and thus can be used to treat a subject having or at risk for a disorder characterized by unwanted Erk1/2 expression, e.g., lung cancer.

In another preferred embodiment the iRNA agent silences the PCNA(p21) gene, and thus can be used to treat a subject having or at risk for a disorder characterized by unwanted PCNA expression, e.g., lung cancer.

In a preferred embodiment the iRNA agent silences the MYB gene, and thus can be used to treat a subject having or at risk for a disorder characterized by unwanted MYB expression, e.g., colon cancer or chronic myelogenous leukemia.

In a preferred embodiment the iRNA agent silences the c-MYC gene, and thus can be used to treat a subject having or at risk for a disorder characterized by unwanted c-MYC expression, e.g., Burkitt's lymphoma or neuroblastoma.

In another preferred embodiment the iRNA agent silences the JUN gene, and thus can be used to treat a subject having or at risk for a disorder characterized by unwanted JUN expression, e.g., ovarian, prostate or breast cancers.

In another preferred embodiment the iRNA agent silences the FOS gene, and thus can be used to treat a subject having or at risk for a disorder characterized by unwanted FOS expression, e.g., skin or prostate cancers.

In a preferred embodiment the iRNA agent silences the BCL-2 gene, and thus can be used to treat a subject having or at risk for a disorder characterized by unwanted BCL-2 expression, e.g., lung or prostate cancers or Non-Hodgkin lymphoma.

In a preferred embodiment the iRNA agent silences the Cyclin D gene, and thus can be used to treat a subject having or at risk for a disorder characterized by unwanted Cyclin D expression, e.g., esophageal and colon cancers.

In a preferred embodiment the iRNA agent silences the VEGF gene, and thus can be used to treat a subject having or at risk for a disorder characterized by unwanted VEGF expression, e.g., esophageal and colon cancers.

In a preferred embodiment the iRNA agent silences the EGFR gene, and thus can be used to treat a subject having or at risk for a disorder characterized by unwanted EGFR expression, e.g., breast cancer.

In another preferred embodiment the iRNA agent silences the Cyclin A gene, and thus can be used to treat a subject having or at risk for a disorder characterized by unwanted Cyclin A expression, e.g., lung and cervical cancers.

In another preferred embodiment the iRNA agent silences the Cyclin E gene, and thus can be used to treat a subject having or at risk for a disorder characterized by unwanted Cyclin E expression, e.g., lung and breast cancers.

In another preferred embodiment the iRNA agent silences the WNT-1 gene, and thus can be used to treat a subject having or at risk for a disorder characterized by unwanted WNT-1 expression, e.g., basal cell carcinoma.

In another preferred embodiment the iRNA agent silences the beta-catenin gene, and thus can be used to treat a subject having or at risk for a disorder characterized by unwanted beta-catenin expression, e.g., adenocarcinoma or hepatocellular carcinoma.

In another preferred embodiment the iRNA agent silences the c-MET gene, and thus can be used to treat a subject having or at risk for a disorder characterized by unwanted c-MET expression, e.g., hepatocellular carcinoma.

In another preferred embodiment the iRNA agent silences the PKC gene, and thus can be used to treat a subject having or at risk for a disorder characterized by unwanted PKC expression, e.g., breast cancer.

In a preferred embodiment the iRNA agent silences the NFKB gene, and thus can be used to treat a subject having or at risk for a disorder characterized by unwanted NFKB expression, e.g., breast cancer.

In a preferred embodiment the iRNA agent silences the STAT3 gene, and thus can be used to treat a subject having or at risk for a disorder characterized by unwanted STAT3 expression, e.g., prostate cancer.

In another preferred embodiment the iRNA agent silences the survivin gene, and thus can be used to treat a subject having or at risk for a disorder characterized by unwanted survivin expression, e.g., cervical or pancreatic cancers.

In another preferred embodiment the iRNA agent silences the Her2/Neu gene, and thus can be used to treat a subject having or at risk for a disorder characterized by unwanted Her2/Neu expression, e.g., breast cancer.

In another preferred embodiment the iRNA agent silences the topoisomerase I gene, and thus can be used to treat a subject having or at risk for a disorder characterized by unwanted topoisomerase I expression, e.g., ovarian and colon cancers.

In a preferred embodiment the iRNA agent silences the topoisomerase II alpha gene, and thus can be used to treat a subject having or at risk for a disorder characterized by unwanted topoisomerase II expression, e.g., breast and colon cancers.

In a preferred embodiment the iRNA agent silences mutations in the p73 gene, and thus can be used to treat a subject having or at risk for a disorder characterized by unwanted p73 expression, e.g., colorectal adenocarcinoma.

In a preferred embodiment the iRNA agent silences mutations in the p21(WAF1/CIP1) gene, and thus can be used to treat a subject having or at risk for a disorder characterized by unwanted p21(WAF1/CIP1) expression, e.g., liver cancer.

In a preferred embodiment the iRNA agent silences mutations in the p27(KIP1) gene, and thus can be used to treat a subject having or at risk for a disorder characterized by unwanted p27(KIP1) expression, e.g., liver cancer.

In a preferred embodiment the iRNA agent silences mutations in the PPM gene, and thus can be used to treat a subject having or at risk for a disorder characterized by unwanted PPM1D expression, e.g., breast cancer.

In a preferred embodiment the iRNA agent silences mutations in the RAS gene, and thus can be used to treat a subject having or at risk for a disorder characterized by unwanted RAS expression, e.g., breast cancer.

In another preferred embodiment the iRNA agent silences mutations in the caveolin I gene, and thus can be used to treat a subject having or at risk for a disorder characterized by unwanted caveolin I expression, e.g., esophageal squamous cell carcinoma.

In another preferred embodiment the iRNA agent silences mutations in the MIB I gene, and thus can be used to treat a subject having or at risk for a disorder characterized by unwanted MIB I expression, e.g., male breast carcinoma (MBC).

In another preferred embodiment the iRNA agent silences mutations in the MTAI gene, and thus can be used to treat a subject having or at risk for a disorder characterized by unwanted MTAI expression, e.g., ovarian carcinoma.

In another preferred embodiment the iRNA agent silences mutations in the M68 gene, and thus can be used to treat a subject having or at risk for a disorder characterized by unwanted M68 expression, e.g., human adenocarcinomas of the esophagus, stomach, colon, and rectum.

In preferred embodiments the iRNA agent silences mutations in tumor suppressor genes, and thus can be used as a method to promote apoptotic activity in combination with chemotherapeutics.

In a preferred embodiment the iRNA agent silences mutations in the p53 tumor suppressor gene, and thus can be used to treat a subject having or at risk for a disorder characterized by unwanted p53 expression, e.g., gall bladder, pancreatic and lung cancers.

In a preferred embodiment the iRNA agent silences mutations in the p53 family member DN-p63, and thus can be used to treat a subject having or at risk for a disorder characterized by unwanted DN-p63 expression, e.g., squamous cell carcinoma In a preferred embodiment the iRNA agent silences mutations in the pRb tumor suppressor gene, and thus can be used to treat a subject having or at risk for a disorder characterized by unwanted pRb expression, e.g., oral squamous cell carcinoma In a preferred embodiment the iRNA agent silences mutations in the APC1 tumor suppressor gene, and thus can be used to treat a subject having or at risk for a disorder characterized by unwanted APC1 expression, e.g., colon cancer.

In a preferred embodiment the iRNA agent silences mutations in the BRCA1 tumor suppressor gene, and thus can be used to treat a subject having or at risk for a disorder characterized by unwanted BRCA1 expression, e.g., breast cancer.

In a preferred embodiment the iRNA agent silences mutations in the PTEN tumor suppressor gene, and thus can be used to treat a subject having or at risk for a disorder characterized by unwanted PTEN expression, e.g., hamartomas, gliomas, and prostate and endometrial cancers.

In a preferred embodiment the iRNA agent silences MLL fusion genes, e.g., MLL-AF9, and thus can be used to treat a subject having or at risk for a disorder characterized by unwanted MLL fusion gene expression, e.g., acute leukemias.

In another preferred embodiment the iRNA agent silences the BCR/ABL fusion gene, and thus can be used to treat a subject having or at risk for a disorder characterized by unwanted BCR/ABL fusion gene expression, e.g., acute and chronic leukemias.

In another preferred embodiment the iRNA agent silences the TEL/AML1 fusion gene, and thus can be used to treat a subject having or at risk for a disorder characterized by unwanted TEL/AML1 fusion gene expression, e.g., childhood acute leukemia.

In another preferred embodiment the iRNA agent silences the EWS/FLI1 fusion gene, and thus can be used to treat a subject having or at risk for a disorder characterized by unwanted EWS/FLI1 fusion gene expression, e.g., Ewing Sarcoma.

In another preferred embodiment the iRNA agent silences the TLS/FUS 1 fusion gene, and thus can be used to treat a subject having or at risk for a disorder characterized by unwanted TLS/FUS1 fusion gene expression, e.g., Myxoid liposarcoma.

In another preferred embodiment the iRNA agent silences the PAX3/FKHR fusion gene, and thus can be used to treat a subject having or at risk for a disorder characterized by unwanted PAX3/FKHR fusion gene expression, e.g., Myxoid liposarcoma.

In another preferred embodiment the iRNA agent silences the AML1/ETO fusion gene, and thus can be used to treat a subject having or at risk for a disorder characterized by unwanted AML1/ETO fusion gene expression, e.g., acute leukemia.

In another aspect, the invention features, a method of treating a subject, e.g., a human, at risk for or afflicted with a disease or disorder that may benefit by angiogenesis inhibition e.g., cancer. The method includes:

providing an iRNA agent, e.g., an iRNA agent having a structure described herein, which iRNA agent is homologous to and can silence, e.g., by cleavage, a gene which mediates angiogenesis;

administering the iRNA agent to a subject, thereby treating the subject.

In a preferred embodiment the iRNA agent silences the alpha v-integrin gene, and thus can be used to treat a subject having or at risk for a disorder characterized by unwanted alpha V integrin, e.g., brain tumors or tumors of epithelial origin.

In a preferred embodiment the iRNA agent silences the Flt-1 receptor gene, and thus can be used to treat a subject having or at risk for a disorder characterized by unwanted Flt-1 receptors, eg. Cancer and rheumatoid arthritis.

In a preferred embodiment the iRNA agent silences the tubulin gene, and thus can be used to treat a subject having or at risk for a disorder characterized by unwanted tubulin, eg. Cancer and retinal neovascularization.

In a preferred embodiment the iRNA agent silences the tubulin gene, and thus can be used to treat a subject having or at risk for a disorder characterized by unwanted tubulin, eg. Cancer and retinal neovascularization.

In another aspect, the invention features a method of treating a subject infected with a virus or at risk for or afflicted with a disorder or disease associated with a viral infection. The method includes:

providing an iRNA agent, e.g., and iRNA agent having a structure described herein, which iRNA agent is homologous to and can silence, e.g., by cleavage, a viral gene of a cellular gene which mediates viral function, e.g., entry or growth;

administering the iRNA agent to a subject, preferably a human subject, thereby treating the subject.

Thus, the invention provides for a method of treating patients infected by the Human Papilloma Virus (HPV) or at risk for or afflicted with a disorder mediated by HPV, e.g., cervical cancer. HPV is linked to 95% of cervical carcinomas and thus an antiviral therapy is an attractive method to treat these cancers and other symptoms of viral infection.

In a preferred embodiment, the expression of a HPV gene is reduced. In another preferred embodiment, the HPV gene is one of the group of E2, E6, or E7.

In a preferred embodiment the expression of a human gene that is required for HPV replication is reduced.

The invention also includes a method of treating patients infected by the Human Immunodeficiency Virus (HIV) or at risk for or afflicted with a disorder mediated by HIV, e.g., Acquired Immune Deficiency Syndrome (AIDS).

In a preferred embodiment, the expression of a HIV gene is reduced. In another preferred embodiment, the HIV gene is CCR5, Gag, or Rev.

In a preferred embodiment the expression of a human gene that is required for HIV replication is reduced. In another preferred embodiment, the gene is CD4 or Tsg101.

The invention also includes a method for treating patients infected by the Hepatitis B Virus (HBV) or at risk for or afflicted with a disorder mediated by HBV, e.g., cirrhosis and heptocellular carcinoma.

In a preferred embodiment, the expression of a HBV gene is reduced. In another preferred embodiment, the targeted HBV gene encodes one of the group of the tail region of the HBV core protein, the pre-cregious (pre-c) region, or the cregious (c) region. In another preferred embodiment, a targeted HBV-RNA sequence is comprised of the poly(A) tail.

In preferred embodiment the expression of a human gene that is required for HBV replication is reduced.

The invention also provides for a method of treating patients infected by the Hepatitis A Virus (HAV), or at risk for or afflicted with a disorder mediated by HAV.

In a preferred embodiment the expression of a human gene that is required for HAV replication is reduced.

The present invention provides for a method of treating patients infected by the Hepatitis C Virus (HCV), or at risk for or afflicted with a disorder mediated by HCV, e.g., cirrhosis In a preferred embodiment, the expression of a HCV gene is reduced.

In another preferred embodiment the expression of a human gene that is required for HCV replication is reduced.

The present invention also provides for a method of treating patients infected by the any of the group of Hepatitis Viral strains comprising hepatitis D, E, F, G, or H, or patients at risk for or afflicted with a disorder mediated by any of these strains of hepatitis.

In a preferred embodiment, the expression of a Hepatitis, D, E, F, G, or H gene is reduced.

In another preferred embodiment the expression of a human gene that is required for hepatitis D, E, F, G or H replication is reduced.

Methods of the invention also provide for treating patients infected by the Respiratory Syncytial Virus (RSV) or at risk for or afflicted with a disorder mediated by RSV, e.g, lower respiratory tract infection in infants and childhood asthma, pneumonia and other complications, e.g., in the elderly.

In a preferred embodiment, the expression of a RSV gene is reduced. In another preferred embodiment, the targeted HBV gene encodes one of the group of genes N, L, or P.

In a preferred embodiment the expression of a human gene that is required for RSV replication is reduced.

Methods of the invention provide for treating patients infected by the Herpes Simplex Virus (HSV) or at risk for or afflicted with a disorder mediated by HSV, e.g, genital herpes and cold sores as well as life-threatening or sight-impairing disease mainly in immunocompromised patients.

In a preferred embodiment, the expression of a HSV gene is reduced. In another preferred embodiment, the targeted HSV gene encodes DNA polymerase or the helicase-primase.

In a preferred embodiment the expression of a human gene that is required for HSV replication is reduced.

The invention also provides a method for treating patients infected by the herpes Cytomegalovirus (CMV) or at risk for or afflicted with a disorder mediated by CMV, e.g., congenital virus infections and morbidity in immunocompromised patients.

In a preferred embodiment, the expression of a CMV gene is reduced.

In a preferred embodiment the expression of a human gene that is required for CMV replication is reduced.

Methods of the invention also provide for a method of treating patients infected by the herpes Epstein Barr Virus (EBV) or at risk for or afflicted with a disorder mediated by EBV, e.g., NK/T-cell lymphoma, non-Hodgkin lymphoma, and Hodgkin disease.

In a preferred embodiment, the expression of a EBV gene is reduced.

In a preferred embodiment the expression of a human gene that is required for EBV replication is reduced.

Methods of the invention also provide for treating patients infected by Kaposi's Sarcoma-associated Herpes Virus (KSHV), also called human herpesvirus 8, or patients at risk for or afflicted with a disorder mediated by KSHV, e.g., Kaposi's sarcoma, multicentric Castleman's disease and AIDS-associated primary effusion lymphoma.

In a preferred embodiment, the expression of a KSHV gene is reduced.

In a preferred embodiment the expression of a human gene that is required for KSHV replication is reduced.

The invention also includes a method for treating patients infected by the JC Virus (JCV) or a disease or disorder associated with this virus, e.g., progressive multifocal leukoencephalopathy (PML).

In a preferred embodiment, the expression of a JCV gene is reduced.

In preferred embodiment the expression of a human gene that is required for JCV replication is reduced.

Methods of the invention also provide for treating patients infected by the myxovirus or at risk for or afflicted with a disorder mediated by myxovirus, e.g., influenza.

In a preferred embodiment, the expression of a myxovirus gene is reduced.

In a preferred embodiment the expression of a human gene that is required for myxovirus replication is reduced.

Methods of the invention also provide for treating patients infected by the rhinovirus or at risk for of afflicted with a disorder mediated by rhinovirus, e.g., the common cold.

In a preferred embodiment, the expression of a rhinovirus gene is reduced.

In preferred embodiment the expression of a human gene that is required for rhinovirus replication is reduced.

Methods of the invention also provide for treating patients infected by the coronavirus or at risk for of afflicted with a disorder mediated by coronavirus, e.g., the common cold.

In a preferred embodiment, the expression of a coronavirus gene is reduced.

In preferred embodiment the expression of a human gene that is required for coronavirus replication is reduced.

Methods of the invention also provide for treating patients infected by the flavivirus West Nile or at risk for or afflicted with a disorder mediated by West Nile Virus.

In a preferred embodiment, the expression of a West Nile Virus gene is reduced. In another preferred embodiment, the West Nile Virus gene is one of the group comprising E, NS3, or NS5.

In a preferred embodiment the expression of a human gene that is required for West Nile Virus replication is reduced.

Methods of the invention also provide for treating patients infected by the St. Louis Encephalitis flavivirus, or at risk for or afflicted with a disease or disorder associated with this virus, e.g., viral haemorrhagic fever or neurological disease.

In a preferred embodiment, the expression of a St. Louis Encephalitis gene is reduced.

In a preferred embodiment the expression of a human gene that is required for St. Louis Encephalitis virus replication is reduced.

Methods of the invention also provide for treating patients infected by the Tick-borne encephalitis flavivirus, or at risk for or afflicted with a disorder mediated by Tick-borne encephalitis virus, e.g., viral haemorrhagic fever and neurological disease.

In a preferred embodiment, the expression of a Tick-borne encephalitis virus gene is reduced.

In a preferred embodiment the expression of a human gene that is required for Tick-borne encephalitis virus replication is reduced.

Methods of the invention also provide for methods of treating patients infected by the Murray Valley encephalitis flavivirus, which commonly results in viral haemorrhagic fever and neurological disease.

In a preferred embodiment, the expression of a Murray Valley encephalitis virus gene is reduced.

In a preferred embodiment the expression of a human gene that is required for Murray Valley encephalitis virus replication is reduced.

The invention also includes methods for treating patients infected by the dengue flavivirus, or a disease or disorder associated with this virus, e.g., dengue haemorrhagic fever.

In a preferred embodiment, the expression of a dengue virus gene is reduced.

In a preferred embodiment the expression of a human gene that is required for dengue virus replication is reduced.

Methods of the invention also provide for treating patients infected by the Simian Virus 40 (SV40) or at risk for or afflicted with a disorder mediated by SV40, e.g., tumorigenesis.

In a preferred embodiment, the expression of a SV40 gene is reduced.

In a preferred embodiment the expression of a human gene that is required for SV40 replication is reduced.

The invention also includes methods for treating patients infected by the Human T Cell Lymphotropic Virus (HTLV), or a disease or disorder associated with this virus, e.g., leukemia and myelopathy.

In a preferred embodiment, the expression of a HTLV gene is reduced. In another preferred embodiment the HTLV 1 gene is the Tax transcriptional activator.

In a preferred embodiment the expression of a human gene that is required for HTLV replication is reduced.

Methods of the invention also provide for treating patients infected by the Moloney-Murine Leukemia Virus (Mo-MuLV) or at risk for or afflicted with a disorder mediated by Mo-MuLV, e.g., T-cell leukemia.

In a preferred embodiment, the expression of a Mo-MuLV gene is reduced.

In a preferred embodiment the expression of a human gene that is required for Mo-MuLV replication is reduced.

Methods of the invention also provide for treating patients infected by the encephalomyocarditis virus (EMCV) or at risk for or afflicted with a disorder mediated by EMCV, e.g. myocarditis. EMCV leads to myocarditis in mice and pigs and is capable of infecting human myocardial cells. This virus is therefore a concern for patients undergoing xenotransplantation.

In a preferred embodiment, the expression of a EMCV gene is reduced.

In a preferred embodiment the expression of a human gene that is required for EMCV replication is reduced.

The invention also includes a method for treating patients infected by the measles virus (MV) or at risk for or afflicted with a disorder mediated by MV, e.g. measles.

In a preferred embodiment, the expression of a MV gene is reduced.

In a preferred embodiment the expression of a human gene that is required for MV replication is reduced.

The invention also includes a method for treating patients infected by the Vericella zoster virus (VZV) or at risk for or afflicted with a disorder mediated by VZV, e.g. chicken pox or shingles (also called zoster).

In a preferred embodiment, the expression of a VZV gene is reduced.

In a preferred embodiment the expression of a human gene that is required for VZV replication is reduced.

The invention also includes a method for treating patients infected by an adenovirus or at risk for or afflicted with a disorder mediated by an adenovirus, e.g. respiratory tract infection.

In a preferred embodiment, the expression of an adenovirus gene is reduced.

In a preferred embodiment the expression of a human gene that is required for adenovirus replication is reduced.

The invention includes a method for treating patients infected by a yellow fever virus (YFV) or at risk for or afflicted with a disorder mediated by a YFV, e.g. respiratory tract infection.

In a preferred embodiment, the expression of a YFV gene is reduced. In another preferred embodiment, the preferred gene is one of a group that includes the E, NS2A, or NS3 genes.

In a preferred embodiment the expression of a human gene that is required for YFV replication is reduced.

Methods of the invention also provide for treating patients infected by the poliovirus or at risk for or afflicted with a disorder mediated by poliovirus, e.g., polio.

In a preferred embodiment, the expression of a poliovirus gene is reduced.

In a preferred embodiment the expression of a human gene that is required for poliovirus replication is reduced.

Methods of the invention also provide for treating patients infected by a poxvirus or at risk for or afflicted with a disorder mediated by a poxvirus, e.g., smallpox In a preferred embodiment, the expression of a poxvirus gene is reduced.

In a preferred embodiment the expression of a human gene that is required for poxvirus replication is reduced.

In another, aspect the invention features methods of treating a subject infected with a pathogen, e.g., a bacterial, amoebic, parasitic, or fungal pathogen. The method includes:

providing a iRNA agent, e.g., a siRNA having a structure described herein, where siRNA is homologous to and can silence, e.g., by cleavage of a pathogen gene;

administering the iRNA agent to a subject, preferably a human subject, thereby treating the subject.

The target gene can be one involved in growth, cell wall synthesis, protein synthesis, transcription, energy metabolism, e.g., the Krebs cycle, or toxin production.

Thus, the present invention provides for a method of treating patients infected by a *plasmodium* that causes malaria.

In a preferred embodiment, the expression of a *plasmodium* gene is reduced. In another preferred embodiment, the gene is apical membrane antigen 1 (AMA1).

In a preferred embodiment the expression of a human gene that is required for *plasmodium* replication is reduced.

The invention also includes methods for treating patients infected by the *Mycobacterium ulcerans*, or a disease or disorder associated with this pathogen, e.g. Buruli ulcers.

In a preferred embodiment, the expression of a *Mycobacterium ulcerans* gene is reduced.

In a preferred embodiment the expression of a human gene that is required for *Mycobacterium ulcerans* replication is reduced.

The invention also includes methods for treating patients infected by the *Mycobacterium tuberculosis*, or a disease or disorder associated with this pathogen, e.g. tuberculosis.

In a preferred embodiment, the expression of a *Mycobacterium tuberculosis* gene is reduced.

In a preferred embodiment the expression of a human gene that is required for *Mycobacterium tuberculosis* replication is reduced.

The invention also includes methods for treating patients infected by the *Mycobacterium leprae*, or a disease or disorder associated with this pathogen, e.g. leprosy.

In a preferred embodiment, the expression of a *Mycobacterium leprae* gene is reduced.

In a preferred embodiment the expression of a human gene that is required for *Mycobacterium leprae* replication is reduced.

The invention also includes methods for treating patients infected by the bacteria *Staphylococcus aureus*, or a disease or disorder associated with this pathogen, e.g. infections of the skin and muscous membranes.

In a preferred embodiment, the expression of a *Staphylococcus aureus* gene is reduced.

In a preferred embodiment the expression of a human gene that is required for *Staphylococcus aureus* replication is reduced.

The invention also includes methods for treating patients infected by the bacteria *Streptococcus pneumoniae*, or a disease or disorder associated with this pathogen, e.g. pneumonia or childhood lower respiratory tract infection.

In a preferred embodiment, the expression of a *Streptococcus pneumoniae* gene is reduced.

In a preferred embodiment the expression of a human gene that is required for *Streptococcus pneumoniae* replication is reduced.

The invention also includes methods for treating patients infected by the bacteria *Streptococcus pyogenes*, or a disease or disorder associated with this pathogen, e.g. Strep throat or Scarlet fever.

In a preferred embodiment, the expression of a *Streptococcus pyogenes* gene is reduced.

In a preferred embodiment the expression of a human gene that is required for *Streptococcus pyogenes* replication is reduced.

The invention also includes methods for treating patients infected by the bacteria *Chlamydia pneumoniae*, or a disease or disorder associated with this pathogen, e.g. pneumonia or childhood lower respiratory tract infection In a preferred embodiment, the expression of a *Chlamydia pneumoniae* gene is reduced.

In a preferred embodiment the expression of a human gene that is required for *Chlamydia pneumoniae* replication is reduced.

The invention also includes methods for treating patients infected by the bacteria *Mycoplasma pneumoniae*, or a disease or disorder associated with this pathogen, e.g. pneumonia or childhood lower respiratory tract infection In a preferred embodiment, the expression of a *Mycoplasma pneumoniae* gene is reduced.

In a preferred embodiment the expression of a human gene that is required for *Mycoplasma pneumoniae* replication is reduced.

In one aspect, the invention features, a method of treating a subject, e.g., a human, at risk for or afflicted with a disease or disorder characterized by an unwanted immune response, e.g., an inflammatory disease or disorder, or an autoimmune disease or disorder. The method includes:

providing an iRNA agent, e.g., an iRNA agent having a structure described herein, which iRNA agent is homologous to and can silence, e.g., by cleavage, a gene which mediates an unwanted immune response;

administering the iRNA agent to a subject, thereby treating the subject.

In a preferred embodiment the disease or disorder is an ischemia or reperfusion injury, e.g., ischemia or reperfusion injury associated with acute myocardial infarction, unstable angina, cardiopulmonary bypass, surgical intervention e.g., angioplasty, e.g., percutaneous transluminal coronary angioplasty, the response to a transplantated organ or tissue, e.g., transplanted cardiac or vascular tissue; or thrombolysis.

In a preferred embodiment the disease or disorder is restenosis, e.g., restenosis associated with surgical intervention e.g., angioplasty, e.g., percutaneous transluminal coronary angioplasty.

In a preferred embodiment the disease or disorder is Inflammatory Bowel Disease, e.g., Crohn Disease or Ulcerative Colitis.

In a preferred embodiment the disease or disorder is inflammation associated with an infection or injury.

In a preferred embodiment the disease or disorder is asthma, lupus, multiple sclerosis, diabetes, e.g., type II diabetes, arthritis, e.g., rheumatoid or psoriatic.

In particularly preferred embodiments the iRNA agent silences an integrin or co-ligand thereof, e.g., VLA4, VCAM, ICAM.

In particularly preferred embodiments the iRNA agent silences a selectin or co-ligand thereof, e.g., P-selectin, E-selectin (ELAM), 1-selectin, P-selectin glycoprotein-1 (PSGL-1). In particularly preferred embodiments the iRNA agent silences a component of the complement system, e.g., C3, C5, C3aR, C5aR, C3 convertase, C5 convertase.

In particularly preferred embodiments the iRNA agent silences a chemokine or receptor thereof, e.g., TNFI, TNFJ, IL-1I, IL-1J, IL-2, IL-2R, IL-4, IL-4R, IL-5, IL-6, IL-8, TNFRI, TNFRII, IgE, SCYA11, CCR3.

In other embodiments the iRNA agent silences GCSF, Gro1, Gro2, Gro3, PF4, MIG, Pro-Platelet Basic Protein (PPBP), MIP-1I, MIP-1J, RANTES, MCP-1, MCP-2, MCP-3, CMBKR1, CMBKR2, CMBKR3, CMBKR5, AIF-1, I-309.

In one aspect, the invention features, a method of treating a subject, e.g., a human, at risk for or afflicted with acute pain or chronic pain. The method includes:

providing an iRNA agent, which iRNA is homologous to and can silence, e.g., by cleavage, a gene which mediates the processing of pain;

administering the iRNA to a subject, thereby treating the subject.

In particularly preferred embodiments the iRNA agent silences a component of an ion channel.

In particularly preferred embodiments the iRNA agent silences a neurotransmitter receptor or ligand.

In one aspect, the invention features, a method of treating a subject, e.g., a human, at risk for or afflicted with a neurological disease or disorder. The method includes:

providing an iRNA agent which iRNA is homologous to and can silence, e.g., by cleavage, a gene which mediates a neurological disease or disorder;

administering the iRNA agent to a subject, thereby treating the subject.

In a preferred embodiment the disease or disorder is Alzheimer's Disease or Parkinson Disease.

In particularly preferred embodiments the iRNA agent silences an amyloid-family gene, e.g., APP; a presenilin gene, e.g., PSEN1 and PSEN2, or I-synuclein.

In a preferred embodiment the disease or disorder is a neurodegenerative trinucleotide repeat disorder, e.g., Huntington disease, dentatorubral pallidoluysian atrophy or a spinocerebellar ataxia, e.g., SCA1, SCA2, SCA3 (Machado-Joseph disease), SCA7 or SCA8.

In particularly preferred embodiments the iRNA agent silences HD, DRPLA, SCA1, SCA2, MJD1, CACNL1A4, SCA7, SCA8.

The loss of heterozygosity (LOH) can result in hemizygosity for sequence, e.g., genes, in the area of LOH. This can result in a significant genetic difference between normal and disease-state cells, e.g., cancer cells, and provides a useful difference between normal and disease-state cells, e.g., cancer cells. This difference can arise because a gene or other sequence is heterozygous in euploid cells but is hemizygous in cells having LOH. The regions of LOH will often include a gene, the loss of which promotes unwanted proliferation, e.g., a tumor suppressor gene, and other sequences including, e.g., other genes, in some cases a gene which is essential for normal function, e.g., growth. Methods of the invention rely, in part, on the specific cleavage or silencing of one allele of an essential gene with an iRNA agent of the invention. The iRNA agent is selected such that it targets the single allele of the essential gene found in the cells having LOH but does not silence the other allele, which is present in cells which do not show LOH. In essence, it discriminates between the two alleles, preferentially silencing the selected allele. In essence polymorphisms, e.g., SNPs of essential genes that are affected by LOH, are used as a target for a disorder characterized by cells having LOH, e.g., cancer cells having LOH.

E.g., one of ordinary skill in the art can identify essential genes which are in proximity to tumor suppressor genes, and which are within a LOH region which includes the tumor suppressor gene. The gene encoding the large subunit of human RNA polymerase II, POLR2A, a gene located in close proximity to the tumor suppressor gene p53, is such a gene. It frequently occurs within a region of LOH in cancer cells. Other genes that occur within LOH regions and are lost in many cancer cell types include the group comprising replication protein A 70-kDa subunit, replication protein A 32-kD, ribonucleotide reductase, thymidilate synthase, TATA associated factor 2H, ribosomal protein S14, eukaryotic initiation factor 5A, alanyl tRNA synthetase, cysteinyl tRNA synthetase, NaK ATPase, alpha-1 subunit, and transferrin receptor.

Accordingly, the invention features, a method of treating a disorder characterized by LOH, e.g., cancer. The method includes:

optionally, determining the genotype of the allele of a gene in the region of LOH and preferably determining the genotype of both alleles of the gene in a normal cell;

providing an iRNA agent which preferentially cleaves or silences the allele found in the LOH cells;

administering the iRNA to the subject, thereby treating the disorder.

The invention also includes a iRNA agent disclosed herein, e.g, an iRNA agent which can preferentially silence, e.g., cleave, one allele of a polymorphic gene In another aspect, the invention provides a method of cleaving or silencing more than one gene with an iRNA agent. In these embodiments the iRNA agent is selected so that it has sufficient homology to a sequence found in more than one gene. For example, the sequence AAGCTGGCCCTGGA-CATGGAGAT (SEQ ID NO:28) is conserved between mouse lamin B1, lamin B2, keratin complex 2-gene 1 and lamin A/C. Thus an iRNA agent targeted to this sequence would effectively silence the entire collection of genes.

The invention also includes an iRNA agent disclosed herein, which can silence more than one gene.

Route of Delivery

For ease of exposition the formulations, compositions and methods in this section are discussed largely with regard to unmodified iRNA agents. It should be understood, however, that these formulations, compositions and methods can be practiced with other iRNA agents, e.g., modified iRNA agents, and such practice is within the invention. A composition that includes a iRNA can be delivered to a subject by a variety of routes. Exemplary routes include: intravenous, topical, rectal, anal, vaginal, nasal, pulmonary, ocular.

The iRNA molecules of the invention can be incorporated into pharmaceutical compositions suitable for administration. Such compositions typically include one or more species of iRNA and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering the iRNA in aerosol form. The vascular endothelial cells could be targeted by coating a balloon catheter with the iRNA and mechanically introducing the DNA.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water, syrups, elixirs or non-aqueous media, tablets, capsules, lozenges, or troches. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the nucleic acid compositions can be combined with emulsifying and suspending agents. If desired, certain sweetening and/or flavoring agents can be added.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers.

Topical Delivery

For ease of exposition the formulations, compositions and methods in this section are discussed largely with regard to unmodified iRNA agents. It should be understood, however, that these formulations, compositions and methods can be practiced with other iRNA agents, e.g., modified iRNA agents, and such practice is within the invention. In a preferred embodiment, an iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof) is delivered to a subject via topical administration. "Topical administration" refers to the delivery to a subject by contacting the formulation directly to a surface of the subject. The most common form of topical delivery is to the skin, but a composition disclosed herein can also be directly applied to other surfaces of the body, e.g., to the eye, a mucous membrane, to surfaces of a body cavity or to an internal surface. As mentioned above, the most common topical delivery is to the skin. The term encompasses several routes of administration including, but not limited to, topical and transdermal. These modes of administration typically include penetration of the skin's permeability barrier and efficient delivery to the target tissue or stratum. Topical administration can be used as a means to penetrate the epidermis and dermis and ultimately achieve systemic delivery of the composition. Topical administration can also be used as a means to selectively deliver oligonucleotides to the epidermis or dermis of a subject, or to specific strata thereof, or to an underlying tissue.

The term "skin," as used herein, refers to the epidermis and/or dermis of an animal. Mammalian skin consists of two major, distinct layers. The outer layer of the skin is called the epidermis. The epidermis is comprised of the stratum corneum, the stratum granulosum, the stratum spinosum, and the stratum basale, with the stratum corneum being at the surface of the skin and the stratum basale being the deepest portion of the epidermis. The epidermis is between 50 μm and 0.2 mm thick, depending on its location on the body.

Beneath the epidermis is the dermis, which is significantly thicker than the epidermis. The dermis is primarily composed of collagen in the form of fibrous bundles. The collagenous bundles provide support for, inter alia, blood vessels, lymph capillaries, glands, nerve endings and immunologically active cells.

One of the major functions of the skin as an organ is to regulate the entry of substances into the body. The principal permeability barrier of the skin is provided by the stratum corneum, which is formed from many layers of cells in various states of differentiation. The spaces between cells in the stratum corneum is filled with different lipids arranged in lattice-like formations that provide seals to further enhance the skins permeability barrier.

The permeability barrier provided by the skin is such that it is largely impermeable to molecules having molecular weight greater than about 750 Da. For larger molecules to cross the skin's permeability barrier, mechanisms other than normal osmosis must be used.

Several factors determine the permeability of the skin to administered agents. These factors include the characteristics of the treated skin, the characteristics of the delivery agent, interactions between both the drug and delivery agent and the drug and skin, the dosage of the drug applied, the form of treatment, and the post treatment regimen. To selectively target the epidermis and dermis, it is sometimes possible to formulate a composition that comprises one or more penetration enhancers that will enable penetration of the drug to a preselected stratum.

Transdermal delivery is a valuable route for the administration of lipid soluble therapeutics. The dermis is more permeable than the epidermis and therefore absorption is much more rapid through abraded, burned or denuded skin. Inflammation and other physiologic conditions that increase blood flow to the skin also enhance transdermal adsorption. Absorption via this route may be enhanced by the use of an oily vehicle (inunction) or through the use of one or more penetration enhancers. Other effective ways to deliver a composition disclosed herein via the transdermal route include hydration of the skin and the use of controlled release topical patches. The transdermal route provides a potentially effective means to deliver a composition disclosed herein for systemic and/or local therapy.

In addition, iontophoresis (transfer of ionic solutes through biological membranes under the influence of an electric field) (Lee et al., Critical Reviews in Therapeutic Drug Carrier Systems, 1991, p. 163), phonophoresis or sonophoresis (use of ultrasound to enhance the absorption of various therapeutic agents across biological membranes, notably the skin and the cornea) (Lee et al., Critical Reviews in Therapeutic Drug Carrier Systems, 1991, p. 166), and optimization of vehicle characteristics relative to dose position and retention at the site of administration (Lee et al., Critical Reviews in Therapeutic Drug Carrier Systems, 1991, p. 168) may be useful methods for enhancing the transport of topically applied compositions across skin and mucosal sites.

The compositions and methods provided may also be used to examine the function of various proteins and genes in vitro in cultured or preserved dermal tissues and in animals. The invention can be thus applied to examine the function of any gene. The methods of the invention can also be used therapeutically or prophylactically. For example, for the treatment of animals that are known or suspected to suffer from diseases such as psoriasis, lichen planus, toxic epidermal necrolysis, ertythema multiforme, basal cell carcinoma, squamous cell carcinoma, malignant melanoma, Paget's disease, Kaposi's sarcoma, pulmonary fibrosis, Lyme disease and viral, fungal and bacterial infections of the skin.

Pulmonary Delivery

For ease of exposition the formulations, compositions and methods in this section are discussed largely with regard to unmodified iRNA agents. It should be understood, however, that these formulations, compositions and methods can be practiced with other iRNA agents, e.g., modified iRNA agents, and such practice is within the invention. A composition that includes an iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof) can be administered to a subject by pulmonary delivery. Pulmonary delivery compositions can be delivered by inhalation by the patient of a dispersion so that the composition, preferably iRNA, within the dispersion can reach the lung where it can be readily absorbed through the alveolar region directly into blood circulation. Pulmonary delivery can be effective both for systemic delivery and for localized delivery to treat diseases of the lungs.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self contained. Dry powder dispersion devices, for example, deliver drugs that may be readily formulated as dry powders. A iRNA composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The term "powder" means a composition that consists of finely dispersed solid particles that are free flowing and capable of being readily dispersed in an inhalation device and subsequently inhaled by a subject so that the particles reach the lungs to permit penetration into the alveoli. Thus, the powder is said to be "respirable." Preferably the average particle size is less than about 10 µm in diameter preferably with a relatively uniform spheroidal shape distribution. More preferably the diameter is less than about 7.5 µm and most preferably less than about 5.0 µm. Usually the particle size distribution is between about 0.1 µm and about 5 µm in diameter, particularly about 0.3 µm to about 5 µm.

The term "dry" means that the composition has a moisture content below about 10% by weight (% w) water, usually below about 5% w and preferably less it than about 3% w. A dry composition can be such that the particles are readily dispersible in an inhalation device to form an aerosol.

The term "therapeutically effective amount" is the amount present in the composition that is needed to provide the desired level of drug in the subject to be treated to give the anticipated physiological response.

The term "physiologically effective amount" is that amount delivered to a subject to give the desired palliative or curative effect.

The term "pharmaceutically acceptable carrier" means that the carrier can be taken into the lungs with no significant adverse toxicological effects on the lungs.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. A preferred group of carbohydrates includes lactose, threhalose, raffinose maltodextrins, and mannitol. Suitable polypeptides include aspartame. Amino acids include alanine and glycine, with glycine being preferred.

Additives, which are minor components of the composition of this invention, may be included for conformational stability during spray drying and for improving dispersibility of the powder. These additives include hydrophobic amino acids such as tryptophan, tyrosine, leucine, phenylalanine, and the like.

Suitable pH adjusters or buffers include organic salts prepared from organic acids and bases, such as sodium citrate, sodium ascorbate, and the like; sodium citrate is preferred.

Pulmonary administration of a micellar iRNA formulation may be achieved through metered dose spray devices with propellants such as tetrafluoroethane, heptafluoroethane, dimethylfluoropropane, tetrafluoropropane, butane, isobutane, dimethyl ether and other non-CFC and CFC propellants.

Oral or Nasal Delivery

For ease of exposition the formulations, compositions and methods in this section are discussed largely with regard to unmodified iRNA agents. It should be understood, however, that these formulations, compositions and methods can be practiced with other iRNA agents, e.g., modified iRNA agents, and such practice is within the invention. Both the oral and nasal membranes offer advantages over other routes of administration. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized and removed easily.

In oral delivery, compositions can be targeted to a surface of the oral cavity, e.g., to sublingual mucosa which includes the membrane of ventral surface of the tongue and the floor of the mouth or the buccal mucosa which constitutes the lining of the cheek. The sublingual mucosa is relatively permeable thus giving rapid absorption and acceptable bioavailability of many drugs. Further, the sublingual mucosa is convenient, acceptable and easily accessible.

The ability of molecules to permeate through the oral mucosa appears to be related to molecular size, lipid solubility and peptide protein ionization. Small molecules, less than 1000 daltons appear to cross mucosa rapidly. As molecular size increases, the permeability decreases rapidly. Lipid soluble compounds are more permeable than non-lipid soluble molecules. Maximum absorption occurs when molecules are un-ionized or neutral in electrical charges. Therefore charged molecules present the biggest challenges to absorption through the oral mucosae.

A pharmaceutical composition of iRNA may also be administered to the buccal cavity of a human being by spraying into the cavity, without inhalation, from a metered dose spray dispenser, a mixed micellar pharmaceutical formulation as described above and a propellant. In one embodiment, the dispenser is first shaken prior to spraying the pharmaceutical formulation and propellant into the buccal cavity.

Devices

For ease of exposition the devices, formulations, compositions and methods in this section are discussed largely with regard to unmodified iRNA agents. It should be understood, however, that these devices, formulations, compositions and methods can be practiced with other iRNA agents, e.g., modified iRNA agents, and such practice is within the invention. An iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof) can be disposed on or in a device, e.g., a device which implanted or otherwise placed in a subject. Exemplary devices include devices which are introduced into the vasculature, e.g., devices inserted into the lumen of a vascular tissue, or which devices themselves form a part of the vasculature, including stents, catheters, heart valves, and other vascular devices. These devices, e.g., catheters or stents, can be placed in the vasculature of the lung, heart, or leg.

Other devices include non-vascular devices, e.g., devices implanted in the peritoneum, or in organ or glandular tissue, e.g., artificial organs. The device can release a therapeutic substance in addition to a iRNA, e.g., a device can release insulin.

Other devices include artificial joints, e.g., hip joints, and other orthopedic implants.

In one embodiment, unit doses or measured doses of a composition that includes iRNA are dispensed by an implanted device. The device can include a sensor that monitors a parameter within a subject. For example, the device can include pump, e.g., and, optionally, associated electronics.

Tissue, e.g., cells or organs, such as the kidney, can be treated with An iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof) ex vivo and then administered or implanted in a subject.

The tissue can be autologous, allogeneic, or xenogeneic tissue. For example, tissue (e.g., kidney) can be treated to reduce graft v. host disease. In other embodiments, the tissue is allogeneic and the tissue is treated to treat a disorder characterized by unwanted gene expression in that tissue, such as in the kidney. In another example, tissue containing hematopoietic cells, e.g., bone marrow hematopoietic cells, can be treated to inhibit unwanted cell proliferation.

Introduction of treated tissue, whether autologous or transplant, can be combined with other therapies.

In some implementations, the iRNA treated cells are insulated from other cells, e.g., by a semi-permeable porous barrier that prevents the cells from leaving the implant, but enables molecules from the body to reach the cells and molecules produced by the cells to enter the body. In one embodiment, the porous barrier is formed from alginate.

In one embodiment, a contraceptive device is coated with or contains an iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof). Exemplary devices include condoms, diaphragms, IUD (implantable uterine devices, sponges, vaginal sheaths, and birth control devices. In one embodiment, the iRNA is chosen to inactive sperm or egg. In another embodiment, the iRNA is chosen to be complementary to a viral or pathogen RNA, e.g., an RNA of an STD. In some instances, the iRNA composition can include a spermicide.

Dosage

In one aspect, the invention features a method of administering an iRNA agent, e.g., a double-stranded iRNA agent, or sRNA agent, to a subject (e.g., a human subject). The method includes administering a unit dose of the iRNA agent, e.g., a sRNA agent, e.g., double stranded sRNA agent that (a) the double-stranded part is 19-25 nucleotides (nt) long, preferably 21-23 nt, (b) is complementary to a target RNA (e.g., an endogenous or pathogen target RNA), and, optionally, (c) includes at least one 3' overhang 1-5 nucleotide long. In one embodiment, the unit dose is less than 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g. about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA agent per kg of bodyweight.

The defined amount can be an amount effective to treat or prevent a disease or disorder, e.g., a disease or disorder associated with the target RNA, such as an RNA present in the kidney. The unit dose, for example, can be administered by injection (e.g., intravenous or intramuscular), an inhaled dose, or a topical application. Particularly preferred dosages are less than 2, 1, or 0.1 mg/kg of body weight.

In a preferred embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time.

In one embodiment, the effective dose is administered with other traditional therapeutic modalities. In one embodiment, the subject has a viral infection and the modality is an anti-viral agent other than an iRNA agent, e.g., other than a double-stranded iRNA agent, or sRNA agent. In another embodiment, the subject has atherosclerosis and the effective dose of an iRNA agent, e.g., a double-stranded iRNA agent, or sRNA agent, is administered in combination with, e.g., after surgical intervention, e.g., angioplasty.

In one embodiment, a subject is administered an initial dose and one or more maintenance doses of an iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof). The maintenance dose or doses are generally lower than the initial dose, e.g., one-half less of the initial dose. A maintenance regimen can include treating the subject with a dose or doses ranging from 0.01 µg to 1.4 mg/kg of body weight per day, e.g., 10, 1, 0.1, 0.01, 0.001, or 0.00001 mg per kg of bodyweight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once for every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

In one embodiment, the iRNA agent pharmaceutical composition includes a plurality of iRNA agent species. In another embodiment, the iRNA agent species has sequences that are non-overlapping and non-adjacent to another species with respect to a naturally occurring target sequence. In another embodiment, the plurality of iRNA agent species is specific for different naturally occurring target genes. In another embodiment, the iRNA agent is allele specific.

In some cases, a patient is treated with a iRNA agent in conjunction with other therapeutic modalities. For example, a patient being treated for a kidney disease, e.g., early stage renal disease, can be administered an iRNA agent specific for a target gene known to enhance the progression of the disease in conjunction with a drug known to inhibit activity of the target gene product. For example, a patient who has early stage renal disease can be treated with an iRNA agent that targets an SGLT2 RNA, in conjunction with the small molecule phlorizin, which is known to block sodium-glucose cotransport and to subsequently reduce single nephron glomerular filtration rate. In another example, a patient being treated for a cancer of the kidney can be administered an iRNA agent specific for a target essential for tumor cell proliferation in conjunction with a chemotherapy.

Following successful treatment, it may be desirable to have the patient undergo maintenance therapy to prevent the recurrence of the disease state, wherein the compound of the invention is administered in maintenance doses, ranging from 0.01 µg to 100 g per kg of body weight (see U.S. Pat. No. 6,107, 094).

The concentration of the iRNA agent composition is an amount sufficient to be effective in treating or preventing a disorder or to regulate a physiological condition in humans. The concentration or amount of iRNA agent administered will depend on the parameters determined for the agent and the method of administration, e.g. nasal, buccal, pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof) can include a single treatment or, preferably, can include a series of treatments. It will also be appreciated that the effective dosage of a iRNA agent such as a sRNA agent used for treatment may increase or decrease over the course of a particular treatment. Changes in dosage may result and become apparent from the results of diagnostic assays as described herein. For example, the subject can be monitored after administering a iRNA agent composition. Based on information from the monitoring, an additional amount of the iRNA agent composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that express a human gene, e.g. a gene that produces a target RNA. The transgenic animal can be deficient for the corresponding endogenous RNA. In another embodiment, the composition for testing includes a iRNA agent that is complementary, at least in an internal region, to a sequence that is conserved between the target RNA in the animal model and the target RNA in a human.

The inventors have discovered that iRNA agents described herein can be administered to mammals, particularly large mammals such as nonhuman primates or humans in a number of ways.

In one embodiment, the administration of the iRNA agent, e.g., a double-stranded iRNA agent, or sRNA agent, composition is parenteral, e.g. intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, pulmonary, intranasal, urethral or ocular. Administration can be provided by the subject or by another person, e.g., a health care provider. The medication can be provided in measured doses or in a dispenser which delivers a metered dose. Selected modes of delivery are discussed in more detail below.

The invention provides methods, compositions, and kits, for rectal administration or delivery of iRNA agents described herein.

Accordingly, an iRNA agent, e.g., a double-stranded iRNA agent, or sRNA agent, (e.g., a precursor, e.g., a larger iRNA agent which can be processed into a sRNA agent, or a DNA which encodes a an iRNA agent, e.g., a double-stranded iRNA agent, or sRNA agent, or precursor thereof) described herein, e.g., a therapeutically effective amount of a iRNA agent described herein, e.g., a iRNA agent having a double stranded region of less than 40, and preferably less than 30 nucleotides and having one or two 1-3 nucleotide single strand 3' overhangs can be administered rectally, e.g., introduced through the rectum into the lower or upper colon. This approach is particularly useful in the treatment of, inflammatory disorders, disorders characterized by unwanted cell proliferation, e.g., polyps, or colon cancer.

The medication can be delivered to a site in the colon by introducing a dispensing device, e.g., a flexible, camera-guided device similar to that used for inspection of the colon or removal of polyps, which includes means for delivery of the medication.

The rectal administration of the iRNA agent is by means of an enema. The iRNA agent of the enema can be dissolved in a saline or buffered solution. The rectal administration can also by means of a suppository, which can include other ingredients, e.g., an excipient, e.g., cocoa butter or hydropropylmethylcellulose.

Any of the iRNA agents described herein can be administered orally, e.g., in the form of tablets, capsules, gel capsules, lozenges, troches or liquid syrups. Further, the composition can be applied topically to a surface of the oral cavity.

Any of the iRNA agents described herein can be administered buccally. For example, the medication can be sprayed into the buccal cavity or applied directly, e.g., in a liquid, solid, or gel form to a surface in the buccal cavity. This administration is particularly desirable for the treatment of inflammations of the buccal cavity, e.g., the gums or tongue, e.g., in one embodiment, the buccal administration is by spraying into the cavity, e.g., without inhalation, from a dispenser, e.g., a metered dose spray dispenser that dispenses the pharmaceutical composition and a propellant.

Any of the iRNA agents described herein can be administered to ocular tissue. For example, the medications can be applied to the surface of the eye or nearby tissue, e.g., the inside of the eyelid. They can be applied topically, e.g., by spraying, in drops, as an eyewash, or an ointment. Administration can be provided by the subject or by another person, e.g., a health care provider. The medication can be provided in measured doses or in a dispenser which delivers a metered dose. The medication can also be administered to the interior of the eye, and can be introduced by a needle or other delivery device which can introduce it to a selected area or structure. Ocular treatment is particularly desirable for treating inflammation of the eye or nearby tissue.

Any of the iRNA agents described herein can be administered directly to the skin. For example, the medication can be applied topically or delivered in a layer of the skin, e.g., by the use of a microneedle or a battery of microneedles which penetrate into the skin, but preferably not into the underlying muscle tissue. Administration of the iRNA agent composition can be topical. Topical applications can, for example, deliver the composition to the dermis or epidermis of a subject. Topical administration can be in the form of transdermal patches, ointments, lotions, creams, gels, drops, suppositories, sprays, liquids or powders. A composition for topical administration can be formulated as a liposome, micelle, emulsion, or other lipophilic molecular assembly. The transdermal administration can be applied with at least one penetration enhancer, such as iontophoresis, phonophoresis, and sonophoresis.

Any of the iRNA agents described herein can be administered to the pulmonary system. Pulmonary administration can be achieved by inhalation or by the introduction of a delivery device into the pulmonary system, e.g., by introducing a delivery device which can dispense the medication. A preferred method of pulmonary delivery is by inhalation. The medication can be provided in a dispenser which delivers the medication, e.g., wet or dry, in a form sufficiently small such that it can be inhaled. The device can deliver a metered dose of medication. The subject, or another person, can administer the medication.

Pulmonary delivery is effective not only for disorders which directly affect pulmonary tissue, but also for disorders which affect other tissue.

iRNA agents can be formulated as a liquid or nonliquid, e.g., a powder, crystal, or aerosol for pulmonary delivery.

Any of the iRNA agents described herein can be administered nasally. Nasal administration can be achieved by introduction of a delivery device into the nose, e.g., by introducing a delivery device which can dispense the medication. Methods of nasal delivery include spray, aerosol, liquid, e.g., by drops, or by topical administration to a surface of the nasal cavity. The medication can be provided in a dispenser with delivery of the medication, e.g., wet or dry, in a form sufficiently small such that it can be inhaled. The device can deliver a metered dose of medication. The subject, or another person, can administer the medication.

Nasal delivery is effective not only for disorders which directly affect nasal tissue, but also for disorders which affect other tissue iRNA agents can be formulated as a liquid or nonliquid, e.g., a powder, crystal, or for nasal delivery.

An iRNA agent can be packaged in a viral natural capsid or in a chemically or enzymatically produced artificial capsid or structure derived therefrom.

The dosage of a pharmaceutical composition including a iRNA agent can be administered in order to alleviate the symptoms of a disease state, e.g., cancer or a cardiovascular disease. A subject can be treated with the pharmaceutical composition by any of the methods mentioned above.

Gene expression in a subject can be modulated by administering a pharmaceutical composition including an iRNA agent.

A subject can be treated by administering a defined amount of an iRNA agent, e.g., a double-stranded iRNA agent, or sRNA agent, (e.g., a precursor, e.g., a larger iRNA agent which can be processed into a sRNA agent) composition that is in a powdered form, e.g., a collection of microparticles, such as crystalline particles. The composition can include a plurality of iRNA agents, e.g., specific for one or more different endogenous target RNAs. The method can include other features described herein.

A subject can be treated by administering a defined amount of an iRNA agent composition that is prepared by a method that includes spray-drying, i.e. atomizing a liquid solution, emulsion, or suspension, immediately exposing the droplets to a drying gas, and collecting the resulting porous powder particles. The composition can include a plurality of iRNA agents, e.g., specific for one or more different endogenous target RNAs. The method can include other features described herein.

The iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof), can be provided in a powdered, crystallized or other finely divided form, with or without a carrier, e.g., a micro- or nano-particle suitable for inhalation or other pulmonary delivery. This can include providing an aerosol preparation, e.g., an aerosolized spray-dried composition. The aerosol composition can be provided in and/or dispensed by a metered dose delivery device.

The subject can be treated for a condition treatable by inhalation, e.g., by aerosolizing a spray-dried iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof) composition and inhaling the aerosolized composition. The iRNA agent can be an sRNA. The composition can include a plurality of iRNA agents, e.g., specific for one or more different endogenous target RNAs. The method can include other features described herein.

A subject can be treated by, for example, administering a composition including an effective/defined amount of an iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof), wherein the composition is prepared by a method that includes spray-drying, lyophilization, vacuum drying, evaporation, fluid bed drying, or a combination of these techniques In another aspect, the invention features a method that includes: evaluating a parameter related to the abundance of a transcript in a cell of a subject; comparing the evaluated parameter to a reference value; and if the evaluated parameter has a preselected relationship to the reference value (e.g., it is greater), administering a iRNA agent (or a precursor, e.g., a larger iRNA agent which can be processed into a sRNA agent, or a DNA which encodes a iRNA agent or precursor thereof) to the subject. In one embodiment, the iRNA agent includes a sequence that is complementary to the evaluated transcript. For example, the parameter can be a direct measure of transcript levels, a measure of a protein level, a disease or disorder symptom or characterization (e.g., rate of cell proliferation and/or tumor mass, viral load).

In another aspect, the invention features a method that includes: administering a first amount of a composition that comprises an iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof) to a subject, wherein the iRNA agent includes a strand substantially complementary to a target nucleic acid; evaluating an activity associated with a protein encoded by the target nucleic acid; wherein the evaluation is used to determine if a second amount should be administered. In a preferred embodiment the method includes administering a second amount of the composition, wherein the timing of administration or dosage of the second amount is a function of the evaluating. The method can include other features described herein.

In another aspect, the invention features a method of administering a source of a double-stranded iRNA agent (ds iRNA agent) to a subject. The method includes administering or implanting a source of a ds iRNA agent, e.g., a sRNA agent, that (a) includes a double-stranded region that is 19-25 nucleotides long, preferably 21-23 nucleotides, (b) is complementary to a target RNA (e.g., an endogenous RNA or a pathogen RNA), and, optionally, (c) includes at least one 3' overhang 1-5 nt long. In one embodiment, the source releases ds iRNA agent over time, e.g. the source is a controlled or a slow release source, e.g., a microparticle that gradually releases the ds iRNA agent. In another embodiment, the source is a pump, e.g., a pump that includes a sensor or a pump that can release one or more unit doses.

In one aspect, the invention features a pharmaceutical composition that includes an iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof) including a nucleotide sequence complementary to a target RNA, e.g., substantially and/or exactly complementary. The target RNA can be a transcript of an endogenous human gene. In one embodiment, the iRNA agent (a) is 19-25 nucleotides long, preferably 21-23 nucleotides, (b) is complementary to an endogenous target RNA, and, optionally, (c) includes at least one 3' overhang 1-5 nt long. In one embodiment, the pharmaceutical composition can be an emulsion, microemulsion, cream, jelly, or liposome.

In one example the pharmaceutical composition includes an iRNA agent mixed with a topical delivery agent. The topical delivery agent can be a plurality of microscopic vesicles. The microscopic vesicles can be liposomes. In a preferred embodiment the liposomes are cationic liposomes.

In another aspect, the pharmaceutical composition includes an iRNA agent, e.g., a double-stranded iRNA agent, or sRNA agent (e.g., a precursor, e.g., a larger iRNA agent which can be processed into a sRNA agent, or a DNA which encodes an iRNA agent, e.g., a double-stranded iRNA agent, or sRNA agent, or precursor thereof) admixed with a topical penetration enhancer. In one embodiment, the topical penetration enhancer is a fatty acid. The fatty acid can be arachidonic acid, oleic acid, lauric acid, caprylic acid, capric acid, myristic acid, palmitic acid, stearic acid, linoleic acid, linolenic acid, dicaprate, tricaprate, monolein, dilaurin, glyceryl 1-monocaprate, 1-dodecylazacycloheptan-2-one, an acylcarnitine, an acylcholine, or a $C_{1-10}$ alkyl ester, monoglyceride, diglyceride or pharmaceutically acceptable salt thereof.

In another embodiment, the topical penetration enhancer is a bile salt. The bile salt can be cholic acid, dehydrocholic acid, deoxycholic acid, glucholic acid, glycholic acid, glycodeoxycholic acid, taurocholic acid, taurodeoxycholic acid, chenodeoxycholic acid, ursodeoxycholic acid, sodium tauro-24,25-dihydro-fusidate, sodium glycodihydrofusidate, polyoxyethylene-9-lauryl ether or a pharmaceutically acceptable salt thereof.

In another embodiment, the penetration enhancer is a chelating agent. The chelating agent can be EDTA, citric acid, a salicyclate, a N-acyl derivative of collagen, laureth-9, an N-amino acyl derivative of a beta-diketone or a mixture thereof.

In another embodiment, the penetration enhancer is a surfactant, e.g., an ionic or nonionic surfactant. The surfactant can be sodium lauryl sulfate, polyoxyethylene-9-lauryl ether, polyoxyethylene-20-cetyl ether, a perfluorchemical emulsion or mixture thereof.

In another embodiment, the penetration enhancer can be selected from a group consisting of unsaturated cyclic ureas, 1-alkyl-alkones, 1-alkenylazacyclo-alakanones, steroidal anti-inflammatory agents and mixtures thereof. In yet another embodiment the penetration enhancer can be a glycol, a pyrrol, an azone, or a terpenes.

In one aspect, the invention features a pharmaceutical composition including an iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof) in a form suitable for oral delivery. In one embodiment, oral delivery can be used to deliver an iRNA agent composition to a cell or a region of the gastro-intestinal tract, e.g., small intestine, colon (e.g., to treat a colon cancer), and so forth. The oral delivery form can be tablets, capsules or gel capsules. In one embodiment, the iRNA agent of the pharmaceutical composition modulates expression of a cellular adhesion protein, modulates a rate of cellular proliferation, or has biological activity against eukaryotic pathogens or retroviruses. In another embodiment, the pharmaceutical composition includes an enteric material that substantially prevents dissolution of the tablets, capsules or gel capsules in a mammalian stomach. In a preferred embodiment the enteric material is a coating. The coating can be acetate phthalate, propylene glycol, sorbitan monoleate, cellulose acetate trimellitate, hydroxy propyl methylcellulose phthalate or cellulose acetate phthalate.

In another embodiment, the oral dosage form of the pharmaceutical composition includes a penetration enhancer. The penetration enhancer can be a bile salt or a fatty acid. The bile salt can be ursodeoxycholic acid, chenodeoxycholic acid, and salts thereof. The fatty acid can be capric acid, lauric acid, and salts thereof.

In another embodiment, the oral dosage form of the pharmaceutical composition includes an excipient. In one example the excipient is polyethyleneglycol. In another example the excipient is precirol.

In another embodiment, the oral dosage form of the pharmaceutical composition includes a plasticizer. The plasticizer can be diethyl phthalate, triacetin dibutyl sebacate, dibutyl phthalate or triethyl citrate.

In one aspect, the invention features a pharmaceutical composition including an iRNA agent and a delivery vehicle. In one embodiment, the iRNA agent is (a) is 19-25 nucleotides long, preferably 21-23 nucleotides, (b) is complementary to an endogenous target RNA, and, optionally, (c) includes at least one 3' overhang 1-5 nucleotides long.

In one embodiment, the delivery vehicle can deliver an iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof) to a cell by a topical route of administration. The delivery vehicle can be microscopic vesicles. In one example the microscopic vesicles are liposomes. In a preferred embodiment the liposomes are cationic liposomes. In another example the microscopic vesicles are micelles. In one aspect, the invention features a pharmaceutical composition including an iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof) in an injectable dosage form. In one embodiment, the injectable dosage form of the pharmaceutical composition includes sterile aqueous solutions or dispersions and sterile powders. In a preferred embodiment the sterile solution can include a diluent such as water; saline solution; fixed oils, polyethylene glycols, glycerin, or propylene glycol.

In one aspect, the invention features a pharmaceutical composition including an iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof) in oral dosage form. In one embodiment, the oral dosage form is selected from the group consisting of tablets, capsules and gel capsules. In another embodiment, the pharmaceutical composition includes an enteric material that substantially prevents dissolution of the tablets, capsules or gel capsules in a mammalian stomach. In a preferred embodiment the enteric material is a coating. The coating can be acetate phthalate, propylene glycol, sorbitan monoleate, cellulose acetate trimellitate, hydroxy propyl methyl cellulose phthalate or cellulose acetate phthalate. In one embodiment, the oral dosage form of the pharmaceutical composition includes a penetration enhancer, e.g., a penetration enhancer described herein.

In one aspect, the invention features a pharmaceutical composition including an iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof) in a rectal dosage form. In one embodiment, the rectal dosage form is an enema. In another embodiment, the rectal dosage form is a suppository.

In one aspect, the invention features a pharmaceutical composition including an iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof) in a vaginal dosage form. In one embodiment, the vaginal dosage form is a suppository. In another embodiment, the vaginal dosage form is a foam, cream, or gel.

In one aspect, the invention features a pharmaceutical composition including an iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof) in a pulmonary or nasal dosage form. In one embodiment, the iRNA agent is incorporated into a particle, e.g., a macroparticle, e.g., a microsphere. The particle can be produced by spray drying, lyophilization, evaporation, fluid bed drying, vacuum drying, or a combination thereof. The microsphere can be formulated as a suspension, a powder, or an implantable solid.

In one aspect, the invention features a spray-dried iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof) composition suitable for inhalation by a subject, including: (a) a therapeutically effective amount of a iRNA agent suitable for treating a condition in the subject by inhalation; (b) a pharmaceutically acceptable excipient selected from the group consisting of carbohydrates and amino acids; and (c) optionally, a dispersibility-enhancing amount of a physiologically-acceptable, water-soluble polypeptide.

In one embodiment, the excipient is a carbohydrate. The carbohydrate can be selected from the group consisting of monosaccharides, disaccharides, trisaccharides, and polysaccharides. In a preferred embodiment the carbohydrate is a monosaccharide selected from the group consisting of dextrose, galactose, mannitol, D-mannose, sorbitol, and sorbose. In another preferred embodiment the carbohydrate is a disaccharide selected from the group consisting of lactose, maltose, sucrose, and trehalose.

In another embodiment, the excipient is an amino acid. In one embodiment, the amino acid is a hydrophobic amino acid. In a preferred embodiment the hydrophobic amino acid is selected from the group consisting of alanine, isoleucine, leucine, methionine, phenylalanine, proline, tryptophan, and valine. In yet another embodiment the amino acid is a polar amino acid. In a preferred embodiment the amino acid is selected from the group consisting of arginine, histidine, lysine, cysteine, glycine, glutamine, serine, threonine, tyrosine, aspartic acid and glutamic acid.

In one embodiment, the dispersibility-enhancing polypeptide is selected from the group consisting of human serum albumin, α-lactalbumin, trypsinogen, and polyalanine.

In one embodiment, the spray-dried iRNA agent composition includes particles having a mass median diameter (MMD) of less than 10 microns. In another embodiment, the spray-dried iRNA agent composition includes particles having a mass median diameter of less than 5 microns. In yet another embodiment the spray-dried iRNA agent composition includes particles having a mass median aerodynamic diameter (MMAD) of less than 5 microns.

In certain other aspects, the invention provides kits that include a suitable container containing a pharmaceutical formulation of an iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof). In certain embodiments the individual components of the pharmaceutical formulation may be provided in one container. Alternatively, it may be desirable to provide the components of the pharmaceutical formulation separately in two or more containers, e.g., one container for an iRNA agent preparation, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

In another aspect, the invention features a device, e.g., an implantable device, wherein the device can dispense or administer a composition that includes an iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof), e.g., a iRNA agent that silences an endogenous transcript. In one embodiment, the device is coated with the composition. In another embodiment the iRNA agent is disposed within the device. In another embodiment, the device includes a mechanism to dispense a unit dose of the composition. In other embodiments the device releases the composition continuously, e.g., by diffusion. Exemplary devices include stents, catheters, pumps, artificial organs or organ components (e.g., artificial heart, a heart valve, etc.), and sutures.

As used herein, the term "crystalline" describes a solid having the structure or characteristics of a crystal, i.e., particles of three-dimensional structure in which the plane faces intersect at definite angles and in which there is a regular internal structure. The compositions of the invention may have different crystalline forms. Crystalline forms can be prepared by a variety of methods, including, for example, spray drying.

The invention is further illustrated by the following examples, which should not be construed as further limiting.

EXAMPLES

Example 1

Diethyl2-azabutane-1,4-dicarboxylate AA

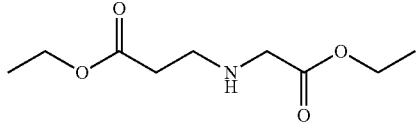

AA

A 4.7M aqueous solution of sodium hydroxide (50 mL) was added into a stirred, ice-cooled solution of ethyl glycinate hydrochloride (32.19 g, 0.23 mole) in water (50 mL). Then, ethyl acrylate (23.1 g, 0.23 mole) was added and the mixture was stirred at room temperature until the completion of reaction was ascertained by TLC (19 h). After 19 h which it was partitioned with dichloromethane (3×100 mL). The organic layer was dried with anhydrous sodium sulfate, filtered and evaporated. The residue was distilled to afford AA (28.8 g, 61%).

Example 2

3-{Ethoxycarbonylmethyl-[6-(9H-fluoren-9-yl-methoxycarbonyl-amino)-hexanoyl]-amino}-propionic acid ethyl ester AB

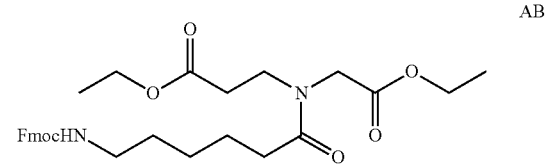

AB

Fmoc-6-amino-hexanoic acid (9.12 g, 25.83 mmol) was dissolved in dichloromethane (50 mL) and cooled with ice. Diisopropylcarbodiimde (3.25 g, 3.99 mL, 25.83 mmol) was added to the solution at 0° C. It was then followed by the addition of Diethyl2-azabutane-1,4-dicarboxylate (5 g, 24.6 mmol) and dimethylamino pyridine (0.305 g, 2.5 mmol). The solution was brought to room temperature and stirred further for 6 h. the completion of the reaction was ascertained by TLC. The reaction mixture was concentrated in vacuum and to the ethylacetate was added to precipitate diisopropyl urea. The suspension was filtered. The filtrate was washed with 5% aqueous hydrochloric acid, 5% sodium bicarbonate and water. The combined organic layer was dried over sodium sulfate and concentrated to give the crude product which was purified by column chromatography (50% EtOAC/Hexanes) to yield 11.87 g (88%) of AB

Example 3

3-[(6-Amino-hexanoyl)-ethoxycarbonylmethyl-amino]-propionic acid ethyl ester AC

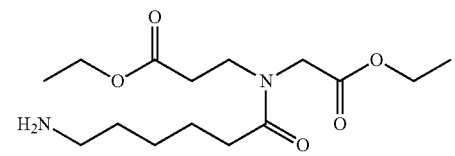

AC

3-{Ethoxycarbonylmethyl-[6-(9H-fluoren-9-ylmethoxycarbonylamino)-hexanoyl]-amino}-propionic acid ethyl ester AB (11.5 g, 21.3 mmol) was dissolved in 20% piperidine in dimethylformamide at 0° C. The solution was continued stirring for 1 h. The reaction mixture was concentrated in vacuum and the residue water was added and the product was extracted with ethyl acetate. The crude product was purified by converting into hydrochloride salt.

Example 4

3-({6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}ethoxycarbonylmethyl-amino)-propionic acid ethyl ester AD

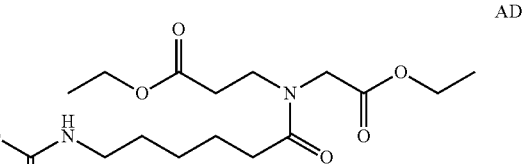

AD

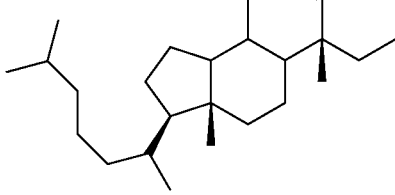

Hydrochloride salt of 3-[(6-Amino-hexanoyl)-ethoxycarbonylmethyl-amino]-propionic acid ethyl ester AC (4.7 g, 14.8 mmol) was taken in dichloromethane. The suspension was cooled to 0° C. with ice. To the suspension diisopropylethylamine (3.87 g, 5.2 mL, 30 mmol) was added. To the resulting solution cholesteryl chloroformate (6.675 g, 14.8 mmol) was added. The reaction mixture was stirred overnight. The reaction mixture was diluted with dichloromethane and washed with 10% hydrochloric acid. The product was purified flash chromatography (10.3 g, 92%).

Example 5

1-{6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}-4-oxo-pyrrolidine-3-carboxylic acid ethyl ester AE

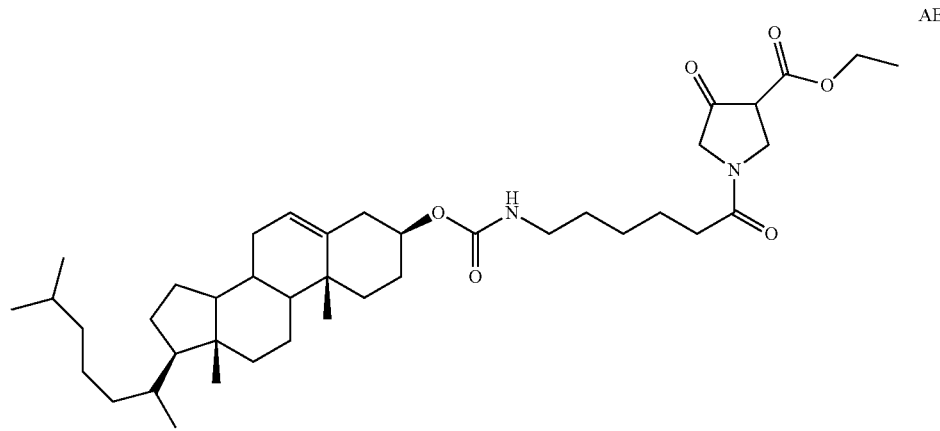 [SMILES: CCOC(=O)C1CN(C(=O)CCCCCNC(=O)O[C@H]2CC[C@@]3(C)C(=CCC4C3CC[C@@]3(C)C4CC[C@@H]3C(C)CCCC(C)C)C2)CC1=O]

Potassium t-butoxide (1.1 g, 9.8 mmol) was slurried in 30 mL of dry toluene. The mixture was cooled to 0° C. and 5 g (6.6 mmol) of diester was added slowly with stirring within 20 mins. The temperature was kept below 5° C. during the addition. The stirring was continued for 30 mins at 0° C. and 1 mL of glacial acetic acid was added, immediately followed by 4 g of $NaH_2PO_4.H_2O$ in 40 mL of water The resultant mixture was extracted with two 100 mL of dichloromethane and the combined organic extracts were washed twice with 10 mL of phosphate buffer, dried, and evaporated to dryness. The residue was dissolved in 60 mL of toluene, cooled to 0° C. and extracted with three 50 mL portions of cold pH 9.5 carbonate buffer. The aqueous extracts were converted to pH 3 with phosphoric acid, and extracted with five 40 mL portions of chloroform which were combined, dried and evaporated to a residue. The residue was purified by column chromatography using 25% ethylacetate/hexanes to afford 1.9 g of β-ketoester was obtained (39%).

Example 6

[6-(3-Hydroxy-4-hydroxymethyl-pyrrolidin-1-yl)-6-oxo-hexyl]-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AF

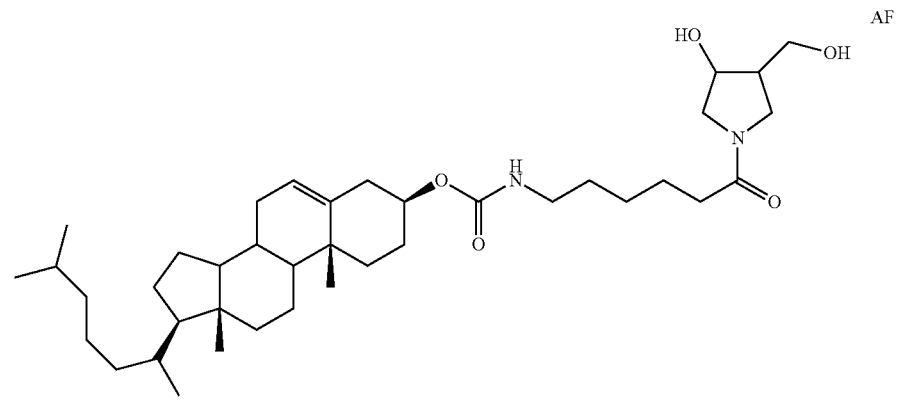 [SMILES: CC(C)CCCC(C)[C@H]1CCC2C3CC=C4C[C@@H](OC(=O)NCCCCCC(=O)N5CC(O)C(CO)C5)CC[C@]4(C)C3CC[C@@]21C]

Methanol (2 mL) was added dropwise over a period of 1 h to a refluxing mixture of ketoester AE (1.5 g, 2.2 mmol) and sodium borohydride (0.226 g, 6 mmol) in tetrahydrofuran (10 mL). Stirring is continued at reflux temperature for 1 h. After cooling to room temperature, 1 N HCl (12.5 mL) was added, the mixture was extracted with ethylacetate (3×40 mL). The combined ethylacetate layer was dried over anhydrous sodium sulfate and concentrated in vacuum to yield the product which purified by column chromatography (10% MeOH/CHCl$_3$). (89%).

Example 7

(6-{3-[Bis-(4-methoxy-phenyl)-phenyl-methoxymethyl]-4-hydroxy-pyrrolidin-1-yl}-6-oxo-hexyl)-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AG

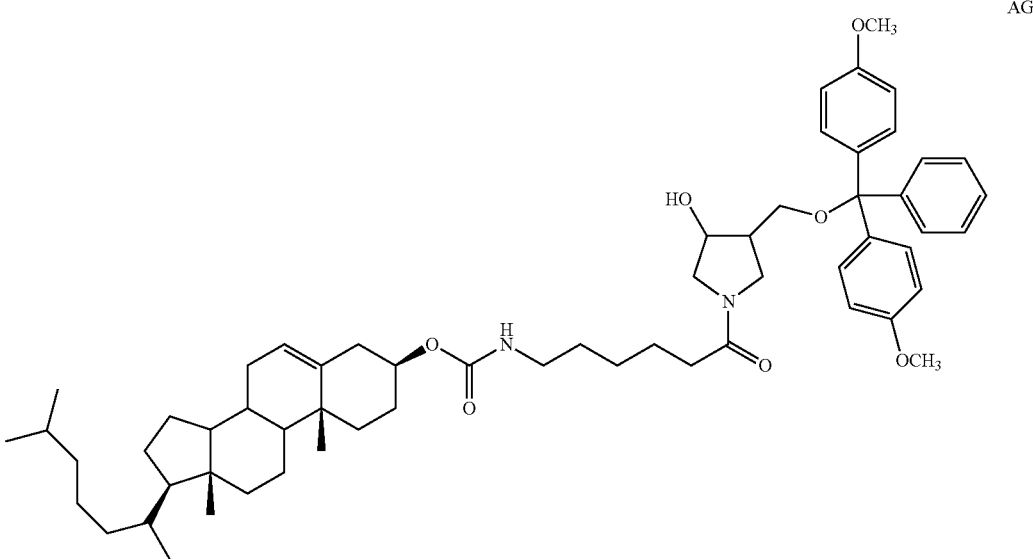 [SMILES: COc1ccc(C(OCC2CN(C(=O)CCCCCNC(=O)O[C@H]3CC[C@@]4(C)C(=CCC5C4CC[C@@]4(C)C5CC[C@@H]4C(C)CCCC(C)C)C3)CC2O)(c2ccccc2)c2ccc(OC)cc2)cc1]

Diol AF (1.25 gm 1.994 mmol) was dried by evaporating with pyridine (2×5 mL) in vacuo. Anhydrous pyridine (10 mL) and 4,4'-dimethoxytritylchloride (0.724 g, 2.13 mmol) were added with stirring. The reaction was carried out at room temperature for overnight. The reaction was quenched by the addition of methanol. The reaction mixture was concentrated in vacuum and to the residue dichloromethane (50 mL) was added. The organic layer was washed with 1M aqueous sodium bicarbonate. The organic layer was dried over anhydrous sodium sulfate, filtered and concentrated. The residual pyridine was removed by evaporating with toluene. The crude product was purified by column chromatography (2% MeOH/Chloroform, R$_f$=0.5 in 5% MeOH/CHCl$_3$). (1.75 g, 95%)

Example 8

Succinic acid mono-(4-[bis-(4-methoxy-phenyl)-phenyl-methoxymethyl]-1-{6-[17-(1,5-dimethyl-hexyl)-10,13-dimethyl 2,3,4,7,8,9,10,11,12,13,14,15,16,17-tetradecahydro-1H cyclopenta[a]phenanthren-3-yloxycarbonylaminophexanoyl]-hexanoyl}-pyrrolidin-3-yl) ester AH

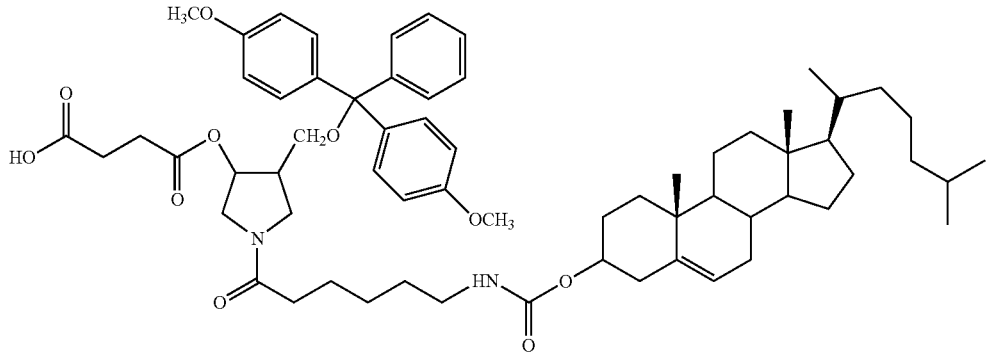

Compound AG (1.0 g, 1.05 mmol) was mixed with succinic anhydride (0.150 g, 1.5 mmol) and DMAP (0.073 g, 0.6 mmol) and dried in a vacuum at 40° C. overnight. The mixture was dissolved in anhydrous dichloroethane (3 mL), triethylamine (0.318 g, 0.440 mL, 3.15 mmol) was added and the solution was stirred at room temperature under argon atmosphere for 16 h. It was then diluted with dichloromethane (40 mL) and washed with ice cold aqueous citric acid (5 wt %, 30 mL) and water (2×20 mL). The organic phase was dried over anhydrous sodium sulfate and concentrated to dryness. The residue was used as such for the next step.

Example 9

Cholesterol Derivatised CPG AI

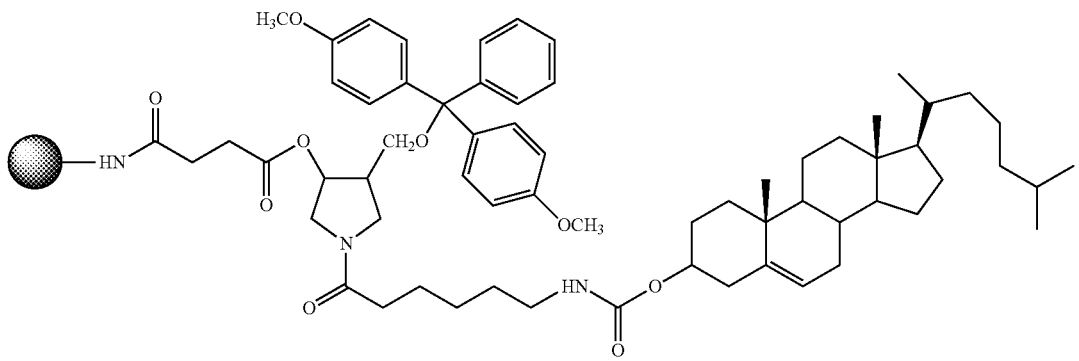

AI

Succinate A11 (0.254 g, 0.242 mmol) was dissolved in mixture of dichloromethane/acetonitrile (3:2, 3 mL). To that solution DMAP (0.0296 g, 0.242 mmol) in acetonitrile (1.25 mL), 2,2'-Dithio-bis(5-nitropyridine) (0.075 g, 0.242 mmol) in acetonitrile/dichloroethane (3:1, 1.25 mL) were added successively. To the resulting solution triphenylphosphine (0.064 g, 0.242 mmol) in acetonitrile (0.6 ml) was added. The reaction mixture turned bright orange in color. The solution was agitated briefly using wrist-action shaker (5 mins). Long chain alkyl amine-CPG (LCAA-CPG) (1.5 g, 61 µm/g) was added. The suspension was agitated for 2 h. The CPG was filtered through a sintered funnel and washed with acetonitrile, dichloromethane and ether successively. Unreacted amino groups were masked using acetic anhydride/pyridine. The loading capacity of the CPG was measured by taking UV measurement. (37 µM/g).

Example 10

(4-[bis-(4-methoxy-phenyl)-phenyl-methoxymethyl]-1-{6-[17-(1,5-dimethyl-hexyl)-10,13-dimethyl 2,3,4,7,8,9,10,11,12,13,14,15,16,17-tetradecahydro-1H cyclopenta[a]phenanthren-3-yloxycarbonylamino]-hexanoyl}-pyrrolidin-3-yl)phosphoramidite AJ

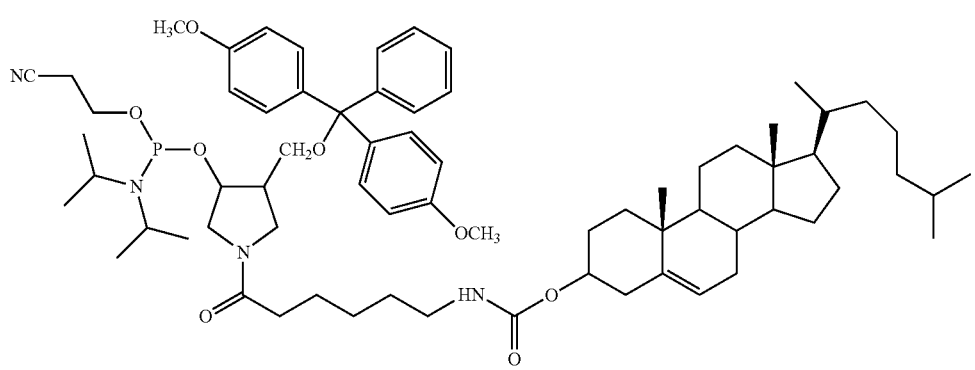

AJ

Compound AG (0.15 g, 0.158 mmol) was coevaporated with toluene (5 mL). To the residue N,N-tetraisopropylammonium tetrazolide (0.0089 g, 0.079 mmol) was added and the mixture was dried over $P_2O_5$ in a vacuum oven for overnight at 40° C. The reaction mixture was dissolved in the mixture of anhydrous acetonitrile/dichloromethane (2;1, 1 mL) and 2-cyanoethyl-N,N,N',N'-tetraisopropylphosphoramidite (0.0714 g, 0.0781 mL, 0.237 mmol) was added. The reaction mixture was stirred at ambient temperature for overnight. The completion of the reaction was ascertained by TLC (1;1 ethyl acetate:hexane). The solvent was removed under reduced pressure and the residue was dissolved in ethyl acetate (10 mL) and washed with 5% $NaHCO_3$ (4 mL) and brine (4 mL). The ethyl acetate layer was dried over anhydrous $Na_2SO_4$ and concentrated under reduced pressure. The resulting mixture was chromatographed (50:49:1, EtOAc: Hexane:triethlyamine) to afford AJ as white foam (0.152 g, 84%).

Example 11

RNA Synthesis, Deprotection and Purification Protocol

1. Synthesis:

The RNA molecules were synthesized on a 394 ABI machine using the standard 93 step cycle written by the manufacturer with modifications to a few wait steps as described below. The solid support was controlled pore glass (CPG, 1 µmole, 500 Å, Glen Research, Sterling Va.) and the monomers were RNA phosphoramidites with standard protecting groups ($N^6$-benzoyl-5'-O-dimethoxytrityladenosine-2'tbutyldimethylsilyl-3'-O—N,N'-diisopropyl-2-cyanoethylphosphoramidite, 5'-O-dimethoxytrityluridine-2' tbutyldimethylsilyl-3'-O—N,N'-diisopropyl-2-cyanoethylphosphoramidite, $N^2$-isobutyryl-5'-O-dimethoxytritylguanosine-2'tbutyldimethylsilyl, 3'-O—N,N'-diisopropyl-2-cyanoethylphosphoramidite, and N4-benzoyl-5'-O-dimethoxytritylcytidine-2'tbutyldimethylsilyl-3'-O—N,N'-diisopropyl-2-cyanoethylphosphoramidite from Chemgenes Corp MA) used at a concentration of 0.15M in acetonitrile ($CH_3CN$) and a coupling time of 7.5 min. The activator was thiotetrazole (0.25M), For the PO-oxidation Iodine/Water/Pyridine was used and the PS-oxidation Beaucage reagent 0.5M solution in acetomitrile was used. All reagents for synthesis were also from Glen Research.

2. Deprotection-I (Oligomer Cleavage, Base and Phosphate Deprotection)

After completion of synthesis the controlled pore glass (CPG) was transferred to a screw cap vial (Fisher, catalog number 03-340-5N) or a screw cap RNase free microfuge tube. The oligonucleotide was cleaved from the CPG with simultaneous deprotection of base and phosphate groups with 1.0 mL of a mixture of ethanolic ammonia [ammonia:ethanol (3:1)] for 6 hours to overnight at 55° C. The vial was cooled briefly on ice and then the ethanolic ammonia mixture was transferred to a new microfuge tube. The CPG was washed with 3×0.25 mL portions of 50% acetonitrile (70% $CH_3CN$ for cholesterol and such hydrophobic conjugated oligomers). The approximate 1.75 mL of solution is best divided equally into two microfuge tubes, capped tightly and then cooled at −80° C. for 15 min, before drying in a speed vac/lyophilizer for about 90 min.

3. Deprotection-II (Removal of 2' TBDMS Group)

The white residue obtained was resuspended in 200 µL of triethylamine trihydrofluoride (TEA.3HF, Aldrich) and heated at 65° C. for 1.5 h to remove the tertbutyldimethylsilyl (TBDMS) groups at the 2' position. The reaction was then quenched with 400 µL of isopropoxytrimethylsilane (iPrOMe$_3$Si Aldrich) and further incubated on the heating block leaving the caps open for 15 min; (This causes the volatile isopropoxytrimethylsilylfluoride adduct to vaporize). The residual quenching reagent was removed by drying in a speed vac. The oligomer was then precipitated in anhydrous methanol (MeOH, 800 µL). The liquid was removed very carefully after spinning in a centrifuge for 5 minutes on the highest speed available. Residual methanol was removed by drying briefly in a speed vac after freezing at −80° C. The crude RNA was obtained as a white fluffy material in the microfuge tube.

4. Quantitation of Crude Oligomer or Raw Analysis

Samples were dissolved in 50% aqueous acetonitrile (0.5 mL) and quantitated as follows: Blanking was first performed with 50% aqueous acetonitrile alone (1 mL).

5 µL of sample and 995 µL of 50% acetonitrile, were mixed well in a microfuge tube, transferred to cuvette and absorbance reading obtained at 260 nm. The crude material is dried down and stored at −20° C.

5. Purification of Oligomers

The crude oligomers were analyzed and purified by HPLC (Mono Q Pharmacia Biotech 5/50). The buffer system is A=100 mM Tris HCl 10% HPLC grade acetonitrile pH=8, B=100 mM Tris-HCl pH 8, 10% HPLC grade acetonitrile 1M NaCl, flow 1.0 mL/min, wavelength 260 nm. For the unmodified RNA 21mer a gradient of 0-0.6M NaCl is usually adequate. One can purify a small amount of material (~5 OD) and analyze by CGE or MS. Once the identity of this material is confirmed the crude oligomer can then be purified using a larger amount of material. i.e 40 OD's per run, flow rate of 1 mL/min and a less sensitive wavelength of 280 nm to avoid saturation of the detector. Fractions containing the full length oligonucleotides are then pooled together, evaporated and finally desalted as described below.

6. Desalting of Purified Oligomer

The purified dry oligomer was then desalted using either C-18 Sepak cartridges (Waters) or Sephadex G-25M (Amersham Biosciences). The cartridge was conditioned with 10 mL each of acetonitrile, followed 50% acetonitrile, 100 mM buffer (this can be triethylammonium acetate, sodium acetate or ammonium acetate). Finally the purified oligomer dissolved thoroughly in 10 mL RNAse free water was applied to the cartridge with very slow dropwise elution. The cartridge was washed with water (10 mL) to remove salts. And finally the salt free oligomer was eluted with 50% acetonitrile or 50% methanol directly into a screw cap vial.

7. Capillary Gel Electrophoresis (CGE) and Electrospray LC/Ms

1 µL of approximately 0.04 OD oligomer is first dried down, redissolved in water (2 µL) and then pipetted in special vials for CGE and LC/MS analysis. In general, desalting should be carried out prior to analysis.

TABLE 4

List of RNA oligonucleotides synthesized siRNA Sequence 1S   5'-CUUACGCUGAGUACUUCGAdTdT-3' (SEQ ID NO: 29)

1AS  5'-UCGAAGUACUCAGCGUAAGdTdT-3' (SEQ ID NO: 30)

2S   5'-CUUACGCUGAGUACUUCGAUU-3' (all RNA) (SEQ ID NO: 31)

2AS  5'-UCGAAGUACUCAGCGUAAGUU-3' (all RNA) (SEQ ID NO: 32)

3S   5'-CUUACGCUGAGUACUUCGAdT*dT-3' * = PS (SEQ ID NO: 33)

3AS  5'-UCGAAGUACUCAGCGUAAGdT*dT-3' * = PS (SEQ ID NO: 34)

4S   5'-C*UUACGCUGAGUACUUCGAdT*dT-3' * = PS (SEQ ID NO: 35)

4AS  5'-U*CGAAGUACUCAGCGUAAGdT*dT-3' * = PS (SEQ ID NO: 36)

5S   5'-C*UUACGCUGAGUACUUCGA*dT*dT-3' * = PS (SEQ ID NO: 37)

5AS  5'-U*CGAAGUACUCAGCGUAAGdT*dT-3' * = PS (SEQ ID NO: 38)

6S   5' CUUACGCUGAGUACUUCGAU$_{2'OMe}$U$_{2'OMe}$ 3' (SEQ ID NO: 39)

6AS  5'-UCGAAGUACUCAGCGUAAGU$_{2'OMe}$U$_{2'OMe}$-3' (SEQ ID NO: 40)

7S   5' CUUACGCUGAGUACUUCGAU*$_{2'OMe}$U$_{2'OMe}$ 3' * = PS (SEQ ID NO: 41)

7AS  5'-UCGAAGUACUCAGCGUAAGU*$_{2'OMe}$U$_{2'OMe}$-3' * = PS (SEQ ID NO: 42)

8S   5' C*UUACGCUGAGUACUUCGAU*$_{2'OMe}$U$_{2'OMe}$ 3' * = PS (SEQ ID NO: 43)

8AS  5'-U*CGAAGUACUCAGCGUAAGU*$_{2'OMe}$U$_{2'OMe}$-3'* = PS (SEQ ID NO: 44)

9S   5'-M1CUUACGCUGAGUACUUCGAdTdTM2-3' (SEQ ID NO: 45)

9AS  5'-M1UCGAAGUACUCAGCGUAAGdTdTM2-3' (SEQ ID NO: 46)

10S  5'-M1*CUUACGCUGAGUACUUCGAdTdT*M2-3' (SEQ ID NO: 47)

10AS 5'-M1*UCGAAGUACUCAGCGUAAGdTdT*M2-3' (SEQ ID NO: 48)

11S  5'-CUUACGCUGAGUACUUCGAdTdTM3-3' (SEQ ID NO: 49)

11AS 5'-UCGAAGUACUCAGCGUAAGdTdTM3-3' (SEQ ID NO: 50)

12S  5'-CUUACGCUGAGUACUUCGAdTdT*M3-3'* = PS (SEQ ID NO: 51)

12AS 5'-UCGAAGUACUCAGCGUAAGdTdT*M3-3'* = PS (SEQ ID NO: 52)

M1 = 3'-OMe-U, in which the 3' substituent of the (U) sugar is -OCH3.
M2 = 3'-OMe-U, in which the 3' substituent of the (U) sugar is -OCH3.
M3 = 3' pyrrolidine cholesterol
* = PS = phosphorothioate linkage
U$_{2'OMe}$ means that the 2' substituent of the (U) sugar is -OCH3.
dT = deoxythymidine

TABLE 5

Mass data for olignucleotides in Table 4

| siRNA | Expected Mass (amu) | LC/MS (amu) |
|---|---|---|
| 1S | 6606.09 | 6606.67 |
| 1AS | 6693.06 | 6692.93 |
| 2S | 6610.91 | 6610.68 |
| 2AS | 6697.01 | 6696.782 |
| 3S | 6623.03 | 6622.76 |
| 3AS | 6709.13 | 6708.71 |
| 4S | 6639.09 | |
| 4AS | 6725.2 | 6724 |
| 5S | 6655.16 | |
| 5AS | 6741.26 | 6740.56 |
| 6S | 6638.96 | 6638.66 |
| 6AS | 6725.06 | 6724.67 |
| 7S | 6655.02 | 6654.57 |
| 7AS | 6741.13 | |
| 8S | 6671.09 | 6670.79 |
| 8AS | 6757.19 | 6756.84 |
| 9S | 7247.29 | 7246.67 |
| 9AS | 7333.4 | 7333.11 |
| 10S | 7263.36 | |
| 10AS | 7349.46 | |
| 11S | 7312.41 | 7313.06 |
| 11AS | 7398.51 | 7397 |

TABLE 5-continued

Mass data for olignucleotides in Table 4

| siRNA | Expected Mass (amu) | LC/MS (amu) |
|---|---|---|
| 12S | 7328.48 | 7329 |
| 12AS | 7414.58 | 7415.39 |

Example 12

In Vitro Activity and Cytotoxicity of Chemically Modified siRNAs

Synthetic siRNAs

Firefly luciferase targeting oligoribonucleotides (antisense 5'-UCGAAGUACUCUAGCGUAAGNN-3') (SEQ ID NO:53) were synthesized and characterized as described above. Twelve unique sense and twelve unique antisense strands were mixed in all possible combinations to yield 144 distinct siRNA duplexes. Sense and antisense strands were arrayed into 96-well PCR plates (VWR, West Chester, Pa.) in annealing buffer (100 mM KOAc, 30 mM HEPES, 2 mM MgOAc, pH 7.4) to give a final concentration of 10 µM duplex. Annealing was performed employing a thermal cycler (ABI PRISM 7000, Applied Biosystems, Foster City, Calif.) capable accommodating the PCR plates. The plates were held at 90° C. for one minute and 37° C. for one hour. Duplex formation was verified by native agarose gel electrophoresis of a random sample of the 144 sense and antisense combinations.

Cell Culture

HeLa SS6 cells were grown at 37° C. in Dulbecco's modified Eagle medium (DMEM) supplemented with 10% fetal bovine serum (FBS), 100 units/mL penicillin, and 100 g/mL streptomycin (Invitrogen, Carlsbad, Calif.). Cells were passaged regularly to maintain exponential growth. Twenty-four hours prior to siRNA transfection, cells were seeded on opaque, white 96-well plates (Costar, Corning, N.Y.) at a concentration of 15,000 cells/well in 150 µL antibiotic-free, phenol red-free DMEM (Invitrogen).

Dual Luciferase Gene Silencing Assays

In vitro activity of siRNAs was determined using a high-throughput 96-well plate format luciferase silencing assay. Cells were first transiently transfected with plasmids encoding firefly (target) and renilla (control) luciferase. DNA transfections were performed using Lipofectamine 2000 (Invitrogen) (0.5 µL/µg total DNA) and the plasmids gWiz-Luc (Aldevron, Fargo, N. Dak.) (200 ng/well) and pRL-CMV (Promega, Madison, Wis.) (200 ng/well). After 2 h, the plasmid transfection medium was removed, and the firefly luciferase targeting siRNAs were added to the cells at 100 nM concentration. siRNA transfections were performed using TransIT-TKO (Mirus, Madison, Wis.) (0.3 L/well). After 24 h, cells were analyzed for both firefly and *renilla* luciferase expression using a plate luminometer (VICTOR², PerkinElmer, Boston, Mass.) and the Dual-Glo Luciferase Assay kit (Promega). Firefly/*renilla* luciferase expression ratios were used to determine percent gene silencing relative to mock-treated (no siRNA) controls.

Cytotoxicity Assays

Cytotoxicity assays were performed in parallel with the gene silencing assays. These assays were carried out in the exact manner as the gene silencing assays (see above) with the exception that 24 h post siRNA tranfection, cells were analyzed for cytotoxicity instead of gene silencing. Relative cell viability was determined by quantification of cellular ATP content using the CellTiter-Glo Luminescent Cell Viability Assay kit (Promega).

Figure 15:
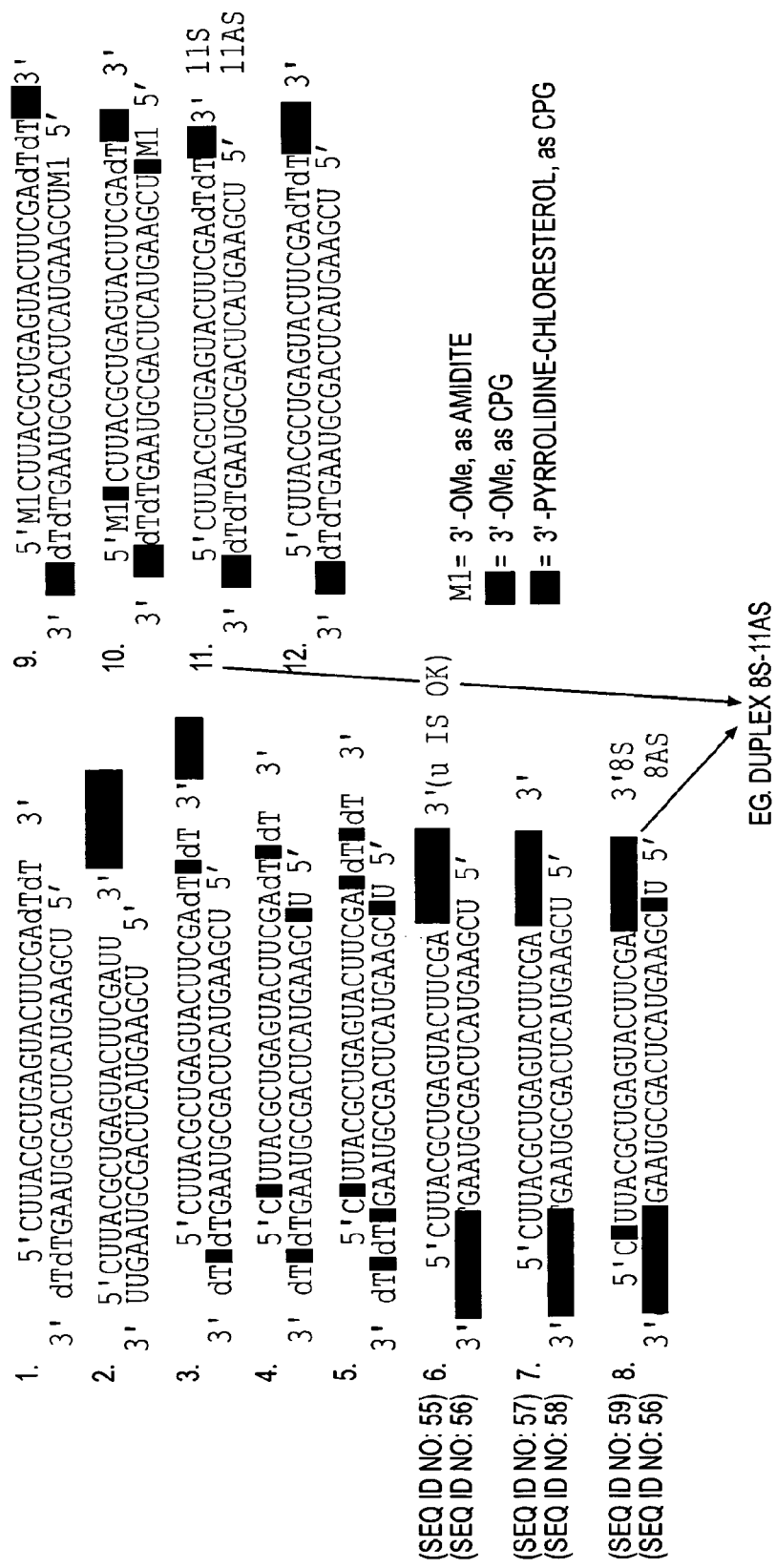
FIG. 15 is a list of control and candidate iRNA agents. SEQ ID NOs for the sense and antisense strands of the duplexes are as follows (sense strand/antisense strand): Duplex #1 (SEQ ID NO. 29/SEQ ID NO. 30), Duplex #2 (SEQ ID NO. 31/SEQ ID NO. 32), Duplex #3 (SEQ ID NO. 33/SEQ ID NO. 34), Duplex #4 (SEQ ID NO. 35/SEQ ID NO. 36), Duplex #5 (SEQ ID NO. 37/SEQ ID NO. 38), Duplex #6 (SEQ ID NO. 55/SEQ ID NO. 56), Duplex #7 (SEQ ID NO. 57/SEQ ID NO.

A control and candidate iRNA agents are delineated in FIG. 15.

Relative cell viability results and activity results are represented graphically in FIGS. 16 and 17, respectively. Essentially no activity was observed with duplexes with 12 AS; about 50% activity was observed with 9-11 AS; and full activity was observed with 1-8 AS.

Representative cholesterol-tethered RRMS monomers are shown in FIG. 18. An RRMS monomer having a linked solid support (bottom left) can be incorporated at the 3' end of an RNA, e.g., an iRNA agent. An RRMS monomer having an amidite (bottom left) can be incorporated at the 5' end or internal position of an RNA, e.g., an iRNA agent.

LCMS data for a 3' cholesterol conjugate after PAGE purification is shown in FIG. 19.

Example 13

To evaluate the cell permeation properties of cholesterol conjugated siRNAs 11 sense strand containing 3' cholesterol conjugate was annealed with 1 antisense strand and applied to the cell culture without any transfection agent. The 1S-1AS duplex was used as an unmodified control. Luciferase expression was silenced by the 11S-1AS duplex with a dose response without the transfection agent, while the unmodified duplex 1S-1AS did not show any gene silencing (see FIG. 20).

Example 14

5' CHOLESTEROL-CUUACGCUGAGUACUUCGAdTdT-3' (SEQ ID NO: 54)

Compound 14-a (described e.g., at page 67)was used to synthesize siRNA conjugates where cholesterol was conjugated at the 5' end of RNA molecules.

The phosphoramidite 14-a was dissolved in acetomitrile/ methylene chloride 1:1 solution to give a 0.2M solution. This was used for the terminal coupling during the oligonucleotide synthesis. For the PO-oxidation Iodine/Water/Pyridine was used and the PS-oxidation Beaucage reagent 0.5M solution in acetomitrile was used. The diamathoxy triotyl group was removed in the synthesizer and the purification and characterization were carried out as described in example 11.

Example 15

Additional Ligand-Conjugated Monomer Syntheses

Scheme and compound numbers refer to those recited in Example 15.

Synthesis of 4-hydroxy-L-prolinol Linker

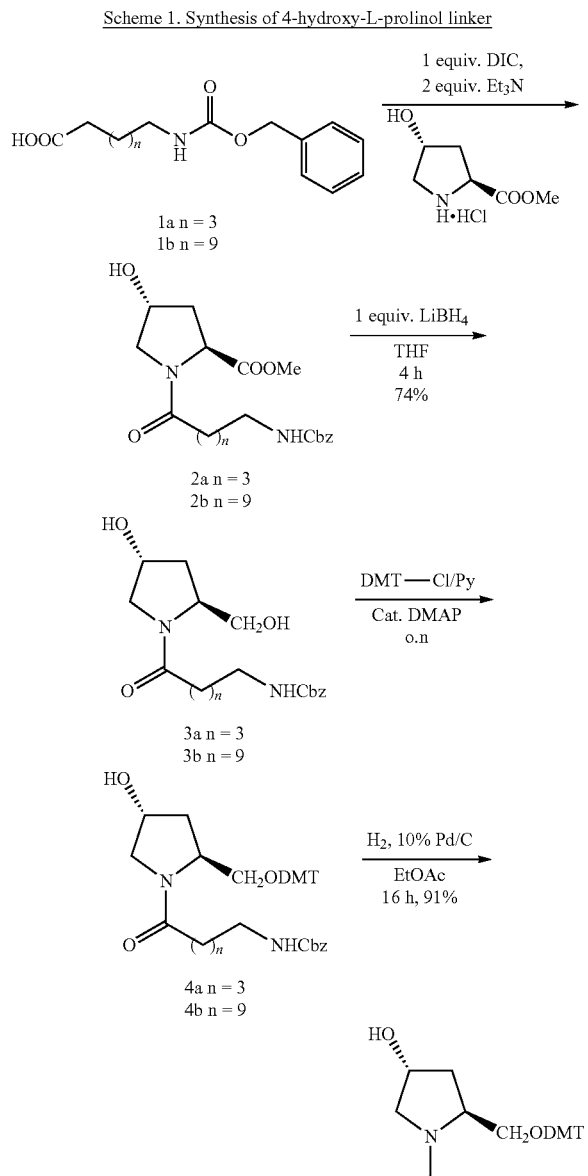

Scheme 1. Synthesis of 4-hydroxy-L-prolinol linker

1-(6-Benzyloxycarbonylamino-hexanoyl)-4-hydroxy-pyrrolidine-2-carboxylic acid methyl ester (2a)

Referring to scheme 1,6-benzyloxyamino hexanoic acid (13.25 g, 50 mmol) was dissolved in anhydrous dichloromethane (50 mL) and cooled to 0° C. To the solution were added diisopropyl carbodiimide (6.31 g, 7.7 mL, 50 mmol) and triethylamine (10.2 g, 13.7 mL, 100 mmol). After stirring for 20 mins at 0° C., 4-hydroxy-L-proline methyl ester hydrochloride (9.6 g, 50 mmol) was added and the stirring was continued at room temperature under argon for over night. The reaction mixture was evaporated to dryness. To the residue ethyl acetate (100 mL) was added and the filtered to remove diisopropyl urea. The precipitate was washed with ethyl acetate (50 mL). The combined organic layer was washed with 2N HCl, saturated sodium bicarbonate and water. The organic layer was dried over sodium sulfate, filtered and evaporated to dryness. Compound 2a ($R_f$=0.6 in 10% MeOH/CHCl$_3$, 22 g) was obtained, which was directly used for the next step without further purification.

[6-(4-Hydroxy-2-hydroxymethyl-pyrrolidin-1-yl)-6-oxo-hexyl]-carbamic acid benzyl ester (3a)

To the solution of lithium borohydride (1.34 g) in anhydrous tetrahydrofuran (50 mL) was added a solution of methyl ester 2a in THF (50 mL) over a period of 30 mins at 0° C. After the addition the reaction mixture was brought to room temperature and stirred further under argon. The completion of the reaction was ascertained by TLC after 4 h. ($R_f$=0.4 in 10% MeOH/CHCl$_3$). The reaction mixture was evaporated to dryness and cooled to 0° C. To the residue 3N HCl (100 mL) was added slowly. After stirring for 30 mins the product was extracted with dichloromethane (3×100 mL). The combined organic layer was washed with brine and dried over sodium sulfate. Organic layer was filtered and evaporated to dryness. Compound 3a was purified by column chromatography first by eluting with ethyl acetate to remove impurities followed by dichloromethane/methanol (5%) gave 14.3 g (70%)

$^1$H NMR (400 MHz, DMSO-d$_6$): Observed rotamers due to amide bond at the ring. δ 7.35 (m, 5H), 5.0 (s, 2H), 4.92 (d, OH, D$_2$O exchangeable, 4.78 (t, OH, D$_2$O exchangeable) 4.28 (m, 1H), 3.95 (m, 1H), 3.2-3.48 (m, 5H), 2.92-3.0 (m, 2H), 2.1-2.3 (m, 2H), 1.7-2.0 (2H), 1.34-1.52 (m, 4H), 1.2-1.3 (m, 2H).

$^{13}$C NMR (100 MHz, DMSO-d$_6$): δ171.3, 171.1 (minor due to rotamer which disappears while performing at 80° C.), 156.1, 137.3, 128.3, 127.7, 68.2, 65.1, 61.9, 57.5, 55.1, 36.1, 34.2, 29.3, 26.1, 25.9, 24.6, 24.1, 20.77, 14.09.

(6-{2-[Bis-(4-methoxy-phenyl)-phenyl-methoxymethyl]-4-hydroxy-pyrrolidin-1-yl}-6-oxo-hexyl)-carbamic acid benzyl ester (4a)

Referring to scheme 1, compound 3a (14 g, 38.4 mmol) was co-evaporated with anhydrous pyridine three times and then dissolved in pyridine (60 mL). To this solution dimethylamino pyridine (0.488 g, 4 mmol) and DMT-Cl (13.6 g, 40.3 mmol, 1.05 equiv.) were added at room temperature. The reaction mixture was stirred at room temperature for 16 h. The excess DMT-Cl was quenched by the addition of methanol (25 mL). The solution was dried under reduced pressure. To the residue was suspended in ethyl acetate (300 mL) and washed with saturated bicarbonate solution, brine and water. The organic layer was dried over anhydrous sodium sulfate, filtered and evaporated. 24.2 g of the crude product was obtained after removal of the solvent. Upon purification over silica gel using 2% MeOH/DCM compound 4a (21.3 g, 83%) was obtained as white foamy solid.

$^1$H NMR (400 MHz, DMSO-d$_6$): δ 7.18-7.38 (m, 14H), 6.2-6.5 (m, 4H), 5.0 (s, 2H), 4.9 (d, —OH, D$_2$O exchangeable), 4.4 (m, 1H), 4.15 (m, 1H), 3.7 (s, 6H), 3.56 (m, 1H), 3.32 (m, 1H), 3.14 (m, 1H), 2.9-3.0 (m, 4H), 2.18 (m, 2H), 1.8-2.1 (m, 2H), 1.1-1.5 (m, 6H).

$^{13}$C NMR (100 MHz, CDCl$_3$): δ 174.7, 172.7, 171.9, 171.3, 171.2, 158.8, 158.7, 158.6, 158.5, 158.4, 158.3, 156.7, 156.7, 156.6, 147.5, 145.8, 145.2, 144.9, 144.7, 144.4, 139.6, 137.1, 137.04, 137.01, 136.9, 136.82, 136.78, 136.55, 136.47, 136.45, 136.3, 136.28, 135.93, 135.85, 135.81, 130.2, 130.1, 130.0, 129.9, 129.3, 128.69, 128.66, 128.22, 128.16, 128.0, 127.99, 127.94, 127.91, 127.77, 113.52, 113.43, 113.35, 113.3, 113.24, 113.19, 113.03, 86.8, 86.1, 85.9, 73.0, 71.6, 71.5, 70.5, 69.3, 67.3, 67.1, 68.76, 68.71, 64.38, 63.7, 60.58, 60.0, 56.4, 55.8, 55.7, 55.45, 55.41, 55.35, 55.33, 40.97, 40.87, 40.77, 37.13, 36.83, 35.13, 35.00, 34.81, 34.6, 33.3, 29.8, 26.73, 25.5, 26.4, 26.2, 24.9, 24.6, 24.5, 24.3, 24.2, 21.1, 14.3.

6-Amino-1-{2-[bis-(4-methoxy-phenyl)-phenyl-methoxymethyl]-4-hydroxy-pyrrolidin-1-yl}-hexan-1-one (5)

Compound 4a (14.5 g, 21.7 mmol) was dissolved in ethyl acetate (100 mL) and purged with argon. To the solution was added 10% palladium on carbon (2 g). The flask was purged with hydrogen 2 times and stirred further at room temperature under hydrogen atmosphere for overnight. The disappearance of the starting material was confirmed by the TLC. The reaction mixture was filtered through a pad of Celite and washed with ethyl acetate. The combined organic layer was concentrated under reduced pressure to afford compound 5 (10.56 g, 91%) as white solid. This was used as such for the next step.

$^1$H NMR (400 MHz, DMSO-d$_6$): δ 7.16-7.32 (m, 9H), 6.86 (m, 4H), 5.0 (bs, 1H), 4.4 (m, 1H), 3.9-4.25 (m, 2H), 3.72 (s, 6H), 3.56 (m, 1H), 3.32 (m, 1H), 3.14 (m, 1H), 2.98-3.0 (m, 2H), 2.45 (m, 2H), 2.2 (m, 2H), 1.8-2.04 (m, 3H), 1.1-1.45 (m, 4H).

$^{13}$C NMR (100 MHz, DMSO-d$_6$): δ 17.9, 157.9, 145.1, 144.76, 135.8 135.7, 129.5, 127.8, 127.7, 127.5, 126.5, 113.2, 113.1, 85.7, 85.0, 68.5, 67.4, 63.3, 54.9, 41.6, 36.2, 34.2, 33.3, 32.5, 26.2, 24.7, 24.4.

Compound 4b

The desired compound 4b is obtained from N$^{Cbz}$-12-aminododecanoic acid (1b) and trans-4-hydroxyproline methyl ester hydrochloride in three steps as described for the synthesis of compound 4a from compound 1a.

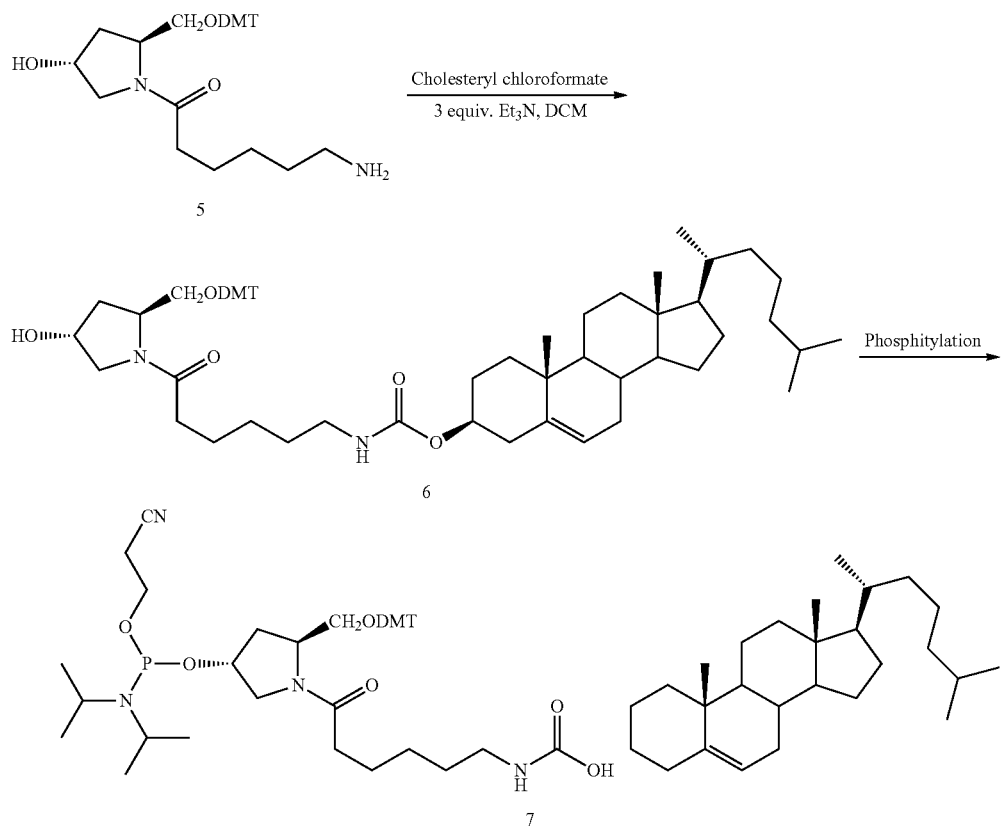

Scheme 2. Synthesis of 4-hydroxy-L-prolinol cholesterol-phosphoramidite

Synthesis of 4-hydroxy-L-prolinol cholesterol phosphoramidite (6-{2-[Bis-(4-methoxy-phenyl)-phenyl-methoxymethyl]-4-hydroxy-pyrrolidin-1-yl}-6-oxo-hexyl)-carbamic acid 10,13-dimethyl-17-octyl-2,3,4,7,8,9,10,11,12,13,14,15,16,17-tetradecahydro-1H-cyclopenta[a]phenanthren-3-yl ester (6)

Referring to scheme 2, compound 5 (13.3 g, 25 mmol) was dissolved in anhydrous dichloromethane (100 mL) and cooled to 0° C. To the solution were added triethylamine (7.5 g, 10 mL, 75 mmol) and cholesteryl chloroformate (11.24 g, 25 mmol) successively. The reaction temperature was brought to ambient temperature and stirred further for 2 h. The completion of the reaction was ascertained by TLC (10% MeOH/CHCl$_3$). The reaction mixture was evaporated under the vacuum to afford the crude product. Compound 6 (22.1 g, 93%) was obtained as a white foamy solid after column chromatography over silica gel.

$^1$H NMR (400 MHz, DMSO-d$_6$): δ 7.12-7.3 (m, 8H), 6.95 (m, 1H), 6.84 (m, 4H), 5.3 (bs, 1H), 4.92 and 4.84 (d, OH, exchangeable with D$_2$O), 4.21-4.38 (m, 2H), 4.35 (m, 1H), 3.7 (s, 6H), 3.54 (m, 1H), 3.28 (m, 2H), 3.12 (m, 1H), 2.84-2.98 (m, 3H), 2.12-2.28 (m, 3H), 1.7-2.0 (m, 7H), 0.8-1.52 (m, 40H), 0.6 (s, 3H).

$^{13}$C NMR (100 MHz, DMSO-d$_6$): δ 170.8, 158.0, 157.9, 155.6, 145.0, 139.7, 135.8, 135.7, 129.5, 127.7, 127.5, 121.7, 113.1, 113.0, 85.7, 85.1, 72.7, 68.5, 63.3, 56.1, 55.5, 54.9, 49.4, 41.8, 36.5, 35.2, 31.3, 27.7, 27.3, 26.0, 24.1, 23.8, 23.2, 22.6, 22.3, 20.5, 18.9, 18.5, 11.6.

4-Hydroxy-L-prolinol-cholesterol-phosphoramidite (2)

Compound 6 (4.0 g, 4.23 mmol) was coevaporated with anhydrous toluene (25 mL). To the residue N,N-tetraisopropylammonium tetrazolide (0.238 g, 2.1 mmol) was added and the mixture was dried over P$_2$O$_5$ in a vacuum oven for overnight at 40° C. The reaction mixture was dissolved in dichloromethane (25 mL) and 2-cyanoethyl-N,N,N',N'-tetraisopropylphosphorodiamidite (1.9 g, 2.1 mL, 6.3 mmol) was added. The reaction mixture was stirred at ambient temperature for overnight. The completion of the reaction was ascertained by TLC (R$_f$=0.5 in 1:1 ethyl acetate:hexane). The reaction mixture was diluted with dichloromethane (50 mL) and washed with 5% NaHCO$_3$ (50 mL) and brine (50 mL). The organic layer was dried over anhydrous Na$_2$SO$_4$ filtered and concentrated under reduced pressure. The residue was purified over silica gel (50:49:1, EtOAc:Hexane:triethlyamine) to afford 7 as white foam (4.35 g, 89%).

$^1$H NMR (400 MHz, CDCl$_3$): δ 7.14-7.38 (m, 9H), 6.8 (m, 4H), 5.36 (bs, 1H), 4.34-4.7 (m, 4H), 3.4-3.82 (m, 13H), 3.15 (m, 3H), 2.58 (m, 2H), 1.8-2.38 (m, 12H), 0.84-1.68 (m, 49H), 0.76 (s, 3H).

$^{31}$P NMR (161.82 MHz, CDCl$_3$): δ 145.9, 145.7, 145.4, 145.0 (1:2 ratio, 4 peaks due to rotamers).

$^{13}$C NMR (100 MHz, CDCl$_3$): δ 171.8, 158.7, 158.5, 156.3, 145.3, 144.7, 140.1, 136.4, 136.36, 136.32, 135.8, 130.1, 129.2, 128.4, 128.27, 128.21, 128.13, 127.9, 127.1, 126.9, 125.5, 122.6, 111.8, 117.7, 113.4, 113.2, 86.16, 86.1, 74.3, 72.3, 58.5, 58.3, 58.1, 56.8, 56.3, 55.9, 55.8, 55.4, 55.3, 52.2, 43.4, 43.3, 42.5, 40.8, 39.9, 39.7, 38.7, 37.2, 36.7, 36.3, 36.0, 35.0, 32.1, 32.0, 30.0, 28.45, 28.4, 28.2, 26.8, 24.8, 24.7, 24.69, 24.6, 24.5, 24.0, 23.0, 22.7, 21.6, 21.2, 20.6, 20.59, 20.52, 19.5, 18.9, 12.0

Synthesis of Solid Support with Immobilized Cholesterol

Scheme 3. Synthesis of solid support with immobilized cholesterol

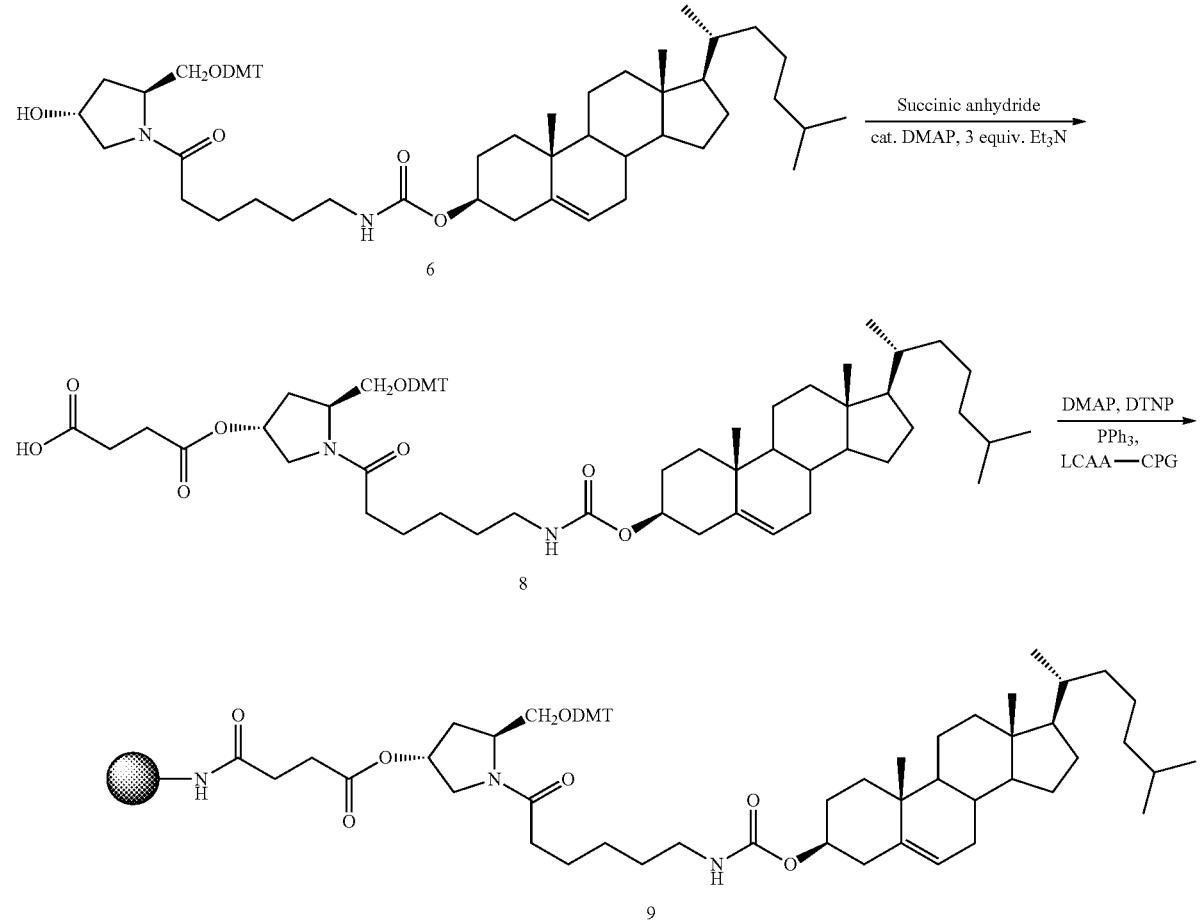

Succinic acid mono-{5-[bis-(4-methoxy-phenyl)-phenyl-methoxymethyl]-1-[6-(10,13-dimethyl-17-octyl-2,3,4,7,8,9,10,11,12,13,14,15,16,17-tetradecahydro-1H-cyclopenta[a]phenanthren-3-yloxycarbonylamino)-hexanoyl]-pyrrolidin-3-yl}ester (8)

Referring to scheme 3, Compound 6 (22 g, 23.2 mmol) was mixed with succinic anhydride (3.48 g, 34.8 mmol) and DMAP (0.283 g, 2.32 mmol) and dried in a vacuum at 40° C. overnight. The mixture was dissolved in anhydrous dichloromethane (50 mL), triethylamine (7 g, 9.6 mL, 70 mmol) was added and the solution was stirred at room temperature under argon atmosphere for 16 h. It was then diluted with dichloromethane (100 mL) and washed with ice cold aqueous citric acid (5% wt., 100 mL) and water (2×100 mL). The organic phase was dried over anhydrous sodium sulfate and concentrated to dryness. The crude product was purified by column chromatography to afford compound 8 as white solid (21.7 g, 89% yield; $R_f$=0.5 in 10% MeOH/CHCl$_3$).

$^1$H NMR (400 MHz, CDCl$_3$): δ 7.32-7.36 (m, 2H), 7.2-7.28 (m, 7H), 6.76-6.8 (m, 4H), 5.4 (bs, 1H), 4.46 (m, 2H), 3.78 (s, 6H), 3.42 (m, 1H), 3-3.18 (m, 3H), 2.5-2.6 (m, 3H), 2.12-2.38 (m, 6H), 1.78-2.02 (m, 7H), 0.8-1.6 (m, 42H), 0.66 (s, 3H)

$^{13}$C NMR (100 MHz, CDCl$_3$): δ 176.59, 172.22, 158.78, 158.62, 145.16, 139.8, 136.39, 136.22, 130.18, 130.14, 128.23, 128.0, 126.97, 122.91, 113.28, 56.88, 56.32, 55.45, 55.4, 50.19, 45.47, 42.51, 39.93, 39.72, 38.67, 37.14, 36.74, 36.38, 36.0, 32.1, 32.06, 28.44, 28.22, 24.5, 24.0, 23.04, 22.77, 21.24, 19.55, 18.92, 12.07, 8.72

Solid Support Immobilized with Cholesterol (9)

Succinate 8 (10.45 g, 10 mmol) was dissolved in dichloroethane (50 mL). To that solution DMAP (1.22 g, 10 mmol) was added. 2,2'-Dithio-bis(5-nitropyridine) (3.1 g, 10 mmol) in acetonitrile/dichloroethane (3:1, 50 mL) was added successively. To the resulting solution triphenylphosphine (2.63 g, 10 mmol) in acetonitrile (25 ml) was added. The reaction mixture turned bright orange in color. The solution was agitated briefly using wrist-action shaker (5 mins). Long chain alkyl amine-CPG (LCAA-CPG) (70 g, 155 μm/g) was added. The suspension was agitated for 16 h. The CPG was filtered through a sintered funnel and washed with acetonitrile, dichloromethane and ether successively. Unreacted amino groups were masked using acetic anhydride/pyridine. The loading capacity of the CPG was measured by taking UV measurement. (62 μM/g).

Scheme 4. Synthesis of 4-hydroxy-L-prolinol-rac-dioctadecy glyceryl amidite

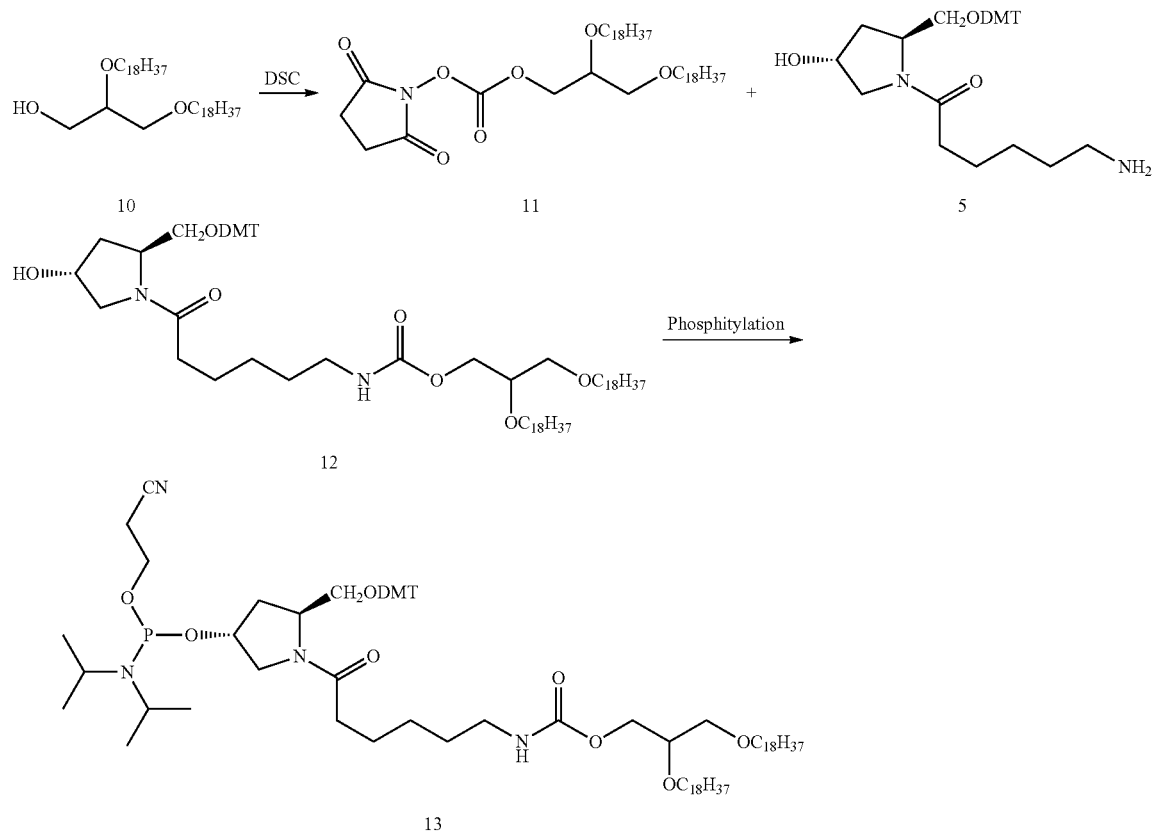

Synthesis of 4-hydroxy-L-prolinol-rac-dioctadecy glyceryl amidite 1,2-Di-O-octadecyl-rac-glycerol succinimidyl carbamate (11)

Referring to scheme 4, 1,2-Di-O-octadecyl-rac-glycerol (10 g, 16.74 mmol) was dissolved in anhydrous dichloromethane (150 mL). To the solution were added disuccinimidyl carbonate (6.4 g, 25.1 mmol), triethylamine (10 mL) and acetonitrile (50 mL). The reaction mixture was stirred at room temperature under argon for 6 h and then evaporated

(6-{2-[Bis-(4-methoxy-phenyl)-phenyl-methoxymethyl]-4-hydroxy-pyrrolidin-1-yl}-6-oxo-hexyl)-carbamic acid 2,3-bis-octadecyloxy-propyl ester (12)

Amine 5 (10.5 g, 19.7 mmol) was dissolved in anhydrous dichloromethane (50 mL) and cooled to 0° C. To the solution were added pyridine (10 mL) and compound 11 (12.5 g, 17.3 mmol) successively. The reaction temperature was brought to ambient temperature and stirred further for 3 h. The completion of the reaction was ascertained by TLC (10% MeOH/ CHCl₃). The reaction mixture was diluted with dichloromethane and washed with saturated NaHCO₃, water followed by brine. The organic layer was dried over sodium sulfate, filtered and concentrated under vacuum to afford the crude product. Compound 12 (17.8 g, 89%) was obtained as a white solid after column chromatography over silica gel.

$^1$H NMR (400 MHz, DMSO-$d_6$): δ 7.2-7.38 (m, 9H), 6.76 (m, 4H), 5.4 (s, 3H), 4.0 (m, 2H), 3.25 (s, 6H), 2.96 (m, 2H), 2.0 (m, 3H), 3-3.18 (m, 3H), 2.5-2.6 (m, 3H), 2.12-2.38 (m, 6H), 1.78-2.02 (m, 7H), 1.2-1.6 (m, 76H), 0.8 (m, 3H)

$^{13}$C NMR (100 MHz, DMSO-$d_6$): δ 171.89, 171.38, 158.74, 158.56, 156.70, 156.6, 145.28, 144.77, 136.49, 136.33, 135.89, 135.8, 130.19, 130.15, 128.25, 128.20, 128.09, 127.94, 127.13, 126.90, 113.37, 113.21, 86.68, 86.05, 71.98, 70.8, 70.69, 70.61, 69.40, 65.6, 64.38, 63.8, 60.61, 40.93, 38.48, 36.97, 35.0, 33.3, 32.13, 31.21, 29.9, 29.86, 29.72, 29.56, 26.59, 26.30, 26.24, 24.66, 22.89, 21.26, 14.39, 14.33

4-Hydroxy-L-prolinol-rac-dioctadecy glyceryl amidite (13)

Compound 12 (10.0 g, 8.65 mmol) was coevaporated with anhydrous toluene (50 mL). To the residue N,N-tetraisopropylammonium tetrazolide (0.488 g, 4.32 mmol) was added and the mixture was dried over $P_2O_5$ in a vacuum oven for overnight at 40° C. The reaction mixture was dissolved in dichloromethane (50 mL) and 2-cyanoethyl-N,N,N',N'-tetraisopropylphosphorodiamidite (3.91 g, 4.28 mL, 13 mmol) was added. The reaction mixture was stirred at ambient temperature for overnight. The completion of the reaction was ascertained by TLC ($R_f$=0.6 in 1:1 ethyl acetate:hexane). The reaction mixture was diluted with dichloromethane (100 mL) and washed with 5% NaHCO₃ (100 mL) and brine (100 mL). The organic layer was dried over anhydrous Na₂SO₄ filtered and concentrated under reduced pressure. The residue was purified over silica gel (50:49:1, EtOAc:Hexane:triethylamine) to afford 13 as white solid (15.37 g, 93%).

$^1$H NMR (400 MHz, CDCl₃): δ 7.16-7.38 (m, 9H), 6.78 (m, 4H), 4.62-4.78 (m, 2H), 4.27 (m, 1H), 4.04-4.2 (m, 3H), 3.7-3.8 (m, 10H), 3.4-3.6 (m, 11H), 3.16 (m, 4H), 2.58-2.7 (m, 4H), 2.22 (m, 3H), 2.12 (m, 1H), 1.15-1.4 (m, 75H), 0.95 (m, 6H), $^{31}$P NMR (161.82 MHz, CDCl₃): δ 145.96, 145.76, 145.45, 145.07

$^{13}$C NMR (100 MHz, CDCl₃): δ 171.79, 171.61, 158.75, 158.58, 156.59, 145.31, 144.77, 136.47, 136.35, 136.31, 135.86, 130.22, 130.19, 128.28, 128.20, 128.11, 127.95, 127.15, 126.91, 113.39, 113.24, 86.11, 71.98, 70.81, 70.69, 72.93, 72.2, 71.98, 70.81, 70.81, 70.69, 64.37, 63.92, 58.55, 58.35, 58.36, 58.16, 59.57, 55.86, 55.44, 55.39, 46.31, 44.70, 44.65, 43.36, 43.34, 41.08, 35.08, 33.45, 32.13, 30.23, 29.92, 29.88, 29.72, 29.58, 26.32, 26.26, 24.85, 24.78, 24.68, 22.9, 20.58, 14.34

Synthesis of Solid Support with Immobilized Rac-Dioctadecy Glycerol (15)

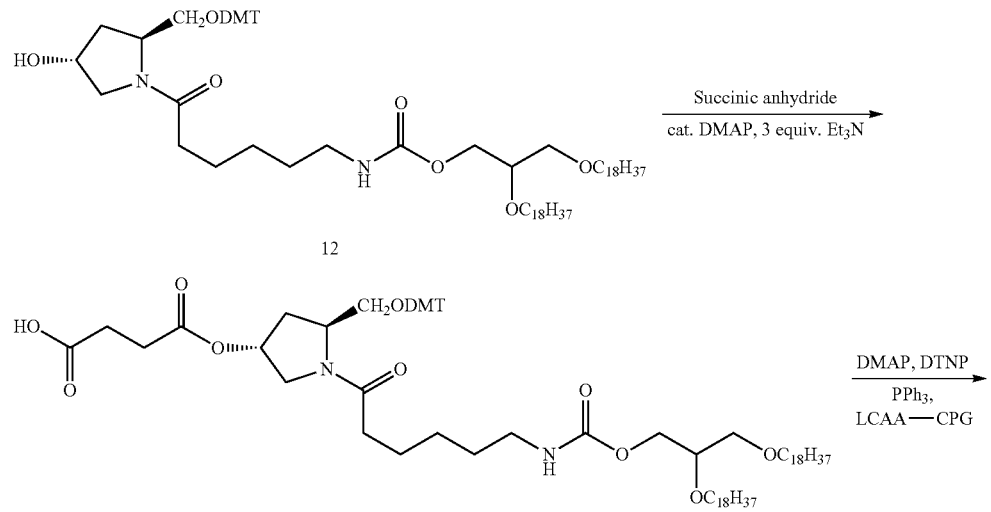

Scheme 5. Synthesis of solid support with immobilized rac-dioctadecy glycerol

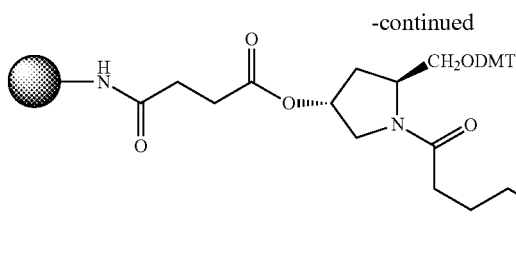

15

Succinic acid mono-{5-[bis-(4-methoxy-phenyl)-phenyl-methoxymethyl]-1-[6-(2,3-bis-octadecyloxy-propoxycarbonylamino)-hexanoyl]-pyrrolidin-3-yl}ester (14)

Referring to scheme 5, Compound 12 (5.6 g, 4.8 mmol) was mixed with succinic anhydride (0.727 g, 7.26 mmol) and DMAP (0.062 g, 0.5 mmol) and dried in a vacuum at 40° C. overnight. The mixture was dissolved in anhydrous dichloromethane (20 mL), triethylamine (1.52 g, 2 mL, 15 mmol) was added and the solution was stirred at room temperature under argon atmosphere for 16 h. It was then diluted with dichloromethane (50 mL) and washed with ice cold aqueous citric acid (5% wt., 50 mL) and water (2×50 mL). The organic phase was dried over anhydrous sodium sulfate and concentrated to dryness. The crude product was purified by column chromatography to afford compound 14 as white solid (2.85 g, 47% yield; $R_f$=0.65 in 10% MeOH/CHCl$_3$).

$^1$H NMR (400 MHz, DMSO-d$_6$): δ 12.2 (bs, 1H), 7.18-7.4 (m, 9H), 6.82 (m, 4H), 4.62-4.78 (m, 2H), 4.27 (m, 1H), 4.04-4.2 (m, 3H), 3.7-3.8 (m, 10H), 3.4-3.6 (m, 11H), 3.16 (m, 4H), 2.58-2.7 (m, 4H), 2.22 (m, 3H), 2.12 (m, 1H), 1.15-1.4 (m, 75H), 0.95 (m, 6H), $^{13}$C NMR (100 MHz, DMSO-d$_6$): δ 178.26, 174.23, 171.79, 171.61, 158.75, 158.58, 156.59, 145.31, 144.77, 136.47, 136.35, 136.31, 135.86, 130.22, 130.19, 128.28, 128.20, 128.11, 127.95, 127.15, 126.91, 113.39, 113.24, 86.11, 71.98, 70.81, 70.69, 72.93, 72.2, 71.98, 70.81, 70.81, 70.69, 64.37, 63.92, 58.55, 58.35, 58.36, 58.16, 59.57, 55.86, 55.44, 55.39, 46.31, 44.70, 44.65, 43.36, 43.34, 41.08, 35.08, 33.45, 32.13, 30.23, 29.92, 29.88, 29.72, 29.58, 28.41, 26.32, 26.26, 24.85, 24.78, 24.68, 22.9, 20.58, 14.34.

Solid Support with Immobilized Rac-Dioctadecy Glycerol (15)

Succinate 14 (2 g, 1.6 mmol) was dissolved in dichloroethane (8 mL). To that solution DMAP (0.194 g, 1.6 mmol) was added. 2,2'-Dithio-bis(5-nitropyridine) (0.496 g, 1.6 mmol) in acetonitrile/dichloroethane (3:1, 8 mL) was added successively. To the resulting solution triphenylphosphine (0.419 g, 1.6 mmol) in acetonitrile (4 ml) was added. The reaction mixture turned bright orange in color. The solution was agitated briefly using wrist-action shaker (5 mins). Long chain alkyl amine-CPG (LCAA-CPG) (5.16 g, 800 μmoles, 1551 m/g) was added. The suspension was agitated for 4 h. The CPG was filtered through a sintered funnel and washed with acetonitrile, dichloromethane and ether successively. Unreacted amino groups were masked using acetic anhydride/pyridine. The loading capacity of the CPG was measured by taking UV measurement. (76 μM/g).

Synthesis of 4-hydroxy-L-prolinol-vitamin E amidite

Scheme 6: Synthesis of hydroxy-prolinol-dialkyl Vit E phosphoramidite

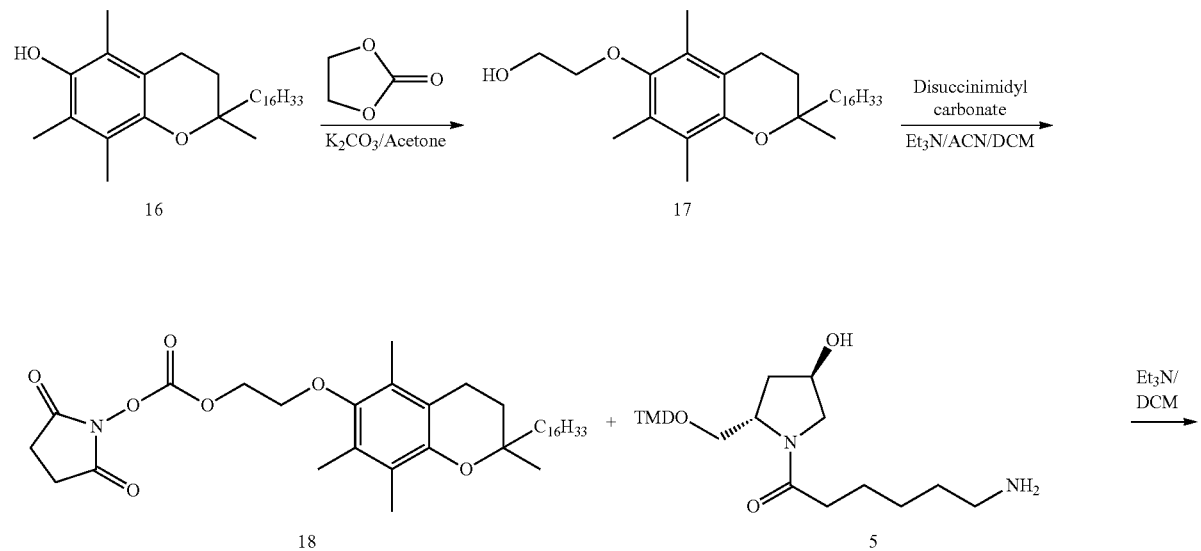

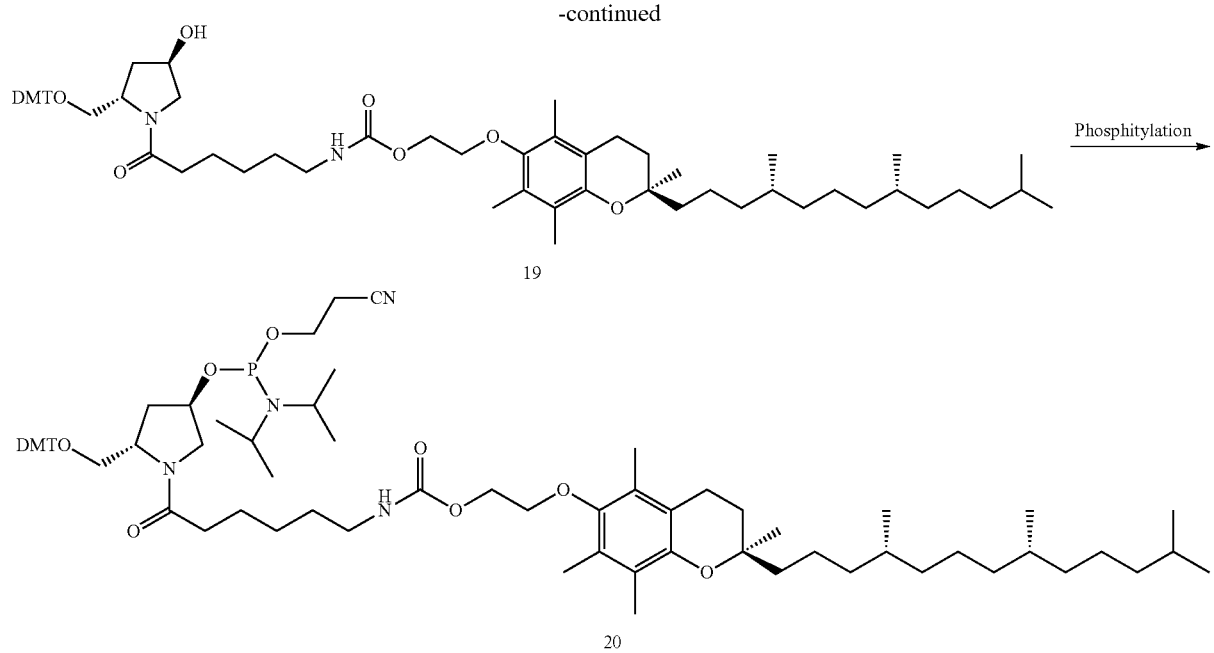

2-(2-Hexadecyl-2,5,7,8-tetramethyl-chroman-6-yloxy)-ethanol (17)

Referring to scheme 6, vitamin E (16.0 g, 37 mmol) was dissolved in acetone (100 mL). Potassium carbonate (25.5 g, 185 mmol), ethylene carbonate (6.5 g, 75 mmol) were added to the solution. The suspension was stirred at reflux temperature for over night. Even though the reaction did not go to completion, the reaction mixture was concentrated in the vacuum, and the residue was taken in ethyl acetate and washed with water. The organic layer was dried over sodium sulfate, filtered and evaporated. The crude product was purified by column chromatography using hexane/ethyl acetate to afford compound 17 in 65% yield (11.5 g, $R_f$=0.8 in 25% EtOAc/Hexane).

$^1$H NMR (400 MHz, CDCl$_3$): δ 4.13 (m, 2H), 3.98 (m, 2H), 2.6 (t, 2H), 2.15 (s, 3H), 2.1 (s, 6H), 1.7-1.8 (m, 2H), 1.1-1.5 (m, 14H), 0.8-0.88 (m, 12H)

$^{13}$C NMR (100 MHz, CDCl$_3$): δ 145.75, 144.74, 122.83, 121.2, 118.66, 117.58, 77.43, 74.74, 60.63, 40.08, 40.01, 39.59, 37.80, 37.79, 37.71, 37.67, 37.6, 37.55, 37.50, 33.01, 33.0, 32.91, 31.8, 31.57, 31.69, 28.20, 25.04, 25.02, 24.66, 24.01, 22.95, 22.85, 21.28, 20.98, 19.97, 19.9, 19.86, 19.81, 14.42, 14.35, 12.43, 12.0, 11.5

Carbonic acid 2,5-dioxo-pyrrolidin-1-yl ester 2-(2-hexadecyl-2,5,7,8-tetramethyl-chroman-6-yloxy)-ethyl ester (18)

Compound 17 (10.5 g, 22 mmol) was dissolved in anhydrous dichloromethane (150 mL). To the solution were added disuccinimidyl carbonate (8.45 g, 33 mmol), triethylamine (20 mL) and acetonitrile (50 mL). The reaction mixture was stirred at room temperature under argon for over night and then evaporated dryness. The residue was dissolved in dichloromethane (300 mL). It was washed with saturated NaHCO$_3$ aqueous solution (3×100 mL). The organic layer was dried over Na$_2$SO$_4$, filtered and evaporated to dryness. Compound 18 (10.4 g, 77%) was obtained as colorless powder after drying in high vacuum, which was directly used for the next step without further purification.

$^1$H NMR (400 MHz, CDCl$_3$): δ 7.2-7.4 (m, 4H), 3.1 (m, 1H), 2.7 (s, 4H), 2.58 (t, 2H), 2.08-2.14 (m, 9H), 1.7-1.82 (m, 2H), 1-1.6 (m, 23H), 0.8-0.88 (m, 12H)

$^{13}$C NMR (100 MHz, CDCl$_3$): δ 168.76, 168.66, 150.6, 150.37, 141.36, 138.09, 129.24, 128.44, 126.73, 125.51, 125.1, 123.74, 117.97, 77.72, 75.56, 39.58, 37.71, 37.65, 37.59, 37.48, 32.98, 32.88, 31.16, 31.11, 28.19, 25.83, 25.75, 25.7, 25.02, 25.01, 24.64, 24.07, 24.07, 22.93, 22.84, 21.67, 21.22, 20.73, 20.38, 19.96, 19.89, 19.86, 19.82, 12.77, 11.98, 11.94

(6-{2-[Bis-(4-methoxy-phenyl)-phenyl-methoxymethyl]-4-hydroxy-pyrrolidin-1-yl}-6-oxo-hexyl)-carbamic acid 2-(2-hexadecyl-2,5,7,8-tetramethyl-chroman-6-yloxy)-ethyl ester (19)

Amine 5 (8.7 g, 16.3 mmol) was dissolved in anhydrous dichloromethane (40 mL) and cooled to 0° C. To the solution were added triethylamine (5.06 g, 6.73 mL, 50 mmol) and compound 18 (10 g, 16.2 mmol) successively. The reaction temperature was brought to ambient temperature and stirred further for 6 h. The completion of the reaction was ascertained by TLC (10% MeOH/CHCl$_3$). The reaction mixture was diluted with dichloromethane and washed with saturated NaHCO$_3$, water followed by brine. The organic layer was dried over sodium sulfate, filtered and concentrated under vacuum to afford the crude product. Compound 19 (14.5 g, 88%) was obtained as a white foamy solid after column chromatography over silica gel.

$^1$H NMR (400 MHz, DMSO-d$_6$): δ 7.72 (m, 1H, —NH), 7.3 (m, 4H), 7.18 (m, 5H), 6.86 (m, 4H), 4.98 (s, —OH), 4.38 (m, 2H), 4.12 (m, 2H), 3.72 (s, 6H), 3.56 (m, 1H), 3.22-3.32 (m, 2H), 3.16 (m, 1H), 3.0 (m, 3H), 2.2 (m, 2H), 1.98 (m, 4H), 1-9 (m, 7H), 1.8 (m, 1H), 1.72 (m, 2H), 1-1.5 (m, 32H), 0.82 (m, 12H)

$^{13}$C NMR (100 MHz, DMSO-d$_6$): δ 171.20, 158.29, 158.16, 154.83, 148.31, 145.26, 140.65, 136.04, 135.90, 135.58, 129.78, 127.97, 127.75, 127.43, 126.79, 125.91, 121.58, 117.10, 113.28, 86.0, 85.32, 74.71, 68.71, 63.46, 55.13, 36.91, 36.8, 36.35, 32.25, 27.75, 26.06, 24.36, 23.91, 23.68, 22.68, 22.59, 19.75, 19.68, 12.74, 11.89, 11.64

4-Hydroxy-L-prolinol-vitamin E amidite (20)

Compound 19 (9.2 g, 9 mmol) was coevaporated with anhydrous toluene (50 mL). To the residue N,N-tetraisopropylammonium tetrazolide (0.51 g, 4.5 mmol) was added and the mixture was dried over $P_2O_5$ in a vacuum oven for overnight at 40° C. The reaction mixture was dissolved in dichloromethane (50 mL) and 2-cyanoethyl-N,N,N',N'-tetraisopropylphosphorodiamidite (4 g, 4.45 mL, 13.5 mmol) was added. The reaction mixture was stirred at ambient temperature for overnight. The completion of the reaction was ascertained by TLC ($R_f$=0.65 in 1:1 ethyl acetate:hexane). The reaction mixture was diluted with dichloromethane (100 mL) and washed with 5% $NaHCO_3$ (100 mL) and brine (100 mL). The organic layer was dried over anhydrous $Na_2SO_4$ filtered and concentrated under reduced pressure. The residue was purified over silica gel (50:49:1, EtOAc:Hexane:triethlyamine) to afford 20 as white foamy solid (10.5 g, 95%).

$^1$H NMR (400 MHz, $CDCl_3$): δ 7.38 (m, 2H), 7.18-7.28 (m, 7H), 6.82 (m, 4H), 5.18 (m, 1H), 4.65 (m, 2H), 4.38 (m, 2H), 4.1 (m, 1H), 3.7-3.8 (m, 9H), 3.58 (m, 3H), 3.4 (m, 1H), 3.28 (m, 2H), 3.18 (m, 2H), 2.58 (m, 4H), 2.26 (m, 3H), 2-2.1 (m, 10H), 1.5-1.8 (m, 10H), 1.05-1.3 (m, 32H), 0.84-0.88 (m, 14H).

$^{31}$P NMR (161.82 MHz, $CDCl_3$): δ 145.92, 145.78, 145.45, 145.04

$^{13}$C NMR (100 MHz, $CDCl_3$): δ 172.1, 171.82, 171.63, 158.74, 158.67, 155.17, 149.34, 145.31, 144.77, 140.58, 136.44, 136.34, 136.3, 135.85, 135.8, 130.18, 128.25, 128.19, 128.11, 127.95, 127.82, 127.13, 126.90, 126.0, 123.0, 117.87, 117.78, 117.42, 113.4, 113.29, 113.23, 86.77, 86.15, 86.10, 77.42, 75.15, 72.39, 72.21, 72.01, 63.92, 58.65, 58.53, 58.47, 58.35, 58.13, 56.49, 55.96, 55.85, 55.44, 55.37, 54.65, 43.44, 43.31, 41.22, 40.33, 39.55, 37.74, 37.64, 37.58, 37.47, 35.06, 33.44, 32.97, 32.9, 31.3, 30.1, 28.17, 26.7, 26.74, 26.68, 25.12, 24.99, 24.84, 24.77, 24.64, 24.57, 24.11, 22.92, 22.83, 21.23, 21.25, 20.76, 20.63, 20.56, 20.50, 19.95, 19.88, 19.84, 19.82, 19.78, 13.05, 12.20, 11.97.

Synthesis of Solid Support with Immobilized Vitamin E (22)

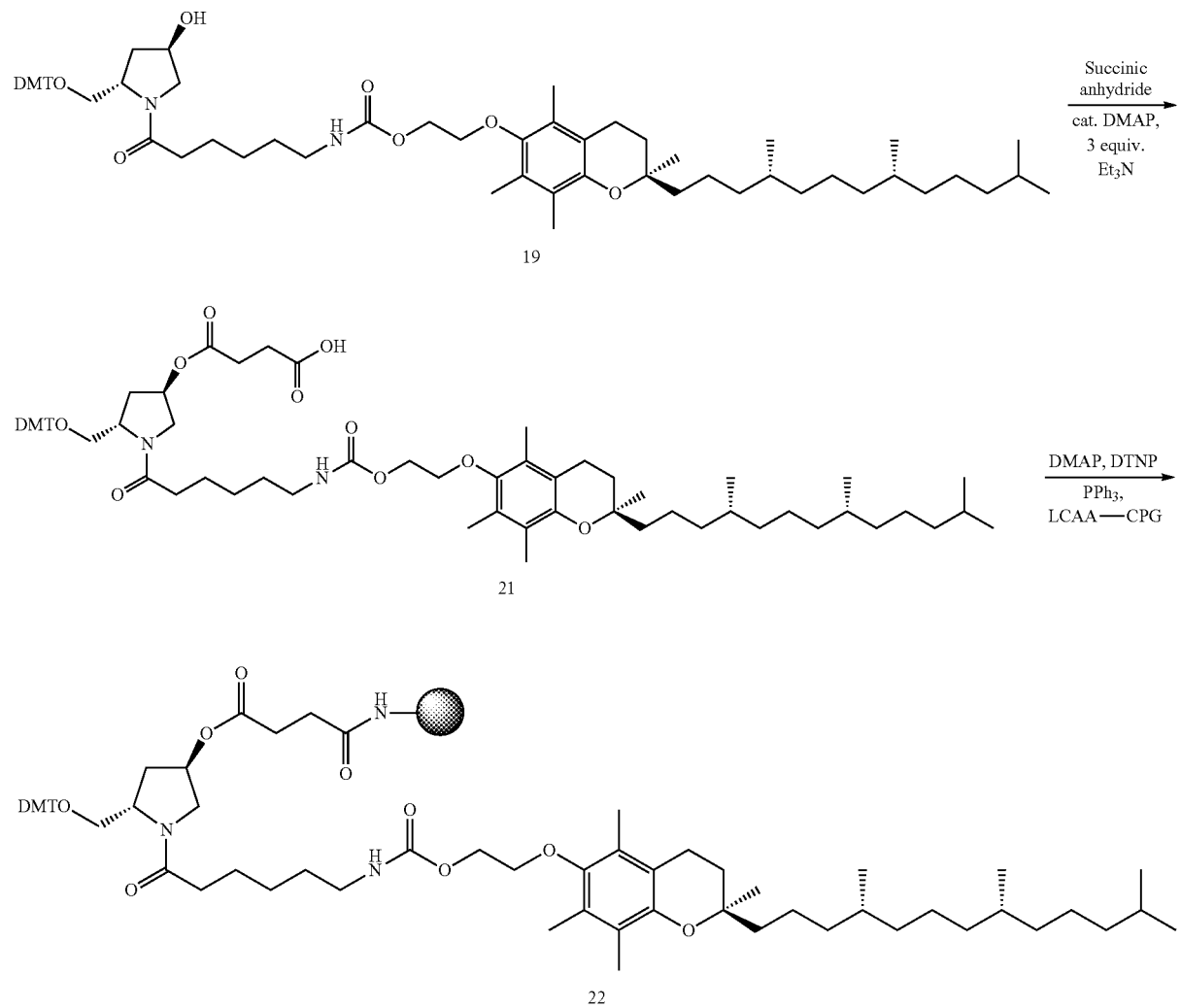

Succinic acid mono-(5-[bis-(4-methoxy-phenyl)-phenyl-methoxymethyl]-1-{6-[2-(2-hexadecyl-2,5,7,8-tetramethyl-chroman-6-yloxy)-ethoxycarbonylamino]-hexanoyl}-pyrrolidin-3-yl) ester (21)

Referring to scheme 7, Compound 19 (5.1 g, 5 mmol) was mixed with succinic anhydride (0.75 g, 7.5 mmol) and DMAP (0.062 g, 0.5 mmol) and dried in a vacuum at 40° C. overnight. The mixture was dissolved in anhydrous dichloromethane (25 mL), triethylamine (1.52 g, 2 mL, 15 mmol) was added and the solution was stirred at room temperature under argon atmosphere for 16 h. It was then diluted with dichloromethane (50 mL) and washed with ice cold aqueous citric acid (5% wt., 50 mL) and water (2×50 mL). The organic phase was dried over anhydrous sodium sulfate and concentrated to dryness. The crude product was purified by column chromatography to afford compound 21 as white foamy solid (2.85 g, 51% yield; $R_f$=0.65 in 10% MeOH/CHCl$_3$).

$^1$H NMR (400 MHz, DMSO-d$_6$): δ 12.3 (bs, 1H), 7.6 (m, 1H), 7.2-7.4 (m, 9H), 6.86 (m, 4H), 5.32 (m, 2H), 4.18 (m, 2H), 3.62-3.8 (s, 6H), 3.54 (m, 1H), 3.42 (m, 1H), 3.34 (s, 6H), 3.21 (m, 1H), 3.0 (m, 2H), 2.46 (m, 4H), 2.2 (m, 4H), 1.9 (m, 4H), 1.72 (m, 3H), 1-1.5 (m, 30H), 0.82 (m, 12H).

$^{13}$C NMR (100 MHz, DMSO-d$_6$): δ 173.61, 172.26, 171.17, 165.43, 159.77, 158.34, 158.22, 157.02, 154.88, 153.72, 148.68, 148.36, 145.17, 144.85, 143.74, 141.94, 140.63, 135.93, 129.83, 128.06, 127.77, 127.46, 125.97, 121.63, 117.25, 113.35, 85.50, 74.86, 73.08, 55.19, 36.88, 32.17, 28.97, 28.80, 27.58, 24.34, 23.85, 22.75, 22.66, 19.84, 19.78, 12.8, 11.94, 11.72.

Solid Support with Immobilized Vitamin E (22)

Succinate 21 (2.8 g, 2.5 mmol) was dissolved in dichloroethane (12 mL). To that solution DMAP (0.306 g, 2.5 mmol) was added. 2,2'-Dithio-bis(5-nitropyridine) (0.775 g, 2.5 mmol) in acetonitrile/dichloroethane (3:1, 12 mL) was added successively. To the resulting solution triphenylphosphine (0.656 g, 2.5 mmol) in acetonitrile (7 ml) was added. The reaction mixture turned bright orange in color. The solution was agitated briefly using wrist-action shaker (5 mins). Long chain alkyl amine-CPG (LCAA-CPG) (8.0 g, 1240 μmoles, 1551m/g) was added. The suspension was agitated for 2 h. The CPG was filtered through a sintered funnel and washed with acetonitrile, dichloromethane and ether successively. Unreacted amino groups were masked using acetic anhydride/pyridine. The loading capacity of the CPG 22 was measured by taking UV measurement. (76 μM/g).

Synthesis of 4-hydroxy-L-prolinol-thiocholesterol amidite (26)

Scheme 8. Synthesis of 4-hydroxy-L-prolinol-thiocholesterol phosphoramidite

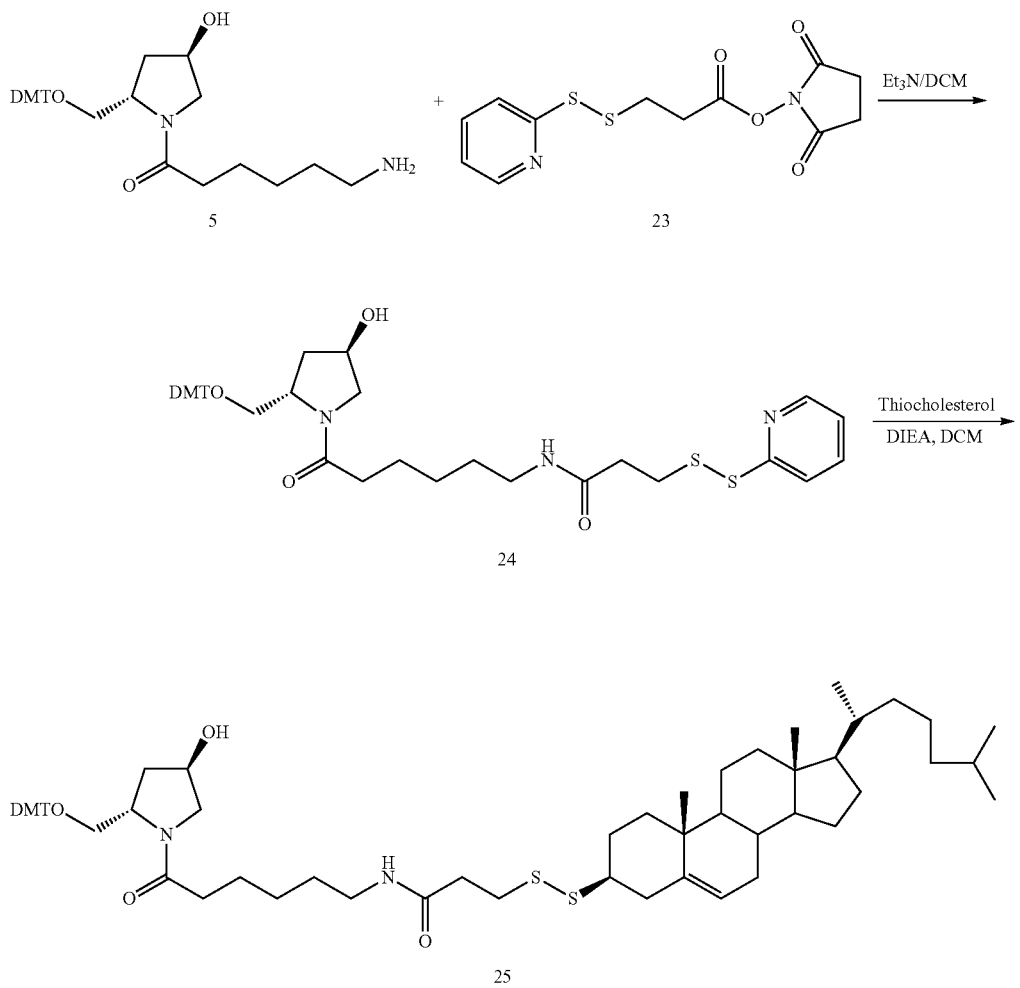

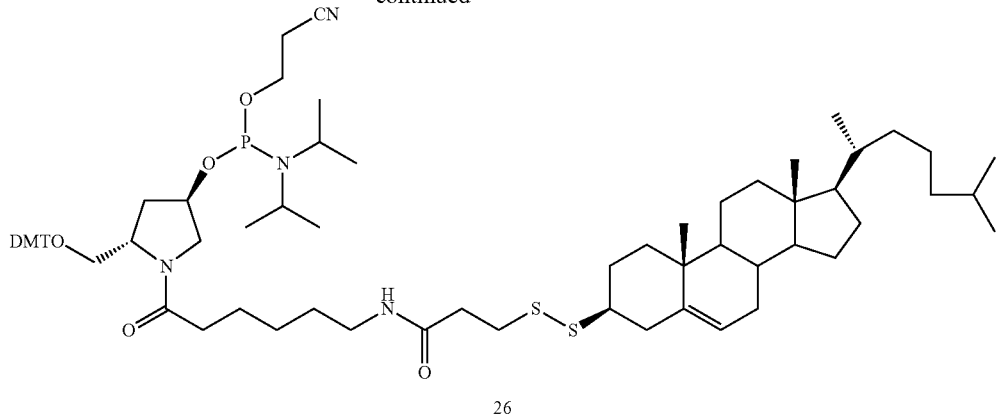

26

N-(6-{2-[Bis-(4-methoxy-phenyl)-phenyl-methoxymethyl]-4-hydroxy-pyrrolidin-1-yl}-6-oxo-hexyl)-3-(pyridin-2-yldisulfanyl)-propionamide (24)

Referring to scheme 8, amine 5 (7.7 g, 14.5 mmol) was dissolved in anhydrous dichloromethane (40 mL) and cooled to 0° C. To the solution were added triethylamine (3.0 g, 4.2 mL, 30 mmol) and 3-(Pyridin-2-yldisulfanyl)-propionic succinate ester 23 (SPDP) (4.5 g, 14.4 mmol) successively. The reaction temperature was brought to ambient temperature and stirred further for 16 h. The completion of the reaction was ascertained by TLC (10% MeOH/CHCl$_3$, R$_f$=0.6). The reaction mixture was diluted with dichloromethane and washed with saturated NaHCO$_3$, water followed by brine. The organic layer was dried over sodium sulfate, filtered and concentrated under vacuum to afford the crude product. Compound 24 (10.58 g, 78%) was obtained as a white foamy solid after column chromatography over silica gel.

$^1$H NMR (400 MHz, DMSO-d$_6$): δ 8.45 (d, 1H), 7.9 (m, 1H), 7.8 (m, 1H), 7.76 (m, 1H), 7.3 (m, 4H), 7.18 (m, 5H), 6.86 (m, 4H), 4.98 (d, —OH, 1H), 4.38 (m, 1H), 4.1 (m, 1H) (s, 6H), 3.56 (m, 1H), 3.46 (m, 1H), 3.21-3.34 (m, 3H), 3.14 (m, 1H), 3 (m, 2H), 2.48 (m, 2H), 2.2 (m, 2H), 1.8-2.02 (m, 2H), 1.1-1.5 (4H).

$^{13}$C NMR (100 MHz, DMSO-d$_6$): δ.171.32, 169.97, 159.36, 158.31, 158.18, 149.80, 145.27, 138.08, 136.1, 135.9, 129.8, 128.0, 127.7, 121.4, 119.3, 113.3, 85.338, 68.7, 55.3, 34.75, 34.28, 29.1, 26.3, 24.36.

4-Hydroxy-L-prolinol-thiocholesterol-DMT-alcohol 25

Compound 24 (7.5 g, 10.28 mmol) was dissolved in anhydrous dichloromethane (75 mL) under argon and cooled to 0° C. To this solution were added diisopropylethyl amine (2.71 g, 3.66 mL, 21 mmol) followed by thiocholesterol (4.145 g, 10.28 mmol). The reaction mixture was brought to ambient temperature and stirred further for 16 h. The completion of the reaction was ascertained by TLC (100% ethyl acetate, R$_f$=0.6). The reaction mixture was concentrated under reduced pressure and the residue was subjected to column chromatography on silica gel. Even though there was good separation in hexane/ethyl acetate system, compound precipitates in that mixture. After eluting with 4 L of ethyl acetate, the column was eluted with 5% MeOH/dichloromethane (2 L) to obtain compound 25 as white foamy solid (8 g, 76%).

$^1$H NMR (400 MHz, DMSO-d$_6$): δ 7.88 (m, 1H), 7.3 (m, 4H), 7.17 (m, 5H), 6.84 (m, 4H), 5.3 (bs, 1H), 4.89 (d, —OH), 4.38 (m, 1H), 4.1 (m, 1H), 3.72 (s, 6H), 3.56 (m, 1H), 3.32 (m, 1H), 3.14 (m, 1H), 3 (m, 3H), 2.84 (m, 2H), 2.64 (m, 1H), 2.42 (m, 2H), 2.2 (m, 3H), 1.8-2.0 (m, 7H), 0.8-1.54 (m, 35H), 0.62 (s, 3H).

$^{13}$C NMR (100 MHz, DMSO-d$_6$): δ 170.8, 158.0, 157.9, 155.6, 145.0, 139.7, 135.8, 135.7, 129.5, 127.7, 127.5, 121.7, 113.1, 113.0, 85.7, 85.1, 72.7, 68.5, 63.3, 60.72, 56.1, 55.5, 55.28, 54.9, 49.4, 41.8, 36.5, 35.2, 31.3, 30.35, 27.7, 27.3, 26.0, 24.1, 23.8, 23.2, 22.6, 22.3, 21.11, 20.5, 19.43, 18.9, 18.5, 14.4, 11.6.

4-Hydroxy-L-prolinol-thiocholesterol phosphoramidite (26)

Compound 25 (5.7 g, 5.58 mmol) was coevaporated with anhydrous toluene (50 mL). To the residue N,N-tetraisopropylammonium tetrazolide (0.315 g, 2.79 mmol) was added and the mixture was dried over P$_2$O$_5$ in a vacuum oven for overnight at 40° C. The reaction mixture was dissolved in dichloromethane (20 mL) and 2-cyanoethyl-N,N,N',N'-tetraisopropylphosphorodiamidite (2.48 g, 2.72 mL, 8.25 mmol) was added. The reaction mixture was stirred at ambient temperature for overnight. The completion of the reaction was ascertained by TLC (R$_f$=0.9 in ethyl acetate). The reaction mixture was diluted with dichloromethane (50 mL) and washed with 5% NaHCO$_3$ (50 mL) and brine (50 mL). The organic layer was dried over anhydrous Na$_2$SO$_4$ filtered and concentrated under reduced pressure. The residue was purified over silica gel (50:49:1, EtOAc:Hexane:triethlyamine) to afford 26 as white foamy solid (6.1 g, 89%).

$^1$H NMR (400 MHz, C$_6$D$_6$): δ 7.62 (m, 2H), 7.45 (m, 5H), 7.24 (m, 2H), 7.1 (m, 1H), 6.82 (m, 4H), 5.64 (m, 1H), 5.38 (m, 1H), 4.7 (m, 1H), 4.54 (m, 2H), 3.78 (m, 2H), 3.5 (m, 3H), 3.36 (m, 9H), 3.22 (m, 4H), 3.06 (m, 3H), 2.72 (m, 1H), 2.32-2.54 (m, 5H), 1.8-2.2 (m, 10H), 1.08-1.74 (m, 28H), 1.3 (m, 6H), 0.94 (m, 12H), 0.67 (s, 3H).

$^{31}$P NMR (161.82 MHz, C$_6$D$_6$): δ 146.05, 145.91, 145.66, 145.16

$^{13}$C NMR (100 MHz, C$_6$D$_6$): δ 171.43, 171.25, 169.87, 159.25, 159.11, 146.08, 141.59, 136.66, 136.6, 130.62, 130.54, 128.63, 127.53, 127.02, 121.53, 117.73, 117.57, 113.66, 113.57, 86.59, 86.54, 64.36, 58.56, 58.37, 58.30, 56.96, 56.51, 56.07, 54.86, 54.77, 50.57, 50.27, 43.48, 43.35, 42.55, 40.13, 39.9, 39.75, 39.56, 38.70, 36.94, 36.64, 36.29, 36.19, 35.90, 34.58, 32.24, 32.08, 29.48, 29.03, 28.98, 28.6, 28.38, 26.54, 24.68, 24.61, 24.54, 23.6, 23.0, 22.74, 21.26, 20.03, 19.9, 19.38, 19.01, 12.06.

Synthesis of Polymer Support Immobilized with Thiocholesterol 28

$^{13}$C NMR (100 MHz, DMSO-d$_6$): δ 173.35, 171.94, 170.63, 169.64, 157.99, 144.96, 141.02, 135.72, 129.61, 127.81, 127.55, 113.12, 56.15, 54.99, 52.28, 49.58, 49.06, 41.82, 36.17, 34.97, 33.41, 33.09, 31.32, 27.39, 23.16, 22.68, 22.39, 20.56, 18.95, 18.54, 11.66, 6.02, 5.0

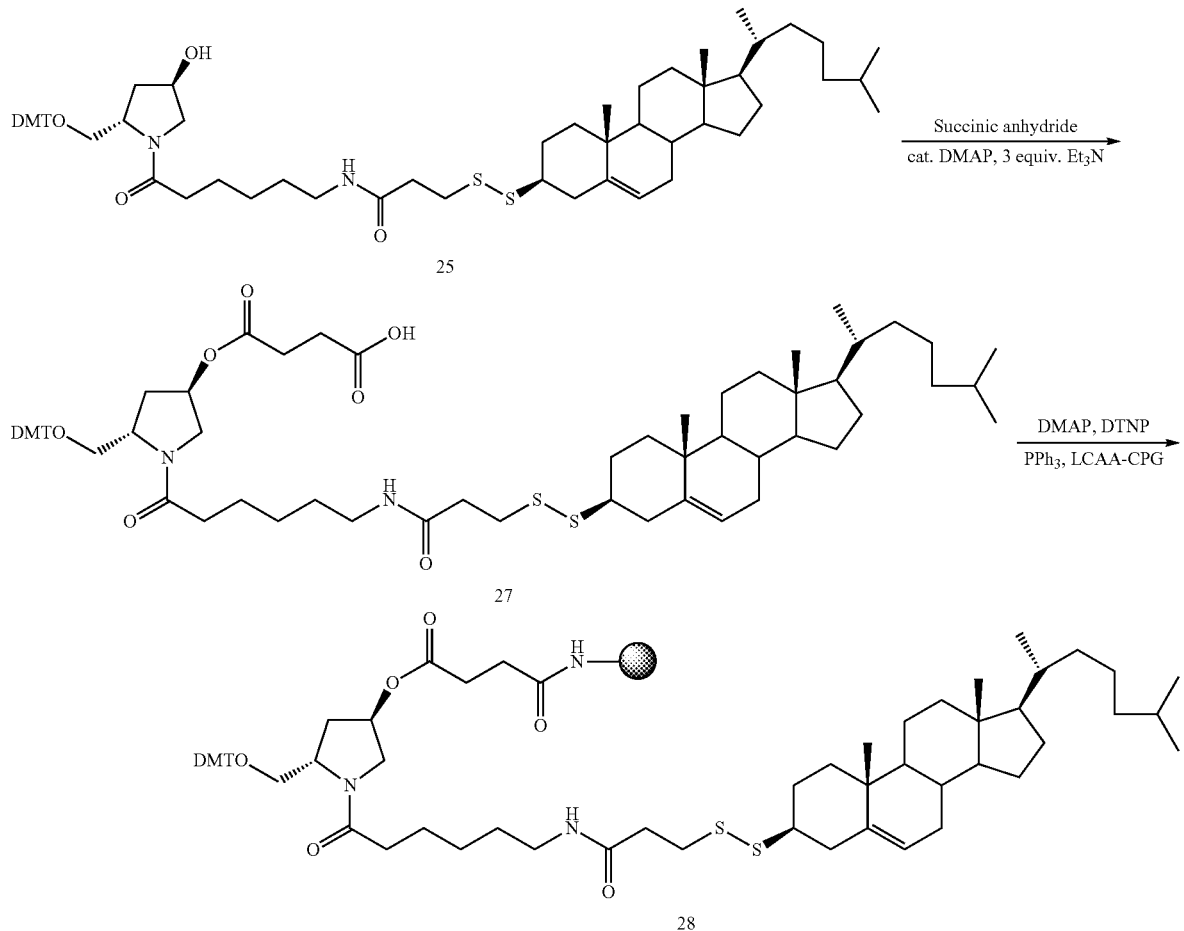

Scheme 9. Synthesis of polymer support immobilized with thiocholesterol

4-Hydroxy-L-prolinol-thiocholesterol-succinate 27

Referring to scheme 9, Compound 25 (2.2 g, 2.15 mmol) was mixed with succinic anhydride (0.323 g, 3.23 mmol) and DMAP (0.026 g, 0.215 mmol) and dried in a vacuum at 40° C. overnight. The mixture was dissolved in anhydrous dichloromethane (10 mL), triethylamine (0.708 g, 0.976 mL, 7 mmol) was added and the solution was stirred at room temperature under argon atmosphere for 16 h. It was then diluted with dichloromethane (50 mL) and washed with ice cold aqueous citric acid (5% wt., 25 mL) and water (2×25 mL). The organic phase was dried over anhydrous sodium sulfate and concentrated to dryness. The crude product was purified by column chromatography to afford compound 27 as white foamy solid (2.2 g, 92% yield; R$_f$=0.6s in 10% MeOH/CHCl$_3$).

$^1$H NMR (400 MHz, DMSO-d$_6$): δ 12.22 (bs, 1H), 7.84 (m, 1H), 7.25 (m, 4H), 7.2 (m, 5H), 6.86 (m, 4H), 5.36 (m, 2H), 4.18 (bs, 1H), 3.72 (s, 6H), 3.4-3.6 (m, 2H), 3.2 (m, 1H), 3.0 (m, 4H), 2.84 (m, 2H), 2.64 (m, 2H), 2.4-2.52 (m, 12H), 2.2 (m, 6H), 1.9 (m, 8H), 0.8-1.52 (m, 28H), 0.65 (s, 3H).

Solid Support with Immobilized Thiocholesterol (28)

Succinate 27 (2.1 g, 1.9 mmol) was dissolved in dichloroethane (8 mL). To that solution DMAP (0.228 g, 1.9 mmol) was added. 2,2'-Dithio-bis(5-nitropyridine) (0.58 g, 1.9 mmol) in acetonitrile/dichloroethane (3:1, 8 mL) was added successively. To the resulting solution triphenylphosphine (0.49 g, 1.9 mmol) in acetonitrile (4 ml) was added. The reaction mixture turned bright orange in color. The solution was agitated briefly using wrist-action shaker (5 mins). Long chain alkyl amine-CPG (LCAA-CPG) (12 g, 1860 μmoles, 1551m/g) was added. The suspension was agitated for 4 h. The CPG was filtered through a sintered funnel and washed with acetonitrile, dichloromethane and ether successively. Unreacted amino groups were masked using acetic anhydride/pyridine. The loading capacity of the CPG 28 was measured by taking UV measurement. (57 μM/g).

Synthesis of 4-hydroxy-L-prolinol
cholesterol-phosphoramidite (N-alkyl linkage) (33)
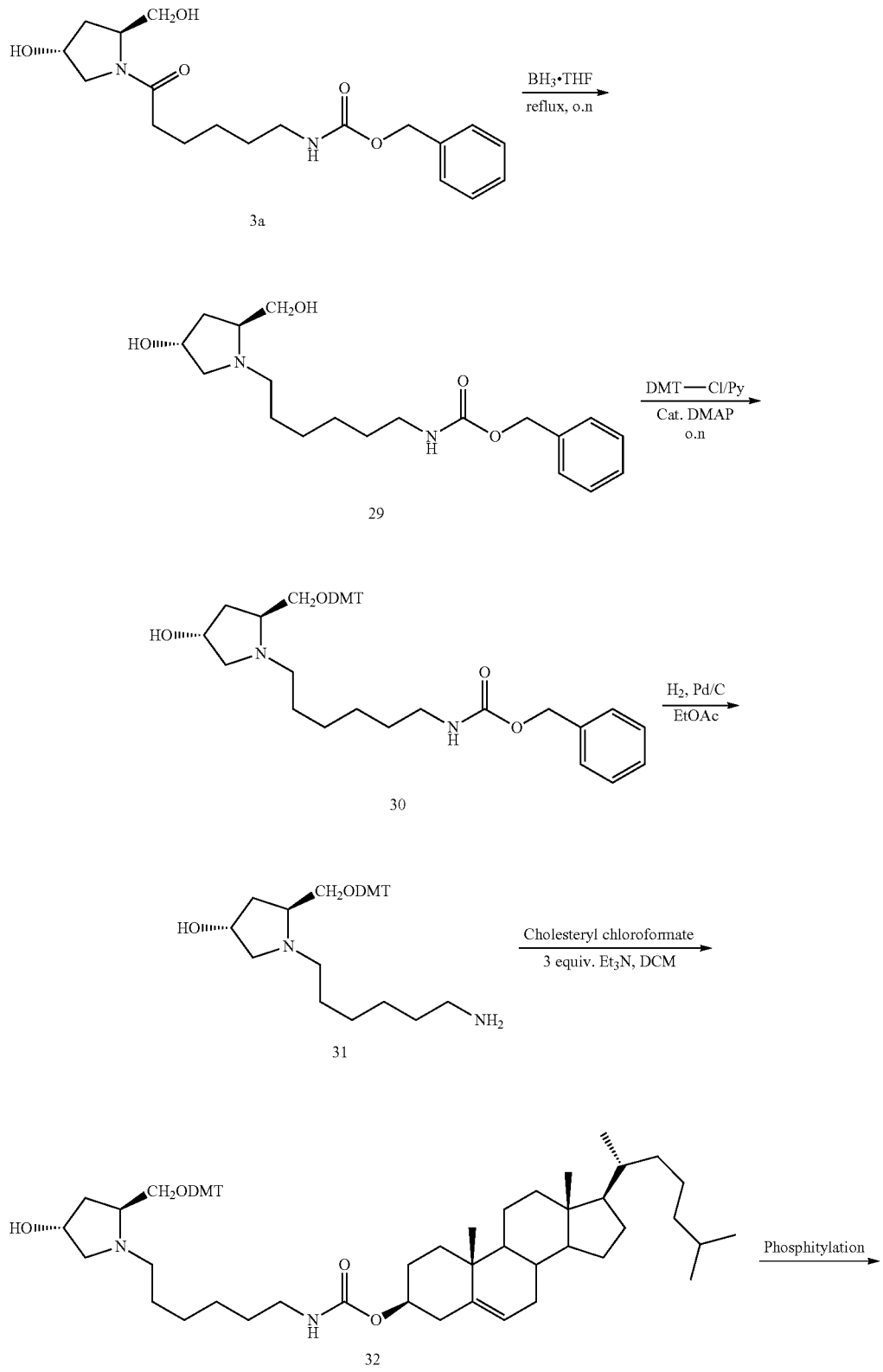
Scheme 10. Synthesis of 4-hydroxy-L-prolinol cholesterol-phosphoramidite

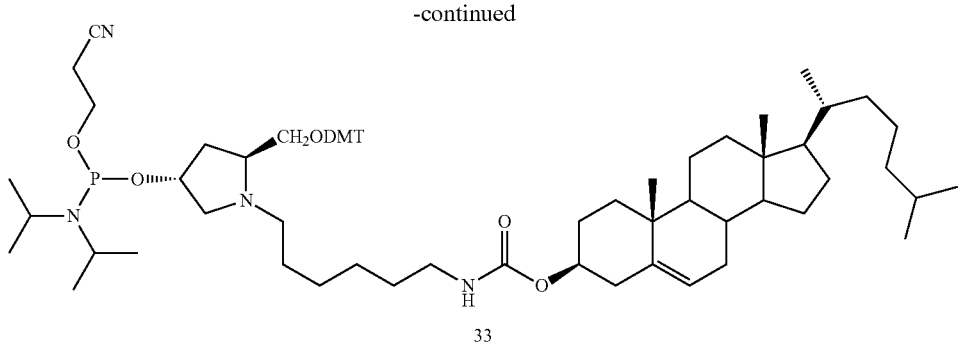

33

[6-(4-Hydroxy-2-hydroxymethyl-pyrrolidin-1-yl)-hexyl]carbamic acid benzyl ester (29)

Referring to scheme 10, compound 3a (7 g, 19.2 mmol) was dissolved in anhydrous THF and cooled to 0° C. under argon atmosphere. Borane-THF (50 mL, 1M soln. in THF, 2.5 equiv.) was added slowly over a period of 15 mins. The reaction mixture was brought to room temperature and stirred at reflux temperature for over night. After 16 h, the reaction mixture was cooled and concentrated under vacuum to dryness. To the residue, saturated solution of ammonium chloride (200 mL) was added and the product extracted with ethyl acetate (3×100 mL). The combined organic layer was dried over anhydrous sodium sulfate, filtered and concentrated under reduced pressure. The crude was purified by column chromatography over silica gel to afford compound 29 as a viscous liquid (6.2 g, 92%).
$^1$H NMR (400 MHz, DMSO-$d_6$): δ 7.33 (m, 5H), 5.1 (s, 2H), 4.94 (d, OH, $D_2O$ exchangeable, 4.76 (t, OH, $D_2O$ exchangeable) 3.68 (m, 1H), 3.95 (m, 2H), 2.92-3.0 (m, 4H), 2.1-2.3 (m, 3H), 1.7-2.0 (2H), 1.34-1.52 (m, 6H), 1.2-1.3 (m, 4H).
$^{13}$C NMR (100 MHz, DMSO-$d_6$): 156.1, 137.3, 128.3, 127.7, 68.2, 65.1, 61.9, 57.5, 56.2, 55.1, 36.1, 34.2, 29.3, 26.1, 25.9, 24.6, 24.1.

(6-{2-[Bis-(4-methoxy-phenyl)-phenyl-methoxymethyl]-4-hydroxy-pyrrolidin-1-yl}-hexyl)-carbamic acid benzyl ester (30)

Compound 29 (6 g, 17 mmol) was co-evaporated with anhydrous pyridine three times and then dissolved in pyridine (60 mL). To this solution dimethylamino pyridine (0.207 g, 1.7 mmol) and DMT-Cl (6 g, 17.9 mmol, 1.05 equiv.) were added at room temperature. The reaction mixture was stirred at room temperature for 16 h. The excess DMT-Cl was quenched by the addition of methanol (25 mL). The solution was dried under reduced pressure. To the residue was suspended in ethyl acetate (300 mL) and washed with saturated bicarbonate solution, brine and water. The organic layer was dried over anhydrous sodium sulfate, filtered and evaporated. 24.2 g of the crude product was obtained after removal of the solvent. Upon purification over silica gel using 2% MeOH/DCM compound 30 (8.7 g, 79%) was obtained as white foamy solid.
$^1$H NMR (400 MHz, DMSO-$d_6$): δ 7.18-7.38 (m, 14H), 6.2-6.5 (m, 4H), 5.0 (s, 2H), 4.9 (d, —OH, $D_2O$ exchangeable), 4.4 (m, 1H), 4.15 (m, 1H), 3.7 (s, 6H), 3.56 (m, 1H), 3.32 (m, 1H), 3.14 (m, 1H), 2.9-3.0 (m, 6H), 2.18 (m, 2H), 1.8-2.1 (m, 2H), 1.1-1.5 (m, 6H).

1-(6-Amino-hexyl)-5-[bis-(4-methoxy-phenyl)-phenyl-methoxymethyl]-pyrrolidin-3-ol (31)

Compound 30 (6.52 g, 10 mmol) was dissolved in ethyl acetate (100 mL) and purged with argon. To the solution was added 10% palladium on carbon (2 g). The flask was purged with hydrogen 2 times and stirred further at room temperature under hydrogen atmosphere for overnight. The disappearance of the starting material was confirmed by the TLC. The reaction mixture was filtered through a pad of Celite and washed with ethyl acetate. The combined organic layer was concentrated under reduced pressure to afford compound 31 (4.8 g, 93%) as white solid. This was used as such for the next step.

(6-{2-[Bis-(4-methoxy-phenyl)-phenyl-methoxymethyl]-4-hydroxy-pyrrolidin-1-yl}-hexyl)-carbamic acid 10,13-dimethyl-17-octyl-2,3,4,7,8,9,10,11,12, 13,14,15,16,17-tetradecahydro-1H-cyclopenta[a] phenanthren-3-yl ester (32)

Compound 31 (4.5 g, 8.67 mmol) was dissolved in anhydrous dichloromethane (100 mL) and cooled to 0° C. To the solution were added triethylamine (2.52 g, 3.36 mL, 25 mmol) and cholesteryl chloroformate (3.89 g, 8.67 mmol) successively. The reaction temperature was brought to ambient temperature and stirred further for 2 h. The completion of the reaction was ascertained by TLC (10% MeOH/CHCl$_3$). The reaction mixture was evaporated under the vacuum to afford the crude product. Compound 32 (3.05 g, 37%) was obtained as a white foamy solid after column chromatography over silica gel.
$^1$H NMR (400 MHz, DMSO-$d_6$): δ 7.1-7.4 (m, 9H), 6.8 (m, 4H), 5.25 (b, 1H), 4.65 (s, 1H), 5.35 (bs, 1H), 4.05 (m, 1H), 3.65 (s, 6H), 3.32 9s, 1H), 3.14 (m, 2H), 2.6-2.9 (m, 8H), 2-2.2 (m, 4H), 0.6-1.8 (m, 48H).
$^{13}$C NMR (100 MHz, DMSO-$d_6$): 157.922, 148.38, 140.26, 138.89, 129.78, 129.02, 127.74, 127.55, 112.87, 85.41, 67.72, 59.91, 55.1, 54.97, 54.83, 22.53, 22.34, 20.87, 19.22, 14.18.

4-Hydroxy-L-prolinol-cholesterol-phosphoramidite (N-alkyl linkage) (33)

Compound 32 (2.0 g, 2.14 mmol) was coevaporated with anhydrous toluene (25 mL). To the residue N,N-tetraisopropylammonium tetrazolide (0.118 g, 1.05 mmol) was added and the mixture was dried over $P_2O_5$ in a vacuum oven for overnight at 40° C. The reaction mixture was dissolved in dichloromethane (5 mL) and 2-cyanoethyl-N,N,N',N'-tetraisopropylphosphorodiamidite (0.97 g, 1.1 mL, 3.22 mmol) was added. The reaction mixture was stirred at ambient temperature for overnight. The completion of the reaction was ascertained by TLC ($R_f$=0.5 in 1:1 ethyl acetate:hexane). The reaction mixture was diluted with dichloromethane (50 mL) and washed with 5% NaHCO$_3$ (50 mL) and brine (50 mL). The organic layer was dried over anhydrous Na$_2$SO$_4$ filtered and concentrated under reduced pressure. The residue was purified over silica gel (50:49:1, EtOAc:Hexane:triethylamine) to afford 33 as white solid (2.1 g, 86%).

$^1$H NMR (400 MHz, C$_6$D$_6$): δ 7.72 (m, 2H), 7.56 (m, 3H), 7.21 (m, 2H), 7-7.1 (m, 3H), 6.8 (m, 3H), 5.4 (bs, 1H), 4.94 (bs, 1H), 4.56 (m, 1H), 3.54 (m, 3H), 3.42 (m, 1H), 3.2-3.38 (m, 9H), 3.1 (m, 2H), 2.94 (m, 1H), 2.78 (m, 1H), 2.68 (m, 2H), 2.4-2.6 (m, 3H), 2.22 (m, 1H), 2-2.12 (m, 8H), 0.9-1.9 (m, 63H), 0.66 (s, 3H).

$^{31}$P NMR (161.82 MHz, C$_6$D$_6$): δ 145.48, 145.33 (NO rotamers observed after removing amide bond)

$^{13}$C NMR (100 MHz, C$_6$D$_6$): δ 159.07, 155.86, 146.20, 140.19, 140.19, 137.83, 136.95, 130.65, 129.27, 128.77, 128.51, 127.55, 126.93, 125.64, 126.66, 117.5, 113.5, 86.51, 74.63, 72.62, 72.44, 67.37, 63.39, 58.64, 58.46, 56.90, 56.46, 54.72, 50.25, 44.84, 44.72, 48.38, 43.41, 43.26, 43.29, 42.55, 40.10, 39.0, 39.38, 37.31, 36.8, 36.63, 36.19, 32.27, 32.14, 29.41, 28.86, 28.61, 28.38, 27.60, 27.01, 24.74, 24.67, 24.62, 24.56, 24.51, 24.32, 24.07, 24.01, 23.00, 22.74, 21.37, 21.33, 20.03, 20.0, 19.97, 19.47, 19.01, 12.05.

Synthesis of Solid Support with Immobilized Cholesterol (N-Alkyl Linkage) (35)

Succinic acid mono-{5-[bis-(4-methoxy-phenyl)-phenyl-methoxymethyl]-1-[6-(10,13-dimethyl-17-octyl-2,3,4,7,8,9,10,11,12,13,14,15,16,17-tetradecahydro-1H-cyclopenta[a]phenanthren-3-yloxycarbonylamino)-hexyl]-pyrrolidin-3-yl}ester (34)

Referring to scheme 11, Compound 33 (1 g, 1.07 mmol) was mixed with succinic anhydride (0.16 g, 1.61 mmol) and DMAP (0.012 g, 0.1 mmol) and dried in a vacuum at 40° C. overnight. The mixture was dissolved in anhydrous dichloromethane (10 mL), triethylamine (0.328 g, 0.45 mL, 3.25 mmol) was added and the solution was stirred at room temperature under argon atmosphere for 16 h. It was then diluted with dichloromethane (50 mL) and washed water (2×25 mL). The organic phase was dried over anhydrous sodium sulfate and concentrated to dryness. The product 34 was used as such for next step without further purification (1.2 g, Quantitative).

$^1$H NMR (400 MHz, CDCl$_3$): δ 7.32-7.36 (m, 2H), 7.2-7.28 (m, 7H), 6.76-6.8 (m, 4H), 5.4 (bs, 1H), 4.46 (m, 2H), 3.78 (s, 6H), 3.42 (m, 1H), 3-3.18 (m, 3H), 2.5-2.6 (m, 3H), 2.12-2.38 (m, 6H), 1.78-2.02 (m, 7H), 0.8-1.6 (m, 42H), 0.66 (s, 3H)

$^{13}$C NMR (100 MHz, CDCl$_3$): δ 158.78, 158.62, 145.16, 139.8, 136.39, 136.22, 130.18, 130.14, 128.23, 128.0, 126.97, 122.91, 113.28, 56.88, 56.32, 55.45, 55.4, 50.19,

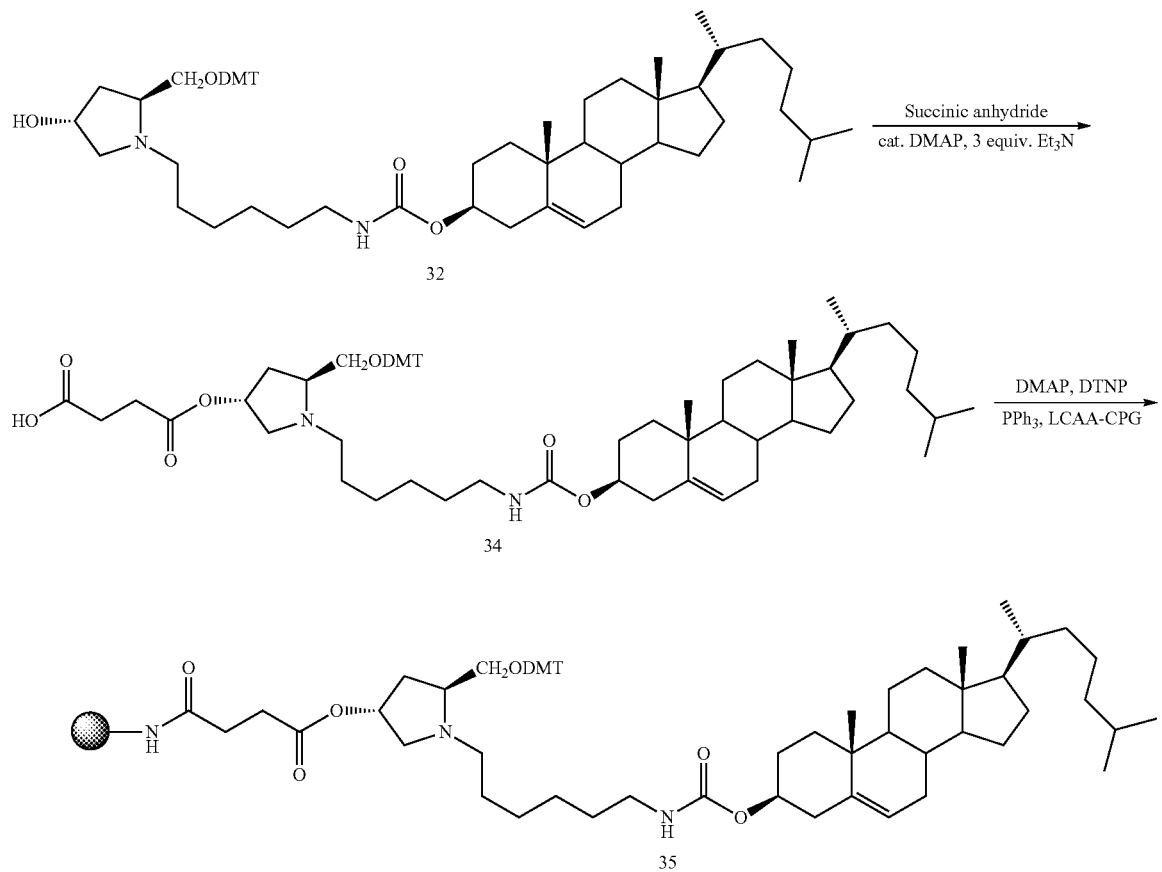

Scheme 11. Synthesis of solid support with immobilized cholesterol 45.47, 42.51, 39.93, 39.72, 38.67, 37.14, 36.74, 36.38, 36.0, 32.1, 32.06, 28.44, 28.22, 24.5, 24.0, 23.04, 22.77, 21.24, 19.55, 18.92, 12.07, 8.72

Solid Support with Immobilized Cholesterol (N-Alkyl Linkage) (35)

Succinate 34 (1.2 g, 1.16 mmol) was dissolved in dichloroethane (5 mL). To that solution DMAP (0.142 g, 1.16 mmol) was added. 2,2'-Dithio-bis(5-nitropyridine) (0.347 g, 1.16 mmol) in acetonitrile/dichloroethane (3:1, 5 mL) was added successively. To the resulting solution triphenylphosphine (0.304 g, 1.15 mmol) in acetonitrile (2.5 ml) was added. The reaction mixture turned bright orange in color. The solution was agitated briefly using wrist-action shaker (5 mins). Long chain alkyl amine-CPG (LCAA-CPG) (6 g, 900 μmoles, 1551m/g) was added. The suspension was agitated for 4 h. The CPG was filtered through a sintered funnel and washed with acetonitrile, dichloromethane and ether successively. Unreacted amino groups were masked using acetic anhydride/pyridine. The loading capacity of the CPG 35 was measured by taking UV measurement. (63 μM/g).

Synthesis of hydroxy-prolinol-phthalimido phosphoramidite (45)

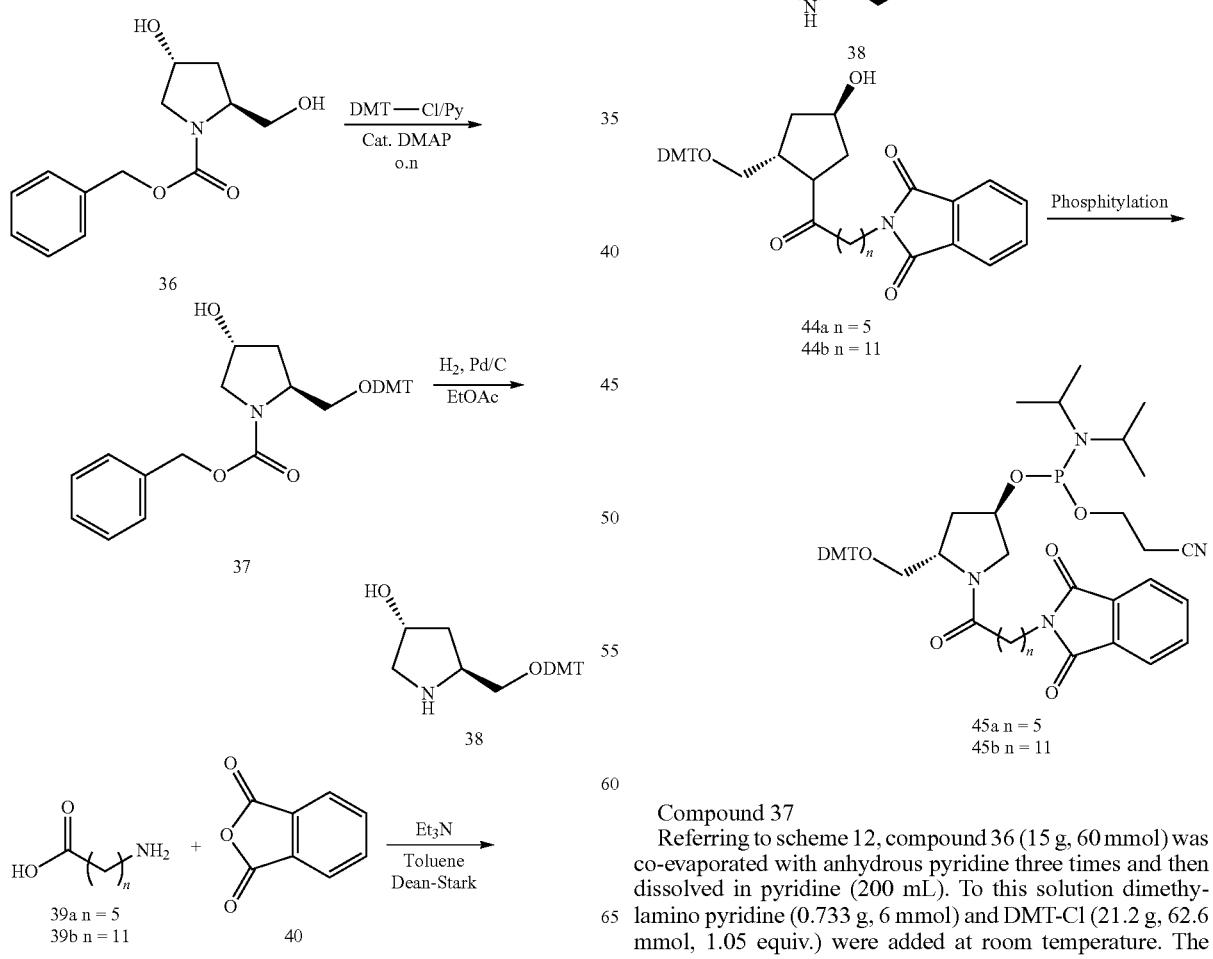

Compound 37

Referring to scheme 12, compound 36 (15 g, 60 mmol) was co-evaporated with anhydrous pyridine three times and then dissolved in pyridine (200 mL). To this solution dimethylamino pyridine (0.733 g, 6 mmol) and DMT-Cl (21.2 g, 62.6 mmol, 1.05 equiv.) were added at room temperature. The reaction mixture was stirred at room temperature for 16 h. The excess DMT-Cl was quenched by the addition of methanol (50 mL). The solution was dried under reduced pressure. To the residue was suspended in ethyl acetate (500 mL) and washed with saturated bicarbonate solution, brine and water. The organic layer was dried over anhydrous sodium sulfate, filtered and evaporated. Upon purification over silica gel using 3% MeOH/DCM compound 37 (33 g, 77%) was obtained as white foamy solid.

$^1$H NMR (400 MHz, DMSO-$d_6$): δ7.22-7.38 (m, 8H), 7.16-7.2 9m, 5H), 7.06 (m, 1H), 6.84 (m, 4H), 5.34 (bs, 1H), 4.88-4.96 (m, 2H), 4.25 (m, 1H), 4 (bs, 1H), 3.7 (s, 6H), 3.4 (m, 2H), 3.04 (m, 2H), 1.86 (m, 2H).

$^{13}$C NMR (10 MHz, DMSO-$d_6$): δ 158.0, 154.28, 154.22, 149.62, 145.04, 137.15, 136.64, 135.74, 136.67, 129.58, 129.53, 128.4, 128.26, 127.81, 127.73, 127.55, 127.29, 126.65, 126.65, 123.91, 113.12, 85.24, 85.14, 68.45, 67.83, 65.96, 65.64, 64.39, 63.4, 54.99, 37.67, 36.68.

5-[Bis-(4-methoxy-phenyl)-phenyl-methoxymethyl]-pyrrolidin-3-ol (38)

Compound 37 (8.25 g, 14.9 mmol) was dissolved in methanol (20 mL) and purged with nitrogen. To the solution were added ammonium formate (14.1 g, 223 mmol) and 10% Pd/C (0.825 g). The suspension was stirred at room temperature for 1 h. The reaction mixture was filtered through a pad of Celite and washed with methanol. The solution was concentrated to dryness under vacuum. The residue was dissolved in ethyl acetate 9250 mL) and washed with water (2×25 mL). The organic layer was dried over sodium sulfate, filtered and evaporated to dryness under reduced pressure. Product 38 (6.25 g, 98%) was used without purification for the next step.

$^1$H NMR (400 MHz, DMSO-$d_6$): δ 8.28 (bs, 1H), 7.36 (m, 2H), 7.18-7.3 (m, 7H), 6.84 (d, 4H), 4.2 (m, 1H), 3.7 (s, 6H), 3.6 (m, 1H), 3.02 (m, 3H), 2.8 (d, 1H), 1.74 (dd, 1H), 1.48 (m, 1H).

$^{13}$C NMR (10 MHz, DMSO-$d_6$): δ 165.02, 158.06, 149.9, 135.5, 129.74, 127.81, 127.72, 126.67, 113.15, 85.58, 69.6, 59.76, 56.81, 55.02, 53.6237.66, 14.08.

6-(1,3-Dioxo-1,3-dihydro-isoindol-2-yl)-hexanoic acid (41a)

6-amino hexanoic acid 39a (13.1 g, 100 mmol) and phthalic anhydride (40) (14.8 g, 100 mmol) were mixed in toluene (150 mL). To the suspension was added triethyl amine (13 mL). The suspension was refluxed using Dean-stark for 16 h. When collection of water ceased, the reaction was cooled and evaporated to dryness. The residue was suspended in water and conc. hydrochloric acid (1.5 mL) was added. The suspension was stirred for 30 mins and filtered. The precipitate was washed with water and dried over sodium sulfate to afford compound 41a (24.5 g, 93%) which was used as such for the next step.

6-(1,3-Dioxo-1,3-dihydro-isoindol-2-yl)-hexanoic acid pentafluorophenyl ester (43a)

Referring to scheme 12, compound 41a (13.3 g, 51 mmol) was dissolved in anhydrous dichloromethane (40 mL) and cooled to 0° C. under argon. To the solution were added diisopropyl carbodiimide (6.31 g, 7.7 mL, 50 mmol) and pentafluoro phenol (42, 9.2 g, 50 mmol). After overnight the reaction mixture was evaporated to dryness. To the residue ethyl acetate (100 mL) was added and the filtered to remove diisopropyl urea. The precipitate was washed with ethyl acetate (50 mL). The combined organic layer was washed with saturated sodium bicarbonate and water. The organic layer was dried over sodium sulfate, filtered and evaporated to dryness. Compound 43a ($R_f$=0.8 in 10% EtOAc/Hexane, 21.65 g, 92%) was obtained, which was directly used for the next step without further purification.

$^1$H NMR (400 MHz, CDCl$_3$): δ 7.82 (m, 2H), 7.7 (m, 2H), 3.7 (t, 2H), 2.65 (t, 2H), 1.7-1.85 (m, 4H), 1.48 (m, 2H).

$^{13}$C NMR (100 MHz, CDCl$_3$): δ 169.46, 168.62, 142.5, 140.84, 139.29, 138.32, 136.75, 134.13, 132.28, 123.39, 37.78, 33.3, 28.33, 26.21, 24.46.

2-(6-{2-[Bis-(4-methoxy-phenyl)-phenyl-methoxymethyl]-4-hydroxy-pyrrolidin-1-yl}-6-oxo-hexyl)-isoindole-1,3-dione (44a)

Amine 38 (9.32 g, 22.2 mmol) and triethyl amine (4.55 g, 6.27 mL, 45 mmol) weres dissolved in anhydrous dichloromethane (20 mL) and cooled to 0° C. under argon. To that solution was added compound 43a (9.5 g, 22.2 mmol) at 0° C. The reaction mixture was brought to ambient temperature and stirred further. After 30 mins, disappearance of starting materials were ascertained by TLC. (10% MeOH/CHCl$_3$). The reaction mixture was diluted with dichloromethane (100 mL) and washed with 5% NaOH solution (3×50 mL) followed by water and brine. The organic layer was dried over anhydrous sodium sulfate, filtered and evaporated to dryness. Upon purification over silica gel compound 44a was obtained as foamy white solid in good yield. (13.2 g, 89%).

$^1$H NMR (400 MHz, DMSO-$d_6$): δ 7.84 (m, 4H), 7.3 (m, 4H), 7.18 (m, 5H), 6.86 (m, 4H), 4.98 (d, —OH), 4.38 (m, 1H), 4.1 (m, 1H), 3.72 (d, 6H), 3.55 (m, 3H), 3.3 (m, 2H), 3.12 (m, 1H), 2.97 (m, 1H), 2.2 (t, 2H), 2.0 (m, 1H), 1.9 (m, 1H), 1.82 (m, 1H), 1.44-1.6 (m, 1H), 1.3 (m, 2H), 1.14 (m, 1H), $^{13}$C NMR (100 MHz, DMSO-$d_6$): δ 172.78, 172.11, 168.74, 168.67, 158.74, 158.55, 158.54, 145.24, 144.72, 136.46, 136.27, 137.87, 135.84, 134.18, 134.13, 134.09, 132.3, 132.27, 130.18, 130.11, 129.33, 128.22, 128.20, 128.08, 128.03, 127.93, 127.12, 126.89, 123.41, 123.38, 113.35, 113.2, 86.7, 86.06, 70.7, 69.46, 65.51, 63.67, 56.61, 56.0, 55.9, 55.42, 55.36, 54.2, 38.44, 38.0, 37.98, 36.9, 35.0, 33.4, 28.6, 28.5, 28.4, 26.79, 26.71, 25.0, 24.6, 24.5.

4-Hydroxy-prolinol-phthalimido phosphoramidite (45a)

Compound 44a (9.0 g, 13.57 mmol) was coevaporated with anhydrous toluene (50 mL). To the residue N,N-tetraisopropylammonium tetrazolide (0.766 g, 6.8 mmol) was added and the mixture was dried over P$_2$O$_5$ in a vacuum oven for overnight at 40° C. The reaction mixture was dissolved in dichloromethane (20 mL) and 2-cyanoethyl-N,N,N',N'-tetraisopropylphosphorodiamidite (6.13 g, 6.7 mL, 20.35 mmol) was added. The reaction mixture was stirred at ambient temperature for overnight. The completion of the reaction was ascertained by TLC ($R_f$=0.7 in 1:1 ethyl acetate:hexane). The reaction mixture was diluted with dichloromethane (100 mL) and washed with 5% NaHCO$_3$ (100 mL) and brine (100 mL). The organic layer was dried over anhydrous Na$_2$SO$_4$ filtered and concentrated under reduced pressure. The residue was purified over silica gel (50:49:1, EtOAc:Hexane:triethlyamine) to afford compound 45a as white solid (10.5 g, 89%).

$^1$H NMR (400 MHz, C$_6$D$_6$): δ 7.62 (m, 2H), 7.42 (m, 6H), 7.22 (t, 2H), 7.08 (m, 1H), 6.88 (dd, 2H), 6.78 (m, 4H), 4.66 (m, 1H), 4.56 (m, 1H), 3.72 (m, 1H), 3.5 (m, 5H), 3.3 (m, 7H), 3.22 (m, 1H), 2.1 (m, 5H), 1.74 (m, 4H), 1.56 (m, 2H), 1.26 (m, 2H), 1.1 (m, 13H).

$^{31}$P NMR (161.82 MHz, C$_6$D$_6$): δ 145.98, 145.8, 145.63, 146.3 (Rotamers observed after due to amide bond at the ring)

$^{13}$C NMR (100 MHz, C$_6$D$_6$): δ 171.03, 170.08, 167.98, 159.23, 159.0, 146.1, 136.76, 136.69, 136.64, 136.27, 133.35, 132.7, 130.59, 130.54, 130.46, 128.65, 128.56, 127.55, 126.97, 128.24, 128.0, 127.7, 122.84, 113.62, 113.53, 113.51, 86.57, 86.51, 72.67, 72.5, 72.33, 64.48, 58.59, 58.46, 58.41, 58.28, 57.77, 56.03, 55.97, 54.81, 54.73, 43.47, 43.35, 37.87, 36.42, 36.32, 34.94, 34.88, 33.37, 28.77, 26.94, 24.67, 24.6, 24.51, 20.10, 20.04, 19.98.

Compound 45b:

The phosphoramidite 45b is obtained from 39b in four steps as described for the synthesis of compound 45a from 39a.

4.18 (m, 1H), 3.7 (s, 6H), 3.53 (m, 3H), 3.32 (m, 2H), 3.2 (m, 1H), 3.0 (m, 1H), 2.94 (s, 2H), 2.4 (m, 6H), 2.2 (m, 3H), 2.0 (m, 1H), 1.5 (m, 4H), 1.28 (m, 2H), 1.16 (m, 1H).

$^{13}$C NMR (100 MHz, DMSO-d$_6$): δ 172.95, 171.95, 168.78, 168.64, 158.77, 158.59, 145.18, 144.67, 136.44, 136.23, 135.8, 134.13, 133.33, 132.29, 130.21, 130.13, 128.25, 128.13, 127.98, 126.94, 123.45, 113.40, 113.26, 106.61, 86.11, 73.59, 63.67, 55.76, 55.39, 53.31, 39.64, 38.03, 35.1, 35.51, 28.56, 26.82, 24.45.

The succinate (2.7 g, 3.5 mmol) was dissolved in dichloroethane (15 mL). To that solution DMAP (0.0427 g, 3.5 mmol) was added. 2,2'-Dithio-bis(5-nitropyridine) (1.086 g, 3.5 mmol) in acetonitrile/dichloroethane (3:1, 15 mL) was added successively. To the resulting solution triphenylphosphine (0.918 g, 3.5 mmol) in acetonitrile (7 ml) was added.

Scheme 13. Synthesis of solid support immobilized with phthalimido group

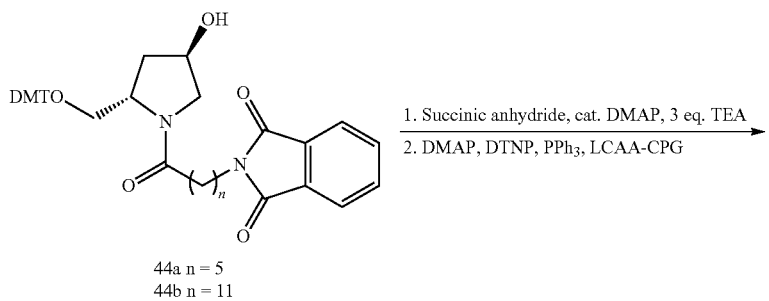

44a n = 5
44b n = 11

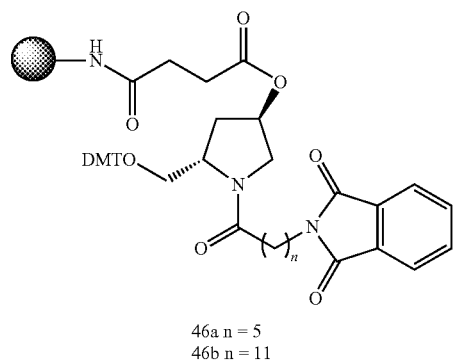

46a n = 5
46b n = 11

Synthesis of Solid Support Immobilized with Phthalimido Group (46a)

Referring to scheme 13, Compound 44a (3 g, 4.5 mmol) was mixed with succinic anhydride (0.675 g, 6.75 mmol) and DMAP (0.055 g, 0.45 mmol) and dried in a vacuum at 40° C. overnight. The mixture was dissolved in anhydrous dichloromethane (10 mL), triethylamine (1.37 g, 1.8 mL, 13.5 mmol) was added and the solution was stirred at room temperature under argon atmosphere for 16 h. It was then diluted with dichloromethane (150 mL) and washed with 5% ice-cold citric acid (2×50 mL) followed by water (2×50 mL) and brine. The organic phase was dried over anhydrous sodium sulfate and concentrated to dryness. The succinate was obtained after purification over silica gel (3.2 g, 93%).

$^1$H NMR (400 MHz, DMSO-d$_6$): δ 8.08 (m, 1H), 7.82 (m, 3H), 7.28 (m, 4H), 7.16 (m, 5H), 6.84 (m, 4H), 5.32 (m, 1H),

The reaction mixture turned bright orange in color. The solution was agitated briefly using wrist-action shaker (5 mins). Long chain alkyl amine-CPG (LCAA-CPG) (10.5 g, 1620 mmoles, 155 μm/g) was added. The suspension was agitated for 4 h. The CPG was filtered through a sintered funnel and washed with acetonitrile, dichloromethane and ether successively. Unreacted amino groups were masked using acetic anhydride/pyridine. The loading capacity of the CPG 46a was measured by taking UV measurement. (63 μM/g).

Synthesis of Solid Support Immobilized with Phthalimido Group (46b)

The desired compound 46b is obtained from compound 44b in two steps as described for the preparation of compound 46a from the corresponding precursor 44a.

Serinol as a Linker
Synthesis of Solid Support Immobilized with Cholesterol-Serinol Linker (54)
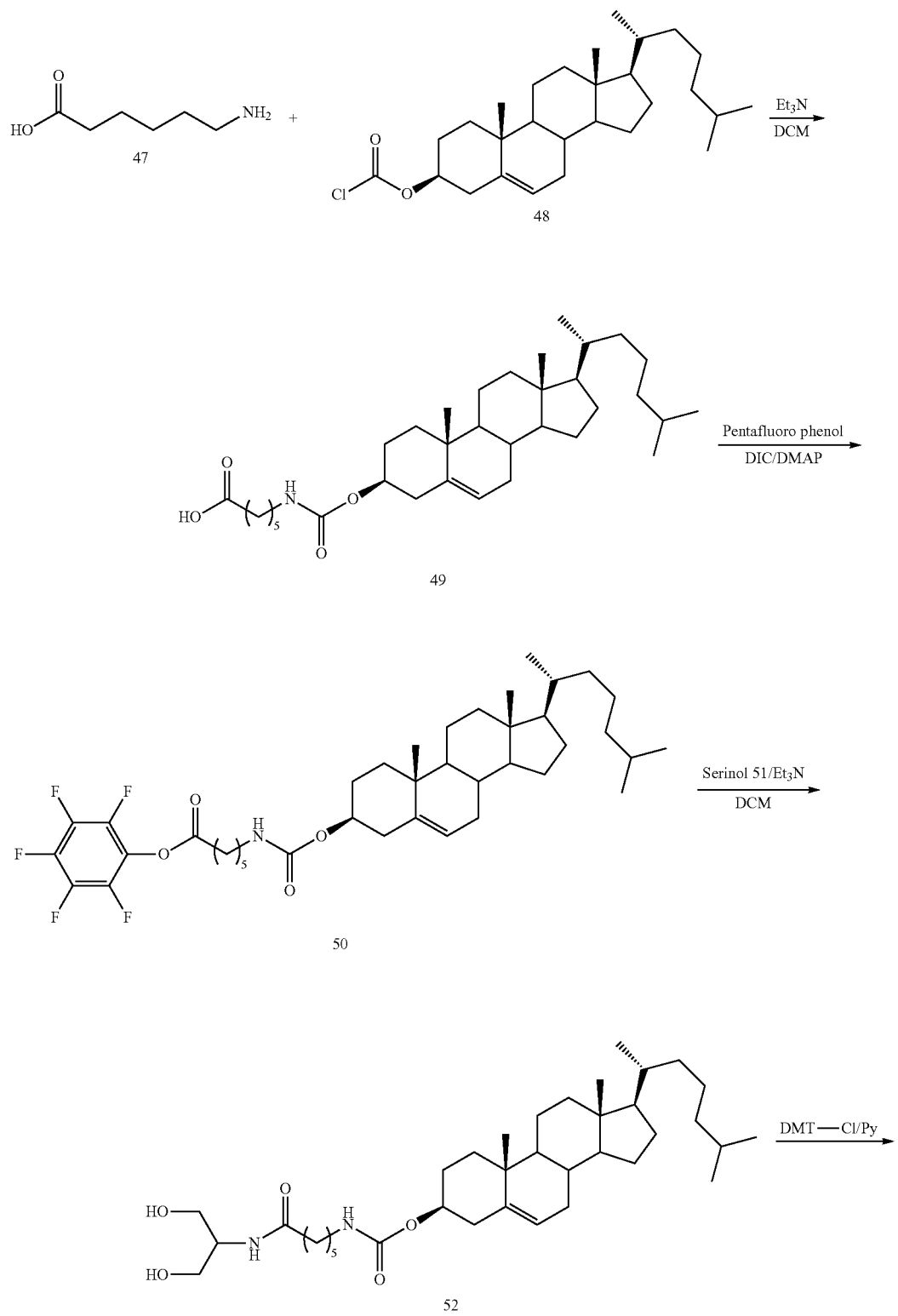

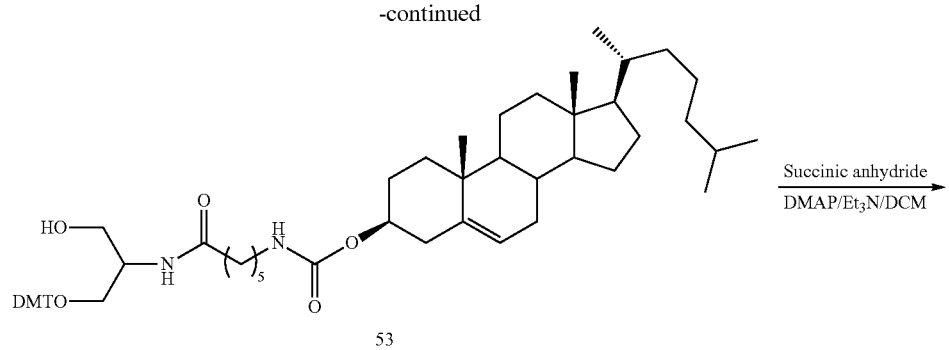

53

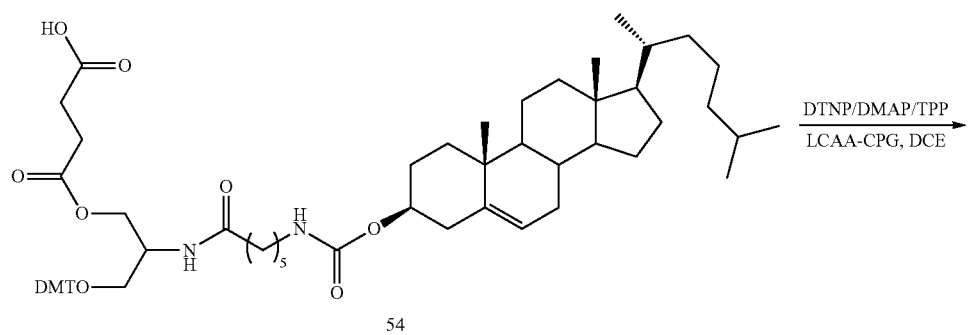

54

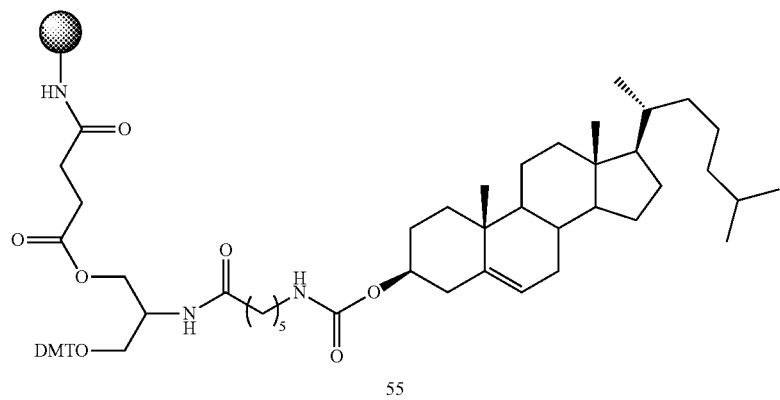

55

ε-N-cholesteryloxycarbonylaminocaproic Acid (49)

Referring to Scheme 14, ε-aminocaproic acid (3.93 g, 30 mmol) was suspended in pyridine (60 mL). The flask was flushed with nitrogen and to the mixture was added N,O-bis (trimethylsilyl)acetamide (10 mL, 70 mmol) under stirring. The reaction mixture was stirred at room temperature for 30 min. Then cooled in ice bath. Cholesteryl chloroformate (13.5 g, 30 mmol) was added into reaction mixture in two portions over 2 h. The reaction was continued by stirring at room temperature for another 4 h. 2% HCl aqueous solution (150 ml) was added under cooling with ice bath. The mixture was stirred for 5 min. and then poured into a separating funnel. The product was extracted with dichloromethane (3×150 mL). The combined organic layer was washed with 2% HCl solution (2×150 mL) and with brine (2×150 mL), dried over anhydrous sodium sulfate, filtered and evaporated to dryness giving a yellow foam (14.44 g, 87%)

$^1$H NMR (400 MHz, CDCl$_3$): δ 5.36 (m, 1H), 4.48 (m, 1H), 3.15 (m, 2H), 2.38 (t, 2H), 1.8-2.04 (m, 5H), 1.32-1.7 (m, 19H), 0.88-1.2 (m, 22H), 0.67 (s, 3H)

$^{13}$C NMR (100 MHz, CDCl$_3$): δ 179.17, 156.42, 139.94, 126.64, 74.43, 56.82, 56.28, 50.14, 42.45, 39.88, 39.67, 38.69, 37.13, 36.69, 36.34, 35.97, 34.08, 32.05, 32.01, 29.78, 28.48, 28.30, 28.17, 26.32, 24.47, 24.44, 24.0, 23.0, 22.73, 21.19, 19.5, 18.87, 12.01.

ε-N-pentalfluorophenyl cholesteryloxycarbonylamino caproate (50)

Referring to scheme 14, E-N-cholesteryloxycarbonylaminocaproic acid (49) (22.71 g, 41.9 mmol) was dissolved in anhydrous dichloromethane (40 mL) and cooled to 0° C. To the solution were added diisopropyl carbodiimide (5.17 g, 6.4 mL, 41 mmol) and triethylamine (10.2 g, 13.7 mL, 100 mmol). After stirring for 20 mins at 0° C., pentafluorophenol (7.71 g, 41.9 mmol) was added and the stirring was continued at room temperature under argon for over night. The reaction mixture was evaporated to dryness. To the residue ethyl acetate (100 mL) was added and the filtered to remove diisopropyl urea. The precipitate was washed with ethyl acetate (50 mL). The combined organic layer was washed with saturated sodium bicarbonate and water. The organic layer was dried over sodium sulfate, filtered and evaporated to dryness. Compound 50 ($R_f$=0.7 in 10% EtOAc/hexane, 25.4 g, 86%) was obtained, which was directly used for the next step without further purification.

$^1$H NMR (400 MHz, $CDCl_3$): δ 5.38 (m, 1H), 4.47 (m, 1H), 3.2 (m, 2H), 2.36 (t, 2H), 1.81-2.05 (m, 5H), 1.3-1.7 (m, 19H), 0.89-1.21 (m, 22H), 0.68 (s, 3H)

$^{13}$C NMR (100 MHz, $CDCl_3$): δ 179.2, 156.2, 139.84, 139.29, 138.32, 136.75, 134.13, 132.28, 126.64, 123.39, 74.43, 56.82, 56.28, 50.14, 42.45, 39.88, 39.67, 38.69, 37.13, 36.69, 36.34, 35.97, 34.08, 32.05, 32.01, 29.78, 28.48, 28.30, 28.17, 26.32, 24.47, 24.44, 24.0, 23.0, 22.73, 21.19, 19.5, 18.87, 12.01.

Synthesis of [5-(2-Hydroxy-1-hydroxymethyl-ethylcarbamoyl)-pentyl]-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester (52)

Serinol (51) (1.37 g, 15 mmol) and triethyl amine (3.03 g, 4.15 mL, 30 mmol) were dissolved in anhydrous dichloromethane (20 mL) and cooled to 0° C. under argon. To that solution was added compound 50 (7.1 g, 10 mmol) at 0° C. The reaction mixture was brought to ambient temperature and stirred further. After 3 h, disappearance of starting materials were ascertained by TLC. (10% MeOH/$CHCl_3$). The reaction mixture was diluted with dichloromethane (100 mL) and washed with 5% NaOH solution (3×50 mL) followed by water and brine. The organic layer was dried over anhydrous sodium sulfate, filtered and evaporated to dryness. Upon purification over silica gel using 5% MeOH/DCM, compound 52 was obtained as foamy white solid in good yield. (5.61 g, 90%).

$^1$H NMR (400 MHz, DMSO-$d_6$): δ 5.32 (m, 1H), 4.58 (t, 2H), 4.28 (m, 2H), 3.58 (m, 1H), 3.38 (m, 4H), 2.91 (t, 2H), 2.2 (m, 2H), 2.06 (t, 2H), 1.72-1.98 (m, 5H), 0.82-1.58 (m, 37H), 0.74 (s, 3H).

M/S(m/z): Calculated: 616.48 Observed: 617.5 ($M^+$+1), 636.4 ($M^+$+Na).

Synthesis of (5-{1-[Bis-(4-methoxy-phenyl)-phenyl-methoxymethyl]-2-hydroxy-ethylcarbamoyl}-pentyl)-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester (54)

Diol 52 (5.6 g, 9.1 mmol) was co-evaporated with anhydrous pyridine three times and then dissolved in pyridine (10 mL). To this solution dimethylamino pyridine (0.110 g, 0.91 mmol) and DMT-Cl (3.23 g, 9.53 mmol, 1.05 equiv.) were added at room temperature. The reaction mixture was stirred at room temperature for 16 h. Due to the presence of two primary hydroxyl groups, the reaction never went to completion. The solution was dried under reduced pressure and co-evaporated with toluene to remove residual pyridine. To the residue was suspended in ethyl acetate (200 mL) and washed with saturated bicarbonate solution, brine and water. The organic layer was dried over anhydrous sodium sulfate, filtered and evaporated. The crude product was obtained after removal of the solvent. Upon purification over silica gel using 2% MeOH/DCM compound 53 (0.680 g, 10%) was obtained as white foamy solid.

$^1$H NMR (400 MHz, DMSO-$d_6$): δ 7.62 (d, 1H), 7.36 (m, 2H), 7.18-7.3 (m, 6H), 7.1 (m, 1H), 6.86 (m, 4H), 5.32 (bs, 1H), 4.6 (t, 1H), 4.28 (m, 1H), 3.98 (m, 1H), 3.72 (s, 6H), 3.42 (m, 2H), 2.98 (m, 1H), 2.9 (m, 3H), 1.72-2.3 (m, 9H), 0.8-1.58 (m, 39H), 0.64 (s, 3H).

Synthesis of Succinic acid mono-(3-[bis-(4-methoxy-phenyl)-phenyl-methoxy]-2-{6-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoylamino}-propyl) ester (54)

DMT-alcohol 53 (0.650 g, 0.707 mmol) was mixed with succinic anhydride (0.100 g, 1 mmol) and DMAP (0.0123 g, 0.1 mmol) and dried in a vacuum at 40° C. overnight. The mixture was dissolved in anhydrous dichloromethane (5 mL), triethylamine (0.203 g, 0.27 mL, 2 mmol) was added and the solution was stirred at room temperature under argon atmosphere for 16 h. It was then diluted with dichloromethane (20 mL) and washed with ice cold aqueous citric acid (5% wt., 25 mL) and water (2×25 mL). The organic phase was dried over anhydrous sodium sulfate and concentrated to dryness. The crude product was purified by column chromatography to afford compound 54 as white solid (0.54 g, 78% yield; $R_f$=0.5 in 10% MeOH/$CHCl_3$).

$^1$H NMR (400 MHz, $CDCl_3$): δ 7.26-7.32 (m, 5H), 7.16-7.18 (m, 4H), 6.84 (m, 4H), 5.38 (bs, 1H), 4.6 (t, 1H), 4.2-4.6 (m, 4H), 3.8 (s, 6H), 3.62 (m, 2H), 3.18 (m, 4H), 2.6-2.72 (m, 4H), 2.2-2.38 (m, 3H), 1.82-2.04 (m, 9H), 0.84-1.62 (m, 39H), 0.66 (s, 3H).

Synthesis of Cholesterol Immolized on Solid Support with Serinol Linker (55)

Succinate 54 (0.51 g, 0.5 mmol) was dissolved in dichloroethane (2 mL). To that solution DMAP (0.061 g, 0.5 mmol) was added. 2,2'-Dithio-bis(5-nitropyridine) (0.155 g, 0.5 mmol) in acetonitrile/dichloroethane (3:1, 2 mL) was added successively. To the resulting solution triphenylphosphine (0.131 g, 0.5 mmol) in acetonitrile (1 ml) was added. The reaction mixture turned bright orange in color. The solution was agitated briefly using wrist-action shaker (5 mins). Long chain alkyl amine-CPG (LCAA-CPG) (2.2 g, 115 μm/g) was added. The suspension was agitated for 3 h. The CPG was filtered through a sintered funnel and washed with acetonitrile, dichloromethane and ether successively. Unreacted amino groups were masked using acetic anhydride/pyridine. The loading capacity of the CPG was measured by taking UV measurement. (35 μM/g).

Scheme 15. Synthesis of cholesterol phosphoramidite with serinol linker

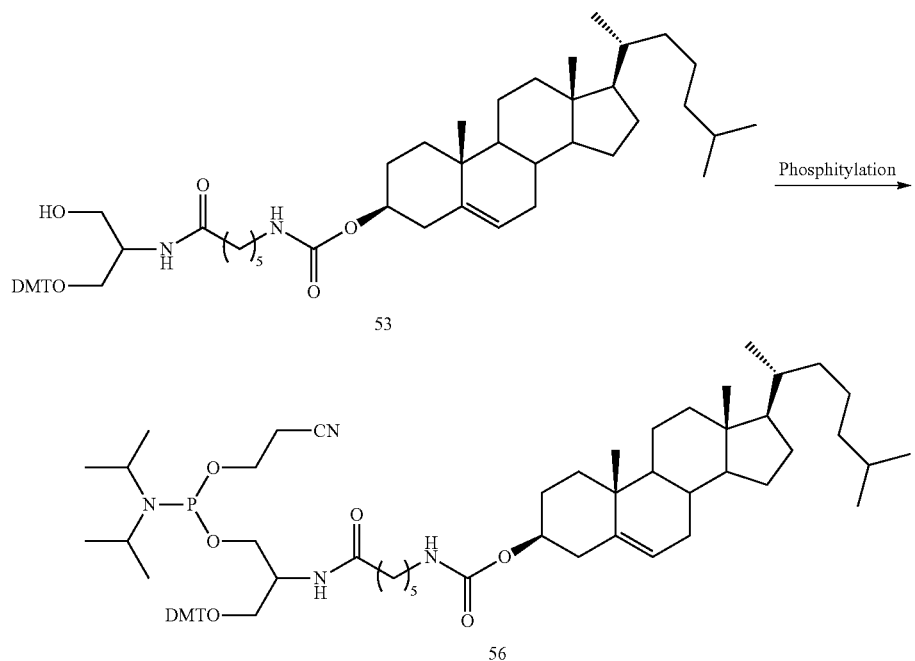

Serinol-cholesterol-phosphoramidite (56)

Referring to Scheme 15, Compound 53 (0.92 g, 1 mmol) is coevaporated with anhydrous toluene (25 mL). To the residue N,N-tetraisopropylammonium tetrazolide (0.056 g, 0.5 mmol) is added and the mixture is dried over $P_2O_5$ in a vacuum oven for overnight at 40° C. The reaction mixture is dissolved in dichloromethane (25 mL) and 2-cyanoethyl-N, N,N',N'-tetraisopropylphosphorodiamidite (1.9 g, 2.1 mL, 6.3 mmol) is added. The reaction mixture is stirred at ambient temperature for overnight. The completion of the reaction is ascertained by TLC. The reaction mixture is diluted with dichloromethane (25 mL) and washed with 5% $NaHCO_3$ (50 mL) and brine (50 mL). The organic layer is dried over anhydrous $Na_2SO_4$ filtered and concentrated under reduced pressure. The residue is purified over silica gel (50:49:1, EtOAc: Hexane:triethlyamine) to afford amidite 56.

Synthesis of Pyrrolidine-Cholesterol Phosphoramidite

Scheme 16. Synthesis of pyrrolidine-cholesterol-phosphoramidite

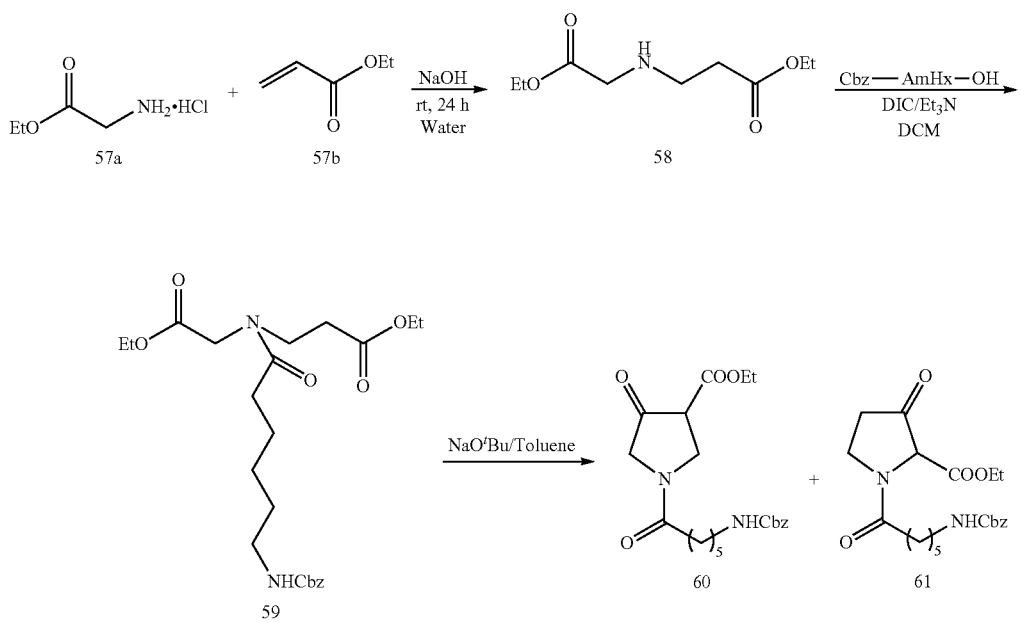

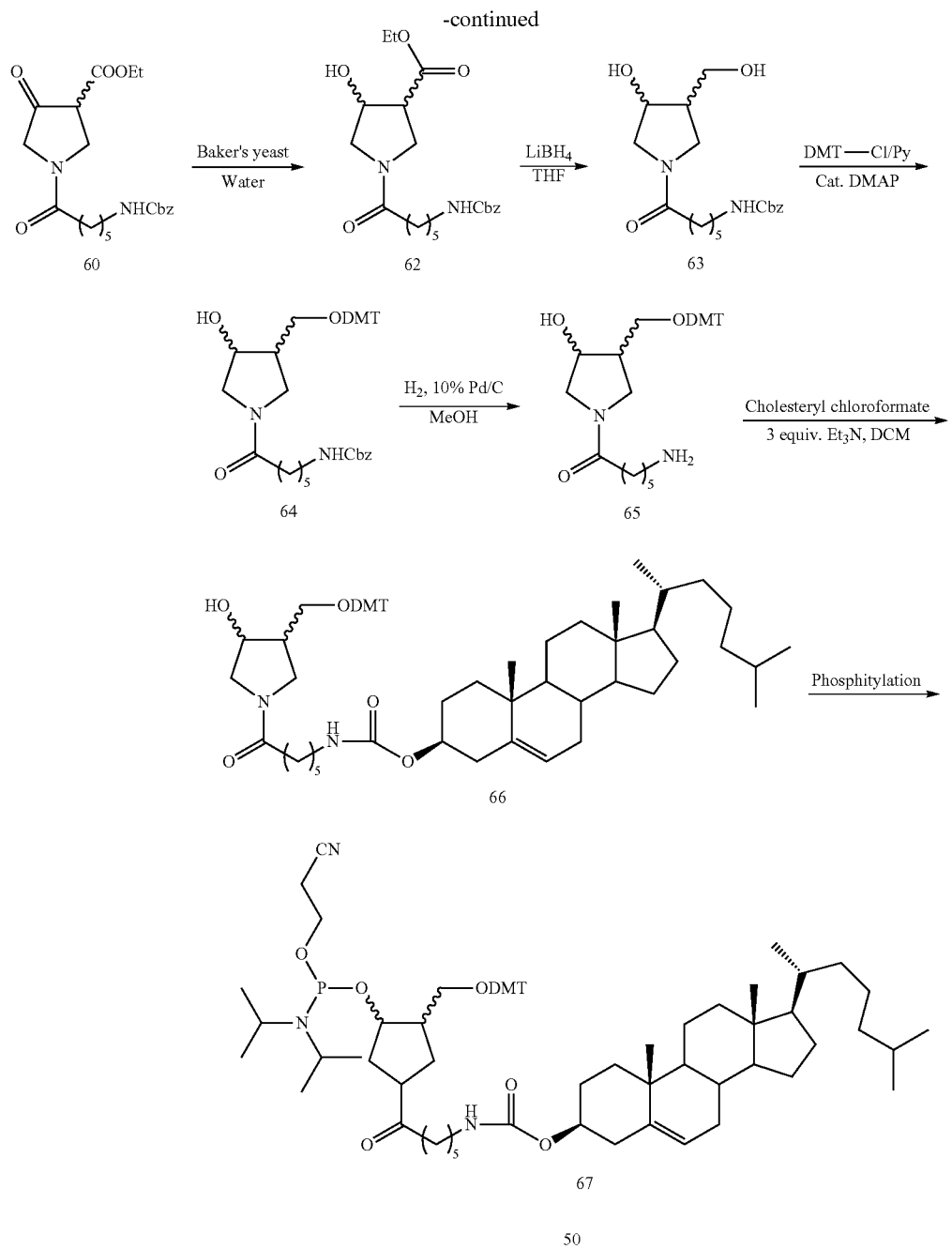

Synthesis of
3-(Ethoxycarbonylmethyl-amino)-propionic acid
ethyl ester (58)

Referring to scheme 16, a 4.7M aqueous solution of sodium hydroxide (50 mL) was added into a stirred, ice-cooled solution of ethyl glycinate hydrochloride (32.19 g, 0.23 mole) in water (50 mL). Then, ethyl acrylate (23.1 g, 0.23 mole) was added and the mixture was stirred at room temperature until the completion of reaction was ascertained by TLC (19 h). After 19 h which it was partitioned with dichloromethane (3×100 mL). The organic layer was dried with anhydrous sodium sulfate, filtered and evaporated. The residue was distilled to afford 58 (28.8 g, 61%).

$^1$H NMR (CDCl$_3$, 400 MHz): δ 4.1-4.2 (m, 4H), 3.4 (s, 2H), 2.8 (t, J=6.7 Hz, 2H), 2.4 (t, J=6.7 Hz, 2H), 1.25 (m, 6H).

Synthesis of 3-[(6-Benzyloxycarbonylamino-hex-anoyl)-ethoxycarbonylmethyl-amino]-propionic acid ethyl ester (59)

6-benzyloxyamino hexanoic acid (13.25 g, 50 mmol) was dissolved in anhydrous dichloromethane (50 mL) and cooled to 0° C. To the solution were added diisopropyl carbodiimide (6.31 g, 7.7 mL, 50 mmol) and triethylamine (10.2 g, 13.7 mL, 100 mmol). After stirring for 20 mins at 0° C., compound 58 (10.16 g, 50 mmol) was added and the stirring was continued at room temperature under argon for over night. The reaction mixture was evaporated to dryness. To the residue ethyl acetate (100 mL) was added and the filtered to remove diisopropyl urea. The precipitate was washed with ethyl acetate (50 mL). The combined organic layer was washed with 2N HCl, saturated sodium bicarbonate and water. The organic layer was dried over sodium sulfate, filtered and evaporated to dryness. Compound 59 ($R_f$=0.5 in 25% EtOAc/Hexane, 20.5 g) was obtained, which was directly used for the next step without further purification.

$^1$H NMR (CDCl$_3$, 400 MHz): δ 7.36 (m, 5H), 5.1 (s, 2H), 4.06-4.22 (m, 6H), 3.6-3.7 (m, 2H), 3.2 (m, 2H), 2.6 (m, 2H), 2.42 (m, 2H), 2.14 (m, 2H), 1.2-1.7 (m, 12H).

Synthesis of 1-(6-Benzyloxycarbonylamino-hexanoyl)-4-oxo-pyrrolidine-3-carboxylic acid ethyl ester (60)

To a suspension of potassium t-butoxide (7.12 g, 64 mmol) in toluene (150 mL) at 0° C. under nitrogen, was added diester 59 (20 g, 44 mmol) in toluene (25 mL) over a 10 min period. The solution was stirred for 30 min at 0° C. and 5 mL of glacial acetic acid was added, immediately followed by 25 g of NaH$_2$PO$_4$.H$_2$O in 250 mL of ice-cold water. The resultant mixture was extracted with chloroform (3×200 mL), and the combined organic extracts were washed twice with phosphate buffer (2×25 mL, pH=7.0), dried over anhydrous sodium sulfate and evaporated to dryness. The residue was dissolved in toluene (300 mL), cooled to 0° C., and extracted with cold pH 9.5 carbonate buffer (3×150 mL). The aqueous extracts were converted to pH 3 with phosphoric acid, and extracted with chloroform (5×125 mL) which were combined, dried, and evaporated to a afford keto ester 60 (12 g, 45%).

The toluene fraction was washed with water (25 mL), dried and evaporated to afford ketoester 61 (7.6 g, 28%).

$^1$H NMR (CDCl$_3$, 400 MHz): δ 7.35 (m, 5H), 5.1 (s, 2H), 4.05-4.34 (m, 6H), 3.8 (m, 1H), 3.2 (m, 4H), 2.6 (m, 1H), 2.2-2.4 (m, 1H), 1.68 (m, 1H), 1.52 (m, 1H), 1.24-1.4 (m, 6H).

Synthesis of 1-(6-Benzyloxycarbonylamino-hexanoyl)-4-hydroxy-pyrrolidine-3-carboxylic acid ethyl ester (62)

To a solution of sucrose (3 g) in distilled water (40 mL) was added Baker's yeast (2 g). The suspension was heated at 32° C. for 1 h. The content of the flask was then poured into a flask containing ketoester 60 (4 g, 9.88 mmol, dissolved in 4 mL of methanol). Stirring was continued at 32° C. for 24 h after which additional sucrose (3 g) in warm (40° C.) distilled water was added. After 48 h, the suspension was filtered through a pad of Celite. The pad was washed with water and the aqueous layer was extracted with ethyl acetate (3×250 mL). The combined organic layer was dried over anhydrous sodium sulfate, filtered and concentrated under reduced pressure. The residue was subjected to flash chromatography (30% EtOAc/Hexane) to afford alcohol 62 (1.7 g, 42%).

$^1$H NMR (CDCl$_3$, 400 MHz): δ 7.32 (m, 5H), 5.12 (s, 2H), 4.56 (m, 1H), 4.2 (m, 2H), 3.9 (m, 1H), 3.83 (m, 1H), 3.63 (m, 1H), 3.48 (m, 1H), 2.82-3.06 (m, 3H), 2.2 (t, 2H), 1.22-1.41 (m, 9H). (Also observed minor rotamer due to amide bond)

$^{13}$C NMR (CDCl$_3$, 100 MHz): δ 173.2, 172.5, 171.41, 156.78, 136.74, 128.60, 128.17, 128.11, 70.19, 68.38, 66.56, 60.56, 58.22, 57.71, 55.36, 54.60, 52.36, 40.78, 37.73, 34.2, 29.64, 24.22, 21.66, 14.29.

Synthesis of [6-(3-Hydroxy-4-hydroxymethyl-pyrrolidin-1-yl)-6-oxo-hexyl]-carbamic acid benzyl ester (63)

To the solution of lithium borohydride (0.305 g, 13 mmol) in anhydrous tetrahydrofuran (25 mL) was added a solution of ethyl ester 62 (3.74 g, 9.2 mmol) in THF (25 mL) over a period of 30 mins at 0° C. After the addition the reaction mixture was brought to room temperature and stirred further under argon. The completion of the reaction was ascertained by TLC after 4 h. ($R_f$=0.4 in 10% MeOH/CHCl$_3$). The reaction mixture was evaporated to dryness and cooled to 0° C. To the residue 3N HCl (40 mL) was added slowly. After stirring for 30 mins the product was extracted with dichloromethane (3×75 mL). The combined organic layer was washed with brine and dried over sodium sulfate. Organic layer was filtered and evaporated to dryness. Compound 63 was purified by column chromatography first by eluting with dichloromethane/methanol (5%) (3.2 g, 92%).

$^1$H NMR (CDCl$_3$, 400 MHz): δ 7.34 (m, 5H), 5.16 (s, 2H), 4.64 (m, 1H), 4.4 (bs, 1H), 4.2 (m, 1H), 3.78 (m, 2H), 3.62 (m, 3H), 3.5 (m, 2H), 2.06 (m, 4H), 1.55 (m, 4H), 1.2 (m, 2H).

Synthesis of (6-{3-[Bis-(4-methoxy-phenyl)-phenyl-methoxymethyl]-4-hydroxy-pyrrolidin-1-yl}-6-oxo-hexyl)-carbamic acid benzyl ester (64)

Referring to scheme 16, compound 63 (3.65 g, 10 mmol) was co-evaporated with anhydrous pyridine three times and then dissolved in pyridine (10 mL). To this solution dimethylamino pyridine (0.122 g, 1 mmol) and DMT-Cl (3.55 g, 10.5 mmol, 1.05 equiv.) were added at room temperature. The reaction mixture was stirred at room temperature for 16 h. The excess DMT-Cl was quenched by the addition of methanol (10 mL). The solution was dried under reduced pressure. To the residue was suspended in ethyl acetate (200 mL) and washed with saturated bicarbonate solution, brine and water. The organic layer was dried over anhydrous sodium sulfate, filtered and evaporated. The crude product was obtained after removal of the solvent. Upon purification over silica gel using 3% MeOH/DCM compound 64 (5.9 g, 88%) was obtained as white foamy solid.

$^1$H NMR (CDCl$_3$, 400 MHz): δ 7.24-7.38 (m, 13H), 7.18 (m, 2H), 6.84 (m, 3H), 5.1 (s, 2H), 4.96 (m, 1H), 4.36 (m, 2H), 3.74-3.8 (m, 8H), 3.52 (m, 2H), 3.2 (m, 3H), 1.88-2.38 (m, 4H), 1.28-1.72 (m, 6H)

$^{13}$C NMR (100 MHz, CDCl$_3$): δ 174.7, 172.7, 171.9, 171.3, 171.2, 158.8, 158.7, 158.6, 158.5, 158.4, 158.3, 156.7, 156.7, 156.6, 147.5, 145.8, 145.2, 144.9, 144.7, 144.4, 139.6, 137.1, 137.04, 137.01, 136.9, 136.82, 136.78, 136.55, 136.47, 136.45, 136.3, 136.28, 135.93, 135.85, 135.81, 130.2, 130.1, 130.0, 129.9, 129.3, 128.69, 128.66, 128.22, 128.16, 128.0, 127.99, 127.94, 127.91, 127.77, 113.52, 113.43, 113.35, 113.3, 113.24, 113.19, 113.03, 86.8, 86.1, 85.9, 73.0, 71.6, 71.5, 70.5, 69.3, 67.3, 67.1, 68.76, 68.71, 64.38, 63.7, 60.58, 60.0, 56.4, 55.8, 55.7, 55.45, 55.41, 55.35, 55.33, 40.97, 40.87, 40.77, 37.13, 36.83, 35.13, 35.00, 34.81, 34.6, 33.3, 29.8, 26.73, 25.5, 26.4, 26.2, 24.9, 24.6, 24.5, 24.3, 24.2, 21.1, 14.3.

Synthesis of 6-Amino-1-{3-[bis-(4-methoxy-phenyl)-phenyl-methoxymethyl]-4-hydroxy-pyrrolidin-1-yl}-hexan-1-one (65)

Compound 64 (5.9 g, 8.84 mmol) was dissolved in methanol (10 mL) and purged with argon. To the solution was added 10% palladium on carbon (0.6 g). The flask was purged with hydrogen 2 times and stirred further at room temperature under hydrogen atmosphere for overnight. The disappearance of the starting material was confirmed by the TLC. The reaction mixture was filtered through a pad of Celite and washed with methanol. The combined organic layer was concentrated under reduced pressure to afford compound 65 (4.3 g, 92%) as white solid. This was used as such for the next step.

¹H NMR (DMSO-d₆, 400 MHz): δ 7.16-7.36 (m, 9H), 6.88 (m, 4H), 4.4 (m, 1H), 4.16 (m, 1H), 3.72 (m, 6H), 3.56 (dd, 1H), 3.34 (m, 1H), 3.14 (m, 1H), 3.0 (m, 1H), 2.7 (m, 2H), 2.2 (m, 2H), 1.8-2.1 (m, 3H), 1.28-1.58 (m, 6H), 1.16 (m, 2H).

¹³C NMR (DMSO-d₆, 100 MHz): δ 170.84 (Minor disappears at 80° C.), 170.75, 165.82, 158.1, 157.98, 145.1, 144.76, 135.86, 135.74, 129.61, 129.57, 127.91, 127.81, 127.57, 126.61, 113.23, 113.31, 85.79, 85.11, 68.55 63.33, 56.76, 55.07, 55.02, 38.63, 36.27, 33.89, 32.34, 27.12, 27.05, 23.91, 20.77, 14.09.

Synthesis of (6-{3-[Bis-(4-methoxy-phenyl)-phenyl-methoxymethyl]-4-hydroxy-pyrrolidin-1-yl}-6-oxo-hexyl)-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester (66)

Referring to scheme 16, compound 65 (7.75 g, 14.5 mmol) was dissolved in anhydrous dichloromethane (50 mL) and cooled to 0° C. To the solution were added triethylamine (3 g, 4.2 mL, 30 mmol) and cholesteryl chloroformate (6.5 g, 29 mmol) successively. The reaction temperature was brought to ambient temperature and stirred further for 2 h. The completion of the reaction was ascertained by TLC (10% MeOH/CHCl₃). The reaction mixture was evaporated under the vacuum to afford the crude product. Compound 66 (12.4 g, 88%) was obtained as a white foamy solid after column chromatography over silica gel using 3% MeOH/DCM.

¹H NMR (400 MHz, DMSO-d₆): δ 7.12-7.3 (m, 8H), 6.95 (m, 1H), 6.84 (m, 4H), 5.3 (bs, 1H), 4.92 and 4.84 (d, OH, exchangeable with D₂O), 4.21-4.38 (m, 2H), 4.35 (m, 1H), 3.7 (s, 6H), 3.54 (m, 1H), 3.28 (m, 2H), 3.12 (m, 1H), 2.84-2.98 (m, 3H), 2.12-2.28 (m, 3H), 1.7-2.0 (m, 7H), 0.8-1.52 (m, 40H), 0.6 (s, 3H).

¹³C NMR (100 MHz, DMSO-d₆): δ 170.8, 158.0, 157.9, 155.6, 145.0, 139.7, 135.8, 135.7, 129.5, 127.7, 127.5, 121.7, 113.1, 113.0, 85.7, 85.1, 72.7, 68.5, 63.3, 56.1, 55.5, 54.9, 49.4, 41.8, 36.5, 35.2, 31.3, 27.7, 27.3, 26.0, 24.1, 23.8, 23.2, 22.6, 22.3, 20.5, 18.9, 18.5, 11.6.

M/S (ESI): Calculated: 944.63 Observed: 967.6 (M⁺+Na).

Synthesis of pyrrolidine-cholesterol phosphoramidite (67)

Compound 66 (0.15 g, 0.158 mmol) was coevaporated with toluene (5 mL). To the residue N,N-tetraisopropylammonium tetrazolide (0.0089 g, 0.079 mmol) was added and the mixture was dried over P₂O₅ in a vacuum oven for overnight at 40° C. The reaction mixture was dissolved in the mixture of anhydrous acetonitrile/dichloromethane (2;1, 1 mL) and 2-cyanoethyl-N,N,N',N'-tetraisopropylphosphorodiamidite (0.0714 g, 0.0781 mL, 0.237 mmol) was added. The reaction mixture was stirred at ambient temperature for overnight. The completion of the reaction was ascertained by TLC (1;1 ethyl acetate:hexane). The solvent was removed under reduced pressure and the residue was dissolved in ethyl acetate (10 mL) and washed with 5% NaHCO₃ (4 mL) and brine (4 mL). The ethyl acetate layer was dried over anhydrous Na₂SO₄ and concentrated under reduced pressure. The resulting mixture was chromatographed (50:49:1, EtOAc:Hexane:triethlyamine) to afford 67 as white foam (0.152 g, 84%).

¹H NMR (CDCl₃, 400 MHz): δ 7.36 (m, 2H), 7.24 (m, 7H), 6.8 (m, 4H), 5.38 (m, 1H), 4.7 (m, 1H), 4.5 (m, 1H), 4.36 (m, 1H), 3.5-3.8 (m, 9H), 3.36-3.6 (m, 4H), 3.14 (m, 3H), 2.58 (m, 2H), 1.8-2.38 (m, 12H), 0.84-1.68 (m, 51H), 0.66 (s, 3H).

³¹P NMR (161.82 MHz, CDCl₃): δ 146.3, 146.2, 145.98, 145.8, 145.63, 145.4 (multiple peaks due mixer of diastereomer and Rotamers observed after due to amide bond at the ring)

¹³C NMR (CDCl₃, 100 MHz): δ 171.6, 158.75, 158.58, 156.36, 145.32, 144.78, 140.10, 136.48, 136.36, 136.32, 135.84, 130.19, 129.24, 128.44, 128.27, 128.21, 128.13, 127.97, 127.15, 126.92, 125.51, 122.62, 117.87, 117.79, 113.40, 113.25, 86.16, 86.11, 74.31, 72.39, 63.92, 58.5, 58.3, 58.1, 56.8, 56.3, 55.9, 55.8, 55.4, 55.3, 52.2, 43.4, 43.3, 42.5, 40.8, 39.9, 39.7, 38.7, 37.2, 36.7, 36.3, 36.0, 35.0, 32.1, 32.0, 30.0, 28.45, 28.4, 28.2, 26.8, 24.8, 24.7, 24.69, 24.6, 24.5, 24.0, 23.0, 22.7, 21.6, 21.2, 20.6, 20.59, 20.52, 19.5, 18.9, 11.6

Synthesis of Succinic acid mono-(4-[bis-(4-methoxy-phenyl)-phenyl-methoxymethyl]-1-{6-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}-pyrrolidin-3-yl) ester (68)

Referring to scheme 17, Compound 66 (12 g, 12.69 mmol) was mixed with succinic anhydride (1.9 g, 19 mmol) and DMAP (1.56 g, 13 mmol) and dried in a vacuum at 40° C. overnight. The mixture was dissolved in anhydrous dichloromethane (50 mL), triethylamine (2 g, 3.6 mL, 26 mmol) was added and the solution was stirred at room temperature under argon atmosphere for 16 h. It was then diluted with dichloromethane (100 mL) and washed with ice cold aqueous citric acid (5% wt., 100 mL) and water (2×100 mL). The organic phase was dried over anhydrous sodium sulfate and concentrated to dryness. The crude product was purified by column chromatography to afford compound 68 as white solid (12.1 g, 91% yield; R$_f$=0.5 in 10% MeOH/CHCl₃).

¹H NMR (400 MHz, DMSO-d₆): δ 7.12-7.32 (m, 9H), 6.82 (m, 4H), 5.3 (m, 2H), 4.26 (m, 1H), 4.06 (m, 1H), 3.6-3.78 (m, 8H), 3.52 (m, 1H), 3.2 (m, 1H), 3 (m, 2H), 2.88 (m, 2H), 2.7 (m, 1H), 2.1-2.24 (m, 6H), 1.84-2.04 (m, 3H), 1.75 (m, 4H), 0.8-1.52 (m, 39H), 0.62 (m, 3H)

¹³C NMR (100 MHz, DMSO-d₆): δ 173.42, 171.97, 170.66, 158.12, 157.99, 156.63, 144.97, 144.67, 139.77, 135.73, 135.59, 135.38, 129.61, 127.88, 127.8, 127.57, 126.61, 121.8, 113.2. 113.12, 85.96, 85.26, 72.81, 72.73, 63.24, 56.12, 55.58, 55.0, 54.97, 54.84, 49.47, 41.85, 36.60, 35.66, 35.22, 33.09, 31.38, 29.33, 28.84, 28.74, 27.9, 27.8, 27.4, 25.96, 24.40, 23.86, 23.23, 22.66, 22.39, 20.57, 18.98, 18.53, 11.66, 10.01.

Scheme 17. Synthesis of cholesterol immobilized solid support with pyrrolidine linker

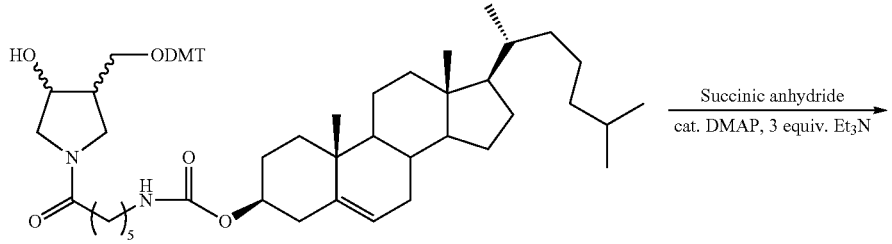

66

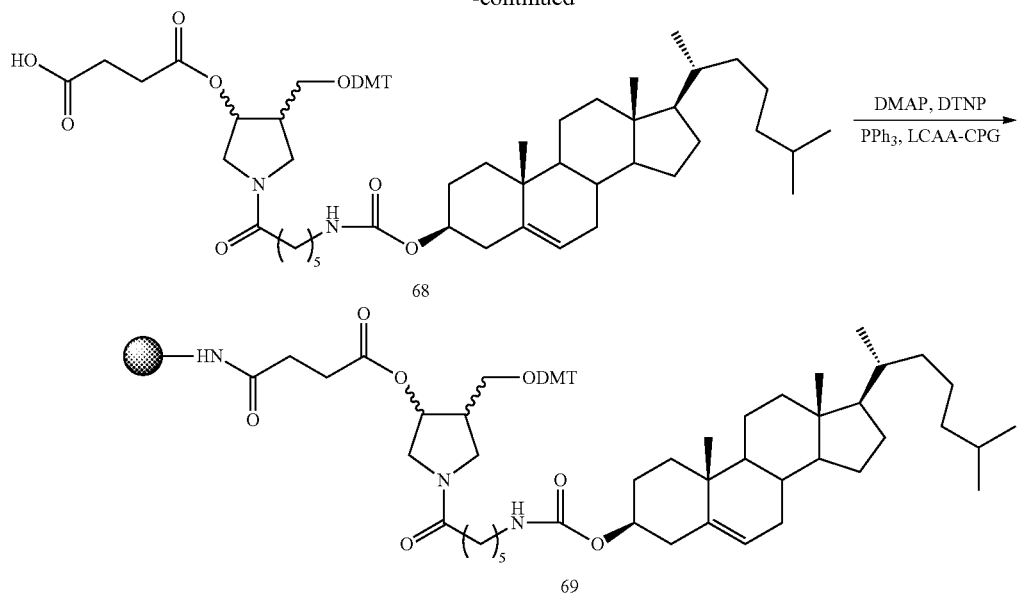

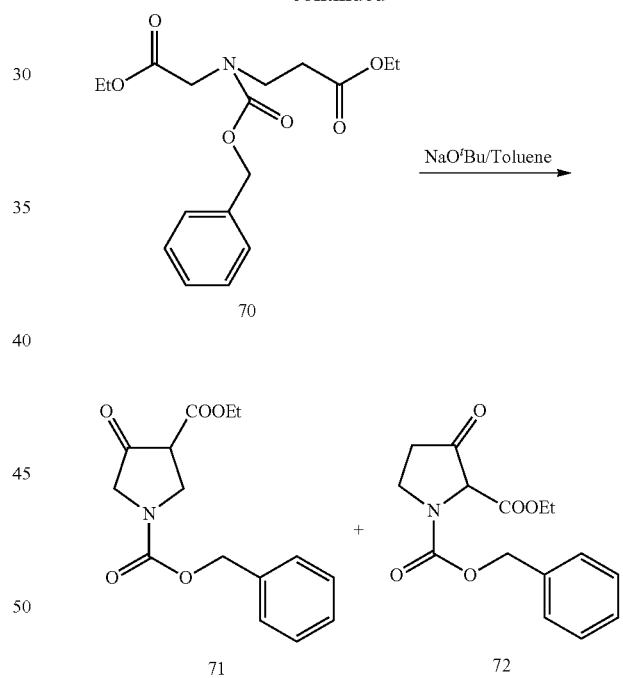

Synthesis of Cholesterol Immobilized Solid Support with Pyrrolidine Linker (69)

Succinate 68 (8.4 g, 8 mmol) was dissolved in dichloroethane (40 mL). To that solution DMAP (0.977 g, 8 mmol) was added. 2,2'-Dithio-bis(5-nitropyridine) (2.49 g, 8 mmol) in acetonitrile/dichloroethane (3:1, 40 mL) was added successively. To the resulting solution triphenylphosphine (2.1 g, 8 mmol) in acetonitrile (20 ml) was added. The reaction mixture turned bright orange in color. The solution was agitated briefly using wrist-action shaker (5 mins). Long chain alkyl amine-CPG (LCAA-CPG) (30 g, 155 μm/g) was added. The suspension was agitated for 4 h. The CPG was filtered through a sintered funnel and washed with acetonitrile, dichloromethane and ether successively. Unreacted amino groups were masked using acetic anhydride/pyridine. The loading capacity of the CPG was measured by taking UV measurement. (82 μM/g).

Synthesis of Phthalimido-Pyrrolidine Phosphoramidite

Scheme 18. Synthesis of hydroxy-prolinol-phthalimido phosphoramidite

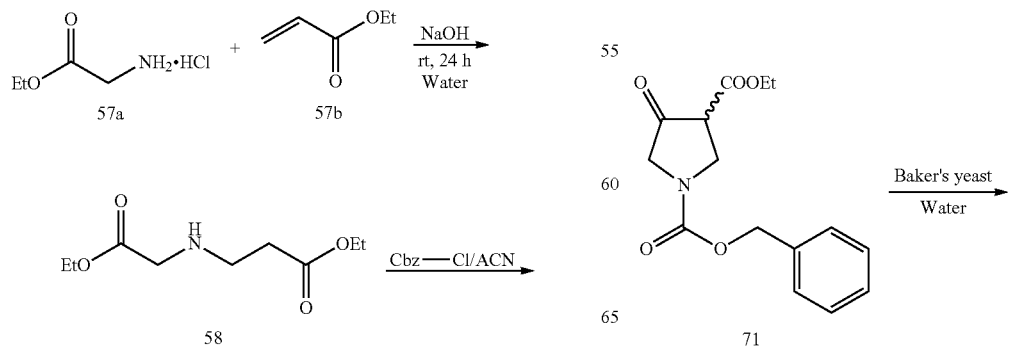

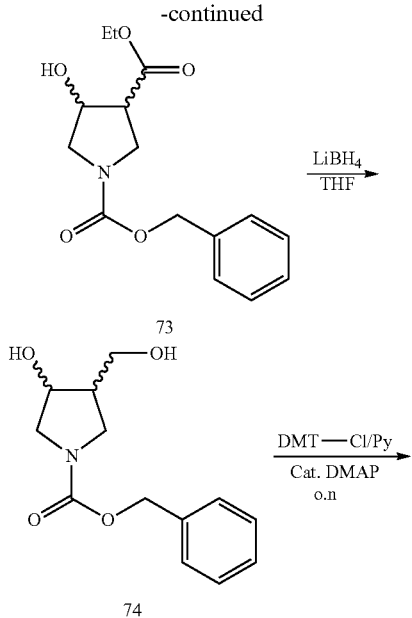

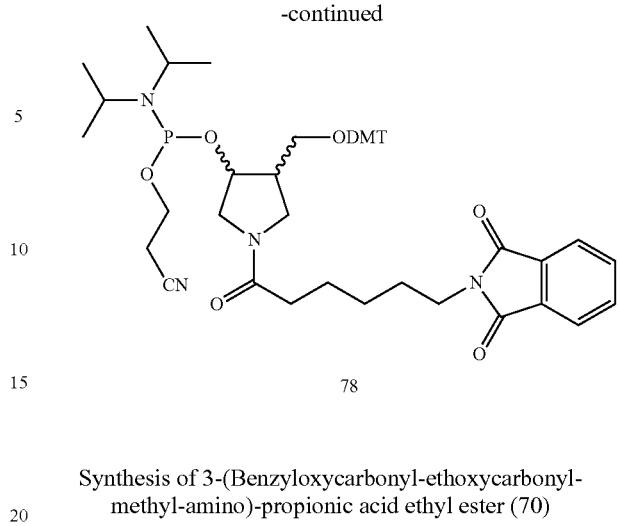

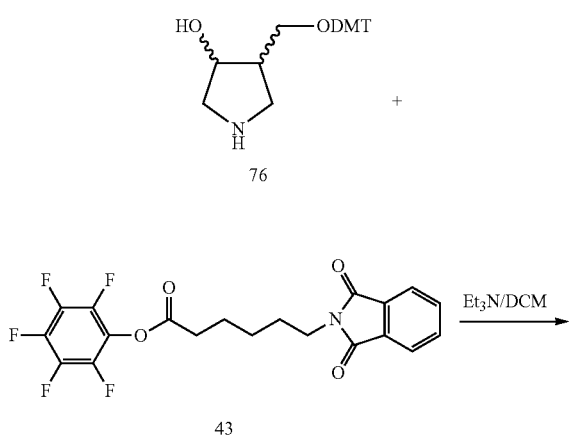

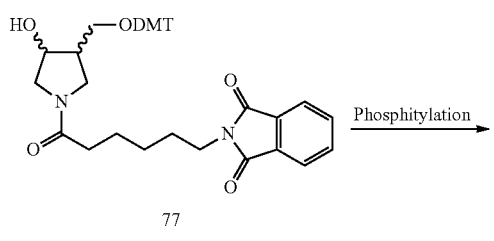

Synthesis of 3-(Benzyloxycarbonyl-ethoxycarbonyl-methyl-amino)-propionic acid ethyl ester (70)

To a solution of diester 58 (3.88 g, 20.2 mmol) in dry acetonitrile (40 mL) at 0° C., under Argon, was added slowly benzyl chloroformate (3.17 mL, 1.1 equiv.). The solution was stirred at 0° C. for 1 h after which it was poured into water (50 mL). The phases were separated and the aqueous layer was extracted with dichloromethane (3×50 mL). the combined organic extracts were washed with 5% HCl, water, brine and dried over anhydrous sodium sulfate. Evaporation of the solvents was followed by distillation to afford compound 70 as a colorless oil (5.4 g, 80%).

$^1$H NMR (400 MHz, CDCl$_3$): δ 7.18-7.4 (m, 5H), 5.13 (s, 2H), 4.12 (q, 2H, J=7.1 Hz), 4.06 (q, 2H, J=7.1 Hz), 3.58 (t, 2H, J=6.4 Hz), 2.6 (t, 2H, J=6.4 Hz), 1.18 (t, 3H, J=7.1 Hz), 1.2 (t, 3H, J=7.1 Hz).

$^{13}$C NMR (100 MHz, CDCl$_3$): δ 172.7, 170.4, 156.7, 136.8, 129, 128.9, 128.4, 128.3, 128.2, 68, 61.6, 61.1, 50.9, 45.8, 34.6, 14.6.

Synthesis of 4-Oxo-pyrrolidine-1,3-dicarboxylic acid 1-benzyl ester 3-ethyl ester (71)

To a suspension of potassium t-butoxide (2.52 g, 22.4 mmol, 1.4 equiv.) in toluene (50 mL) at 0° C. under nitrogen, was added diester 70 (5.41 g, 16 mmol) in toluene (10 mL) over a 10 min period. The solution was stirred for 30 min at 0° C. and 2 mL of glacial acetic acid was added, immediately followed by 10 g of NaH$_2$PO$_4$.H$_2$O in 100 mL of ice-cold water. The resultant mixture was extracted with chloroform (3×150 mL), and the combined organic extracts were washed twice with phosphate buffer (2×25 mL, pH=7.0), dried over anhydrous sodium sulfate and evaporated to dryness. The residue was dissolved in toluene (200 mL), cooled to 0° C., and extracted with cold pH 9.5 carbonate buffer (3×150 mL). The aqueous extracts were converted to pH 3 with phosphoric acid, and extracted with chloroform (5×125 mL) which were combined, dried, and evaporated to a afford keto ester 71 (2.2 g, 42%).

The toluene fraction was washed with water (10 mL), dried and evaporated to afford ketoester 72 (1.3 g, 24%).

$^1$H NMR (400 MHz, CDCl$_3$): δ 7.2 (m, 5H), 5.18 (s, 2H), 4.25 (m, 4H), 4.1 (m, 1H), 3.94 (m, 1H), 3.62 (m, 1H), 1.3 (m, 3H).

$^{13}$C NMR (100 MHz, CDCl$_3$): δ 203.29, 166.14, 153.56, 136.36, 127.89, 127.34, 127.04, 65.96, 60.75, 52.77, 51.84, 45.55, 13.41

Synthesis of 4-Hydroxy-pyrrolidine-1,3-dicarboxylic acid 1-benzyl ester 3-ethyl ester (73)

To a solution of sucrose (3 g) in distilled water (40 mL) was added Baker's yeast (2 g). The suspension was heated at 32° C. for 1 h. The content of the flask was then poured into a flask containing ketoester 71 (2.9 g, 9.88 mmol, dissolved in 4 mL of methanol). Stirring was continued at 32° C. for 24 h after which additional sucrose (3 g) in warm (40° C.) distilled water was added. After 48 h, the suspension was filtered through a pad of Celite. The pad was washed with water and the aqueous layer was extracted with ethyl acetate (3×250 mL). The combined organic layer was dried over anhydrous sodium sulfate, filtered and concentrated under reduced pressure. The residue was subjected to flash chromatography (30% EtOAc/Hexane) to afford alcohol 73 (1.2 g, 41%).

$^1$H NMR (CDCl$_3$, 400 MHz): δ 7.36 (m, 5H), 5.1 (m, 3H), 4.1 (m, 3H), 3.88 (m 2H), 3.5 (m, 1H), 3.34 (m, 2H), 1.2 (m, 3H) (Also observed minor rotamer due to amide bond).

Synthesis of 3-Hydroxy-4-hydroxymethyl-pyrrolidine-1-carboxylic acid benzyl ester (74)

To the solution of lithium borohydride (0.305 g, 13 mmol) in anhydrous tetrahydrofuran (25 mL) was added a solution of ethyl ester 73 (2.69 g, 9.2 mmol) in THF (25 mL) over a period of 30 mins at 0° C. After the addition the reaction mixture was brought to room temperature and stirred further under argon. The completion of the reaction was ascertained by TLC after 4 h. (R$_f$=0.3 in 10% MeOH/CHCl$_3$). The reaction mixture was evaporated to dryness and cooled to 0° C. To the residue 3N HCl (40 mL) was added slowly. After stirring for 30 mins the product was extracted with dichloromethane (3×75 mL). The combined organic layer was washed with brine and dried over sodium sulfate. Organic layer was filtered and evaporated to dryness. Compound 74 was purified by column chromatography first by eluting with dichloromethane/methanol (5%) (1.98 g, 85%).

$^1$H NMR (CDCl$_3$, 400 MHz): δ 7.36 (m, 5H), 5.16 (s, 2H), 4.62 (m, 1H), 4.4 (bs, 1H), 4.2 (m, 1H), 3.8 (m, 2H), 3.64 (m, 3H), 3.5 (m, 2H). (Also observed minor rotamer due to amide bond).

Synthesis of 3-[Bis-(4-methoxy-phenyl)-phenyl-methoxymethyl]-4-hydroxy-pyrrolidine-1-carboxylic acid benzyl ester (75)

Referring to scheme 18, compound 74 (4.39 g, 17.5 mmol) was co-evaporated with anhydrous pyridine three times and then dissolved in pyridine (30 mL). To this solution dimethylamino pyridine (0.213 g, 1.75 mmol) and DMT-Cl (6.22 g, 18.4 mmol, 1.05 equiv.) were added at room temperature. The reaction mixture was stirred at room temperature for 16 h. The excess DMT-Cl was quenched by the addition of methanol (10 mL). The solution was dried under reduced pressure. To the residue was suspended in ethyl acetate (300 mL) and washed with saturated bicarbonate solution, brine and water. The organic layer was dried over anhydrous sodium sulfate, filtered and evaporated. The crude product was obtained after removal of the solvent. Upon purification over silica gel using 3% MeOH/DCM compound 75 (8.46 g, 87%) was obtained as white foamy solid.

$^1$H NMR (CDCl$_3$, 400 MHz): δ 7.18-7.4 (m, 14H), 6.8 (m, 4H), 5.1 (s, 2H), 5.0 (m, 1H), 4.54 (m, 1H), 4.18 (m, 2H), 3.78 (s, 6H), 3.6 (m, 2H), 3.14 (m, 1H), 2.02 (m, 1H), 1.74 (m, 1H). (Also observed minor rotamer due to amide bond).

$^{13}$C NMR (CDCl$_3$, 100 MHz): δ 158.81, 158.59, 147.52, 145.18, 139.65, 136.64, 136.31, 130.17, 129.33, 128.76, 128.58, 128.37, 128.28, 128.18, 128.05, 127.96, 127.28, 126.93, 113.35, 113.24, 86.1, 81.62, 69.93, 67.66, 67.16, 66.81, 55.45, 55.39, 37.64.

Synthesis of 4-[Bis-(4-methoxy-phenyl)-phenyl-methoxymethyl]-pyrrolidin-3-ol (76)

Compound 75 (8.25 g, 14.9 mmol) was dissolved in methanol (20 mL) and purged with argon. To the solution was added 10% palladium on carbon (0.825 g). The flask was purged with hydrogen 2 times and stirred further at room temperature under hydrogen atmosphere for 3 h. The disappearance of the starting material was confirmed by the TLC. The reaction mixture was filtered through a pad of Celite and washed with methanol. The combined organic layer was concentrated under reduced pressure to afford amine 76 (6.12 g, 98%) as white solid. This was used as such for the next step.

$^1$H NMR (DMSO-d$_6$, 400 MHz): δ 8.3 (s, 1H), 7.38 (m, 2H), 7.22 (m, 7H), 6.84 (m, 4H), 4.2 (m, 1H), 3.7 (s, 6H), 3.6 (m, 1H), 3.0 (m, 3H), 2.8 (m, 1H), 1.74 (m, 1H), 1.5 (m, 1H).

$^{13}$C NMR (DMSO-d$_6$, 100 MHz): δ 165.02, 158.06, 144.90, 135.55, 129.74, 127.81, 127.72, 126.67, 113.15, 85.58, 69.6, 59.76, 56.81, 55.02, 53.62.

Synthesis of 2-(6-{3-[Bis-(4-methoxy-phenyl)-phenyl-methoxymethyl]-4-hydroxy-pyrrolidin-1-yl}-6-oxo-hexyl)-isoindole-1,3-dione (77)

Referring to scheme 18, compound 76 (4.2 g, 10 mmol) was dissolved in anhydrous dichloromethane (25 mL) and cooled to 0° C. To the solution were added triethylamine (1.01 g, 1.4 mL, 10 mmol) and ester 43 (4.3 g, 10 mmol) successively. The reaction temperature was brought to ambient temperature and stirred further for 2 h. The completion of the reaction was ascertained by TLC (10% MeOH/CHCl$_3$). The reaction mixture was diluted with DCM (100 mL) and washed with 10% NaOH solution. The organic layer was washed with brine, water and dried over anhydrous sodium sulfate and filtered. The crude product was obtained by evaporating the solvent under the vacuum. Compound 77 (5.4 g, 81%) was obtained as a white foamy solid after column chromatography over silica gel using 4% MeOH/DCM.

$^1$H NMR (DMSO-d$_6$, 400 MHz): δ 7.84 (m, 4H), 7.28 (m, 4H), 7.18 (m, 5H), 6.86 (m, 4H), 4.98 (d, —OH, D$_2$O exchangeable), 4.38 (m, 1H), 4.3 (m, 1H), 3.72 (s, 6H), 3.53 (m, 3H), 3.3 (m, 1H), 3.14 (m, 1H), 2.98 (m, 2H), 2.2 (m, 2H), 2.0 (m, 2H), 1.44-1.62 (m, 2H), 1.3 (m, 2H), 1.13 (m, 1H)

$^{13}$C NMR (DMSO-d$_6$, 100 MHz): δ 172.78, 172.11, 168.74, 168.67, 158.74, 158.55, 158.54, 145.24, 144.72, 136.46, 136.27, 137.87, 135.84, 134.18, 134.13, 134.09, 132.3, 132.27, 130.18, 130.11, 129.33, 128.22, 128.20, 128.08, 128.03, 127.93, 127.12, 126.89, 123.41, 123.38, 113.35, 113.2, 86.7, 86.06, 70.7, 69.46, 65.51, 63.67, 56.61, 56.0, 55.9, 55.42, 55.36, 54.2, 38.44, 38.0, 37.98, 36.9, 35.0, 33.4, 28.6, 28.5, 28.4, 26.79, 26.71, 25.0, 24.6, 24.5.

Pyrrolidine-phthalimido phosphoramidite (78)

Compound 77 (1.5 g, 2.26 mmol) was coevaporated with anhydrous toluene (25 mL). To the residue N,N-tetraisopropylammonium tetrazolide (0.127 g, 1.13 mmol) was added and the mixture was dried over P$_2$O$_5$ in a vacuum oven for overnight at 40° C. The reaction mixture was dissolved in acetonitrile/dichloroethane (10 mL) and 2-cyanoethyl-N,N, N',N'-tetraisopropylphosphorodiamidite (1.362 g, 1.49 mL, 4.52 mmol) was added. The reaction mixture was stirred at ambient temperature for overnight. The completion of the reaction was ascertained by TLC ($R_f$=0.4 in 1:1 ethyl acetate: hexane). The reaction mixture was concentrated under-vacuum and the residue was dissolved in ethyl acetate (100 mL). The organic layer was washed with 5% $NaHCO_3$ (100 mL) and brine (100 mL). The organic layer was dried over anhydrous $Na_2SO_4$ filtered and concentrated under reduced pressure. The residue was purified over silica gel (50:49:1, EtOAc:Hexane:triethlyamine) to afford compound 78 as white solid (1.66 g, 85%).

$^1$H NMR (400 MHz, $C_6D_6$): δ 7.62 (m, 2H), 7.42 (m, 6H), 7.22 (t, 2H), 7.08 (m, 1H), 6.88 (dd, 2H), 6.78 (m, 4H), 4.66 (m, 1H), 4.56 (m, 1H), 3.72 (m, 1H), 3.5 (m, 5H), 3.3 (m, 7H), 3.22 (m, 1H), 2.1 (m, 5H), 1.74 (m, 4H), 1.56 (m, 2H), 1.26 (m, 2H), 1.1 (m, 13H).

$^{31}$P NMR (161.82 MHz, $C_6D_6$): δ 146.3, 146.2, 145.98, 145.8, 145.63, 145.4 (multiple peaks due mixer of diastereomer and Rotamers observed after due to amide bond at the ring)

$^{13}$C NMR (100 MHz, $C_6D_6$): δ 171.03, 170.08, 167.98, 159.23, 159.0, 146.1, 136.76, 136.69, 136.64, 136.27, 133.35, 132.7, 130.59, 130.54, 130.46, 128.65, 128.56, 127.55, 126.97, 128.24, 128.0, 127.7, 122.84, 113.62, 113.53, 113.51, 86.57, 86.51, 72.67, 72.5, 72.33, 64.48, 58.59, 58.46, 58.41, 58.28, 57.77, 56.03, 55.97, 54.81, 54.73, 43.47, 43.35, 37.87, 36.42, 36.32, 34.94, 34.88, 33.37, 28.77, 26.94, 24.67, 24.6, 24.51, 20.10, 20.04, 19.98.

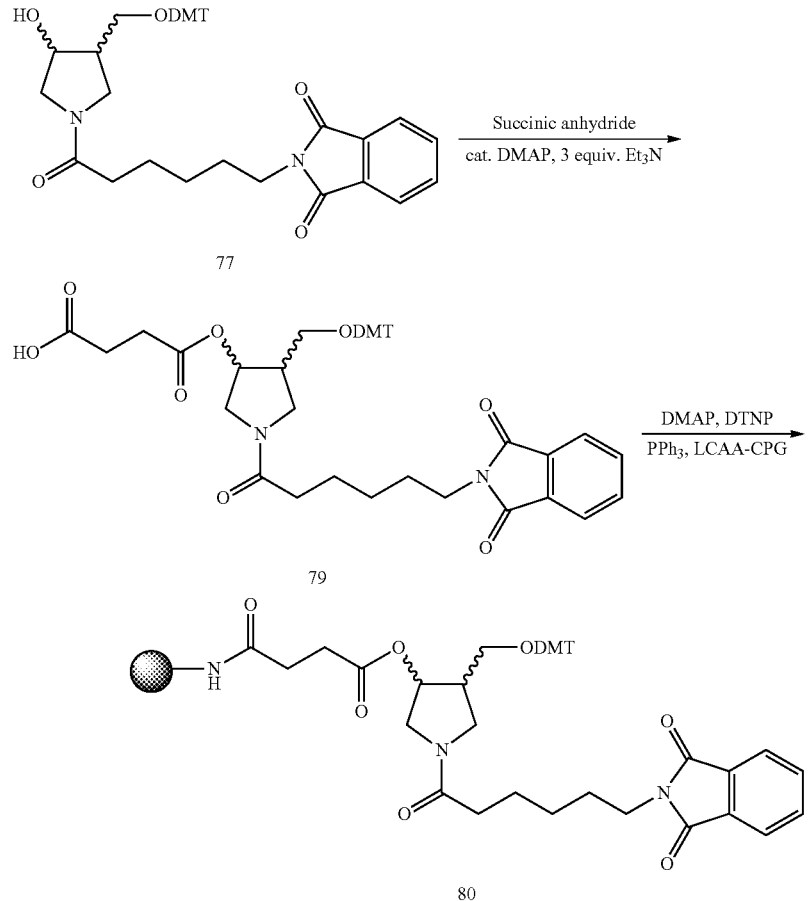

Scheme 19. Synthesis of phthalimido-pyrrolidine immoblilized on a solid support

Synthesis of Succinic acid mono-{4-[bis-(4-methoxy-phenyl)-phenyl-methoxymethyl]-1-[6-(1,3-dioxo-1,3-dihydro-isoindol-2-yl)-hexanoyl]-pyrrolidin-3-yl}ester (79)

Referring to scheme 19, Compound 77 (2 g, 3 mmol) was mixed with succinic anhydride (0.600 g, 6 mmol) and DMAP (0.366 g, 3 mmol) and dried in a vacuum at 40° C. overnight. The mixture was dissolved in anhydrous dichloromethane (5 mL), triethylamine (0.913 g, 1.25 mL, 9 mmol) was added and the solution was stirred at room temperature under argon atmosphere for 4 h. It was then diluted with dichloromethane (50 mL) and washed with ice cold aqueous citric acid (5% wt., 50 mL) and water (2×50 mL). The organic phase was dried over anhydrous sodium sulfate and concentrated to dryness. The crude product was purified by column chromatography using 6% MeOH/DCM to afford compound 79 as white solid (2.05 g, 89% yield; $R_f$=0.4 in 10% MeOH/$CHCl_3$).

$^1$H NMR (400 MHz, DMSO-$d_6$): δ 7.8 (m, 4H), 7.26 (m, 4H), 7.14 (m, 5H), 6.83 (m, 4H), 4.92 (d, —OH, $D_2O$ exchangeable), 4.38 (m, 1H), 4.1 (m, 1H), 3.68 (s, 6H), 3.52 (m, 2H), 3.3 (m, 2H), 3.1 (m, 1H), 2.95 (m, 1H), 2.18 (m, 6H), 1.98 (m, 2H), 1.44-1.58 (m, 4H), 1.26 (m, 2H)

$^{13}$C NMR (100 MHz, DMSO-$d_6$): δ 170.78, 167.94, 158.07, 157.96, 145.07, 135.86, 135.44, 134.36, 131.61, 129.6, 127.78, 127.57, 126.58, 122.99, 113.10, 85.10, 68.56, 54.98, 37.28, 27.87, 26.01, 24.03.

Synthesis of Phthalimido-Pyrrolidine Immobilized on a Solid Support (80)

Succinate 79 (0.900 g, 1.17 mmol) was dissolved in dichloroethane:ACN (1:1, 5 mL). To that solution DMAP (0.144 g, 1.17 mmol) was added. 2,2'-Dithio-bis(5-nitropyridine) (0.360 g, 1.17 mmol) in acetonitrile/dichloroethane (3:1, 5 mL) was added successively. To the resulting solution triphenylphosphine (0.306 g, 1.17 mmol) in acetonitrile (2.5 ml) was added. The reaction mixture turned bright orange in color. The solution was agitated briefly using wrist-action shaker (5 mins). Long chain alkyl amine-CPG (LCAA-CPG) (3.5 g, 155 µm/g) was added. The suspension was agitated for 4 h. The CPG was filtered through a sintered funnel and washed with acetonitrile, dichloromethane and ether successively. Unreacted amino groups were masked using acetic anhydride/pyridine. The loading capacity of the CPG 80 was measured by taking UV measurement. (87 µM/g)

Synthesis of Extended Steroid Conjugates with Hydroxyl-Prolinol Linker

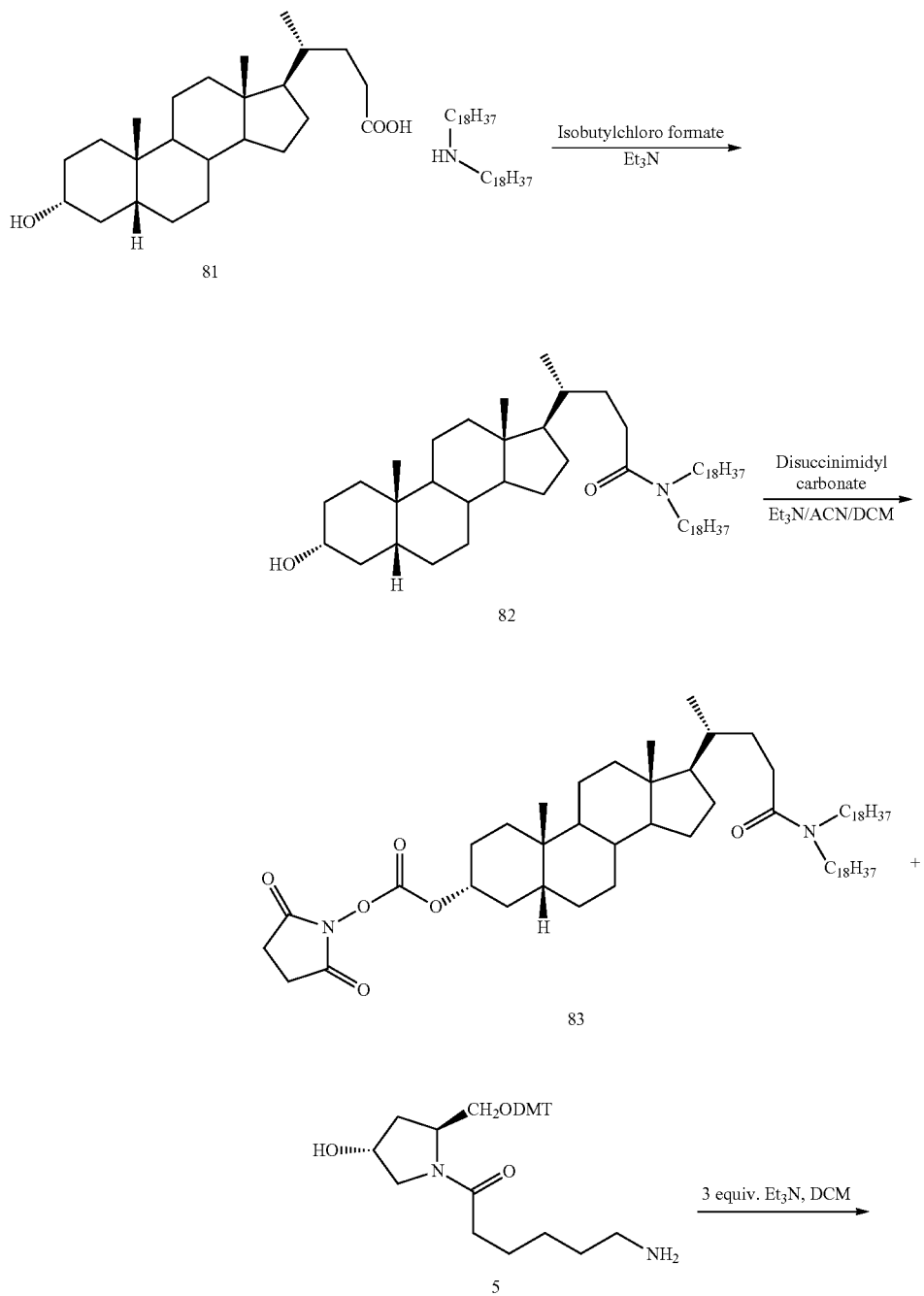

Scheme 20. Synthesis of extended steroid conjugates phosphoramidite wth hydroxyl-prolinol linker

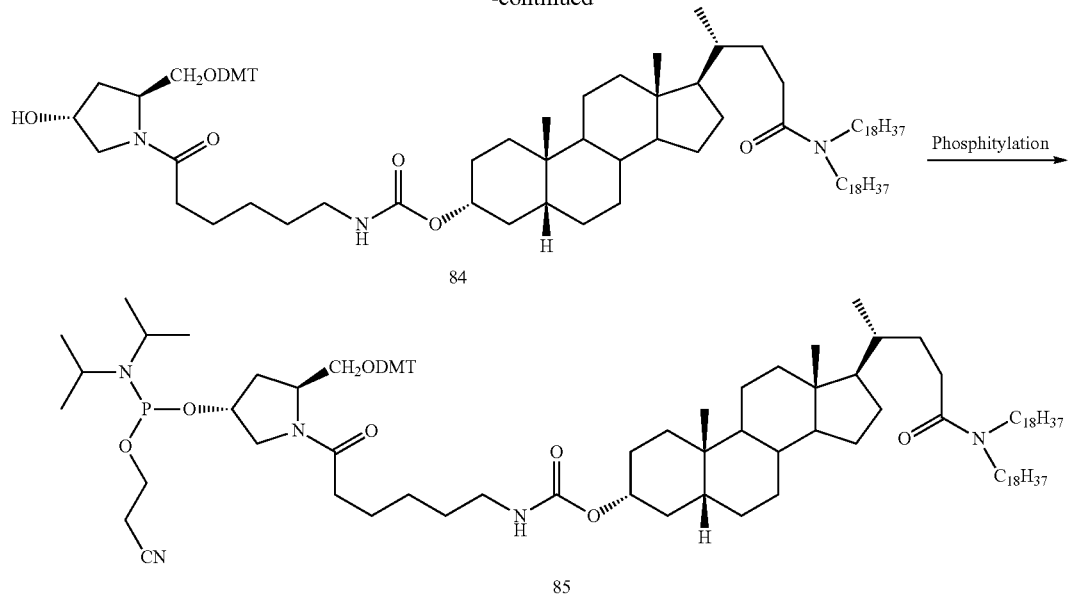

Synthesis of 4-(3-Hydroxy-10,13-dimethyl-hexadecahydro-cyclopenta[a]phenanthren-17-yl)-pentanoic acid dioctadecylamide (82)

Lithocholic acid (81) (7.1 g, 18.8 mmol) was dissolved in anhydrous tetrahydrofuran (60 mL). Isobutylchloroformate (2.6 g, 2.6 mL, 18.8 mmol) was added followed by the addition of triethylamine (3.84 g, 5.3 mL, 38 mmol) and dioctadecylamine (9.8 g, 18.77 g). The reaction mixture was brought to ambient temperature and allowed to stir over night. The reaction mixture was concentrated under vacuum, and the residue was dissolved in dichloromethane (250 mL). The organic layer was washed with 5% sodium bicarbonate, 3% aqueous HCl and water. After drying over anhydrous sodium sulfate, the solvent was removed under reduced pressure to afford amide 82 (15.5 g) in 93% yield. This was used as such for the next step.

$^1$H NMR (400 MHz, CDCl$_3$): δ 3.84 (d, —OH, D$_2$O exchangeable), 3.64 (m, 1H), 3.16-3.34 (m, 4H), 2.32 (m, 1H), 2.18 (m, 1H), 1.22-1.98 (m, 83H), 0.84-1.18 (m, 17H), 0.64 (s, 3H)

$^{13}$C NMR (100 MHz, CDCl$_3$): δ 173.3, 72.1, 71.04, 56.7, 56.3, 56.19, 48.2, 46.07, 42.96, 42.32, 40.65, 40.41, 36.70, 36.07, 35.87, 35.57, 34.79, 32.13, 31.92, 30.77, 30.37, 29.83, 29.8, 29.78, 29.72, 29.68, 29.4, 28.47, 28.3, 28.03, 27.41, 27.29, 27.13, 27.09, 26.63, 24.45, 23.59, 22.9, 21.05, 19.41, 18.76, 18.48, 14.32, 12.28.

Synthesis of Carbonic acid 17-(3-dioctadecylcarbamoyl-1-methyl-propyl)-10,13-dimethyl-hexadecahydro-cyclopenta[a]phenanthren-3-yl ester 2,5-dioxo-pyrrolidin-1-yl ester (83)

Referring to scheme 20, amide 82 (15.5 g, 17.6 mmol) was dissolved in anhydrous dichloromethane (150 mL). To the solution were added disuccinimidyl carbonate (6.76 g, 26.4 mmol), triethylamine (10 mL) and acetonitrile (50 mL). The reaction mixture was stirred at room temperature under argon for 6 h and then evaporated dryness. The residue was dissolved in dichloromethane (300 mL). It was washed with saturated NaHCO$_3$ aqueous solution (3×100 mL). The organic layer was dried over Na$_2$SO$_4$, filtered and evaporated to dryness. Compound 83 (12.3 g, 71%) was obtained as colorless powder after drying in high vacuum, which was directly used for the next step without further purification.

$^1$H NMR (400 MHz, CDCl$_3$): δ 4.7 (m, 1H), 3.15-3.34 (m, 4H), 2.82 (s, 4H), 2.32 (m, 1H), 2.16 (m, 1H), 1.66-2.0 (m, 10H), 1.2-1.58 (m, 78H), 0.86-1.12 (14H), 0.64 (s, 3H).

$^{13}$C NMR (100 MHz, CDCl$_3$): δ 173.34, 168.98, 151.08, 83.17, 71.37, 56.58, 56.31, 48.21, 46.06, 42.91, 42.09, 40.61, 40.26, 35.95, 35.81, 35.33, 34.96, 34.75, 34.69, 32.10, 31.19, 31.88, 29.89, 29.85, 29.79, 29.54, 28.41, 28.27, 27.96, 27.26, 27.09, 27.06, 26.42, 25.82, 25.77, 25.73, 25.66, 25.6, 24.38, 23.56, 23.34, 22.87, 21.02, 20.35, 19.37, 18.83, 18.73, 18.53, 14.3, 12.25.

Synthesis of (6-{2-[Bis-(4-methoxy-phenyl)-phenyl-methoxymethyl]-4-hydroxy-pyrrolidin-1-yl}-6-oxo-hexyl)-carbamic acid 17-(3-dioctadecylcarbamoyl-1-methyl-propyl)-10,13-dimethyl-hexadecahydro-cyclopenta[a]phenanthren-3-yl ester (84)

Amine 5 (4.22 g, 7.9 mmol) was dissolved in anhydrous dichloromethane (25 mL) and cooled to 0° C. To the solution were added pyridine (10 mL) and compound 83 (8.1 g, 7.9 mmol) successively. The reaction temperature was brought to ambient temperature and stirred further for 3 h. The completion of the reaction was ascertained by TLC (EtOAc, R$_f$=0.8). The reaction mixture was diluted with dichloromethane and washed with saturated NaHCO$_3$, water followed by brine. The organic layer was dried over sodium sulfate, filtered and concentrated under vacuum to afford the crude product. Compound 12 (8.8 g, 77%) was obtained as a white solid after column chromatography over silica gel.

$^1$H NMR (400 MHz, DMSO-d$_6$): δ 7.2-7.38 (m, 9H), 6.76 (m, 4H), 4.0 (m, 2H), 3.72 (s, 6H), 3-3.18 (m, 3H), 2.96 (m, 2H), 2.5-2.6 (m, 3H), 2.12-2.38 (m, 6H), 1.22-1.98 (m, 89H), 0.84-1.18 (m, 23H), 0.64 (s, 3H)

$^{13}$C NMR (100 MHz, DMSO-d$_6$): δ 171.89, 171.38, 158.74, 158.56, 156.70, 156.6, 145.28, 144.77, 136.49, 136.33, 135.89, 135.8, 130.19, 130.15, 128.25, 128.20, 128.09, 127.94, 127.13, 126.90, 113.37, 113.21, 72.1, 71.04, 56.7, 56.3, 56.19, 48.2, 46.07, 42.96, 42.32, 40.65, 40.41, 36.70, 36.07, 35.87, 35.57, 34.79, 32.13, 31.92, 30.77, 30.37, 29.83, 29.8, 29.78, 29.72, 29.68, 29.4, 28.47, 28.3, 28.03, 27.41, 27.29, 27.13, 27.09, 26.63, 24.45, 23.59, 22.9, 21.05, 19.41, 18.76, 18.48, 14.32, 12.28.

Synthesis of Extended Steroid Conjugates Phosphoramidite with Hydroxyl-Prolinol Linker (85)

Compound 84 (5.8 g, 4 mmol) was coevaporated with anhydrous toluene (50 mL). To the residue N,N-tetraisopropylammonium tetrazolide (0.225 g, 2 mmol) was added and the mixture was dried over $P_2O_5$ in a vacuum oven for overnight at 40° C. The reaction mixture was dissolved in dichloromethane (25 mL) and 2-cyanoethyl-N,N,N',N'-tetraisopropylphosphorodiamidite (1.8 g, 1.97 mL, 6 mmol) was added. The reaction mixture was stirred at ambient temperature for overnight. The completion of the reaction was ascertained by TLC ($R_f$=0.7 in 1:1 ethyl acetate:hexane). The reaction mixture was diluted with dichloromethane (100 mL) and washed with 5% $NaHCO_3$ (100 mL) and brine (100 mL). The organic layer was dried over anhydrous $Na_2SO_4$ filtered and concentrated under reduced pressure. The residue was purified over silica gel (50:49:1, EtOAc:Hexane:triethlyamine) to afford 85 as white solid (5.45 g, 83%).

$^1$H NMR (400 MHz, $C_6D_6$): δ 7.62 (m, 2H), 7.46 (m, 4H), 7.24 (m, 2H), 7.08 (m, 1H), 6.8 (m, 4H), 4.9 (m, 1H), 4.6 (m, 2H), 3.74 (m, 1H), 3.5 (m, 3H), 3.4 (m, 2H), 3.36 (2s, 6H), 3-3.22 (m, 4H), 0.8-2.4 (m, 133H), 0.62 (s, 3H)

$^{31}$P NMR (161.82 MHz, $CDCl_3$): δ 148.26 (high in integration), 148.01, 147.6 (due to rotamer $^{13}$C NMR (100 MHz, $CDCl_3$): δ 171.79, 171.61, 158.75, 158.58, 156.59, 145.31, 144.77, 136.47, 136.35, 136.31, 135.86, 130.22, 130.19, 128.28, 128.20, 128.11, 127.95, 127.15, 126.91, 113.39, 113.24, 86.11, 71.98, 70.81, 70.69, 72.93, 72.2, 71.98, 70.81, 70.81, 70.69, 64.37, 63.92, 58.55, 58.35, 58.36, 58.16, 59.57, 55.86, 55.44, 55.39, 46.31, 44.70, 44.65, 43.36, 43.34, 41.08, 35.08, 33.45, 32.13, 30.23, 29.92, 29.88, 29.72, 29.58, 26.32, 26.26, 24.85, 24.78, 24.68, 22.9, 20.58, 14.34.

Synthesis of Succinic acid mono-(5-[bis-(4-methoxy-phenyl)-phenyl-methoxymethyl]-1-{6-[17-(3-dioctadecylcarbamoyl-1-methyl-propyl)-10,13-dimethyl-hexadecahydro-cyclopenta[a]phenanthren-3-yloxycarbonylamino]-hexanoyl}-pyrrolidin-3-yl) ester (86)

Referring to scheme 21, Compound 84 (1.44 g, 1 mmol) was mixed with succinic anhydride (0.15 g, 1.5 mmol) and DMAP (0.0122 g, 0.1 mmol) and dried in a vacuum at 40° C. overnight. The mixture was dissolved in anhydrous dichloromethane (5 mL), triethylamine (0.101 g, 0.14 mL, 1 mmol) was added and the solution was stirred at room temperature under argon atmosphere for 16 h. It was then diluted with dichloromethane (50 mL) and washed with ice cold aqueous citric acid (5% wt., 25 mL) and water (2×25 mL). The organic phase was dried over anhydrous sodium sulfate and concentrated to dryness. The crude product was purified by column chromatography to afford compound 86 as white solid (1.1 g, 71% yield; $R_f$=0.5 in 10% MeOH/$CHCl_3$).

$^1$H NMR (400 MHz, DMSO-$d_6$): δ 7.62 (m, 2H), 7.46 (m, 4H), 7.24 (m, 2H), 7.08 (m, 1H), 6.8 (m, 4H), 4.9 (m, 1H), 4.6 (m, 2H), 3.74 (m, 1H), 3.5 (m, 3H), 3.4 (m, 2H), 3.36 (2s, 6H), 2.82 (s, 4H), 2.32 (m, 1H), 2.16 (m, 1H), 1.66-2.0 (m, 10H), 1.2-1.58 (m, 78H), 0.86-1.12 (14H), 0.64 (s, 3H).

$^{13}$C NMR (100 MHz, DMSO-$d_6$): δ 176.59, 172.22, 158.78, 158.62, 145.16, 139.8, 136.39, 136.22, 130.18, 130.14, 128.23, 128.0, 126.97, 122.91, 113.28, 72.1, 71.04, 56.7, 56.3, 56.19, 48.2, 46.07, 42.96, 42.32, 40.65, 40.41, 36.70, 36.07, 35.87, 35.57, 34.79, 32.13, 31.92, 30.77, 30.37, 29.83, 29.8, 29.78, 29.72, 29.68, 29.4, 28.47, 28.3, 28.03, 27.41, 27.29, 27.13, 27.09, 26.63, 24.45, 23.59, 22.9, 21.05, 19.41, 18.76, 18.48, 14.32, 12.28.

Scheme 21. Synthesis of extended steroid conjugates immobilized on solid support with hydroxyl-prolinol linker

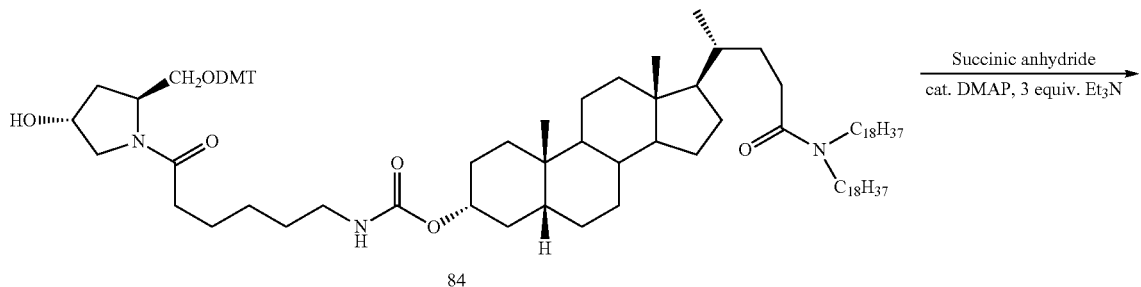

84

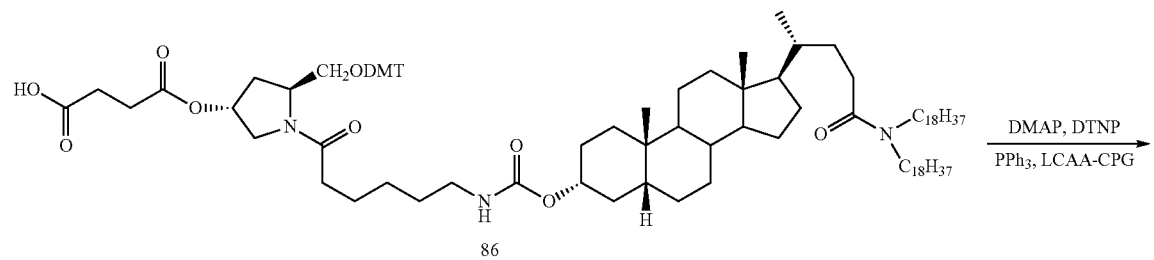

86

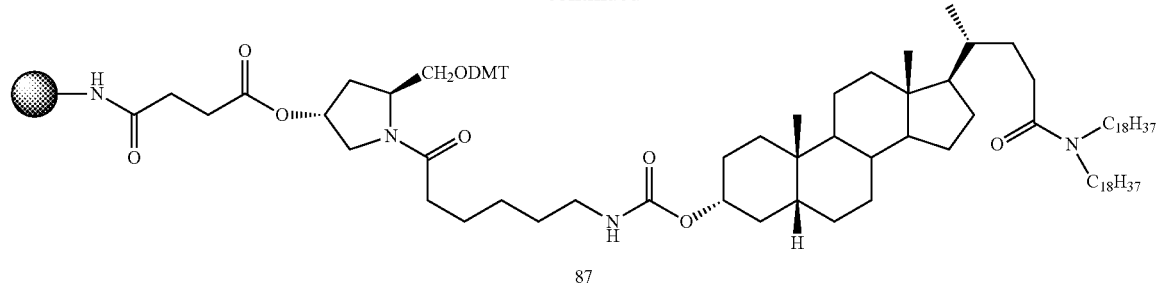

87

Synthesis of Extended Steroid Conjugates Immobilized on Solid Support with Hydroxyl-Prolinol Linker (87)

Succinate 86 (1 g, 0.649 mmol) was dissolved in dichloroethane (3 mL). To that solution DMAP (0.079 g, 0.649 mmol) was added. 2,2'-Dithio-bis(5-nitropyridine) (0.202 g, 0.649 mmol) in acetonitrile/dichloroethane (3:1, 3 mL) was added successively. To the resulting solution triphenylphosphine (0.17 g, 0.65 mmol) in acetonitrile (1.5 ml) was added. The reaction mixture turned bright orange in color. The solution was agitated briefly using wrist-action shaker (5 mins). Long chain alkyl amine-CPG (LCAA-CPG) (4 g, 155 μm/g) was added. The suspension was agitated for 16 h. The CPG was filtered through a sintered funnel and washed with acetonitrile, dichloromethane and ether successively. Unreacted amino groups were masked using acetic anhydride/pyridine. The loading capacity of the CPG was measured by taking UV measurement. (62 μM/g).

Synthesis of Extended Steroid Conjugates with Hydroxyl-Prolinol Linker

Scheme 22. Synthesis of extended steroid conjugates phosphoramidite wth hydroxyl-prolinol linker

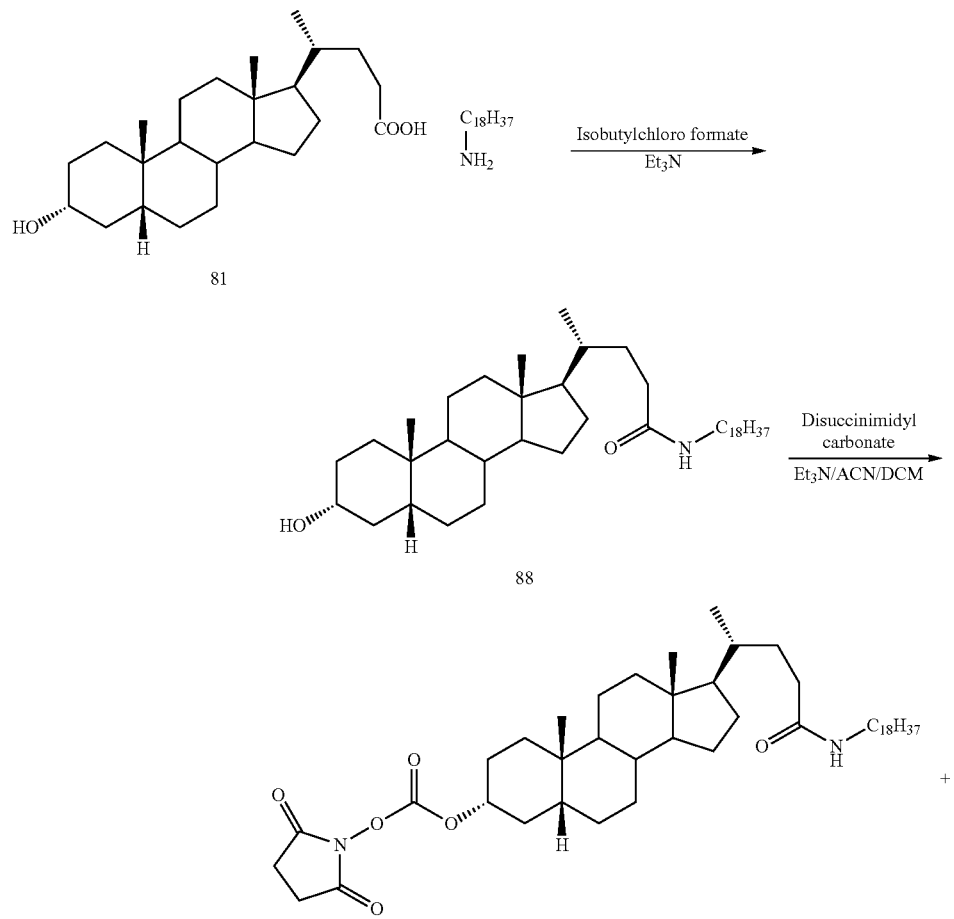

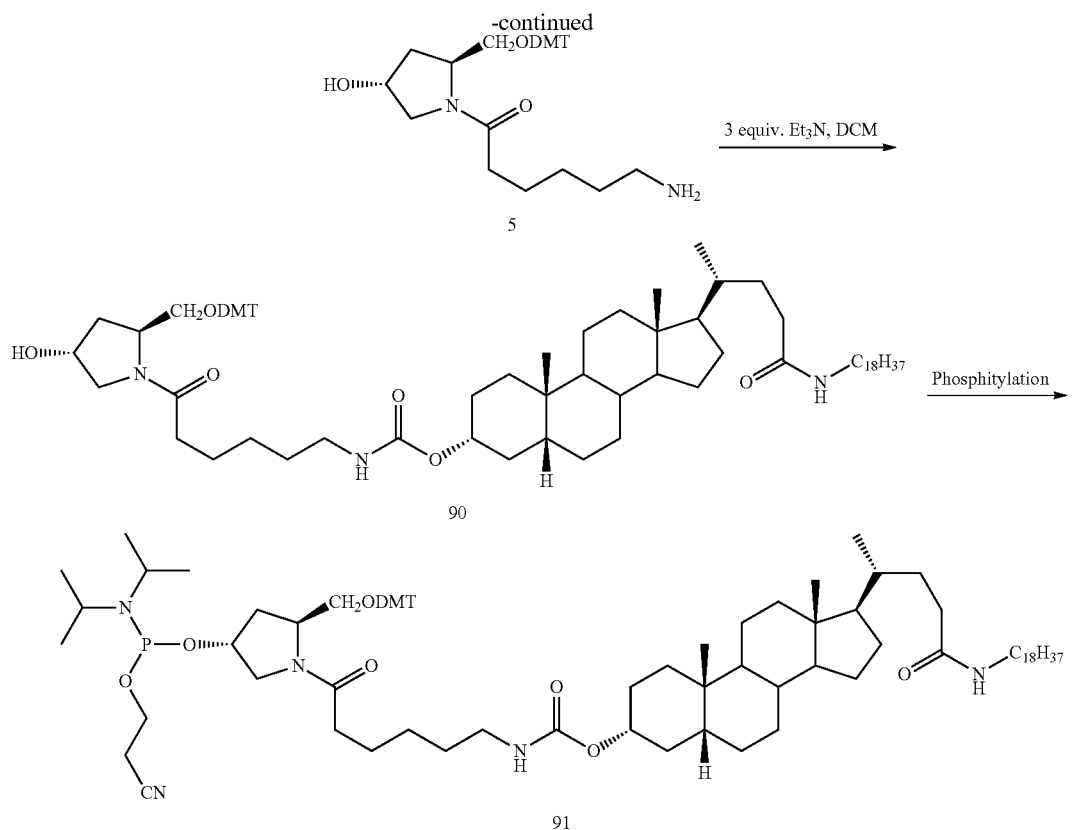

Synthesis of 4-(3-Hydroxy-10,13-dimethyl-hexadecahydro-cyclopenta[a]phenanthren-17-yl)-pentanoic acid octadecylamide (88)

Lithocholic acid (81) (9.78 g, 26 mmol) was dissolved in anhydrous tetrahydrofuran (60 mL). Isobutylchloroformate (3.55 g, 3.55 mL, 26 mmol) was added followed by the addition of triethylamine (5.26 g, 7.25 mL, 52 mmol) and dioctadecylamine (7 g, 26 g). The reaction mixture was brought to ambient temperature and allowed to stir over night. The reaction mixture was concentrated under vacuum, and the residue was dissolved in dichloromethane (250 mL). The organic layer was washed with 5% sodium bicarbonate, 3% aqueous HCl and water. After drying over anhydrous sodium sulfate, the solvent was removed under reduced pressure to afford amide 88 (14.5 g) in 89% yield. This was used as such for the next step.

Synthesis of Carbonic acid 10,13-dimethyl-17-(1-methyl-3-octadecylcarbamoyl-propyl)-hexadecahydro-cyclopenta[a]phenanthren-3-yl ester 2,5-dioxo-pyrrolidin-1-yl ester (89)

Referring to scheme 22, amide 88 (14.5 g, 23 mmol) was dissolved in anhydrous dichloromethane (150 mL). To the solution were added disuccinimidyl carbonate (8.87 g, 34 mmol), triethylamine (15 mL) and acetonitrile (50 mL). The reaction mixture was stirred at room temperature under argon for 6 h and then evaporated dryness. The residue was dissolved in dichloromethane (300 mL). It was washed with saturated $NaHCO_3$ aqueous solution (3×100 mL). The organic layer was dried over $Na_2SO_4$, filtered and evaporated to dryness. Compound 89 (14.3 g, 81%) was obtained as colorless powder after drying in high vacuum, which was directly used for the next step without further purification.

Synthesis of (6-{2-[Bis-(4-methoxy-phenyl)-phenyl-methoxymethyl]-4-hydroxy-pyrrolidin-1-yl}-6-oxo-hexyl)-carbamic acid 10,13-dimethyl-17-(1-methyl-3-octadecylcarbamoyl-propyl)-hexadecahydro-cyclopenta[a]phenanthren-3-yl ester (90)

Amine 5 (4.22 g, 7.9 mmol) is dissolved in anhydrous dichloromethane (25 mL) and cooled to 0° C. To the solution are added pyridine (10 mL) and compound 89 (9.3 g, 7.9 mmol) successively. The reaction temperature was brought to ambient temperature and stirred further. The completion of the reaction is ascertained by TLC (EtOAc). The reaction mixture is diluted with dichloromethane and washed with saturated $NaHCO_3$, water followed by brine. The organic layer is dried over sodium sulfate, filtered and concentrated under vacuum to afford the crude product. Compound 90 is obtained as a white solid after column chromatography over silica gel.

Synthesis of Extended Steroid Conjugates Phosphoramidite with Hydroxyl-Prolinol Linker (91)

Compound 90 (4.75 g, 4 mmol) is coevaporated with anhydrous toluene (50 mL). To the residue N,N-tetraisopropylammonium tetrazolide (0.225 g, 2 mmol) is added and the mixture is dried over $P_2O_5$ in a vacuum oven for overnight at 40° C. The reaction mixture is dissolved in dichloromethane (25 mL) and 2-cyanoethyl-N,N,N',N'-tetraisopropylphosphorodiamidite (1.8 g, 1.97 mL, 6 mmol) is added. The reaction mixture is stirred at ambient temperature for overnight. The completion of the reaction is ascertained by TLC (1:1 ethyl acetate:hexane). The reaction mixture is diluted with dichloromethane (100 mL) and washed with 5% NaHCO₃ (100 mL) and brine (100 mL). The organic layer is dried over anhydrous Na₂SO₄ filtered and concentrated under reduced pressure. The residue was purified over silica gel (50:49:1, EtOAc:Hexane:triethlyamine) to afford 91.

romethane (5 mL), triethylamine (0.101 g, 0.14 mL, 1 mmol) is added and the solution is allowed to stir at room temperature under argon atmosphere for 16 h. It is then diluted with dichloromethane (50 mL) and washed with ice cold aqueous citric acid (5% wt., 25 mL) and water (2×25 mL). The organic phase is dried over anhydrous sodium sulfate and concentrated to dryness. The crude product was purified by column chromatography to afford compound 92.

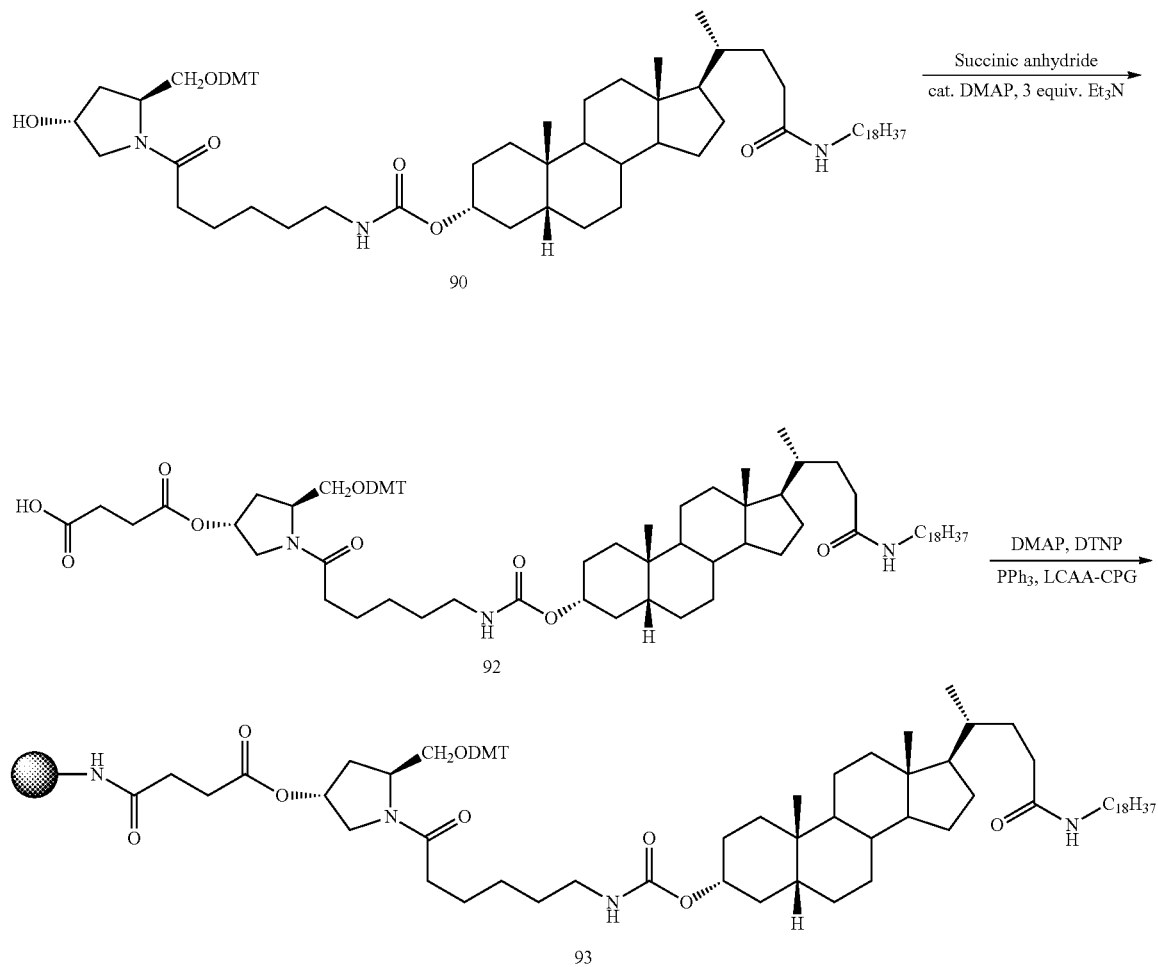

Scheme 23. Synthesis of extended steroid conjugates immobilized on solid support with hydroxyl-prolinol linker Synthesis of (6-{2-[Bis-(4-methoxy-phenyl)-phenyl-methoxymethyl]-4-hydroxy-pyrrolidin-1-yl}-6-oxo-hexyl)-carbamic acid 10,13-dimethyl-17-(1-methyl-3-octadecylcarbamoyl-propyl)-hexadecahydro-cyclopenta[a]phenanthren-3-yl ester (92)

Referring to scheme 23, Compound 90 (1.185 g, 1 mmol) is mixed with succinic anhydride (0.15 g, 1.5 mmol) and DMAP (0.0122 g, 0.1 mmol) and dried in a vacuum at 40° C. overnight. The mixture is dissolved in anhydrous dichlo- Synthesis of Extended Steroid Conjugates Immobilized on Solid Support with Hydroxyl-Prolinol Linker (93)

Succinate 92 (0.833 g, 0.649 mmol) is dissolved in dichloroethane (3 mL). To that solution DMAP (0.079 g, 0.649 mmol) is added. 2,2'-Dithio-bis(5-nitropyridine) (0.202 g, 0.649 mmol) in acetonitrile/dichloroethane (3:1, 3 mL) is added successively. To the resulting solution triphenylphosphine (0.17 g, 0.65 mmol) in acetonitrile (1.5 ml) is added. The reaction mixture turned bright orange in color. The solution is agitated briefly using wrist-action shaker (5 mins). Long chain alkyl amine-CPG (LCAA-CPG) (2.5 g, 155 μm/g) is added. The suspension is agitated further. The CPG is filtered through a sintered funnel and washed with acetonitrile, dichloromethane and ether successively. Unreacted amino groups are masked using acetic anhydride/pyridine. The loading capacity of the CPG is measured by taking UV measurement.

Scheme 24. Synthesis of dimethylamino phosphoramidite with hydroxyl-prolinol linker

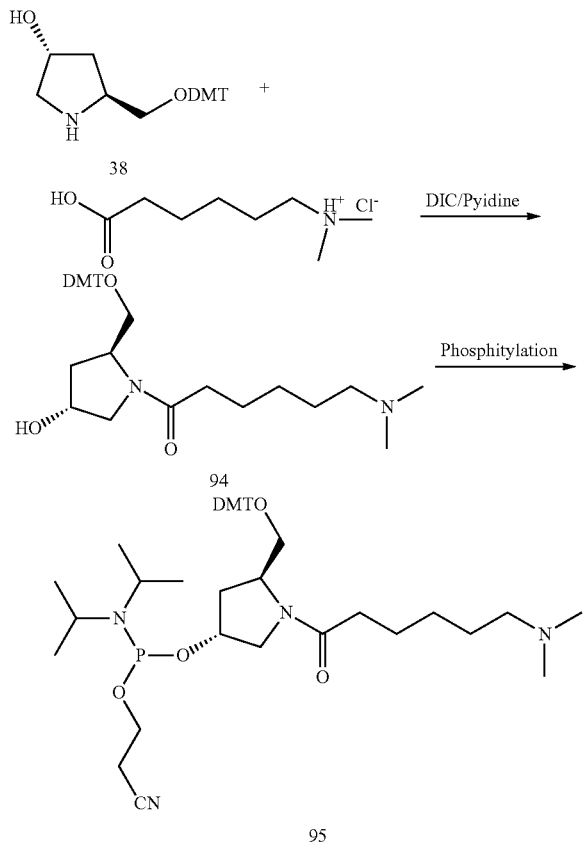

Synthesis of Dimethylamino Phosphoramidite with Hydroxyl-Prolinol Linker

1-{2-[Bis-(4-methoxy-phenyl)-phenyl-methoxymethyl]-4-hydroxy-pyrrolidin-1-yl}-6-dimethylamino-hexan-1-one (94)

Hydrochloride salt of 5-dimethylamino-pentanoic acid (1.95 g, 10 mmol) is suspended in anhydrous pyridine (50 mL). To the suspension is added diisopropylcarbodiimide (1.262 g, 1.55 mL, 10 mmol) followed by amine 38 (4.2 g, 10 mmol). The stirring is allowed to continue for 16 h. The reaction mixture is concentrated under vacuum, to the residue ethyl acetate is added and washed with, 5% $NaHCO_3$ solution, brine and water. After drying over anhydrous sodium sulfate the solvent is removed to afford crude product. DMT-alcohol 94 is obtained after purification over silica gel.

Synthesis of Dimethylamino Phosphoramidite with Hydroxyl-Prolinol Linker (95)

Compound 94 (2.35 g, 4.2 mmol) is coevaporated with anhydrous toluene (25 mL). To the residue N,N-tetraisopropylammonium tetrazolide (0.238 g, 2.1 mmol) is added and the mixture was dried over $P_2O_5$ in a vacuum oven for overnight at 40° C. The reaction mixture is dissolved in dichloromethane (25 mL) and 2-cyanoethyl-N,N,N',N'-tetraisopropylphosphorodiamidite (1.9 g, 2.1 mL, 6.3 mmol) is added. The reaction mixture was stirred at ambient temperature for overnight. The completion of the reaction is ascertained by TLC (1:1 ethyl acetate:hexane). The reaction mixture is diluted with dichloromethane (50 mL) and washed with 5% $NaHCO_3$ (50 mL) and brine (50 mL). The organic layer is dried over anhydrous $Na_2SO_4$ filtered and concentrated under reduced pressure. The residue was purified over silica gel (50:49:1, EtOAc:Hexane:triethlyamine) to afford 95.

Scheme 25. Synthesis of dimethylamino immobilized solid support with hydroxyl-prolinol linker

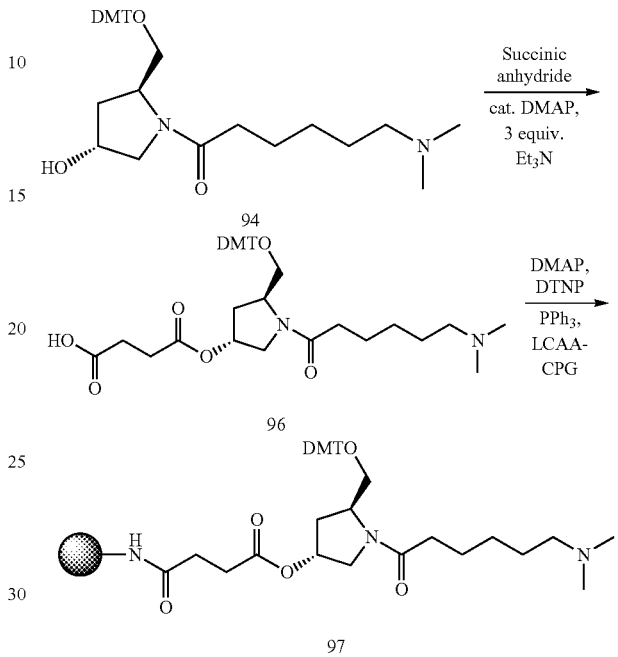

Synthesis of Succinic acid mono-[5-[bis-(4-methoxy-phenyl)-phenyl-methoxymethyl]-1-(6-dimethylamino-hexanoyl)-pyrrolidin-3-yl]ester (96)

Referring to scheme 25, Compound 94 (1.2 g, 2 mmol) is mixed with succinic anhydride (0.200 g, 2 mmol) and DMAP (0.244 g, 13 mmol) and dried in a vacuum at 40° C. overnight. The mixture is dissolved in anhydrous dichloromethane (5 mL), triethylamine (0.476 g, 0.64 mL, 4 mmol) is added and the solution stirred at room temperature under argon atmosphere for 16 h. It is then diluted with dichloromethane (100 mL) and washed with ice cold aqueous citric acid (5% wt., 100 mL) and water (2×100 mL). The organic phase is dried over anhydrous sodium sulfate and concentrated to dryness. The crude product is purified by column chromatography to afford compound 96.

Synthesis of Dimethylamino Immobilized Solid Support with Hydroxyl-Prolinol Linker (97)

Succinate 96 (1 g, 1.5 mmol) is dissolved in dichloroethane (7 mL). To that solution DMAP (0.183 g, 1.5 mmol) is added. 2,2'-Dithio-bis(5-nitropyridine) (0.470 g, 1.5 mmol) in acetonitrile/dichloroethane (3:1, 7 mL) is added successively. To the resulting solution triphenylphosphine (0.395 g, 1.5 mmol) in acetonitrile (3 ml) is added. The reaction mixture turned bright orange in color. The solution is agitated briefly using wrist-action shaker (5 mins). Long chain alkyl amine-CPG (LCAA-CPG) (4 g, 155 μm/g) is added. The suspension was agitated for 4 h. The CPG is filtered through a sintered funnel and washed with acetonitrile, dichloromethane and ether successively. Unreacted amino groups are masked using acetic anhydride/pyridine. The loading capacity of the CPG is measured by taking UV measurement.

Scheme 26. Synthesis of nalidixic phosphoramidite with hydroxyl-prolinol linker

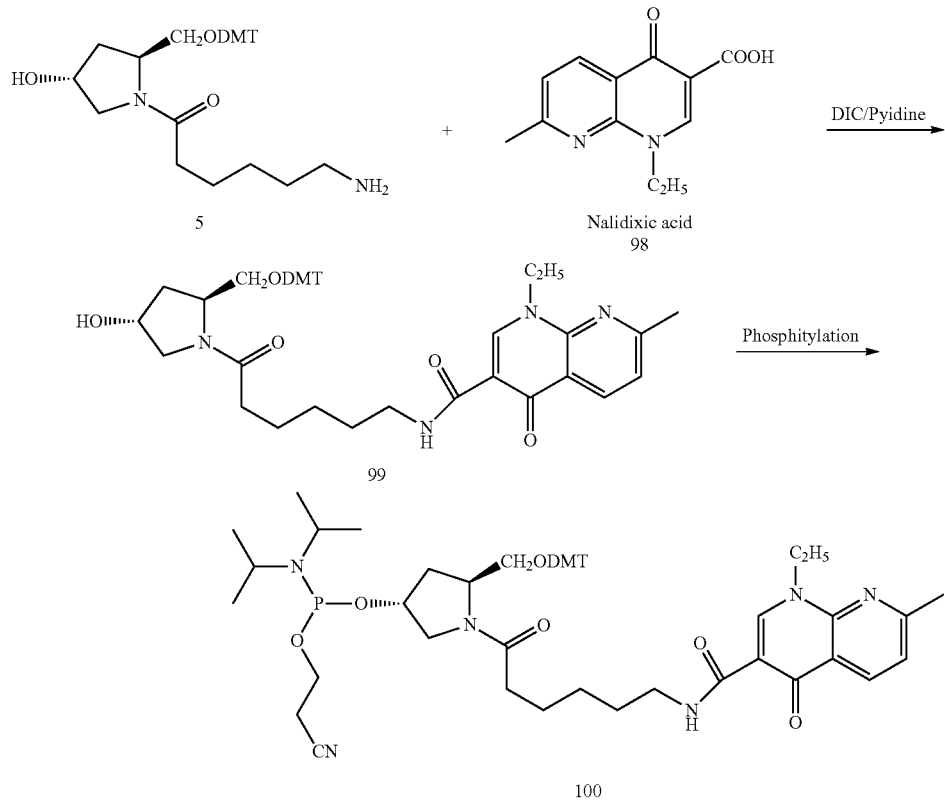

Synthesis of Nalidixic Phosphoramidite with Hydroxyl-Prolinol Linker

1-Ethyl-7-methyl-4-oxo-1,4-dihydro-[1,8]naphthyridine-3-carboxylic acid (6-{2-[bis-(4-methoxy-phenyl)-phenyl-methoxymethyl]-4-hydroxy-pyrrolidin-1-yl}-6-oxo-hexyl)-amide (99)

Nalidixic acid (2.32 g, 10 mmol) is suspended in anhydrous pyridine (50 mL). To the suspension is added diisopropylcarbodiimide (1.262 g, 1.55 mL, 10 mmol) followed by amine 5 (5.32 g, 10 mmol). The stirring is allowed to continue for 16 h. The reaction mixture is concentrated under vacuum, to the residue ethyl acetate is added and washed with, 5% $NaHCO_3$ solution, brine and water. After drying over anhydrous sodium sulfate the solvent is removed to afford crude product. DMT-alcohol 99 is obtained after purification over silica gel.

Synthesis of Nalidixic Phosphoramidite with Hydroxyl-Prolinol Linker (100)

Compound 99 (3.12 g, 4.2 mmol) is coevaporated with anhydrous toluene (25 mL). To the residue N,N-tetraisopropylammonium tetrazolide (0.238 g, 2.1 mmol) is added and the mixture was dried over $P_2O_5$ in a vacuum oven for overnight at 40° C. The reaction mixture is dissolved in dichloromethane (25 mL) and 2-cyanoethyl-N,N,N',N'-tetraisopropylphosphorodiamidite (1.9 g, 2.1 mL, 6.3 mmol) is added. The reaction mixture was stirred at ambient temperature for overnight. The completion of the reaction is ascertained by TLC (1:1 ethyl acetate:hexane). The reaction mixture is diluted with dichloromethane (50 mL) and washed with 5% $NaHCO_3$ (50 mL) and brine (50 mL). The organic layer is dried over anhydrous $Na_2SO_4$ filtered and concentrated under reduced pressure. The residue was purified over silica gel (50:49:1, EtOAc:Hexane:triethlyamine) to afford 100.

Scheme 27. Synthesis of nalidixic immobilized solid support with hydroxyl-prolinol linker

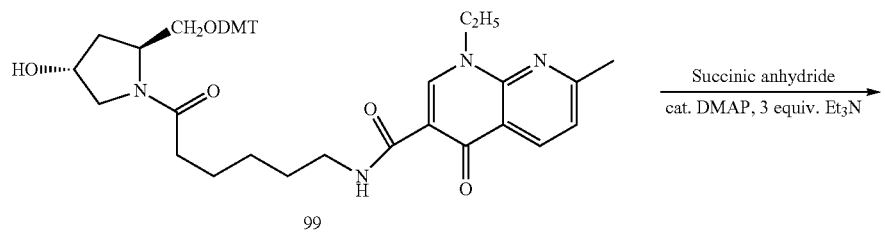

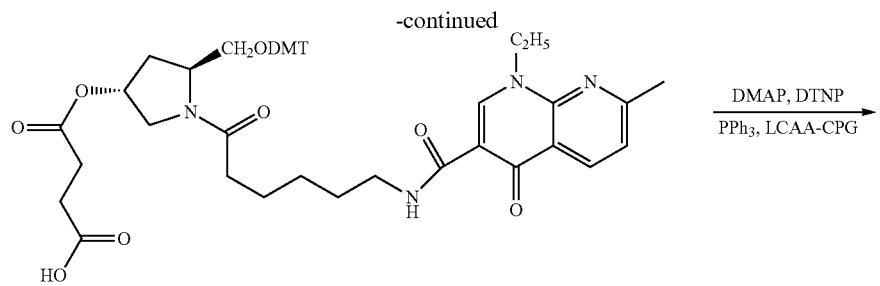

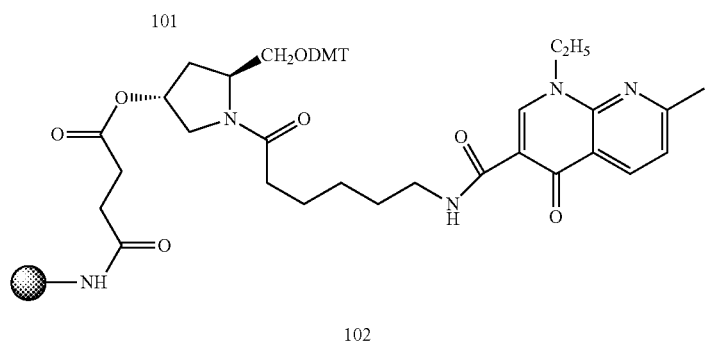

Synthesis of Succinic acid mono-(5-[bis-(4-methoxy-phenyl)-phenyl-methoxymethyl]-1-{6-[(1-ethyl-7-methyl-4-oxo-1,4-dihydro-[1,8]naphthyridine-3-carbonyl)-amino]-hexanoyl}-pyrrolidin-3-yl)ester (101)

Referring to scheme 27, Compound 99 (1.48 g, 2 mmol) is mixed with succinic anhydride (0.200 g, 2 mmol) and DMAP (0.244 g, 13 mmol) and dried in a vacuum at 40° C. overnight. The mixture is dissolved in anhydrous dichloromethane (5 mL), triethylamine (0.606 g, 0.96 mL, 6 mmol) is added and the solution stirred at room temperature under argon atmosphere for 16 h. It is then diluted with dichloromethane (100 mL) and washed with ice cold aqueous citric acid (5% wt., 100 mL) and water (2×100 mL). The organic phase is dried over anhydrous sodium sulfate and concentrated to dryness. The crude product is purified by column chromatography to afford compound 101.

Synthesis of Nalidixic Immobilized Solid Support with Hydroxyl-Prolinol Linker (102)

Succinate 100 (1.26 g, 1.5 mmol) is dissolved in dichloroethane (7 mL). To that solution DMAP (0.183 g, 1.5 mmol) is added. 2,2'-Dithio-bis(5-nitropyridine) (0.470 g, 1.5 mmol) in acetonitrile/dichloroethane (3:1, 7 mL) is added successively. To the resulting solution triphenylphosphine (0.395 g, 1.5 mmol) in acetonitrile (3 ml) is added. The reaction mixture turned bright orange in color. The solution is agitated briefly using wrist-action shaker (5 mins). Long chain alkyl amine-CPG (LCAA-CPG) (4 g, 155 μm/g) is added. The suspension was agitated for 4 h. The CPG is filtered through a sintered funnel and washed with acetonitrile, dichloromethane and ether successively. Unreacted amino groups are masked using acetic anhydride/pyridine. The loading capacity of the CPG is measured by taking UV measurement.

Diosgenein Phosphoramidite with Hydroxyl-Prolinol Linker

Scheme 28. Synthesis of Diosgenein phosphoramidite with hydroxyl-prolinol linker

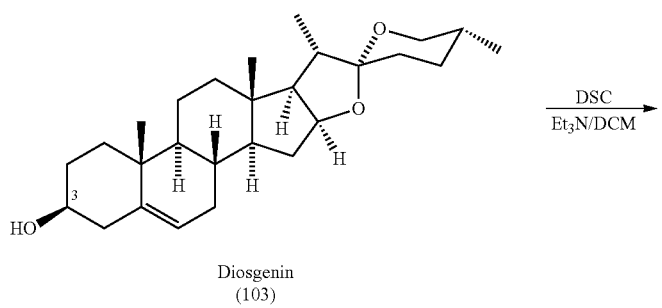

Diosgenin (103)

-continued

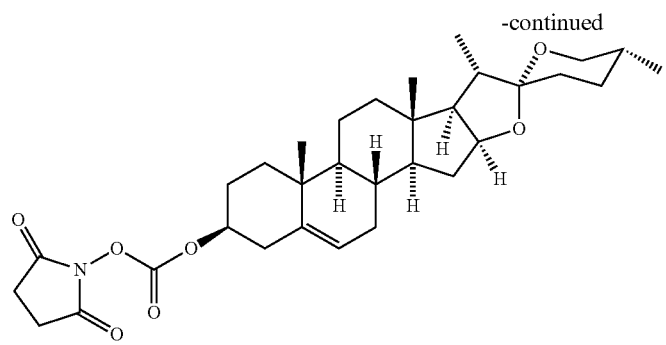

104

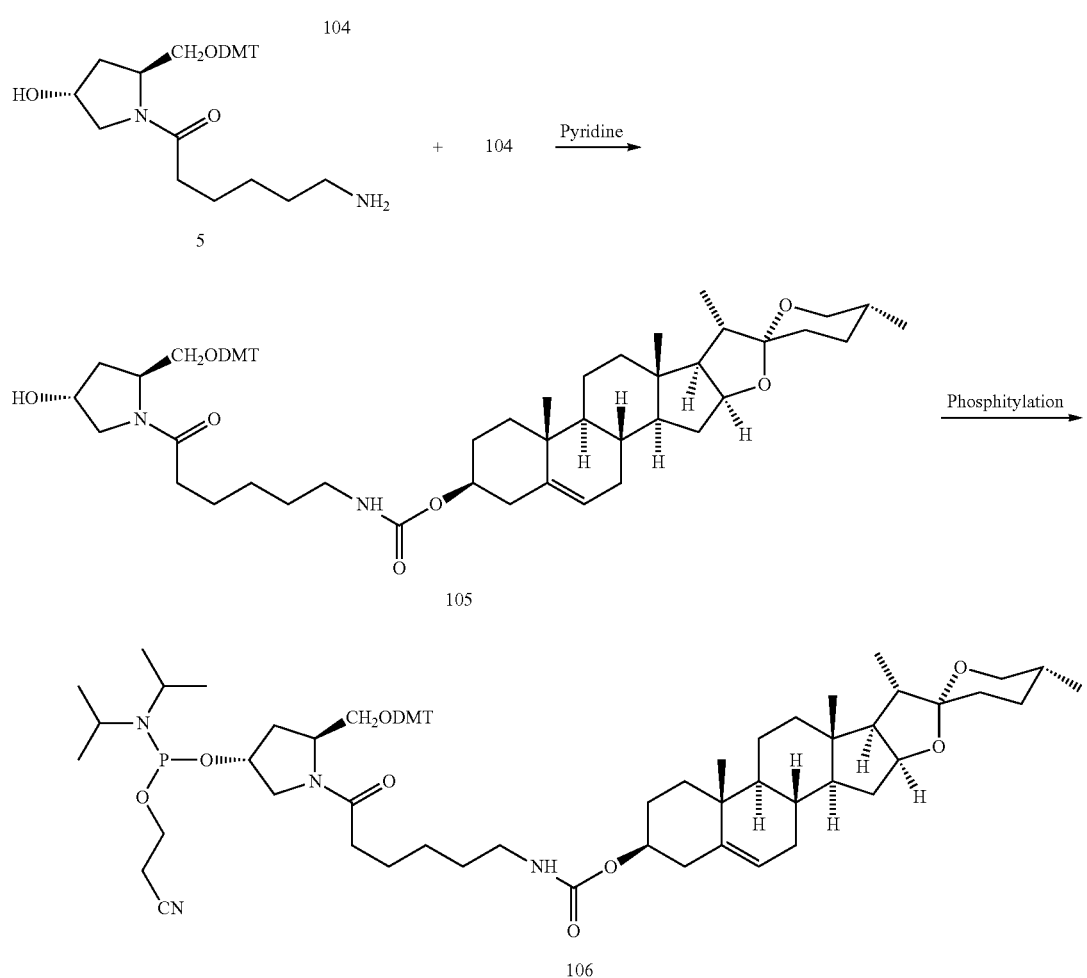

Diosgenin Succinimidyl Carbamate (104)

Referring to scheme 28, diosgenin (6.9 g, 16.74 mmol) is dissolved in anhydrous dichloromethane (150 mL). To the solution are added disuccinimidyl carbonate (6.4 g, 25.1 mmol), triethylamine (10 mL) and acetonitrile (50 mL). The reaction mixture is stirred at room temperature under argon for 6 h and then evaporated dryness. The residue is dissolved in dichloromethane (300 mL). It is washed with saturated $NaHCO_3$ aqueous solution (3×100 mL). The organic layer is dried over $Na_2SO_4$, filtered and evaporated to dryness. Compound 104 is obtained as colorless powder after drying in high vacuum, which is directly used for the next step without further purification.

Synthesis of Diosgenin DMT-Alcohol 105

Amine 5 (10.5 g, 19.7 mmol) is dissolved in anhydrous dichloromethane (50 mL) and cooled to 0° C. To the solution were added pyridine (10 mL) and compound 104 (9.62 g, 17.3 mmol) successively. The reaction temperature is brought to ambient temperature and stirred further for 3 h. The completion of the reaction is ascertained by TLC (10% MeOH/ $CHCl_3$). The reaction mixture is diluted with dichloromethane and washed with saturated $NaHCO_3$, water followed by brine. The organic layer is dried over sodium sulfate, filtered and concentrated under vacuum to afford the crude product. Compound 105 is obtained as a white solid after column chromatography over silica gel.

Synthesis of Diosgenin Phosphoramidite with Hydroxyl-Prolinol Linker (106)

Compound 105 (4.1 g, 4.2 mmol) is coevaporated with anhydrous toluene (25 mL). To the residue N,N-tetraisopropylammonium tetrazolide (0.238 g, 2.1 mmol) is added and the mixture was dried over $P_2O_5$ in a vacuum oven for overnight at 40° C. The reaction mixture is dissolved in dichloromethane (25 mL) and 2-cyanoethyl-N,N,N',N'-tetraisopropylphosphorodiamidite (1.9 g, 2.1 mL, 6.3 mmol) is added. The reaction mixture was stirred at ambient temperature for overnight. The completion of the reaction is ascertained by TLC (1:1 ethyl acetate:hexane). The reaction mixture is diluted with dichloromethane (50 mL) and washed with 5% $NaHCO_3$ (50 mL) and brine (50 mL). The organic layer is dried over anhydrous $Na_2SO_4$ filtered and concentrated under reduced pressure. The residue was purified over silica gel (50:49:1, EtOAc:Hexane:triethlyamine) to afford 106.

overnight. The mixture is dissolved in anhydrous dichloromethane (5 mL), triethylamine (0.676 g, 0.96 mL, 6 mmol) is added and the solution stirred at room temperature under argon atmosphere for 16 h. It is then diluted with dichloromethane (100 mL) and washed with ice cold aqueous citric acid (5% wt., 100 mL) and water (2×100 mL). The organic phase is dried over anhydrous sodium sulfate and concentrated to dryness. The crude product is purified by column chromatography to afford compound 107.

Synthesis of Diosgenin Immobilized Solid Support with Hydroxyl-Prolinol Linker (108)

Succinate 107 (1.61 g, 1.5 mmol) is dissolved in dichloroethane (7 mL). To that solution DMAP (0.183 g, 1.5 mmol) is added. 2,2'-Dithio-bis(5-nitropyridine) (0.470 g, 1.5 mmol) in acetonitrile/dichloroethane (3:1, 7 mL) is added successively. To the resulting solution triphenylphosphine (0.395 g,

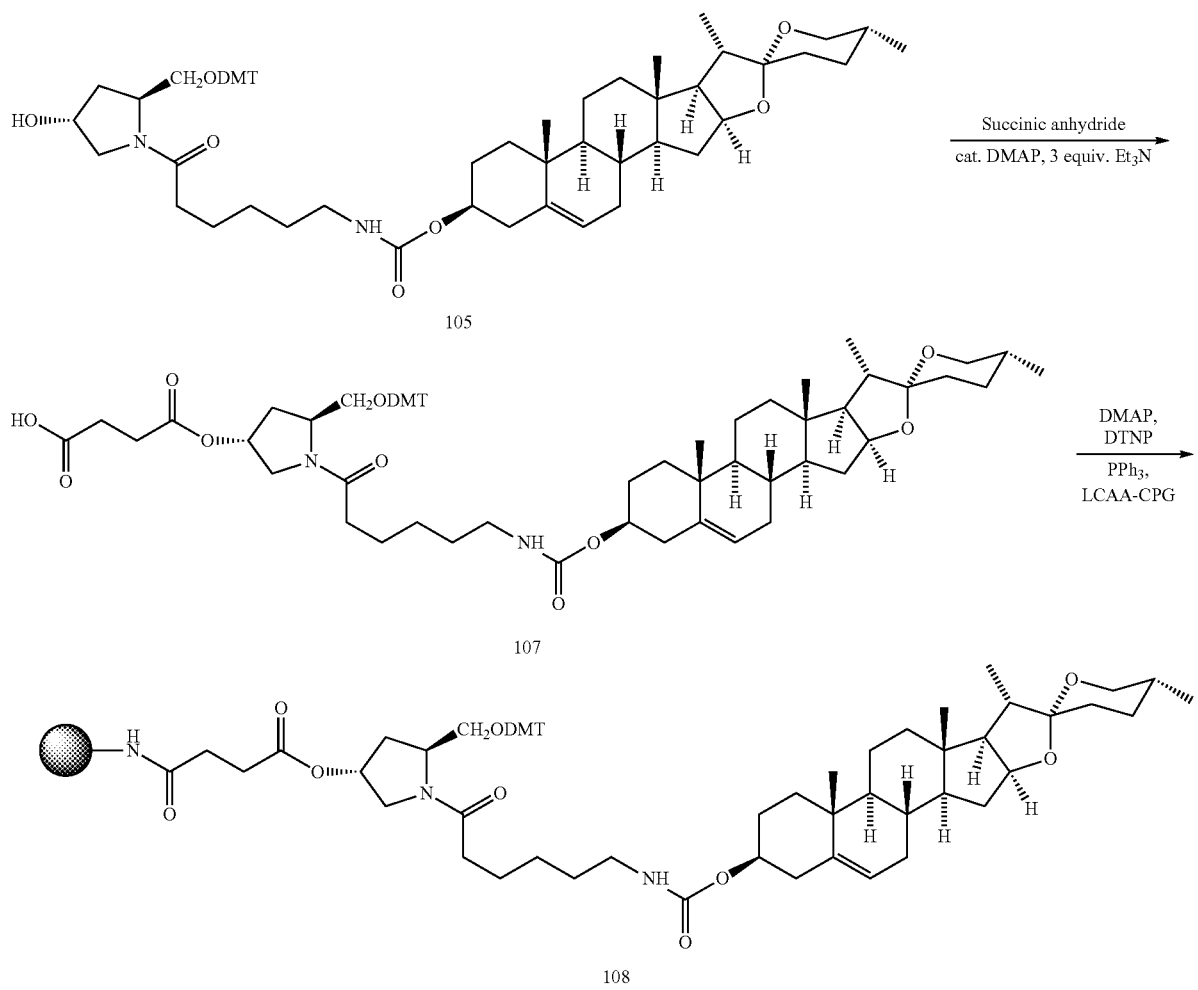

Scheme 29. Synthesis of Diosgenein immobilized on solid support with hydroxyl-prolinol linker

Synthesis of Diosgenin-Hydroxy-Prolinol Succinate 107

Referring to scheme 29, Compound 105 (1.95 g, 2 mmol) is mixed with succinic anhydride (0.200 g, 2 mmol) and DMAP (0.244 g, 13 mmol) and dried in a vacuum at 40° C.

1.5 mmol) in acetonitrile (3 ml) is added. The reaction mixture turned bright orange in color. The solution is agitated briefly using wrist-action shaker (5 mins). Long chain alkyl amine-CPG (LCAA-CPG) (4 g, 155 μm/g) is added. The suspension was agitated for 4 h. The CPG is filtered through a sintered funnel and washed with acetonitrile, dichloromethane and ether successively. Unreacted amino groups are masked using acetic anhydride/pyridine. The loading capacity of the CPG is measured by taking UV measurement.

Epifriedelanol Phosphoramidite with Hydroxyl-Prolinol Linker

To the solution are added disuccinimidyl carbonate (6.4 g, 25.1 mmol), triethylamine (10 mL) and acetonitrile (50 mL). The reaction mixture is stirred at room temperature under argon for 6 h and then evaporated dryness. The residue is dissolved in dichloromethane (300 mL). It is washed with saturated $NaHCO_3$ aqueous solution (3×100 mL). The

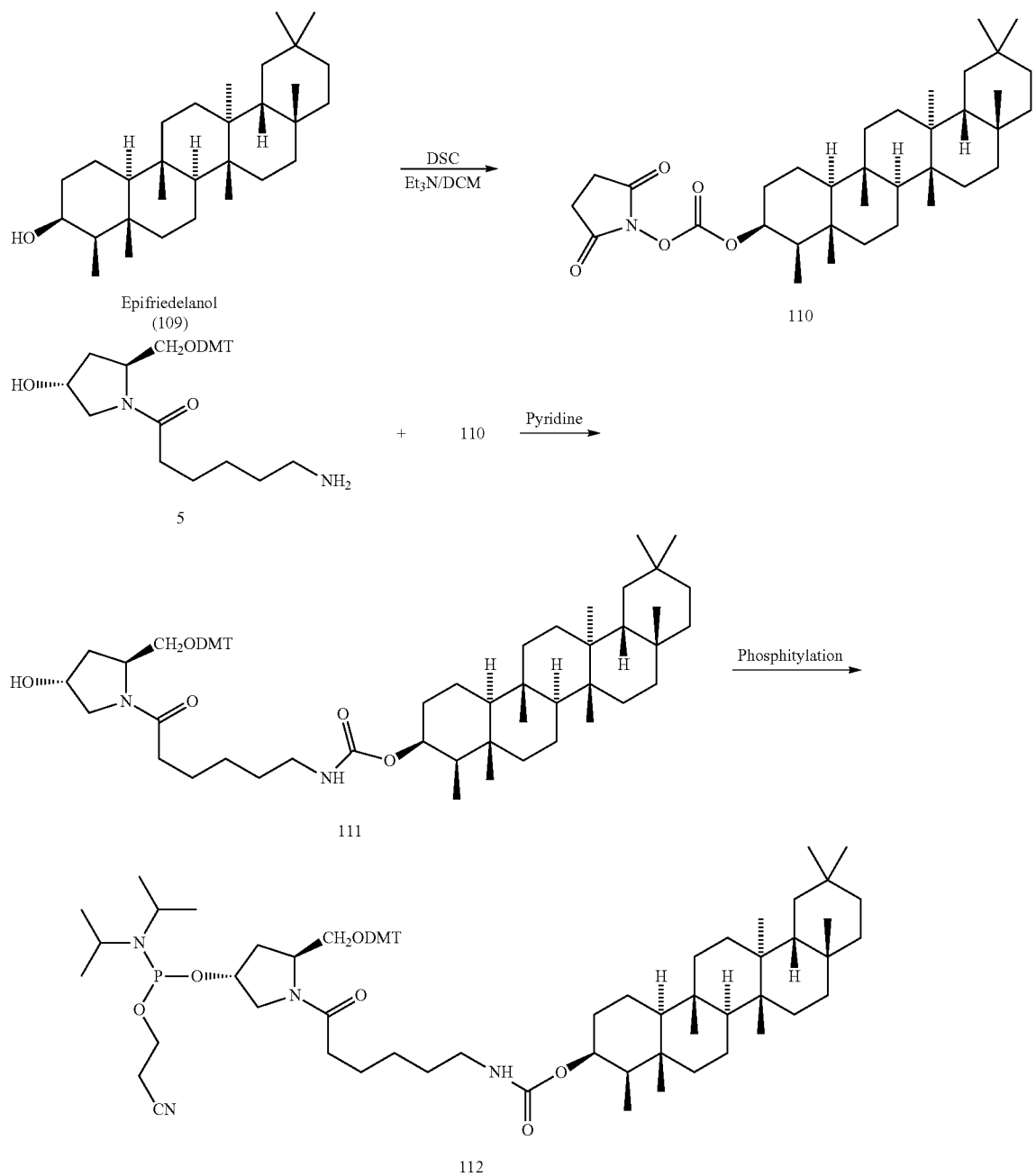

Epifriedelanol Succinimidyl Carbamate (110)

Referring to scheme 30, Epifriedelanol (7.2 g, 16.74 mmol) is dissolved in anhydrous dichloromethane (150 mL).

organic layer is dried over $Na_2SO_4$, filtered and evaporated to dryness. Compound 110 is obtained as colorless powder after drying in high vacuum, which is directly used for the next step without further purification.

Synthesis of Epifriedelanol DMT-Alcohol 111

Amine 5 (10.5 g, 19.7 mmol) is dissolved in anhydrous dichloromethane (50 mL) and cooled to 0° C. To the solution were added pyridine (10 mL) and compound 110 (9.85 g, 17.3 mmol) successively. The reaction temperature is brought to ambient temperature and stirred further for 3 h. The completion of the reaction is ascertained by TLC (10% MeOH/CHCl$_3$). The reaction mixture is diluted with dichloromethane and washed with saturated NaHCO$_3$, water followed by brine. The organic layer is dried over sodium sulfate, filtered and concentrated under vacuum to afford the crude product. Compound 111 is obtained as a white solid after column chromatography over silica gel.

Synthesis of Epifriedelanol Phosphoramidite with Hydroxyl-Prolinol Linker (112)

Compound 111 (4.14 g, 4.2 mmol) is coevaporated with anhydrous toluene (25 mL). To the residue N,N-tetraisopropylammonium tetrazolide (0.238 g, 2.1 mmol) is added and the mixture was dried over P$_2$O$_5$ in a vacuum oven for overnight at 40° C. The reaction mixture is dissolved in dichloromethane (25 mL) and 2-cyanoethyl-N,N,N',N'-tetraisopropylphosphorodiamidite (1.9 g, 2.1 mL, 6.3 mmol) is added. The reaction mixture was stirred at ambient temperature for overnight. The completion of the reaction is ascertained by TLC (1:1 ethyl acetate:hexane). The reaction mixture is diluted with dichloromethane (50 mL) and washed with 5% NaHCO$_3$ (50 mL) and brine (50 mL). The organic layer is dried over anhydrous Na$_2$SO$_4$ filtered and concentrated under reduced pressure. The residue was purified over silica gel (50:49:1, EtOAc:Hexane:triethlyamine) to afford 112.

Scheme 31. Synthesis of Epifriedelanol immobilized on solid support with hydroxyl-prolinol linker

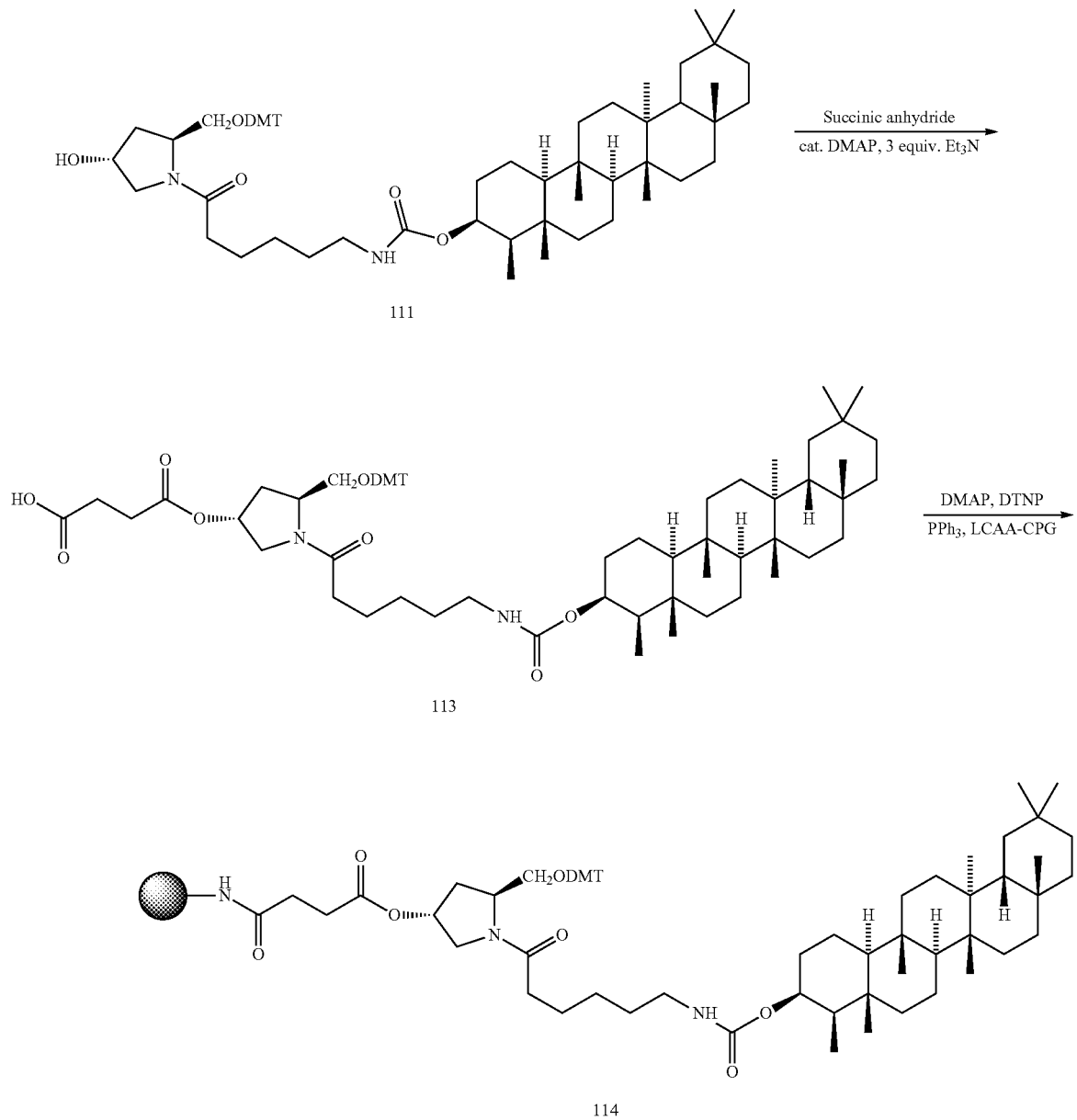

323

Synthesis of Epifriedelanol-Hydroxy-Prolinol Succinate 113

Referring to scheme 31, Compound 111 (1.975 g, 2 mmol) is mixed with succinic anhydride (0.200 g, 2 mmol) and DMAP (0.244 g, 13 mmol) and dried in a vacuum at 40° C. overnight. The mixture is dissolved in anhydrous dichloromethane (5 mL), triethylamine (0.676 g, 0.96 mL, 6 mmol) is added and the solution stirred at room temperature under argon atmosphere for 16 h. It is then diluted with dichloromethane (100 mL) and washed with ice cold aqueous citric acid (5% wt., 100 mL) and water (2×100 mL). The organic phase is dried over anhydrous sodium sulfate and concentrated to dryness. The crude product is purified by column chromatography to afford compound 113.

324

Synthesis of Epifriedelanol Immobilized Solid Support with Hydroxyl-Prolinol Linker (114)

Succinate 113 (1.63 g, 1.5 mmol) is dissolved in dichloroethane (7 mL). To that solution DMAP (0.183 g, 1.5 mmol) is added. 2,2'-Dithio-bis(5-nitropyridine) (0.470 g, 1.5 mmol) in acetonitrile/dichloroethane (3:1, 7 mL) is added successively. To the resulting solution triphenylphosphine (0.395 g, 1.5 mmol) in acetonitrile (3 ml) is added. The reaction mixture turned bright orange in color. The solution is agitated briefly using wrist-action shaker (5 mins). Long chain alkyl amine-CPG (LCAA-CPG) (4 g, 155 µm/g) is added. The suspension was agitated for 4 h. The CPG is filtered through a sintered funnel and washed with acetonitrile, dichloromethane and ether successively. Unreacted amino groups are masked using acetic anhydride/pyridine. The loading capacity of the CPG is measured by taking UV measurement.

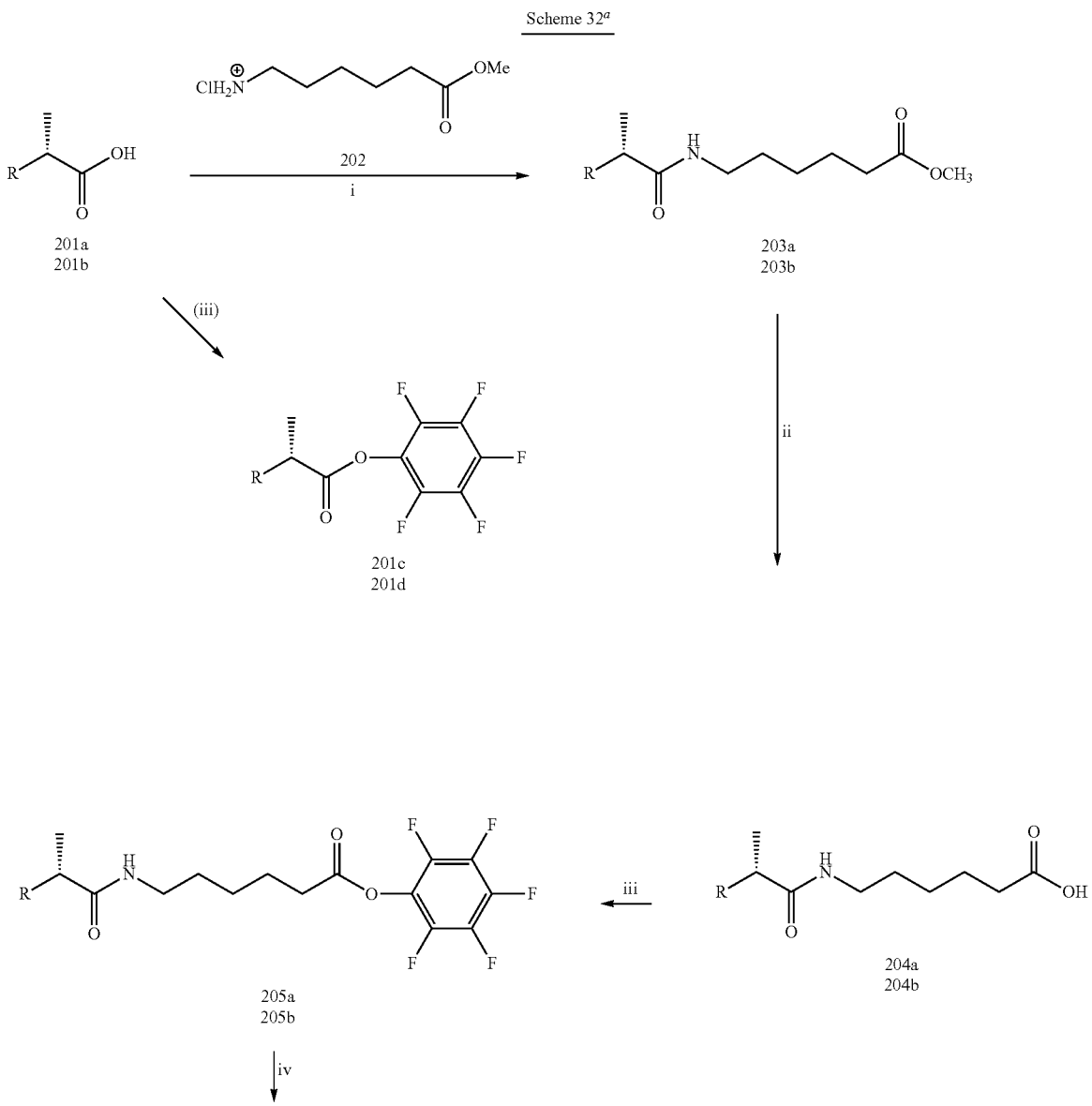

Scheme 32[a]

-continued

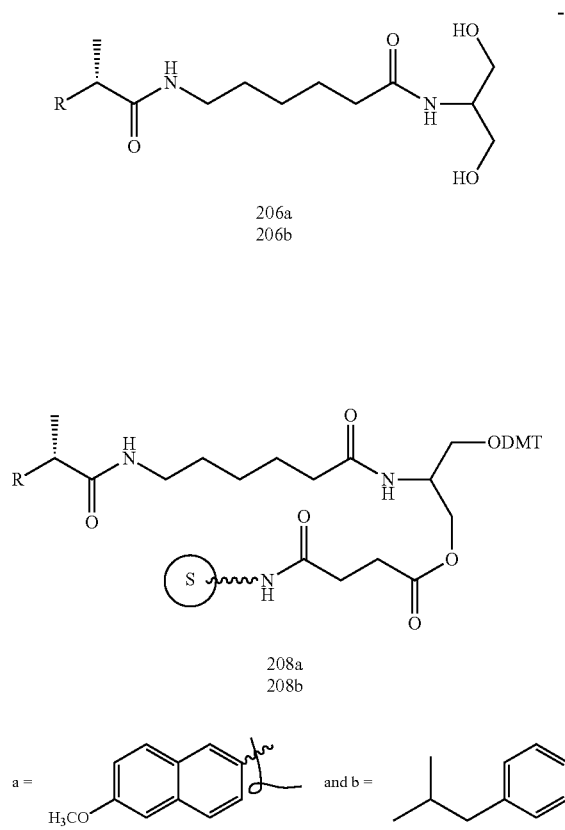

206a
206b

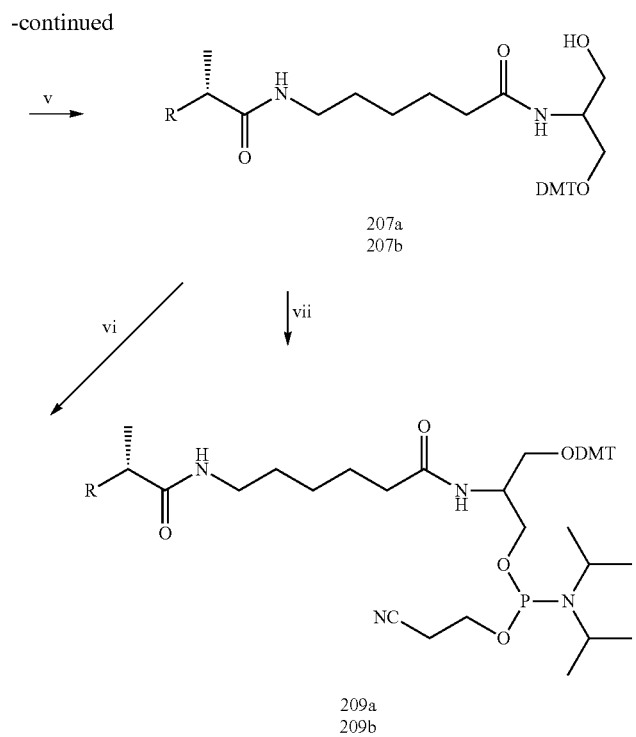

207a
207b 208a
208b 209a
209b $^a$(i) DCC, DMAP, DIEA/Dichloromethane; (ii) LiOH/THF-H$_2$O; (iii) DCC, DMAP, Pentafluorophenol/Dichloromethane; (iv) Serinol, TEA/Dichloromethane; (v) DMT-Cl, DMAP/Py; (vi) (a) Succinic anhydride, DMAP/Dichloroethane and (b) DTNP, DMAP, Ph$_3$P, Aminoalkyl solid support and (vii) N,N-diisopropylamino β-cyanoethylphosphonamidic chloride {[(CH$_3$)$_2$CH]$_2$N—P(Cl)—OCH$_2$CH$_2$CN}, DIEA/Dichloromethane or 2-Cyanoethyl-N,N, N′, N′-tetraisopropylphosphorodiamidite, tetrazole (or tetrazolediisopropylammonium salt)/Acetonitrile.

Compound 203a:

The ester 203a was prepared according to reported procedure from the literature (*Org. Syn.*, 1984, 63, 183). Naproxen (201a 10.00 g, 43.427 mmol, purchased from Aldrich) and 4-(Dimethylamino)pyridine (DMAP, 0.53 g, 4.338 mmol, purchased from Aldrich) were dissolved in anhydrous N,N-dimethylformamide (DMF) and 1,3-diisopropylcarbodiimide (DICC, 6.8 mL, 43.914 mmol, purchased from Aldrich) was added into the solution and stirred at ambient temperature for 5 minute. 6-aminohexanoic acid methyl ester hydrochloride (202, 10.00 g, 57.408 mmol, purchased from Fluka) and diisopropylethylamine (DIEA, 10 mL, purchased from Aldrich) were added into the stirring solution after 5 minute of addition of DICC and stirred overnight at ambient temperature. DMF was removed from the reaction in vacuo, the product was extracted into ethyl acetate (EtOAc, 200 mL), washed successively with aqueous KHSO$_4$, water, sodium bicarbonate solution and water. The organic layer was dried over anhydrous sodium sulfate (Na$_2$SO$_4$) and filtered. A white solid was precipitated out from the EtOAc extract by adding hexane to afford the desired compound 203a, 11.20 g (72.14%). $^1$H NMR (400 MHz, [D$_6$]DMSO, 25° C.): δ 7.95-7.92 (t, J(H,H)=5.2 & 5.6 Hz, 1H), 7.76-7.68 (m, 3H), 7.43-7.40 (dd, J′(H,H)=1.6 and J″(H,H)=8.4 Hz, 1H), 7.25-7.24 (d, J(H,H)=2.0 Hz, 1H), 7.13-7.11 (dd, J′(H,H)=2.4 and J″(H,H)= 8.8 Hz, 1H), 3.84 (s, 3H), 3.70-3.65 (q, J(H,H)=6.8 and 7.2 Hz, 1H), 3.54 (s, 3H), 3.00-2.97 (q, J(H,H)=6.8 Hz, 2H), 2.21-2.17 (t, 2H), 1.48-1.29 (m, 7H), 1.19-1.13 (m, 2H).

Compound 204a:

Hydrolysis of the ester 203a was performed as reported earlier (Rajeev et al., 2002, 4, 4395). Compound 203a (10.80 g, 30.24 mmol) was suspended in tetrahydrofuran-water (THF-H$_2$O) mixture (4:1, 40 mL) and stirred with LiOH (1.65 g, 39.32 mmol) for 4 h at ambient temperature. THF was removed from the reaction in vacuo and free acid was precipitated out from water by adding concentrated KHSO$_4$ solution, thoroughly washed with water, filtered through a sintered filter, triturated with diethyl ether and dried over P$_2$O$_5$ under vacuum overnight to obtain the acid 204a as a white solid, 10.22 g (98.4%). $^1$H NMR (400 MHz, [D$_6$]DMSO, 25° C.): δ 11.96 (bs, 1H), 7.95-7.92 (t, J(H,H)=5.37 Hz, 1H), 7.77-7.68 (m, 3H), 7.43-7.41 (d, J(H,H)=8.3 Hz, 1H), 7.25-7.24 (d, J(H,H)=2.44 Hz, 1H), 7.13-7.11 (dd, J′(H,H)=1.95, 2.44 and J″(H,H)=8.79, 9.27 Hz, 1H), 3.84 (s, 3H), 3.71-3.65 (q, J(H,H)=6.84, 7.33 Hz, 1H), 3.02-2.97 (m, 2H), 2.13-2.09 (t, J(H,H)=7.33 Hz, 2H), 1.46-1.30 (m, 7H), 1.21-1.15 (m, 2H).

Compound 205a:

Compound 204a (5.00 g, 14.57 mmol), DMAP (0.18 g, 1.47 mmol) and pentafluorophenol (3.50 g, 19.02 mmol, purchased from Aldrich) were taken in dichloromethane (40 mL) and DCC (3.00 g, 14.54 mmol) was added into the solution. Reaction mixture was stirred at ambient temperature for 8 h. The reaction mixture was diluted to 100 mL by adding EtOAc and precipitated DCU was removed by filtration. Combined filtrate, evaporated solvent in vacuo, and the residue was subsequently filtered through a column of silica gel, eluent hexane/EtOAc 4:1 to obtain a mixture (7.90 g) of the desired ester 205a and excess pentafluorophenol from the reaction. The crude product thus obtained was directly used for proceeding experiments without further purification.

Compound 206a:

Pentafluorophenol ester 205a was stirred with serinol in the presence of TEA to obtain compound 206a (*J. Org. Chem.*, 1991, 56, 1713). Compound 205a (4.00 g, 7.86 mmol) and serinol (1.5 g, 16.46 mmol, purchased from Aldrich) were suspended in dichloromethane (30 mL) and triethylamine (TEA, 2.3 mL, purchased from Aldrich) was added into the suspension, stirred at ambient temperature for 2 h. A white precipitate was formed during the course of the reaction. After 2 h, the precipitate was filtered through a sintered filter, washed successively with excess of dichloromethane, water and diethyl ether to afford desired product 206a (2.82 g, 86.2%). $^1$H NMR (400 MHz, [D$_6$]DMSO, 25° C.): δ 7.95-7.92 (t, J(H,H)=5.49 Hz, 1H, exchangeable with D$_2$O), 7.77-7.68 (m, 3H), 7.43-7.39 (m, 2H, accounted for 1H after D$_2$O exchange), 7.26-7.25 (d, J(H,H)=2.14 Hz, 1H), 7.13-7.11 (dd, J'(H,H)=2.44 and J''(H,H)=8.85 Hz, 1H), 4.58-4.55 (t, J(H,H)=5.49 Hz, 2H, exchangeable with D$_2$O), 3.84 (s, 3H), 3.71-3.65 (m, 2H), 3.37-3.35 (t, became doublet after D$_2$O exchange, 4H), 3.02-2.95 (m, 2H), 2.03-2.01 (t, J(H,H)=7.32, 7.63 Hz, 2H), 1.46-1.30 (m, 7H), 1.20-1.12 (m, 2H).

Compound 207a:

Compound 206a was prepared by modifying reported literature procedure (Rajeev et al., *Org. Lett.*, 2003, 5, 3005). A solid mixture of compound 206a (2.50 g, 6.01 mmol) and DMAP (0.075 g, 0.61 mmol) was dried over P$_2$O$_5$ under vacuum overnight. The solid mixture was suspended in anhydrous pyridine (100 mL) under argon and heated to obtain a homogenous solution. The temperature of the mixture was brought to room temperature and stirred. 4,4'-Di-O-methyltrityl chloride (2.24 g, 6.61 mmol, purchased from Chem Genes Corporation) was separately dissolved in 20 mL of anhydrous dichloromethane and added drop-wise into the stirring pyridine solution over a period of 45 minute under argon. Reaction mixture was further stirred overnight. Solvents were removed form the reaction mixture and the product was extracted into EtOAc (150 mL) and washed successively with water, NaHCO$_3$ solution and water, dried over anhydrous Na$_2$SO$_4$ and evaporated to solid mass. Desired product was purified by flash silica gel column chromatography: (a) eluent: 1% methylalcohol (MeOH) in dichloromethane—1.60 g of undesired bis DMT derivative (26.1%) and (b) 5% MeOH in dichloromethane—2.50 g of desired product 207a (57.9%). $^1$H NMR (400 MHz, [D$_6$]DMSO, 25° C.): δ 7.94-7.91 (t, J(H,H)=5.49 Hz, 1H, exchangeable with D$_2$O), 7.7-7.68 (m, 3H), 7.60-7.58 (d, J(H,H)=8.55 Hz, 1H, exchangeable with D$_2$O), 7.43-7.10 (m, 12H), 6.86-6.84 (d, 4H), 4.62-4.59 (t, J(H,H)=5.18, 5.49 Hz, 1H, exchangeable with D$_2$O), 4.01-3.96 (m, 1H), 3.83 (s, 3H), 3.71-3.65 (m, 7H), 3.44-3.42 (t, J(H,H)=5.19, 5.49 Hz, 2H), 3.03-2.87 (m, 4H), 2.05-2.01 (t, J(H,H)=7.33, 7.63 Hz, 2H), 1.48-1.30 (m, 7H), 1.21-1.14 (m, 2H).

Compound 208a:

The desired solid support 208a was prepared according to reported procedures (References for succinilation: Rajeev et al., *Org. Lett.*, 2003, 5, 3005 and for conjugation to CPG: Kumar et al., *Nucleosides Nucleotides*, 1996, 15, 879). A mixture of compound 207a (1.00 g, 1.39 mmol), succinic anhydride (0.17 g, 1.69 mmol, purchased from Aldrich) and DMAP (0.21 g, 1.72 mmol) were suspended in 7 mL of anhydrous ethylene dichloride for 24 h. Reaction mixture was diluted to 50 mL by adding dichloromethane and washed with dilute aqueous citric acid solution (20 mL), dried over anhydrous Na$_2$SO$_4$ and evaporated to dryness. The residue obtained was further dried over P$_2$O$_5$ under vacuum to afford an almost pure but crude monosuccinate as a white solid (1.10 g, 96.5%). The product obtained was directly used for subsequent reaction without further purification. $^1$H NMR (400 MHz, [D$_6$]DMSO, 25° C.): δ 7.94-7.91 (t, J(H,H)=5.19, 5.49 Hz, 1H, exchangeable with D$_2$O), 7.83-7.81 (d, J(H,H)=7.94 Hz, 1H, exchangeable with D$_2$O), 7.76-7.68 (m, 3H), 7.42-7.10 (m, 12H), 6.88-6.86 (d, 4H), 4.18-4.12 (m, 2H), 4.07-3.98 (m, 2H), 3.83 (s, 3H), 3.71-3.66 (m, 7H), 3.00-2.91 (m, 4H), 2.40 (s, 4H), 2.04-2.00 (t, J(H,H)=7.32 Hz, 2H), 1.44-1.22 (m, 7H), 1.19-1.15 (m, 2H).

2,2'-Dithiobis(5-nitropyridine) (0.38 g, 1.22 mmol, DTNP, purchased from Adrich) was dissolved in a 1:1 mixture of acetonitrile and ethylene dichloride (5 mL) and added into a suspension of naproxen-6-aminohexanoic acid-serinol conjugate mono DMT mono succinate (1.00 g, 1.21 mmol) and DMAP (0.16 g, 1.31 mmol) in 2 mL of anhydrous acetonitrile. Triphenylphosphine (Ph$_3$P, 0.32 g, 1.22 mmol, purchased from Aldrich) was added into the reaction mixture and shaken for 3-4 minute. 5.5 g of long chain aminoalkyl controlled pore glass (CPG) with 500 Å size and a loading of 112.7 μM/g (purchased from Millipore), and excess of acetonitrile (to soak the CPG completely) were added into the reaction mixture and the suspension was shaken (agitated) for 45 minute at ambient temperature. CPG was filtered through a sintered funnel, washed extensively with acetonitrile, dichloromethane and diethyl ether and subsequently re-suspended in pyridine-dichloromethane and treated with acetic anhydride in the presence of DIEA to cap unreacted amino groups on the CPG. After 10 minute, CPG was filtered and extensively washed with dichloromethane, acetonitrile and diethyl ether followed by drying under vacuum to obtain the desired CPG 208a with a loading 54.12 μM/g.

The loading was determined as reported in the literature (Prakash et al., *J. Org. Chem.*, 2002, 67, 357 and references cited therein).

Compound 209a:

The phosphoramidite was prepared as reported in the literature (Rajeev et al., *Org. Lett.*, 2003, 5, 3005 and references cited therein). Compound 207a (1.00 g, 1.39 mmol) and diisopropylammonium tetrazolide (0.12 g, 0.70 mmol) were dried over P$_2$O$_5$ vacuum overnight and subsequently suspended in anhydrous acetonitrile (5 mL) under argon atmosphere. 2-Cyanoethyl-N,N,N',N'-tetraisopropylphosphorodiamidite (0.69 mL, 2.09 mmol) was added into the suspension and stirred at ambient temperature for 14 h. Solvent was removed form the reaction in vacuo and residue was suspended in EtOAc (40 mL) and washed with dilute NaHCO$_3$ solution followed by standard work. Desired amidite 209a was purified by flash silica gel column chromatography; eluent: 100 EtOAc, yield 0.79 g (61.8%). $^{31}$P NMR (161.8 MHz, CDCl$_3$, 25° C.): δ 146.01, 145.69.

Compound 201c:

Naproxen (201, 11.25 g, 48.86 mmol), pentafluorophenol (10.00 g, 54.33 mmol) and DMAP (0.60 g, 4.91 mmol) were dissolved in DMF (40 mL) and stirred at ambient temperature. 1,3-dicyclohexylcarbodiimide (DCC, 11.00 g, 53.31 mmol) was added into the solution and continued stirring overnight. 1,3-dicyclohexylurea (DCU) was precipitated out during the course of the reaction. The precipitated DCU was filtered off, washed with DMF, combined filtrate and removed DMF in vacuo. Oily residue obtained was filtered through a small column of silica gel, eluent 10% EtOAc in hexane to remove dissolved DCU to afford a mixture of the desired ester 201c and excess pentafluorophenol (20.30 g). The crude product thus obtained was directly used for proceeding experiments without further purification. $^1$H NMR (400 MHz, [D$_6$]DMSO, 25° C.): δ 7.85-7.81 (m, 3H), 7.48-7.46 (dd, J'(H,H)=1.53 and J"(H,H)=8.55 Hz, 1H), 7.32-7.31 (d, J(H,H)=2.44 Hz, 1H), 7.18-7.16 (dd, J'(H,H)=2.44 and J"(H, H)=8.85 Hz, 1H), 4.47-4.44 (q, J(H,H)=7.02 Hz), 3.86 (s, 3H), 1.63-1.61 (d, J(H,H)=7.34 Hz, 3H).

Compound 203b:

Ibuprofen (201b, 5.0 g, 24.23 mmol, purchased from Acros Organic), methyl 6-aminohexanoic acid monohydrochloride (202, 6.60 g, 36.33 mmol, purchased from Fluka) and DMAP (0.30 g, 2.46 mmol) were suspended in dichloromethane (60 mL) in a 200 mL round bottom flask and DCC (5.00 g, 24.23 mmol) was added into the suspension, stirred for 3 minute. After 3 minute, 3.6 mL (25.83 mmol) of TEA was added into the reaction and continued stirring at ambient temperature for 18 h. Solvent and excess TEA were removed from the reaction in vacuo and residue obtained was triturated with diethyl ether, filtered through a sintered funnel to remove DCU. Combined filtrate and evaporated on a rotary evaporator. Residue was redissolved in EtOAc (100 mL) and successively washed with KHSO$_4$ solution, water, NaHCO$_3$ solution and water followed by drying over anhydrous Na$_2$SO$_4$ and evaporation of solvent in vacuo to obtain yellowish viscous residue of compound 203b (8.0 g). The crude product thus obtained was directly used for subsequent reaction without further purification. $^1$H NMR (400 MHz, [D$_6$]DMSO, 25° C.): δ 7.86-7.84 (bt, J(H,H)=5.39, 5.00 Hz, 1H, exchangeable with D$_2$O), 7.19-7.03 (m, 4H), 3.56 (s, 3H), 3.53-3.47 (q, J(H,H)= 7.05 Hz, 1H), 3.00-2.95 (q, J(H,H)=6.64, 5.81 Hz, 2H), 2.39-2.37 (m, 2H, mixture of rotamers), 2.23-2.20 (t, J(H,H)= 7.45, 7.05 Hz, 2H), 1.81-1.74 (m, 1H), 1.49-1.41 (m, 2H), 1.36-1.26 (m, 5H), 1.19-1.11 (m, 2H), 0.84-0.82 (m, 6H, mixture of rotamers).

Compound 204b:

Compound 203b (8.00 g, 24.01 mmol) was stirred with LiOH (1.21 g, 28.84 mmol) in THF-H$_2$O (4:1, 40 mL) for 4 h. Solvents were removed from the reaction mixture in vacuo and the residue was washed with concentrated KHSO$_4$ solution. Unlike the corresponding naproxen analogue 204a, the free acid 204b did not precipitate out from the aqueous phase, so the aqueous phase was repeatedly extracted with EtOAc, combined extract, dried over Na$_2$SO$_4$ and evaporated in vacuo to obtain slightly yellowish viscous residue, 6.60 g (86.1%). The acid 204b thus obtained was directly used for subsequent experiments without further purification. $^1$H NMR (400 MHz, [D$_6$]DMSO, 25° C.): δ 11.96 (bs, 1H, exchangeable with D$_2$O), 7.87-7.84 (t, J(H,H)=5.39 Hz, 1H, exchangeable with D$_2$O), 7.19-7.04 (m, 4H), 4.04-3.99 (q, J(H,H)=7.05 Hz, 1H), 3.62-3.57 (q, J(H,H)=7.05 Hz, 0.1H, minor rotamer), 3.53-3.47 (q, J(H,H)=7.05 Hz, 1.9H), 3.00-2.95 (q, J(H,H)=6.22 Hz, 2H), 2.41-2.37 (m, 2H, mixture of rotamers), 2.14-2.10 (t, J(H,H)=7.47, 7.05 Hz, 2H), 1.81-1.74 (m, 1H), 1.46-1.40 (m, 2H), 1.36-1.26 (m, 5H), 1.20-1.12 (m, 2H), 0.85-0.82 (m, 6H, mixture of rotamers).

Compound 206b:

Compound 204b (6.60 g, 20.676 mmol), DMAP (0.26 g, 2.128 mmol) and pentafluorophenol (5.70 g, 30.97 mmol) were dissolved in dichloromethane (60 mL) and DCC (4.27 g, 20.70 mmol) was added into the stirring solution. The reaction mixture was allowed to stir for 8 h. Precipitated DCU was removed by filtration and the filtrate was evaporated to obtain a crude oil containing the desired ester 205b. The crude 205b thus obtained was stirred with serinol (3.5 g, 38.42 mmol) in dichloromethane in the presence of TEA (8 mL) for 2 h. A white precipitate was formed during the course of the reaction, which was filtered washed successively with dichloromethane, water and diethyl ether and dried over P$_2$O$_5$ to obtain 2.4 g of the product 206b. Extraction of the aqueous phase with EtOAc afforded another 1.05 g of the desired product 206b. Combined yield was 42.5%. $^1$H NMR (400 MHz, [D$_6$]DMSO, 25° C.): δ 7.87-7.84 (t, J(H,H)=5.86, 5.37 Hz, 1H, exchangeable with D$_2$O), 7.42-7.40 (d, J(H,H)=7.81 Hz, 1H, exchangeable with D$_2$O), 7.19-7.17 (d, J(H,H)=8.30 Hz, 2H), 7.06-7.04 (d, J(H,H)=8.30 Hz, 2H), 4.57 (bs, 2H, exchangeable with D$_2$O), 3.69-3.63 (m, 1H), 3.53-3.47 (q, J(H,H)=6.83 Hz, 1H), 3.36-3.34 (d, J(H,H)=5.37 Hz, 4H), 3.02-2.91 (m, 2H), 2.39-2.37 (d, J(H,H)=7.34 Hz, 2H), 2.04-2.00 (t, J(H,H)=7.33 Hz, 2H), 1.81-1.75 (m, 1H), 1.44-1.26 (m, 7H), 1.18-1.12 (m, 2H), 0.84-0.83 (d, J(H,H)=6.35 Hz, 6H).

Compound 207b:

A solid mixture of compound 206b (3.00 g, 7.65 mmol), 4,4'-dimethoxytrityl chloride (2.85 g, 8.41 mmol) and DMAP (0.20 g, 1.64 mmol) was taken in a 200 mL RB and dried over P$_2$O$_5$ under vacuum overnight Anhydrous pyridine (40 mL) was added into the mixture under argon and stirred for overnight. Pyridine was removed from the reaction and residue was suspended in EtOAc (100 mL) followed by standard workup. Desired mono DMT and bis DMT products were separated by flash silica gel column chromatography, eluent: 2-3% methanol in dichloromethane, 170 g (22.3%, bis DMT derivative) and eluent: 4% methanol in dichloromethane, 1.89 g (35.6%, desired mono DMT product 207b). $^1$H NMR (400 MHz, [D$_6$]DMSO, 25° C.): δ 7.83-7.80 (t, J(H,H)=5.37 Hz, 1H, exchangeable with D$_2$O), 7.58-7.55 (d, J(H,H)=8.79 Hz, 1H, exchangeable with D$_2$O), 7.34-7.32 (d, J(H,H)=7.33 Hz, 2H), 7.26-7.14 (m, 9H), 7.02-7.00 (d, J(H,H)=7.81 Hz, 2H), 6.83-6.81 (d, J(H,H)=8.79 Hz, 4H), 4.58-4.56 (t, J(H, H)= 5.37, 4.88 Hz, 1H, exchangeable with D$_2$O), 3.95-3.93 (m, 1H), 3.68 (s, 6H), 3.48-3.45 (q, J(H,H)=7.34 Hz, 1H), 3.41-3.38 (t, J(H,H)=5.37 Hz, 2H), 2.96-2.84 (m, 4H), 2.34-2.33 (d, J(H,H)=7.33 Hz, 2H), 2.02-1.98 (t, J(H,H)=7.33, 7.81 Hz, 2H), 1.76-1.69 (m, 1H), 1.44-1.36 (m, 2H), 1.33-1.23 (m, 5H), 1.16-1.08 (m, 2H), 0.80-0.78 (d, J(H,H)=6.35 Hz, 6H). $^{13}$C NMR (100 MHz, [D$_6$]DMSO, 25° C.): δ 174.0, 172.8, 158.3, 145.4, 139.9, 139.7, 136.2, 130.1, 129.2, 128.2, 128.1, 127.3, 113.5, 85.5, 61.0, 55.4, 51.1, 45.1, 44.6, 35.7, 30.0, 29.1, 26.3, 25.4, 22.5, 18.8.

Compound 208b:

The desired succinate (0.98 g, 85.7%) was synthesized from the corresponding precursor 207b (1.00 g, 1.44 mmol), DMAP (0.27 g, 2.21 mmol) and succinic anhydride (0.22 g, 2.20 mmol) as described for the corresponding naproxen derivative. The succinic acid derivative was purified by flash silica gel column chromatography, eluent: 5% methanol in dichloromethane. $^1$H NMR (400 MHz, [D$_6$]DMSO, 25° C.): δ 7.86-7.80 (m, 2H, exchangeable with D$_2$O), 7.34-7.32 (d, J(H,H)=7.33 Hz, 2H), 7.28-7.13 (m, 9H), 7.02-7.00 (d, J(H, H)=8.30 Hz, 2H), 6.85-6.83 (d, J(H,H)=8.79 Hz, 4H), 4.14-1.10 (bm, 2H), 4.02-3.98 (m, 1H), 3.68 (s, 6H), 3.50-3.44 (q, J(H,H)=7.33, 6.83 Hz, 2H), 2.96-2.87 (m, 2H), 2.35-2.33 (m, 6H), 2.51-2.45 (m, 7H, 2H+ DMSO-d$_6$), 2.01-1.96 (t, J(H, H)= 7.32 Hz, 2H), 1.77-1.69 (m, 1H), 1.42-1.22 (m, 7H), 1.15-1.07 (m, 2H), 0.80-0.78 (d, J(H,H)=6.35 Hz, 6H). $^{13}$C NMR (100 MHz, [D$_6$]DMSO, 25° C.): δ 174.9, 174.3, 173.2, 158.5, 145.3, 139.9, 139.8, 136.0, 130.2, 129.3, 128.4, 128.1, 127.4, 113.6, 85.8, 55.5, 46.1, 46.1, 45.3, 44.7, 35.6, 30.1, 29.0, 26.2, 25.4, 22.6, 18.8.

The desired CPG 208b (4.50 g) with a loading capacity of 85.62 μM/g was prepared from 0.92 g (1.16 mmol) of the ibuprofen succinate thus obtained, 2,2'-Dithiobis(5-nitropyridine) (0.37 g, 1.18 mmol), DMAP (0.15 g, 1.23 mmol), Ph$_3$P (0.31 g, 1.18 mmol) and long chain aminoalkyl controlled pore glass (CPG) with 500 Å size and a loading of 162.5 µM/g as described for the preparation of the corresponding naproxen analogue 208a.

Compound 209b:

The desired amidite 209b is prepared as described for compound 209a in Example 1.

Compound 201d:

Ibuprofen pentafluorophenol ester (201d) was prepared from ibuprofen (201b, 5.00 g, 24.23 mmol), pentafluorophenol (5.4 g, 29.02 mmol), DCC (5.00 g, 24.23 mmol) and DMAP (0.30 g, 2.46 mmol) as described for the synthesis of pentafluorophenol ester (201c) of naproxen (201a).

mL) for 1 h. The reaction mixture was diluted to 50 mL and washed with aqueous sodium bicarbonate followed by standard workup. Compound 210a was obtained as a white foamy solid after flash silica gel column chromatography, eluent: 3-4% methanol in dichloromethane, yield: 5.45 g (quant.). $^1$H NMR (400 MHz, [D$_6$]DMSO, 25° C.): δ 7.92-7.88 (m, 1H); 7.76-7.68 (m, 3H); 7.43-7.41 (d, J(H,H)=8.5 Hz, 1H); 7.31-7.08 (m, 11H); 6.87-6.83 (m, 4H); 4.97 (bd, 0.7H, exchangeable with D$_2$O); 4.88 (bd, 0.3H, exchangeable with D$_2$O); 4.39-4.35 (m, 0.7H); 4.29-4.26 (m, 0.3H); 4.14-4.10 (m, 0.7H), 3.83-3.82 (d, J(H,H)=2 Hz, 3H, changed to multiplet after D$_2$O exchange); 3.71-3.65 (m, 7H); 3.54-3.50 (m,

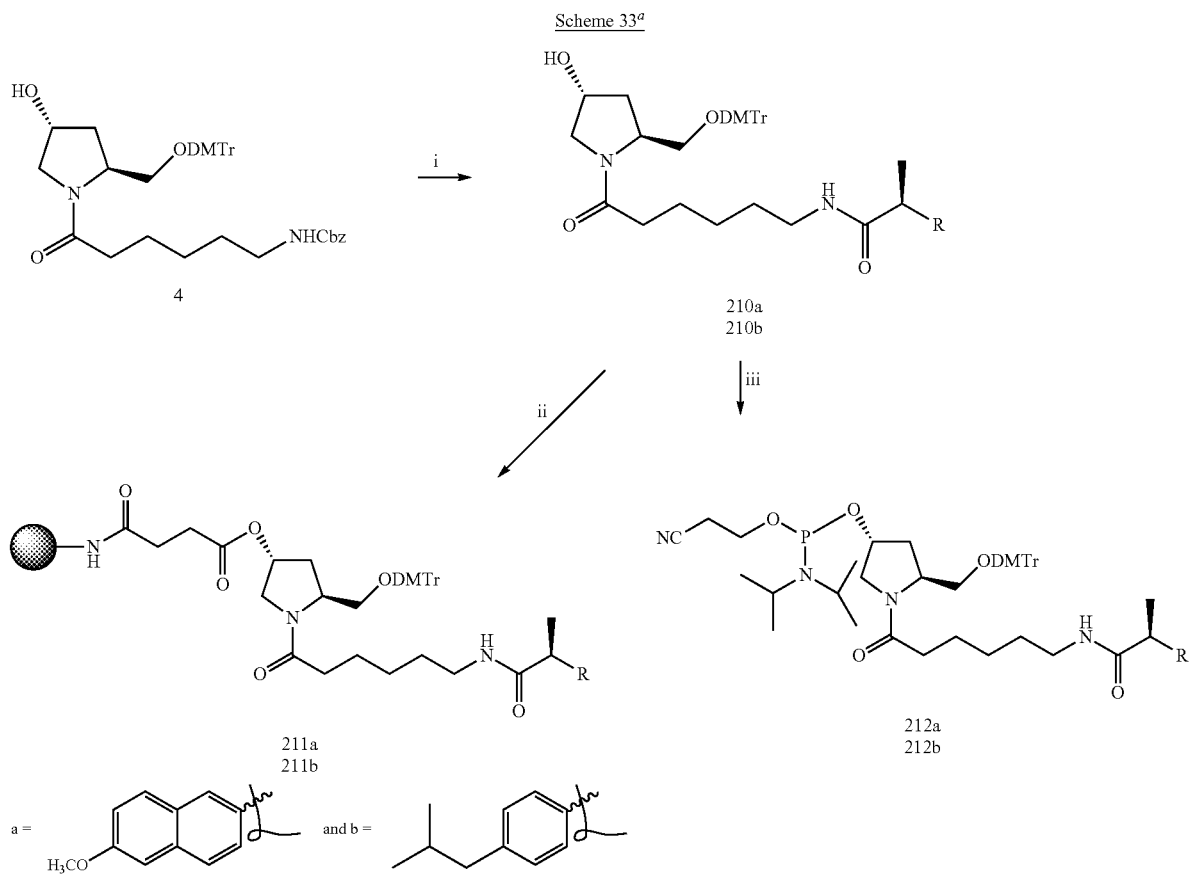

$^a$(i) (a) H$_2$/Pd-C/EtOAc-MeOH (4:1) and (b) Naporxen pantaflurophenol ester (or Ibuprofen pentafluorophenol ester), TEA/dichloromethane; (ii) (a) Succinic anhydride, DMAP/Dichloroethane and (b) DTNP, DMAP, Ph$_3$P, Aminoalkyl solid support and (iii) N,N-diisopropylamino b-cyanoethylphosphonamidic chloride {[(CH$_3$)$_2$CH]$_2$N—P(Cl)—OCH$_2$CH$_2$CN}, DIEA/Dichloromethane or 2-Cyanoethyl-N,N, N', N'-tetraisopropylphosphorodiamidite, tetrazole (or tetrazolediisopropylammonium salt)/Acetonitrile.

Compound 210a:

Compound 4 (4.90 g, 7.35 mmol) was dissolved in ethyl acetate-methanol (4:1, 16 mL) and purged with argon. To the solution was added 10% palladium on carbon (2 g, wet, Degussa type E101 NE/W). The flask was purged with hydrogen 2 times and stirred further at room temperature under hydrogen at 1 atm for 2 h. The disappearance of the starting material was confirmed by TLC analysis. The reaction mixture was filtered through a bed of Celite and washed with ethyl acetate-methanol (4:1). The combined filtrate was concentrated under reduced pressure to afford free amine. The free amine obtained was stirred with compound 101c (3.1 g, 7.82 mmol) in the presence of TEA in dichloromethane (20

0.7H), 3.43-3.40 (m, 0.3H); 3.28-3.22 (m, 1H); 315-3.10 (m, 1H); 3.01-2.95 (m, 3H); 2.12-1.80 (m, 5H); 1.42-1.04 (m, 8H).

Compound 211a:

The solid support 211a is prepared from compound 210a as described in Example 1 for the preparation of compound 208a.

Compound 212a:

The phosphoramidite 212a is prepared from compound 210a as described in Example 1 for the preparation of compound 209a.

Compound 210b:

Compound 210b is obtained from compound 4 and compound 201d as described in Example 3 for the preparation of compound 210a.

Compound 211b:

The solid support 211b is prepared from compound 210b as described in Example 1 for the preparation of compound 208a.

Compound 212b:

The phosphoramidite 212b is prepared from compound 210b as described in Example 1 for the preparation of compound 209a.

Compound 214a:

DMT-dT-C5-Amino linker (213, 1.00 g, 1.43 mmol) from Chem Genes was stirred with cholesteryl chloroformate (0.77 g, 1.71 mmol) in dichloromethane (10 mL) in the presence of TEA (1.0 mL) at ambient temperature for 2 h. Completion of the reaction was confirmed by TCL monitoring. The reaction mixture was diluted to 50 mL by adding more dichloromethane and washed successively with $NaHCO_3$ solution and water followed by standard workup. Residue obtained was purified by flash silica gel column chromatography to afford 214a (0.66 g, 37.75%). $^1$H NMR (400 MHz, [D$_6$] DMSO, 25° C.): δ 11.61 (s, 1H, exchangeable with D$_2$-O),

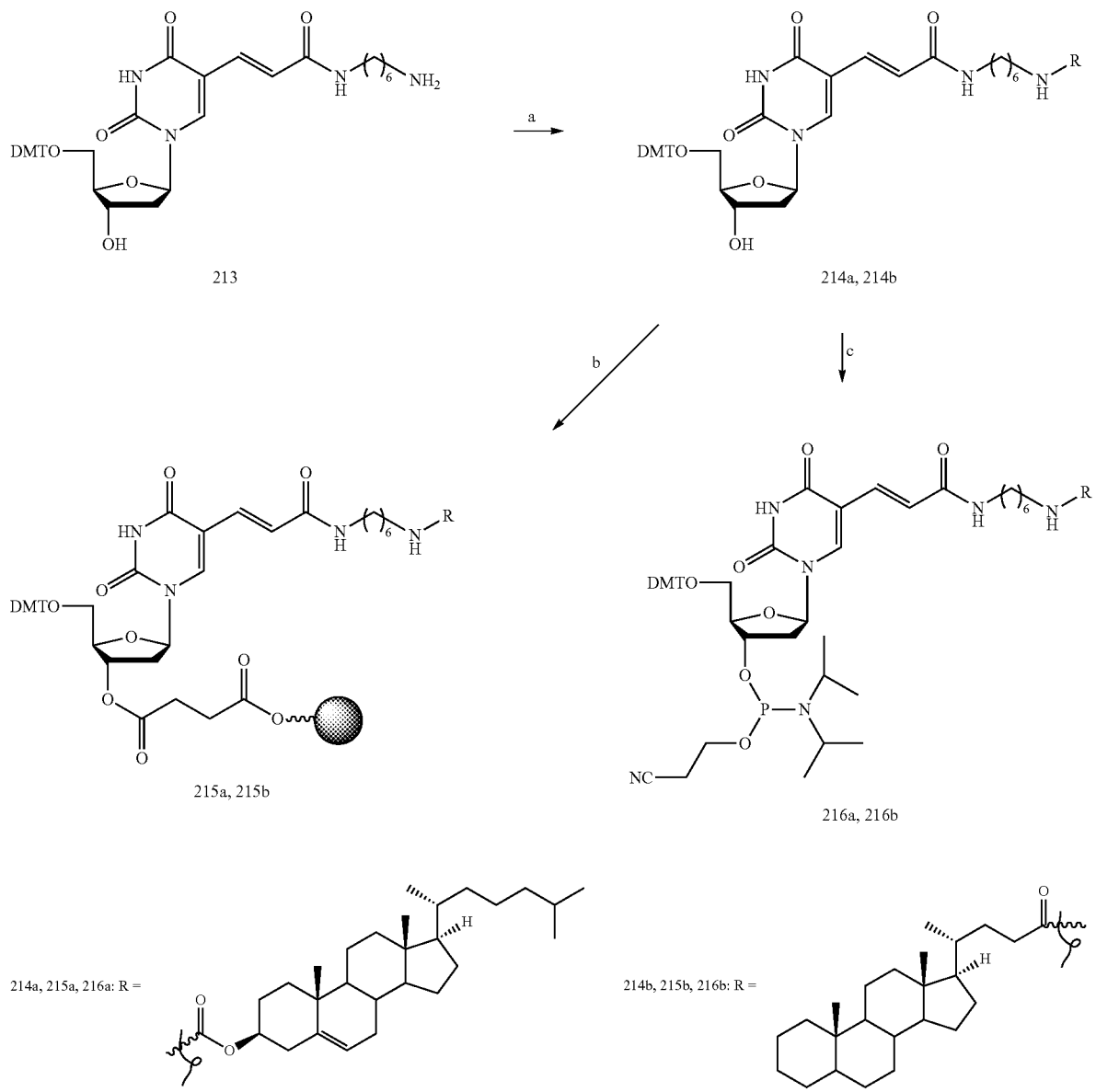

Scheme 34$^a$ $^a$ (i) For 2a: Cholesterylchloroformate, TEA/Dichloromethane; for 2b: 5β-cholanic acid pentafluorophenol ester, TEA/Dichloromethane; (ii) (a) Succinic anhydride, DMAP/Dichloroethane and (b) DTNP, DMAP, Ph$_3$P, Aminoalkyl solid support; (iii) N,N-diisopropylamino β-cyanoethylphosphonamidic chloride
{[(CH$_3$)$_2$CH]$_2$N—P(Cl)—OCH$_2$CH$_2$CN}, DIEA/Dichloromethane or 2-Cyanoethyl-N,N, N′, N′-tetraisopropylphosphorodiamidite, tetrazole (or tetrazolediisopropylammonium salt)/Acetonitrile 8.01-7.98 (t, J(H,H)=5.39 Hz, 1H, exchangeable with D$_2$O), 7.92 (s, 1H), 7.37-6.99 (m, 12H), 6.87-6.83 (m, 4H), 6.17-6.14 (t, J(H,H)=6.64 Hz, 1H), 5.30 (s, 1H), 5.28-5.27 (d, J(H,H)=4.56 Hz, 1H, exchangeable with D$_2$O), 4.32-4.20 (m, 2H), 3.87-3.84 (m, 1H), 3.71-3.63 (m, 7H), 3.21-3.03 (m, 4H), 2.95-2.88 (m, 2H), 2.33-2.13 (m, 4H), 1.97-1.73 (m, 5H), 1.54-0.82 (m, 40H), 0.63 (s, 3H).

Compound 215a

Compound 214a (0.55 g, 0.495 mmol) and succinic anhydride (0.075 g, 0.749 mmol) were suspended in anhydrous dichloromethane (5 mL) and stirred at ambient temperature in the presence of DMAP (0.18 g, 1.49 mmol) overnight. After confirming completion of the reaction, the reaction mixture was diluted to 50 mL by adding dichloromethane and washed with dilute citric acid solution; organic layer was dried over anhydrous Na$_2$SO$_4$ and evaporated in vacuo. Residue obtained was purified by flash silica gel column chromatography, eluent 6% methanol in dichloromethane, to afford the corresponding succinic acid derivative (0.50 g, 83.4%). $^1$H NMR (400 MHz, [D$_6$]DMSO, 25° C.): δ 12.24 (bs, 1H, exchangeable with D$_2$O), 11.64 (s, 1H, exchangeable with D$_2$O), 8.02-7.99 (bm, 2H), 7.36-7.00 (m, 12H), 6.87-6.81 (m, 4H), 6.15-6.11 (t, J(H,H)=6.84 Hz, 1H), 5.30 (bs, 1H), 5.17-5.14 (bm, 1H), 4.31-4.24 (m, 1H), 4.05 (bm, 1H), 3.70-3.66 (m, 8H), 3.34-3.08 (m, 6H), 2.94-2.88 (m, 4H), 2.31-2.13 (m, 3H), 1.96-1.71 (bm, 5H), 1.55-0.80 (m, 40H), 0.63 (s, 3H).

The succinnate thus obtained was conjugated to long chain aminoalkyl controlled glass support (CPG) with a loading of 155 μM/g loading as described in the literature by Kumar et al. (*Nucleosides and Nucleotides*, 1996, 15, 879) to obtain the desired the desired CPG solid support 215a (1.70 g) with a loading of 78.42 μM/g. The loading of the support 215a was determined as described in the literature (Prakash et al., *J. Org. Chem.*, 2002, 67, 357).

Compound 216a

The phosphoramidite 216a is prepared from compound 214a by reacting with 2-Cyanoethyl-N,N,N',N'-tetraisopropylphosphorodiamidite in the presence of tetrazolediisopropylammonium salt in acetonitrile according to reported procedures (Rajeev et al., *Org. Lett.*, 2003, 5, 3005).

Compound 214b

5β-Cholanic acid (5.00 g, 13.87 mmol, purchased from Sigma), pentafluorophenol (2.81 g, 15.27 mmol, purchased from Aldrich) and DMAP (0.20 g, 1.64 mmol) were dissolved in dichloromethane and N,N'-dicyclohexycarbodiimide (DCC, 2.86 g, 13.86 mmol) was added into the solution at ambient temperature. The reaction mixture was stirred for 4 h. N,N'-Dicyclohexylurea was filtered off from the reaction and the filtrate was evaporated to obtain pentafluorophenol ester of 5β-cholanic acid. The ester (0.90 g, 1.708 mmol) thus obtained was stirred with compound 213 (1.00 g, 1.431 mmol) in the presence of TEA in dichloromethane (8 mL) for 2 h. The reaction was complete after 2 h as evident from TLC analysis. Reaction mixture was diluted to 50 mL by adding more dichloromethane and washed with dilute NaHCO$_3$ solution followed by standard workup. Residue was purified by flash silica gel column chromatography, eluent 3-4% methanol in dichloromethane, to afford the desired compound 214b (1.46 g, 98.04%).

$^1$H NMR (400 MHz, [D$_6$]DMSO, 25° C.): δ 11.62 (bs, 1H exchangeable with D$_2$O); 8.03-8.00 (t, J(H,H)=5.38 Hz, 1H, exchangeable with D$_2$O), 7.92 (s, 1H), 7.74-7.71 (t, 1H, exchangeable with D$_2$O); 7.37-7.02 (m, 11H), 6.88-6.84 (m, 4H), 6.17-6.14 (t, J(H.H)=6.35, 6.69 Hz, 1H), 4.22-4.19 (m, 1H), 3.88-3.85 (m, 1H), 3.70-3.69 (d, J(H,H)=3.91 Hz, 6H); 3.20-2.89 (m, 6H), 2.33-2.27 (m, 1H), 2.18-2.12 (m, 1H), 2.08-2.00 (m, 1H), 1.99-1.84 (m, 2H), 1.84-1.56 (m, 6H), 1.54-0.94 (m, 33H), 0.87-0.79 (m, 7H), 0.57 (s, 3H).

$^{13}$C NMR (100 MHz, [D$_6$]DMSO, 25° C.): δ 173.5, 166.1, 162.2, 158.5, 149.7, 145.2, 142.9, 136.0, 135.9, 132.5, 130.1, 128.4, 128.1, 127.2, 122.4, 113.6, 109.8, 107.3, 86.1, 85.9, 85.4, 70.6, 64.2, 56.5, 56.0, 55.4, 55.2, 46.2, 43.5, 42.7, 40.4, 38.7, 37.5, 35.8, 35.3, 32.9, 32.1, 29.5, 29.4, 28.2, 27.5, 27.1, 26.9, 26.6, 26.5, 24.4, 24.3, 21.2, 20.9, 18.6, 12.2, 9.1.

Compound 215b

Compound 215b was prepared from compound 214b as described in Example 1 for the synthesis of compound 215aa. Loading of the support 215b (2.7 g) prepared was determined as 81 μM/g.

Compound 216b

The phosphoramidite 216b is prepared from compound 214b by reacting with 2-Cyanoethyl-N,N,N',N'-tetraisopropylphosphorodiamidite in the presence of tetrazolediisopropylammonium salt in acetonitrile according to reported procedures (Rajeev et al., *Org. Lett.*, 2003, 5, 3005).

Scheme 35$^a$

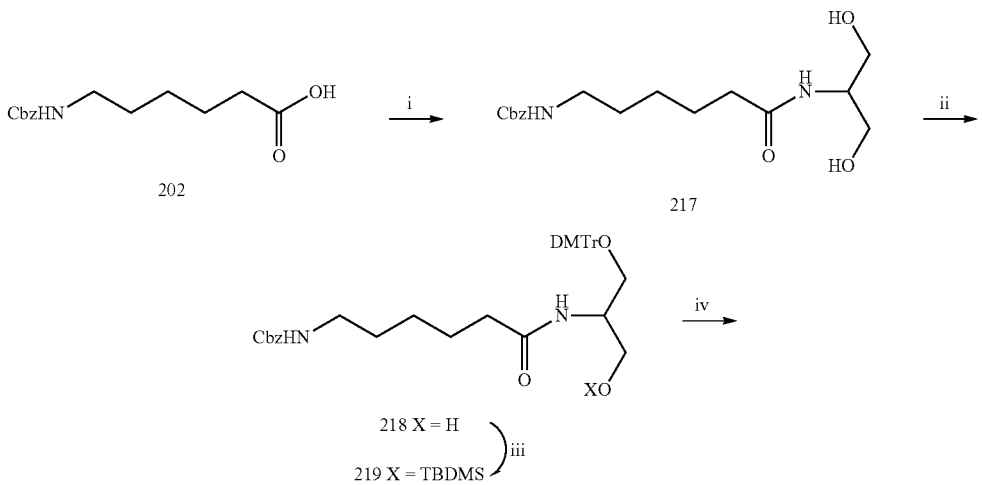

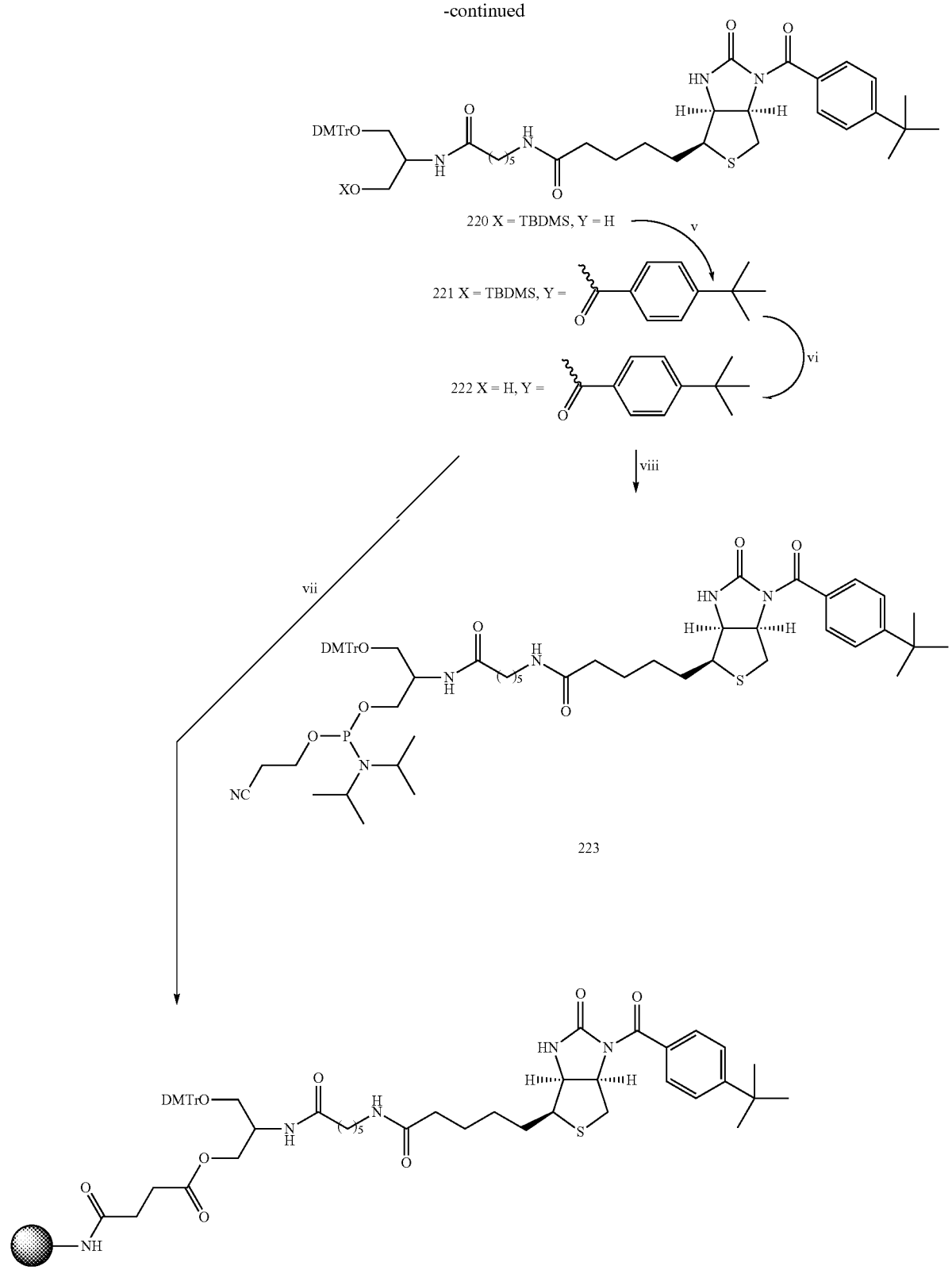

-continued

220 X = TBDMS, Y = H
221 X = TBDMS, Y = 4-tBu-benzoyl
222 X = H, Y = 4-tBu-benzoyl
223
224

[a] (i) (a) Pentafluorophenol, DCC, DMAP/Dichlorromethane and (b) Serinol, TEA/dichloromethane; (ii) DMT-Cl, DMAP/Py; (iii) TBDMS-Cl, Imidazole/Py; (iv) (a) Pd-C (10%), ammonium formate and (b) Biotin-NHS ester, TEA/DMF and (v) 4-tBu-Bz-Cl, DMAP/DCM; (vi) TEA·3HF, TEA/THF; (vii) (a) Succinic anhydride, DMAP/Dichloroethane and (b) DTNP, DMAP, Ph₃P, Aminoalkyl solid support and (viii) N,N-diisopropylamino β-cyanoethylphosphonamidic chloride{[(CH₃)₂CH]₂N—P(Cl)—OCH₂CH₂CN}, DIEA/Dichloromethane or 2-Cyanoethyl-N,N N′, N′-tetraisopropylphosphorodiamidite, tetrazole (or tetrazolediisopropylammonium salt)/Acetonitrile.

Compound 217:

N-Cbz-6-aminohexanoic acid (202, 30.31 g, 114.25 mmol, purchased from Novabiochem), pentafluorophenol (25.00 g, 135.83 mmol) and DMAP (1.54 g, 12.60 mmol) were taken in dichloromethane (100 mL) and to this DCC (26.00 g, 121.01 mmol) added slowly under stirring. During the course of addition, temperature of the reaction rose and dichloromethane started boiling out, so it was cooled down to room temperature and allowed to stir overnight. Reaction mixture was diluted to 200 mL by adding diethyl ether and subsequently filtered through a sintered funnel to remove DCU, washed residue with diethyl ether, combined washing and evaporated to dryness. The desired ester was purified by flash silica gel column chromatography, eluent: hexane/EtOAc 2:1, yield 43.54 g (88.4%). $^1$H NMR (400 MHz, [D$_6$]DMSO, 25° C.): δ 7.36-7.23 (m, 6H), 4.99 (s, 2H), 3.01-2.96 (q, J(H,H)=6.35 Hz, 2H), 2.78-2.52 (q, J(H,H)=7.33 Hz, 2H), 1.69-1.61 (m, 2H), 1.47-1.29 (m, 4H).

The pentafluorophenol ester (26.00 g, 60.31 mmol) and serinol (5.00 g, 54.88 mmol) were suspended in 200 mL of dichloromethane and stirred in the presence of TEA (17 mL, 121. 97 mmol) at ambient temperature overnight. A thick white precipitate was formed during the course of the reaction. The reaction mixture was diluted to 200 mL by adding diethyl ether, triturated and filtered. The precipitate was thoroughly washed with diethyl ether and dried under vacuum over P$_2$O$_5$ to obtain 16.51 g (81.0%) of the desired compound 217 as a white solid. $^1$H NMR (400 MHz, [D$_6$]DMSO, 25° C.): δ 7.44-7.42 (d, J(H,H)=7.81 Hz, 1H, exchangeable with D$_2$O), 7.37-7.27 (m, 5H), 7.24-7.20 (t, J(H,H)=5.86, 5.37 Hz, 1H, exchangeable with D$_2$O), 4.99 (s, 2H), 4.58-4.55 (t, J(H,H)=5.37 Hz, 2H, exchangeable with D$_2$O), 3.70-3.65 (m, 1H), 3.37-3.34 (t, J(H,H)=5.86, 3.37 Hz, changed to doublet after D$_2$O exchange, J(H,H, after D$_2$O exchange)=5.37 Hz, 4H), 2.98-2.92 (q, J(H,H)=6.84, 6.35 Hz, 2H), 2.06-2.02 (t, J(H,H)=7.33 Hz, 2H), 1.49-1.33 (m, 4H), 1.24-1.16 (m, 2H).

Compound 218:

Compound 217 (14.10 g, 41.66 mmol) and DMAP 0.60 g, 4.91 mmol) were taken in a 200 mL RB and dried under vacuum over P$_2$O$_5$. The solid mixture then suspended in 50 mL of anhydrous pyridine under argon. 4,4-Dimethoxytrityl chloride (15.5 g, 44.27 mmol) was separately dissolved in 40 mL of anhydrous dichloromethane and added into the stirring pyridine solution under argon. The reaction mixture was allowed to stir at ambient temperature overnight.

Solvents were removed from the reaction mixture and residue was extracted into EtOAC (200 mL), washed with NaHCO$_3$ solution followed by standard workup. The desired product 218 was purified by flash silica gel column chromatopgraphy, eluent: hexane/EtOAc 3:2, 8.62 g (28.0%, bis DMT derivative) and 3-4% MeOH in chloroform, 15.28 g (57.3%, desired mono DMT derivative 218). $^1$H NMR (400 MHz, [D$_6$]DMSO, 25° C.): δ 7.63-7.60 (d, J(H,H)=8.79 Hz, 1H, exchangeable with D$_2$O), 7.38-7.17 (m, 15H, accounted for 14H after D$_2$O exchange), 6.87-6.84 (d, J(H,H)=8.79 Hz, 4H), 4.98 (s, 2H), 4.62-4.59 (t, J(H,H)=5.37 Hz, 1H, exchangeable with D$_2$O), 4.00-3.95 (m, 1H), 3.72 (s, 6H), 3.46-3.41 (t, J(H,H)=5.37 Hz, 2H), 3.00-2.87 (m, 4H), 2.08-2.04 (t, J(H,H)=7.33 Hz, 2H) 1.50-1.33 (m, 4H), 1.25-1.16 (m, 2H).

Compound 219:

Compound 218 (12.91 g, 20.16 mmol) in anhydrous pyridine (50 mL) was stirred with TBDMS-Cl (4.60 g, 30.52 mmol) in the presence of imidazole (6.30 g, 92.54 mmol) at ambient temperature for 6 h. After 6 h pyridine was removed in vacuo and the product was extracted into ethyl acetate (100 mL), washed with sodium bicarbonate solution followed by standard workup. The residue was purified by flash silica gel column chromatography, eluent: 2-3% methanol in dichloromethane to afford compound 219 (15.10 g, 99.3%). $^1$H NMR (400 MHz, [D$_6$]DMSO, 25° C.): δ 7.65-7.63 (bd, J(H,H)=8.30 Hz, 1H, exchangeable with D$_2$O); 7.38-7.17 (m, 14H); 6.86-6.84 (d, J(H,H)=8.79 Hz, 4H); 5.00 (s, 2H); 4.01-3.96 (m, 1H); 3.71 (s, 6H); 3.58-3.52 (m, 2H), 3.04-2.99 (m, 1H); 2.98-2.89 (m, 3H); 2.09-2.05 (t, 2H); 1.50-1.43 (m, 2H); 1.42-1.38 (m, 2H); 124-1.19 (m, 2H); 0.75 (s, 9H); −0.05 (s, 3H); −0.06 (s, 3H).

Compound 220:

Compound 219 (7.05 g, 9.33 mmol) and ammonium formate (3.00 g, 47.573) were suspended in 40 mL of methanol/ethyl acetate (1:2) and to this Pd—C (10%, 0.70 g) was added at ambient temperature. The suspension was initially warmed by blowing hot air and subsequently stirred at ambient temperature for 4 h. Completion of the reaction was monitored by TLC and after 4 h, the reaction mixture was filtered over a celite column, washed residue with methanol/ethyl acetate (1:2), combined filtrate and evaporated to dryness. Residue obtained was extracted into ethyl acetate (100 mL) and washed with aqueous sodium bicarbonate and water. Organic layer was dried over anhydrous Na$_2$SO$_4$ and evaporate to obtain the free amine. $^1$H NMR (400 MHz, [D$_6$]DMSO, 25° C.): δ 7.72-7.61 (m, 1.5H); 7.43-7.06 (m, 10H); 6.86-6.84 (d, J(H,H)=8.79 Hz, 4H); 4.20-3.97 (bm, 1H); 3.71 (s, 6H); 3.59-3.52 (bm, 2H); 3.07-3.00 (m, 2H); 2.93-2.88 (m, 2H); 2.72-2.98 (t, 1H); 2.10-2.05 (m, 2H); 1.53-1.44 (m, 4H), 1.28-1.22 (m, 2H), 0.75 (s, 9H); −0.05 (s, 3H); −0.07 (s, 3H).

The free amine (2.0 g, 3.22 mmol) was stirred with biotin-NHS ester (1.0 g, 2.93 mmol, purchased from Sigma) in the presence of triethylamine in DMF for 4 h. Progress of the reaction was monitored by TLC. Removed DMF in vacuo and the product was extracted into ethyl acetate (50 mL) and washed with water followed by standard workup. Compound 220 was purified by flash silica gel column chromatography; eluent: 5% methanol in dichloromethane, yield: 1.43 g (57.7%). $^1$H NMR (400 MHz, [D$_6$]DMSO, 25° C.): δ 7.73-7.70 (t, J(H,H)=5.38 Hz, 1H, exchangeable with D$_2$O); 7.66-7.63 (d, J(H,H)=8.79 Hz, 1H, exchangeable with D$_2$O); 7.38-7.18 (m, 9H); 6.86-6.84 (d, J(H,H)=8.30 Hz, 4H); 6.42-6.35 (d, J(H,H)=27.35 Hz, 2H, changes to δ 5.62-5.61 with J(H,H)=0.98 Hz after D$_2$O exchange); 4.29-4.26 (m, 1H), 4.12-4.08 (m, 1H), 4.00-3.98 (m, 1H), 3.72 (s, 6H), 3.57-3.53 (m, 2H), 3.08-2.77 (m, 6H); 2.57-2.54 (d, J(H,H)=12.70 Hz, 1H), 2.10-2.06 (t, J(H,H)=8.79, 5.86 Hz, 2H); 2.04-2.00 (t, J(H,H)=7.32 Hz, 2H), 1.61-1.19 (m, 12H); 0.75 (s, 9H), −0.05 (s, 3H); −.06 (s, 3H).

Compound 221:

Compound 220 (1.3 g, 1.54 mmol) was stirred with 4-tert-butylbenzoyl chloride (1 mL, 5.08 mmol) in the presence of DMAP (0.02 g, 0.163 mmol) in anhydrous pyridine (5 mL) under argon atmosphere for 4 h. Excess of 4-tert-butylbenzoyl chloride was quenched by adding methanol and subsequently removed pyridine and methanol in vacuo. The product was extracted into ethyl acetate (50 mL) and washed with aqueous sodium bicarbonate followed by standard workup. Residue obtained was subjected to flash column chromatography to afford compound 221 (0.64 g, 41.4%). $^1$H NMR (400 MHz, [D$_6$]DMSO, 25° C.): δ 7.72-7.69 (t, J(H,H)=5.37 Hz, 1H, exchangeable with D$_2$O); 7.64-7.62 (d, J(H,H)=8.79 Hz, 1H, exchangeable with D$_2$O); 7.53-7.17 (m, 14H); 6.83-6.81 (d, J(H,H)=8.79 Hz, 4H); 5.11-5.10 (d, J(H,H)=1.95 Hz, 2H); 4.01-3.98 (m, 1H); 3.71 (s, 6H); 3.61-3.55 (m, 3H); 3.18-3.15 (m, 1H); 3.03-2.88 (m, 4H); 2.07-1.99 (m, 4H); 1.62-1.58 (m, 1H); 1.47-1.19 (m, 22H); 0.75 (s, 9H), −0.05 (s, 3H); −0.07 (s, 3H).

$^{13}$C NMR (100 MHz, [D$_6$]DMSO, 25° C.): δ 173.0, 172.9, 172.8, 172.7, 170.5, 170.0, 158.4, 155.5, 155.4, 152.2, 145.4, 136.2, 136.1, 132.0, 131.6, 130.2, 129.3, 129.1, 128.2, 128.1, 127.1, 125.2, 113.5, 85.6, 62.4, 62.2, 60.0, 59.9, 55.5, 55.2, 54.2, 50.8, 35.8, 35.1, 31.2, 31.1, 29.2, 29.0, 28.7, 26.4, 26.1, 25.6, 18.2, −5.1, −5.0.

Compound 222:

A solution of compound 221 (0.64 g, 0.64 mmol) in anhydrous THF (5 mL) was stirred with TEA.3HF (purchased from Aldrich, 1 mL) in the presence of anhydrous TEA (5 mL) at ambient temperature for 24. Solvents were removed from the reaction mixture under vacuum and the product was extracted into ethyl acetate, washed with aqueous sodium bicarbonate followed by standard workup. Flash silica gel column chromatography (eluent: 5% methanol in dichloromethane) of the residue afforded compound 222 (0.54 g, 95%). $^1$H NMR (400 MHz, [D$_6$]DMSO, 25° C.): δ 7.91 (bs, 1H, exchangeable with D$_2$O); 7.73 (bt, 1H, exchangeable with D$_2$O); 7.63-7.61 (d, J(H,H)=8.79 Hz, 1H, exchangeable with D$_2$O); 7.39-7.19 (m, 13H); 6.87-6.84 (d, J(H,H)=8.79 Hz, 4H); 5.05-5.02 (m, 1H); 4.62-4.60 (t, J(H,H)=5.37 Hz, 1H, exchangeable with D$_2$O); 4.21-4.17 (m, 1H); 4.00-3.96 (m, 1H); 3.72 (s, 6H); 3.45-3.42 (t, J(H,H)=5.37 Hz, 2H, changed to a doublet after D$_2$O exchange); 3.28-3.22 (m, 1H); 3.04-2.84 (m, 6H), 2.10-1.94 (m, 4H); 1.71-1.62 (m, 1H); 1.57-1.18 (m, 22H).

$^{13}$C NMR (100 MHz, [D$_6$]DMSO, 25° C.): δ 172.8, 172.7, 169.5, 158.3, 155.8, 154.2, 145.4, 136.2, 132.8, 130.1, 128.8, 128.1, 128.0, 127.0, 124.6, 113.4, 85.4, 63.0, 62.1, 61.0, 57.6, 55.4, 55.2, 55.1, 51.1, 57.6, 55.4, 55.2, 55.1, 38.7, 37.7, 35.8, 35.6, 35.0, 31.3, 29.2, 28.6, 28.2, 26.4, 25.6, 25.5.

Compound 223:

The phosphoramidite 223 is prepared from compound 222 by reacting with 2-Cyanoethyl-N,N,N',N'-tetraisopropylphosphorodiamidite in the presence of tetrazolediisopropylammonium salt in acetonitrile according to reported procedures (Rajeev et al., Org. Lett., 2003, 5, 3005).

Compound 224:

Compound 222 (0.50 g, 0.56 mmol) was stirred with succinic anhydride (0.115 g, 1.15 mmol) in the presence of DMAP (0.21 g, 1.72 mmol) in anhydrous ethylene dichloride under argon at 55° C. for 3 h. The reaction mixture was diluted to 20 mL by adding dichloromethane and washed with cold 10% citric acid solution, dried over anhydrous sodium sulfate and evaporated to dryness. The acid formed was purified by flash silica gel column chromatography (eluent: 10% methanol in dichloromethane); yield: 0.50 g (89.9%). $^1$H NMR (400 MHz, [D$_6$]DMSO, 25° C.): δ 12.12 (s, 1H, exchangeable with D$_2$O); 7.91 (bs, 1H, exchangeable with D$_2$O); 7.86-7.84 (bd, 1H, exchangeable with D$_2$O); 7.74-7.72 (bd, 1H, exchangeable with D$_2$O); 7.52-7.16 (m, 13H); 6.88-6.86 (d, J(H,H)= 8.79 Hz, 4H); 5.06-5.02 (m, 1H), 5.02-4.95 (m, 0.4H); 4.82-4.76 (m, 0.6H); 4.27-3.89 (m, 5H); 3.79-3.76 (m, 0.4H); 3.72 (s, 6H); 3.54-3.48 (m, 0.6H); 3.41-2.81 (m, 9H, accounted for 8H after D$_2$O exchange); 2.52 (bm, 4H); 2.07-1.94 (bm, 4H); 1.71-1.62 (m, 1H); 1.54-1.13 (m, 22H).

$^{13}$C NMR (100 MHz, [D$_6$]DMSO, 25° C.): δ 174.5, 174.1, 173.3, 173.2, 172.9, 172.7, 169.8, 158.6, 156.1, 155.9, 154.5, 145.3, 136.0, 132.9, 130.2, 129.3, 129.0, 128.5, 128.1, 127.4, 125.4, 124.8, 113.7, 85.8, 63.5, 62.3, 57.8, 55.6, 55.4, 55.2, 57.8, 55.6, 55.4, 55.2, 48.0, 37.9, 35.8, 35.2, 31.4, 31.4, 29.2, 29.1, 29.0, 28.8, 28.4, 26.4, 25.8, 25.6.

Compound 224 (2.0 with 56.15 μM/g loading) was prepared from the acid (0.45 g, 0.45 mmol), DMAP (0.068 g, 0.56 mmol), triphenylphosphine (0.135 mg, 0.51 mmol) and 2,2'-Dithiobis(5-nitropyridine) (DTNP, 0.16 g, 0.52 mmol) as described for the synthesis of compound 208a.

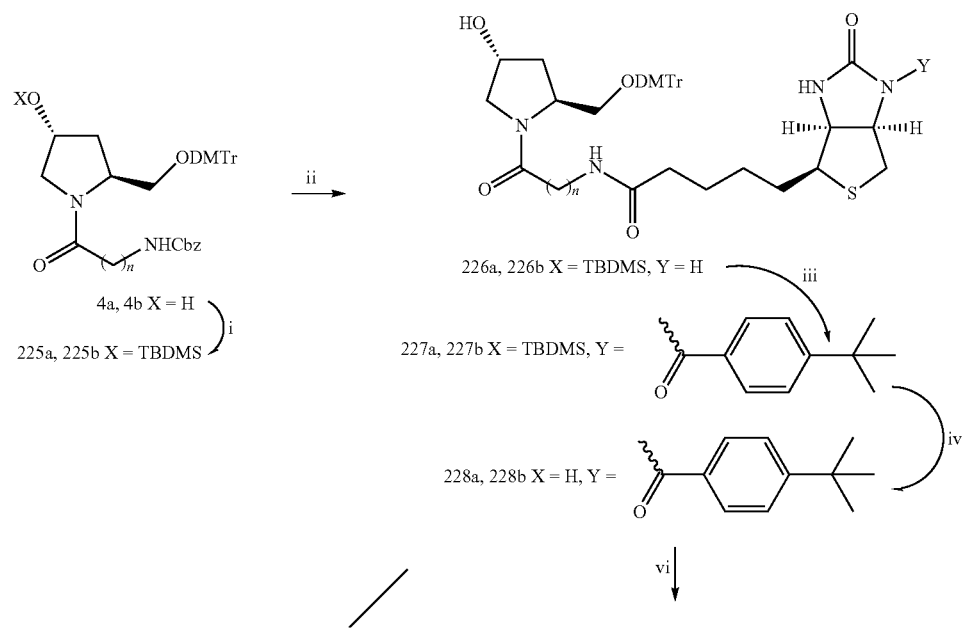

-continued

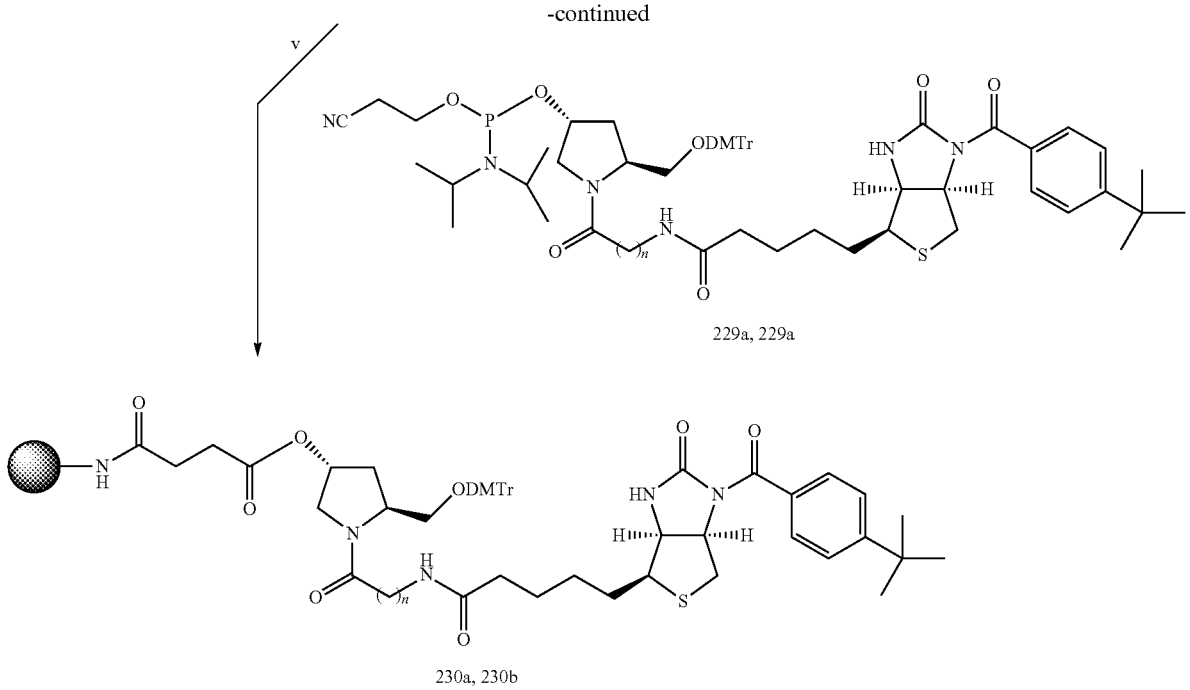

4a, 225a, 226a, 227a, 228a, 229a and 230a n = 5
4b, 225b, 226b, 227b, 228b, 229b and 230b n = 11

$^a$ (i) TBDMS-Cl, Imidazole/Py; (ii) (a) H$_2$ (1 atm), Pd-C (10%)/EtOAc-MeOH (4:1) and (b) Biotin-NHS ester, TEA/DMF and (iii) 4-tBu-Bz-Cl, DMAP/DCM; (iv) TEA•3HF, TEA/THF (v) (a) Succinic anhydride, DMAP/Dichloroethane and (b) DTNP, DMAP, Ph$_3$P, Aminoalkyl solid support and (vi) N,N-diisopropylamino β-cyanoethylphosphonamidic chloride {[(CH$_3$)$_2$CH]$_2$N—P(Cl)—OCH$_2$CH$_2$CN}, DIEA/Dichloromethane or 2-Cyanoethyl-N,N, N', N'-tetraisopropylphosphorodiamidite, tetrazole (or tetrazolediisopropylammonium salt)/Acetonitrile.

Compound 225a:

Compound 4a (12.09 g, 18.23 mmol) was stirred with TBDMS-Cl (4.00 g, 26.54 mmol) in the presence of imidazole (5.42 g, 79.61 mmol) in anhydrous pyridine (60 mm) overnight. After removing pyridine, the product was extracted into ethyl acetate (150 mL), washed with aqueous sodium bicarbonate, followed by standard workup. Residue obtained was subjected to flash silica gel column chromatography using 1% methanol in dichloromethane as eluent to afford compound 225a. $^1$H NMR (500 MHz, [D$_6$]DMSO, 25° C.): δ 7.33-7.13 (bm, 15H, accounted for 14H after D$_2$O exchange); 6.87-6.82 (bm, 4H); 5.01 (s, 0.2H, rotamer minor); 4.99 (s, 1.8H, rotamer major), 4.68-4.64 (m, 0.72 H, major rotamer); 4.14-4.07 (bm, 1H), 3.72 (s, 7H), 3.38-3.36 (m, 0.6H, rotamer minor); 3.26-3.21 (m, 1.4H, rotamer major); 3.08-3.07 (m, 0.3H, rotamer, minor); 2.99-2.89 (m, 2.7H, rotamer, major); 2.22-2.12 (m, 2H), 2.04-1.78 (m, 2H); 1.48-1.23 (m, 6H), 0.84, 0.82 (s, 9H, rotamers major and minor); 0.05 (d, J(H,H)=1.5 Hz, 4.3H, rotamer major); 0.03-0.02 (d, J(H,H)=5.5 Hz, 1.7H).

Compound 226a

Compound 225a (12.22 g, 15.67 mmol) was hydrogenated at 1 atm over 10% Pd—C (1.12 g, wet Degussa type E101 NE/W) in ethyl acetate/methanol (4:1) for 4 h as described for the synthesis of compound 210a. The free amine obtained was stirred with biotin-NHS ester (5.42 g, 15.87 mmol, purchased from ChemGenes Corporation Wilmington, Mass.) in the presence of TEA for 6 h in dichloromethane/methanol (9:1, 100 mL). Solvents were removed from the reaction mixture and the product was extracted into dichloromethane (400 mL), washed with aqueous sodium bicarbonate followed by standard workup. The crude product thus obtained was used for next reaction without further purification or characterization.

Compound 227a:

The crude 226a and DMAP (0.31 g, 2.57 mmol) were taken in anhydrous pyridine and stirred over an ice bath. To the stirring solution, 4-tert-butylbenzoyl chloride (5.0 mL, 25.42 mmol) was added drop-wise over ten minute. After the addition, the reaction mixture was brought to room temperature over 2 h and continued stirring overnight. After quenching excess 4-tert-butylbenzoyl chloride by adding methanol, solvents were removed from the reaction mixture and the product was extracted into ethyl acetate (300 mL), washed with aqueous sodium bicarbonate followed by standard workup. The desired product 227a was purified by flash silica gel column chromatography using dichloromethane containing 4-6% of methanol as eluent. Yield: 9.53 g (58.9%). $^1$H NMR (500 MHz, [D$_6$]DMSO, 25° C.): δ 7.90 (m, 1H, exchangeable with D$_2$O); 7.73-7.72 (bm, 1H, exchangeable with D$_2$O); 7.39 (s, 4H); 7.32-7.16 (m, 9H), 6.88-6.86 (m, 4H); 5.05-5.02 (m, 1H); 4.68-4.64 (m, 0.7H, rotamer, major); 4.57-4.53 (m, 0.3H, rotamer, minor); 4.20-4.17 (m, 1H), 4.13-4.08 (m, 1H); 3.72 (s, 6H), 3.38-3.20 (m, 3H); 3.08-2.81 (m, 5H); 2.24-1.77 (m, 6H); 1.68-0.98 (m, 23H); 0.84-0.81 (m, 9H), 0.05-0.02 (m, 6H).

Compound 228a

Compound 227a (6.43 g, 6. 22 mmol) was taken in a 250 ml RB and to this 3 mL of anhydrous TEA and 20 mL of 1M TBAF in anhydrous THF (purchased from Aldrich) were added under argon and stirred at ambient temperature for 4 h. Progress of the reaction was monitored by TLC, and after 4 h, THF was removed in vacuo. Residue was extracted into ethyl acetate (100 mL), washed with aqueous sodium bicarbonate followed by standard workup. Compound 228a was obtained as a white foamy solid after flash silica gel column chromatography (eluent: 5-6% methanol in dichloromethane), yield: 5.51 g (96.3%). $^1$H NMR (500 MHz, [D$_6$]DMSO, 25° C.): δ

.90 (bs, 1H, exchangeable with D$_2$O); 7.76-7.74 (m, 1H, exchangeable with D$_2$O); 7.39 (s, 4H), 7.32-7.15 (m, 9H); 6.88-6.84 (m, 4H); 5.08-5.01 (m, 1H), 4.98-4.97 (d, 0.7H, exchangeable with D$_2$O); 4.89-4.88 (d, 0.3H, exchangeable with D$_2$O), 4.40-4.38 (m, 0.85H), 4.30-4.27 (m, 0.3H); 4.21-4.18 (m, 0.85H); 4.17-4.05 (m, 1H); 3.72 (s, 6H);

3.58-3.52 (m, 0.85H), 3.44-3.38 (m, 0.5H); 3.34-3.28 (m, 0.85H); 3.27-3.22 (m, 1H), 3.19-3.14 (m, 0.8H); 3.04-2.81 (m, 5H), 2.21-1.77 (m, 6H), 1.68-1.20 (m, 22H).

Compound 229a:

After drying over P$_2$O$_5$ under vacuum, compound 228a (1.49 g, 1.62 mmol) was taken in anhydrous dichloroethane (10 mL) under argon and stirred at ambient temperature. To the solution anhydrous TEA (0.70 mL, 5.02 mmol) and N,N-diisopropylamino β-cyanoethylphosphonamidic chloride (0.80 mL, 3.38 mmol, purchased from ChemGenes Corporation, Wilmington, Mass.) were added and stirred for 3 h. After completion of the reaction, solvent and excess TEA were removed under vacuum and the product was extracted into ethyl acetate, washed with aqueous sodium bicarbonate solution followed by standard workup. Phosphoramidite 229a was purified by flash silica gel column chromatography using ethyl acetate as eluent, yield: 0.48 g (26.4%). $^{31}$P NMR (162 MHz, [D$_6$]DMSO, 25° C.): δ 149.02 (major); 148.90 (minor); 148.62 (minor); 148.02 (major).

Compound 230a:

Compound 228a (1.55 g, 1.68 mmol) and DMAP (1.0 g, 8.18 mmol) were taken in anhydrous dichloroethane (5 mL) and stirred at ambient temperature. Succinic anhydride (0.30 g, 2.99 mmol) was added into the stirring solution and the stirring was continued overnight. The succinate derivative was obtained as a gray white solid (0.61 g, 35.5%) after workup and purification as described for the preparation of compound 224. $^1$H NMR (500 MHz, [D$_6$]DMSO, 25° C.): δ 12.15 (s, 1H, exchangeable with D$_2$O); 7.75-7.58 (bm, 1.4H, exchangeable with D$_2$O); 7.54-7.47 (m, 4H); 7.32-7.16 (m, 9H); 6.89-6.81 (m, 4H); 5.38-5.33 (m, 0.7H); 5.28-5.20 (m, 0.3H); 5.06-5.00 (m, 0.3H); 4.99-4.95 (m, 0.7H); 4.82-4.77 (m, 1H); 4.28-4.22 (m, 0.25H); 4.21-4.15 (m, 0.75H); 3.80-3.60 (m, 7H); 3.57-3.42 (m, 2H); 3.22-2.80 (m, 7H); 2.28-1.90 (m, 6H), 1.58-1.41 (m, 24H).

$^{13}$C NMR (100 MHz, [D$_6$]DMSO, 25° C.): δ 174.3, 174.2, 173.2, 173.1, 172.7, 171.8, 170.3, 158.7, 158.5, 158.4, 155.9, 152.5, 145.4, 145.1, 140.6, 136.3, 136.1, 135.9, 131.9, 130.2, 129.4, 129.2, 128.4, 128.1, 127.3, 125.3, 113.8, 113.7, 113.3, 85.9, 73.4, 72.5, 63.6, 59.9, 55.6, 55.2, 52.8, 5.9, 35.8, 35.3, 35.0, 34.6, 33.5, 31.6, 31.4, 31.3, 29.3, 29.1, 28.6, 28.5, 28.1, 26.5, 25.5, 24.6.

The solid support 230a (2.05 g with a loading of 66.88 μM/g) was obtained from the succinate (0.57 g, 0.55 mmol), DMAP (0.085 g, 0.69 mmol), triphenylphosphine (0.15 g, 0.57 mmol), DTNP (0.18 g, 0.58 mmol) and lca-CPG (155 μM/g loading with a mean pore diameter of 484 Å, purchased from Millipore) as described for the preparation of compound 208a.

Compound 225b:

Compound 225b is prepared from compound 4b as described for the synthesis of compound 225a.

Compound 226b:

The desired compound is obtained from compound 225b as described for the preparation of compound 226a from compound 225a.

Compound 227b:

The desired compound is obtained from compound 226b as described for the preparation of compound 227a from compound 226a.

Compound 228b:

Compound 228b is prepared from compound 227b as described for the synthesis of compound 228a from compound 227a.

Compound 229b:

The desired compound is obtained from compound 228b as described for the preparation of compound 229a from compound 228a.

Compound 230b:

Compound 230b is prepared from compound 228b as described for the synthesis of compound 230a from compound 228a.

Scheme 37$^a$

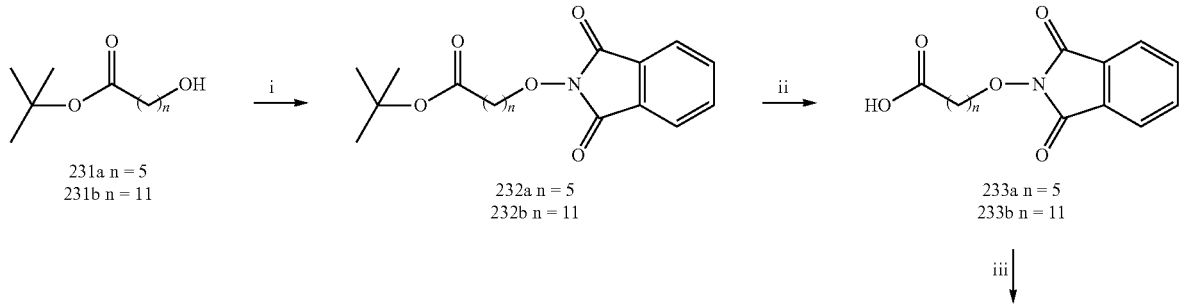

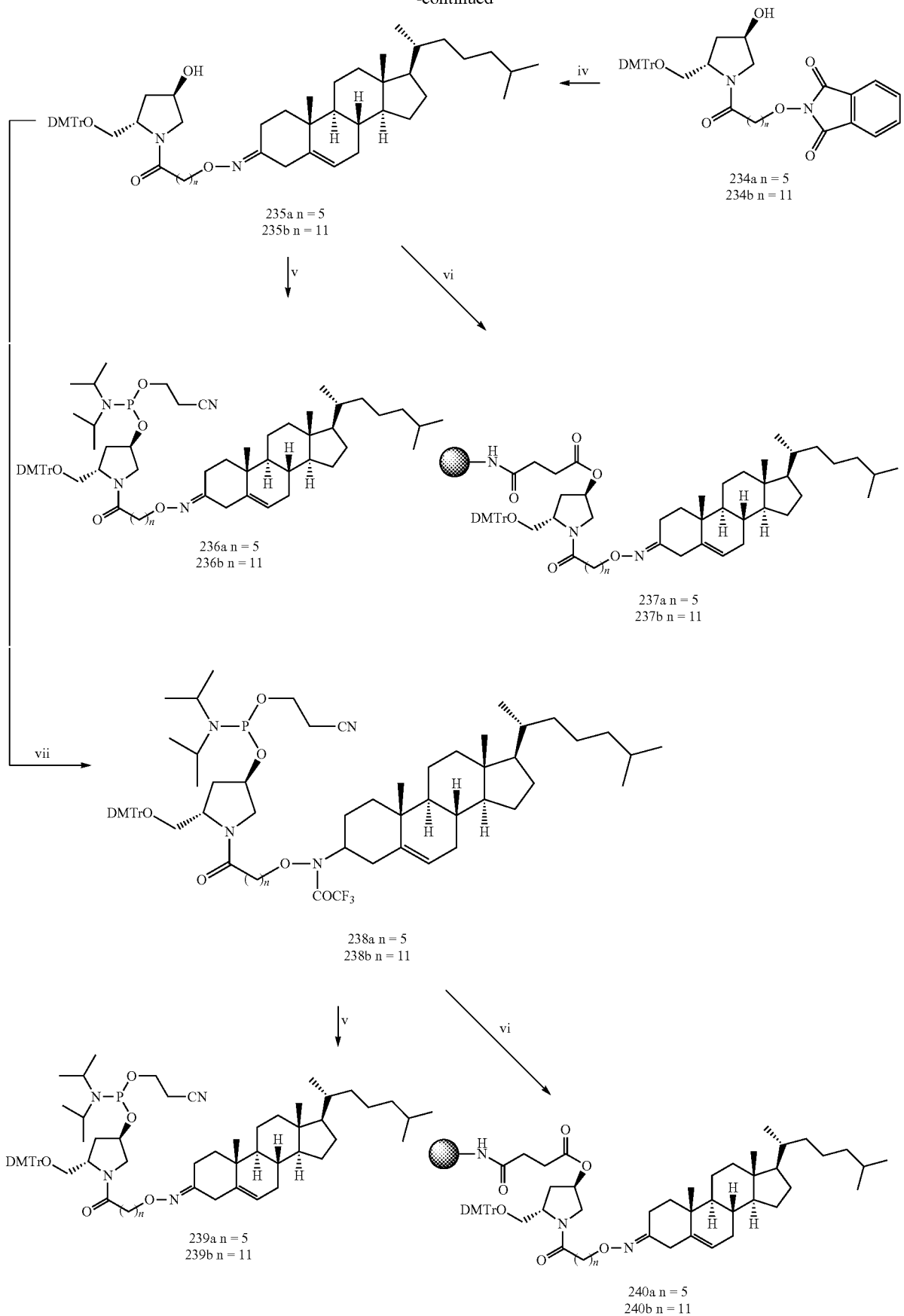

*a* (i) N-Hydroxyphthalimide, PPh₃, DEAD/THF (ii) TFA; (iii) DCC, DMAP, N-hydroxysuccinimide, 38/DMF; (iv) (a) hydrazinium hydrate/Py and (b) 5-Cholesten-3-one; (v) 2-Cyanoethyl-N,N, N', N'-tetraisopropylphosphorodiamidite, tetrazole (or tetrazolediisopropylammonium salt)/ Acetonitrile; (vi) (a) Succinic anhydride, DMAP/Dichloroethane and (b) DTNP, DMAP, Ph₃P, Aminoalkyl solid support and (vii) (a) NABH₃CN/THF and ethyl trifluoroacetate, TEA/dichloromethane.

Compound 232a:

Tert-Butyl ester (231a) of 6-hydroxyhexanoic acid is prepared as reported in the literature (Larock and Leach, *J. Org. Chem*, 1984, 49, 2144). Compound 231a is reacted with N-hydroxyphthalimide under Mitsunobu conditions to obtain compound 232a (as reported by Katajisto et. al., *Bioconjugate Chem.*, 2004, 15, 890.

Compound 233a:

Compound 232a is treated with trifluoroacetic acid to obtain compound 233a.

Compound 234a:

The free acid 233a is stirred with N-hydroxysuccinimide and DCC in the presence of DAMP in DMF for 30 min and subsequently compound 38 is added into the reaction mixture to obtain the desired compound 234a.

Compound 235a:

Compound 234a is treated with hydrazine.hydrate in pyridine and subsequently with 5-cholesten-3-one (purchased from Aldrich) to obtain compound 235a.

Compound 236a:

The phosphoramidite 236a is prepared from 235a as described for the compound 7 from compound 6 using 2-cyanoethyl-N,N,N',N''-tetraisopropylphosphorodiamidite as the phosphitylation agent.

Compound 237a:

The solid support 237a is obtained from compound 235a as described for the synthesis of compound 208a.

Compound 238a:

Compound 235a is treated with sodium cyanoborohydride to reduce the C=N double bond. The crude product of the sodium cyanoborohydride reaction is subsequently treated with ethyl trifluoroacetate in the presence of TEA in dichloromethane to obtain compound 238a.

Compound 239a:

The phosphoramidite 239a is prepared from 238a as described for the compound 7 from compound 6 using 2-cyanoethyl-N,N,N',N''-tetraisopropylphosphorodiamidite as the phosphitylation agent.

Compound 240a:

The solid support 240a is obtained from compound 238a as described for the synthesis of compound 208a.

Compound 232b:

Compound 231b is prepared as reported in the literature by Noguchi et al. (Tetrahedron, 1995, 51, 10531). Compound 231b is converted to 232b as described for the preparation of compound 232a.

Compound 236b:

The desired prosphoramidite is obtained from compound 232b in four steps as described for the preparation of compound 236a from 232a.

Compound 237b:

The CPG support is obtained from compound 235b as described for the synthesis of compound 208a from 207a.

Compound 238b:

Compound 238b is prepared from compound 235b as described for the preparation of compound 238a from 235a.

Compound 239b:

The phosphoramidite 239b is prepared from 238b as described for the compound 7 from compound 6 using 2-cyanoethyl-N,N,N',N''-tetraisopropylphosphorodiamidite as the phosphitylation agent.

Compound 240b:

The solid support 240b is obtained from compound 238b as described for the synthesis of compound 208a.

Scheme 38*a*

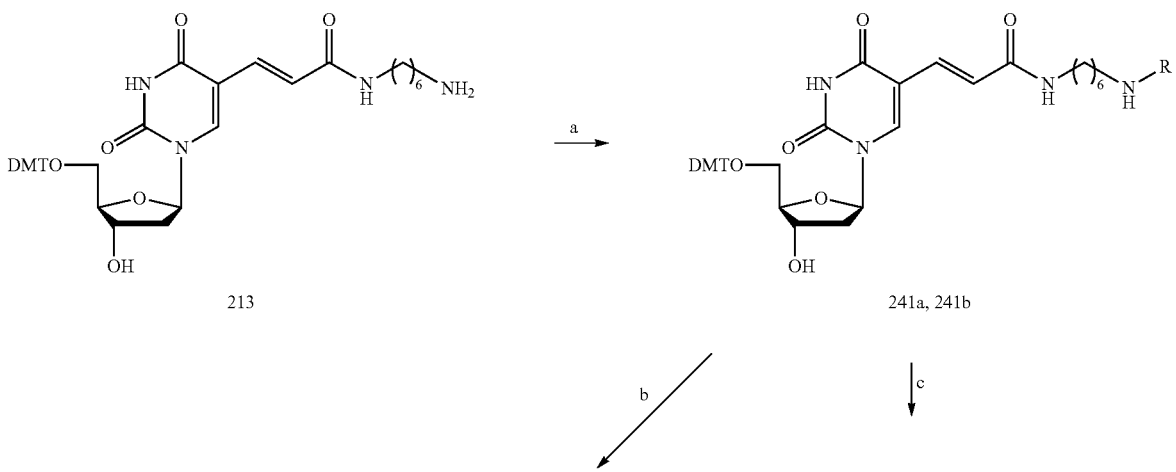

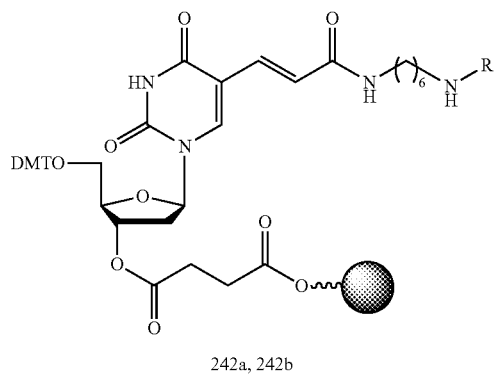

242a, 242b

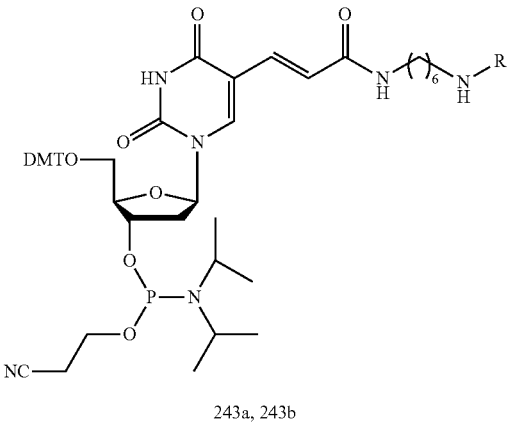

243a, 243b

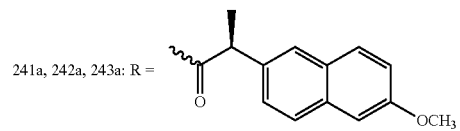

241a, 242a, 243a: R =

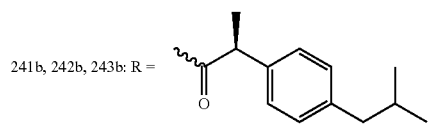

241b, 242b, 243b: R =

[a] (i) For 241a: Naproxen pentafluorophenol ester, TEA/Dichloromethane; for 241b: Ibuprofen pentafluorophenol ester, TEA/Dichloromethane; (ii) (a) Succinic anhydride, DMAP/Dichloroethane and (b) DTNP, DMAP, Ph₃P, Aminoalkyl solid support; (iii) N,N-diisopropylamino β-cyanoethylphosphonamidic chloride {[(CH₃)₂CH]₂N—P(Cl)—OCH₂CH₂CN}, DIEA/Dichloromethane or 2-Cyanoethyl-N,N, N', N''-tetraisopropylphosphorodiamidite, tetrazole (or tetrazolediisopropylammonium salt)/Acetonitrile Compound 241a:

Naproxen pentafluorophenol ester (1.3 g, 3.28 mmol) was added into a solution of compound 213 (1.5 g, 2.14 mmol, purchased from ChemGenes Corporation, Wilmington, Mass.) and TEA (4.6 mL, 33.0 mmol) and stirred overnight. Solvent and excess TEA were removed from the reaction in vacuo and the product was extracted into ethyl acetate (80 mL), washed with aqueous sodium bicarbonate solution followed by standard workup. Flash silica gel column chromatography of the residue using dichloromethane containing 4% methanol as eluent yielded 0.85 g (43.5%) of compound 241a as a grayish white solid. $^1$H NMR (400 MHz, [D$_6$]DMSO, 25° C.): δ 11.62 (s, 1H, exchangeable with D$_2$O); 7.99-7.91 (bm, 3H), 7.76-7.68 (m, 3H); 7.43-7.01 (m, 13H); 6.87-6.84 (m, 4H); 6.17-6.14 (t, J'(H,H)=6.41 and J"(H,H)=6.71 Hz, 1H), 5.28-5.27 (d, J(H,H)=4.88 Hz, 1H, exchangeable with D$_2$O); 4.23-4.19 (m, 1H); 3.88-3.81 (bm, 4H), 3.69-3.68 (bm, 8H); 3.20-2.97 (m, 6H); 2.34-2.27 (m, 1H); 2.19-2.13 (m, 1H); 1.38-1.17 (bm, 11H).

Compound 242a:

Compound 241a (0.65 g, 0.71 mmol) and DMAP (0.13 g, 1.06 mmol) were taken in dichloroethane (5 mL) in an RB and stirred at ambient temperature. Succinic anhydride (0.11 g, 1.09 mmol) was added into the stirring solution and the stirring was continued for 24 h. Progress of the reaction was monitored by TLC and after 24 h, the reaction mixture was diluted to 50 mL by adding ethyl acetate. Organic layer was washed with cold dilute citric acid solution followed by water. Organic layer was dried over anhydrous sodium sulfate and evaporated in vacuo to obtain the corresponding succinic acid derivative (0.67 g, 92.8%, crude yield) of compound 241a.

The succinate (0.51 g, 0.50 mmol) thus obtained was converted to compound 242a (2.8 g, with a loading of 11.6 μM/g) by coupling to lca-CPG (2.8 g with initial loading of 112.7 μM/g with mean pore size 505 A, purchased from Millipore) using triphenylphosphine (0.132 g, 0.503 mmol), DAMP (0.07 g, 0.57 mmol) and 2,2'-dithiobis(5-nitropyridine) (DTNP, 0.156 g, 0.50 mmol) as coupling agents as described for the synthesis of compound 208a.

Compound 243a:

The phosphoramidite 243a is prepared from 241a as described for the compound 7 from compound 6 using 2-cyanoethyl-N,N,N',N''-tetraisopropylphosphorodiamidite as the phosphitylation agent.

Example 16

Oligonucleotide Synthesis, Purification and Analysis

Synthesis:

The Oligonucleotide molecules were synthesized on a 394 ABI machine using the standard 93 step cycle written by the manufacturer with modifications to a few wait steps as described below. The solid support was available in house and the monomers were RNA phosphoramidites with fast protecting groups (5'-O-dimethoxytrityl N6-phenoxyacetyl-2'-O-t-butyldimethylsilyladenosine-3'-O—N,N'-diisopropyl-cyanoethylphosphoramidite, 5'-O-dimethoxytrityl-N4-acetyl-2'-O-t-butyldimethylsilylcytidine-3'-O—N,N'-diisopropyl-2-cyanoethylphosphoramidite, 5'-O-dimethoxytrityl-N2-p-isopropylphenoxyacetyl-2'-O-t-butyldimethylsilylguanosine-3'-O—N,N'-diisopropyl-2-cyanoethylphosphoramidite, and 5'-O-dimethoxytrityl-2'-O-t-butyldimethylsilyluridine-3'-O—N,N'-diisopropyl-2-cyanoethylphosphoramidite from Pierce Nucleic Acids Technologies. All 2'-O-Me amidites were received from Glen Research. All amidites were used at a concentration of 0.15M in acetonitrile (CH$_3$CN) and a coupling time of 12-15 min. The activator was 5-(ethylthio)-1H-tetrazole (0.25M), for the PO-oxidation Iodine/Water/Pyridine was used and for PS-oxidation, 2% Beaucage reagent (Iyer et al., *J. Am. Chem.*

Soc., 1990, 112, 1253) in anhydrous acetonitrile was used. The sulphurization time was about 6 min.

Deprotection-I (Nucleobase Deprotection)

After completion of synthesis the support was transferred to a screw cap vial (VWR Cat #20170-229) or screw caps RNase free microfuge tube. The oligonucleotide was cleaved from the support with simultaneous deprotection of base and phosphate groups with 1.0 mL of a mixture of ethanolic ammonia [ammonia:ethanol (3:1)] for 15 h at 55° C. The vial was cooled briefly on ice and then the ethanolic ammonia mixture was transferred to a new microfuge tube. The CPG was washed with 2×0.1 mL portions of RNase free deionised water. Combined washings, cooled over a dry ice bath for 10 min and subsequently dried in speed vac.

Deprotection-II for RNA Oligonucleotides (Removal of 2' TBDMS Group)

The white residue obtained was resuspended in 400 µl of triethylamine, triethylamine trihydrofluoride (TEA.3HF) and NMP (4:3:7) and heated at 50° C. for overnight to remove the tert-butyldimethylsilyl (TBDMS) groups at the 2' position (Wincott et al., *Nucleic Acids Res.*, 1995, 23, 2677). The reaction was then quenched with 400 µl of isopropoxytrimethylsilane (iPrOMe$_3$Si, purchased from Aldrich) and further incubated on the heating block leaving the caps open for 10 min; (This causes the volatile isopropxytrimethylsilylfluoride adduct to vaporize). The residual quenching reagent was removed by drying in a speed vac. Added 1.5 ml of 3% triethylamine in diethyl ether and pelleted by centrifuging. The supernatant was pipetted out without disturbing the pellet and the pellet was dried in speed vac. The crude RNA was obtained as a white fluffy material in the microfuge tube.

Quantitation of Crude Oligomer or Raw Analysis

Samples were dissolved in RNase free deionied water (1.0 mL) and quantitated as follows: Blanking was first performed with water alone (1 mL) 20 µL of sample and 980 µL of water were mixed well in a microfuge tube, transferred to cuvette and absorbance reading obtained at 260 nm. The crude material is dried down and stored at –20° C.

5. Purification of Oligomers:

PAGE Purification

PAGE purification of oligomers synthesized was performed as reported by Sambrook et al. (Molecular Cloning: a Laboratory Manual, Second Edition, Cold Spring Harbor Laboratory Press, Cold Spring Harbor, N.Y., 1989). The 12% denaturing gel was prepared for purification of unmodified and modified oligoribonucleotides. Took 120 mL Concentrate+105 mL Diluents+25 mL Buffer (National Diagnostics) then added 50 µL TEMED and 1.5 mL 10% APS. Pour the gel and leave it for ½ h to polymerize. Suspended the RNA in 20 µL water and 80 µL formamide. Load the gel tracking dye on left lane followed by the sample slowly on to the gel. Run the gel on 1×TBE buffer at 36 W for 4-6 h. Once run is completed, Transfer the gel on to preparative TLC plates and see under UV light. Cut the bands. Soak and crushed in Water. Leave in shaker for overnight. Remove the eluent, Dry in speed vac.

HPLC Analysis and Purification

Analysis was performed on an Agilent 1100 series HPLC using a Dionex 4×250 mm DNAPak column. Buffer A was 1 mM EDTA, 25 mM Tris pH9, 50 mM NaClO$_4$, 20% MeCN. Buffer B was 1 mM EDTA, 25 mM Tris pH 9, 0.4M NaClO$_4$, 20% MeCN. Separation was performed on a 0-65% B segmented gradient with buffers and column heated to 65° C.

Materials were purified on an ÄKTA Explorer equipped with a column packed with TSKgel Q 5PW (Tosoh Biosciences). Buffer A was 1 mM EDTA, 25 mM Tris pH 9. Buffer B was 1 mM EDTA, 25 mM Tris pH 9, 0.4M NaClO$_4$. Buffers were heated by a 4 kW buffer heater set at 65° C., giving a column outlet temperature of 45° C. The solution containing the crude material was diluted 4-6 fold and loaded onto the column and eluted with a segmented gradient from 0-60% B. Appropriate fractions were pooled Desalting of Purified Oligomer The purified dry oligomer was then desalted using Sephadex G-25 M (Amersham Biosciences). The cartridge was conditioned with 10 mL of RNase free deionised water thrice. Finally the purified oligomer was dissolved in 2.5 mL RNase-free water and passed through the cartridge with very slow drop wise elution. The salt free oligomer was eluted with 3.5 mL of RNase free water directly into a screw cap vial. All olgonucleotides were finally analyzed by LC-MS and capillary gel electrophoresis.

TABLE 6

List of ligand oligonucleotides (sense and antisense strand).

| Sequence ID | Sequence | Cal Mass amu | Found Mass amu | CGE (%) |
|---|---|---|---|---|
| 100 | 5' CUU ACG CUG AGU ACU UCG A dTdT 3' | 6606.00 | 6606.45 | 99.25 |
| 101 | 5' UCG AAG UAC UCA GCG UAA G dT dT 3' | 6696.32 | 6693.0 | 89.0 |
| 102 | 5' CUU ACG CUG AGU ACU UCG A dTdT L$_1$3' | 7084.19 | 7084.58 | 96.90 |
| 103 | 5' UCG AAG UAC UCA GCG UAA G dT dT L$_1$ 3' | 7170.29 | 7170.89 | 92.00 |
| 104 | 5' CUU ACG CUG AGU ACU UCG A dT dT* L$_1$ 3' | 7100.19 | 7099.12 | 92.99 |
| 105 | 5' UCG AAG UAC UCA GCG UAA G dT dT* L$_1$ 3' | 7157.29 | 7156.2 | 89.00 |
| 106 | 5'G*G*U*G*U*A U G G C U U C A A C C* C* U* U*$_{2'OMe}$ U*$_{2'OMe}$ L$_1$ 3' | 7293.00 | 7237.06 | 97.50 |
| 107 | 5'A* G* G* G* U U G A A G C C A U* A C* A* C* C* U*$_{2'OMe}$ U$_{2'OMe}$ L$_1$ 3' | 7362.73 | 7338.4 | 96.00 |
| 108 | 5' CUU ACG CUG AGU ACU UCG A dT dT L$_2$ 3' | 7064.96 | 7064.91 | 90.0% |
| 109 | 5' UCG AAG UAC UCA GCG UAA G dT dT L$_2$3' | 7154.00 | 7153.2 | 90.72 |
| 110 | 5' UCG AAG UAC UCA GCG UAA G UU L$_2$ 3' | 7153.98 | 7151.13 | 92.20 |
| 111 | 5' L$_1$CUU ACG CUG AGU ACU UCG A dTdT 3' | | | |

TABLE 6-continued

List of ligand oligonucleotides (sense and antisense strand).

| Sequence ID | Sequence | Cal Mass amu | Found Mass amu | CGE (%) |
|---|---|---|---|---|
| 112 | 5' $L_1$UCG AAG UAC UCA GCG UAA G dT dT 3' | | | |
| 113 | 5' $L_2$CUU ACG CUG AGU ACU UCG A dTdT 3' | | | |
| 114 | 5' $L_2$UCG AAG UAC UCA GCG UAA G dT dT 3' | | | |
| 115 | 5' CUU ACG CUG AGU ACU UCG A dTdT$L_3$ 3' | | | |
| 116 | 5' UCG AAG UAC UCA GCG UAA G dT dT$L_3$ 3' | | | |
| 117 | 5' $L_3$ CUU ACG CUG AGU ACU UCG A dTdT 3' | | | |
| 118 | 5' $L_3$ UCG AAG UAC UCA GCG UAA G dT dT 3' | | | |
| 119 | 5' CUU ACG CUG AGU ACU UCG A dTdT $L_4$3' | | | |
| 120 | 5' UCG AAG UAC UCA GCG UAA G dT dT $L_4$ 3' | | | |
| 121 | 5' $L_4$CUU ACG CUG AGU ACU UCG A dTdT 3' | | | |
| 122 | 5' $L_4$ UCG AAG UAC UCA GCG UAA G dT dT 3' | | | |
| 123 | 5' CUU ACG CUG AGU ACU UCG A dT dT $L_5$3' | | | |
| 124 | 5' UCG AAG UAC UCA GCG UAA G dT dT $L_5$ 3' | | | |
| 125 | 5' $L_5$CUU ACG CUG AGU ACU UCG A dT dT 3' | | | |
| 126 | 5' $L_5$UCG AAG UAC UCA GCG UAA G dT dT 3' | | | |
| 127 | 5' CUU ACG CUG AGU ACU UCG A dT dT $L_6$3' | | | |
| 128 | 5' UCG AAG UAC UCA GCG UAA G dT dT $L_6$ 3' | | | |
| 129 | 5' $L_6$CUU ACG CUG AGU ACU UCG A dT dT 3' | | | |
| 130 | 5' $L_6$UCG AAG UAC UCA GCG UAA G dT dT 3' | | | |
| 131 | 5' CUU ACG CUG AGU ACU UCG A dT dT $L_7$ 3' | | | |
| 132 | 5' UCG AAG UAC UCA GCG UAA G dT dT $L_7$3' | | | |
| 133 | 5' $L_7$CUU ACG CUG AGU ACU UCG A dT dT 3' | | | |
| 134 | 5' $L_7$UCG AAG UAC UCA GCG UAA G dT dT 3' | | | |
| 135 | 5' CUU ACG CUG AGU ACU UCG A dT dT $L_8$ 3' | | | |
| 136 | 5' UCG AAG UAC UCA GCG UAA G dT dT $L_8$3' | | | |
| 137 | 5' $L_8$CUU ACG CUG AGU ACU UCG A dT dT 3' | | | |
| 138 | 5' $L_8$UCG AAG UAC UCA GCG UAA G dT dT 3' | | | |
| 139 | 5' CUU ACG CUG AGU ACU UCG A dT dT $L_9$ 3' | | | |
| 140 | 5' UCG AAG UAC UCA GCG UAA G dT dT $L_9$3' | | | |
| 141 | 5' $L_9$CUU ACG CUG AGU ACU UCG A dT dT 3' | | | |
| 142 | 5' $L_9$UCG AAG UAC UCA GCG UAA G dT dT 3' | | | |
| 143 | 5' CUU ACG CUG AGU ACU UCG A dT dT $L_{10}$3' | | | |
| 144 | 5' UCG AAG UAC UCA GCG UAA G dT dT $L_{10}$ 3' | | | |
| 145 | 5' $L_{10}$CUU ACG CUG AGU ACU UCG A dT dT 3' | | | |
| 146 | 5' $L_{10}$UCG AAG UAC UCA GCG UAA G dT dT 3' | | | |
| 147 | 5' CUU ACG CUG AGU ACU UCG A dT dT $L_{11}$ 3' | | | |
| 148 | 5' UCG AAG UAC UCA GCG UAA G dT dT $L_{11}$3' | | | |

TABLE 6-continued

List of ligand oligonucleotides (sense and antisense strand).

| Sequence ID | Sequence | Cal Mass amu | Found Mass amu | CGE (%) |
|---|---|---|---|---|
| 149 | 5' $L_{11}$CUU ACG CUG AGU ACU UCG A dT dT 3' | | | |
| 150 | 5' $L_{11}$UCG AAG UAC UCA GCG UAA G dT dT 3' | | | |
| 151 | 5' CUU ACG CUG AGU ACU UCG A dT dT $L_{12}$ 3' | | | |
| 152 | 5' UCG AAG UAC UCA GCG UAA G dT dT $L_{12}$3' | | | |
| 153 | 5' $L_{12}$CUU ACG CUG AGU ACU UCG A dT dT 3' | | | |
| 154 | 5' $L_{12}$UCG AAG UAC UCA GCG UAA G dT dT 3' | | | |
| 155 | 5' CUU ACG CUG AGU ACU UCG A dT dT $L_{13}$ 3' | | | |
| 156 | 5' UCG AAG UAC UCA GCG UAA G dT dT $L_{13}$3' | | | |
| 157 | 5' $L_{13}$CUU ACG CUG AGU ACU UCG A dT dT 3' | | | |
| 158 | 5' $L_{13}$UCG AAG UAC UCA GCG UAA G dT dT 3' | | | |
| 159 | 5' CUU ACG CUG AGU ACU UCG A dT dT $L_{14}$ 3' | | | |
| 160 | 5' UCG AAG UAC UCA GCG UAA G dT dT $L_{14}$3' | | | |
| 161 | 5' $L_{14}$CUU ACG CUG AGU ACU UCG A dT dT 3' | | | |
| 162 | 5' $L_{14}$UCG AAG UAC UCA GCG UAA G dT dT 3' | | | |
| 163 | 5' CUU ACG CUG AGU ACU UCG A dT dT $L_{15}$ 3' | | | |
| 164 | 5' UCG AAG UAC UCA GCG UAA G dT dT $L_{15}$3' | | | |
| 165 | 5' $L_{15}$CUU ACG CUG AGU ACU UCG A dT dT 3' | | | |
| 166 | 5' $L_{15}$UCG AAG UAC UCA GCG UAA G dT dT 3' | | | |
| 167 | 5' CUU ACG CUG AGU ACU UCG A dT dT $L_{16}$ 3' | | | |
| 168 | 5' UCG AAG UAC UCA GCG UAA G dT dT $L_{16}$3' | | | |
| 169 | 5' $L_{16}$CUU ACG CUG AGU ACU UCG A dT dT 3' | | | |
| 170 | 5' $L_{16}$UCG AAG UAC UCA GCG UAA G dT dT 3' | | | |
| 171 | 5' CUU ACG CUG AGU ACU UCG A dT dT $L_{17}$ 3' | | | |
| 172 | 5' UCG AAG UAC UCA GCG UAA G dT dT $L_{17}$3' | | | |
| 173 | 5' $L_{17}$CUU ACG CUG AGU ACU UCG A dT dT 3' | | | |
| 174 | 5' $L_{17}$UCG AAG UAC UCA GCG UAA G dT dT 3' | | | |

$L_1$ = Naproxen 6-aminohexanoic acid with Serinol linker
$L_2$ = Ibuprofen 6-aminohexanoic acid with Serinol linker
$L_3$ = Cholesterol 6-aminohexanoic acid with trans-4-hydroxy-L-prolinol linker
$L_4$ = Cholesterol 6-aminohexanoic acid with serinol linker
$L_6$ = Cholesterol with trans-4-hydroxy-L-prolinol linker containing cationic tert-amine moiety
$L_7$ = Thiocholesterol with trans-4-hydroxy-L-prolinol linker
$L_8$ = Cholesterol 6-aminohexanoic acid with 3-hydroxy-4-(hydorxy)methylpyrrolidine linker
$L_8$ = Biotin 6-aminohexanoic acid with trans-4-hydroxy-L-prolinol linker
$L_9$ = Biotin 6-aminohexanoic acid with serinol linker
$L_{10}$ = Biotin 12-aminododecanoic acid with trans-4-hydroxy-L-prolinol linker
$L_{10}$ = ω-aminocaproyl with trans-4-hydroxy-L-prolinol linker
$L_{11}$ = ω-aminododecyl with trans-4-hydroxy-L-prolinol linker
$L_{12}$ = Vitamin E 6-aminohexanoic acid with trans-4-hydroxy-L-prolinol linker
$L_{13}$ = Dialkylglyceride 6-aminohexanoic acid with trans-4-hydroxy-L-prolinol linker
$L_{14}$ = Naproxen 6-aminohexanoic acid with trans-4-hydroxy-L-prolinol linker
$L_{15}$ = N,N-Dimethyl 6-aminohexanoic acid with trans-4-hydroxy-L-prolinol linker
$L_{16}$ = N,N-Dimethyl 12-aminododecanoic acid with trans-4-hydroxy-L-prolinol linker
$L_{17}$ = Nadixic 6-aminohexanoic acid with trans-4-hydroxy-L-prolinol linker
* = PS

Example 17 siRNA Modifications Enhanced Duplex Stability

Radiolabel Method for Monitoring Serum Stability of siRNA Duplexes:

siRNA duplexes were prepared at a stock concentration of 1 μM in which either the sense (S) or antisense strand (AS) contained a trace amount of 5'-$^{32}$P labeled material (e.g. $^{32}$P-S/AS and S/$^{32}$P-AS). The presence of the end-labeled sense or antisense strand allowed for monitoring of the individual strand within the context of the siRNA duplex. Therefore, two duplex preparations were made for each siRNA sequence tested. siRNA duplexes were incubated in 90% human serum at a final concentration of 100 nM duplex. Samples were removed and quenched in a stop mix at appropriate times. For a typical time course, 10 seconds, 15 minutes, 30 minutes, 1 hour, 2 hours and 4 hours time points were taken. Samples were analyzed by denaturing polyacrylamide gel electrophoresis along with a control sample (4 hour buffer-alone incubation) and a partial alkaline hydrolysis ladder of the labeled sense or antisense strand as a marker. The gel was imaged using a Fuji phosphorimager to detect the full length sense and antisense strands along with any degradation fragments that were generated by serum nucleases during incubation.

Since there is the possibility of losing the 5' phosphate label due to phosphatase activity in the serum, an alternative to 5' end labeling is to place an internal $^{32}$P or $^{33}$P label within either the sense or antisense strand. This labeling method is much more laborious than 5' end labeling and currently we have no evidence that dephosphorylation occurs during serum incubation.

A series of chemical modifications that fall into the following categories; backbone modification, sugar modification, nucleobase modification and 3' conjugate, were tested and showed enhanced serum stability as compared to a unmodified siRNA duplex. A description of each modification, its location within the siRNA duplex, and the serum stability data follows.

Serum Stability of Unmodified Parent Duplex:

The unmodified parent duplex, AL-DUP-1000, was used to establish the serum stability baseline for evaluating the effect of chemical modifications on nuclease resistance.

AL-DUP-1000

```
ALN-SEQ-1000
                              SEQ ID NO: 54
5'-CUUACGCUGAGUACUUCGAdTdT-3'

ALN-SEQ-1001
                              SEQ ID NO: 61
3'dTdTGAAUGCGACUCAUGAAGCU-5'
```

AL-DUP-1000 was subjected to the serum stability assay to evaluate its inherent nuclease resistance and to define its degradation pattern (FIG. 21). Denaturing gel electrophoresis was used analyze AL-DUP-1000 in a human serum stability assay. An siRNA duplex containing 5' end-labeled sense RNA (*s/as) and a duplex containing 5' end-labeled antisense RNA (as/s*) were each incubated in 90% human serum and time points were assayed at 10 seconds, 5 min, 15 min, 30 min, 1 hour, 2 hours and 4 hours. The control was a 4 hour time point for siRNA duplex incubated in PBS buffer alone, OH— was the partial alkaline hydrolysis marker. This unmodified duplex was observed to be degraded by both 3'-5' exonucleases and endonucleases (FIG. 21).

Cleavage of the 3' end of both the sense and antisense strands by 3'-5' exonucleases occurs within the first 5 minutes of incubation resulting in the loss of the 3' terminal dT residues (top vertical lines in s*/as and s/as* panels of FIG. 21). In addition to exonuclease degradation, both strands were cleaved by endonucleases. There was a major endonuclease site at position sixteen of the antisense strand (bottom vertical lines in s*/as and s/as* panels of FIG. 21) that appears as early as 10 seconds. Very little full length sense or antisense strand was remaining after 1 hour in human serum. Chemical modifications were introduced within the context of the parent duplex to evaluate their effect on nuclease resistance. These chemical modifications fall within one of the following classes: backbone modification, sugar modification, nucleobase modification, cationic modification and conjugate.

Backbone Modifications Enhanced Nuclease Resistance:

Specific phophodiester linkages of the siRNA duplex were replaced by either phosphorothioate or methylphosphonate and their stability was evaluated in the human serum stability assay. Table 7 contains the sequences of the duplexes tested. Substitution of the phosphodiester linkage at the 3' end of both the sense and antisense strands inhibited exonucleolytic degradation of the 3' overhangs (FIGS. 22A and 22B) as compared to the unmodified parent duplex (refer to FIG. 21). Full length starting material was present for four hours for both the sense and antisense strands. The endonucleolytic cleavage pattern seen in the unmodified duplex was unchanged. Similar results were obtained for duplexes that contained additional phosphorothioates at their 3' ends (data not shown). The placement of phosphorothioates at the endonucleolytic cleavage sites (duplexes 1419, 1420 and 1421) did not inhibit endonucleolytic cleavage at these sites (data not shown). In summary, a single phosphorothioate or methylphosphonate between the two 3' terminal nucleotides was sufficient to protect the 3' ends from exonuclease degradation. Additional phosphorothioates at the 3' ends appear to enhance this effect, which may be necessary for long term exposure to serum nucleases.

TABLE 7 siRNA duplexes containing backbone modifications.

| Alnylam Duplex | Duplex Sequence | Alnylam Sequence |
|---|---|---|
| AL-DUP-1393 | 5'-CUUACGCUGAGUACUUCGAdT*dT-3' | AL-SEQ-1026 |
| | 3'-dT*dTGAAUGCGACUCAUGAAGCU-5' | AL-SEQ-1027 |
| AL-DUP-1394 | 5'-CUUACGCUGAGUACUUCGA*dT*dT-3' | AL-SEQ-1028 |
| | 3'-dT*dT*GAAUGCGACUCAUGAAGCU-5' | AL-SEQ-1029 |
| AL-DUP-1395 | 5'-CUUACGCUGAGUACUUCG*A*dT*dT-3' | AL-SEQ-1030 |
| | 3'-dT*dT*G*AAUGCGACUCAUGAAGCU-5' | AL-SEQ-1031 |
| AL-DUP-1396 | 5'-CUUACGCUGAGUACUUC*G*A*dT*dT-3' | AL-SEQ-1032 |
| | 3'-dT*dT*G*A*AUGCGACUCAUGAAGCU-5' | AL-SEQ-1033 |
| AL-DUP-1419 | 5'-CUUACGCUGAGU*ACUUCGAdTdT-3' | AL-SEQ-2182 |
| | 3'-dTdTGAAUGCGACUCA*UGAAGCU-5' | AL-SEQ-2184 |

TABLE 7-continued siRNA duplexes containing backbone modifications.

| Alnylam Duplex | Duplex Sequence | Alnylam Sequence |
|---|---|---|
| AL-DUP-1420 | 5'-CUU*ACGCUGAGU*ACUUCGAdTdT-3' | AL-SEQ-2183 |
|  | 3'-dTdTGAA*UGCGACUCA*UGAAGCU-5' | AL-SEQ-2185 |
| AL-DUP-1421 | 5'-CUU*ACGCUGAGU*ACUUCGAdT*dT-3' | AL-SEQ-2186 |
|  | 3'-dT*dTGAA*UGCGACUCA*UGAAGCU-5' | AL-SEQ-2188 |
| AL-DUP-1329 | 5'-CUUACGCUGAGUACUUCGAdTmpdT-3' | AL-SEQ-1038 |
|  | 3'-dTmpdTGAAUGCGACUCAUGAAGCU-5' | AL-SEQ-1039 |

(* = phosphorothioate, mp = methylphosphonate)

SEQ ID NOs 62-77, respectively.

Sugar Modifications Enhanced Nuclease Resistance:

The effect of replacing the 2'OH with 2'OMe was evaluated at the sites of endonucleolytic cleavage as well as at the 3' ends of the siRNA duplex. The duplexes tested in the human serum stability assay are shown in Table 2. Some of these duplexes also contained phosphorothioate linkages to evaluate whether the combination of the two modifications enhance nuclease resistance more significantly. Substitution of the terminal dT residues with 2'OMe-U (AL-DUP-1027) reduced 3'-5' exonuclease degradation slightly over the unmodified parent duplex (data not shown); however, the extent of exonuclease protection by 2'OMe-U was far less than that achieved by placing a

TABLE 8 siRNA duplexes containing 2'OMe Substitutions

| Alnylam Duplex | Duplex Sequence | Alnylam Sequence |
|---|---|---|
| AL-DUP-1027 | 5'-CUUACGCUGAGUACUUCGA<u>UU</u>-3' | AL-SEQ-1006 |
|  | 3'-<u>UU</u>GAAUGCGACUCAUGAAGCU-5' | AL-SEQ-1007 |
| AL-OUP-1036 | 5'-C*UUACGCUGAGUACUUCGA<u>U</u>*<u>U</u>-3' | AL-SEQ-1008 |
|  | 3'-<u>U</u>*<u>U</u>GAAUGCGACUCAUGAAGC*<u>U</u>-5' | AL-SEQ-1009 |
| AL-DUP-13ff | 5'-C*U<u>U</u>ACGCUGAGUACUUCGA<u>U</u>*<u>U</u>,-3' | AL-SEQ-gggg |
|  | 3'-<u>U</u>*<u>U</u>GAA<u>U</u>GCGACUCAUGAAGC*<u>U</u>-5' | AL-SEQ-hhhh |
| AL-DUP-1363 | 5'-C*U<u>U</u>ACGCUGAG<u>U</u>ACUUCGA<u>U</u>*<u>U</u>-3' | AL-SEQ-1162 |
|  | 3'-<u>U</u>*<u>U</u>GAA<u>U</u>GCGAC<u>U</u>C<u>A</u><u>U</u>GAAGC*<u>U</u>-5' | AL-SEQ-1163 |

(<u>U</u> = 2'OMe-uridine, * = phosphorothioate)

SEQ ID NOs 78-85, respectively.

phosphorothioate between the two terminal dT residues (see FIG. 22A). Addition of a single phosphorothioate between the two terminal 2'OMe-uridine residues effectively inhibited 3'-5' exonucleolytic cleavage as seen in FIG. 23 for duplexes AL-DUP-1036, AL-DUP-13ff, and AL-DUP-1363. 2'OMe substitution on its own was much more effective at protecting from endonucleolytic cleavage when placed at the internal cleavage sites. The parent duplex was cleaved 3' of U at two UpA sites within the duplex. Both strands are cleaved due to the symmetry of this dinucleotide repeat and mapping data was used to confirm the sites of cleavage (data not shown). Placement of 2'OMe at the strong endonucleolytic site ((FIG. 23, star in s/*as gel, AL-DUP-13ff) resulted in inhibition of cleavage at this site. The second, weaker endonucleolytic site (FIG. 23, black star in *s/as), however, was slightly enhanced when the strong site was protected with 2'OMe (FIG. 23, compare AL-DUP-13ff to AL-DUP-1036). Protection of both sites with 2'OMe (AL-DUP-1363) resulted in reduced endonucleolytic cleavage at both sites (FIG. 23). The inhibitory effect of the 2'OMe substitution is consistent with the mechanism of endonucleolytic cleavage, which requires the 2'OH as a nucleophile in the cleavage reaction. 2'OMe modification will also be an effective means to protect the 3' overhang of single overhang siRNA duplexes where the 3' overhang is composed of ribonucleotides. In this situation, 2'OMe substitution can be used to block the possible loss of the terminal two nucleotides by endonucleolytic cleavage and phosphorothioate can be used to protect from exonuclease degradation.

Cationic Modifications Enhanced Nuclease Resistance:

The effect of three different cationic chemical modifications on nuclease resistance was tested and compared to the parent unmodified duplex. The structures of the three cationic modifications tested are shown below.

a.

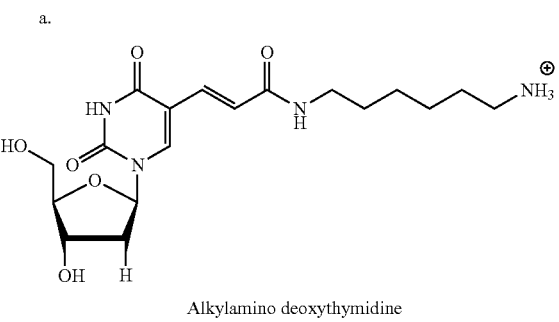

Alkylamino deoxythymidine b.

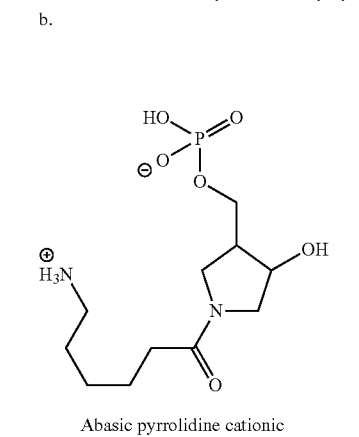

Abasic pyrrolidine cationic c.

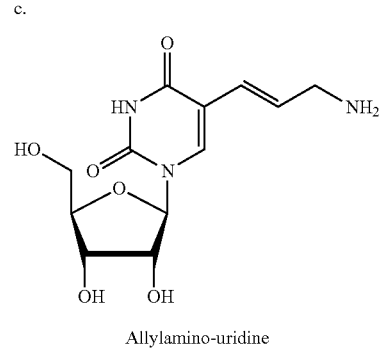

Allylamino-uridine

TABLE 9 siRNA duplexes containing cationic substances

| Alnylam Duplex | Duplex Sequence | Alnylam Sequence |
|---|---|---|
| AL-DUP-10aa | 5'-CUUACGCUGAGUACUUCGAdTaadT-3' | AL-SEQ-1017 |
|  | 3'-aadTdTGAAUGCGACUCAUGAAGCU-5' | AL-SEQ-1018 |
| AL-DUP-10bb | 5'-CUUACGCUGAGUACUUCGAaadTaadT-3' | AL-SEQ-1015 |
|  | 3'-aadTaadTGAAUGCGACUCAUGAAGCU-5' | AL-SEQ-1016 |
| AL-DUP-1ccc | 5'-CUUACGCUGAGUACUUCGAdTdTAbP-3' | AL-SEQ-dddd |
|  | 3'-AbPdTdTGAAUGCGACUCAUGAAGCU-5' | AL-SEQ-eeee |
| AL-DUP-1403 | 5'-C*UaaUACGCUGAGUACUUCGAU*U-3' | AL-SEQ-2080 |
|  | 3'-U*UGAAaaUGCGACUCAUGAAGC*U-5' | AL-SEQ-2081 |
| AL-DUP-1406 | 5'-C*UaaUACGCUGAGaaUACUUCGAU*U-3' | AL-SEQ-2082 |
|  | 3'-U*UGAAaaUGCGACUCAaaUGAAGC*U-5' | AL-SEQ-2083 |

(aadT = alkylamine-dt, abP = abasic pyrrolidine cationic, aaU = allylamine-U, * = phosphorothioate, U = 2'OMe-U)

SEQ ID NOs 86-95, respectively.

The sequences of the duplexes assayed in the human serum stability assay are shown in Table 9. Both alkylamino-dT and abasic pyrrolidine cationic modifications were placed at the 3' terminal overhang to evaluate their effect on 3'-5' exonuclease degradation. Allylamino-uridines were placed at the internal endonucleolytic cleavage sites to evaluate their ability to inhibit endonucleolytic cleavage. As seen in FIG. 24, replacing the 3' terminal dT residue with a single alkylamino-dT efficiently inhibited 3'-5' exonucleolytic degradation (FIG. 24, AL-DUP-10aa, left gel image). Replacement of both dT residues in the overhang with alkylamino-dT resulted in a similar extent of inhibition (data not shown). Addition of an abasic pyrrolidine cationic modification at the 3' terminus of each strand also protected against exonucleolytic degradation (FIG. 24, middle gel image). Both the alkylamino-dT and abasic pyrrolidine modifications protected from 3'-5' exonucleolytic cleavage up to 23 hours (data not shown). Placement of allylamino-U at the internal cleavage sites inhibited endonucleolytic cleavage as shown in FIG. 24 for duplex AL-DUP-1403. The ends of this duplex were stabilized from exonucleolytic degradation by 2'OMe-U and phosphorothioate substitutions in order to separate the two different cleavage events. Endonucleolytic cleavage was inhibited at both internal cleavage sites by allylamino-U substitution for AL-DUP-1406 (data not shown).

3' Conjugates Enhanced Nuclease Resistance:

Conjugation of naproxen and ibuprofen to the 3' end of the siRNA were tested for their ability to inhibit 3'-5' exonucleolytic degradation. The structure of naproxen is shown in below:

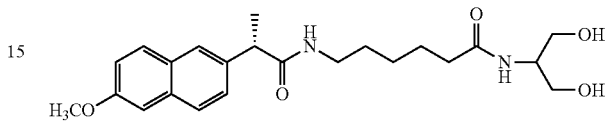

Table 10 lists the siRNAs that were tested in the human serum stability assay. Conjugation of either naproxen or ibuprofen to the 3' end inhibited exonucleolytic degradation. FIG. 18 shows the serum stability data for the naproxen modified duplex (AL-DUP-1069) and similar results were obtained for AL-DUP1413. Presumably the conjugates inhibit exonucleolytic cleavage by sterically blocking the exonuclease from binding to the 3' end of the siRNA duplex. Similar data was also obtained for AL-DUP-1069 in pooled mouse serum.

TABLE 10 siRNA duplexes containing 3' conjugates

| Alnylam Duplex | Duplex Sequence | Alnylam Sequence |
|---|---|---|
| AL-DUP-1069 | 5'-CUUACGCUGAGUACUUCGAdTdTNap-3' 3'-NapdTdTGAAUGCGACUCAUGAAGCU-5' | |
| AL-DUP-1413 | 5'-CUUACGCUGAGUACUUCGAdTdTIbu-3' 3'-NapdTdTGAAUGCGACUCAUGAAGCU-5' | |

(Nap = Naproxen, Ibu = Ibuprofen)

SEQ ID NOs 96-99, respectively.

A number of embodiments of the invention have been described. Nevertheless, it will be understood that various modifications may be made without departing from the spirit and scope of the invention. Accordingly, other embodiments are within the scope of the following claims.

---

What is claimed is:

1. An iRNA agent comprising a first strand and a second strand, wherein at least two subunits having a formula (I) are incorporated into at least one of said strands:

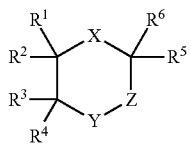

(I)

wherein:
X is $N(CO)R^7$, $NR^7$ or $CH_2$;
Y is $NR^8$, O, S, $CR^9R^{10}$, or absent;
Z is $CR^{11}R^{12}$ or absent;
each of $R^1$, $R^2$, $R^3$, $R^4$, $R^9$, and $R^{10}$ is, independently, H, $OR^a$, $OR^b$, $(CH_2)_nOR^a$, or $(CH_2)_nOR^b$, provided that at least one of $R^1$, $R^2$, $R^3$, $R^4$, $R^9$, and $R^{10}$ is $OR^a$ or $OR^b$ and that at least one of $R^1$, $R^2$, $R^3$, $R^4$, $R^9$, and $R^{10}$ is $(CH_2)_nOR^a$, or $(CH_2)_nOR^b$;

each of $R^5$, $R^6$, $R^{11}$, and $R^{12}$ is, independently, H, $C_1$-$C_6$ alkyl optionally substituted with 1-3 $R^{13}$, or $C(O)NHR^7$; or $R^5$ and $R^{11}$ together are $C_3$-$C_8$ cycloalkyl optionally substituted with $R^{14}$;

$R^7$ is $R^d$; or $C_1$-$C_{20}$ alkyl substituted with $NR^cR^d$ or $NHC(O)R^d$;
$R^8$ is $C_1$-$C_6$ alkyl;
$R^{13}$ is hydroxy, $C_1$-$C_4$ alkoxy, or halo;
$R^{14}$ is $NR^cR^7$;
$R^a$ is H or

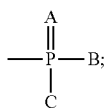

$R^b$ is H or

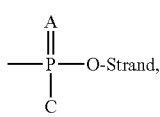

wherein the Strand in each occurrence is independently the first strand or second strand of the iRNA agent;

each of A and C is, independently, O or S; and
B is OH, O⁻, or

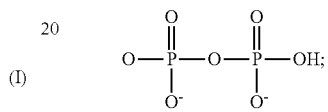

$R^c$ is H or $C_1$-$C_6$ alkyl;
$R^d$ is H or a ligand; and
n is 1-4.

2. The iRNA agent of claim 1, wherein three subunits having a formula (I) are incorporated into at least one of said strands.

3. The iRNA agent of claim 2, wherein the three subunits having a formula (I) are placed at positions 1, 2 and 3 of the 3' end of a sense strand.

4. The iRNA agent of claim 1, wherein X is $N(CO)R^7$ or $NR^7$, Y is $CR^9R^{10}$, and Z is absent.

5. The iRNA agent of claim 4, wherein one of $R^1$, $R^2$, $R^3$, $R^4$, $R^9$, and $R^{10}$ is $OR^a$ or $OR^b$; and one of $R^1$, $R^2$, $R^3$, $R^4$, $R^9$, and $R^{10}$ is $(CH_2)_nOR^a$ or $(CH_2)_nOR^b$.

6. The iRNA agent of claim 4, wherein $R^2$, $R^3$, $R^4$, $R^5$, $R^6$, and $R^{10}$ are H.

7. The iRNA agent of claim 4, wherein $R^9$ is $OR^a$ or $OR^b$, and $R^1$ is $(CH_2)_nOR^a$ or $(CH_2)_nOR^b$.

8. The iRNA agent of claim 1, $R^1$ can be $CH_2OR^a$ and $R^9$ can be $OR^b$.

9. The iRNA agent of claim 8, wherein $R^1$ and $R^9$ are cis.

10. The iRNA agent of claim 8, wherein $R^1$ and $R^9$ are trans.

11. The iRNA agent of claim 1, wherein $R^d$ is selected from the group consisting of a folic acid radical, a cholesterol radical, a carbohydrate radical, a vitamin A radical, a vitamin E radical, and a vitamin K radical.

12. The iRNA agent of claim 1, wherein $R^d$ is a cholesterol radical.

13. The iRNA agent of claim 1, wherein $R^d$ is a carbohydrate radical.

14. The iRNA agent of claim 1, wherein $R^d$ is a steroid radical, which is optionally tethered to at least one carbohydrate radical.

15. The iRNA agent of claim 1, wherein at least one of said strands leads to the cleavage of a complementary target sequence via a RISC-dependent mechanism.

16. The iRNA agent of claim 1, wherein A is O in each occurrence.

17. The iRNA agent of claim 1, wherein A is S in at least one occurrence.

18. The iRNA agent of claim 1, wherein formula (I) is incorporated into a sense strand.

19. The iRNA agent of claim 1, wherein formula (I) is incorporated into positions 1, 2 and 3 of the 3' end of a sense strand.

20. The iRNA agent of claim 1, wherein the iRNA agent is 21 nucleotides in length and has a duplex region of about 19 pairs.

21. The iRNA agent of claim 1, wherein the iRNA agent includes a duplex region between 17 and 23 pairs in length.

22. The iRNA agent of claim 1, wherein $R^d$ is a ligand selected from the group consisting of a lipophile, a lipid, a steroid, a terpene, a vitamin, a carbohydrate, a protein, a protein binding agent, an integrin targeting molecule, polycationic, a peptide or peptide mimic, a polyamine, a dye, an intercalating agent, a cross-linker, a porphyrin, a polycyclic aromatic hydrocarbon, an artificial endonuclease, a lipophilic molecule, a glycerol or ester or ether thereof, a geranyloxyhexyl group, a hexadecylglycerol, a borneol, a menthol, a 1,3-propanediol, a heptadecyl group, a palmitic acid, a myristic acid, an O3-(oleoyl)lithocholic acid, an O3-(oleoyl)cholenic acid, a dimethoxytrityl, a phenoxazine, a peptide conjugate, an alkylating agent, a phosphate, an amino, a mercapto, a PEG, a MPEG, a $[MPEG]_2$, an alkyl or substituted alkyl, a radiolabeled marker, an enzyme, a hapten, a transport/absorption facilitator, a synthetic ribonuclease, a dinitrophenyl, a HRP, an AP, and a derivative and a combination thereof.

23. A kit comprising an iRNA agent of claim 1, a sterile container in which the iRNA agent is enclosed, and instructions for use.

* * * * *

SEQUENCE LISTING

```
<160> NUMBER OF SEQ ID NOS: 174

<210> SEQ ID NO 1
<211> LENGTH: 16
<212> TYPE: PRT
<213> ORGANISM: Artificial Sequence
<220> FEATURE:
<223> OTHER INFORMATION: Exemplary Cell Permeation Peptide

<400> SEQUENCE: 1

Arg Gln Ile Lys Ile Trp Phe Gln Asn Arg Arg Met Lys Trp Lys Lys
 1               5                   10                  15

<210> SEQ ID NO 2
<211> LENGTH: 14
```

```
<212> TYPE: PRT
<213> ORGANISM: Artificial Sequence
<220> FEATURE:
<223> OTHER INFORMATION: Exemplary Cell Permeation Peptide

<400> SEQUENCE: 2

Gly Arg Lys Lys Arg Arg Gln Arg Arg Pro Pro Gln Cys
1               5                   10

<210> SEQ ID NO 3
<211> LENGTH: 27
<212> TYPE: PRT
<213> ORGANISM: Artificial Sequence
<220> FEATURE:
<223> OTHER INFORMATION: Exemplary Cell Permeation Peptide

<400> SEQUENCE: 3

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 4
<211> LENGTH: 18
<212> TYPE: PRT
<213> ORGANISM: Artificial Sequence
<220> FEATURE:
<223> OTHER INFORMATION: Exemplary Cell Permeation Peptide

<400> SEQUENCE: 4

Leu Leu Ile Ile Leu Arg Arg Arg Ile Arg Lys Gln Ala His Ala His
1               5                   10                  15

Ser Lys

<210> SEQ ID NO 5
<211> LENGTH: 26
<212> TYPE: PRT
<213> ORGANISM: Artificial Sequence
<220> FEATURE:
<223> OTHER INFORMATION: Exemplary Cell Permeation Peptide

<400> SEQUENCE: 5

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 6
<211> LENGTH: 18
<212> TYPE: PRT
<213> ORGANISM: Artificial Sequence
<220> FEATURE:
<223> OTHER INFORMATION: Amphiphilic model peptide

<400> SEQUENCE: 6

Lys Leu Ala Leu Lys Leu Ala Leu Lys Ala Leu Lys Ala Ala Leu Lys
1               5                   10                  15

Leu Ala

<210> SEQ ID NO 7
<211> LENGTH: 9
<212> TYPE: PRT
<213> ORGANISM: Artificial Sequence
<220> FEATURE:
<223> OTHER INFORMATION: Exemplary Cell Permeation Peptide
```

```
<400> SEQUENCE: 7

Arg Arg Arg Arg Arg Arg Arg Arg Arg
1               5

<210> SEQ ID NO 8
<211> LENGTH: 10
<212> TYPE: PRT
<213> ORGANISM: Artificial Sequence
<220> FEATURE:
<223> OTHER INFORMATION: Exemplary Cell Permeation Peptide

<400> SEQUENCE: 8

Lys Phe Phe Lys Phe Phe Lys Phe Phe Lys
1               5                   10

<210> SEQ ID NO 9
<211> LENGTH: 37
<212> TYPE: PRT
<213> ORGANISM: Artificial Sequence
<220> FEATURE:
<223> OTHER INFORMATION: Exemplary Cell Permeation Peptides

<400> SEQUENCE: 9

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 10
<211> LENGTH: 31
<212> TYPE: PRT
<213> ORGANISM: Artificial Sequence
<220> FEATURE:
<223> OTHER INFORMATION: Exemplary Cell Permeation Peptides

<400> SEQUENCE: 10

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 11
<211> LENGTH: 30
<212> TYPE: PRT
<213> ORGANISM: Artificial Sequence
<220> FEATURE:
<223> OTHER INFORMATION: Exemplary Cell Permeation Peptides

<400> SEQUENCE: 11

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 12
<211> LENGTH: 36
<212> TYPE: PRT
<213> ORGANISM: Artificial Sequence
<220> FEATURE:
<223> OTHER INFORMATION: Exemplary Cell Permeation Peptides

<400> SEQUENCE: 12
```

```
Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
            20                  25                  30

Lys Cys Cys Lys
        35
```

<210> SEQ ID NO 13
<211> LENGTH: 12
<212> TYPE: PRT
<213> ORGANISM: Artificial Sequence
<220> FEATURE:
<223> OTHER INFORMATION: Exemplary Cell Permeation Peptides

<400> SEQUENCE: 13

```
Arg Lys Cys Arg Ile Val Val Ile Arg Val Cys Arg
1               5                   10
```

<210> SEQ ID NO 14
<211> LENGTH: 42
<212> TYPE: PRT
<213> ORGANISM: Artificial Sequence
<220> FEATURE:
<223> OTHER INFORMATION: Exemplary Cell Permeation Peptides

<400> SEQUENCE: 14

```
Arg Arg Arg Pro Arg Pro Pro Tyr Leu Pro Arg Pro Arg Pro Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro Gly Lys Arg
        35                  40
```

<210> SEQ ID NO 15
<211> LENGTH: 13
<212> TYPE: PRT
<213> ORGANISM: Artificial Sequence
<220> FEATURE:
<223> OTHER INFORMATION: Exemplary Cell Permeation Peptides

<400> SEQUENCE: 15

```
Ile Leu Pro Trp Lys Trp Pro Trp Trp Pro Trp Arg Arg
1               5                   10
```

<210> SEQ ID NO 16
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 16

```
Ala Ala Val Ala Leu Leu Pro Ala Val Leu Leu Ala Leu Leu Ala Pro
1               5                   10                  15
```

<210> SEQ ID NO 17
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 17

Ala Ala Leu Leu Pro Val Leu Leu Ala Ala Pro

<210> SEQ ID NO 18
<211> LENGTH: 13
<212> TYPE: PRT
<213> ORGANISM: Human immunodeficiency virus

<400> SEQUENCE: 18

Gly Arg Lys Lys Arg Arg Gln Arg Arg Arg Pro Pro Gln
1               5                   10

<210> SEQ ID NO 19
<211> LENGTH: 16
<212> TYPE: PRT
<213> ORGANISM: Drosophila Antennapedia

<400> SEQUENCE: 19

Arg Gln Ile Lys Ile Trp Phe Gln Asn Arg Arg Met Lys Trp Lys Lys
1               5                   10                  15

<210> SEQ ID NO 20
<211> LENGTH: 21
<212> TYPE: DNA
<213> ORGANISM: Artificial Sequence
<220> FEATURE:
<223> OTHER INFORMATION: "Dual targeting" siRNAs
<220> FEATURE:
<221> NAME/KEY: misc_feature
<222> LOCATION: 20, 21
<223> OTHER INFORMATION: n = dT= deoxythymidine

<400> SEQUENCE: 20
uaccagcacc caggugcugn n                                              21

<210> SEQ ID NO 21
<211> LENGTH: 21
<212> TYPE: DNA
<213> ORGANISM: Artificial Sequence
<220> FEATURE:
<223> OTHER INFORMATION: "Dual targeting" siRNAs
<220> FEATURE:
<221> NAME/KEY: misc_feature
<222> LOCATION: 20, 21
<223> OTHER INFORMATION: n = dT= deoxythymidine

<400> SEQUENCE: 21
ccgggcaucc ggacgaguun n                                              21

<210> SEQ ID NO 22
<211> LENGTH: 21
<212> TYPE: DNA
<213> ORGANISM: Artificial Sequence
<220> FEATURE:
<223> OTHER INFORMATION: Dual targeting  siRNA
<220> FEATURE:
<221> NAME/KEY: misc_feature
<222> LOCATION: 1, 2
<223> OTHER INFORMATION: n = dT= deoxythymidine

<400> SEQUENCE: 22
nnaugguagu gggucgacga c                                              21

<210> SEQ ID NO 23
<211> LENGTH: 21
<212> TYPE: DNA
<213> ORGANISM: Artificial Sequence
<220> FEATURE:
<223> OTHER INFORMATION: "Dual targeting" siRNAs
<220> FEATURE:
<221> NAME/KEY: misc_feature
<222> LOCATION: 1, 2
<223> OTHER INFORMATION: n = dT= deoxythymidine

<400> SEQUENCE: 23
nnggcccguc gcccagcuca a                                              21

<210> SEQ ID NO 24
<211> LENGTH: 21
<212> TYPE: DNA
<213> ORGANISM: Artificial Sequence
<220> FEATURE:
<223> OTHER INFORMATION: Pseudocomplementary, bifunctional siRNA
<220> FEATURE:
<221> NAME/KEY: misc_feature
<222> LOCATION: 5
<223> OTHER INFORMATION: n = A* = 2-aminoadenine
<220> FEATURE:
<221> NAME/KEY: misc_feature
<222> LOCATION: 20, 21
<223> OTHER INFORMATION: n = dT= deoxythymidine

<400> SEQUENCE: 24
uaccngcacc caggugcugn n                                              21

<210> SEQ ID NO 25
<211> LENGTH: 21
<212> TYPE: DNA
<213> ORGANISM: Artificial Sequence
<220> FEATURE:
<223> OTHER INFORMATION: Pseudocomplementary, bifunctional siRNA
<220> FEATURE:
<221> NAME/KEY: misc_feature
<222> LOCATION: 16
<223> OTHER INFORMATION: n = A* = 2-aminoadenine
<220> FEATURE:
<221> NAME/KEY: misc_feature
<222> LOCATION: 20, 21
<223> OTHER INFORMATION: n = dT= deoxythymidine

<400> SEQUENCE: 25
ccgggcaucc ggacgnguun n                                              21

<210> SEQ ID NO 26
<211> LENGTH: 21
<212> TYPE: DNA
<213> ORGANISM: Artificial Sequence
<220> FEATURE:
<223> OTHER INFORMATION: Pseudocomplementary, bifunctional siRNA
<220> FEATURE:
<221> NAME/KEY: misc_feature
<222> LOCATION: 1, 2
<223> OTHER INFORMATION: n = dT= deoxythymidine
<220> FEATURE:
<221> NAME/KEY: misc_feature
<222> LOCATION: 7
<223> OTHER INFORMATION: n = U* = 2-thiouracil

<400> SEQUENCE: 26
nnauggnagu gggucgacga c                                              21

<210> SEQ ID NO 27
<211> LENGTH: 21
<212> TYPE: DNA
<213> ORGANISM: Artificial Sequence
<220> FEATURE:
<223> OTHER INFORMATION: Pseudocomplementary, bifunctional siRNA
<220> FEATURE:
<221> NAME/KEY: misc_feature
<222> LOCATION: 1, 2

```
<223> OTHER INFORMATION: n = dT= deoxythymidine
<220> FEATURE:
<221> NAME/KEY: misc_feature
<222> LOCATION: 18
<223> OTHER INFORMATION: n = U* 2-thiouracil

<400> SEQUENCE: 27
nnggcccguc gcccagcnca a                                              21

<210> SEQ ID NO 28
<211> LENGTH: 23
<212> TYPE: DNA
<213> ORGANISM: Mus musculus

<400> SEQUENCE: 28
aagctggccc tggacatgga gat                                            23

<210> SEQ ID NO 29
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_ feature
<222> LOCATION: 20, 21
<223> OTHER INFORMATION: n = dT= deoxythymidine

<400> SEQUENCE: 29
cuuacgcuga guacuucgan n                                              21

<210> SEQ ID NO 30
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 30
ucgaaguacu cagcguaagn n                                              21

<210> SEQ ID NO 31
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 31
cuuacgcuga guacuucgau u                                              21

<210> SEQ ID NO 32
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 32
ucgaaguacu cagcguaagu u                                              21

<210> SEQ ID NO 33
<211> LENGTH: 21
```

<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = dT* =deoxythymidine, phosphorothioate
    linkage
<220> FEATURE:
<221> NAME/KEY: misc_feature
<222> LOCATION: 21
<223> OTHER INFORMATION: n = dT =deoxythymidine

<400> SEQUENCE: 33
cuuacgcuga guacuucgan n                                           21

<210> SEQ ID NO 34
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = dT* =deoxythymidine, phosphorothioate
    linkage
<220> FEATURE:
<221> NAME/KEY: misc_RNA
<222> LOCATION: 21
<223> OTHER INFORMATION: n = dT =deoxythymidine

<400> SEQUENCE: 34
ucgaaguacu cagcguaagn n                                           21

<210> SEQ ID NO 35
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: n = C* = Cys phosphorothioate linkage
<220> FEATURE:
<221> NAME/KEY: misc_feature
<222> LOCATION: 20
<223> OTHER INFORMATION: n = dT* =deoxythymidine, phosphorothioate
    linkage
<220> FEATURE:
<221> NAME/KEY: misc_feature
<222> LOCATION: 21
<223> OTHER INFORMATION: n = dT =deoxythymidine

<400> SEQUENCE: 35
nuuacgcuga guacuucgan n                                           21

<210> SEQ ID NO 36
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: n = U* = phosphorothioate linkage
<220> FEATURE:
<221> NAME/KEY: misc_feature
<222> LOCATION: 20
<223> OTHER INFORMATION: n = dT* =deoxythymidine, phosphorothioate

```
                                    linkage
<220> FEATURE:
<221> NAME/KEY: misc_feature
<222> LOCATION: 21
<223> OTHER INFORMATION: n = dT=deoxythymidine

<400> SEQUENCE: 36
ncgaaguacu cagcguaagn n                                             21

<210> SEQ ID NO 37
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: n = C* = Cys phosphorothioate linkage
<220> FEATURE:
<221> NAME/KEY: misc_feature
<222> LOCATION: 19
<223> OTHER INFORMATION: n = Ala* =  Ala phosphorothioate linkage
<220> FEATURE:
<221> NAME/KEY: misc_feature
<222> LOCATION: 20
<223> OTHER INFORMATION: n = dT* = deoxythymidine, phosphorothioate
                                    linkage
<220> FEATURE:
<221> NAME/KEY: misc_feature
<222> LOCATION: 21
<223> OTHER INFORMATION: n = dT = deoxythymidine

<400> SEQUENCE: 37
nuuacgcuga guacuucgnn n                                             21

<210> SEQ ID NO 38
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: n =U* = U phosphorothioate linkage
<220> FEATURE:
<221> NAME/KEY: misc_feature
<222> LOCATION: 20
<223> OTHER INFORMATION: n = dT* =deoxythymidine, phosphorothioate
                                    linkage
<220> FEATURE:
<221> NAME/KEY: misc_feature
<222> LOCATION: 21
<223> OTHER INFORMATION: n = dT =deoxythymidine

<400> SEQUENCE: 38
ncgaaguacu cagcguaagn n                                             21

<210> SEQ ID NO 39
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 39
cuuacgcuga guacuucgau                                               20

<210> SEQ ID NO 40
<211> LENGTH: 20
```

```
<212> TYPE: RNA
<213> ORGANISM: Artificial Sequence
<220> FEATURE:
<223> OTHER INFORMATION: Synthetically generated oligonucleotide

<400> SEQUENCE: 40
ucgaaguacu cagcguaagu                                               20

<210> SEQ ID NO 41
<211> LENGTH: 20
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = U* = phosphorothioate linkage

<400> SEQUENCE: 41
cuuacgcuga guacuucgan                                               20

<210> SEQ ID NO 42
<211> LENGTH: 20
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = U* = phosphorothioate linkage

<400> SEQUENCE: 42
ucgaaguacu cagcguaagn                                               20

<210> SEQ ID NO 43
<211> LENGTH: 20
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: n = C* = Cys phosphorothioate linkage
<220> FEATURE:
<221> NAME/KEY: misc_feature
<222> LOCATION: 20
<223> OTHER INFORMATION: n = U* = phosphorothioate linkage

<400> SEQUENCE: 43
nuuacgcuga guacuucgan                                               20

<210> SEQ ID NO 44
<211> LENGTH: 20
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1, 20
<223> OTHER INFORMATION: n = U* = phosphorothioate linkage

<400> SEQUENCE: 44
ncgaaguacu cagcguaagn                                               20

<210> SEQ ID NO 45
```

```
<211> LENGTH: 23
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: n = 3'-OMe-U, in which the 3' substituent of
      the (U) sugar is -OCH3
<220> FEATURE:
<221> NAME/KEY: misc_feature
<222> LOCATION: 21, 22
<223> OTHER INFORMATION: n = dT =deoxythymidine,
<220> FEATURE:
<221> NAME/KEY: misc_feature
<222> LOCATION: 23
<223> OTHER INFORMATION: n = M2 = 3'-OMe-U, in which the 3' substituent
      of the (U) sugar is -OCH3

<400> SEQUENCE: 45
ncuuacgcug aguacuucga nnn                                            23

<210> SEQ ID NO 46
<211> LENGTH: 23
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: n = M1 = 3'-OMe-U, in which the 3' substituent
      of the (U) sugar is -OCH3
<220> FEATURE:
<221> NAME/KEY: misc_feature
<222> LOCATION: 21, 22
<223> OTHER INFORMATION: n = dT =deoxythymidine
<220> FEATURE:
<221> NAME/KEY: misc_feature
<222> LOCATION: 23
<223> OTHER INFORMATION: n = M2 = 3'-OMe-U, in which the 3' substituent
      of the (U) sugar is -OCH3

<400> SEQUENCE: 46
nucgaaguac ucagcguaag nnn                                            23

<210> SEQ ID NO 47
<211> LENGTH: 23
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: n = 3'-OMe-U, phosphorothioate linkage
<220> FEATURE:
<221> NAME/KEY: misc_feature
<222> LOCATION: 21
<223> OTHER INFORMATION: n = dT = deoxythymidine
<220> FEATURE:
<221> NAME/KEY: misc_feature
<222> LOCATION: 22
<223> OTHER INFORMATION: n = dT* =deoxythymidine, phosphorothioate
      linkage
<220> FEATURE:
<221> NAME/KEY: misc_feature
<222> LOCATION: 23
<223> OTHER INFORMATION: n = M2 = 3'-OMe-U, in which the 3' substituent
      of the (U) sugar is -OCH3

<400> SEQUENCE: 47
ncuuacgcug aguacuucga nnn                                            23
```

```
<210> SEQ ID NO 48
<211> LENGTH: 23
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: n = 3'-OMe-U, phosphorothioate linkage
<220> FEATURE:
<221> NAME/KEY: misc_feature
<222> LOCATION: 21
<223> OTHER INFORMATION: n = dT = deoxythymidine
<220> FEATURE:
<221> NAME/KEY: misc_feature
<222> LOCATION: 22
<223> OTHER INFORMATION: n = dT* = deoxythymidine, phosphorothioate
      linkage
<220> FEATURE:
<221> NAME/KEY: misc_feature
<222> LOCATION: 23
<223> OTHER INFORMATION: n = M2 = 3'-OMe-U, in which the 3' substituent
      of the (U) sugar is -OCH3

<400> SEQUENCE: 48
nucgaaguac ucagcguaag nnn                                             23

<210> SEQ ID NO 49
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT = deoxythymidine

<400> SEQUENCE: 49
cuuacgcuga guacuucgan n                                               21

<210> SEQ ID NO 50
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT = deoxythymidine

<400> SEQUENCE: 50
ucgaaguacu cagcguaagn n                                               21

<210> SEQ ID NO 51
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = dT = deoxythymidine
<220> FEATURE:
<221> NAME/KEY: misc_feature
<222> LOCATION: 21
<223> OTHER INFORMATION: n = dT* = deoxythymidine, phosphorothioate
      linkage
```

-continued

```
<400> SEQUENCE: 51
cuuacgcuga guacuucgan n                                      21

<210> SEQ ID NO 52
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = dT = deoxythymidine
<220> FEATURE:
<221> NAME/KEY: misc_feature
<222> LOCATION: 21
<223> OTHER INFORMATION: n = dT* = deoxythymidine, phosphorothioate
      linkage

<400> SEQUENCE: 52
ucgaaguacu cagcguaagn n                                      21

<210> SEQ ID NO 53
<211> LENGTH: 22
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21, 22
<223> OTHER INFORMATION: n = A, C, G, U, T, dT, U2'OMe, or 3'OMe-U

<400> SEQUENCE: 53
ucgaaguacu cuagcguaag nn                                     22

<210> SEQ ID NO 54
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT = deoxythymidine

<400> SEQUENCE: 54
cuuacgcuga guacuucgan n                                      21

<210> SEQ ID NO 55
<211> LENGTH: 19
<212> TYPE: RNA
<213> ORGANISM: Artificial Sequence
<220> FEATURE:
<223> OTHER INFORMATION: Synthetically generated si RNA

<400> SEQUENCE: 55
cuuacgcuga guacuucga                                         19

<210> SEQ ID NO 56
<211> LENGTH: 19
<212> TYPE: RNA
<213> ORGANISM: Artificial Sequence
<220> FEATURE:
<223> OTHER INFORMATION: Synthetically generated siRNA

<400> SEQUENCE: 56
```
ucgaaguacu cagcguaag                                                  19

<210> SEQ ID NO 57
<211> LENGTH: 19
<212> TYPE: RNA
<213> ORGANISM: Artificial Sequence
<220> FEATURE:
<223> OTHER INFORMATION: Synthetically generated siRNA

<400> SEQUENCE: 57
cuuacgcuga guacuucga                                                  19

<210> SEQ ID NO 58
<211> LENGTH: 19
<212> TYPE: RNA
<213> ORGANISM: Artificial Sequence
<220> FEATURE:
<223> OTHER INFORMATION: Synthetically generated siRNA

<400> SEQUENCE: 58
ucgaaguacu cagcguaag                                                  19

<210> SEQ ID NO 59
<211> LENGTH: 19
<212> TYPE: RNA
<213> ORGANISM: Artificial Sequence
<220> FEATURE:
<223> OTHER INFORMATION: Synthetically generated siRNA
<220> FEATURE:
<221> NAME/KEY: misc_difference
<222> LOCATION: 1
<223> OTHER INFORMATION: n = C* = Cys phosphorothioate linkage

<400> SEQUENCE: 59
nuuacgcuga guacuucga                                                  19

<210> SEQ ID NO 60
<211> LENGTH: 19
<212> TYPE: RNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 2
<223> OTHER INFORMATION: n = C* = Cys phosphorothioate linkage

<400> SEQUENCE: 60
ungaaguacu cagcguaag                                                  19

<210> SEQ ID NO 61
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT = deoxythymidine

<400> SEQUENCE: 61
ucgaaguacu cagcguaagn n                                               21

<210> SEQ ID NO 62
<211> LENGTH: 21
<212> TYPE: DNA

```
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 20
<223> OTHER INFORMATION: n = dT* = deoxythymidine, phosphorothioate
      linkage
<220> FEATURE:
<221> NAME/KEY: misc_feature
<222> LOCATION: 21
<223> OTHER INFORMATION: n = dT = deoxythymidine

<400> SEQUENCE: 62
cuuacgcuga guacuucgan n                                              21

<210> SEQ ID NO 63
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 20
<223> OTHER INFORMATION: n = dT= deoxythymidine
<220> FEATURE:
<221> NAME/KEY: misc_feature
<222> LOCATION: 21
<223> OTHER INFORMATION: n = dT* = deoxythymidine, phosphorothioate
      linkage

<400> SEQUENCE: 63
ucgaaguacu cagcguaagn n                                              21

<210> SEQ ID NO 64
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 19
<223> OTHER INFORMATION: n = A* = adenine, phosphorothioate linkage
<220> FEATURE:
<221> NAME/KEY: misc_feature
<222> LOCATION: 20
<223> OTHER INFORMATION: n = dT* =deoxythymidine, phosphorothioate
      linkage
<220> FEATURE:
<221> NAME/KEY: misc_feature
<222> LOCATION: 21
<223> OTHER INFORMATION: n = dT= deoxythymidine

<400> SEQUENCE: 64
cuuacgcuga guacuucgnn n                                              21

<210> SEQ ID NO 65
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 20, 21
<223> OTHER INFORMATION: n = dT* =deoxythymidine, phosphorothioate
      linkage

<400> SEQUENCE: 65
ucgaaguacu cagcguaagn n                                              21
```

<210> SEQ ID NO 66
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 18
<223> OTHER INFORMATION: n = G* = guanine, phosphorothioate linkage
<220> FEATURE:
<221> NAME/KEY: misc_feature
<222> LOCATION: 19
<223> OTHER INFORMATION: n = A* = adenine, phosphorothioate linkage
<220> FEATURE:
<221> NAME/KEY: misc_feature
<222> LOCATION: 20
<223> OTHER INFORMATION: n = dT* =deoxythymidine, phosphorothioate
      linkage
<220> FEATURE:
<221> NAME/KEY: misc_feature
<222> LOCATION: 21
<223> OTHER INFORMATION: n = dT= deoxythymidine

<400> SEQUENCE: 66
cuuacgcuga guacuucnnn n                                              21

<210> SEQ ID NO 67
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 19
<223> OTHER INFORMATION: n = G* = guanine, phosphorothioate linkage
<220> FEATURE:
<221> NAME/KEY: misc_feature
<222> LOCATION: 20, 21
<223> OTHER INFORMATION: n = dT* =deoxythymidine, phosphorothioate
      linkage

<400> SEQUENCE: 67
ucgaaguacu cagcguaann n                                              21

<210> SEQ ID NO 68
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 17
<223> OTHER INFORMATION: n = C* = cytosine  phosphorothioate linkage
<220> FEATURE:
<221> NAME/KEY: misc_feature
<222> LOCATION: 18
<223> OTHER INFORMATION: n = G* = guanine, phosphorothioate linkage
<220> FEATURE:
<221> NAME/KEY: misc_feature
<222> LOCATION: 19
<223> OTHER INFORMATION: n = A* = adenine, phosphorothioate linkage
<220> FEATURE:
<221> NAME/KEY: misc_feature
<222> LOCATION: 20
<223> OTHER INFORMATION: n = dT* =deoxythymidine, phosphorothioate
      linkage
<220> FEATURE:
<221> NAME/KEY: misc_feature
<222> LOCATION: 21
<223> OTHER INFORMATION: n = dT= deoxythymidine

<400> SEQUENCE: 68
cuuacgcuga guacuunnnn n                    21

<210> SEQ ID NO 69
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 18
<223> OTHER INFORMATION: n = A* = adenine, phosphorothioate linkage
<220> FEATURE:
<221> NAME/KEY: misc_feature
<222> LOCATION: 19
<223> OTHER INFORMATION: n = G* = guanine, phosphorothioate linkage
<220> FEATURE:
<221> NAME/KEY: misc_feature
<222> LOCATION: 20, 21
<223> OTHER INFORMATION: n = dT* =deoxythymidine, phosphorothioate
      linkage

<400> SEQUENCE: 69
ucgaaguacu cagcguannn n                    21

<210> SEQ ID NO 70
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 12
<223> OTHER INFORMATION: n =U* = uracil, phosphorothioate linkage
<220> FEATURE:
<221> NAME/KEY: misc_feature
<222> LOCATION: 20, 21
<223> OTHER INFORMATION: n = dT= deoxythymidine

<400> SEQUENCE: 70
cuuacgcuga gnacuucgan n                    21

<210> SEQ ID NO 71
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 8
<223> OTHER INFORMATION: n = A* = adenine, phosphorothioate linkage
<220> FEATURE:
<221> NAME/KEY: misc_feature
<222> LOCATION: 20, 21
<223> OTHER INFORMATION: n = dT= deoxythymidine

<400> SEQUENCE: 71
ucgaaguncu cagcgunagn n                    21

<210> SEQ ID NO 72
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature

```
<222> LOCATION: 3, 12
<223> OTHER INFORMATION: n =U* = uracil, phosphorothioate linkage
<220> FEATURE:
<221> NAME/KEY: misc_feature
<222> LOCATION: 20, 21
<223> OTHER INFORMATION: n = dT= deoxythymidine

<400> SEQUENCE: 72
cunacgcuga gnacuucgan n                                              21

<210> SEQ ID NO 73
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 8, 17
<223> OTHER INFORMATION: n = A* = adenine, phosphorothioate linkage
<220> FEATURE:
<221> NAME/KEY: misc_feature
<222> LOCATION: 20, 21
<223> OTHER INFORMATION: n = dT= deoxythymidine

<400> SEQUENCE: 73
ucgaaguncu cagcgunagn n                                              21

<210> SEQ ID NO 74
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 3, 12
<223> OTHER INFORMATION: n =U* = uracil, phosphorothioate linkage
<220> FEATURE:
<221> NAME/KEY: misc_feature
<222> LOCATION: 20
<223> OTHER INFORMATION: n = dT* =deoxythymidine, phosphorothioate
      linkage
<220> FEATURE:
<221> NAME/KEY: misc_feature
<222> LOCATION: 21
<223> OTHER INFORMATION: n = dT= deoxythymidine

<400> SEQUENCE: 74
cunacgcuga gnacuucgan n                                              21

<210> SEQ ID NO 75
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 8, 17
<223> OTHER INFORMATION: n = A* = adenine, phosphorothioate linkage
<220> FEATURE:
<221> NAME/KEY: misc_feature
<222> LOCATION: 20
<223> OTHER INFORMATION: n = dT= deoxythymidine
<220> FEATURE:
<221> NAME/KEY: misc_feature
<222> LOCATION: 21
<223> OTHER INFORMATION: n = dT* =deoxythymidine, phosphorothioate
      linkage

<400> SEQUENCE: 75
```
ucgaaguncu cagcgunagn n          21

<210> SEQ ID NO 76
<211> LENGTH: 22
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 20, 22
<223> OTHER INFORMATION: n = dT= deoxythymidine
<220> FEATURE:
<221> NAME/KEY: misc_feature
<222> LOCATION: 21
<223> OTHER INFORMATION: n = mp = methylphosphonate

<400> SEQUENCE: 76
cuuacgcuga guacuucgan nn          22

<210> SEQ ID NO 77
<211> LENGTH: 22
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 20, 22
<223> OTHER INFORMATION: n = dT= deoxythymidine
<220> FEATURE:
<221> NAME/KEY: misc_feature
<222> LOCATION: 21
<223> OTHER INFORMATION: n = mp = methylphosphonate

<400> SEQUENCE: 77
ucgaaguacu cagcguaagn nn          22

<210> SEQ ID NO 78
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 20, 21
<223> OTHER INFORMATION: n = U = 2'OMe-uridine

<400> SEQUENCE: 78
cuuacgcuga guacuucgan n          21

<210> SEQ ID NO 79
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 20, 21
<223> OTHER INFORMATION: n = U = 2'OMe-uridine

<400> SEQUENCE: 79
ucgaaguacu cagcguaagn n          21

<210> SEQ ID NO 80
<211> LENGTH: 21
<212> TYPE: DNA
<213> ORGANISM: Artificial Sequence -continued

```
<220> FEATURE:
<223> OTHER INFORMATION: Synthetically generated si RNA
<220> FEATURE:
<221> NAME/KEY: misc_feature
<222> LOCATION: 1
<223> OTHER INFORMATION: n = C* = cytosine  phosphorothioate linkage
<220> FEATURE:
<221> NAME/KEY: misc_feature
<222> LOCATION: 20
<223> OTHER INFORMATION: n = U* = 2'OMe-uridine, phosphorothioate
      linkage
<220> FEATURE:
<221> NAME/KEY: misc_feature
<222> LOCATION: 21
<223> OTHER INFORMATION: n = U = 2'OMe-uridine

<400> SEQUENCE: 80
nuuacgcuga guacuucgan n                                             21

<210> SEQ ID NO 81
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 2
<223> OTHER INFORMATION: n = C* = cytosine  phosphorothioate linkage
<220> FEATURE:
<221> NAME/KEY: misc_feature
<222> LOCATION: 20
<223> OTHER INFORMATION: n = U = 2'OMe-uridine
<220> FEATURE:
<221> NAME/KEY: misc_feature
<222> LOCATION: 21
<223> OTHER INFORMATION: n = U* = 2'OMe-uridine, phosphorothioate
      linkage

<400> SEQUENCE: 81
ungaaguacu cagcguaagn n                                             21

<210> SEQ ID NO 82
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 1
<223> OTHER INFORMATION: n = C* = cytosine  phosphorothioate linkage
<220> FEATURE:
<221> NAME/KEY: misc_feature
<222> LOCATION: 3, 21
<223> OTHER INFORMATION: n = U = 2'OMe-uridine
<220> FEATURE:
<221> NAME/KEY: misc_feature
<222> LOCATION: 20
<223> OTHER INFORMATION: n = U* = 2'OMe-uridine, phosphorothioate
      linkage

<400> SEQUENCE: 82
nunacgcuga guacuucgan n                                             21

<210> SEQ ID NO 83
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
```

```
<222> LOCATION: 2
<223> OTHER INFORMATION: n = C* = cytosine  phosphorothioate linkage
<220> FEATURE:
<221> NAME/KEY: misc_feature
<222> LOCATION: 16, 20
<223> OTHER INFORMATION: n = U = 2'OMe-uridine
<220> FEATURE:
<221> NAME/KEY: misc_feature
<222> LOCATION: 21
<223> OTHER INFORMATION: n = U* = 2'OMe-uridine, phosphorothioate
      linkage

<400> SEQUENCE: 83
ungaaguacu cagcgnaagn n                                           21

<210> SEQ ID NO 84
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 1
<223> OTHER INFORMATION: n = C* = cytosine  phosphorothioate linkage
<220> FEATURE:
<221> NAME/KEY: misc_feature
<222> LOCATION: 3, 12, 21
<223> OTHER INFORMATION: n = U = 2'OMe-uridine
<220> FEATURE:
<221> NAME/KEY: misc_feature
<222> LOCATION: 20
<223> OTHER INFORMATION: n = U* = 2'OMe-uridine, phosphorothioate
      linkage

<400> SEQUENCE: 84
nunacgcuga gnacuucgan n                                           21

<210> SEQ ID NO 85
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 2
<223> OTHER INFORMATION: n = C* = cytosine  phosphorothioate linkage
<220> FEATURE:
<221> NAME/KEY: misc_feature
<222> LOCATION: 7, 16, 20
<223> OTHER INFORMATION: n = U = 2'OMe-uridine
<220> FEATURE:
<221> NAME/KEY: misc_feature
<222> LOCATION: 21
<223> OTHER INFORMATION: n = U* = 2'OMe-uridine, phosphorothioate
      linkage

<400> SEQUENCE: 85
ungaagnacu cagcgnaagn n                                           21

<210> SEQ ID NO 86
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 20
<223> OTHER INFORMATION: n = dT= deoxythymidine
<220> FEATURE:
<221> NAME/KEY: misc_feature
```

<222> LOCATION: 21
<223> OTHER INFORMATION: n = aadT = alkylamine-deoxythymidine

<400> SEQUENCE: 86
cuuacgcuga guacuucgan n                                              21

<210> SEQ ID NO 87
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 20
<223> OTHER INFORMATION: n = deoxythymidine
<220> FEATURE:
<221> NAME/KEY: misc_feature
<222> LOCATION: 21
<223> OTHER INFORMATION: n = aadT = alkylamine-deoxythymidine

<400> SEQUENCE: 87
ucgaaguacu cagcguaagn n                                              21

<210> SEQ ID NO 88
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 20, 21
<223> OTHER INFORMATION: n = aadT = alkylamine-deoxythymidine

<400> SEQUENCE: 88
cuuacgcuga guacuucgan n                                              21

<210> SEQ ID NO 89
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 20, 21
<223> OTHER INFORMATION: n = aadT = alkylamine-deoxythymidine

<400> SEQUENCE: 89
ucgaaguacu cagcguaagn n                                              21

<210> SEQ ID NO 90
<211> LENGTH: 22
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 20, 21
<223> OTHER INFORMATION: n = dT= deoxythymidine
<220> FEATURE:
<221> NAME/KEY: misc_feature
<222> LOCATION: 22
<223> OTHER INFORMATION: n = AbP = abasic pyrrolidine cationic

<400> SEQUENCE: 90
cuuacgcuga guacuucgan nn                                             22

```
<210> SEQ ID NO 91
<211> LENGTH: 22
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 20, 21
<223> OTHER INFORMATION: n = dT= deoxythymidine
<220> FEATURE:
<221> NAME/KEY: misc_feature
<222> LOCATION: 22
<223> OTHER INFORMATION: n = AbP = abasic pyrrolidine cationic

<400> SEQUENCE: 91
ucgaaguacu cagcguaagn nn                                              22

<210> SEQ ID NO 92
<211> LENGTH: 22
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 1
<223> OTHER INFORMATION: n = C* = cytosine  phosphorothioate linkage
<220> FEATURE:
<221> NAME/KEY: misc_feature
<222> LOCATION: 3
<223> OTHER INFORMATION: n = aaU = Allylamino-uridine
<220> FEATURE:
<221> NAME/KEY: misc_feature
<222> LOCATION: 20
<223> OTHER INFORMATION: n = U* = 2'OMe-uridine, phosphorothioate
      linkage
<220> FEATURE:
<221> NAME/KEY: misc_feature
<222> LOCATION: 21
<223> OTHER INFORMATION: n = U = 2'OMe-uridine

<400> SEQUENCE: 92
nunacgcuga guacuucgan nn                                              22

<210> SEQ ID NO 93
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 2
<223> OTHER INFORMATION: n = C* = cytosine  phosphorothioate linkage
<220> FEATURE:
<221> NAME/KEY: misc_feature
<222> LOCATION: 16
<223> OTHER INFORMATION: n = aaU = Allylamino-uridine
<220> FEATURE:
<221> NAME/KEY: misc_feature
<222> LOCATION: 20
<223> OTHER INFORMATION: n = U = 2'OMe-uridine
<220> FEATURE:
<221> NAME/KEY: misc_feature
<222> LOCATION: 21
<223> OTHER INFORMATION: n = U* = 2'OMe-uridine, phosphorothioate
      linkage

<400> SEQUENCE: 93
ungaaguacu cagcgnaagn n                                               21
```

```
<210> SEQ ID NO 94
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 1
<223> OTHER INFORMATION: n = C* = cytosine  phosphorothioate linkage
<220> FEATURE:
<221> NAME/KEY: misc_feature
<222> LOCATION: 3, 12
<223> OTHER INFORMATION: n = aaU = Allylamino-uridine
<220> FEATURE:
<221> NAME/KEY: misc_feature
<222> LOCATION: 20
<223> OTHER INFORMATION: n = U* = 2'OMe-uridine, phosphorothioate
      linkage
<220> FEATURE:
<221> NAME/KEY: misc_feature
<222> LOCATION: 21
<223> OTHER INFORMATION: n = U = 2'OMe-uridine

<400> SEQUENCE: 94
nunacgcuga gnacuucgan n                                              21

<210> SEQ ID NO 95
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 2
<223> OTHER INFORMATION: n = C* = cytosine  phosphorothioate linkage
<220> FEATURE:
<221> NAME/KEY: misc_feature
<222> LOCATION: 7, 16
<223> OTHER INFORMATION: n = aaU = Allylamino-uridine
<220> FEATURE:
<221> NAME/KEY: misc_feature
<222> LOCATION: 20
<223> OTHER INFORMATION: n = U = 2'OMe-uridine
<220> FEATURE:
<221> NAME/KEY: misc_feature
<222> LOCATION: 21
<223> OTHER INFORMATION: n = U* = 2'OMe-uridine, phosphorothioate
      linkage

<400> SEQUENCE: 95
ungaagnacu cagcgnaagn n                                              21

<210> SEQ ID NO 96
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 20, 21
<223> OTHER INFORMATION: n = dT= deoxythymidine

<400> SEQUENCE: 96
cuuacgcuga guacuucgan n                                              21

<210> SEQ ID NO 97
<211> LENGTH: 22
<212> TYPE: DNA
<213> ORGANISM: Artificial Sequence
<220> FEATURE:
```

<223> OTHER INFORMATION: Synthetically generated si RNA
<220> FEATURE:
<221> NAME/KEY: misc_feature
<222> LOCATION: 20, 21
<223> OTHER INFORMATION: n = dT= deoxythymidine

<400> SEQUENCE: 97
ucgaaguacu cagcguaagn nn                                                 22

<210> SEQ ID NO 98
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 20, 21
<223> OTHER INFORMATION: n = dT= deoxythymidine

<400> SEQUENCE: 98
cuuacgcuga guacuucgan n                                                  21

<210> SEQ ID NO 99
<211> LENGTH: 21
<212> TYPE: DNA
<213> ORGANISM: Artificial Sequence
<220> FEATURE:
<223> OTHER INFORMATION: Synthetically generated si RNA
<220> FEATURE:
<221> NAME/KEY: misc_feature
<222> LOCATION: 20, 21
<223> OTHER INFORMATION: n = dT= deoxythymidine

<400> SEQUENCE: 99
ucgaaguacu cagcguaagn n                                                  21

<210> SEQ ID NO 100
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 100
cuuacgcuga guacuucgan n                                                  21

<210> SEQ ID NO 101
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 101
ucgaaguacu cagcguaagn n                                                  21

<210> SEQ ID NO 102
<211> LENGTH: 21
<212> TYPE: DNA
<213> ORGANISM: Artificial Sequence

```
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 102
cuuacgcuga guacuucgan n                                              21

<210> SEQ ID NO 103
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 103
ucgaaguacu cagcguaagn n                                              21

<210> SEQ ID NO 104
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = dT= deoxythymidine
<220> FEATURE:
<221> NAME/KEY: misc_feature
<222> LOCATION: 21
<223> OTHER INFORMATION: n = dT* =deoxythymidine, phosphorothioate
      linkage

<400> SEQUENCE: 104
cuuacgcuga guacuucgan n                                              21

<210> SEQ ID NO 105
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = dT= deoxythymidine
<220> FEATURE:
<221> NAME/KEY: misc_feature
<222> LOCATION: 21
<223> OTHER INFORMATION: n = dT* =deoxythymidine, phosphorothioate
      linkage

<400> SEQUENCE: 105
ucgaaguacu cagcguaagn n                                              21

<210> SEQ ID NO 106
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1, 2, 4
```

```
<223> OTHER INFORMATION: n = G* = guanine, phosphorothioate
<220> FEATURE:
<221> NAME/KEY: misc_feature
<222> LOCATION: 17, 18
<223> OTHER INFORMATION: n = C* = cytosine  phosphorothioate
<220> FEATURE:
<221> NAME/KEY: misc_feature
<222> LOCATION: 3, 5, 19
<223> OTHER INFORMATION: n =U* = uracil, phosphorothioate linkage
<220> FEATURE:
<221> NAME/KEY: misc_feature
<222> LOCATION: 20, 21
<223> OTHER INFORMATION: n = U* = 2'Ome-uridine, phosphorothioate
      linkage

<400> SEQUENCE: 106
nnnnnauggc uucaacnnnn n                                             21

<210> SEQ ID NO 107
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1, 17
<223> OTHER INFORMATION: n = A* = adenine, phosphorothioate linkage
<220> FEATURE:
<221> NAME/KEY: misc_feature
<222> LOCATION: 2, 3, 4,
<223> OTHER INFORMATION: n = G* = guanine, phosphorothioate linkage
<220> FEATURE:
<221> NAME/KEY: misc_feature
<222> LOCATION: 14
<223> OTHER INFORMATION: n =U* = uracil, phosphorothioate linkage
<220> FEATURE:
<221> NAME/KEY: misc_feature
<222> LOCATION: 16, 18, 19
<223> OTHER INFORMATION: n = C* = cytosine  phosphorothioate linkage
<220> FEATURE:
<221> NAME/KEY: misc_feature
<222> LOCATION: 20, 21
<223> OTHER INFORMATION: n = U* = 2'Ome-uridine, phosphorothioate
      linkage

<400> SEQUENCE: 107
nnnnuugaag ccanannnnn n                                             21

<210> SEQ ID NO 108
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 108
cuuacgcuga guacuucgan n                                             21

<210> SEQ ID NO 109
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine
```

-continued

<400> SEQUENCE: 109
ucgaaguacu cagcguaagn n                                          21

<210> SEQ ID NO 110
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 110
ucgaaguacu cagcguaagu u                                          21

<210> SEQ ID NO 111
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 111
cuuacgcuga guacuucgan n                                          21

<210> SEQ ID NO 112
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 112
ucgaaguacu cagcguaagn n                                          21

<210> SEQ ID NO 113
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 113
cuuacgcuga guacuucgan n                                          21

<210> SEQ ID NO 114
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 114
ucgaaguacu cagcguaagn n                                    21

<210> SEQ ID NO 115
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 115
cuuacgcuga guacuucgan n                                    21

<210> SEQ ID NO 116
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 116
ucgaaguacu cagcguaagn n                                    21

<210> SEQ ID NO 117
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 117
cuuacgcuga guacuucgan n                                    21

<210> SEQ ID NO 118
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 118
ucgaaguacu cagcguaagn n                                    21

<210> SEQ ID NO 119
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 119

-continued cuuacgcuga guacuucgan n                                                   21

<210> SEQ ID NO 120
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 120
ucgaaguacu cagcguaagn n                                                   21

<210> SEQ ID NO 121
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 121
cuuacgcuga guacuucgan n                                                   21

<210> SEQ ID NO 122
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 122
ucgaaguacu cagcguaagn n                                                   21

<210> SEQ ID NO 123
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 123
cuuacgcuga guacuucgan n                                                   21

<210> SEQ ID NO 124
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

```
<400> SEQUENCE: 124
ucgaaguacu cagcguaagn n                                              21

<210> SEQ ID NO 125
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 125
cuuacgcuga guacuucgan n                                              21

<210> SEQ ID NO 126
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 126
ucgaaguacu cagcguaagn n                                              21

<210> SEQ ID NO 127
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 127
cuuacgcuga guacuucgan n                                              21

<210> SEQ ID NO 128
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 128
ucgaaguacu cagcguaagn n                                              21

<210> SEQ ID NO 129
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine
```

-continued

<400> SEQUENCE: 129
cuuacgcuga guacuucgan n                                              21

<210> SEQ ID NO 130
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 130
ucgaaguacu cagcguaagn n                                              21

<210> SEQ ID NO 131
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 131
cuuacgcuga guacuucgan n                                              21

<210> SEQ ID NO 132
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 132
ucgaaguacu cagcguaagn n                                              21

<210> SEQ ID NO 133
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 133
cuuacgcuga guacuucgan n                                              21

<210> SEQ ID NO 134
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21

<223> OTHER INFORMATION: n = dT= deoxythymidine

<400> SEQUENCE: 134
ucgaaguacu cagcguaagn n    21

<210> SEQ ID NO 135
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 135
cuuacgcuga guacuucgan n    21

<210> SEQ ID NO 136
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 136
ucgaaguacu cagcguaagn n    21

<210> SEQ ID NO 137
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 137
cuuacgcuga guacuucgan n    21

<210> SEQ ID NO 138
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 138
ucgaaguacu cagcguaagn n    21

<210> SEQ ID NO 139
<211> LENGTH: 20
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature

```
<222> LOCATION: 20, 21
<223> OTHER INFORMATION: n = dT= deoxythymidine

<400> SEQUENCE: 139
cuuacgcuga guacuucgan                                                    20

<210> SEQ ID NO 140
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 140
ucgaaguacu cagcguaagn n                                                  21

<210> SEQ ID NO 141
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 141
cuuacgcuga guacuucgan n                                                  21

<210> SEQ ID NO 142
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 142
ucgaaguacu cagcguaagn n                                                  21

<210> SEQ ID NO 143
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 143
cuuacgcuga guacuucgan n                                                  21

<210> SEQ ID NO 144
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
```

<221> NAME/KEY: misc_feature
<222> LOCATION: 20, 21
<223> OTHER INFORMATION: n = dT= deoxythymidine

<400> SEQUENCE: 144
ucgaaguacu cagcguaagn n          21

<210> SEQ ID NO 145
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 145
cuuacgcuga guacuucgan n          21

<210> SEQ ID NO 146
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 146
ucgaaguacu cagcguaagn n          21

<210> SEQ ID NO 147
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 147
cuuacgcuga guacuucgan n          21

<210> SEQ ID NO 148
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 148
ucgaaguacu cagcguaagn n          21

<210> SEQ ID NO 149
<211> LENGTH: 21
<212> TYPE: DNA
<213> ORGANISM: Artificial Sequence
<220> FEATURE:
<223> OTHER INFORMATION: Synthetically generated oligonucleotide

```
<220> FEATURE:
<221> NAME/KEY: misc_feature
<222> LOCATION: 20, 21
<223> OTHER INFORMATION: n = dT= deoxythymidine

<400> SEQUENCE: 149
cuuacgcuga guacuucgan n                                              21

<210> SEQ ID NO 150
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 150
ucgaaguacu cagcguaagn n                                              21

<210> SEQ ID NO 151
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 151
cuuacgcuga guacuucgan n                                              21

<210> SEQ ID NO 152
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 152
ucgaaguacu cagcguaagn n                                              21

<210> SEQ ID NO 153
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 153
cuuacgcuga guacuucgan n                                              21

<210> SEQ ID NO 154
<211> LENGTH: 21
<212> TYPE: DNA
<213> ORGANISM: Artificial Sequence
<220> FEATURE:
```

<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 154
ucgaaguacu cagcguaagn n					21

<210> SEQ ID NO 155
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 155
cuuacgcuga guacuucgan n					21

<210> SEQ ID NO 156
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 156
ucgaaguacu cagcguaagn n					21

<210> SEQ ID NO 157
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 157
cuuacgcuga guacuucgan n					21

<210> SEQ ID NO 158
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 158
ucgaaguacu cagcguaagn n					21

<210> SEQ ID NO 159
<211> LENGTH: 21
<212> TYPE: DNA
<213> ORGANISM: Artificial Sequence

```
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 159
cuuacgcuga guacuucgan n                                            21

<210> SEQ ID NO 160
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 160
ucgaaguacu cagcguaagn n                                            21

<210> SEQ ID NO 161
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 161
cuuacgcuga guacuucgan n                                            21

<210> SEQ ID NO 162
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 162
ucgaaguacu cagcguaagn n                                            21

<210> SEQ ID NO 163
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 163
cuuacgcuga guacuucgan n                                            21

<210> SEQ ID NO 164
<211> LENGTH: 21
<212> TYPE: DNA
```

```
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 164
ucgaaguacu cagcguaagn n                                           21

<210> SEQ ID NO 165
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 165
cuuacgcuga guacuucgan n                                           21

<210> SEQ ID NO 166
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 166
ucgaaguacu cagcguaagn n                                           21

<210> SEQ ID NO 167
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 167
cuuacgcuga guacuucgan n                                           21

<210> SEQ ID NO 168
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 168
ucgaaguacu cagcguaagn n                                           21

<210> SEQ ID NO 169
<211> LENGTH: 21
```

```
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 169
cuuacgcuga guacuucgan n                                              21

<210> SEQ ID NO 170
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 170
ucgaaguacu cagcguaagn n                                              21

<210> SEQ ID NO 171
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 171
cuuacgcuga guacuucgan n                                              21

<210> SEQ ID NO 172
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 172
ucgaaguacu cagcguaagn n                                              21

<210> SEQ ID NO 173
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 173
cuuacgcuga guacuucgan n                                              21

<210> SEQ ID NO 174
```

```
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT= deoxythymidine

<400> SEQUENCE: 174
ucgaaguacu cagcguaagn n                                          21
```